(12) United States Patent
Banno et al.

(10) Patent No.: US 8,436,043 B2
(45) Date of Patent: May 7, 2013

(54) HETEROCYCLIC COMPOUND

(75) Inventors: Yoshihiro Banno, Osaka (JP); Ryoma Hara, Osaka (JP); Ryosuke Tokunoh, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 203 days.

(21) Appl. No.: 12/920,973

(22) PCT Filed: Mar. 4, 2009

(86) PCT No.: PCT/JP2009/054095
§ 371 (c)(1),
(2), (4) Date: Sep. 3, 2010

(87) PCT Pub. No.: WO2009/110520
PCT Pub. Date: Sep. 11, 2009

(65) Prior Publication Data
US 2012/0053173 A1 Mar. 1, 2012
US 2012/0270865 A2 Oct. 25, 2012

(30) Foreign Application Priority Data

Mar. 5, 2008 (JP) ................. 2008-055250
Feb. 6, 2009 (JP) ................. 2009-025511

(51) Int. Cl.
*A61K 31/343* (2006.01)
*C07D 307/80* (2006.01)

(52) U.S. Cl.
USPC .......................... 514/469; 549/467

(58) Field of Classification Search ........... 514/469; 549/467
See application file for complete search history.

(56) References Cited

U.S. PATENT DOCUMENTS

| | | | |
|---|---|---|---|
| 7,598,285 B2 | 10/2009 | Parmee et al. |
| 7,687,534 B2 | 3/2010 | Stelmach et al. |
| 7,799,818 B2 | 9/2010 | Parmee et al. |
| 7,799,820 B2 | 9/2010 | Takahashi et al. |
| 7,968,589 B2 | 6/2011 | Stelmach et al. |
| 2005/0272794 A1 | 12/2005 | Parmee et al. |
| 2008/0085926 A1 | 4/2008 | Stelmach et al. |
| 2009/0118304 A1 | 5/2009 | Takahashi et al. |
| 2009/0176854 A1 | 7/2009 | Parmee et al. |
| 2009/0247746 A1 | 10/2009 | Yasuma et al. |
| 2010/0004158 A1 | 1/2010 | Stelmach et al. |
| 2010/0144824 A1 | 6/2010 | Stelmach et al. |

FOREIGN PATENT DOCUMENTS

| | | |
|---|---|---|
| EP | 2 210 876 | 7/2010 |
| JP | 2006/112549 | 10/2006 |
| JP | 2007/037534 | 4/2007 |
| WO | 00/69810 | 11/2000 |
| WO | 03/048109 | 6/2003 |
| WO | 2004/002480 | 1/2004 |
| WO | 2004/069158 | 8/2004 |
| WO | 2004/098528 | 11/2004 |
| WO | 2004/100875 | 11/2004 |
| WO | 2006/102067 | 9/2006 |
| WO | 2007/106181 | 9/2007 |
| WO | 2010/050445 | 5/2010 |

OTHER PUBLICATIONS

International Search Report issued May 19, 2009 in International (PCT) Application No. PCT/JP2009/054095.
Opposition against corresponding Costa Rican patent application and English translation thereof, published Dec. 10, 2010.

*Primary Examiner* — Taofiq A Solola
(74) *Attorney, Agent, or Firm* — Wenderoth, Lind & Ponack, L.L.P.

(57) ABSTRACT

Provision of a prophylactic or therapeutic agent for diabetes, which has superior efficacy.
A compound represented by the formula:

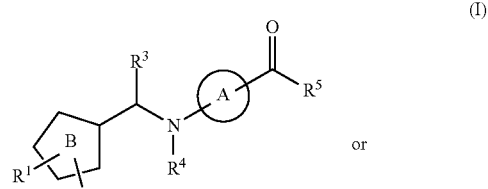

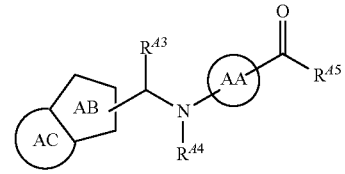

wherein each symbol is as described in the specification, or a salt thereof.

10 Claims, No Drawings

SEQUENCE LISTING

<160> NUMBER OF SEQ ID NOS: 2

<210> SEQ ID NO 1
<211> LENGTH: 31
<212> TYPE: DNA
<213> ORGANISM: Artificial sequence
<220> FEATURE:
<223> OTHER INFORMATION: Synthetic construct; PCR primer

<400> SEQUENCE: 1
aatagaattc atgccccct gccagccaca g                                31

<210> SEQ ID NO 2
<211> LENGTH: 36
<212> TYPE: DNA
<213> ORGANISM: Artificial sequence
<220> FEATURE:
<223> OTHER INFORMATION: Synthetic construst; PCR primer

<400> SEQUENCE: 2
ctaagcggcc gctcagaagg ggctctcagc caatct                          36

HETEROCYCLIC COMPOUND

This application is a U.S. national stage of International Application No. PCT/JP2009/054095 filed Mar. 4, 2009.

TECHNICAL FIELD

The present invention relates to a heterocyclic compound having a glucagon antagonistic action, which is useful for the prophylaxis or treatment of diabetes and the like.

BACKGROUND OF THE INVENTION

Glucagon is a straight chain peptide hormone having 29 amino acids, which is secreted from pancreatic α cells and promotes glycogenolysis and gluconeogenesis in the liver. Diabetes patients generally show promoted secretion and reactiveness of glucagon, which is one cause of hyperglycemia. Therefore, glucagon receptor antagonists can suppress excess sugar production from the liver by shutting off the action of glucagons, and are useful as therapeutic drugs for diabetes.

As glucagon antagonists, the following compounds are known.

1) a compound represented by the following formula:

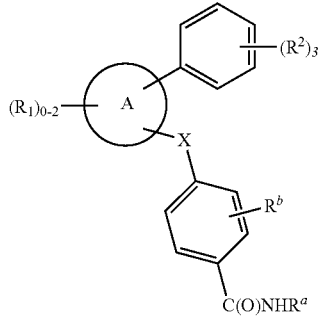

wherein ring A is 6- to 10-membered aryl, 6- to 10-membered aromatic heterocyclic group, 6-membered aryl condensed with 5- or 6-membered carbocycle; $R_1$ is, when it is present, (a) halogen, OH, $CO_2R^4$, $SO_pR^5$, CN, $NO_2$, $C(O)NR^6R^7$ or $NR^6R^7$, (b) $C_{1-6}$ alkyl, $C(O)C_{1-6}$ alkyl or $C(O)C_{1-6}$ alkyl (substitutable with (a)), (c) 6- to 10-membered aryl, aryloxy or arylthio, or 5- to 10-s membered aromatic heterocyclic group, aromatic heterocyclyl-oxy or aromatic heterocyclyl-thio (each substitutable with (a) or (b); these groups are further substitutable with pyrazole, imidazole, tetrazole, pyrrole, triazole, thiazole, furan, thiophene, thiadiazole or oxazole (each substitutable with (a) or (b))); $R^2$ is H, or substituent (a) or (b); X is —O—, —S—, —$C(R^3)_2)_{1-2}$—, —$OC(R^3)_2$— or —$C(R^3)_2O$—; $R^3$ is H, or $C_{1-10}$ alkyl, $C_{2-4}$ alkenyl, aryl or aromatic heterocyclic group (substitutable with (a) or (b); one of $R^3$ is other than H or $C_{1-10}$ alkyl); $R^4$ is H or $C_{1-6}$ alkyl; $R^5$ is $C_{1-10}$ alkyl, aryl or aryl-$C_{1-10}$ alkyl; $R^6$ and $R^7$ are each H or $C_{1-3}$ alkyl; p is 0-2; $R^a$ is $CH_2CH_2CO_2R^4$, $CH_2CH(OH)CO_2R^4$ or 5-tetrazolyl; and $R^b$ is H, or substituent (a) or (b)] (patent document 1: WO2006/102067).

2) A compound represented by the following formula:

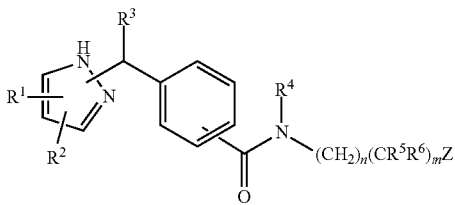

wherein $R^1$ is (a) $C_{1-10}$ alkyl, $C_{2-10}$ alkenyl or $C_{2-10}$ alkynyl (each substitutable), or (b) aryl, aromatic heterocyclic group or nonaromatic heterocyclic group (each substitutable); $R^2$ is H or $R^1$; $R^3$ and $R^4$ are each H or $C_{1-10}$ alkyl; $R^5$ is H or F; $R^6$ is H, OH, F or $C_{1-3}$ alkyl, or $R^5$ and $R^6$ form oxo; $R^8$ is H, or $C_{1-10}$ alkyl (substitutable with phenyl, OH, $OC_{1-6}$ alkyl, $CO_2H$, $CO_2C_{1-6}$ alkyl, halo); m is 0-2; n is 1-6; when one of m and n is other than 0, Z is $COR^8$, 5-tetrazolyl or 5-(2-oxo-1,3,4-oxadiazolyl), and when m and n are both 0, Z is 5-tetrazolyl or 5-(2-oxo-1,3,4-oxadiazolyl)] (patent document 2: WO2004/069158).

3) A compound represented by the following formula:

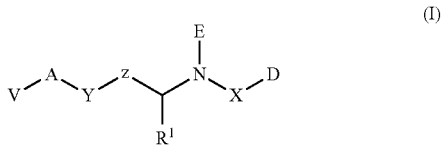

wherein V is —$C(O)OR^2$, —$C(O)NR^2R^3$, —$C(O)NR^2OR^3$, —$S(O)_2OR^2$,

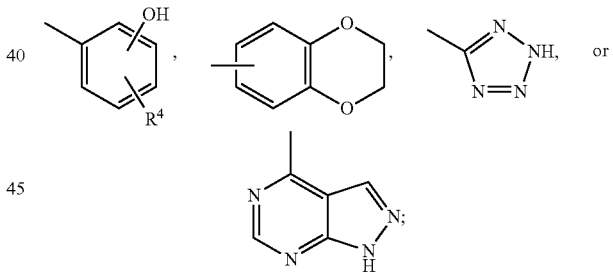

$R^2$ and $R^3$ are each independently H or $C_{1-6}$ alkyl; $R^4$ is H, halogen and the like; A is

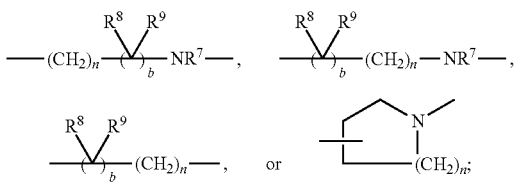

b is 0 or 1; n is 0-3; $R^7$ is H, $C_{1-6}$ alkyl and the like; $R^8$ and $R^9$ are each independently H or $C_{1-6}$ alkyl; Y is —C(O)—, —$S(O)_2$—, —O— or a bond; Z is phenyl, 5-6-membered aromatic heterocycle (each substitutable with halo etc.); $R^1$ is H or $C_{1-6}$ alkyl; X is

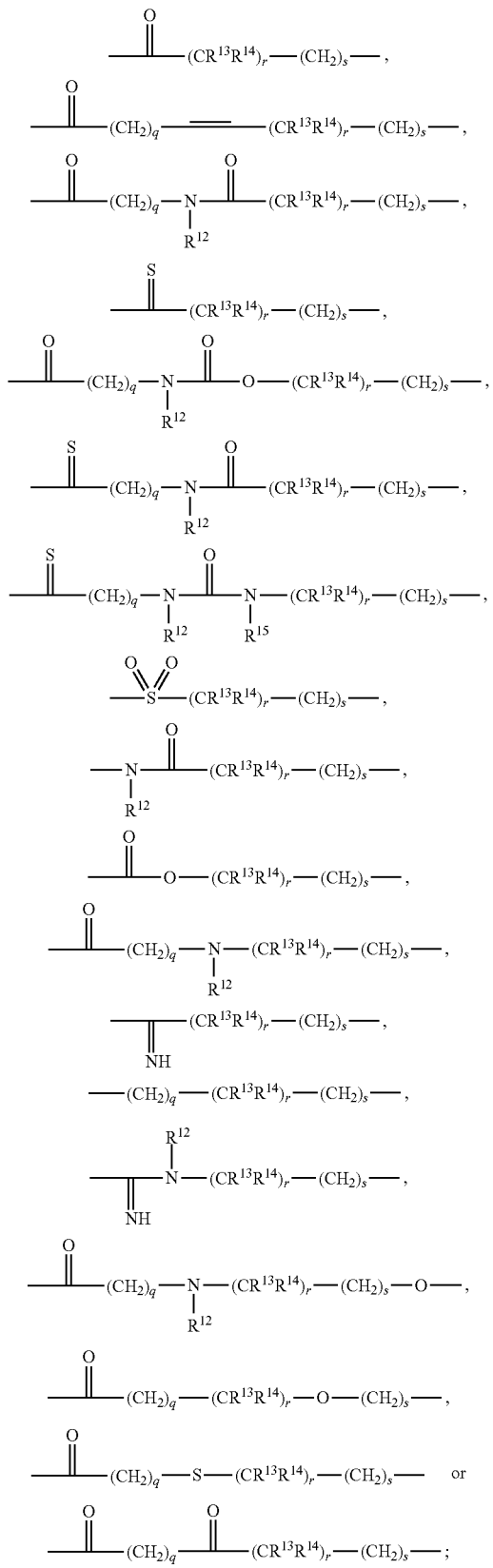

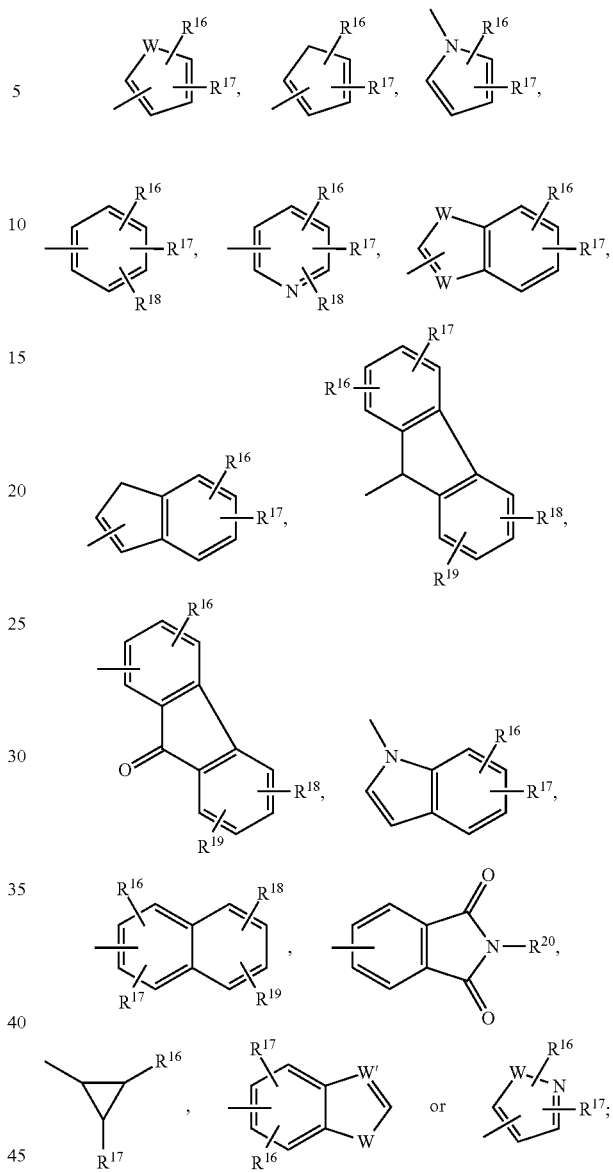

W is —O—, —S—, —S(O)$_2$— or —NR$^{20}$—; W' is =CR$^{20'}$— or —N=; R$^{16}$, R$^{17}$, R$^{18}$ and R$^{19}$ are each independently H, —C(O)NR$^{21}$R$^{22}$, —C(O)R$^{21}$ and the like; R$^{20}$ and R$^{20'}$ are each H, C$_{1-6}$ alkyl, C$_{3-8}$ cycloalkyl or C$_{3-8}$ cycloalkyl-C$_{1-6}$ alkyl; R$^{21}$ and R$^{22}$ are each H, —CF$_3$, C$_{1-6}$ alkyl, aryl, aromatic heterocyclic group and the like; and E is an optionally substituted 3- to 9-membered monocycle or bicyclic ring (patent document 3: WO00/69810).

4) A compound represented by the following formula:

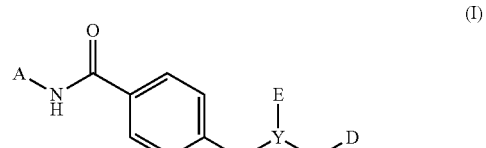

(I)

r is 0 or 1; q and s are each 0-3; R$^{12}$, R$^{13}$, R$^{14}$ and R$^{15}$ are each independently H or alkyl; D is wherein A is

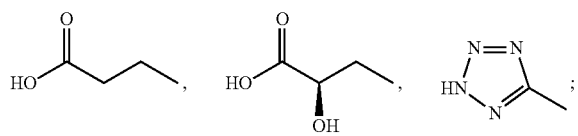

X is a bond, —CR¹R²— or —NR¹—; Y is >CR³— or >N—; R¹, R² and R³ are each independently H or $C_{1-6}$ alkyl, or R¹ and R² optionally form a double bond; E is $C_{1-10}$ alkyl, or $C_{3-10}$ cycloalkyl, $C_{3-10}$ cycloalkyl-$C_{1-6}$ alkyl, aryl, aromatic heterocyclic group or aryl-$C_{1-6}$ alkyl (these are each substitutable with halogen, $C_{1-6}$ alkyl etc.) and the like; B is

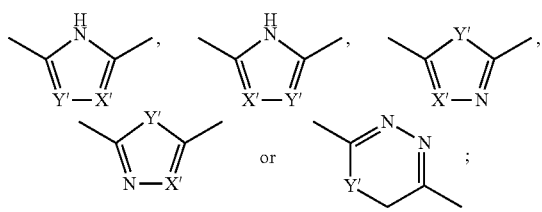

X' is —N= or —CR⁸=; Y' is —S—, —O— or NR⁸—; R⁸ is H, or $C_{1-6}$ alkyl or aryl (these are each substitutable with halogen, $C_{1-6}$ alkyl etc.); R⁹ is H or $C_{1-6}$ alkyl; D is aryl or aromatic heterocyclic group (each substitutable with halogen, $C_{1-10}$ alkyl, $C_{1-6}$ alkoxy, $C_{3-8}$ cycloalkyl, aryl (these rings are substitutable with halogen, $C_{1-10}$ alkyl etc.) and the like) (patent document 4: WO2004/002480).

In addition, the following compounds are known.

5) A compound represented by the following formula

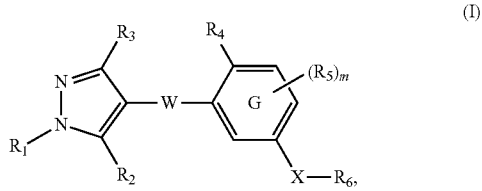

wherein G is phenyl or pyridyl; W is —NH(C=O)(CHR₈)ᵣ—, —CH(R₈)NH—, —NHCH(R₈)—, —CH₂—O— or —(C=O)O—; R₈ is H or alkyl; r is 0, 1 or 2; R₁ is H, optionally substituted alkyl, optionally substituted aryl, optionally substituted aromatic heterocyclic group, optionally substituted cycloalkyl, optionally substituted nonaromatic heterocyclic group and the like; R₂ is H, optionally substituted alkyl, optionally substituted alkoxy, amino and the like; R₃ is H, —CF₃, —OCF₃, halogen, optionally substituted $C_{1-4}$ alkyl, —OR₁₁ and the like; R₄ is H, optionally substituted $C_{1-4}$ alkyl, halogen, —CF₃, —OCF₃, —OR₁₃ and the like; R₅ is —CF₃, —OCF₃, optionally substituted alkyl, optionally substituted cycloalkyl, optionally substituted nonaromatic heterocyclic group, optionally substituted aryl, optionally substituted aromatic heterocyclic group, —OR₁₃, —C(=O)R₁₃, —C(=O)NR₁₃R₁₄ and the like; X is —(C=O)NH—, —NH(C=O)—, —NH(C=O)O—, —SO₂NH—, —CO₂— or a bond; R₆ is H, optionally substituted $C_{1-4}$ alkyl, optionally substituted alkoxy, optionally substituted phenoxy, optionally substituted cycloalkyl, optionally substituted nonaromatic heterocyclic group, optionally substituted aryl, optionally substituted aromatic heterocyclic group and the like; R₆ and R₅ may be bonded to each other to form 5- or 6-membered ring; R₁₁, R₁₃ and R₁₄ are each independently H, optionally substituted alkyl, optionally substituted cycloalkyl, optionally substituted nonaromatic heterocyclic group, optionally substituted aryl or optionally substituted aromatic heterocycle; m is 0, 1, 2 or 3, which is useful as a therapeutic agent for inflammatory diseases, specifically the following compound

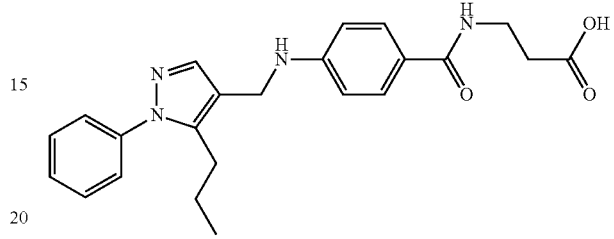

(patent document 5: WO2004/098528).
patent document 1: WO2006/102067
patent document 2: WO2004/069158
patent document 3: WO00/69810
patent document 4: WO2004/002480
patent document 5: WO2004/098528

DISCLOSURE OF THE INVENTION

Problems to be Solved by the Invention

The development of a compound having superior efficacy and useful for the prophylaxis or treatment of diabetes and the like has been desired.

Means of Solving the Problems

The present inventors have found that a compound represented by the following formula (I) or a salt thereof (sometimes to be abbreviated as "compound (I)" in the present specification) and a compound represented by the formula (IA) or a salt thereof (sometimes to be abbreviated as "compound (IA)" in the present specification) have superior glucagon antagonistic action, and superior efficacy as an agent for the prophylactic or treatment of diabetes and the like. Based on the finding, the present inventors have conducted intensive studies and completed the present invention.

Accordingly, the present invention relates to
(1) a compound represented by the following formula:

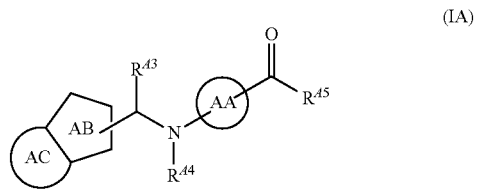

wherein ring AA is an optionally substituted benzene ring, or an optionally substituted 5- or 6-membered aromatic heterocycle;
ring AB is an optionally substituted 5-membered aromatic heterocycle;

ring AC is an optionally substituted benzene ring, or an optionally substituted 5- or 6-membered aromatic heterocycle;

$R^{43}$ is an optionally substituted $C_{1-6}$ alkyl group, an optionally substituted $C_{3-10}$ cycloalkyl group, an optionally substituted $C_{6-14}$ aryl group or an optionally substituted heterocyclic group;

$R^{44}$ is a hydrogen atom or a $C_{1-6}$ alkyl group;

$R^{45}$ is —$(CH_2)_3$—$COOR^{411}$ or —$NR^{46}$—$CR^{47}R^{48}$—$CR^{49}R^{410}$—$COOR^{411}$;

$R^{46}$, $R^{47}$, $R^{48}$, $R^{49}$ and $R^{411}$ are each independently a hydrogen atom or a $C_{1-6}$ alkyl group; and $R^{410}$ is a hydrogen atom, a $C_{1-6}$ alkyl group or a hydroxy group, or a salt thereof;

(2) the compound of the above-mentioned (1), wherein the formula (IA) is the following formula

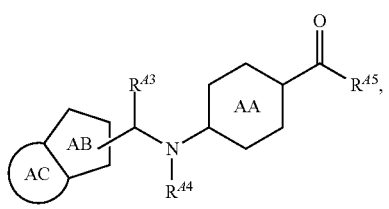

(IA')

and ring AA is a benzene ring or 6-membered aromatic heterocycle;

(3) the compound of the above-mentioned (2), wherein $R^{43}$ is an optionally substituted $C_{1-6}$ alkyl group, an optionally substituted $C_{3-10}$ cycloalkyl group, or an optionally substituted 5- or 6-membered heterocyclic group;

$R^{44}$ is a hydrogen atom;

$R^{45}$ is —$(CH_2)_3$—$COOR^{411}$ or —$NR^{46}$—$(CH_2)_2$—$COOR^{411}$;

$R^{46}$ is a hydrogen atom or methyl; and $R^{411}$ is a hydrogen atom, methyl or ethyl;

(4) 3-{[(4-{[cyclohexyl(3-methyl-1-benzofuran-2-yl)methyl]amino}phenyl)carbonyl](methyl)amino}propanoic acid or a salt thereof;

(5) 3-{[(6-{[cyclohexyl(5-fluoro-3-methyl-1-benzofuran-2-yl)methyl]amino}pyridin-3-yl)carbonyl](methyl)amino}propanoic acid or a salt thereof;

(6) 3-{[(4-{[2-ethyl-1-(5-fluoro-3-methyl-1-benzofuran-2-yl)butyl]amino}phenyl)carbonyl](methyl)amino}propanoic acid or a salt thereof;

(7) 3-[{[4-({1-[5-(cyclopropylmethoxy)-3-methyl-1-benzofuran-2-yl]-2-methylpropyl}amino)phenyl]carbonyl}(methyl)amino]propanoic acid or a salt thereof;

(8) 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid or a salt thereof;

(9) a compound represented by the following formula:

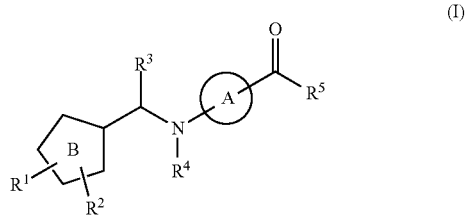

(I)

wherein ring A is an optionally substituted benzene ring, or an optionally substituted 5- or 6-membered aromatic heterocycle;

ring B is pyrazole;

$R^1$ and $R^2$ are each independently an optionally substituted hydrocarbon group, an optionally substituted heterocyclic group, an optionally substituted hydroxy group or acyl;

$R^3$ is an optionally substituted $C_{1-6}$ alkyl group, an optionally substituted $C_{3-10}$ cycloalkyl group, an optionally substituted $C_{6-14}$ aryl group or an optionally substituted heterocyclic group;

$R^4$ is a hydrogen atom or a $C_{1-6}$ alkyl group;

$R^5$ is —$(CH_2)_3$—$COOR^{11}$ or —$NR^6$—$CR^7R^8$—$CR^9R^{10}$—$COOR^{11}$;

$R^6$, $R^7$, $R^9$, $R^9$ and $R^{11}$ are each independently a hydrogen atom or a $C_{1-6}$ alkyl group; and $R^{10}$ is a hydrogen atom, a $C_{3-6}$ alkyl group or a hydroxy group, excluding N-[4-[[(1-phenyl-5-propyl-1H-pyrazol-4-yl)methyl]amino]benzoyl]-β-alanine, or a salt thereof;

(10) the compound of the above-mentioned (9), wherein the formula (I) is the following formula

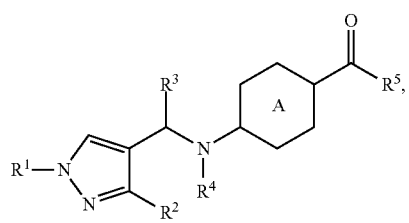

(I')

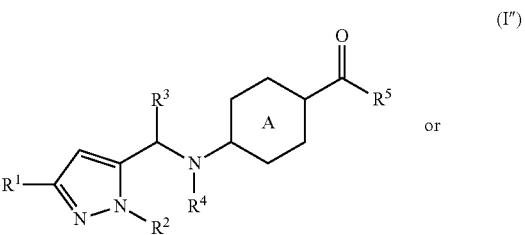

(I'') or

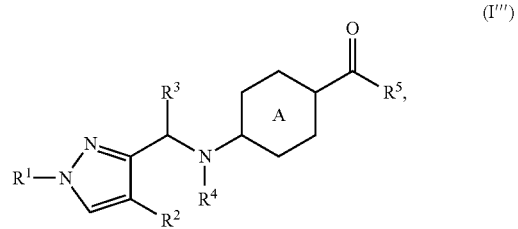

(I''')

and ring A is a benzene ring or 6-membered aromatic heterocycle;

(11) the compound of the above-mentioned (9), wherein $R^1$ is an optionally substituted $C_{1-6}$ alkyl group, an optionally substituted $C_{6-14}$ aryl group, or an optionally substituted 5- or 6-membered aromatic heterocyclic group;

$R^2$ is an optionally substituted $C_{1-6}$ alkyl group, an optionally substituted $C_{1-6}$ alkoxy group, or an optionally substituted $C_{3-10}$ cycloalkyl group;

$R^3$ is an optionally substituted $C_{1-6}$ alkyl group, an optionally substituted $C_{3-10}$ cycloalkyl group, or an optionally substituted 5- or 6-membered heterocyclic group;

$R^4$ is a hydrogen atom;

$R^5$ is —(CH$_2$)$_3$—COOR$^{11}$ or —NR$^6$—CH$_2$—CR$^9$R$^{10}$—COOR$^{11}$;

$R^6$ is a hydrogen atom or methyl;

$R^9$ is a hydrogen atom, methyl or ethyl;

$R^{10}$ is a hydrogen atom, methyl or ethyl; and $R^{11}$ is a hydrogen atom, methyl or ethyl;

(12) 3-[({4-[(cyclohexyl{3-methyl-1-[5-(trifluoromethyl)pyridin-2-yl]-1H-pyrazol-4-yl}methyl)amino]phenyl}carbonyl)amino]propanoic acid or a salt thereof;

(13) 3-[{[4-({cyclohexyl[1-(3-methoxyphenyl)-3-methyl-1H-pyrazol-4-yl]methyl}amino)phenyl]carbonyl}(methyl)amino]propanoic acid or a salt thereof;

(14) 3-[{[4-({cyclohexyl[1-(3-methoxyphenyl)-4-methyl-1H-pyrazol-3-yl]methyl}amino)phenyl]carbonyl}(methyl)amino]propanoic acid or a salt thereof;

(15) a prodrug of the compound of the above-mentioned (1) or (9);

(16) a medicament comprising the compound of the above-mentioned (1) or (9) or a prodrug thereof;

(17) the medicament of the above-mentioned (16) which is a glucagon antagonist;

(18) the medicament of the above-mentioned (16) which is a sugar production-suppressive agent;

(19) the medicament of the above-mentioned (16) which is an agent for the prophylactic or treatment of diabetes;

(20) a method of suppressing sugar production in a mammal, comprising administering the compound of the above-mentioned (1) or a prodrug thereof or the compound of the above-mentioned (9) or a prodrug thereof to the mammal;

(21) a method for the prophylaxis or treatment of diabetes in a mammal, comprising administering the compound of the above-mentioned (1) or a prodrug thereof or the compound of the above-mentioned (9) or a prodrug thereof to the mammal;

(22) use of the compound of the above-mentioned (1) or a prodrug thereof or the compound of the above-mentioned (9) or a prodrug thereof for the production of a medicament for suppressing sugar production;

(23) use of the compound of the above-mentioned (1) or a prodrug thereof or the compound of the above-mentioned (9) or a prodrug thereof for the production of an agent for the prophylaxis or treatment of diabetes;

and the like.

Effect of the Invention

Since the compound of the present invention has a glucagon antagonistic action and superior efficacy (suppression of blood glucose increase, hypoglycemic action and the like), it is useful for the prophylaxis or treatment of diabetes and the like.

DETAILED DESCRIPTION OF THE INVENTION

In the present specification, the "halogen atom" means a fluorine atom, a chlorine atom, a bromine atom or an iodine atom.

In the present specification, examples of the "$C_{1-10}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, examples of the "branched $C_{1-6}$ alkyl group" include isopropyl, isobutyl, sec-butyl, tert-butyl, isopentyl, neopentyl, 1-ethylpropyl, isohexyl, 1,1-dimethylbutyl, 2,2-dimethylbutyl, 3,3-dimethylbutyl, 2-ethylbutyl and the like.

In the present specification, examples of the "$C_{2-10}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

In the present specification, examples of the "$C_{2-10}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

In the present specification, examples of the "$C_{1-6}$ alkoxy group" include methoxy, ethoxy, propoxy, isopropoxy, butoxy, isobutoxy, sec-butoxy, tert-butoxy and the like.

In the present specification, examples of the "$C_{2-6}$ alkenyloxy group" include ethenyloxy and the like.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

In the present specification, examples of the "$C_{3-6}$ cycloalkyl group" include cyclopropyl, cyclobutyl, cyclopentyl, cyclohexyl and the like.

The $C_{3-6}$ cycloalkyl group and $C_{3-10}$ cycloalkyl group may form a fused ring group with a benzene ring and examples of such fused ring group include indanyl and the like.

In the present specification, examples of the "$C_{3-10}$ cycloalkenyl group" include cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl), cycloheptenyl (e.g., 2-cyclohepten-1-yl), cyclooctenyl (e.g., 2-cycloocten-1-yl) and the like.

In the present specification, examples of the "$C_{3-6}$ cycloalkenyl group" include cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) and the like.

The $C_{3-6}$ cycloalkenyl group and $C_{3-10}$ cycloalkenyl group may form a fused ring group with a benzene ring and examples of such fused ring group include dihydronaphthyl and the like.

In the present specification, examples of the "$C_{4-10}$ cycloalkadienyl group" include 2,4-cyclopentadien-1-yl, 2,4-cyclohexadien-1-yl, 2,5-cyclohexadien-1-yl and the like.

The $C_{4-10}$ cycloalkadienyl group may form a fused ring group with a benzene ring and examples of such fused ring group include fluorenyl and the like.

In the present specification, examples of the "$C_{6-14}$ aryl group" include phenyl, naphthyl, anthryl, phenanthryl, acenaphthyl, biphenylyl and the like.

In the present specification, examples of the "$C_{6-40}$ aryl group" include phenyl, naphthyl and the like.

In the present specification, examples of the "$C_{6-14}$ aryloxy group" include phenyloxy and naphthyloxy.

In the present specification, examples of the "$C_{7-13}$ aralkyl group" include benzyl, phenethyl, naphthylmethyl, biphenylylmethyl and the like.

In the present specification, examples of the "$C_{7-43}$ aralkyloxy group" include benzyloxy and the like.

In the present specification, examples of the "$C_{8-13}$ aralkenyl group" include styryl and the like.

In the present specification, examples of the "heterocyclic group" include the following aromatic heterocyclic groups and nonaromatic heterocyclic groups.

In the present specification, examples of the "aromatic heterocyclic group" include a 4- to 12-membered aromatic heterocyclic group, for example, a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom, and a 8- to 12-membered fused aromatic heterocyclic group. Examples of the fused aromatic heterocyclic group include a group derived from a fused ring wherein 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring, and a ring corresponding to a 4- to 7-membered monocyclic aromatic heterocyclic group are condensed, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

In the present specification, examples of the "non-aromatic heterocyclic group" include a 4- to 12-membered non-aromatic heterocyclic group, for example, a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a 8- to 12-membered fused non-aromatic heterocyclic group. Examples of the fused non-aromatic heterocyclic group include a group derived from a fused ring wherein 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring, and a ring corresponding to the 4- to 7-membered monocyclic non-aromatic heterocyclic group are condensed (optionally partially saturated further), and the like.

Preferable examples of the non-aromatic heterocyclic group include
monocyclic non-aromatic heterocyclic groups such as oxetanyl (e.g., 3-oxetanyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like; and the like.

In the present specification, examples of the "5- or 6-membered heterocyclic group" include 5- or 6-membered rings from among the above-mentioned monocyclic aromatic heterocyclic groups and monocyclic nonaromatic heterocyclic groups.

In the present specification, specific examples of the "5- or 6-membered aromatic heterocycle" include rings corresponding to the 5- or 6-membered ring group from among the above-mentioned aromatic heterocyclic group, for example, furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

In the present specification, specific examples of the "5-membered aromatic heterocycle" include rings corresponding to the 5-membered ring group from among the above-mentioned aromatic heterocyclic groups, for example, furan, thiophene, pyrrole, imidazole, pyrazole, thiazole, isothiazole, oxazole, isoxazole, oxadiazole, thiadiazole, triazole, tetrazole and the like.

In the present specification, examples of the "4- to 12-membered aromatic heterocyclyl-oxy group" include groups wherein an oxy group is bonded to the above-mentioned 4- to 12-membered aromatic heterocyclic group, for example, pyridyloxy and the like.

In the present specification, examples of the "4- to 12-membered non-aromatic heterocyclyl-oxy group" include groups wherein an oxy group is bonded to the above-mentioned 4- to 12-membered nonaromatic heterocyclic group, for example, tetrahydropyranyloxy, tetrahydrothiopyranyloxy, 1,1-dioxidotetrahydrothiopyranyloxy and the like.

In the present specification, examples of the "4- to 12-membered aromatic heterocyclyl-carbonyl group" include groups wherein a carbonyl group is bonded to the above-mentioned 4- to 12-membered aromatic heterocyclic group, for example, furylcarbonyl, thienylcarbonyl, pyrazolylcarbonyl, pyrazinylcarbonyl, isooxazolylcarbonyl, pyridylcarbonyl, thiazolylcarbonyl and the like.

In the present specification, examples of the "4- to 12-membered non-aromatic heterocyclyl-carbonyl group" include groups wherein a carbonyl group is bonded to the above-mentioned 4- to 12-membered nonaromatic heterocyclic group, for example, tetrahydrofurylcarbonyl, pyrrolidinylcarbonyl, morpholinylcarbonyl and the like.

In the present specification, examples of the "$C_{1-6}$ alkyl-carbonyl group" include acetyl, propanoyl, butanoyl, isobutanoyl, tert-butanoyl, pentanoyl, isopentanoyl, hexanoyl and the like.

In the present specification, examples of the "$C_{1-6}$ alkyl-carbonyloxy group" include acetyloxy, propanoyloxy, butanoyloxy, isobutanoyloxy, tert-butanoyloxy, pentanoyloxy, isopentanoyloxy, hexanoyloxy and the like.

In the present specification, examples of the "$C_{1-6}$ alkoxy-carbonyl group" include methoxycarbonyl, ethoxycarbonyl, propoxycarbonyl, tert-butoxycarbonyl and the like.

In the present specification, examples of the "$C_{3-10}$ cycloalkyl-carbonyl group" include cyclopropylcarbonyl, cyclopentylcarbonyl, cyclohexylcarbonyl and the like.

In the present specification, examples of the "$C_{6-14}$ aryl-carbonyl group" include benzoyl and the like.

In the present specification, examples of the "$C_{1-6}$ alkylthio group" include methylthio, ethylthio, isopropylthio and the like.

In the present specification, examples of the "$C_{6-14}$ arylthio group" include phenylthio, naphthylthio and the like.

In the present specification, examples of the "$C_{7-13}$ aralkylthio group" include benzylthio and the like.

In the present specification, examples of the "$C_{1-6}$ alkylsulfonyl group" include methylsulfonyl, ethylsulfonyl, isopropylsulfonyl and the like.

In the present specification, examples of the "$C_{6-14}$ arylsulfonyl group" include benzenesulfonyl and the like.

In the present specification, examples of the "$C_{1-3}$ alkylenedioxy group" include methylenedioxy, ethylenedioxy and the like.

In the present specification, examples of the "optionally substituted hydrocarbon group" include optionally substituted $C_{1-10}$ alkyl group, optionally substituted $C_{2-10}$ alkenyl group, optionally substituted $C_{2-10}$ alkynyl group, optionally substituted $C_{3-10}$ cycloalkyl group, optionally substituted $C_{3-10}$ cycloalkenyl group, optionally substituted $C_{4-10}$ cycloalkadienyl group, and optionally substituted $C_{6-14}$ aryl group, optionally substituted $C_{7-13}$ aralkyl group, optionally substituted $C_{8-13}$ arylalkenyl group and the like.

In the present specification, examples of the "optionally substituted hydroxy group" include a hydroxy group optionally substituted by substituent(s) selected from (1) optionally substituted $C_{1-10}$ alkyl group (preferably, optionally substituted $C_{1-6}$ alkyl group),
(2) optionally substituted $C_{2-10}$ alkenyl group,
(3) optionally substituted $C_{3-10}$ cycloalkyl group,
(4) optionally substituted $C_{3-10}$ cycloalkenyl group,
(5) optionally substituted $C_{6-14}$ aryl group,
(6) optionally substituted $C_{7-13}$ aralkyl group,
(7) optionally substituted $C_{8-13}$ arylalkenyl group,
(8) optionally substituted $C_{1-6}$ alkyl-carbonyl group,
(9) optionally substituted heterocyclic group and the like.

In the present specification, the $C_{1-6}$ alkyl group, $C_{1-10}$ alkyl group, $C_{2-10}$ alkenyl group, $C_{2-10}$ alkynyl group and $C_{1-6}$ alkyl-carbonyl group of the "optionally substituted $C_{1-6}$ alkyl group", "optionally substituted $C_{1-10}$ alkyl group", "optionally substituted $C_{2-10}$ alkenyl group", "optionally substituted $C_{2-10}$ alkynyl group", and "optionally substituted $C_{1-6}$ alkyl-carbonyl group" optionally have 1 to 5 (preferably 1 to 3) substituents at each substitutable position(s).

Examples of such substituent include the following substituent group A:
(Substituent Group A)
(1) $C_{3-10}$ cycloalkyl group;
(2) $C_{6-14}$ aryl group optionally substituted by 1 to 3 substituents selected from
(a) $C_{1-6}$ alkyl group optionally substituted by 1 to 3 halogen atoms,
(b) hydroxy group,
(c) $C_{1-6}$ alkoxy group optionally substituted by 1 to 3 halogen atoms, and
(d) halogen atom;
(3) 4- to 12-membered aromatic heterocyclic group optionally substituted by 1 to 3 substituents selected from (a) $C_{1-6}$ alkyl group optionally substituted by 1 to 3 halogen atoms,
(b) hydroxy group,
(c) $C_{1-6}$ alkoxy group optionally substituted by 1 to 3 halogen atoms, and
(d) halogen atom;
(4) 4- to 12-membered nonaromatic heterocyclic group optionally substituted by 1 to 3 substituents selected from
(a) $C_{1-6}$ alkyl group optionally substituted by 1 to 3 halogen atoms,
(b) hydroxy group,
(c) $C_{1-6}$ alkoxy group optionally substituted by 1 to 3 halogen atoms,
(d) halogen atom, and
(e) oxo group;
(5) amino group optionally mono- or di-substituted by substituent(s) selected from
(a) $C_{1-6}$ alkyl group optionally substituted by 1 to 3 substituents selected from
(i) halogen atom, and
(ii) $C_{1-6}$ alkoxy group,
(b) $C_{1-6}$ alkyl-carbonyl group optionally substituted by 1 to 3 halogen atoms,
(c) $C_{1-6}$ alkoxy-carbonyl group optionally substituted by 1 to 3 halogen atoms,
(d) $C_{1-6}$ alkylsulfonyl group optionally substituted by 1 to 3 halogen atoms,
(e) carbamoyl group optionally mono- or di-substituted by $C_{1-6}$ alkyl group optionally substituted by 1 to 3 halogen atoms, and
(f) 4- to 12-membered aromatic heterocyclic group;
(6) $C_{1-6}$ alkyl-carbonyl group optionally substituted by 1 to 3 halogen atoms;
(7) $C_{1-6}$ alkoxy-carbonyl group optionally substituted by 1 to 3 substituents selected from
(a) halogen atom,
(b) $C_{1-6}$ alkoxy group, and
(c) $C_{6-14}$ aryl group;
(8) $C_{1-6}$ alkylsulfonyl group optionally substituted by 1 to 3 halogen atoms;
(9) carbamoyl group optionally mono- or di-substituted by $C_{1-6}$ alkyl group optionally substituted by 1 to 3 halogen atoms;
(10) thiocarbamoyl group optionally mono- or di-substituted by $C_{1-6}$ alkyl group optionally substituted by 1 to 3 halogen atoms;
(11) sulfamoyl group optionally mono- or di-substituted by $C_{1-6}$ alkyl group optionally substituted by 1 to 3 halogen atoms;
(12) carboxy group;
(13) hydroxy group;
(14) $C_{1-6}$ alkoxy group optionally substituted by 1 to 3 substituents selected from
(a) halogen atom,
(b) carboxy group,
(c) $C_{1-6}$ alkoxy group,
(d) $C_{3-6}$ cycloalkyl group,
(e) $C_{1-6}$ alkoxy-carbonyl group optionally substituted by 1 to 3 $C_{6-14}$ aryl groups,
(f) amino group optionally mono- or di-substituted by substituent(s) selected from $C_{1-6}$ alkyl group and $C_{1-6}$ alkoxy-carbonyl group,
(g) 4- to 12-membered aromatic heterocyclic group optionally substituted by 1 to 3 substituents selected from
(i) halogen atom, and
(ii) $C_{1-6}$ alkyl group,
(h) 4- to 12-membered nonaromatic heterocyclic group optionally substituted by 1 to 3 $C_{1-6}$ alkyl groups,
(i) alkylsulfonyl group,
(j) $C_{1-6}$ alkylthio group, and
(k) hydroxy group;
(15) $C_{2-6}$ alkenyloxy group optionally substituted by 1 to 3 halogen atoms;
(16) $C_{7-13}$ aralkyloxy group;
(17) $C_{6-14}$ aryloxy group;
(18) $C_{1-6}$ alkyl-carbonyloxy group;
(19) 4- to 12-membered aromatic heterocyclyl-oxy group optionally substituted by 1 to 3 substituents selected from
(i) $C_{1-6}$ alkyl group optionally substituted by 1 to 3 halogen atoms, and
(ii) cyano group;
(20) 4- to 12-membered non-aromatic heterocyclyl-oxy group;
(21) $C_{6-14}$ aryl-carbonyl group optionally substituted by 1 to 3 substituents selected from
(a) halogen atom, and
(b) $C_{1-6}$ alkyl group optionally substituted by 1 to 3 halogen atoms;
(22) 4- to 12-membered aromatic heterocyclyl-carbonyl group optionally substituted by 1 to 3 substituents selected from $C_{1-6}$ alkyl group optionally substituted by 1 to 3 halogen atoms;
(23) 4- to 12-membered non-aromatic heterocyclyl-carbonyl group optionally substituted by 1 to 3 substituents selected from $C_{1-6}$ alkyl group optionally substituted by 1 to 3 halogen atoms;
(24) mercapto group;
(25) $C_{1-6}$ alkylthio group optionally substituted by 1 to 3 substituents selected from
(a) halogen atom, and
(b) $C_{1-6}$ alkoxycarbonyl group;
(26) $C_{7-13}$ aralkylthio group;
(27) $C_{6-14}$ arylthio group;
(28) cyano group;
(29) nitro group;
(30) halogen atom;
(31) $C_{1-3}$ alkylenedioxy group.

When two or more substituents are used, the respective substituents may be the same or different.

In the present specification, the benzene ring, $C_{6-14}$ aryl group, $C_{3-10}$ cycloalkenyl group, $C_{4-10}$ cycloalkadienyl group, $C_{7-13}$ aralkyl group, and $C_{8-13}$ arylalkenyl group of the "optionally substituted benzene ring", "optionally substituted $C_{6-14}$ aryl group", "optionally substituted $C_{3-10}$ cycloalkenyl group", "optionally substituted $C_{4-10}$ cycloalkadienyl group", "optionally substituted $C_{7-13}$ aralkyl group" and "optionally substituted $C_{8-13}$ arylalkenyl group" each optionally have 1 to 5 (preferably 1 to 3) substituents at substitutable position(s).

Examples of such substituent include the following substituent group B:
(Substituent Group B)
(1) $C_{3-10}$ cycloalkyl group;
(2) $C_{6-14}$ aryl group optionally substituted by 1 to 3 substituents selected from
(a) $C_{1-6}$ alkyl group optionally substituted by 1 to 3 halogen atoms,
(b) hydroxy group,
(c) $C_{1-6}$ alkoxy group optionally substituted by 1 to 3 halogen atoms, and
(d) halogen atom;
(3) 4- to 12-membered aromatic heterocyclic group optionally substituted by 1 to 3 substituents selected from (a) $C_{1-6}$ alkyl group optionally substituted by 1 to 3 halogen atoms,
(b) hydroxy group,
(c) $C_{1-6}$ alkoxy group optionally substituted by 1 to 3 halogen atoms, and
(d) halogen atom;
(4) 4- to 12-membered nonaromatic heterocyclic group optionally substituted by 1 to 3 substituents selected from
(a) $C_{1-6}$ alkyl group optionally substituted by 1 to 3 halogen atoms,
(b) hydroxy group,
(c) $C_{1-6}$ alkoxy group optionally substituted by 1 to 3 halogen atoms,
(d) halogen atom, and
(e) oxo group;
(5) amino group optionally mono- or di-substituted by substituent(s) selected from
(a) $C_{1-6}$ alkyl group optionally substituted by 1 to 3 substituents selected from
(i) halogen atom, and
(ii) $C_{1-6}$ alkoxy group,
(b) $C_{1-6}$ alkyl-carbonyl group optionally substituted by 1 to 3 halogen atoms,
(c) $C_{1-6}$ alkoxy-carbonyl group optionally substituted by 1 to 3 halogen atoms,
(d) $C_{1-6}$ alkylsulfonyl group optionally substituted by 1 to 3 halogen atoms,
(e) carbamoyl group optionally mono- or di-substituted by $C_{1-6}$ alkyl group optionally substituted by 1 to 3 halogen atoms,
(f) 4- to 12-membered aromatic heterocyclic group,
(g) $C_{6-14}$ aryl-carbonyl group (e.g., benzoyl),
(h) $C_{6-14}$ arylsulfonyl group (e.g., benzenesulfonyl), and
(i) $C_{7-13}$ aralkyl group (e.g., benzyl);
(6) $C_{1-6}$ alkyl-carbonyl group optionally substituted by 1 to 3 halogen atoms;
(7) $C_{1-6}$ alkoxy-carbonyl group optionally substituted by 1 to 3 substituents selected from
(a) halogen atom,
(b) $C_{1-6}$ alkoxy group, and
(c) $C_{6-14}$ aryl group;
(8) $C_{1-6}$ alkylsulfonyl group optionally substituted by 1 to 3 halogen atoms;
(9) carbamoyl group optionally mono- or di-substituted by $C_{1-6}$ alkyl group optionally substituted by 1 to 3 halogen atoms;
(10) thiocarbamoyl group optionally mono- or di-substituted by $C_{1-6}$ alkyl group optionally substituted by 1 to 3 halogen atoms;
(11) sulfamoyl group optionally mono- or di-substituted by $C_{1-6}$ alkyl group optionally substituted by 1 to 3 halogen atoms;
(12) carboxy group;
(13) hydroxy group;
(14) $C_{1-6}$ alkoxy group optionally substituted by 1 to 3 substituents selected from
(a) halogen atom,
(b) carboxy group,
(c) $C_{1-6}$ alkoxy group,
(d) $C_{3-6}$ cycloalkyl group,
(e) $C_{1-6}$ alkoxy-carbonyl group optionally substituted by 1 to 3 $C_{6-14}$ aryl groups,
(f) amino group optionally mono- or di-substituted by substituent(s) selected from $C_{1-6}$ alkyl group and $C_{1-6}$ alkoxy-carbonyl group,
(g) 4- to 12-membered aromatic heterocyclic group optionally substituted by 1 to 3 substituents selected from
(i) halogen atom, and
(ii) $C_{1-6}$ alkyl group,
(h) 4- to 12-membered nonaromatic heterocyclic group optionally substituted by 1 to 3 $C_{1-6}$ alkyl groups,
(i) $C_{1-6}$ alkylsulfonyl group,
(j) $C_{1-6}$ alkylthio group, and
(k) hydroxy group;
(15) $C_{2-6}$ alkenyloxy group optionally substituted by 1 to 3 halogen atoms;
(16) $C_{7-13}$ aralkyloxy group;
(17) $C_{6-14}$ aryloxy group;
(18) $C_{1-6}$ alkyl-carbonyloxy group;
(19) 4- to 12-membered aromatic heterocyclyl-oxy group optionally substituted by 1 to 3 substituents selected from
(i) $C_{1-6}$ alkyl group optionally substituted by 1 to 3 halogen atoms, and
(ii) cyano group;
(20) 4- to 12-membered non-aromatic heterocyclyl-oxy group;
(21) $C_{6-14}$ aryl-carbonyl group optionally substituted by 1 to 3 substituents selected from
(a) halogen atom, and
(b) $C_{1-6}$ alkyl group optionally substituted by 1 to 3 halogen atoms;
(22) 4- to 12-membered aromatic heterocyclyl-carbonyl group optionally substituted by 1 to 3 substituents selected from $C_{1-6}$ alkyl group optionally substituted by 1 to 3 halogen atoms;
(23) 4- to 12-membered non-aromatic heterocyclyl-carbonyl group optionally substituted by 1 to 3 substituents selected from $C_{1-6}$ alkyl group optionally substituted by 1 to 3 halogen atoms;
(24) mercapto group;
(25) $C_{1-6}$ alkylthio group optionally substituted by 1 to 3 substituents selected from
(a) halogen atom, and
(b) $C_{1-6}$ alkoxycarbonyl group;
(26) $C_{7-13}$ aralkylthio group;
(27) $C_{6-14}$ arylthio group;
(28) cyano group;
(29) nitro group;
(30) halogen atom;
(31) $C_{1-3}$ alkylenedioxy group;
(32) $C_{1-6}$ alkyl group optionally substituted by 1 to 3 substituents selected from
(a) halogen atom,
(b) carboxy group,
(c) hydroxy group,
(d) $C_{1-6}$ alkoxy-carbonyl group,
(e) $C_{1-6}$ alkoxy group optionally substituted by 1 to 3 $C_{1-6}$ alkoxy groups, and
(f) amino group optionally mono- or di-substituted by $C_{1-6}$ alkyl group(s);
(33) $C_{2-6}$ alkenyl group optionally substituted by 1 to 3 substituents selected from
(a) halogen atom,
(b) carboxy group,
(c) hydroxy group,
(d) $C_{1-6}$ alkoxy-carbonyl group,
(e) $C_{1-6}$ alkoxy group, and
(f) amino group optionally mono- or di-substituted by $C_{1-6}$ alkyl group(s); and
(34) $C_{7-13}$ aralkyl group optionally substituted by 1 to 3 substituents selected from
(a) $C_{1-6}$ alkyl group optionally substituted by 1 to 3 halogen atoms,
(b) hydroxy group, (c) C$_{1-6}$ alkoxy group, and
(d) halogen atom.

When two or more substituents are used, the respective substituents may be the same or different.

In the present specification, the C$_{3-10}$ cycloalkyl group of the "optionally substituted C$_{3-10}$ cycloalkyl group" optionally have 1 to 5 (preferably 1 to 3) substituents at substitutable position(s). Examples of such substituent include the above-mentioned substituent group B and oxo group. When two or more substituents are used, the respective substituents may be the same or different.

In the present specification, when the "heterocyclic group" and "5- or 6-membered heterocyclic group" of the "optionally substituted heterocyclic group" and "optionally substituted 5- or 6-membered heterocyclic group" are aromatic heterocyclic groups, the aromatic heterocyclic groups optionally have 1 to 5 (preferably 1 to 3) substituents at substitutable position(s).

Examples of such substituent include the above-mentioned substituent group B. When two or more substituents are used, the respective substituents may be the same or different.

In the present specification, when the "heterocyclic group" and "5- or 6-membered heterocyclic group" of the "optionally substituted heterocyclic group" and "optionally substituted 5- or 6-membered heterocyclic group" are nonaromatic heterocyclic groups, the nonaromatic heterocyclic groups optionally have 1 to 5 (preferably 1 to 3) substituents at substitutable position(s).

Examples of such substituent include the above-mentioned substituent group B and oxo group. When two or more substituents are used, the respective substituents may be the same or different.

In the present specification, the 5- or 6-membered aromatic heterocycle and 5-membered aromatic heterocycle of the "optionally substituted 5- or 6-membered aromatic heterocycle" and "optionally substituted 5-membered aromatic heterocycle" each optionally have 1 to 5 (preferably 1 to 3) substituents at substitutable position(s). Examples of such substituent include the above-mentioned substituent group B. When two or more substituents are used, the respective substituents may be the same or different.

In the present specification, examples of the "acyl" include groups represented by the formulas: —CO—R$^A$, —CO—OR$^A$, —S(O)$_3$—R$^A$, —S(O)$_2$—R$^A$, —S(O)—R$^A$, —CS—NR$^{A'}$R$^{B'}$, —S(O)$_2$—NR$^{A'}$R$^{B'}$ and the like.

In the formula, R$^A$ is a hydrogen atom, an optionally substituted hydrocarbon group, or an optionally substituted heterocyclic group. R$^{A'}$ and R$^{B'}$ are each independently a hydrogen atom, an optionally substituted hydrocarbon group, or an optionally substituted heterocyclic group, or R$^{A'}$ and R$^{B'}$ form, together with the adjacent nitrogen atom, an optionally substituted nitrogen-containing non-aromatic heterocycle.

Examples of the "nitrogen-containing non-aromatic heterocycle" of the "optionally substituted nitrogen-containing non-aromatic heterocycle" formed by R$^{A'}$ and R$^{B'}$, together with the adjacent nitrogen atom, include 5- to 7-membered nitrogen-containing non-aromatic heterocycle containing, as a ring constituting atom besides carbon atom, at least one nitrogen atom, and optionally further containing 1 or 2 hetero atoms selected from oxygen atom, sulfur atom (the sulfur atom may be oxidized) and nitrogen atom. Preferable examples of such nitrogen-containing non-aromatic heterocycle include pyrrolidine, imidazolidine, pyrazolidine, piperidine, piperazine, morpholine, thiomorpholine and the like.

The nitrogen-containing non-aromatic heterocycle optionally has 1 to 5 (preferably 1 to 3) substituents at substitutable position(s). As such substituent, the above-mentioned substituent group B and oxo group can be mentioned. When two or more substituents are used, the respective substituents may be the same or different.

Preferable examples of the "acyl group" include
(1) formyl group;
(2) carboxy group;
(3) C$_{1-6}$ alkyl-carbonyl group optionally substituted by 1 to 3 substituents selected from
(a) halogen atom,
(b) C$_{1-6}$ alkoxy-carbonyl group,
(c) C$_{6-14}$ aryl group, and
(d) C$_{1-6}$ alkoxy group;
(4) C$_{1-6}$ alkoxy-carbonyl group optionally substituted by 1 to 3 substituents selected from
(a) halogen atom,
(b) C$_{6-14}$ aryl group, and
(c) C$_{1-6}$ alkoxy group;
(5) C$_{3-10}$ cycloalkyl-carbonyl group;
(6) C$_{6-14}$ aryl-carbonyl group optionally substituted by 1 to 3 halogen atoms;
(7) carbamoyl group optionally mono- or di-substituted by substituent(s) selected from
(a) C$_{1-6}$ alkyl group optionally substituted by 1 to 3 substituents selected from
(i) halogen atom,
(ii) C$_{1-6}$ alkoxy-carbonyl group,
(iii) C$_{6-14}$ aryl group,
(iv) C$_{1-6}$ alkoxy group, and
(v) 4- to 12-membered aromatic heterocyclic group,
(b) C$_{3-10}$ cycloalkyl group,
(c) C$_{6-14}$ aryl group optionally substituted by 1 to 3 substituents selected from
(i) halogen atom,
(ii) C$_{1-6}$ alkyl group optionally substituted by 1 to 3 halogen atoms, and
(iii) C$_{1-6}$ alkoxy group, and
(d) 4- to 12-membered aromatic heterocyclic group;
(8) C$_{1-6}$ alkylsulfonyl group optionally substituted by 1 to 3 substituents selected from
(a) halogen atom, and
(b) C$_{6-14}$ aryl group;
(9) C$_{6-14}$ arylsulfonyl group optionally substituted by 1 to 3 halogen atoms;
(10) sulfamoyl group optionally mono- or di-substituted by substituent(s) selected from
(a) halogen atom, and
(b) C$_{1-6}$ alkyl group optionally substituted by 1 to 3 substituents selected from 4- to 12-membered nonaromatic heterocyclic group optionally substituted by oxo group;
(11) thiocarbamoyl group optionally mono- or di-substituted by substituent(s) selected from C$_{1-6}$ alkyl group optionally substituted by 1 to 3 halogen atoms;
(12) 4- to 12-membered aromatic heterocyclyl-carbonyl group optionally substituted by 1 to 3 substituents selected from C$_{1-6}$ alkyl group optionally substituted by 1 to 3 halogen atoms;
(13) 4- to 12-membered non-aromatic heterocyclyl-carbonyl group optionally substituted by 1 to 3 substituents selected from C$_{1-6}$ alkyl group optionally substituted by 1 to 3 halogen atoms;
and the like.

Compound (I) is explained.

Ring A is an optionally substituted benzene ring or optionally substituted 5- or 6-membered aromatic heterocycle.

The 5- or 6-membered aromatic heterocycle for ring A is preferably pyridine.

The "benzene ring" or "5- or 6-membered aromatic heterocycle" of the "optionally substituted benzene ring or optionally substituted 5- or 6-membered aromatic heterocycle" for ring A optionally further has 1 to 4 substituents at substitutable position(s) besides "—NR⁴— group" and "—CO—R⁵ group".

The ring A is preferably a benzene ring or 5- or 6-membered aromatic heterocycle (e.g., pyridine), more preferably benzene or 6-membered aromatic heterocycle (e.g., pyridine), particularly preferably a benzene ring, without a substituent other than the "—NR⁴— group" and "—CO—R⁵ group".

When ring A is benzene or 6-membered aromatic heterocycle, the following part containing ring A in the formula (I):

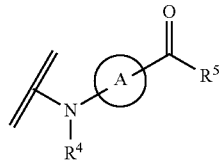

is preferably

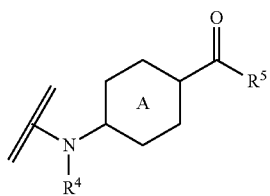

wherein the symbols other than ring A are as defined above.
Ring B is pyrazole.
Specific examples of pyrazole for ring B include

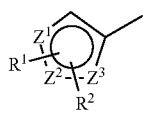

wherein Z¹, Z² and Z³ are: 1) Z¹ and Z² are nitrogen atoms and Z³ is a carbon atom, or 2) Z² and Z³ are nitrogen atoms and Z¹ is a carbon atom; R¹ and R² are as defined above, and these groups are substituted at any substitutable position of a pyrazole ring.
The following part containing ring B in the formula (I):

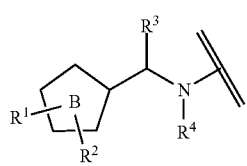

is specifically

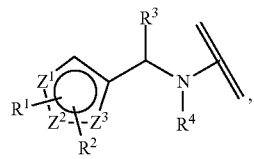

preferably

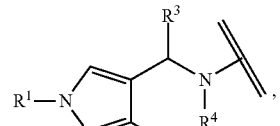

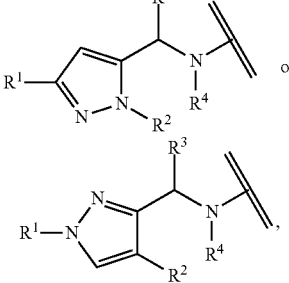

more preferably

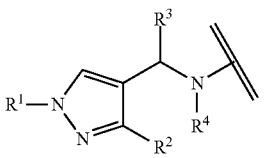

wherein each symbol in the formula is as defined above.
R¹ and R² are each independently an optionally substituted hydrocarbon group, an optionally substituted heterocyclic group, an optionally substituted hydroxy group or acyl.
R¹ is preferably
(1) optionally substituted $C_{1-6}$ alkyl group (e.g., methyl, 1,1-dimethylpropyl),
(2) optionally substituted $C_{6-14}$ aryl group (e.g., phenyl), or
(3) optionally substituted 5- or 6-membered aromatic heterocyclic group (e.g., pyridyl), more preferably
(1) $C_{1-6}$ alkyl group (e.g., methyl, 1,1-dimethylpropyl) optionally substituted by 1 to 3 substituents selected from
(a) halogen atom (e.g., fluorine),
(b) $C_{6-14}$ aryl group (e.g., phenyl), and
(c) $C_{1-6}$ alkoxy group (e.g., methoxy),
(2) $C_{6-14}$ aryl group (e.g., phenyl) optionally substituted by 1 to 3 substituents selected from
(a) halogen atom (e.g., fluorine, chlorine),
(b) $C_{1-6}$ alkyl group (e.g., methyl) optionally substituted by 1 to 3 halogen atoms (e.g., fluorine), and
(c) $C_{1-6}$ alkoxy group (e.g., methoxy, ethoxy) optionally substituted by 1 to 3 halogen atoms (e.g., fluorine), or
(3) 5- or 6-membered aromatic heterocyclic group (e.g., pyridyl) optionally substituted by 1 to 3 substituents selected from (a) halogen atom (e.g., fluorine, chlorine),
(b) $C_{1-6}$ alkyl group (e.g., methyl) optionally substituted by 1 to 3 halogen atoms (e.g., fluorine), and
(c) $C_{1-6}$ alkoxy group (e.g., methoxy) optionally substituted by 1 to 3 halogen atoms (e.g., fluorine).

$R^2$ is preferably
(1) optionally substituted $C_{1-6}$ alkyl group (e.g., methyl, ethyl, t-butyl, n-propyl, isopropyl),
(2) hydroxy group substituted by optionally substituted $C_{1-5}$ alkyl group, namely, optionally substituted $C_{1-6}$ alkoxy group (e.g., methoxy, isopropoxy), or
(3) optionally substituted $C_{3-10}$ cycloalkyl group (e.g., cyclopropyl, cyclohexyl), more preferably
(1) $C_{1-6}$ alkyl group (e.g., methyl, ethyl, t-butyl, n-propyl, isopropyl) optionally substituted by 1 to 3 substituents selected from
(a) halogen atom (e.g., fluorine, chlorine),
(b) $C_{6-14}$ aryl group (e.g., phenyl),
(c) $C_{1-6}$ alkoxy group (e.g., methoxy), and
(d) 4- to 12-membered nonaromatic heterocyclic group (e.g., morpholino),
(2) $C_{1-6}$ alkoxy group (e.g., methoxy, isopropoxy) optionally substituted by 1 to 3 substituents selected from
(a) halogen atom (e.g., fluorine, chlorine),
(b) $C_{6-14}$ aryl group (e.g., phenyl), and
(c) $C_{1-6}$ alkoxy group (e.g., methoxy), or
(3) $C_{3-10}$ cycloalkyl group (e.g., cyclopropyl, cyclohexyl).

$R^3$ is an optionally substituted $C_{1-6}$ alkyl group, optionally substituted $C_{3-10}$ cycloalkyl group, optionally substituted $C_{6-14}$ aryl group or optionally substituted heterocyclic group.

The "optionally substituted heterocyclic group" for $R^3$ is preferably an optionally substituted 5- or 6-membered heterocyclic group.

$R^3$ is preferably
(1) optionally substituted $C_{1-6}$ alkyl group (preferably, branched $C_{1-6}$ alkyl group (e.g., isopropyl, isobutyl, 1-ethylpropyl)),
(2) optionally substituted $C_{3-10}$ cycloalkyl group (e.g., cyclopentyl, cyclohexyl), or
(3) optionally substituted 5- or 6-membered heterocyclic group (e.g., pyridyl, piperidyl, tetrahydrothiopyranyl, 1-oxidotetrahydrothiopyranyl, 1,1-dioxidotetrahydrothiopyranyl), more preferably
(1) $C_{1-6}$ alkyl group (preferably, branched $C_{1-6}$ alkyl group (e.g., isopropyl, isobutyl, 1-ethylpropyl)) optionally substituted by 1 to 3 substituents selected from
(a) $C_{1-6}$ alkoxy group (e.g., methoxy, ethoxy, propoxy) optionally substituted by 1 to 3 $C_{1-6}$ alkoxy groups (e.g., methoxy),
(b) $C_{6-14}$ aryloxy group (e.g., phenyloxy),
(c) $C_{7-13}$ aralkyloxy group (e.g., benzyloxy),
(d) amino group optionally mono- or di-substituted by $C_{1-6}$ alkyl group (e.g., methyl),
(e) 4- to 12-membered nonaromatic heterocyclic group (e.g., piperidyl, morphonyl),
(f) $C_{1-6}$ alkylsulfonyl group (e.g., methylsulfonyl, isopropylsulfonyl), and
(g) $C_{6-14}$ arylsulfonyl group (e.g., benzenesulfonyl),
(2) $C_{3-10}$ cycloalkyl group (e.g., cyclohexyl), or
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 $C_{6-14}$ aryl groups (e.g., phenyl).

$R^4$ is a hydrogen atom or a $C_{1-6}$ alkyl group.
$R^4$ is preferably a hydrogen atom.
$R^5$ is a group represented by $-(CH_2)_3-COOR^{11}$ or $-NR^6-CR^7R^8-CR^9R^{10}-COOR^{11}$ wherein $R^6$, $R^7$, $R^8$, $R^9$ and $R^{11}$ are each independently a hydrogen atom or a $C_{1-6}$ alkyl group, and $R^{10}$ is a hydrogen atom, a $C_{2-6}$ alkyl group or a hydroxy group.

$R^6$ is preferably a hydrogen atom or methyl, more preferably a hydrogen atom.
$R^7$ is preferably a hydrogen atom.
$R^8$ is preferably a hydrogen atom.
$R^9$ is preferably a hydrogen atom, methyl or ethyl, more preferably a hydrogen atom.
$R^{10}$ is preferably a hydrogen atom, methyl or ethyl, more preferably a hydrogen atom.
$R^{11}$ is preferably a hydrogen atom, methyl or ethyl, more preferably a hydrogen atom.
$R^5$ is preferably $-NR^6-CR^7R^8-CR^9R^{10}-COOR^{11}$.

Of compounds (I), a compound wherein
$R^1$ is an optionally substituted $C_{1-6}$ alkyl group, an optionally substituted $C_{6-14}$ aryl group, or an optionally substituted 5- or 6-membered aromatic heterocyclic group;
$R^2$ is an optionally substituted $C_{1-6}$ alkyl group, an optionally substituted $C_{1-6}$ alkoxy group, or an optionally substituted $C_{3-10}$ cycloalkyl group;
$R^3$ is an optionally substituted $C_{1-6}$ alkyl group, an optionally substituted $C_{3-10}$ cycloalkyl group, or an optionally substituted 5- or 6-membered heterocyclic group;
$R^4$ is a hydrogen atom;
$R^5$ is $-(CH_2)_3-COOR^{11}$ or $-NR^6-CH_2-CR^9R^{10}-COOR^{11}$;
$R^6$ is a hydrogen atom or methyl;
$R^9$ is a hydrogen atom, methyl or ethyl;
$R^{10}$ is a hydrogen atom, methyl or ethyl; and
$R^{11}$ is a hydrogen atom, methyl or ethyl is preferable.

When ring A is a benzene ring or 6-membered aromatic heterocycle, specific preferable examples of the formula (I) include the following formulas (I'), (I'') and (I''')

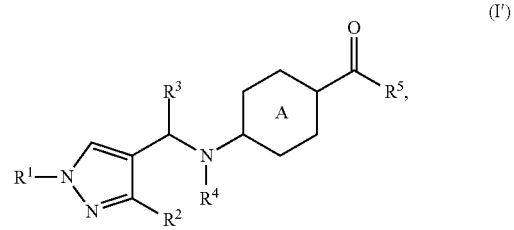

(I')

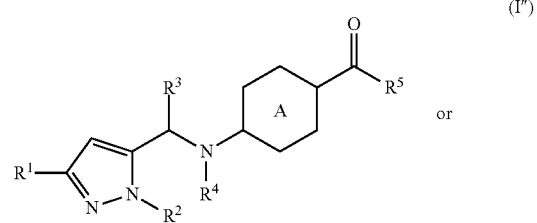

(I'') or

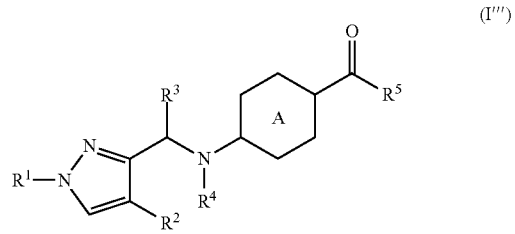

(I''')

wherein each symbol other than ring A is as defined above; compound represented by the above-mentioned formulas (I'), (I'') and (I''') and salts thereof are encompassed in compound (I).

The formula (I) is more preferably the formula (I').

Preferable examples of compound (I) include the following compounds.

(Compound A)

In the formula (I), a compound wherein ring A is a benzene ring or 5- or 6-membered aromatic heterocycle (preferably, pyridine);
ring B is pyrazole;
$R^1$ is
(1) optionally substituted $C_{1-6}$ alkyl group (e.g., methyl, 1,1-dimethylpropyl),
(2) optionally substituted $C_{6-14}$ aryl group (e.g., phenyl), or
(3) optionally substituted 5- or 6-membered aromatic heterocyclic group (e.g., pyridyl);
$R^2$ is
(1) optionally substituted $C_{1-6}$ alkyl group (e.g., methyl, ethyl, t-butyl, n-propyl, isopropyl),
(2) optionally substituted $C_{1-6}$ alkoxy group (e.g., methoxy, isopropoxy), or
(3) optionally substituted $C_{3-10}$ cycloalkyl group (e.g., cyclohexyl);
$R^3$ is
(1) optionally substituted $C_{1-6}$ alkyl group (preferably, branched $C_{1-6}$ alkyl group (e.g., isopropyl, isobutyl, 1-ethylpropyl)),
(2) optionally substituted $C_{3-10}$ cycloalkyl group (e.g., cyclopropyl, cyclohexyl), or
(3) optionally substituted 5- or 6-membered heterocyclic group (e.g., pyridyl, piperidyl, tetrahydrothiopyranyl, 1-oxidotetrahydrothiopyranyl, 1,1-dioxidotetrahydrothiopyranyl);
$R^4$ is a hydrogen atom; and
$R^5$ is —$(CH_2)_3$—$COOR^{11}$ or —$NR^6$—$(CH_2)_2$—$COOR^{11}$ (preferably, —$NR^6$—$(CH_2)_2$—$COOR^{11}$)
wherein $R^6$ is a hydrogen atom or methyl (preferably, a hydrogen atom), and
$R^{11}$ is a hydrogen atom, methyl or ethyl (preferably, a hydrogen atom);
or a salt thereof.

(Compound A-1)

A compound of the formula (I), which is a compound of the formula (I') or (I") (preferably, formula (I')),
wherein, ring A is a benzene ring or 6-membered aromatic heterocycle (e.g., pyridine);
$R^1$ is
(1) $C_{1-6}$ alkyl group (e.g., methyl, 1,1-dimethylpropyl) optionally substituted by 1 to 3 substituents selected from
(a) halogen atom (e.g., fluorine),
(b) $C_{6-14}$ aryl group (e.g., phenyl), and
(c) $C_{1-6}$ alkoxy group (e.g., methoxy),
(2) $C_{6-14}$ aryl group (e.g., phenyl) optionally substituted by 1 to 3 substituents selected from
(a) halogen atom (e.g., fluorine, chlorine),
(b) $C_{1-6}$ alkyl group (e.g., methyl) optionally substituted by 1 to 3 halogen atoms (e.g., fluorine), and
(c) $C_{1-6}$ alkoxy group (e.g., methoxy) optionally substituted by 1 to 3 halogen atoms (e.g., fluorine), or
(3) 5- or 6-membered aromatic heterocyclic group (e.g., pyridyl) optionally substituted by 1 to 3 substituents selected from
(a) halogen atom (e.g., fluorine, chlorine),
(b) $C_{1-6}$ alkyl group (e.g., methyl) optionally substituted by 1 to 3 halogen atoms (e.g., fluorine), and
(c) $C_{1-6}$ alkoxy group (e.g., methoxy) optionally substituted by 1 to 3 halogen atoms (e.g., fluorine);
$R^2$ is
(1) $C_{1-6}$ alkyl group (e.g., methyl, ethyl, t-butyl, n-propyl, isopropyl) optionally substituted by 1 to 3 substituents selected from
(a) halogen atom (e.g., fluorine, chlorine),
(b) $C_{6-14}$ aryl group (e.g., phenyl), and
(c) $C_{1-6}$ alkoxy group (e.g., methoxy),
(2) $C_{1-6}$ alkoxy group (e.g., methoxy, isopropoxy) optionally substituted by 1 to 3 substituents selected from
(a) halogen atom (e.g., fluorine, chlorine),
(b) $C_{6-14}$ aryl group (e.g., phenyl), and
(c) $C_{1-6}$ alkoxy group (e.g., methoxy), or
(3) $C_{3-10}$ cycloalkyl group (e.g., cyclopropyl, cyclohexyl);
$R^3$ is
(1) $C_{1-6}$ alkyl group (preferably, branched $C_{1-6}$ alkyl group (e.g., isobutyl, 1-ethylpropyl)) optionally substituted by 1 to 3 substituents selected from
(a) $C_{1-6}$ alkoxy group (e.g., methoxy, ethoxy, propoxy) optionally substituted by 1 to 3 $C_{1-6}$ alkoxy groups (e.g., methoxy),
(b) $C_{6-14}$ aryloxy group (e.g., phenyloxy),
(c) $C_{7-13}$ aralkyloxy group (e.g., benzyloxy),
(d) amino group optionally mono- or di-substituted by $C_{1-6}$ alkyl group (e.g., methyl),
(e) 4- to 12-membered nonaromatic heterocyclic group (e.g., piperidyl, morpholinyl),
(f) $C_{1-6}$ alkylsulfonyl group (e.g., methylsulfonyl, isopropylsulfonyl), and
(g) $C_{6-14}$ arylsulfonyl group (e.g., benzenesulfonyl),
(2) $C_{3-10}$ cycloalkyl group (e.g., cyclohexyl), or
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 $C_{6-14}$ aryl groups (e.g., phenyl);
$R^4$ is a hydrogen atom; and
$R^5$ is —$(CH_2)_3$—COOH or —$NR^6$—$(CH_2)_2$—COOH, preferably —$NR^6$—$(CH_2)_2$—COOH
wherein $R^6$ is a hydrogen atom or methyl (preferably, hydrogen atom));
or a salt thereof.

(Compound A-2)

A compound of the formula (I), which is a compound of the formula (I'), (I") or (I'") (preferably, formula (I')),
wherein, ring A is a benzene ring or 6-membered aromatic heterocycle (e.g., pyridine);
$R^1$ is
(1) $C_{1-6}$ alkyl group (e.g., methyl, 1,1-dimethylpropyl) optionally substituted by 1 to 3 substituents selected from
(a) halogen atom (e.g., fluorine),
(b) $C_{6-14}$ aryl group (e.g., phenyl), and
(c) $C_{1-6}$ alkoxy group (e.g., methoxy),
(2) $C_{6-14}$ aryl group (e.g., phenyl) optionally substituted by 1 to 3 substituents selected from
(a) halogen atom (e.g., fluorine, chlorine),
(b) $C_{1-6}$ alkyl group (e.g., methyl) optionally substituted by 1 to 3 halogen atoms (e.g., fluorine), and
(c) $C_{1-6}$ alkoxy group (e.g., methoxy, ethoxy) optionally substituted by 1 to 3 halogen atoms (e.g., fluorine), or
(3) 5- or 6-membered aromatic heterocyclic group (e.g., pyridyl) optionally substituted by 1 to 3 substituents selected from
(a) halogen atom (e.g., fluorine, chlorine),
(b) $C_{1-6}$ alkyl group (e.g., methyl) optionally substituted by 1 to 3 halogen atoms (e.g., fluorine) and
(c) alkoxy group (e.g., methoxy) optionally substituted by 1 to 3 halogen atoms (e.g., fluorine);

R² is
(1) C₁₋₆ alkyl group (e.g., methyl, ethyl, t-butyl, n-propyl, isopropyl) optionally substituted by 1 to 3 substituents selected from
(a) halogen atom (e.g., fluorine, chlorine),
(b) C₆₋₁₄ aryl group (e.g., phenyl),
(c) C₁₋₆ alkoxy group (e.g., methoxy), and
(d) 4- to 12-membered nonaromatic heterocyclic group (e.g., morpholino)
(2) C₁₋₆ alkoxy group (e.g., methoxy, isopropoxy) optionally substituted by 1 to 3 substituents selected from
(a) halogen atom (e.g., fluorine, chlorine),
(b) C₆₋₁₄ aryl group (e.g., phenyl), and
(c) C₁₋₆ alkoxy group (e.g., methoxy), or
(3) C₃₋₁₀ cycloalkyl group (e.g., cyclopropyl, cyclohexyl);
R³ is
(1) C₁₋₆ alkyl group (preferably, branched C₁₋₆ alkyl group (e.g., isobutyl, 1-ethylpropyl)) optionally substituted by 1 to 3 substituents selected from
(a) C₁₋₆ alkoxy group (e.g., methoxy, ethoxy, propoxy) optionally substituted by 1 to 3 C₁₋₆ alkoxy groups (e.g., methoxy),
(b) C₆₋₁₄ aryloxy group (e.g., phenyloxy),
(c) C₇₋₁₃ aralkyloxy group (e.g., benzyloxy),
(d) amino group optionally mono- or di-substituted by C₁₋₆ alkyl group (e.g., methyl),
(e) 4- to 12-membered nonaromatic heterocyclic group (e.g., piperidyl, morphonyl),
(f) C₁₋₆ alkylsulfonyl group (e.g., methylsulfonyl, isopropylsulfonyl), and
(g) C₆₋₁₄ arylsulfonyl group (e.g., benzenesulfonyl),
(2) C₃₋₁₀ cycloalkyl group (e.g., cyclohexyl), or
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 C₆₋₁₄ aryl groups (e.g., phenyl);
R⁴ is a hydrogen atom; and
R⁵ is —(CH₂)₃—COOR¹¹ or —NR⁶—CH₂—CR⁹R¹⁰—COOR¹¹, preferably —NR⁶—CH₂—CR⁹R¹⁰—COOR¹¹
wherein R⁶ is a hydrogen atom or methyl (preferably, a hydrogen atom),
R⁹ is a hydrogen atom, methyl or ethyl (preferably, a hydrogen atom),
R¹⁰ is a hydrogen atom, methyl or ethyl (preferably, a hydrogen atom),
R¹¹ is a hydrogen atom, methyl or ethyl (preferably, a hydrogen atom);
or a salt thereof.
(Compound A-3)
3-[({4-[(Cyclohexyl{3-methyl-1-[5-(trifluormethyl)pyridin-2-yl]-1H-pyrazol-4-yl}methyl)amino]phenyl}carbonyl) amino]propanoic acid or a salt thereof (Example 1);
3-[{[4-({cyclohexyl[1-(3-methoxyphenyl)-3-methyl-1H-pyrazol-4-yl]methyl}amino)phenyl]carbonyl}(methyl) amino]propanoic acid or a salt thereof (Example 70); or
3-[{[4-({cyclohexyl[1-(3-methoxyphenyl)-4-methyl-1H-pyrazol-3-yl]methyl}amino)phenyl]carbonyl}(methyl) amino]propanoic acid or a salt thereof (Example 76).
Compound (IA) is explained in the following.
The ring AA is an optionally substituted benzene ring, or an optionally substituted 5- or 6-membered aromatic heterocycle.
The 5- or 6-membered aromatic heterocycle for ring AA is preferably pyridine.
The "benzene ring" or "5- or 6-membered aromatic heterocycle" of the "optionally substituted benzene ring, or an optionally substituted 5- or 6-membered aromatic heterocycle" for ring AA optionally further has 1 to 4 substituents at substitutable position(s) besides the "—NR⁴⁴— group" and "—CO—R⁴⁵ group".

The ring AA is preferably a benzene ring or 5- or 6-membered aromatic heterocycle (e.g., pyridine), more preferably a benzene ring or 6-membered aromatic heterocycle (e.g., pyridine), particularly preferably a benzene ring, which does not have a substituent besides the "—NR⁴⁴— group" and the "—CO—R⁴⁵ group".

When ring AA is a benzene ring or 6-membered aromatic heterocycle, the following part containing ring AA in the formula (IA)

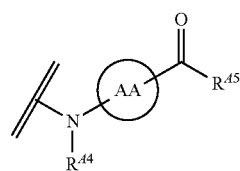

is preferably

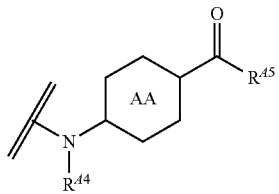

wherein each symbol other than ring AA is as defined above.

Ring AB is an optionally substituted 5-membered aromatic heterocycle.

The 5-membered aromatic heterocycle for ring AB is preferably pyrrole, thiophene, furan, imidazole or pyrazole.

The "5-membered aromatic heterocycle" of the "optionally substituted 5-membered aromatic heterocycle" for ring AB optionally further has 1 or 2 substituents at substitutable position(s) besides the "—CH(R⁴³)— group".

Ring AB is preferably 5-membered aromatic heterocycle (e.g., pyrrole, thiophene, furan, imidazole, pyrazole, pyrrole) optionally substituted by 1 to 3 substituents selected from
(a) C₁₋₆ alkyl group (e.g., methyl, ethyl) optionally substituted by 1 to 3 substituents selected from C₁₋₆ alkoxy group (e.g., methoxy, ethoxy) optionally substituted by 1 to 3 C₁₋₆ alkoxy groups (e.g., methoxy),
(b) C₃₋₁₀ cycloalkyl group (e.g., cyclohexyl),
(c) C₆₋₁₄ aryl group (e.g., phenyl) optionally having 1 to 3 C₁₋₆ alkyl groups (e.g., methyl) optionally substituted by 1 to 3 halogen atoms (e.g., fluorine),
(d) cyano group,
(e) C₁₋₆ alkoxy group (e.g., methoxy), and
(f) halogen atom (e.g., bromine atom).

Ring AC is an optionally substituted benzene ring or optionally substituted 5- or 6-membered aromatic heterocycle.

The 5- or 6-membered aromatic heterocycle for ring AC is preferably pyridine.

The "benzene ring" or "5- or 6-membered aromatic heterocycle" of the "optionally substituted benzene ring or optionally substituted 5- or 6-membered aromatic heterocycle" for ring AC optionally further has 1 to 4 substituents at substitutable position(s).

Ring AC is preferably (1) a benzene ring optionally substituted by 1 to 3 substituents selected from (a) $C_{1-6}$ alkyl group (e.g., methyl, ethyl) optionally substituted by 1 to 3 halogen atoms (e.g., fluorine), (b) $C_{3-10}$ cycloalkyl group (e.g., cyclopropyl, cyclohexyl), (c) $C_{1-6}$ alkoxy group (e.g., methoxy, ethoxy, propoxy, isobutoxy) optionally substituted by 1 to 3 substituents selected from (i) $C_{1-6}$ alkoxy group (e.g., methoxy).

(ii) $C_{3-6}$ cycloalkyl group (e.g., cyclopropyl), (iii) 4- to 12-membered aromatic heterocyclic group (e.g., oxazolyl, isoxazolyl, pyridyl) optionally substituted by 1 to 3 substituents selected from (i') halogen atom (e.g., fluorine, chlorine), and (ii') $C_{1-6}$ alkyl group (e.g., methyl), (iv) 4- to 12-membered nonaromatic heterocyclic group (e.g., oxetanyl, tetrahydrofuryl) optionally substituted by 1 to 3 $C_{1-6}$ alkyl groups (e.g., methyl), (v) $C_{1-6}$ alkylsulfonyl group (e.g., methylsulfonyl), (vi) $C_{1-6}$ alkylthio group (e.g., methylthio), and (vii) hydroxy group, (d) halogen atom (e.g., fluorine, chlorine), (e) $C_{7-13}$ aralkyloxy group (e.g., benzyloxy), (f) 4- to 12-membered non-aromatic heterocyclyl-oxy group (e.g., tetrahydropyranyloxy, tetrahydrothiopyranyloxy, 1,1-dioxidotetrahydrothiopyranyloxy), (g) 4- to 12-membered aromatic heterocyclyl-oxy group (e.g., pyridyloxy) optionally substituted by 1 to 3 substituents selected from (i) $C_{1-6}$ alkyl group (e.g., methyl) optionally substituted by 1 to 3 halogen atoms (e.g., fluorine), and (ii) cyano group, (h) $C_{6-14}$ aryl group (e.g., phenyl), (i) 4- to 12-membered aromatic heterocyclic group (e.g., oxazolyl, isoxazolyl, pyrazolyl, pyridyl) optionally substituted by 1 to 3 substituents selected from (i) $C_{1-6}$ alkyl group (e.g., methyl), and (ii) $C_{1-6}$ alkoxy group (e.g., methoxy), (j) 4- to 12-membered nonaromatic heterocyclic group (e.g., morpholino, thiomorpholino), (k) $C_{7-13}$ aralkyl group (e.g., benzyl), (l) cyano group, (m) amino group optionally mono- or di-substituted by substituent(s) selected from (i) $C_{1-6}$ alkyl group (e.g., methyl, ethyl) optionally substituted by 1 to 3 $C_{1-6}$ alkoxy groups (e.g., methoxy), (ii) $C_{1-6}$ alkyl-carbonyl group (e.g., acetyl), (iii) $C_{1-6}$ alkylsulfonyl group (e.g., methylsulfonyl), (iv) carbamoyl group optionally mono- or di-substituted by $C_{1-6}$ alkyl group (e.g., ethyl), (v) $C_{6-14}$ aryl-carbonyl group (e.g., benzoyl), (vi) $C_{6-14}$ arylsulfonyl group (e.g., benzenesulfonyl), and (vii) $C_{7-13}$ aralkyl group (e.g., benzyl), and (n) $C_{6-14}$ arylsulfonyl group (e.g., benzenesulfonyl), or (2) 5- or 6-membered aromatic heterocycle (e.g., pyridine) optionally substituted by 1 to 3 substituents selected from (a) $C_{1-6}$ alkyl group (e.g., methyl, ethyl) optionally substituted by 1 to 3 halogen atoms (e.g., fluorine), (b) $C_{3-10}$ cycloalkyl group (e.g., cyclohexyl), (c) $C_{1-6}$ alkoxy group (e.g., methoxy, ethoxy) optionally substituted by 1 to 3 substituents selected from (i) $C_{1-6}$ alkoxy group (e.g., methoxy), and (ii) $C_{3-6}$ cycloalkyl group (e.g., cyclopropyl), (d) halogen atom (e.g., fluorine, chlorine, bromine), (e) $C_{7-13}$ aralkyloxy group (e.g., benzyloxy), and (f) 4- to 12-membered non-aromatic heterocyclyl-oxy group (e.g., tetrahydropyranyloxy).

In the formula (IA), the part represented by

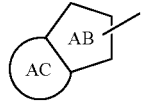

is a group derived from a bicyclic ring formed by ring AB and ring AC having one side of each ring in common (i.e., condensed). Here, the side of ring AB and the side of ring AC involved in the formation of the bicyclic ring are bonded at the same multiplicity. For example, when, in the formula (IA), the part represented by

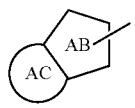

is a group represented by

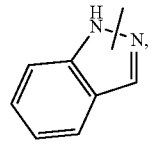

ring AB is "pyrazole" and ring AC is "benzene".

In the fused ring formed by ring AC and ring AB, the "—CH($R^{43}$)— group" is present at any bondable position on ring AB.

$R^{43}$ is an optionally substituted $C_{1-6}$ alkyl group, optionally substituted $C_{3-10}$ cycloalkyl group, optionally substituted $C_{6-14}$ aryl group or optionally substituted heterocyclic group.

The "optionally substituted heterocyclic group" for $R^{43}$ is preferably an optionally substituted 5- or 6-membered heterocyclic group.

$R^{43}$ is preferably (1) optionally substituted $C_{1-6}$ alkyl group (preferably, branched $C_{1-6}$ alkyl group (e.g., isopropyl, isobutyl, 1-ethylpropyl)), (2) optionally substituted $C_{3-10}$ cycloalkyl group (e.g., cyclopentyl, cyclohexyl), or (3) optionally substituted 5- or 6-membered heterocyclic group (e.g., pyridyl, piperidyl, tetrahydrothiopyranyl, 1-oxidotetrahydrothiopyranyl, 1,1-dioxidotetrahydrothiopyranyl), more preferably (1) $C_{1-6}$ alkyl group (preferably, methyl, ethyl, butyl, hexyl, branched $C_{1-6}$ alkyl group (e.g., isopropyl, isobutyl, 1-ethylpropyl)) optionally substituted by 1 to 3 substituents selected from (a) $C_{1-6}$ alkoxy group (e.g., methoxy, ethoxy, propoxy) optionally substituted by 1 to 3 $C_{1-6}$ alkoxy groups (e.g., methoxy), (b) $C_{6-14}$ aryloxy group (e.g., phenyloxy), (c) $C_{7-13}$ aralkyloxy group (e.g., benzyloxy), (d) amino group optionally mono- or di-substituted by $C_{1-6}$ alkyl group (e.g., methyl), (e) 4- to 12-membered nonaromatic heterocyclic group (e.g., piperidyl, morphonyl), (f) $C_{1-6}$ alkylsulfonyl group (e.g., methylsulfonyl, isopropylsulfonyl),
(g) $C_{6-14}$ arylsulfonyl group (e.g., benzenesulfonyl), and
(h) $C_{1-6}$ alkylthio group (e.g., methylthio),
(2) $C_{3-10}$ cycloalkyl group (e.g., cyclopentyl, cyclohexyl),
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 $C_{6-14}$ aryl groups (e.g., phenyl), or
(4) $C_{6-14}$ aryl (e.g., phenyl).
$R^{A4}$ is a hydrogen atom or a $C_{1-6}$ alkyl group.
$R^{A4}$ is preferably a hydrogen atom.
$R^{A5}$ is a group represented by —$(CH_2)_3$—$COOR^{A11}$ or —$NR^{A6}$—$CR^{A7}R^{A8}$—$CR^{A9}R^{A10}$—$COOR^{A11}$, wherein $R^{A6}$, $R^{A7}$, $R^{A8}$, $R^{A9}$ and $R^{A11}$ are each independently a hydrogen atom or a $C_{1-6}$ alkyl group, and $R^{10}$ is a hydrogen atom, a $C_{1-6}$ alkyl group or a hydroxy group.
$R^{A6}$ is preferably a hydrogen atom or methyl, more preferably a hydrogen atom.
$R^{A7}$ is preferably a hydrogen atom.
$R^{A8}$ is preferably a hydrogen atom.
$R^{A9}$ preferably a hydrogen atom.
$R^{A10}$ is preferably a hydrogen atom.
$R^{A11}$ is preferably a hydrogen atom, methyl or ethyl, more preferably a hydrogen atom.
$R^{A5}$ is preferably —$NR^{A6}$—$CR^{A7}R^{A8}$—$CR^{A9}R^{A10}$—$COOR^{A11}$.

When ring AA is a benzene ring or 6-membered aromatic heterocycle, specific preferable examples of the formula (I) include the following formula (IA')

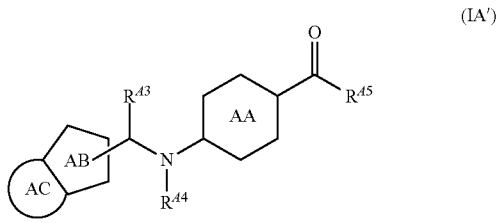

(IA')

(wherein each symbol other than ring AA is as defined above).

A compound represented by the above-mentioned formula (IA') and a salt thereof are encompassed in compound (IA).

Of the compounds represented by the above-mentioned formula (IA'), a compound wherein
$R^{A3}$ is an optionally substituted $C_{1-6}$ alkyl group, an optionally substituted $C_{3-10}$ cycloalkyl group, or an optionally substituted 5- or 6-membered heterocyclic group;
$R^{A4}$ is a hydrogen atom;
$R^{A5}$ is —$(CH_2)_3$—$COOR^{A11}$ or —$NR^{A6}$—$(CH_2)_2$—$COOR^{A11}$;
$R^{A6}$ is a hydrogen atom or methyl; and
$R^{A11}$ is a hydrogen atom, methyl or ethyl is preferable.

Preferable examples of compound (IA) include the following compounds.
(Compound AA)
In the formula (IA), a compound wherein
ring AA is a benzene ring or 5- or 6-membered aromatic heterocycle (e.g., pyridine);
ring AB is an optionally substituted 5-membered aromatic heterocycle (e.g., pyrrole, thiophene, furan, imidazole, pyrazole);
ring AC is an optionally substituted benzene ring, or an optionally substituted 5- or 6-membered aromatic heterocycle (e.g., pyridine);

$R^{A3}$ is
(1) optionally substituted $C_{1-6}$ alkyl group (preferably, branched $C_{1-6}$ alkyl group (e.g., isopropyl, isobutyl, 1-ethylpropyl)),
(2) optionally substituted $C_{3-10}$ cycloalkyl group (e.g., cyclohexyl), or
(3) optionally substituted 5- or 6-membered heterocyclic group (e.g., pyridyl, piperidyl, tetrahydrothiopyranyl, 1-oxidotetrahydrothiopyranyl, 1,1-dioxidotetrahydrothiopyranyl);
$R^{A4}$ is a hydrogen atom; and
$R^{A5}$ is —$(CH_2)_3$—$COOR^{A11}$ or —$NR^{A6}$—$(CH_2)_2$—$COOR^{A11}$, preferably —$NR^{A6}$—$(CH_2)_2$—$COOR^{A11}$
wherein $R^{A6}$ is a hydrogen atom or methyl (preferably, a hydrogen atom),
$R^{A11}$ is a hydrogen atom, methyl or ethyl (preferably, a hydrogen atom);
or a salt thereof.

(Compound AA-1)
A compound of the formula (IA), which is a compound of the formula (IA'), wherein
ring AA is a benzene ring or 6-membered aromatic heterocycle (e.g., pyridine);
ring AB is 5-membered aromatic heterocycle (e.g., thiophene, furan, imidazole, pyrazole) optionally substituted by 1 to 3 substituents selected from
(a) $C_{1-6}$ alkyl group (e.g., methyl, ethyl),
(b) $C_{3-10}$ cycloalkyl group (e.g., cyclohexyl), and
(c) $C_{6-14}$ aryl group (e.g., phenyl);
ring AC is
(1) a benzene ring optionally substituted by 1 to 3 substituents selected from
(a) $C_{1-6}$ alkyl group (e.g., methyl) optionally substituted by 1 to 3 halogen atoms (e.g., fluorine),
(b) $C_{3-10}$ cycloalkyl group (e.g., cyclohexyl),
(c) alkoxy group (e.g., methoxy), and
(d) halogen atom (e.g., fluorine), or
(2) 5- or 6-membered aromatic heterocycle (e.g., pyridine) optionally substituted by 1 to 3 substituents selected from
(a) $C_{1-6}$ alkyl group (e.g., methyl) optionally substituted by 1 to 3 halogen atoms (e.g., fluorine),
(b) $C_{3-10}$ cycloalkyl group (e.g., cyclohexyl),
(c) $C_{1-6}$ alkoxy group (e.g., methoxy), and
(d) halogen atom (e.g., fluorine);
$R^{A3}$ is
(1) a $C_{1-6}$ alkyl group (preferably, branched $C_{1-6}$ alkyl group (e.g., isobutyl, 1-ethylpropyl)) optionally substituted by 1 to 3 substituents selected from
(a) $C_{1-6}$ alkoxy group (e.g., methoxy, ethoxy, propoxy) optionally substituted by 1 to 3 $C_{1-6}$ alkoxy groups (e.g., methoxy),
(b) $C_{6-14}$ aryloxy group (e.g., phenyloxy),
(c) $C_{7-13}$ aralkyloxy group (e.g., benzyloxy),
(d) amino group optionally mono- or di-substituted by $C_{1-6}$ alkyl group (e.g., methyl),
(e) 4- to 12-membered nonaromatic heterocyclic group (e.g., piperidyl, morphonyl),
(f) $C_{1-6}$ alkylsulfonyl group (e.g., methylsulfonyl, isopropylsulfonyl), and
(g) $C_{6-14}$ arylsulfonyl group (e.g., benzenesulfonyl),
(2) a $C_{3-10}$ cycloalkyl group (e.g., cyclohexyl), or
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 $C_{6-14}$ aryl groups (e.g., phenyl);
$R^{A4}$ is a hydrogen atom; and $R^{A5}$ is —$(CH_2)_3$—COOH or —$NR^{A6}$—$(CH_2)_2$—COOH, preferably —$NR^{A6}$—$(CH_2)_2$—COOH
wherein $R^{A6}$ is a hydrogen atom or methyl (preferably, a hydrogen atom);
or a salt thereof.
(Compound AA-2)
  A compound of the formula (IA), which is a compound of the formula (IA'), wherein
ring AA is a benzene ring or 6-membered aromatic heterocycle (e.g., pyridine);
ring AB is 5-membered aromatic heterocycle (e.g., thiophene, furan, imidazole, pyrazole) optionally substituted by 1 to 3 substituents selected from
(a) $C_{1-6}$ alkyl group (e.g., methyl, ethyl) optionally substituted by 1 to 3 $C_{1-6}$ alkoxy groups (e.g., methoxy),
(b) $C_{3-10}$ cycloalkyl group (e.g., cyclohexyl), and
(c) $C_{6-14}$ aryl group (e.g., phenyl);
ring AC is
(1) a benzene ring optionally substituted by 1 to 3 substituents selected from
(a) $C_{1-6}$ alkyl group (e.g., methyl) optionally substituted by 1 to 3 halogen atoms (e.g., fluorine),
(b) $C_{3-10}$ cycloalkyl group (e.g., cyclohexyl),
(c) $C_{1-6}$ alkoxy group (e.g., methoxy, ethoxy) optionally substituted by 1 to 3 substituents selected from
(i) $C_{1-6}$ alkoxy group (e.g., methoxy), and
(ii) $C_{3-6}$ cycloalkyl group (e.g., cyclopropyl),
(d) halogen atom (e.g., fluorine),
(e) $C_{7-13}$ aralkyloxy group (e.g., benzyloxy), and
(f) 4- to 12-membered non-aromatic heterocyclyl-oxy group (e.g., tetrahydropyranyloxy), or
(2) 5- or 6-membered aromatic heterocycle (e.g., pyridine) optionally substituted by 1 to 3 substituents selected from
(a) $C_{1-6}$ alkyl group (e.g., methyl) optionally substituted by 1 to 3 halogen atoms (e.g., fluorine),
(b) $C_{3-10}$ cycloalkyl group (e.g., cyclohexyl),
(c) $C_{1-6}$ alkoxy group (e.g., methoxy, ethoxy) optionally substituted by 1 to 3 substituents selected from (i) $C_{1-6}$ alkoxy group (e.g., methoxy), and
(ii) $C_{3-6}$ cycloalkyl group (e.g., cyclopropyl),
(d) halogen atom (e.g., fluorine),
(e) $C_{7-13}$ aralkyloxy group (e.g., benzyloxy), and
(f) 4- to 12-membered non-aromatic heterocyclyl-oxy group (e.g., tetrahydropyranyloxy);
$R^{A3}$ is
(1) $C_{1-6}$ alkyl group (preferably, branched $C_{1-6}$ alkyl group (e.g., isopropyl, isobutyl, 1-ethylpropyl)) optionally substituted by 1 to 3 substituents selected from
(a) $C_{1-6}$ alkoxy group (e.g., methoxy, ethoxy, propoxy) optionally substituted by 1 to 3 $C_{1-6}$ alkoxy groups (e.g., methoxy),
(b) $C_{6-14}$ aryloxy group (e.g., phenyloxy),
(c) $C_{7-13}$ aralkyloxy group (e.g., benzyloxy),
(d) amino group optionally mono- or di-substituted by $C_{1-6}$ alkyl group (e.g., methyl),
(e) 4- to 12-membered nonaromatic heterocyclic group (e.g., piperidyl, morphonyl),
(f) $C_{1-6}$ alkylsulfonyl group (e.g., methylsulfonyl, isopropylsulfonyl), and
(g) $C_{6-14}$ arylsulfonyl group (e.g., benzenesulfonyl),
(2) $C_{3-10}$ cycloalkyl group (e.g., cyclopentyl, cyclohexyl), or
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 $C_{6-14}$ aryl groups (e.g., phenyl);

$R^{A4}$ is a hydrogen atom; and
$R^{A5}$ is —$(CH_2)_3$—$COOR^{A11}$ or —$NR^{A6}$—$(CH_2)_2$—$COOR^{A11}$, preferably —$NR^{A6}$—$(CH_2)_2$—$COOR^{A11}$
wherein $R^{A6}$ is a hydrogen atom or methyl (preferably, a hydrogen atom), and $R^{A11}$ is a hydrogen atom, methyl or ethyl (preferably, a hydrogen atom)); or a salt thereof.
(Compound AA-3)
  A compound of the formula (IA), which is a compound of the formula (IA'), wherein
ring AA is a benzene ring or 6-membered aromatic heterocycle (e.g., pyridine);
ring AB is a 5-membered aromatic heterocycle (e.g., pyrrole, thiophene, furan, imidazole, pyrazole, pyrrole) optionally substituted by 1 to 3 substituents selected from
(a) $C_{1-6}$ alkyl group (e.g., methyl, ethyl) optionally substituted by 1 to 3 substituents selected from $C_{1-6}$ alkoxy group (e.g., methoxy, ethoxy) optionally substituted by 1 to 3 $C_{1-6}$ alkoxy groups (e.g., methoxy),
(b) $C_{3-10}$ cycloalkyl group (e.g., cyclohexyl),
(c) $C_{6-14}$ aryl group (e.g., phenyl) optionally having 1 to 3 $C_{1-6}$ alkyl groups (e.g., methyl) optionally substituted by 1 to 3 halogen atoms (e.g., fluorine),
(d) cyano group,
(e) $C_{1-6}$ alkoxy group (e.g., methoxy), and
(f) halogen atom (e.g., bromine atom); ring AC is
(1) benzene ring optionally substituted by 1 to 3 substituents selected from
(a) $C_{1-6}$ alkyl group (e.g., methyl) optionally substituted by 1 to 3 halogen atoms (e.g., fluorine),
(b) $C_{3-10}$ cycloalkyl group (e.g., cyclopropyl, cyclohexyl),
(c) $C_{1-6}$ alkoxy group (e.g., methoxy, ethoxy, propoxy, isobutoxy) optionally substituted by 1 to 3 substituents selected from
(i) $C_{1-6}$ alkoxy group (e.g., methoxy),
(ii) $C_{3-6}$ cycloalkyl group (e.g., cyclopropyl),
(iii) 4- to 12-membered aromatic heterocyclic group (e.g., oxazolyl, isoxazolyl, pyridyl) optionally substituted by 1 to 3 substituents selected from
(i') halogen atom (e.g., fluorine, chlorine), and
(ii') $C_{1-6}$ alkyl group (e.g., methyl),
(iv) 4- to 12-membered nonaromatic heterocyclic group (e.g., oxetanyl, tetrahydrofuryl) optionally substituted by 1 to 3 $C_{1-6}$ alkyl groups (e.g., methyl),
(v) $C_{1-6}$ alkylsulfonyl group (e.g., methylsulfonyl),
(vi) $C_{1-6}$ alkylthio group (e.g., methylthio), and
(vii) hydroxy group,
(d) halogen atom (e.g., fluorine, chlorine),
(e) $C_{7-13}$ aralkyloxy group (e.g., benzyloxy),
(f) 4- to 12-membered non-aromatic heterocyclyl-oxy group (e.g., tetrahydropyranyloxy, tetrahydrothiopyranyloxy, 1,1-dioxidotetrahydrothiopyranyloxy),
(g) 4- to 12-membered aromatic heterocyclyl-oxy group (e.g., pyridyloxy) optionally substituted by 1 to 3 substituents selected from
(i) $C_{1-6}$ alkyl group (e.g., methyl) optionally substituted by 1 to 3 halogen atoms (e.g., fluorine), and
(ii) cyano group,
(h) $C_{6-14}$ aryl group (e.g., phenyl),
(i) 4- to 12-membered aromatic heterocyclic group (e.g., oxazolyl, isoxazolyl, pyrazolyl, pyridyl) optionally substituted by 1 to 3 substituents selected from
(i) $C_{1-6}$ alkyl group (e.g., methyl), and
(ii) $C_{1-6}$ alkoxy group (e.g., methoxy),
(j) 4- to 12-membered nonaromatic heterocyclic group (e.g., morpholino, thiomorpholino),
(k) $C_{7-13}$ aralkyl group (e.g., benzyl),
(l) cyano group, (m) amino group optionally mono- or di-substituted by substituent(s) selected from
(i) $C_{1-6}$ alkyl group (e.g., methyl, ethyl) optionally substituted by 1 to 3 $C_{1-6}$ alkoxy groups (e.g., methoxy),
(ii) $C_{1-6}$ alkyl-carbonyl group (e.g., acetyl),
(iii) $C_{1-6}$ alkylsulfonyl group (e.g., methylsulfonyl),
(iv) carbamoyl group optionally mono- or di-substituted by $C_{1-6}$ alkyl group (e.g., ethyl),
(v) $C_{6-14}$ aryl-carbonyl group (e.g., benzoyl),
(vi) $C_{6-14}$ arylsulfonyl group (e.g., benzenesulfonyl), and
(vii) $C_{7-13}$ aralkyl group (e.g., benzyl), and
(n) $C_{6-14}$ arylsulfonyl group (e.g., benzenesulfonyl), or
(2) 5- or 6-membered aromatic heterocycle (e.g., pyridine) optionally substituted by 1 to 3 substituents selected from
(a) $C_{1-6}$ alkyl group (e.g., methyl) optionally substituted by 1 to 3 halogen atoms (e.g., fluorine),
(b) $C_{3-10}$ cycloalkyl group (e.g., cyclohexyl),
(c) $C_{1-6}$ alkoxy group (e.g., methoxy, ethoxy) optionally substituted by 1 to 3 substituents selected from
(i) $C_{1-6}$ alkoxy group (e.g., methoxy), and
(ii) $C_{3-6}$ cycloalkyl group (e.g., cyclopropyl),
(d) halogen atom (e.g., fluorine, chlorine, bromine),
(e) $C_{7-13}$ aralkyloxy group (e.g., benzyloxy), and
(f) 4- to 12-membered non-aromatic heterocyclyl-oxy group (e.g., tetrahydropyranyloxy);
$R^{43}$ is
(1) $C_{1-6}$ alkyl group (preferably, methyl, ethyl, butyl, hexyl, branched $C_{1-6}$ alkyl group (e.g., isopropyl, isobutyl, 1-ethylpropyl)) optionally substituted by 1 to 3 substituents selected from
(a) $C_{1-6}$ alkoxy group (e.g., methoxy, ethoxy, propoxy) optionally substituted by 1 to 3 $C_{1-6}$ alkoxy groups (e.g., methoxy),
(b) $C_{6-14}$ aryloxy group (e.g., phenyloxy),
(c) $C_{7-13}$ aralkyloxy group (e.g., benzyloxy),
(d) amino group optionally mono- or di-substituted by $C_{1-6}$ alkyl group (e.g., methyl),
(e) 4- to 12-membered nonaromatic heterocyclic group (e.g., piperidyl, morphonyl),
(f) $C_{1-6}$ alkylsulfonyl group (e.g., methylsulfonyl, isopropylsulfonyl),
(g) $C_{6-14}$ arylsulfonyl group (e.g., benzenesulfonyl), and
(h) $C_{1-6}$ alkylthio group (e.g., methylthio),
(2) $C_{3-10}$ cycloalkyl group (e.g., cyclopentyl, cyclohexyl),
(3) 5- or 6-membered heterocyclic group (e.g., pyridyl, piperidyl, tetrahydrothiopyranyl, 1-oxidotetrahydrothiopyranyl, 1,1-dioxidotetrahydrothiopyranyl) optionally substituted by 1 to 3 $C_{6-14}$ aryl groups (e.g., phenyl), or
(4) $C_{6-14}$ aryl (e.g., phenyl);
$R^{44}$ is a hydrogen atom; and
$R^{45}$ is —$(CH_2)_3$—$COOR^{411}$ or —$NR^{46}$—$(CH_2)_2$—$COOR^{411}$, preferably, —$NR^{46}$—$(CH_2)_2$—$COOR^{411}$ wherein $R^{46}$ is a hydrogen atom or methyl (preferably, a hydrogen atom), and $R^{411}$ is a hydrogen atom, methyl or ethyl (preferably, a hydrogen atom);
or a salt thereof.
(compound AA-4)
3-{[(4-{[Cyclohexyl(3-methyl-1-benzofuran-2-yl)methyl]amino}phenyl)carbonyl]methyl)amino}propanoic acid or a salt thereof (Example A41);
3-{[(6-{[cyclohexyl(5-fluoro-3-methyl-1-benzofuran-2-yl)methyl]amino}pyridin-3-yl)carbonyl](methyl)amino}propanoic acid or a salt thereof (Example A53);
3-{[(4-{[2-ethyl-1-(5-fluoro-3-methyl-1-benzofuran-2-yl)butyl]amino}phenyl)carbonyl](methyl)amino}propanoic acid or a salt thereof (Example A73);
3-[{[4-({1-[5-(cyclopropylmethoxy)-3-methyl-1-benzofuran-2-yl]-2-methylpropyl}amino)phenyl]carbonyl}(methyl)amino]propanoic acid or a salt thereof (Example A78); or
3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid or a salt thereof (Example A83).

As the salts of compounds (I) and (IA), pharmacologically acceptable salts are preferable. Examples of such salt include a salt with inorganic base, a salt with organic base, a salt with inorganic acid, a salt with organic acid, a salt with basic or acidic amino acid and the like.

Preferable examples of a salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

The prodrug of compound (I) or (IA) means a compound which is converted to compound (I) or (IA) under the physiological condition in the living body by a reaction with an enzyme, a gastric acid, or the like, that is, by enzymatic oxidation, reduction, hydrolysis, etc.; by hydrolysis with gastric acid, etc.

Examples of the prodrug of compound (I) and compound (IA) include a compound obtained by subjecting an amino group in compound (I) and compound (IA) to an acylation, alkylation or phosphorylation (e.g., a compound obtained by subjecting an amino group in compound (I) and compound (IA) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) and compound (IA) to an acylation, alkylation, phosphorylation or boration (e.g., a compound obtained by subjecting a hydroxy group in compound (I) and compound (IA) to an acetylation, palmitoylation, propanoylation, pivaloylation, succinylation, fumarylation, alanylation or dimethylaminomethylcarbonylation); a compound obtained by subjecting a carboxyl group in compound (I) and compound (IA) to an esterification or amidation (e.g., a compound obtained by subjecting a carboxyl group in compound (I) and compound (IA) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) and compound (IA) according to a method known per se.

A prodrug for compound (I) and compound (IA) may also be one which is converted to compound (I) and compound (IA) under a physiological condition, such as those described in IYAKUHIN no KAIHATSU, Development of Pharmaceuticals, Vol. 7, Design of Molecules, p. 163-198, Published by HIROKAWA SHOTEN, 1990.

Compounds (I) and (IA) and prodrugs thereof (these are sometimes to be collectively abbreviated as "the compound of the present invention" in the present specification) include stereoisomers such as cis, trans isomer and the like, optically active forms such as racemate, R compound and S compound and the like. Depending on the kind of ring such as ring A and the like, isomers may be produced by conformation, and such isomers are also included in the compound of the present invention.

The compound of the present invention may be labeled with an isotope (e.g., $^2$H, $^3$H, $^{14}$C, $^{35}$S, $^{125}$I) and the like. The compound of the present invention may be hydrate, non-hydrate, solvate or non-solvate.

The compound of the present invention has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid dosage forms; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, red iron oxide).

Preferable examples of the sweetening agent include sodium saccharin, dipotassium glycyrrhizinate, aspartame and stevia.

Examples of the dosage form of the above-mentioned pharmaceutical composition include oral preparations such as tablets (inclusive of sugar-coated tablets, film-coated tablets, sublingual tablets, orally disintegrating tablets), capsules (inclusive of soft capsules, microcapsules), granules, powders, troches, syrups, emulsions, suspensions, films (e.g., orally disintegrable films) and the like; and parenteral agents such as injections (e.g., subcutaneous injections, intravenous injections, intramuscular injections, intraperitoneal injections, drip infusions), external preparations (e.g., dermal preparations, ointments), suppository (e.g., rectal suppositories, vaginal suppositories), pellets, nasal preparations, pulmonary preparations (inhalants), eye drops and the like. These may be safely administered orally or parenterally (e.g., topically, rectally, intravenously administered).

These preparations may be release control preparations (e.g., sustained-release microcapsule) such as immediate-release preparation, sustained-release preparation and the like.

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, diiron trioxide and the like can be used.

The compound of the present invention shows low toxicity (e.g., acute toxicity, chronic toxicity, genetic toxicity, reproductive toxicity, cardiotoxicity, carcinogenicity and the like) and few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior glucagon antagonistic action.

The compound of the present invention can improve the state involving promoted function of glucagon (e.g., excess sugar production from the liver, excess secretion of growth hormone, excess suppression of gastric motility and the like) by, for example, shutting off the action of glucagon. Hence, the compound of the present invention can be useful as a glucagon antagonist, a sugar production-suppressive agent, a prophylactic or therapeutic agent for diseases involving promoted action of glucagon and the like.

Specifically, the compound of the present invention can be used as a prophylactic or therapeutic agent for obesity, diabetes (e.g., type 1 diabetes, type 2 diabetes, gestational diabetes, obese diabetes), hyperlipidemia (e.g., hypertriglyceridemia, hypercholesterolemia, hypoHDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], metabolic syndrome (pathology containing three or more selected from hyper-triglycerid(TG)emia, hypo-HDL cholesterol (HDL-C) emia, hypertension, abdomen obesity and impaired glucose tolerance), sarcopenia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood glucose level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Moreover, the compound of the present invention can also be used as a prophylactic or therapeutic agent for osteoporosis, cachexia (e.g., carcinocachexia, tuberculous cachexia, diabetic cachexia, hemopathic cachexia, endocrinopathic cachexia, infectious cachexia, cachexia in cardiac disease or cachexia induced by acquired immunodeficiency syndrome), fatty liver, polycystic ovary syndrome, renal diseases (e.g., diabetic nephropathy, glomerulonephritis, glomerulosclerosis, nephrosis syndrome, hypertensive nephrosclerosis, end-stage renal disorder), muscular dystrophy, myocardial infarction, angina pectoris, cerebrovascular disorder (e.g., cerebral infarction, cerebral apoplexy), ischemia, coronary heart disease, non-Q wave myocardial infarction (non-Q wave MI), congestive heart failure, ventricular hypertrophy, cardiac arrhythmia, intermittent claudication, peripheral obstructive arterial disease (e.g., peripheral arterial disorder), Alzheimer's disease, Parkinson's disease, anxiety, dementia, insulin resistance syndrome, syndrome X, hyperinsulinemia, perception disorder in hyperinsulinemia, tumor (e.g., leukemia, breast cancer, prostate cancer, skin cancer, epithelial cancer, glandular cancer), irritable bowel syndrome, acute or chronic diarrhea, inflammatory disease (e.g., chronic rheumatoid arthritis, spondylitis deformans, osteoarthritis, lumbago, gout, gouty arthritis, inflammation after operation or trauma, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, gastric mucosa injury (including gastric mucosa injury caused by aspirin), Lyme disease, rubella arthritis, psoriatic arthritis, conjunctivitis, gastritis, chronic thyroiditis, chronic active hepatitis, Crohn's disease, synovitis, ankylosing spondylitis), small intestinal mucosa injury, malabsorption, testis dysfunction, visceral obesity syndrome, sarcopenia, macular degeneration, hypoplastic anemia, thrombocytopenia, multiple sclerosis, periodontal disease, keloid formation, lung sarcoidosis, myasthenia gravis, Reiter's syndrome, influenza, cerebral malaria, silicosis, bone resorption disease, fever, muscular pain, bone diseases related to multiple myeloma, neurodegenerative diseases due to trauma, traumatic brain injury, giantism, graft vs host reaction, transplant rejection, skin condition (e.g., scar tissue formation, eczema, atopic dermatitis, contact dermatitis, urticaria, scleroderma, psoriasis), allergy or respiratory diseases (e.g., asthma, respiratory distress syndrome, hay fever, allergic rhinitis, chronic lung inflammatory disease (e.g., chronic obliterative pulmonary diseases (COPD)), inflammation relating to autoimmune diseases (e.g., systemic lupus erythematosus, Addison's disease, polyglandular deficiency syndrome, Graves' disease, infectious disease (e.g., sepsis, septic shock, Shigellosis, *helicobacter pylori*), viral disease (e.g., simple herpes virus infection, cytomegalovirus infection, Epstein-Barr virus infection, human immunodeficiency virus infection, A-type, B-type and C-type hepatitis virus infection, angiogenetic disease (e.g., solid tumor, ocular neovasculization, Hemangioma, edema, analgesia, pain (e.g., neuromuscular pain, headache, pain caused by cancer or operation, toothache, arthritic pain), irritable bowel syndrome, leukemia, central nervous system diseases (e.g., due to cerebral ischemia, cerebral infarction, brain edema and the like), renal fibrosis, hepatic fibrosis, prostate fibrosis, lung fibrosis and the like.

Moreover, the compound of the present invention can also be used as a gastrointestinal motility function improver.

The compound of the present invention can also be used for secondary prevention and suppression of progression (e.g., secondary prevention and suppression of progression of cardiovascular events such as myocardial infarction and the like) of the above-mentioned various diseases.

While the subject of administration of the compound of the present invention is not particularly limited, a mammal (e.g., mouse, rat, hamster, rabbit, cat, dog, bovine, sheep, monkey, human and the like) is preferable.

While the dose of the compound of the present invention varies depending on the subject of administration, administration route, target disease, symptom and the like, for example, for oral administration to an adult diabetic patient, it is generally about 0.01 to 100 mg/kg body weight, preferably 0.05 to 30 mg/kg body weight, more preferably 0.1 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and they may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agent for diabetes include insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.)], oral insulin preparation), insulin sensitizer (e.g., pioglitazone or a salt thereof (preferably hydrochloride), TAK-379, rosiglitazone or a salt thereof (preferably maleate), tesaglitazar, Ragaglitazar, muraglitazar, edaglitazone, metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose dependency insulin secretagogue (e.g., TAK-875)], dipeptidyl peptidase IV inhibitor (e.g., alogliptin, Vildagliptin, sitagliptin, saxagliptin, T-6666, TS-021), β3 agonist (e.g., AJ-9677), GPR40 agonist, GLP-1 receptor agonist [e.g., GLP-1, GLP-1MR, NN-2211, AC-2993 (exendin-4), BIM-51077, Aib(8,35)hGLP-1 (7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., tolrestat, epalrestat, zenarestat, zopolrestat, minalrestat, fidarestat, CT-112), neurotrophic factor and an increasing drug thereof (e.g., NGF, NT-3, BDNF, neurotrophin production and secretion promoter described in WO01/14372 (e.g., 4-(4-chlorophenyl)-2-(2-methyl-1-imidazolyl)-5-[3-(2-methylphenoxy)propyl]oxazole)), TAK-583, nerve regeneration promoter (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1 (ASK-1) inhibitor and the like.

Examples of the therapeutic agent for hyperlipidemia include statin compound (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol (γ-oryzanol)) and the like.

Examples of the antihypertensive agent include angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, TAK-491), calcium antagonist (e.g., manidipine, nifedipine, amlodipine, efonidipine, nicardipine), potassium channel opener (e.g., levcromakalim, L-27152, AL 0671, NIP-121), clonidine and the like.

Examples of the antiobesity agent include central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), feeding deterrent (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide and furosemide and the like.

Examples of the antithrombotic agent include heparin (e.g., heparin sodium, heparin calcium, dalteparin sodium (dalteparin sodium)), warfarin (e.g., warfarin potassium), anti-thrombin drug (e.g., aragatroban, dabigatran), thrombolytic agent (e.g., urokinase, tisokinase, alteplase, nateplase, monteplase, pamiteplase), platelet aggregation inhibitor (e.g., ticlopidine hydrochloride, cilostazol), ethyl icosapentate, beraprost sodium, sarpogrelate hydrochloride, E5555, SHC 530348, prasugrel), FXa inhibitor (e.g., TAK-442, rivaroxaban, apixaban, DU-176b, YM150) and the like can be mentioned.

The above-mentioned concomitant drug may be a combination of two or more kinds at an appropriate ratio.

The production methods of the compound of the present invention are explained in the following.

The compound of the present invention can be produced according to a method known per se, for example, the methods described in detail in the following, or a method analogous thereto.

In the following production methods, the starting material compounds may be in the form of salts, and examples of such salt include those similar to the salts of compound (I) and compound (IA).

The compound obtained in each step of the following formulas may be used for the next reaction directly in the form of the reaction mixture or a crude product, or can be isolated and purified by known separation and purification means, for example, concentration, concentration under reduced pressure, solvent extraction, crystallization, recrystallization, phase transfer, chromatography and the like and used for the next reaction.

When the compounds of the following formulas are commercially available, such commercially available products may be directly used.

In each of the following reactions, when the starting material compound has an amino group, a carboxy group or a hydroxy group as a substituent, such group may be protected by a protecting group generally used in the peptide chemistry and the like. In this case, the protecting group is removed as necessary after the reaction to give the object compound.

Examples of the amino-protecting group include a formyl group, a $C_{1-6}$ alkyl-carbonyl group, a $C_{3-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting group can be removed according to a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyliodide, trimethylsilyl bromide and the like) and the like, a reduction method and the like are used.

In each of the following reactions, introduction of substituent and functional group conversion reaction may be further performed by applying a method known per se to the starting material, intermediate and/or resultant product.

Examples of the substituent conversion reaction include methods known per se, for example, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, amination of nitro by reduction, alkylation of hydroxy, substitution and amination of hydroxy; alkylation of ring nitrogen atom of nitrogen-containing heterocycle, introduction of substituent to by coupling reaction (e.g., aryl coupling reaction); substitution of halogen by amine, alcohol or thiol; and the like.

Compound (I) can be produced, for example, by a method shown in the following Reaction scheme 1.

Reaction scheme 1

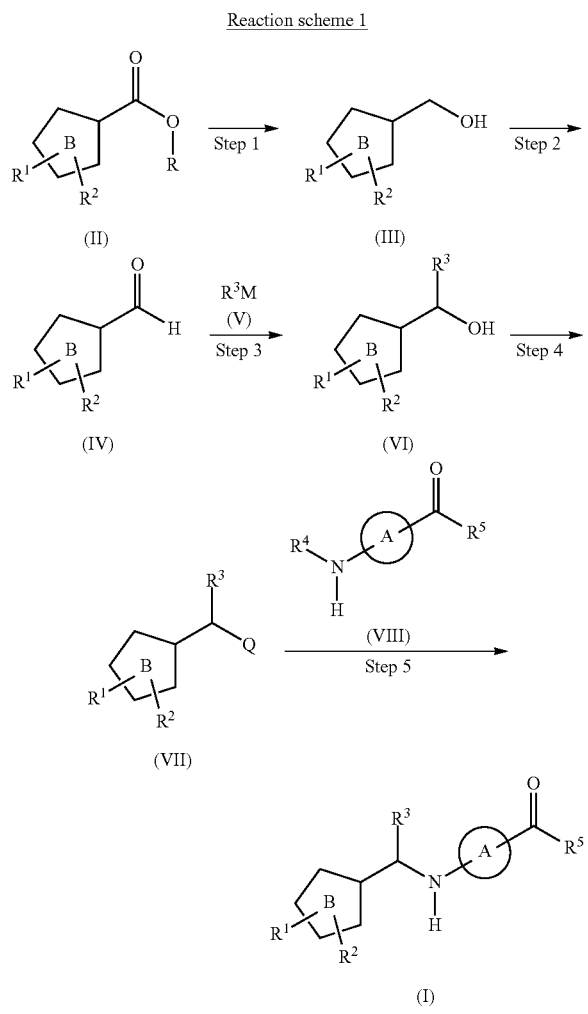

wherein R is a $C_{1-6}$ alkyl group (e.g., methyl, ethyl, n-hexyl); Q is a leaving group (e.g., methanesulfonyloxy group, p-toluenesulfonyloxy group, halogen atom (e.g., chlorine, bromine)); $R^3M$ is an organic metal compound (to be mentioned later), and other symbols are as defined above.

Step 1

Compound (III) can be produced by subjecting starting material compound (II) to a reduction reaction. This reduction reaction can be performed using a reducing agent and according to a conventional method.

Examples of the reducing agent include metal hydrogen compounds such as sodium bis(2-methoxyethoxy)aluminum hydride, diisobutylaluminum hydride (DIBALH) and the like; metal hydrogen complex compounds such as sodium borohydride, sodium cyanoborohydride, lithium aluminum hydride, sodium aluminum hydride and the like and the like.

The amount of the reducing agent to be used is generally 1-20 mol per 1 mol of compound (II).

This reaction is preferably performed in a solvent inert to the reaction. Such solvent is not particularly limited as long as the reaction proceeds and, for example, alcohols such as methanol, ethanol, propanol, isopropanol, butanol, isobutanol, tert-butanol and the like; halogenated hydrocarbons such as dichloromethane, chloroform, carbon tetrachloride, trichloroethylene and the like; aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, dimethoxyethane and the like; mineral acids such as hydrochloric acid, sulfuric acid and the like; organic acids such as formic acid, acetic acid, propionic acid, trifluoroacetic acid, methanesulfonic acid and the like; water; and the like can be mentioned. Two or more kinds of these solvents may be used in a mixture at an appropriate ratio.

The reaction time is generally 10 min-48 hr, preferably 15 min-24 hr.

The reaction temperature is generally −100° C. to 150° C., preferably −20° C. to 100° C.

Compound (II) to be used as a starting material can be synthesized according to a method known per se, for example, the synthesis method described in WO2007/89031, EP94154, WO2003/99793 or EP1176140, or a method analogous thereto.

Step 2 compound (1V) can be produced by subjecting compound (III) to an oxidation reaction. The oxidation reaction can be performed using an oxidant and according to a conventional method.

Examples of the oxidant include active manganese dioxide, pyridinium chlorochromate (PCC), pyridinium dichromate (PDC), Dess-Martin periodinane, dimethyl sulfoxide-acid anhydride (e.g., acetic anhydride, trifluoroacetic anhydride), dimethyl sulfoxide-thionyl chloride, dimethyl sulfoxide-sulfuryl chloride, dimethyl sulfoxide-oxalyl chloride, dimethyl sulfoxide-chlorine, and dimethylsulfoxide-dicyclohexylcarbodiimide (DCC) in the presence of acid (e.g., phosphoric acid, trifluoroacetic acid, dichloroacetic acid) and the like.

The amount of the oxidant to be used is generally 1-20 mol per 1 mol of compound (III).

This reaction is preferably performed in a solvent inert to the reaction. Such solvent is not particularly limited as long as the reaction proceeds and, for example, ethers such as diethyl ether, diisopropyl ether, diphenylether, tetrahydrofuran, 1,4-dioxane, 1,2-dimethoxyethane and the like; ketones such as acetone, methylethyl ketone and the like; halogenated hydrocarbons such as dichloromethane, chloroform, carbon tetrachloride, trichloroethylene and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; mineral acids such as hydrochloric acid, sulfuric acid and the like; organic acids such as formic acid, acetic acid, propionic acid, trifluoroacetic acid, methanesulfonic acid and the like; water; and the like. Two or more kinds of these solvents may be used in a mixture at an appropriate ratio.

The reaction time is generally 10 min-48 hr, preferably 15 min-24 hr.

The reaction temperature is generally −100° C. to 150° C., preferably −20° C. to 100° C.

Step 3

Compound (VI) can be produced by reacting compound (1V) with organic metal compound (V).

This reaction is performed in a solvent inert to the reaction. Such solvent is not particularly limited as long as the reaction proceeds and, for example, ethers such as diethyl ether, tetrahydrofuran, 1,4-dioxane and the like; aliphatic hydrocarbons such as hexane, heptane and the like; aromatic hydrocarbons such as benzene, toluene, xylene and the like; and the like. These solvents may be used in a mixture at an appropriate ratio.

Examples of the organic metal compound (V) include Grignard reagent (e.g., a compound represented by formula: $R^3MgBr$), organic lithium reagent (e.g., a compound represented by formula: $R^3Li$), organic zinc reagent (e.g., a compound represented by formula: $(R^3)_2Zn$), wherein $R^3$ is as defined above) and the like. Such compound can be produced according to a method known per se, for example, the method described in "Jikken Kagaku Kouza (The Chemical Society of Japan ed.), 4th Edition, vol. 25, Synthesis by Organic Metal Reagent" pp. 9-449, Maruzen Press 1992, or a method analogous thereto.

The amount of the organic metal compound (V) to be used is generally about 1-10 mol, preferably about 1-2 mol, per 1 mol of compound (1V).

The reaction temperature is generally −80° C. to 100° C., preferably −20° C. to 50° C.

The reaction time is generally 0.5-20 hr.

Step 4 compound (VII) can be produced by converting the hydroxy group of compound (VI) to a leaving group.

Such conversion to a leaving group can be performed according to a conventional method, for example, by reacting with methanesulfonyl chloride in the presence of an appropriate base, or by reacting with thionyl chloride.

Examples of the base to be used for this reaction include N,N-diisopropylethylamine (DIEA), triethylamine (TEA), pyridine, N,N-dimethylaniline and the like.

The amount of the methanesulfonyl chloride or thionyl chloride to be used is generally about 1-50 mol, preferably about 1-10 mol, per 1 mol of compound (VI).

The amount of the base to be used is generally about 1-50 mol, preferably, about 1-10 mol, per 1 mol of compound (VI).

This reaction is performed in a solvent inert to the reaction. Such solvent is not particularly limited as long as the reaction proceeds and, for example, ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; and the like. These solvents may be used in a mixture at an appropriate ratio.

The reaction temperature is generally −50-150° C., preferably −10-100° C.

The reaction time is generally 0.5-20 hr.

Step 5

Compound (I) can be produced by reacting compound (VII) with compound (VIII) (e.g., ethyl 3-{((4-aminophenyl) carbonyl)amino}propanoate) in the presence of a base. Where necessary, the ester group of the obtained adduct may be hydrolyzed.

Examples of the base to be used for this reaction include alkali metal hydroxides such as lithium hydroxide, sodium hydroxide, potassium hydroxide and the like; alkaline earth is metal hydroxides such as magnesium hydroxide, calcium hydroxide and the like; alkali metal carbonates such as sodium carbonate, potassium carbonate, cesium carbonate and the like; alkali metal hydrogencarbonates such as sodium hydrogen carbonate, potassium hydrogen carbonate and the like; alkali metal alkoxides having 1 to 6 carbon atoms such as sodium methoxide, sodium ethoxide, potassium tert-butoxide and the like; metal hydrides such as sodium hydride, potassium hydride, calcium hydride and the like and the like.

This reaction is preferably performed in a solvent inert to the reaction. Such solvent is not particularly limited as long as the reaction proceeds and, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethylether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; and the like. Two or more kinds of these solvents may be used in a mixture at an appropriate ratio.

In this reaction, 1 equivalent amount to a large excess amount (preferably 1-10 equivalents) of alkali metal iodide such as sodium iodide and the like may be added as a reaction promoter to compound (VII).

The amount of the compound (VIII) to be used is generally about 1-10 mol, preferably about 1-2 mol, per 1 mol of compound (VII).

The amount of the base to be used is generally 1-10 molar equivalents, preferably 1-5 molar equivalents, per 1 mol of compound (VII).

The reaction temperature is generally −30-200° C., preferably 0-150° C.

The reaction time is generally 0.5-20 hr.

The ester group can be hydrolyzed according to a method known per se, for example, the method described in Protective Groups in Organic Synthesis, Third Edition, Wiley-Interscience (1999) or a method analogous thereto.

The production methods of the starting material compounds and reactive derivatives thereof to be used for the above-mentioned methods are explained in the following.

Compound (VIII) can be produced according to, for example, the following Reaction scheme 2.

Reaction scheme 2

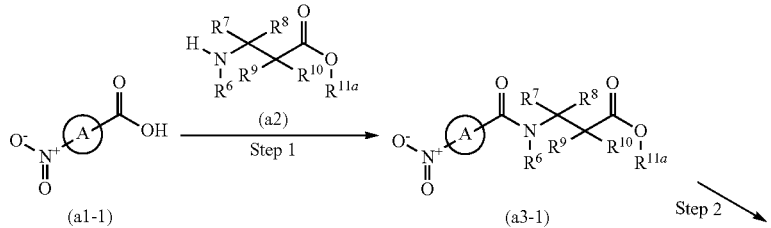

-continued

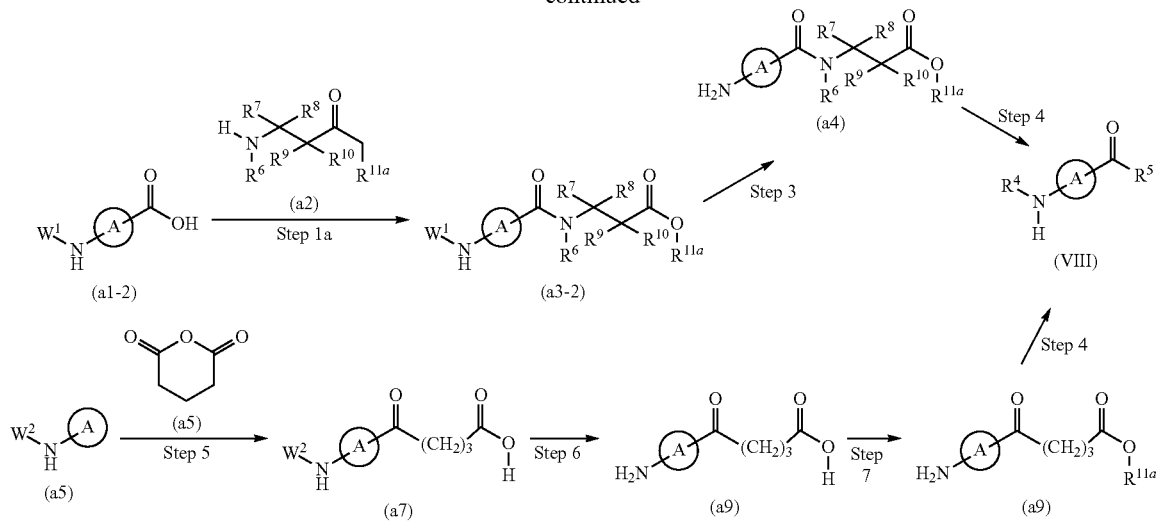

wherein $W^1$ and $W^2$ are each independently an amino-protecting group, $R^{11a}$ is a $C_{1-6}$ alkyl group, and other symbols are as defined above.

Step 1

In this reaction, compound (a1-1) is condensed with compound (a2) to give compound (a3-1).

The condensation reaction can be performed according to a conventional method, for example, a general peptide coupling method. Examples of the method include a method including direct condensation of compound (a1-1) and compound (a2) using a condensation agent, a method including reaction of a reactive derivative of compound (a1-1) with compound (a2) and the like.

Examples of the condensation agent include carbodiimide condensation reagents such as dicyclohexylcarbodiimide (DCC), diisopropylcarbodiimide (DIPC), 1-ethyl-3-(3-dimethylaminopropyl)carbodiimide (EDC), hydrochloride thereof and the like; phosphoric acid condensation reagents such as diethyl cyanophosphate, diphenylphosphoryl azide and the like; carbonyldiimidazole, 2-chloro-1,3-dimethylimidazolium tetrafluoroborate, 2-(7-aza-1H-benzotriazol-1-yl)-1,1,3,3-tetramethyluronium hexafluorophosphate (HATU) and the like.

Examples of the solvent to be used for the condensation reaction include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water; and the like. These solvents may be used in a mixture at an appropriate ratio.

The amount of the compound (a2) to be used is generally 1-10 mol, preferably 1-3 mol, per 1 mol of compound (a1-1).

The amount of the condensation agent to be used is generally 0.1-10 mol, preferably 0.3-3 mol, per 1 mol of compound (a1-1).

When a carbodiimide condensation reagent is used as the condensation agent, the reaction efficiency can be improved by using a suitable condensation promoter (e.g., 1-hydroxy-7-azabenzotriazole, 1-hydroxybenzotriazole, N-hydroxysuccinimide, N-hydroxyphthalimide) as necessary.

When HATU or phosphoric acid condensation reagent is used as the condensation agent, the reaction efficiency can be improved by using an organic amine base such as triethylamine, N,N-diisopropylethylamine and the like.

The amount of the condensation promoter or organic amine base to be used is generally 0.1-10 mol, preferably 0.3-3 mol, per 1 mol of compound (a1-1), respectively.

The reaction temperature is generally −30-120° C., preferably −10-100° C.

The reaction time is generally 0.5-60 hr.

Examples of the reactive derivative of compound (a1-1) include acid halide (e.g., acid chloride, acid bromide), imidazolide, mixed acid anhydride (e.g., anhydride with methyl carbonate, ethyl carbonate or isobutyl carbonate) and the like.

For example, when an acid halide is used, the reaction is generally performed in the presence of a base, and in a solvent that does not adversely influence the reaction.

Examples of the base include amines such as triethylamine, pyridine, N-methylmorpholine, N,N-dimethylaniline, 4-dimethylaminopyridine and the like; alkali metal salt such as lithium hydroxide, sodium hydroxide, potassium hydroxide, sodium hydrogen carbonate, sodium carbonate, potassium carbonate and the like; and the like.

Examples of the solvent that does not adversely influence the reaction include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water; and the like can be mentioned. These solvents may be used in a mixture at an appropriate ratio.

When the above-mentioned amide is used as the solvent, the reaction can also be performed in the absence of a base.

The amount of the compound (a2) to be used is generally 1-10 mol, preferably 1-5 mol, per 1 mol of acid halide of compound (a1-1).

The amount of the base to be used is generally 1-10 mol, preferably 1-5 mol, per 1 mol of acid halide of compound (a1-1).

The reaction temperature is generally −30° C.-120° C., preferably −10-100° C.

The reaction time is generally 0.5-30 hr.

When mixed acid anhydride is used, compound (a1-1) is reacted with chlorocarbonate (e.g., methyl chlorocarbonate, ethyl chlorocarbonate, isobutyl chlorocarbonate) in the presence of a base and then reacted with compound (a2).

Examples of the base to be used for this reaction include the aforementioned, those exemplified as the base to be used for the reaction of a acid halide of compound (a1-1) with compound (a2) and the like.

The amount of the compound (a2) to be used is generally 1-10 mol, preferably 1-5 mol, per 1 mol of compound (a1-1).

The amount of the chlorocarbonate to be used is generally 1-10 mol, preferably 1-5 mol, per 1 mol of compound (a1-1).

The amount of the base to be used is generally 1-10 mol, preferably 1-3 mol, per 1 mol of compound (a1-1).

The reaction temperature is generally −30° C.-120° C., preferably −10-100° C.

The reaction time is generally 0.5-20 hr.

When imidazolide is used, compound (a1-1) is reacted with, for example, N,N'-carbonyldiimidazole (CDI) to give the corresponding imidazolide, which is further reacted with compound (a2).

The amount of the compound (a2) to be used is generally 1-10 mol, preferably 1-5 mol, per 1 mol of compound (a1-1).

The amount of N,N'-carbonyldiimidazole (CDI) to be used is generally 1-10 mol, preferably 1-5 mol, per 1 mol of compound (a1-1).

The reaction temperature is generally −30° C.-120° C., preferably −10-100° C.

The reaction time is generally 0.5-20 hr.

As compound (a1-1) and compound (a2), commercially available products are available, or can be produced using a commercially available compound according to a method known per se or a method analogous thereto.

Step 1a

Compound (a3-2) can be produced in the same manner as in step 1 and using compound (a1-2) and compound (a2).

As compound (a1-2), a commercially available product can be used, or can be produced using a commercially available compound according to a method known per se or a method analogous thereto.

Step 2

Compound (a4) can be produced by subjecting compound (a3-1) to a reduction reaction in the presence of a metal catalyst and a hydrogen source. Such reduction reaction can be performed according to a conventional method in a solvent that does not adversely influence the reaction.

Examples of the metal catalyst to be used for this reaction include palladium-carbon, palladium black, palladium chloride, platinum oxide, platinum black, platinum-palladium, Raney-nickel, Raney cobalt and the like.

Examples of the hydrogen source include hydrogen gas, formic acid, formic acid amine salt, phosphinate salt, hydrazine and the like.

Examples of the solvent that does not adversely influence the reaction include methanol, tetrahydrofuran, N,N-dimethylacetamide and the like.

The amount of the metal catalyst to be used is generally 0.001-1000 mol, preferably 0.01-100 mol, per 1 mol of compound (a3-1).

The reaction temperature is generally −70-150° C., preferably −20-100° C.

The reaction time is generally 0.1-100 hr, preferably 0.1-40 hr.

This reaction can also be performed in the presence of a reducing agent in a solvent that does not adversely influence the reaction.

Examples of the reducing agent include ferric oxide, zinc, tin and the like, and compound (a4) can be produced by the reaction described in "Jikken Kagaku Kouza (The Chemical Society of Japan ed.), 4th Edition, vol. 20, Organic Synthesis II Alcohol and Amine" pp. 279-280, Maruzen Press 1992, or a method analogous thereto.

Step 3

Compound (a4) can be produced by removing the protecting group ($W^1$) of compound (a3-2) by a method known per se, for example, the method described in Protective Groups in Organic Synthesis, Third Edition, Wiley-Interscience (1999) or a method analogous thereto.

Step 4

Compound (VIII) can be produced by subjecting compound (a4) or compound (a9) to a reductive amination reaction.

The reductive amination reaction can be performed by a method known per se, for example, the method described in "Jikken Kagaku Kouza (The Chemical Society of Japan ed.), 4th Edition, vol. 20. Organic Synthesis II Alcohol and Amine" pp. 300-302, Maruzen Press 1992; the method described in Reductions in Organic Chemistry Second Edition, American Chemical Society (1996), pp. 187-189; or a method analogous thereto.

Step 5

Compound (a7) can be synthesized by Friedel-Crafts reaction using compound (a5) and glutaric anhydride (a6) and by the synthesis method described in, for example, WO2004/45616, or a method analogous thereto.

Step 6

Compound (a8) can be produced by removing the protecting group of compound (a7) by a method known per se, for example, the method described in Protective Groups in Organic Synthesis, Third Edition, Wiley-Interscience (1999) or a method analogous thereto.

Step 7

Compound (a9) can be produced by esterification of compound (a8) by a method known per se, for example, the method described in Protective Groups in Organic Synthesis, Third Edition, Wiley-Interscience (1999) or a method analogous thereto.

Compound (IA) can be produced, for example, by the method shown in the following Reaction scheme A1.

In the following Reaction scheme A1, compound (BIa) includes a compound (IA) wherein $R^{411}$ is $C_{1-6}$ alkyl group, and compound (BIb) includes a compound (IA) wherein $R^{411}$ is a hydrogen atom.

Reaction scheme A1

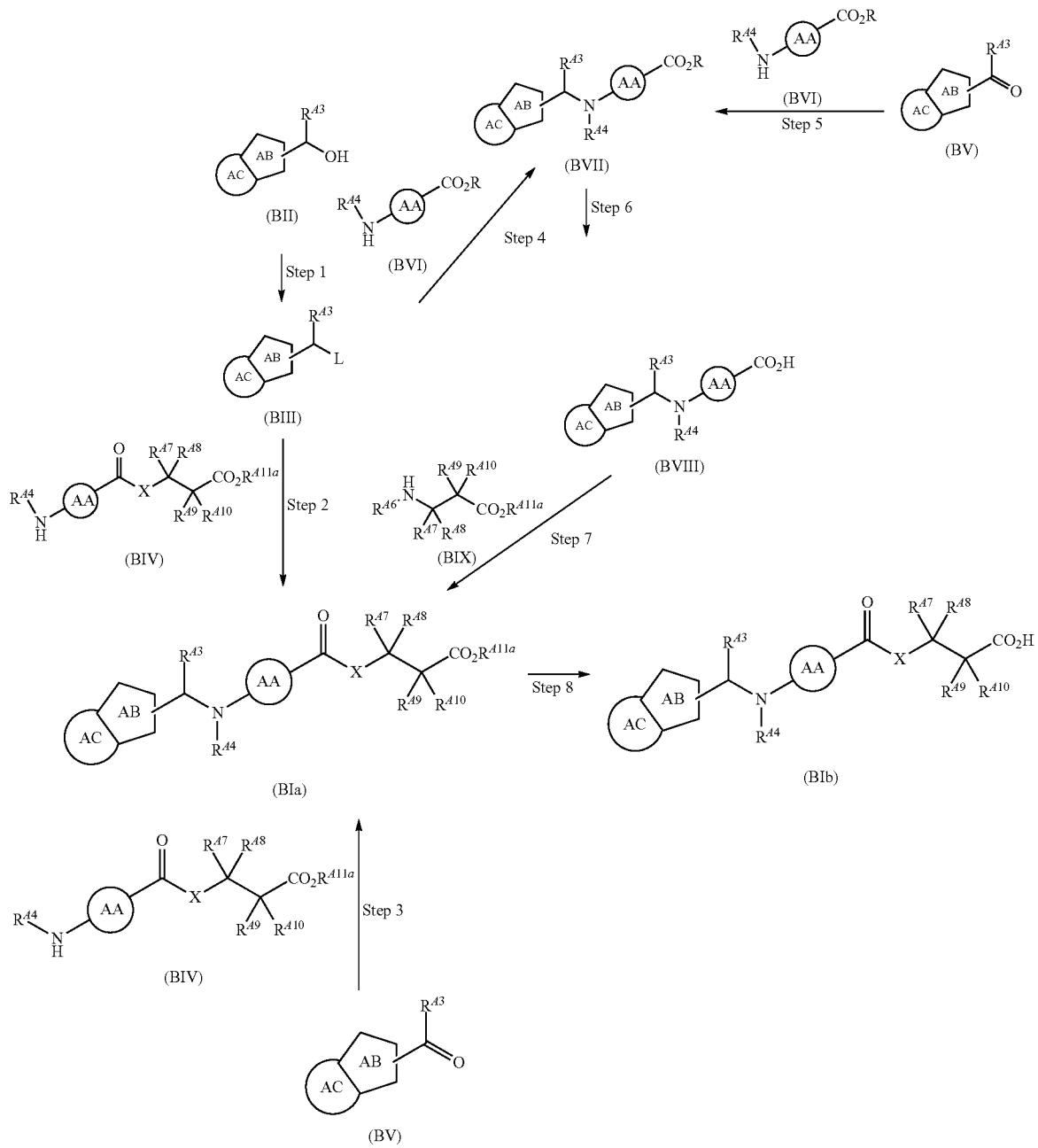

wherein X is $CH_2$ or $NR^{A6}$, $R^{A11a}$ is a $C_{1-6}$ alkyl group, L is a leaving group (e.g., methanesulfonyloxy group, p-toluenesulfonyloxy group, halogen atom (e.g., chlorine, bromine)), and other symbols are each as defined above.

Step 1

Compound (BIII) can be produced, for example, by converting the hydroxy group of compound (BII) to a leaving group. Such conversion to a leaving group can be performed according to a conventional method, for example, reaction with methanesulfonylchloride, phosphoryl chloride or thionyl chloride in the presence of an appropriate base.

Examples of the base include N,N-diisopropylethylamine (DIEA), triethylamine (TEA), pyridine, N,N-dimethylaniline and the like.

The amount of the base to be used is generally 1-10 mol, preferably 1-5 mol, per 1 mol of compound (BII).

The amount of the methanesulfonylchloride, phosphoryl chloride or thionyl chloride to be used is generally 1-10 mol, preferably 1-5 mol, per 1 mol of compound (BII).

This reaction can be performed in a solvent inert to the reaction. Such solvent is not particularly limited as long as the reaction proceeds and, for example, ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; and the like can be mentioned. These solvents may be used in a mixture at an appropriate ratio.

The reaction temperature is generally −80-200° C., preferably −10-150° C.

The reaction time is generally 10 min-20 hr, preferably 15 min-24 hr.

compound (BII) can be produced by the below-mentioned reaction.

Step 2

Compound (BIa) can be produced, for example, by reacting compound (BIII) with compound (BIV) in the presence of a base.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogencarbonates such as sodium hydrogen carbonate, potassium hydrogen carbonate and the like; alkali metal alkoxides having 1 to 6 carbon atoms such as sodium methoxide, sodium ethoxide, potassium tert-butoxide and the like; metal hydrides such as sodium hydride, potassium hydride, calcium hydride and the like; and the like.

The amount of the base to be used is generally 1-10 mol, preferably 1-5 mol, per 1 mol of compound (BIII).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethylether and the like; esters such as ethyl formate, ethyl acetate, isopropyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; and the like can be mentioned. Two or more kinds of these solvents may be used in a mixture at an appropriate ratio.

In this reaction, alkali metal iodide such as sodium iodide, potassium iodide and the like may be added as a reaction promoter, in a proportion of generally 1-20 mol, preferably 1-10 mol, per 1 mol of compound (BIII).

The amount of the compound (BIV) to be used is generally 1-10 mol, preferably 1-3 mol, per 1 mol of compound (BIII).

The reaction temperature is generally −80° C.-200° C., preferably 0° C.-150° C.

The reaction time is generally 10 min-48 hr, preferably 15 min-24 hr.

The compound (BIV) can be produced by the below-mentioned reaction.

Step 3 compound (BIa) can be produced by a method known per se, for example, the method described in Reductions in Organic Chemistry Second Edition, American Chemical Society (1996), pp. 187-189; Journal of Chemical Society Perkin Transactions 1, (2000), pp. 145-146 and the like, or a method analogous thereto, by subjecting compound (BV) and compound (BIV) to reductive amination reaction.

Compound (BV) can be produced by the below-mentioned reaction.

Step 4

Compound (BVII) can be produced, for example, by reacting compound (BIII) with compound (BVI) in the presence of a base according to the production method of compound (BIa) from compound (BIII).

As compound (BVI), a commercially available product can be used, or it can be produced from a commercially available compound by a method known per se or a method analogous thereto.

Step 5

Compound (BVII) can be produced by subjecting compound (BV) and compound (BVI) to a reductive amination reaction according to the production method of, for example, compound (BIa) from compound (BV).

Step 6

Compound (BVIII) can be produced by hydrolysis of the ester of compound (BVII) by a method known per se, for example, the method described in Protective Groups in Organic Synthesis, Third Edition, Wiley-Interscience (1999) or a method analogous thereto.

Step 7

Compound (BIa) can be produced by, for example, condensing compound (BVIII) and compound (BIX).

The condensation reaction can be performed according to a conventional method, for example, a general peptide coupling method. Examples of such method include a method including directly condensing compound (BVIII) and compound (BIX) using a condensation agent, or a method including reacting a reactive derivative of compound (BVIII) with compound (BIX) and the like.

Examples of the condensation agent include carbodiimide condensation reagents such as dicyclohexylcarbodiimide (DCC), diisopropylcarbodiimide (DIPC), 1-ethyl-3-(3-dimethylaminopropyl)carbodiimide (EDC) and hydrochloride thereof and the like; phosphoric acid condensation reagents such as diethyl cyanophosphate, diphenylphosphoryl azide and the like; carbonyldiimidazole, 2-chloro-1,3-dimethylimidazolium tetrafluoroborate, O-(7-azabenzotriazol-1-yl)-1,1,3,3-tetramethyluronium hexafluorophosphate (HATU) and the like.

Examples of the solvent to be used for direct condensation using a condensation agent include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aliphatic hydrocarbons such as hexane, heptane and the like; aromatic hydrocarbons such as benzene, toluene and the like; ethers such as tetrahydrofuran, dioxane, diethyl ether, dimethoxyethane, tert-butyl methyl ether and the like; esters such as methyl acetate, ethyl acetate, isopropyl acetate, n-butyl acetate and the like; nitriles such as acetonitrile, propionitrile and the like; water; and the like. Two or more kinds of these solvents may be used in a mixture at an appropriate ratio.

The amount of the condensation agent to be used is generally 1-10 mol, preferably 1-5 mol, per 1 mol of compound (BVIII).

When carbodiimide condensation reagent is used as the condensation agent, the reaction efficiency can be improved by the use of a suitable condensation promoter (e.g., 1-hydroxy-7-azabenzotriazole, 1-hydroxybenzotriazole, N-hydroxysuccinimide, N-hydroxyphthalimide) as necessary.

When HATU or phosphoric acid condensation reagent is used as the condensation agent, the reaction efficiency can be improved by the use of an organic amine base such as triethylamine, N,N-diisopropylethylamine and the like.

The amount of the condensation promoter or organic amine base to be used is generally 1-10 mol, preferably 1-5 mol, per 1 mol of compound (BVIII), respectively.

The amount of the compound (BIX) to be used is generally 1-10 mol, preferably 1-5 mol, per 1 mol of compound (BVIII).

The reaction time is generally 10 min-60 hr, preferably 15 min-24 hr.

The reaction temperature is generally −50-150° C., preferably −10-100° C.

Examples of the reactive derivative of compound (BVIII) include acid halide (e.g., acid chloride, acid bromide), imidazolide, mixed acid anhydride (e.g., anhydrides with methyl carbonate, ethyl carbonate, isobutyl carbonate and the like) and the like.

When an acid halide is used as a reactive derivative of compound (BVIII), the reaction is generally performed in the presence of a base in a solvent inert to the reaction.

Examples of the base include amines such as triethylamine, N,N-diisopropylethylamine, N-methylmorpholine, N,N-dimethylaniline, 4-dimethylaminopyridine and the like; alkali metal salts such as lithium hydroxide, sodium hydroxide, potassium hydroxide, sodium hydrogen carbonate, sodium carbonate, potassium carbonate and the like; and the like.

The amount of the base to be used is generally 1-10 mol, preferably 1-5 mol, per 1 mol of acid halide of compound (BVIII).

Examples of the solvent to be used for this reaction include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aliphatic hydrocarbons such as hexane, heptane and the like; aromatic hydrocarbons such as benzene, toluene and the like; ethers such as tetrahydrofuran, dioxane, diethyl ether, dimethoxyethane, tert-butyl methyl ether and the like; esters such as methyl acetate, ethyl acetate, isopropyl acetate, n-butyl acetate and the like; nitriles such as acetonitrile, propionitrile and the like; water; and the like. These solvents may be used in a mixture at an appropriate ratio. When the above-mentioned amide is used as a solvent inert to the reaction, the reaction can also be performed in the absence of a base.

The amount of the compound (BIX) to be used is generally 1-10 mol, preferably 1-5 mol, per 1 mol of acid halide of compound (BVIII).

The reaction temperature is generally −30° C.-150° C., preferably −10-100° C.

The reaction time is generally 10 min-48 hr, preferably 15 min-24 hr.

When mixed acid anhydride is used as a reactive derivative of compound (BVIII), compound (BVIII) is reacted with chlorocarbonate (e.g., methyl chlorocarbonate, ethyl chlorocarbonate, isobutyl chlorocarbonate) in the presence of a base and then reacted with compound (BIX).

Examples of the base to be used for this reaction include those exemplified as the base to be used for the aforementioned reaction of acid halide of compound (BVIII) with compound (BIX).

The amount of the chlorocarbonate to be used is generally 1-10 mol, preferably 1-5 mol, per 1 mol of compound (BVIII).

The amount of the base to be used is generally 1-10 mol, preferably 1-5 mol, per 1 mol of compound (BVIII).

The amount of the compound (BIX) to be used is generally 1-10 mol, preferably 1-5 mol, per 1 mol of compound (BVIII).

The reaction temperature is generally −30° C.-120° C., preferably −10-100° C.

The reaction time is generally 10 min-48 hr, preferably 15 min-24 hr.

As compound (BIX), a commercially available product can be used, or it can be produced from a commercially available compound by a method known per se or a method analogous thereto.

Step 8

Compound (BIb) can be produced, for example, by hydrolyzing the ester of compound (BIa) according to the production method of compound (BVIII).

Compound (BII) and compound (BV) which are starting material compounds of Reaction scheme A1 can be produced, for example, by the method shown in the following Reaction scheme A2.

Reaction scheme A2

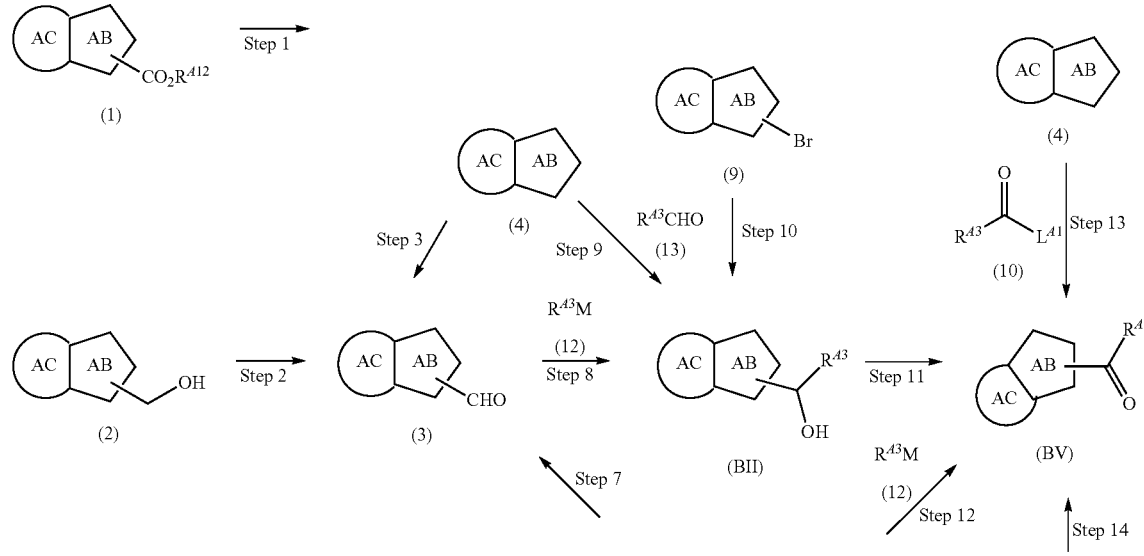

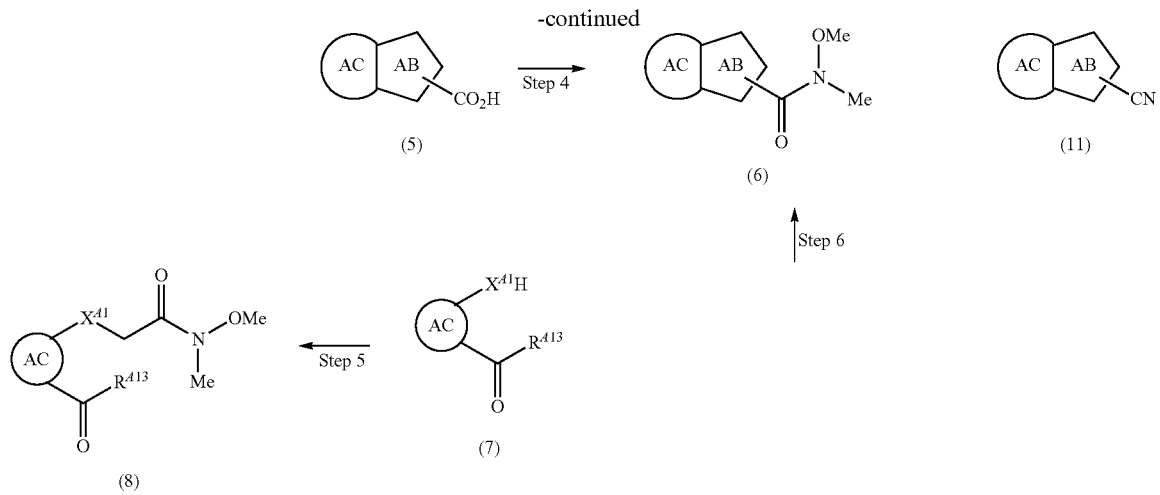

wherein $X^{A1}$ is $NR^{A14}$, O, or S; $R^{A12}$ is a $C_{1-6}$ alkyl group; $R^{A13}$ and $R^{A14}$ are each independently a hydrogen atom, or a substituent that the aforementioned ring AB optionally has; $R^{A13}M$ is an organic metal compound (to be mentioned later); $L^{A1}$ is a leaving group (e.g., halogen atom such as chlorine, bromine and the like), and other symbols are as defined above.

Step 1

Compound (2) can be produced by subjecting compound (I) to a reduction reaction. Reduction reaction can be performed according to a conventional method using a reducing agent.

Examples of the reducing agent include metal hydrogen compounds such as sodium bis(2-methoxyethoxy)aluminum hydride, diisobutylaluminum hydride (DIBALH) and the like; metal hydrogen complex compounds such as sodium borohydride, sodium cyanoborohydride, lithium aluminum hydride, sodium aluminum hydride, calcium borohydride and the like; and the like.

The amount of the reducing agent to be used is generally 1-20 mol, preferably 1-10 mol, per 1 mol of compound (I).

This reaction is preferably performed in a solvent inert to the reaction. Such solvent is not particularly limited as long as the reaction proceeds and, for example, alcohols such as methanol, ethanol, propanol, isopropanol, butanol, isobutanol, tert-butanol and the like; halogenated hydrocarbons such as dichloromethane, chloroform, carbon tetrachloride, trichloroethylene and the like; aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, dimethoxyethane and the like; water; and the like can be mentioned. Two or more kinds of these solvents may be used in a mixture at an appropriate ratio.

The reaction time is generally 10 min-48 hr, preferably 15 min-24 hr.

The reaction temperature is generally −100° C.-150° C., preferably −20° C.-100° C.

As compound (I), a commercially available product can be used, or it can be produced from a commercially available compound by a method known per se or a method analogous thereto.

Step 2

Compound (3) can be produced, for example, by subjecting compound (2) to an oxidation reaction. The oxidation reaction can be performed according to a conventional method and using an oxidant.

Examples of the oxidant include active manganese dioxide, pyridinium chlorochromate (PCC), pyridinium dichromate (PDC), Dess-Martin periodinane, dimethyl sulfoxide-acid anhydride (e.g., acetic anhydride, trifluoroacetic anhydride), dimethyl sulfoxide-thionyl chloride, dimethyl sulfoxide-sulfuryl chloride, dimethyl sulfoxide-oxalyl chloride, dimethyl sulfoxide-chlorine, and dimethyl sulfoxide-dicyclohexylcarbodiimide (DCC) in the presence of acid (e.g., phosphoric acid, trifluoroacetic acid, dichloroacetic acid) and the like.

The amount of the oxidant to be used is generally 1-100 mol, preferably 1-50 mol, per 1 mol of compound (2).

This reaction is preferably performed in a solvent inert to the reaction. Such solvent is not particularly limited as long as the reaction proceeds and, for example, ethers such as diethyl ether, diisopropyl ether, diphenylether, tetrahydrofuran, 1,4-dioxane, 1,2-dimethoxyethane, tert-butylmethylether and the like; ketones such as acetone, methylethyl ketone and the like; halogenated hydrocarbons such as dichloromethane, chloroform, carbon tetrachloride, trichloroethylene and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; mineral acids such as hydrochloric acid, sulfuric acid and the like; organic acids such as formic acid, acetic acid, propionic acid, trifluoroacetic acid, methanesulfonic acid and the like, water; and the like can be mentioned. Two or more kinds of these solvents may be used in a mixture at an appropriate ratio.

The reaction time is generally 10 min-48 hr, preferably 15 min-24 hr.

The reaction temperature is generally −100-150° C., preferably −20-100° C.

Step 3

Compound (3) can be produced by, for example, treating compound (4) with a base and reacting the compound with a formylation agent.

Examples of the base to be used for this reaction include, organic lithium compounds such as n-butyllithium, sec-butyllithium, tert-butyllithium and the like, and alkali amides such as lithium diisopropylamide, lithium tris(trimethylsilyl)amide and the like.

The amount of the base to be used is generally 1-10 mol, preferably 1-5 mol, per 1 mol of compound (4).

Examples of the formylation agent include N,N-dimethylformamide, N-formylpiperidine, ethyl orthoformate and the like.

The amount of the formylation agent to be used is generally 1-10 mol, preferably 1-5 mol, per 1 mol of compound (4).

This reaction is preferably performed in a solvent inert to the reaction. Such solvent is not particularly limited as long as the reaction proceeds and, for example, ethers such as 1,4-dioxane, tetrahydrofuran, diethyl ether, tert-butyl methyl ether, diisopropyl ether, ethylene glycol dimethylether and the like; hydrocarbons such as n-hexane, n-pentane and the like; and the like can be mentioned. Two or more kinds of these solvents may be used in a mixture at an appropriate ratio.

The reaction time is generally 10 min-48 hr, preferably 15 min-24 hr.

The reaction temperature is generally −100-100° C., preferably −80-50° C.

As compound (4), a commercially available product can be used, or it can be produced from a commercially available compound by a method known per se or a method analogous thereto.

Step 4 compound (6) can be produced by condensing compound (5) and N,O-dimethylhydroxylamine according to the production method of, for example, compound (BIa) from compound (BVIII).

As compound (5), a commercially available product can be used, or it can be produced from a commercially available compound by a method known per se or a method analogous thereto.

Step 5

Compound (8) can be produced by reacting, for example, compound (7) with 2-chloro-N-methoxy-N-methylacetamide in the presence of a base according to the production method of compound (BIa) from compound (BIII).

As compound (7), a commercially available product can be used, or it can be produced from a commercially available compound by a method known per se or a method analogous thereto.

Step 6

Compound (6) can be produced, for example, by reacting compound (8) with a base.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogencarbonates such as sodium hydrogen carbonate, potassium hydrogen carbonate and the like; alkali metal alkoxides having 1 to 6 carbon atoms such as sodium methoxide, sodium ethoxide, potassium tert-butoxide and the like; metal hydrides such as sodium hydride, potassium hydride, calcium hydride and the like; organic bases such as 1,8-diazabicyclo[5.4.0]undec-7-ene (DBU), 1,5-diazabicyclo[4.3.0]non-5-ene (DBN), 1,4-diazabicyclo[2.2.2]octane (DABCO) and the like; and the like.

The amount of the base to be used is generally 1-10 mol, preferably 1-5 mol, per 1 mol of compound (8).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethylether and the like; esters such as ethyl formate, ethyl acetate, isopropyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; and the like can be mentioned. Two or more kinds of these solvents may be used in a mixture at an appropriate ratio.

The reaction temperature is generally −80° C.-200° C., preferably 0° C.-150° C.

The reaction time is generally 10 min-48 hr, preferably 15 min-24 hr.

Step 7

Compound (3) can be produced by subjecting, for example, compound (6) to a reduction reaction according to the production method of compound (2).

Step 8 compound (BII) can be produced by reacting, for example, compound (3) with organic metal compound (12).

Examples of the organic metal compound (12) include Grignard reagent (e.g., a compound represented by formula: $R^3MgBr$), organic lithium reagent (e.g., a compound represented by formula: $R^3Li$), organic zinc reagent (e.g., a compound represented by formula: $(R^3)_2Zn$), wherein $R^3$ is as defined above, and the like.

Such organic metal compound can be produced by a method known per se, for example, the method described in "Jikken Kagaku Kouza (The Chemical Society of Japan ed.), 4th Edition, vol. 25, Synthesis by Organic Metal Reagent" pp. 9-449, Maruzen Press 1992, or a method analogous thereto.

The amount of the organic metal compound (12) to be used is generally 1-10 mol, preferably 1-5 mol, per 1 mol of compound (3).

This reaction is performed in a solvent inert to the reaction. Such solvent is not particularly limited as long as the reaction proceeds and, for example, ethers such as diethyl ether, tetrahydrofuran, 1,4-dioxane and the like; aliphatic hydrocarbons such as hexane, heptane and the like; aromatic hydrocarbons such as benzene, toluene, xylene and the like; and the like can be mentioned. Two or more kinds of these solvents may be used in a mixture at an appropriate ratio.

The reaction time is generally 10 min-48 hr, preferably 15 min-24 hr.

The reaction temperature is generally −100-200° C., preferably −80-150° C.

Step 9

Compound (BII) can be produced by, for example, treating compound (4) with a base, and reacting the compound with compound (13).

Examples of the base include those similar to the base described in step 3.

The amount of the base and compound (13) to be used is each generally 1-10 mol, preferably 1-5 mol, per 1 mol of compound (4).

This reaction is preferably performed in a solvent inert to the reaction. Examples of the solvent include those similar to the solvent described in step 3.

The reaction time is generally 10 min-48 hr, preferably 15 min-24 hr.

The reaction temperature is generally −100-100° C., preferably −80-50° C.

As compound (13), a commercially available product can be used, or it can be produced from a commercially available compound by a method known per se or a method analogous thereto.

Step 10

Compound (BII) can be produced by treating, for example, compound (9) with a base, and then reacting the compound with compound (13).

Examples of the base include organic lithium compounds to such as n-butyllithium, sec-butyllithium, tert-butyllithium and the like.

The amount of the base and compound (13) to be used is each generally 1-10 mol, preferably 1-5 mol, per 1 mol of compound (9).

This reaction is preferably performed in a solvent inert to the reaction. Such solvent is not particularly limited as long as the reaction proceeds and, for example, ethers such as 1,4-dioxane, tetrahydrofuran, diethyl ether, tert-butyl methyl ether, diisopropyl ether, ethylene glycol dimethylether and the like; hydrocarbons such as n-hexane, n-pentane and the like; and the like can be mentioned. Two or more kinds of these solvents may be used in a mixture at an appropriate ratio.

The reaction time is generally 10 min-48 hr, preferably 15 min-24 hr.

The reaction temperature is generally −100-100° C., preferably −80-50° C.

As compound (9), a commercially available product can be used, or it can be produced from a commercially available compound by a method known per se or a method analogous thereto.

Step 11

Compound (BV) can be produced, for example, by subjecting compound (BII) to an oxidation reaction according to step 2.

Step 12

Compound (BV) can be produced by reacting compound (6) with organic metal compound (12) according to, for example, step 8.

Step 13

Compound (BV) can be produced by Friedel-Crafts reaction of compound (4) and compound (10)

While this reaction is preferably performed by addition of an acid catalyst, where necessary, it may be performed without addition of an acid catalyst.

Examples of the acid catalyst to be used for the reaction include mineral acids such as sulfuric acid, anhydrous phosphoric acid, polyphosphoric acid and the like, Lewis acids such as aluminum chloride, tin tetrachloride, titanium tetrachloride, boron trifluoride, triethylaluminum, diethylaluminum chloride, zinc chloride and the like, and the like. Preferably, polyphosphoric acid, aluminum chloride, diethylaluminum chloride, zinc chloride and the like are used as acid catalysts.

An acid catalyst can be used in any equivalent amount, generally 0.1-50 mol, preferably 1-20 mol, per 1 mol of compound (4). In some cases, an acid catalyst can also be used as a solvent.

The amount of the compound (10) to be used is generally 1-20 mol, preferably 1-10 mol, per 1 mol of compound (4).

This reaction can be performed without solvent, or after dissolving or suspending in a solvent inert to the reaction. Such solvent is not particularly limited as long as the reaction proceeds and, for example, hydrocarbons such as n-hexane, benzene, toluene and the like; ethers such as 1,4-dioxane, tetrahydrofuran, diethyl ether, dimethoxyethane, tert-butyl methyl ether, diisopropyl ether, ethylene glycol dimethylether, 1,2-dichloroethane and the like; halogenated hydrocarbons such as dichloromethane, chloroform, carbon tetrachloride, trichloroethylene and the like; nitrohydrocarbons such as nitromethane, nitrobenzene and the like; nitriles such as acetonitrile, propionitrile and the like; amides such as formamide, N,N-dimethylformamide, N,N-dimethylacetamide and the like; sulfoxides such as dimethyl sulfoxide and the like; sulfolane; hexamethylphosphoramide; carbon disulfide; and the like can be mentioned. Two or more kinds of these solvents may be used in a mixture at an appropriate ratio.

The reaction time is generally 10 min-48 hr, preferably 15 min-24 hr.

The reaction temperature is generally −100-300° C., preferably 0-200° C.

As compound (10), a commercially available product can be used, or it can be produced from a commercially available compound by a method known per se or a method analogous thereto.

Step 14

Compound (BV) can be produced, for example, by reacting compound (11) with an organic metal reagent according to step 8.

As compound (11), a commercially available product can be used, or it can be produced from a commercially available compound by a method known per se or a method analogous thereto.

compound (BIV) which is a starting material compound in Reaction scheme A1 can be produced, for example, by a method shown in the following Reaction scheme A3.

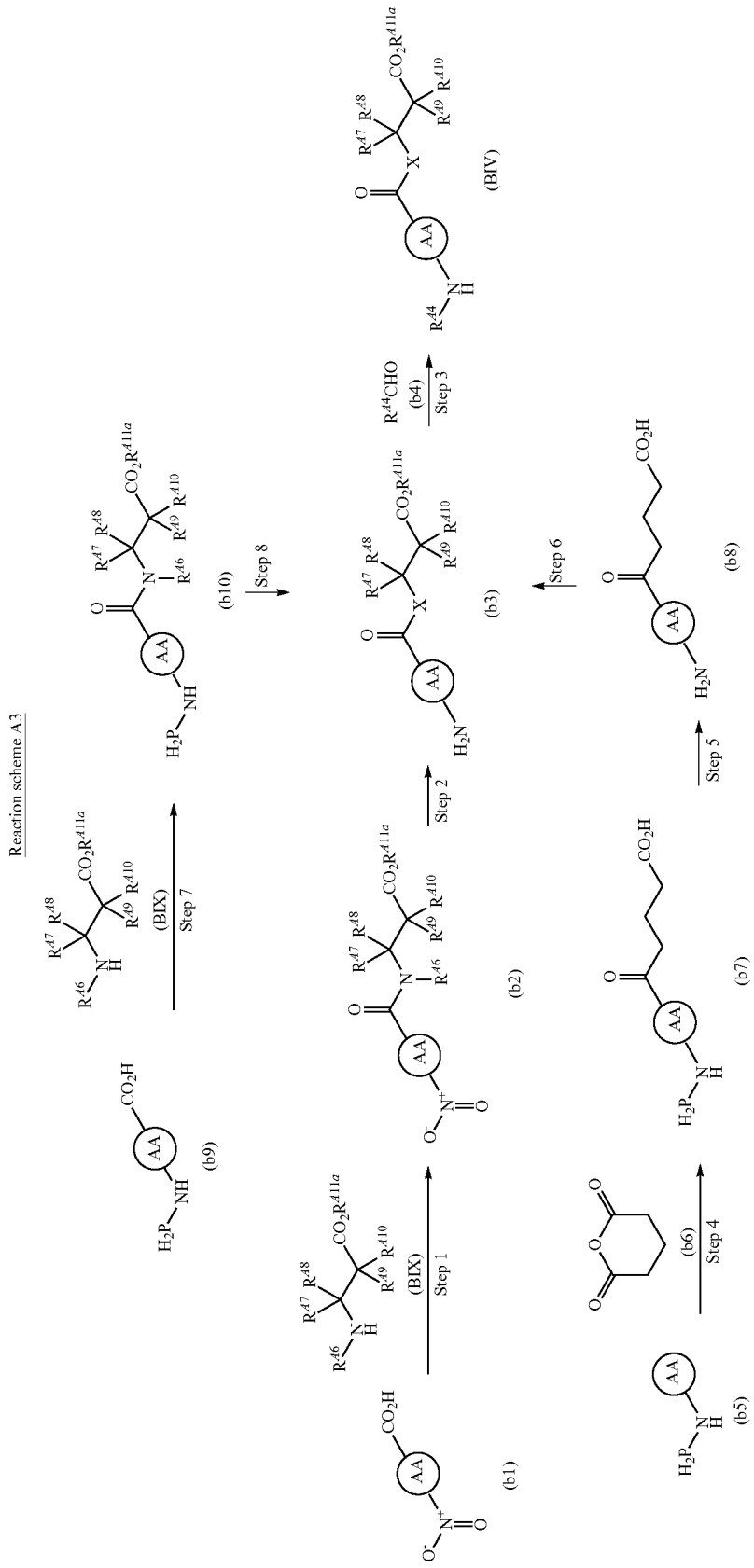

wherein P is an amino-protecting group, and other symbols are each as defined above.

Step 1

Compound (b2) can be produced, for example, by condensing compound (b1) and compound (BIX) according to the production method of compound (BIa) from compound (BVIII).

As compound (A), a commercially available product can be used, or it can be produced from a commercially available compound by a method known per se or a method analogous thereto.

Step 2

Compound (b3) can be produced by subjecting compound (b2) to a reduction reaction in the presence of a metal catalyst and a hydrogen source. Such reduction reaction can be performed according to a conventional method in a solvent that does not adversely influence the reaction.

Examples of the metal catalyst include palladium-carbon, palladium black, palladium chloride, platinum oxide, platinum black, platinum-palladium, Raney-nickel, Raney cobalt and the like.

Examples of the hydrogen source include hydrogen gas, formic acid, formic acid amine salt, phosphinate salt, hydrazine and the like.

Examples of the solvent that does not adversely influence the reaction include methanol, tetrahydrofuran, N,N-dimethylacetamide and the like.

The amount of the metal catalyst to be used is generally 0.001-1000 mol, preferably 0.01-100 mol, per 1 mol of compound (b2).

The reaction temperature is generally −70-150° C., preferably −20-100° C.

The reaction time is generally 0.1-100 hr, preferably 0.1-40 hr.

This reaction can also be performed in the presence of a reducing agent in a solvent that does not adversely influence the reaction.

As the reducing agent, ferric oxide, zinc, tin and the like can be mentioned, and compound (b3) can be produced according to the reaction described in "Jikken Kagaku Kouza (The Chemical Society of Japan ed.), 4th Edition, vol. 20. Organic Synthesis II Alcohol and Amine" pp. 279-280, Maruzen Press 1992, or a method analogous thereto.

The amount of the reducing agent to be used is generally 0.1-20 mol per 1 mol of compound (b2).

Examples of the solvent that does not adversely influence the reaction include alcohols such as methanol, ethanol, propanol, isopropanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, dimethoxyethane and the like; esters such as methyl acetate, ethyl acetate, n-butyl acetate, tert-butyl acetate and the like; amides such as N,N-dimethylformamide, N,N-dimethylacetamide, N-methylpyrrolidone and the like; and the like. Two or more kinds of these solvents may be used in a mixture at an appropriate ratio.

The reaction temperature is generally −70-150° C., preferably −20-100° C.

The reaction time is generally 0.1-100 hr, preferably 0.1-40 hr.

Step 3

Compound (BIV) can be produced by, for example, reductive amination reaction of compound (b3) and compound (b4) according to the production method of compound (BIa) from compound (BV).

As compound (b4), a commercially available product can be used, or it can be produced from a commercially available compound by a method known per se or a method analogous thereto.

Step 4

Compound (b7) can be produced by Friedel-Crafts reaction of compound (b5) and glutaric anhydride (b6) by the synthesis method described in WO2004/45616 or a method analogous thereto.

As compound (b5), a commercially available product can be used, or it can be produced from a commercially available compound by a method known per se or a method analogous thereto.

Step 5

Compound (b8) can be produced by removing the protecting group from compound (b7) by a method known per se, for example, the method described in Protective Groups in Organic Synthesis, Third Edition, Wiley-Interscience (1999) or a method analogous thereto.

Step 6

Compound (b3) ($R^{A7}$, $R^{A8}$, $R^{A9}$ and $R^{A10}$ are hydrogen atoms) can be produced by esterification of compound (b8) by a method known per se, for example, the method described in Protective Groups in Organic Synthesis, Third Edition, Wiley-Interscience (1999) or a method analogous thereto.

Step 7

Compound (b10) can be produced, for example, by condensing compound (b9) and compound (BIX) according to the production method of compound (BIa) from compound (BVIII).

As compound (b9), a commercially available product can be used, or it can be produced from a commercially available compound by a method known per se or a method analogous thereto.

Step 8

Compound (b3) can be produced, for example, by removing the protecting group from compound (b10) according to the method of step 5.

Of compounds (IA), a compound represented by the following formula (BIa-1) [compound (BIa-1)] can be produced according to the following Reaction scheme A4.

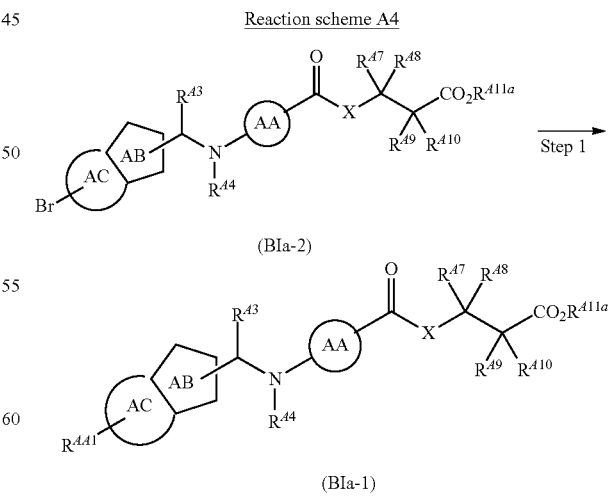

Reaction scheme A4 wherein $R^{AA1}$ is a $C_{1-6}$ alkyl group, a $C_{6-14}$ aryl group, a 4- to 12-membered aromatic heterocyclic group (group bonded via a carbon atom on the ring), a 4- to 12-membered nonaromatic heterocyclic group (group bonded via a carbon atom on the ring), or a cyano group, and other symbols are as defined above.

Step 1

Compound (BIa-1) can be produced, for example, by reacting compound (BIa-2) with an organic metal reagent or metal cyanide in the presence of a metal catalyst.

Examples of the metal catalyst include palladium catalyst (e.g., palladium (II) acetate, tris(dibenzylideneacetone)dipalladium (0), bis(dibenzylideneacetone)palladium (0), tetrakis (triphenylphosphine)palladium (0), [1,1'-bis(diphenylphosphino)ferrocene]dichloropalladium (II) dichloromethane adduct, bis(tris-tert-butylphosphine)palladium (0) etc.); nickel catalyst (e.g., tetrakis(triphenylphosphine)nickel (0), dichloro[1,2-bis(diphenylphosphino)ethane]nickel (II), dichloro[1,3-bis(diphenylphosphino)propane]nickel (II), dichloro[1,4-bis(diphenylphosphino)butane]nickel (II) etc.).

The amount of the metal catalyst to be used is generally 0.01-1 mol, preferably 0.03-0.5 mol, per 1 mol of compound (BIa-2).

Examples of the organic metal reagent include boronic acid, boronate ester, Grignard reagent, organotin reagent, organozinc reagent and the like.

Examples of the metal cyanide include zinc cyanide and the like.

The amount of the organic metal reagent or metal cyanide to be used is generally 1-100 mol, preferably 1-10 mol, per 1 mol of compound (BIa-2).

This reaction may be performed in the presence of a base as necessary.

Examples of such base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogencarbonates such as sodium hydrogen carbonate, potassium hydrogen carbonate and the like; alkali metal alkoxide having a carbon number of 1 to 6 such as sodium methoxide, sodium ethoxide, potassium tert-butoxide and the like. and the like.

The amount of the base to be used is generally 1-100 mol, preferably 1-10 mol, per 1 mol of compound (BIa-2).

This reaction may be performed in the presence of a ligand as necessary.

Examples of such ligand include phosphorus ligand (e.g., triphenylphosphine, 1,3-bis(diphenylphosphino)propane, 1,3-bis(diphenylphosphino)propane, 2,2'-bis(diphenylphosphino)-1,1'-binaphthyl and 4,5-bis(diphenylphosphino)-9,9-dimethylxanthene etc.).

The amount of the ligand to be used is generally 0.01-2 mol, preferably 0.02-1 mol, per 1 mol of compound (BIa-2).

This reaction is preferably performed in a solvent inert to the reaction.

Such solvent is not particularly limited as long as the reaction proceeds and, for example, alcohols such as methanol, ethanol, propanol, isopropanol, butanol, tert-butanol and the like; ethers such as 1,4-dioxane, tetrahydrofuran, diethyl ether, dimethoxyethane, tert-butyl methyl ether, diisopropyl ether, ethylene glycol dimethylether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water and the like can be mentioned. Two or more kinds of these solvents may be used in a mixture at an appropriate ratio.

The reaction temperature is generally −100-180° C., preferably −80° C.-150° C.

The reaction time is generally 0.1 hr-48 hr, preferably 0.1 hr-24 hr.

Compound (BIa-2) can be produced, for example, according to the production method of compound (BIa) in Reaction scheme A1.

Of compounds (BV) described in Reaction scheme A2, a compound represented by the following formula (BV-1) [compound (BV-1)] can be produced according to the following Reaction is scheme A5.

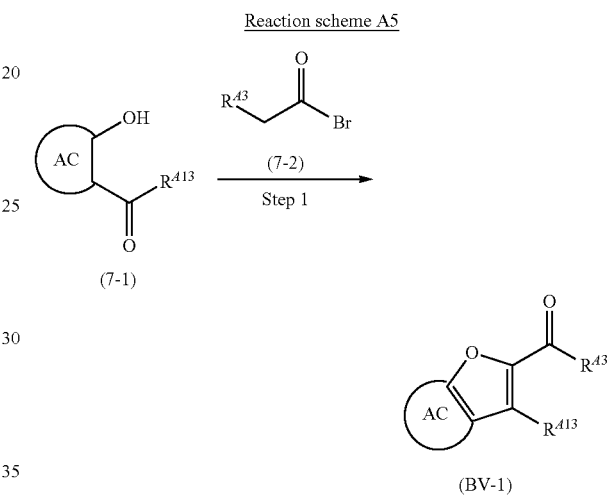

Reaction scheme A5 wherein each symbol is as defined above.

Step 1

Compound (BV-1) can be produced, for example, by reacting compound (7-1) with compound (7-2) in the presence of a base.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogencarbonates such as sodium hydrogen carbonate, potassium hydrogen carbonate and the like; alkali metal alkoxides having 1 to 6 carbon atoms such as sodium methoxide, sodium ethoxide, potassium tert-butoxide and the like; metal hydrides such as sodium hydride, potassium hydride and calcium hydride; organic bases such as 1,8-diazabicyclo [5.4.0]undec-7-ene (DBU), 1,5-diazabicyclo[4.3.0]non-5-ene (DBN), 1,4-diazabicyclo[2.2.2]octane (DABCO) and the like, and the like.

The amount of the base to be used is generally 1-50 mol, preferably 1-20 mol, per 1 mol of compound (7-1).

The amount of the compound (7-2) to be used is generally 1-10 mol, preferably 1-5 mol, per 1 mol of compound (7-1).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethylether and the like; esters such as ethyl formate, ethyl acetate, isopropyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide and the like can be mentioned. Two or more kinds of these solvents may be used in a mixture at an appropriate ratio.

The reaction temperature is generally −80° C.-200° C., preferably 0° C.-150° C.

The reaction time is generally 10 min-48 hr, preferably 15 min-24 hr.

Compound (7-1) can be produced by a method known per se or a method analogous thereto.

Compound (7-2) can be produced by a method known per se or a method analogous thereto.

Of compounds (1), a compound represented by the following formula (I-1) [compound (1-1)] can be produced according to the following Reaction scheme A6.

Reaction scheme A6

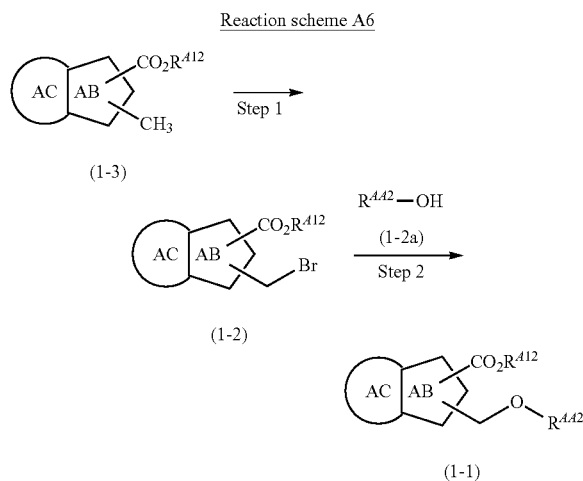

wherein $R^{AA2}$ is a alkyl group, and other symbols are as defined above.

Step 1

Compound (1-2) can be produced, for example, by bromination of compound (1-3).

Examples of the bromination reagent include N-bromoamides such as N-bromosuccinimide, 1,3-dibromo-5,5-dimethylhydantoin and the like.

The amount of the bromination reagent to be used is generally 1-100 mol, preferably 1-10 mol, per 1 mol of compound (1-3).

This reaction may be performed in the co-presence of a radical initiator when desired.

Examples of such radical initiator include azobisisobutyronitrile, benzoyl peroxide and the like.

The amount of the radical initiator to be used is generally 0.001-10 mol, preferably 0.01-5 mol, per 1 mol of compound (1-3).

This reaction is preferably performed in a solvent inert to the reaction. Such solvent is not particularly limited as long as the reaction proceeds and, for example, esters such as ethyl formate, ethyl acetate, n-butyl acetate and the like; halogenated hydrocarbons such as dichloromethane, chloroform, carbon tetrachloride, trichloroethylene and the like; nitriles such as acetonitrile, propionitrile and the like and the like can be mentioned. Two or more kinds of these solvents may be used in a mixture at an appropriate ratio.

The reaction temperature is generally −100-180° C., preferably −80° C.-150° C.

The reaction time is generally 0.1 hr-48 hr, preferably 0.1 hr-24 hr.

Compound (1-3) can be produced by a method known per se or a method analogous thereto.

Step 2

Compound (1-1) can be produced, for example, by reacting compound (1-2) with an alkali metal alkoxide.

Alternatively, compound (1-1) can also be produced, for example, by reacting compound (1-2) with compound (1-2a) in the presence of a base.

Examples of the alkali metal alkoxide include sodium methoxide, potassium methoxide, sodium ethoxide, potassium ethoxide and the like.

The amount of the alkali metal alkoxide to be used is generally 1-50 mol, preferably 1-10 mol, per 1 mol of compound (1-2).

Examples of the base include alkali metal carbonates such as sodium carbonate, potassium carbonate, cesium carbonate and the like; alkali metal hydrogencarbonates such as sodium hydrogen carbonate, potassium hydrogen carbonate and the like; metal hydrides such as sodium hydride, potassium hydride and calcium hydride, and the like.

The amount of the base to be used is generally 1-50 mol, preferably 1-10 mol, per 1 mol of compound (1-2).

The amount of the compound (1-2a) to be used is generally 1-50 mol, preferably 1-10 mol, per 1 mol of compound (1-2).

This reaction is preferably performed in a solvent inert to the reaction. Such solvent is not particularly limited as long as the reaction proceeds and, for example, alcohols such as methanol, ethanol, 1-propanol, 2-propanol, tert-butyl alcohol and the like; ethers such as 1,4-dioxane, tetrahydrofuran, diethyl ether, dimethoxyethane, tert-butyl methyl ether, diisopropyl ether, ethylene glycol dimethylether and the like; esters such as ethyl formate, ethyl acetate, isopropyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide and the like can be mentioned. Two or more kinds of these solvents may be used in a mixture at an appropriate ratio.

In this reaction, alkali metal iodides such as sodium iodide, potassium iodide and the like may be added as a reaction promoter in an amount of generally 1-50 mol, preferably 1-10 mol, per 1 mol of compound (1-2).

The reaction temperature is generally −80° C.-200° C., preferably 0° C.-150° C. The reaction time is generally 0.1 hr-48 hr, preferably 0.1 hr-24 hr.

Compound (1-2a) can be produced by a method known per se or a method analogous thereto.

In compound (BIa) of Reaction scheme A1, a compound represented by the following formula (BIa-3) [compound (BIa-3)] and a compound represented by the formula (BIa-4) [compound (BIa-4)], and in compound (BIb) of Reaction scheme A1, a compound represented by the following formula (BIb-1) [compound (BIb-1)] can be produced, for example, by the methods shown in the following Reaction scheme A7.

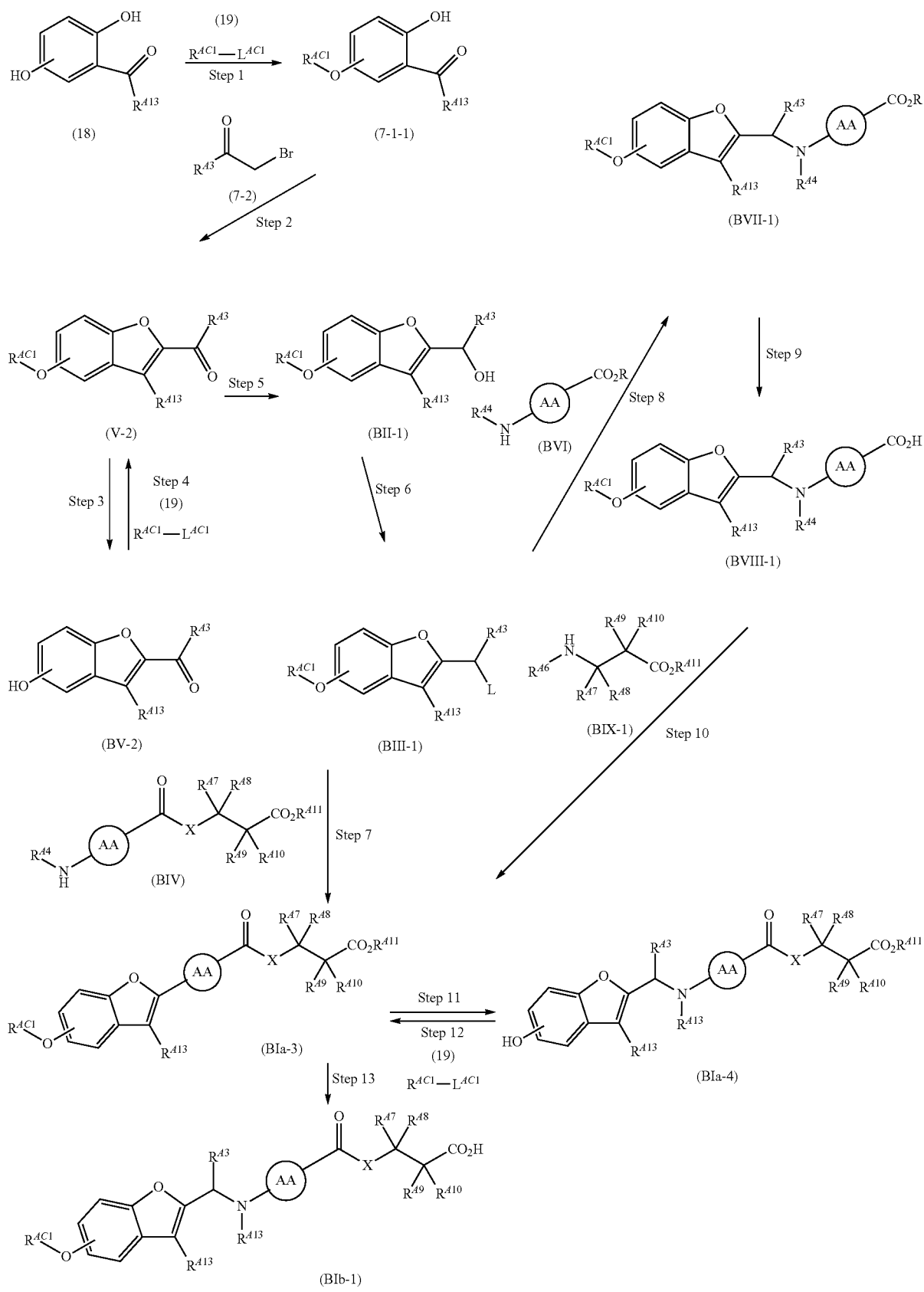
Reaction scheme A7 wherein $R^{AC1}$ is
(1) $C_{1-6}$ alkyl optionally substituted by 1 to 3 substituents selected from
(a) halogen atom,
(b) carboxy group,
(c) $C_{1-6}$ alkoxy group,
(d) $C_{3-6}$ cycloalkyl group,
(e) $C_{1-6}$ alkoxy-carbonyl group optionally substituted by 1 to 3 $C_{6-14}$ aryl groups,
(f) amino group optionally mono- or di-substituted by substituent(s) selected from $C_{1-6}$ alkyl group and $C_{1-6}$ alkoxy-carbonyl group,
(g) 4- to 12-membered aromatic heterocyclic group optionally substituted by 1 to 3 substituents selected from
(i) halogen atom, and
(ii) $C_{1-6}$ alkyl group,
(h) 4- to 12-membered nonaromatic heterocyclic group optionally substituted by 1 to 3 $C_{1-6}$ alkyl groups,
(i) $C_{1-6}$ alkylsulfonyl group,
(j) $C_{1-6}$ alkylthio group, and
(k) hydroxy group;
(2) $C_{7-13}$ aralkyl group;
(3) $C_{6-14}$ aryl group;
(4) $C_{1-6}$ alkyl-carbonyl group;
(5) 4- to 12-membered aromatic heterocyclic group optionally substituted by 1 to 3 substituents selected from
(i) $C_{1-6}$ alkyl group optionally substituted by 1 to 3 halogen atoms, and
(ii) cyano group;
(6) 4- to 12-membered non-aromatic heterocyclyl-oxy group,
$L^{AC1}$ is a leaving group or a hydroxy group,
and other symbols are as defined above.

Examples of the "leaving group" for $L^{AC1}$ include fluorine atom, chlorine atom, bromine atom, iodine atom, benzenesulfonyloxy group, p-toluenesulfonyloxy group, methanesulfonyloxy group, trifluoromethanesulfonyloxy group and the like.

Step 1
In this step, for example, compound (7-1-1) can be produced by reacting compound (18) with compound (19).

When $L^{AC1}$ is a leaving group, this reaction is performed in the presence of a base in a solvent that does not adversely influence the reaction.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, tripotassium phosphate and the like; alkali metal hydroxide such as sodium hydroxide, potassium hydroxide, lithium hydroxide and the like; alkaline earth metal hydroxide such as magnesium hydroxide, calcium hydroxide, barium hydroxide and the like; metal hydrides such as potassium hydride, sodium hydride and the like; alkali metal $C_{1-6}$ alkoxide such as sodium methoxide, sodium ethoxide, potassium tert-butoxide and the like, and the like.

The amount of the base to be used is generally 1-1000 mol, preferably 1-5 mol, per 1 mol of compound (18).

The amount of the compound (19) to be used is generally 1-1000 mol, preferably 1-10 mol, per 1 mol of compound (18).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide, N,N-dimethylacetamide and the like; sulfoxides such as dimethyl sulfoxide and the like; ketones such as acetone and the like; acetonitrile; water. These solvents may be used in a mixture at an appropriate ratio.

The reaction temperature is generally −80° C. to 150° C., preferably −10° C. to 100° C.

The reaction time is generally 0.5-20 hr.

When $L^{AC1}$ is a hydroxy group, this reaction is performed by a method known per se, for example, the method described in Synthesis, page 1 (1981), or a method analogous thereto. That is, this reaction is performed generally in the presence of an organic phosphorus compound and electrophile in a solvent that does not adversely influence the reaction.

Examples of the organic phosphorus compound include triphenylphosphine, tributylphosphine and the like.

Examples of the electrophile include diethyl azodicarboxylate, diisopropyl azodicarboxylate, 1,1'-azodicarbonyldipiperidine and the like.

The amount of the organic phosphorus compound and electrophile to be used is each generally 1-1000 mol, preferably 1-5 mol, per 1 mol of compound (18).

The amount of the compound (19) to be used is generally 1-1000 mol, preferably 1-5 mol, per 1 mol of compound (18).

As the solvent that does not adversely influence the reaction, those similar to the aforementioned can be mentioned.

The reaction temperature is generally −80-150° C., preferably −10-100° C.

Compound (18) and compound (19) can be each produced according to a method known per se.

Step 2
In this step, for example, compound (7-1-1) is reacted with compound (7-2) in the presence of a base to give compound (V-2).

This reaction is performed in the same manner as in Reaction scheme A5, step 1.

Compound (7-2) can be produced according to a method known per se.

Step 3
In this step, for example, $R^{AC1}$ of compound (V-2) is removed to give compound (BV-2).

When $R^{AC1}$ is a benzyl group, this reaction can be performed, for example, in the presence of a metal catalyst such as palladium-carbon, palladium black, palladium-carbon ethylenediamine complex, palladium chloride, platinum oxide, platinum black, platinum-palladium, Raney-nickel, Raney cobalt and the like and a hydrogen source in a solvent that does not adversely influence the reaction.

The amount of the metal catalyst to be used is generally 0.001-1000 mol, preferably 0.01-100 mol, per 1 mol of compound (V-2).

Examples of the hydrogen source include hydrogen gas, formic acid, formic acid amine salt, phosphinate salt, hydrazine and the like.

Examples of the solvent that does not adversely influence the reaction include alcohols such as methanol, ethanol, propanol, 2-propanol, 2-methoxyethanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, 1,2-dimethoxyethane and the like; halogenated hydrocarbons such as dichloromethane, chloroform, 1,2-dichloroethane, 1,1,2,2-tetrachloroethane and the like; amides such as N,N-dimethylformamide, N,N-dimethylacetamide, N-methylpyrrolidone and the like; ethyl acetate, acetic acid and the like. These solvents may be used in a mixture at an appropriate ratio.

The reaction temperature is generally 0-120° C., preferably 10-80° C.

The reaction time is generally 0.5-100 hr.

Step 4

In this step, for example, compound (V-2) can be produced by reacting compound (BV-2) with compound (19). This step is performed in the same manner as in this reaction, step 1.

Step 5

In this step, for example, compound (BII-1) can be produced by subjecting compound (V-2) to a reduction reaction. This reaction is performed in the same manner as in Reaction scheme 1, step 1.

Step 6

In this step, for example, compound (BIII-1) can be produced by converting the hydroxy group of compound (BII-1) to leaving group (L). This reaction is performed in the same manner as in Reaction scheme A1, step 1.

Step 7

In this step, for example, compound (BIa-3) can be produced by reacting compound (BIII-1) with compound (BIV) in the presence of a base. This reaction is performed in the same manner as in Reaction scheme A1, step 2.

Step 8

In this step, for example, compound (BVII-1) can be produced by reacting compound (BIII-1) with compound (BVI) in the presence of a base. This reaction is performed in the same manner as in Reaction scheme A1, step 4.

Step 9

In this step, for example, compound (BVIII-1) can be produced by hydrolyzing the ester of compound (BVII-1). This reaction is performed in the same manner as in Reaction scheme A1, step 6.

Step 10

In this step, for example, compound (BIa-3) can be produced by condensing compound (BVIII-1) and compound (BIX-1). This reaction is performed in the same manner as in Reaction scheme A1, step 7.

As compound (BIX-1), a commercially available product can be used, or it can be produced from a commercially available compound by a method known per se or a method analogous thereto.

Step 11

In this step, for example, compound (BIa-4) can be produced by removing $R^{AC1}$ from compound (BIa-3). This step is performed in the same manner as in this reaction, step 3.

Step 12

In this step, for example, compound (BIa-3) can be produced by reacting (BIa-4) with compound (19). This step is performed in the same manner as in this reaction, step 1.

Step 13

In this step, for example, compound (BIb-1) can be produced by hydrolyzing the ester of compound (BIa-3) according to the production method of compound (BVIII).

Compound (4-1) which is a starting material compound of Reaction scheme A2 can be produced, for example, according to the method shown in the following Reaction scheme A8.

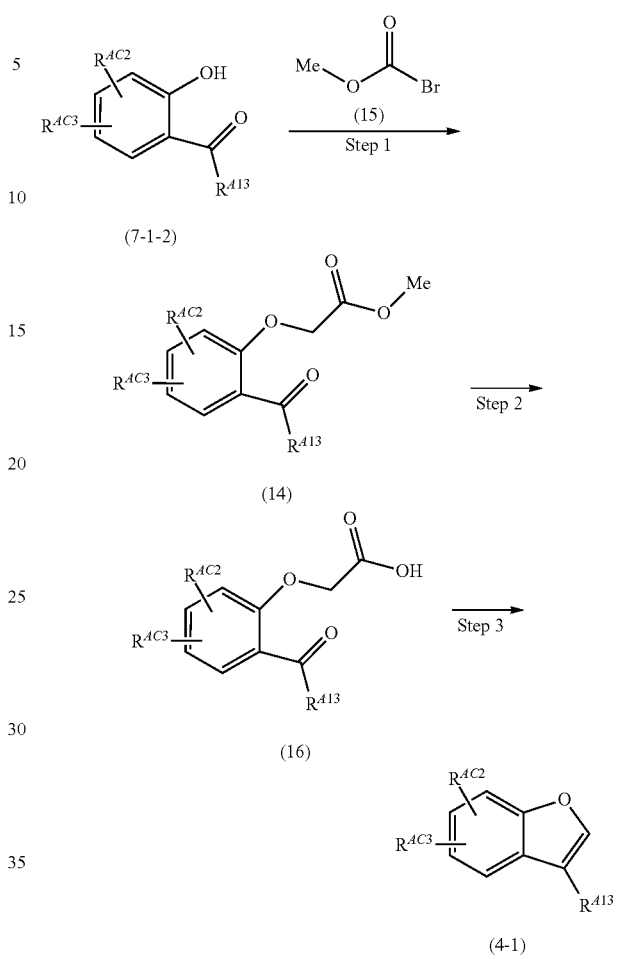

Reaction scheme A8 wherein $R^{AC2}$ and $R^{AC3}$ are each a substituent that the aforementioned ring AC optionally has, and other symbols are as defined above.

Step 1

In this step, for example, compound (14) can be produced by reacting compound (7-1-2) with compound (15) under basic conditions. This reaction is performed in the same manner as in Reaction scheme A5, step 1.

Step 2

In this step, for example, compound (16) can be produced by hydrolyzing the ester of compound (14) according to the production method of compound (BVIII) in Reaction scheme A1.

Step 3

In this step, for example, compound (4-1) can be produced by reacting compound (16) in acetic anhydride.

In this step, sodium acetate may be used as an additive.

The amount of sodium acetate to be used is generally 1-1000 mol, preferably 1-10 mol, per 1 mol of compound (16).

The reaction temperature is generally −80-200° C., preferably −10-150° C.

The reaction time is generally 0.5-20 hr.

Compound (7-1-2) and compound (15) can be produced according to a method known per se.

In compound (BIa-3) of Reaction scheme A7, a compound represented by the following formula (BIa-5) [compound (BIa-5)] can be produced, for example, by the method shown in the following Reaction scheme A9.

Reaction scheme A9

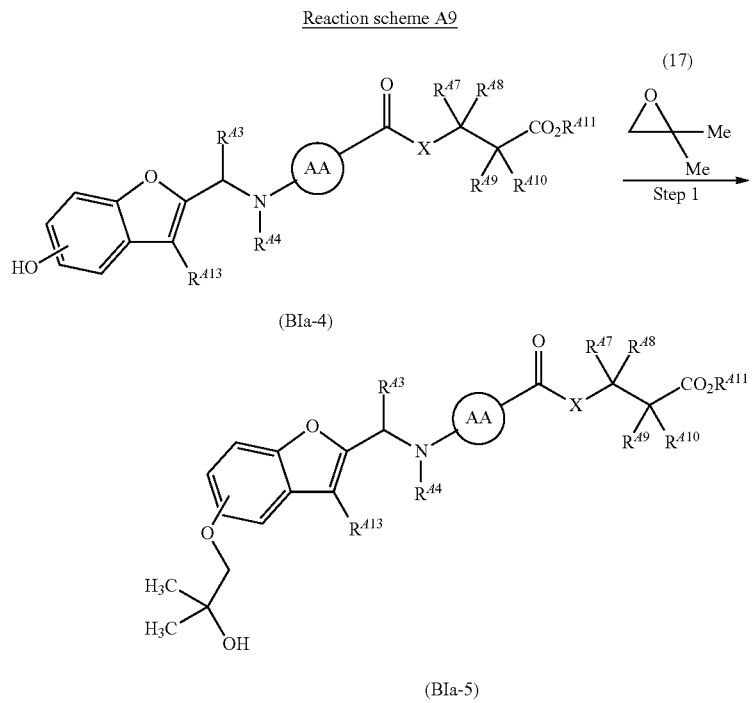

(BIa-4)

(BIa-5)

wherein the symbols are as defined above.
Step 1
In this step, for example, compound (BIa-5) can be produced by reacting compound (BIa-4) with compound (17).

This reaction is performed in the presence of a base in a solvent that does not adversely influence the reaction.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide and the like, and the like.

The amount of the base to be used is generally 1-50 mol, preferably 1-5 mol, per 1 mol of compound (BIa-4).

The amount of the compound (17) to be used is generally 1-50 mol, preferably 1-5 mol, per 1 mol of compound (BIa-4).

In this reaction, sodium iodide or potassium iodide may be further added to the solvent.

The amount of sodium iodide or potassium iodide to be used is generally 1-100 mol, preferably 1-10 mol, per 1 mol of compound (BIa-4).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like; ketones such as acetone and the like; acetonitrile; water. These solvents may be used in a mixture at an appropriate ratio.

The reaction temperature is generally 0-150° C., preferably 0-100° C.

The reaction time is generally 0.5-100 hr.

Compound (BIa-4) can be produced according to Reaction scheme A7.

Compound (17) can be produced according to a method known per se.

The thus-obtained compound (I) and compound (IA) can be isolated and purified by known separation and purification means, for example, concentration, concentration under reduced pressure, solvent extraction, crystallization, recrystallization, phase transfer, chromatography and the like.

In addition, when compound (I) and compound (IA) are obtained as free compounds, they can be converted to object salts by a method known per se or a method analogous thereto. When they are obtained as salts, they can be converted to free forms or other object salts by a method known per se or a method analogous thereto.

When compound (I) or compound (IA) contains an optical isomer, a stereoisomer, a regioisomer or a rotamer, these are also encompassed in compound (I) and compound (IA), and can be obtained as a single product according to synthesis and separation methods known per se. For example, when compound (I) and compound (IA) have an optical isomer, an optical isomer resolved from this compound is also encompassed in compound (I) and compound (IA).

The optical isomer can be prepared according to a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) or compound (IA) contains hydroxy, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, this compound and an optically active amine or an optically active alcohol are subjected to condensation reaction to give diastereomers of the amide compound or the ester compound, respectively. The separated diastereomer is converted to an optical isomer of the original compound by acid hydrolysis or base hydrolysis.

EXAMPLES

The present invention is explained in more detail in the following by referring to Examples, Experimental Examples and Formulation Examples, which are not to be construed as limitative.

$^1$H-NMR spectrum was measured using tetramethylsilane as the internal standard and Varian Gemini 200 (200 MHz), 300 (300 MHz), Bruker 300 (300 MHz) spectrometers, and all δ values are shown by ppm. Unless otherwise specified, the numerical values shown for mixed solvents are volume mixing ratios of respective solvents. Unless otherwise specified, % means weight. In addition, unless otherwise specified, the ratio of elution solvents in silica gel chromatography means a volume mixing ratio. The room temperature (ambient temperature) in the present specification is a temperature of about 20° C. to about 30° C.

Each symbol in the Examples means the following.

DMSO: dimethyl sulfoxide, $CDCl_3$: deuterated chloroform, s: singlet, d: doublet, t: triplet, q: quartet, dd: double doublet, dt: double triplet, quint: quintet, multiplet, brs: broad, J: coupling constant LC/MS analyses in Examples were performed under the following conditions.

measurement device: Waters LC/MS system

HPLC: Agilent HP1100

MS: Micromass ZMD column: CAPCELL PAK c18UG120 S-3 μm, 1.5×35 mm (manufactured by Shiseido Co., Ltd.)

solvent: SOLUTION A; 0.05% aqueous trifluoroacetic acid solution, SOLUTION B; 0.04% trifluoroacetic acid acetonitrile solution gradient cycle: 0 min. (SOLUTION A/SOLUTION B=90/10), 2.00 min. (SOLUTION A/SOLUTION B=5/95), 2.75 min. (SOLUTION A/SOLUTION B=5/95), 2.76 min. (SOLUTION A/SOLUTION B=90/10), 3.60 min. (SOLUTION A/SOLUTION B=90/10)

injection volume: 2 μL, flow rate: 0.5 mL/min, detection method: UV 220 nm,

MS conditions ionization method: ESI

Purification by preparative HLPC in Examples was performed under the following conditions.

instrument: Gilson Inc., High throughput purification system column: YMC CombiPrep ODS-A S-5 μm, 50×20 mm, or CombiPrep Hydrosphere C18 S-5 μm, 50×20 mm solvent: SOLUTION A; 0.1% aqueous trifluoroacetic acid solution, SOLUTION B; 0.1% trifluoroacetic acid acetonitrile solution gradient cycle: 0 min. (SOLUTION A/SOLUTION B=95/5), 1.00 min. (SOLUTION A/SOLUTION B=95/5), 5.20 min. (SOLUTION A/SOLUTION B=5/95), 6.40 min. (SOLUTION A/SOLUTION B=5/95), 6.50 min. (SOLUTION A/SOLUTION B=95/5), 6.60 min. (SOLUTION A/SOLUTION B=95/5), or 0 min. (SOLUTION A/SOLUTION B=98/2), 1.00 min. (SOLUTION A/SOLUTION B=98/2), 5.00 min. (SOLUTION A/SOLUTION B=0/100), 6.40 min. (SOLUTION A/SOLUTION B=0/100), 6.50 min. (SOLUTION A/SOLUTION B=98/2), 6.60 min. (SOLUTION A/SOLUTION B=98/2)

flow rate: 20 mL/min, detection method: UV 220 nm

Example 1

3-[({4-[(cyclohexyl{3-methyl-1-[5-(trifluoromethyl)pyridin-2-yl]-1H-pyrazol-4-yl}methyl)amino]phenyl}carbonyl)amino]propanoic acid

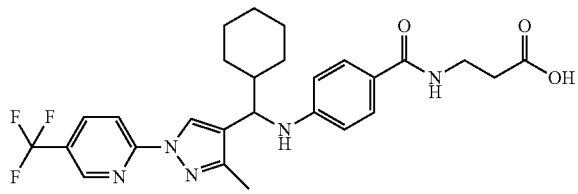 [SMILES: Cc1nn(-c2ccc(C(F)(F)F)cn2)cc1C(Nc1ccc(C(=O)NCCC(=O)O)cc1)C1CCCCC1]

(1) ethyl 3-[(4-nitrobenzoyl)amino]propanoate

To a mixture of 4-nitrobenzoic acid (16.7 g), β-alanine ethyl ester hydrochloride (18.4 g), 1-hydroxybenzotriazole monohydrate (18.4 g), triethylamine (16.7 mL) and N,N-dimethylformamide (200 mL) was added 1-ethyl-3-(3-dimethylaminopropyl)carbodiimide hydrochloride (23.0 g), and the mixture was stirred at room temperature for 8 hr. The reaction mixture was poured into water, and the mixture was extracted with ethyl acetate. The extract was washed with 1N hydrochloric acid and saturated aqueous sodium hydrogen carbonate, dried over magnesium sulfate, and concentrated under reduced pressure to give a white solid. Recrystallization from ethyl acetate-hexane gave the title object compound (26.6 g, 100%) as white crystals.

$^1$H NMR (300 MHz, CDCl$_3$) δ ppm 1.29 (t, J=7.2 Hz, 3H), 2.68 (t, J=6.1 Hz, 2H), 3.76 (q, J=6.1 Hz, 2H), 4.19 (q, J=7.1 Hz, 2H), 7.03 (br. s., 1H), 7.93 (d, J=9.1 Hz, 2H), 8.29 (d, J=8.7 Hz, 2H).

(2) ethyl 3-{[(4-aminophenyl)carbonyl]amino}propanoate

A mixture of ethyl 3-[(4-nitrobenzoyl)amino]propanoate (26.6 g) synthesized above, 5% palladium-carbon (8.9 g), tetrahydrofuran (150 mL) and ethanol (150 mL) was stirred at room temperature overnight under a hydrogen atmosphere. 5% Palladium-carbon was filtered off, and the filtrate was concentrated under reduced pressure to give a white solid. Recrystallization from ethyl acetate-diisopropyl ether gave the title object compound (22.6 g, 95%) as white crystals.

$^1$H NMR (300 MHz, CDCl$_3$) δ ppm 1.27 (t, J=7.2 Hz, 3H), 2.63 (t, J=6.0 Hz, 2H), 3.70 (q, J=6.0 Hz, 2H), 3.94 (br. s., 2H), 4.17 (q, J=7.2 Hz, 2H), 6.66 (d, J=8.7 Hz, 2H), 7.60 (d, J=8.7 Hz, 2H).

(3) methyl 3-methyl-1H-pyrazole-4-carboxylate

A mixture of methyl acetoacetate (30.0 g) and dimethylformamide dimethylacetal (34.7 mL) was stirred at 100° C. for 12 hr, and the mixture was allowed to cool. Ethanol (500 mL) and hydrazine monohydrate (12.6 mL) were added to the reaction mixture at room temperature, and the mixture was heated under reflux for 12 hr. The mixture was allowed to cool, and concentrated under reduced pressure. Water was added to the residue, and the mixture was extracted with ethyl acetate. The extract was concentrated under reduced pressure to give the title object compound (22.3 g, 61%) as a pale-yellow solid.

$^1$H NMR (300 MHz, CDCl$_3$) δ ppm 2.56 (s, 3H), 3.84 (s, 3H), 7.96 (s, 1H).

(4) methyl 3-methyl-1-[5-(trifluoromethyl)pyridin-2-yl]-1H-pyrazole-4-carboxylate To a solution of methyl 3-methyl-1H-pyrazole-4-carboxylate (5.3 g) synthesized above in dimethylformamide (70 mL) was added sodium hydride (1.9 g, 60% in oil) at 0° C., and the mixture was stirred for 10 min. 2-Chloro-5-trifluoromethylpyridine (7.5 g) was added, and the mixture was stirred at room temperature overnight. Aqueous ammonium chloride solution was added to the reaction mixture, and the mixture was extracted with diethyl ether. The extract was washed with brine, dried over magnesium sulfate and concentrated under reduced pressure. The residue was purified by silica gel column chromatography (ethyl acetate:hexane=1:10, volume ratio) to give the title object compound (3.3 g, 31%) as a pale-yellow solid.

$^1$H NMR (300 MHz, CDCl$_3$) δ ppm 2.57 (s, 3H), 3.87 (s, 3H), 7.97-8.17 (m, 2H), 8.63-8.74 (m, 1H), 9.00 (s, 1H).

(5) 3-methyl-1-[5-(trifluoromethyl)pyridin-2-yl]-1H-pyrazole-4-carbaldehyde

Methyl 3-methyl-1-[5-(trifluoromethyl)pyridin-2-yl-1H-pyrazole-4-carboxylate (3.3 g) synthesized above was dissolved in tetrahydrofuran (10 mL), and the solution was added dropwise to a solution (20 mL) of lithium aluminum hydride (0.45 g) in tetrahydrofuran at 0° C. The reaction mixture was stirred at 0° C. for 30 min, and water (0.45 mL) was carefully added dropwise. Furthermore, 1N aqueous sodium hydroxide solution (2.3 mL) was added, and the mixture was stirred at room temperature for 30 min. The reaction mixture was filtered through celite, and the residue was washed with tetrahydrofuran (30 mL). The extracts were combined, dried over magnesium sulfate and concentrated under reduced pressure. The residue was dissolved in toluene (50 mL), manganese dioxide (8.8 g) was added, and the mixture was heated under reflux for 1 hr under dehydrating conditions. After allowing to cool, manganese dioxide was filtered off, and the residue was evaporated under reduced pressure to give the title object compound (2.6 g, 87%) as a pale-yellow solid.

$^1$H NMR (300 MHz, CDCl$_3$) δ 2.57 (s, 3H), 7.97-8.17 (m, 2H), 8.63-8.74 (m, 1H), 9.00 (s, 1H), 9.95 (s, 1H).

(6) cyclohexyl{3-methyl-1-[5-(trifluoromethyl)pyridin-2-yl]-1H-pyrazol-4-yl}methanol To a solution of 3-methyl-1-[5-(trifluoromethyl)pyridin-2-yl]-1H-pyrazole-4-carbaldehyde (2.6 g) synthesized above in tetrahydrofuran (40 mL) was added dropwise 1M cyclohexylmagnesium bromide tetrahydrofuran solution (15 mL) at 0° C. After stirring at 0° C. for 1 hr, aqueous ammonium chloride solution was added, and the mixture was extracted with ethyl acetate. The extract was concentrated under reduced pressure, and the residue was purified by silica gel column chromatography (ethyl acetate:hexane=1:4, volume ratio) to give the title object compound (2.0 g, 36%) as a colorless solid.

$^1$H NMR (300 MHz, CDCl$_3$) δ ppm 0.93-1.93 (m, 11H), 2.36 (s, 3H), 3.62 (br. s., 1H), 4.44 (dd, J=7.2, 3.4 Hz, 1H), 7.91-8.07 (m, 2H), 8.43 (s, 1H), 8.63 (s, 1H).

(7) 3-[({4-[(cyclohexyl{3-methyl-1-[5-(trifluoromethyl)pyridin-2-yl]-1H-pyrazol-4-yl}methyl)amino]phenyl}carbonyl)amino]propanoic acid To a solution (10 mL) of cyclohexyl{3-methyl-1-[5-(trifluoromethyl)pyridin-2-yl]-1H-pyrazol-4-yl}methanol (0.75 g) synthesized above in tetrahydrofuran was added thionyl chloride (0.24 mL) at room temperature, and the mixture was stirred for 30 min. The reaction mixture was poured into aqueous sodium hydrogen carbonate solution at 0° C., and the mixture was extracted with ethyl acetate. The extract was washed with brine, dried over magnesium sulfate and concentrated under reduced pressure. The residue was dissolved in dimethylacetamide (15 mL), and sodium iodide (0.63 g), sodium carbonate (0.45 g) and ethyl 3-{[(4-aminophenyl)carbonyl]amino}propanoate (0.75 g) synthesized in Example 1, (2) were added. The mixture was stirred at 80° C. overnight and allowed to cool. Then, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound in an ethyl ester form (876 mg). This was dissolved in ethanol (4 mL), 1N aqueous sodium hydroxide solution (4 mL) was added at room temperature, and the mixture was stirred for 1 hr. Ethanol was evaporated under reduced pressure, and 1N hydrochloric acid (4 mL) was added to the residue. The precipitate was washed with water to give the title object compound (0.78 g, 70%) as a white solid.

$^1$H NMR (300 MHz, CDCl$_3$) δ ppm 0.81-2.23 (m, 11H), 2.34 (s, 3H), 2.50-2.68 (m, 2H), 3.43-3.74 (m, 2H), 4.20 (d, J=6.4 Hz, 1H), 6.47 (d, J=8.5 Hz, 2H), 6.68 (br. s., 1H), 7.51 (d, J=8.5 Hz, 2H), 7.86-8.05 (m, 2H), 8.31 (s, 1H), 8.57 (s, 1H).

Example 2

3-[({4-[(cyclohexyl{3-methyl-1-[5-(trifluoromethyl) pyridin-2-yl]-1H-pyrazol-4-yl}methyl)amino] phenyl}carbonyl)(methyl)amino]propanoic acid

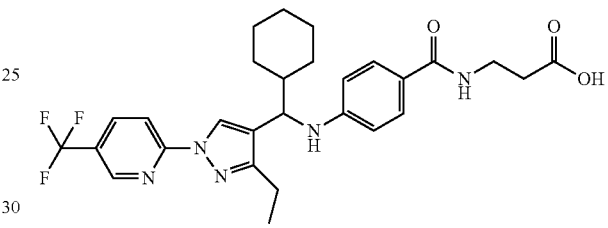

(1) ethyl 3-[methyl(4-nitrobenzoyl)amino]propanoate

Using ethyl 3-(methylamino)propanoate (13.1 g) and in the same manner as in Example 1(1), the title object compound (28.0 g, 100%) was obtained as an oil.

$^1$H NMR (300 MHz, CDCl$_3$) 3 ppm 1.26 (t, J=7.1 Hz, 3H), 2.51-2.78 (m, 2H), 2.99-3.10 (m, 3H), 3.46-3.86 (m, 2H), 4.03-4.28 (m, 2H), 7.50-7.65 (m, 2H), 8.28 (d, J=8.7 Hz, 2H).

(2) ethyl 3-{[(4-aminophenyl)carbonyl](methyl) amino}propanoate

In the same manner as in Example 1(2), the title object compound (26.6 g, 90%) was obtained as an oil.

$^1$H NMR (300 MHz, CDCl$_3$) 3 ppm 1.26 (t, J=7.2 Hz, 3H), 2.64 (t, J=6.4 Hz, 2H), 3.05 (s, 3H), 3.74 (t, J=7.0 Hz, 2H), 3.85 (br. s., 2H), 4.14 (q, J=7.2 Hz, 2H), 6.59-6.72 (m, 2H), 7.23-7.28 (m, 2H).

(3) 3-[({4-[(cyclohexyl{3-methyl-1-[5-(trifluoromethyl)pyridin-2-yl]-1H-pyrazol-4-yl}methyl)amino] phenyl}carbonyl)(methyl)amino]propanoic acid Using cyclohexyl{3-methyl-1-[5-(trifluoromethyl)pyridin-2-yl]-1H-pyrazol-4-yl}methanol (0.75 g) synthesized in Example 1(6) and ethyl 3-{[(4-aminophenyl)carbonyl](methyl)amino}propanoate (0.80 g) synthesized in Example 2(2) and in the same manner as in Example 1 (7), the title object compound (0.74 g, 65%) was obtained as a white solid.

$^1$H NMR (300 MHz, CDCl$_3$) δ ppm 0.95-2.23 (m, 11H), 2.37 (s, 3H), 2.62-2.78 (m, 2H), 3.05 (s, 3H), 3.58-3.84 (m, 2H), 4.21 (d, J=6.1 Hz, 1H), 6.49 (d, J=8.7 Hz, 2H), 7.24 (d, J=8.7 Hz, 2H), 7.90-8.00 (m, 2H), 8.32 (s, 1H), 8.59 (s, 1H).

Example 3

3-[({4-[(cyclohexyl{3-ethyl-1-[5-(trifluoromethyl) pyridin-2-yl]-1H-pyrazol-4-yl}methyl)amino] phenyl}carbonyl)amino]propanoic acid

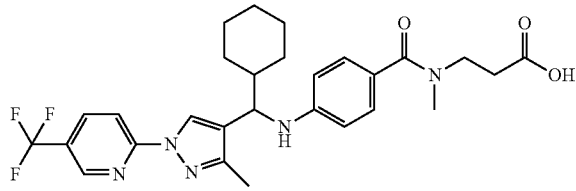 [SMILES: Cc1nn(-c2ccc(C(F)(F)F)cn2)cc1C(Nc1ccc(C(=O)N(C)CCC(=O)O)cc1)C1CCCCC1]

(1) methyl 3-ethyl-1-[5-(trifluoromethyl)pyridin-2-yl]-1H-pyrazole-4-carboxylate A mixture of methyl 3-oxopentanoate (2.6 g) and dimethylformamide dimethylacetal (2.8 mL) was stirred at 100° C. for 12 hr, and allowed to cool. Ethanol (50 mL) and hydrazine monohydrate (1.1 mL) were added to the reaction mixture, and the mixture was treated in the same manner as in Example 1(3) to give a crude product of methyl 3-ethyl-1H-pyrazole-4-carboxylate. This was dissolved in dimethylformamide (30 ml), potassium carbonate (4.2 g) and 2-chloro-5-trifluoromethylpyridine (3.6 g) were added, and the mixture was stirred at 100° C. for 2 hr. In the same manner as in Example 1(4), the title object compound (4.7 g, 79%) was obtained as a yellow solid.

$^1$H NMR (300 MHz, CDCl$_3$) δ ppm 1.33 (t, J=7.5 Hz, 3H), 3.00 (q, J=7.5 Hz, 2H), 3.87 (s, 3H), 7.99-8.18 (m, 2H), 8.68 (s, 1H), 9.00 (s, 1H).

(2) 3-ethyl-1-[5-(trifluoromethyl)pyridin-2-yl]-1H-pyrazole-4-carbaldehyde

Methyl 3-ethyl-1-[5-(trifluoromethyl)pyridin-2-yl]-1H-pyrazole-4-carboxylate (4.7 g) synthesized above was treated in the same manner as in Example 1(5) to give the title object compound (1.1 g, 26%) as a yellow solid.

$^1$H NMR (300 MHz, CDCl$_3$) δ ppm 1.35 (t, J=7.6 Hz, 3H), 3.00 (q, J=7.6 Hz, 2H), 7.98-8.23 (m, 2H), 8.71 (s, 1H), 9.04 (s, 1H), 10.05 (s, 1H).

(3) cyclohexyl{3-ethyl-1-[5-(trifluoromethyl)pyridin-2-yl]-1H-pyrazol-4-yl}methanol 3-Ethyl-1-[5-(trifluoromethyl)pyridin-2-yl]-1H-pyrazole-4-carbaldehyde (1.1 g) synthesized above was treated in the same manner as in Example 1(6) to give the title object compound (1.1 g, 79%) as a yellow oil.

$^1$H NMR (300 MHz, CDCl$_3$) δ ppm 0.80-2.21 (m, 14H), 2.73 (q, J=7.3 Hz, 2H), 4.44 (dd, J=7.2, 3.4 Hz, 1H), 7.87-8.16 (m, 2H), 8.43 (s, 1H), 8.63 (s, 1H).

(4) 3-[({4-[(cyclohexyl{3-ethyl-1-[5-(trifluoromethyl)pyridin-2-yl]-1H-pyrazol-4-yl}methyl)amino]phenyl}carbonyl)amino]propanoic acid Using cyclohexyl{3-ethyl-1-[5-(trifluoromethyl)pyridin-2-yl]-1H-pyrazol-4-yl}methanol (0.55 g) synthesized above and ethyl 3-{[(4-aminophenyl)carbonyl]amino}propanoate (0.37 g) synthesized in Example 1(2) and in the same manner as in Example 1 (7), the title object compound (0.32 g, 38%) was obtained as a white solid.

$^1$H NMR (300 MHz, CDCl$_3$) δ ppm 0.86-2.00 (m, 11H), 1.32 (t, J=7.5 Hz, 3H), 2.38-2.58 (m, 2H), 2.70 (q, J=7.5 Hz, 2H), 3.39-3.69 (m, 2H), 4.22 (d, J=6.0 Hz, 1H), 6.47 (d, J=8.5 Hz, 2H), 6.68 (br. s., 1H), 7.51 (d, J=8.5 Hz, 2H), 7.85-8.08 (m, 2H), 8.30 (s, 1H), 8.56 (s, 1H).

Example 4

3-[({4-[(cyclohexyl{3-ethyl-1-[5-(trifluoromethyl)pyridin-2-yl]-1H-pyrazol-4-yl}methyl)amino]phenyl}carbonyl)(methyl)amino]propanoic acid

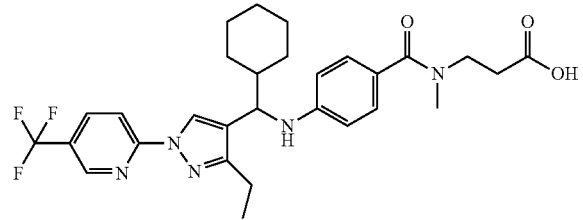 [SMILES: CCc1nn(-c2ccc(C(F)(F)F)cn2)cc1C(Nc1ccc(C(=O)N(C)CCC(=O)O)cc1)C1CCCCC1]

Using cyclohexyl{3-ethyl-1-[5-(trifluoromethyl)pyridin-2-yl]-1H-pyrazol-4-yl}methanol (0.55 g) synthesized in Example 3(3) and ethyl 3-{[(4-aminophenyl)carbonyl](methyl)amino}propanoate (0.39 g) synthesized in Example 2(2) and in the same manner as in Example 1(7), the title object compound (0.35 g, 41%) was obtained as a white solid.

$^1$H NMR (300 MHz, CDCl$_3$) δ ppm 1.19-2.06 (m, 11H), 1.35 (t, J=7.5 Hz, 3H), 2.60-2.81 (m, 4H), 3.05 (s, 3H), 3.72 (d, J=7.5 Hz, 1H), 4.24 (d, J=6.2 Hz, 1H), 6.50 (d, J=8.7 Hz, 2H), 7.26 (d; J=8.7 Hz, 2H), 7.91-8.09 (m, 2H), 8.31 (s, 1H), 8.59 (s, 1H).

Example 5

3-[({4-[(cyclohexyl{3-propyl-1-[5-(trifluoromethyl)pyridin-2-yl]-1H-pyrazol-4-yl}methyl)amino]phenyl}carbonyl)amino]propanoic acid

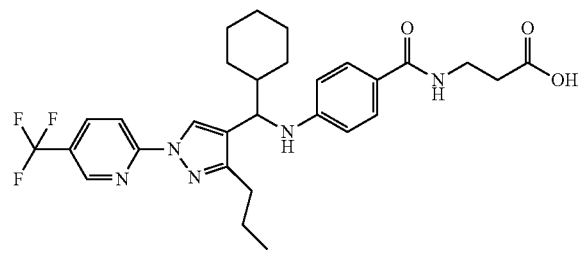 [SMILES: CCCc1nn(-c2ccc(C(F)(F)F)cn2)cc1C(Nc1ccc(C(=O)NCCC(=O)O)cc1)C1CCCCC1]

(1) methyl 3-propyl-1-[5-(trifluoromethyl)pyridin-2-yl]-1H-pyrazole-4-carboxylate A mixture of methyl 3-oxohexanoate (2.1 g) and dimethylformamide dimethylacetal (2.1 mL) was stirred at 100° C. for 12 hr, and the mixture was allowed to cool. To the reaction mixture were added ethanol (50 mL) and hydrazine monohydrate (0.75 mL). In the same manner as in Example 1(3), a crude product of methyl 3-propyl-1H-pyrazole-4-carboxylate was obtained. This was dissolved in dimethylformamide (20 ml), potassium carbonate (3.0 g) and 2-chloro-5-trifluoromethylpyridine (2.7 g) were added, and the mixture was stirred at 100° C. for 2 hr. In the same manner as in Example 1(4), the title object compound (3.3 g, 71%) was obtained as a white solid.

$^1$H NMR (300 MHz, CDCl$_3$) δ ppm 1.02 (t, J=7.4 Hz, 3H), 1.69-1.88 (m, 2H), 2.93 (d, J=7.7 Hz, 2H), 3.87 (s, 3H), 7.98-8.19 (m, 2H), 8.69 (s, 1H), 9.00 (s, 1H).

(2) 3-propyl-1-[5-(trifluoromethyl)pyridin-2-yl]-1H-pyrazole-4-carbaldehyde

Methyl 3-propyl-1-[5-(trifluoromethyl)pyridin-2-yl]-1H-pyrazole-4-carboxylate (3.3 g) synthesized above was treated in the same manner as in Example 1(5) to give the title object compound (1.1 g, 35%) as a yellow oil.

$^1$H NMR (300 MHz, CDCl$_3$) δ ppm 1.03 (t, J=7.3 Hz, 3H), 1.79 (m, 2H), 2.94 (d, J=7.7 Hz, 2H), 8.00-8.23 (m, 2H), 8.71 (s, 1H), 9.04 (s, 1H), 10.05 (s, 1H).

(3) cyclohexyl{3-propyl-1-[5-(trifluoromethyl)pyridin-2-yl]-1H-pyrazol-4-yl}methanol 3-Propyl-1-[5-(trifluoromethyl)pyridin-2-yl]-1H-pyrazole-4-carbaldehyde (1.1 g) synthesized above was treated in the same manner as in Example 1(6) to give the title object compound (1.3 g, 95%) as a yellow oil.

$^1$H NMR (300 MHz, CDCl$_3$) δ ppm 0.80-2.21 (m, 16H), 2.67 (q, J=7.8 Hz, 2H), 4.44 (dd, J=7.5, 3.4 Hz, 1H), 7.90-8.16 (m, 2H), 8.43 (s, 1H), 8.63 (s, 1H).

(4) 3-[({4-[(cyclohexyl{3-propyl-1-[5-(trifluoromethyl)pyridin-2-yl]-1H-pyrazol-4-yl}methyl)amino]phenyl}carbonyl)amino]propanoic acid Using cyclohexyl{3-propyl-1-[5-(trifluoromethyl)pyridin-2-yl]-1H-pyrazol-4-yl}methanol (0.65 g) synthesized above and ethyl 3-{[(4-aminophenyl)carbonyl]amino}propanoate (0.42 g) synthesized in Example 1(2) and in the same manner as in Example 1(7), the title object compound (0.38 g, 39%) was obtained as a white solid.

$^1$H NMR (300 MHz, CDCl$_3$) δ ppm 1.03 (t, J=7.4 Hz, 3H), 1.07-2.04 (m, 13H), 2.49-2.74 (m, 4H), 3.52-3.72 (m, 2H), 4.24 (d, J=6.4 Hz, 1H), 6.50 (d, J=8.7 Hz, 2H), 6.55-6.68 (m, 1H), 7.53 (d, J=8.7 Hz, 2H), 7.86-8.08 (m, 2H), 8.31 (s, 1H), 8.57 (s, 1H).

Example 6

3-[({4-[(cyclohexyl{3-propyl-1-[5-(trifluoromethyl)pyridin-2-yl]-1H-pyrazol-4-yl}methyl)amino]phenyl}carbonyl)(methyl)amino]propanoic acid

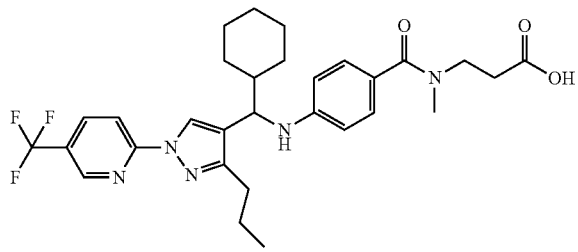 [SMILES: CCCc1nn(-c2ccc(C(F)(F)F)cn2)cc1C(Nc1ccc(C(=O)N(C)CCC(=O)O)cc1)C1CCCCC1]

Using cyclohexyl{3-propyl-1-[5-(trifluoromethyl)pyridin-2-yl]-1H-pyrazol-4-yl}methanol (0.65 g) synthesized in Example 5(3) and ethyl 3-{[(4-aminophenyl)carbonyl](methyl)amino}propanoate (0.44 g) synthesized in Example 2(2) and in the same manner as in Example 1(7), the title object compound (0.34 g, 34%) was obtained as a white solid.

$^1$H NMR (300 MHz, CDCl$_3$) δ ppm 1.03 (t, J=7.2 Hz, 3H), 1.08-2.13 (m, 13H), 2.54-2.78 (m, 4H), 3.05 (s, 3H), 3.71 (t, J=6.2 Hz, 1H), 4.24 (d, J=5.7 Hz, 1H), 6.50 (d, J=8.7 Hz, 2H), 7.26 (d, J=8.7 Hz, 2H), 7.87-8.12 (m, 2H), 8.31 (s, 1H), 8.59 (s, 1H).

Example 7

3-[({4-[(cyclohexyl{3-(1-methylethyl)-1-[5-(trifluoromethyl)pyridin-2-yl]-1H-pyrazol-4-yl}methyl)amino]phenyl}carbonyl)amino]propanoic acid

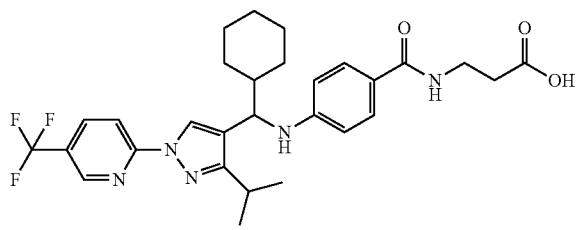 [SMILES: CC(C)c1nn(-c2ccc(C(F)(F)F)cn2)cc1C(Nc1ccc(C(=O)NCCC(=O)O)cc1)C1CCCCC1]

(1) methyl 3-(1-methylethyl)-1-[5-(trifluoromethyl)pyridin-2-yl]-1H-pyrazole-4-carboxylate Using methyl 4-methyl-3-oxopentanoate (2.9 g), dimethylformamide dimethylacetal (2.8 mL) and hydrazine monohydrate (1.1 mL) and in the same manner as in Example 1(3), a crude product of methyl 3-(1-methylethyl)-1H-pyrazole-4-carboxylate was obtained. This was dissolved in dimethylformamide (30 ml), potassium carbonate (4.2 g) and 2-chloro-5-trifluoromethylpyridine (3.6 g) were added, and the mixture was stirred at 100° C. for 2 hr. In the same manner as in an Example 1(4), the title object compound (4.6 g, 73%) was obtained as a white solid.

$^1$H NMR (300 MHz, CDCl$_3$) δ ppm 1.36 (d, J=6.8 Hz, 6H), 3.60 (quint, J=6.8 Hz, 1H), 3.87 (s, 3H), 7.99-8.99 (m, 4H).

(2) 3-(1-methylethyl)-1-[5-(trifluoromethyl)pyridin-2-yl]-1H-pyrazole-4-carbaldehyde Methyl 3-(1-methylethyl)-1-[5-(trifluoromethyl)pyridin-2-yl]-1H-pyrazole-4-carboxylate (4.6 g) synthesized above was treated in the same manner as in Example 1(5) to give the title object compound (1.7 g, 40%) as a white solid.

$^1$H NMR (300 MHz, CDCl$_3$) δ ppm 1.38 (d, J=6.8 Hz, 6H), 3.41-3.64 (m, 1H), 8.01-8.28 (m, 2H), 8.70 (s, 1H), 9.04 (s, 1H), 10.06 (s, 1H).

(3) cyclohexyl{3-(1-methylethyl)-1-[5-(trifluoromethyl)pyridin-2-yl]-1H-pyrazol-4-yl}methanol 3-(1-Methylethyl)-1-[5-(trifluoromethyl)pyridin-2-yl]-1H-pyrazole-4-carbaldehyde (1.7 g) synthesized above was treated in the same manner as in Example 1(6) to give the title object compound (1.5 g, 71%) as a yellow oil.

$^1$H NMR (300 MHz, CDCl$_3$) δ ppm 0.80-2.21 (m, 17H), 3.01 (quint, J=6.9 Hz, 1H), 4.45 (dd, J=7.5, 3.6 Hz, 1H), 7.90-8.10 (m, 2H), 8.43 (s, 1H), 8.62 (s, 1H).

(4) 3-[({4-[(cyclohexyl{3-(1-methylethyl)-1-[5-(trifluoromethyl)pyridin-2-yl]-1H-pyrazol-4-yl}methyl)amino]phenyl}carbonyl)amino]propanoic acid Using cyclohexyl{3-(1-methylethyl)-1-[5-(trifluoromethyl)pyridin-2-yl]-1H-pyrazol-4-yl}methanol (0.50 g) synthesized above and ethyl 3-{[(4-aminophenyl)carbonyl]amino}propanoate (0.32 g) synthesized in Example 1(2) and in the same manner as in Example 1(7), the title object compound (0.11 g, 14%) was obtained as a pale-yellow solid.

$^1$H NMR (300 MHz, CDCl$_3$) δ ppm 1.20-2.06 (m, 11H), 1.28-1.40 (m, 6H), 2.64 (t, J=4.5 Hz, 2H), 2.91-3.17 (m, 1H), 3.54-3.79 (m, 2H), 4.29 (d, J=6.2 Hz, 1H), 6.43-6.65 (m, 3H), 7.54 (d, J=8.7 Hz, 2H), 7.86-8.11 (m, 2H), 8.30 (s, 1H), 8.58 (s, 1H).

Example 8

3-[({4-[(cyclohexyl{3-(1-methylethyl)-1-[5-(trifluoromethyl)pyridin-2-yl]-1H-pyrazol-4-yl}methyl)amino]phenyl}carbonyl)(methyl)amino]propanoic acid

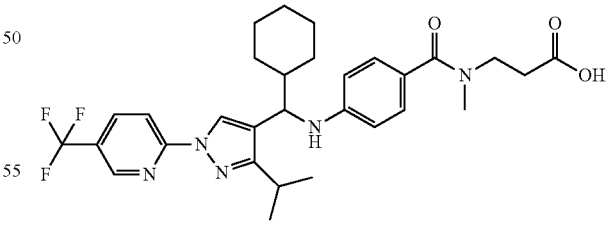

Using cyclohexyl{3-(1-methylethyl)-1-[5-(trifluoromethyl)pyridin-2-yl]-1H-pyrazol-4-yl}methanol (0.65 g) synthesized in Example 7(3) and ethyl 3-{[(4-aminophenyl)carbonyl](methyl)amino}propanoate (0.34 g) synthesized in Example 2(2) and in the same manner as in Example 1(7), the title object compound (0.16 g, 21%) was obtained as a white solid.

$^1$H NMR (300 MHz, CDCl$_3$) δ ppm 1.20-2.05 (m, 11H), 1.32-1.37 (m, 6H), 2.59-2.79 (m, 2H), 2.96-3.20 (m, 4H), 3.73 (t, J=7.5 Hz, 2H), 4.28 (d, J=6.0 Hz, 1H), 6.52 (d, J=8.7 Hz, 2H), 7.26 (d, J=8.7 Hz, 2H), 7.88-8.11 (m, 2H), 8.30 (s, 1H), 8.59 (s, 1H).

Example 9

3-[({4-[(cyclohexyl{3-cyclopropyl-1-[5-(trifluoromethyl)pyridin-2-yl]-1H-pyrazol-4-yl}methyl)amino]phenyl}carbonyl)amino]propanoic acid

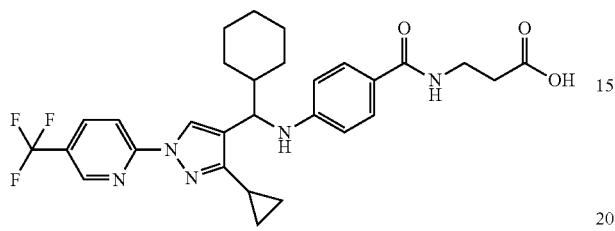

(1) methyl 3-cyclopropyl-1-[5-(trifluoromethyl)pyridin-2-yl]-1H-pyrazole-4-carboxylate Using methyl 3-cyclopropyl-3-oxopropanoate (2.8 g), dimethylformamide dimethylacetal (2.8 mL) and hydrazine monohydrate (1.1 mL) and in the same manner as in Example 1(3), a crude product of methyl 3-cyclopropyl-1H-pyrazole-4-carboxylate was obtained. This was dissolved in dimethylformamide (30 ml), potassium carbonate (4.2 g) and 2-chloro-5-trifluoromethylpyridine (3.6 g) were added, and the mixture was stirred at 100° C. for 2 hr. In the same manner as in Example 1(4), the title object compound (4.8 g, 77%) was obtained as a white solid.
$^{1}$H NMR (300 MHz, CDCl$_3$) δ ppm 1.02-1.10 (m, 4H), 2.55-2.70 (m, 1H), 3.89 (s, 3H), 8.00-8.03 (m, 2H), 8.66 (s, 1H), 8.96 (s, 1H).

(2) 3-cyclopropyl-1-[5-(trifluoromethyl)pyridin-2-yl]-1H-pyrazole-4-carbaldehyde Methyl 3-cyclopropyl-1-[5-(trifluoromethyl)pyridin-2-yl]-1H-pyrazole-4-carboxylate (4.8 g) synthesized above was treated in the same manner as in Example 1(5) to give the title object compound (1.5 g, 36%) as a white solid.
$^{1}$H NMR (300 MHz, CDCl$_3$) δ ppm 1.02-1.15 (m, 4H), 2.50-2.70 (m, 1H), 8.00-8.10 (m, 2H), 8.69 (s, 1H), 8.99 (s, 1H), 10.10 (s, 1H).

(3) cyclohexyl{3-cyclopropyl-1-[5-(trifluoromethyl)pyridin-2-yl]-1H-pyrazol-4-yl}methanol 3-Cyclopropyl-1-[5-(trifluoromethyl)pyridin-2-yl]-1H-pyrazole-4-carbaldehyde (1.5 g) synthesized above was treated in the same manner as in Example 1(6) to give the title object compound (2.1 g, 99%) as a white solid.
$^{1}$H NMR (300 MHz, CDCl$_3$) δ ppm 0.80-2.10 (m, 16H), 4.48 (dd, J=7.3, 3.0 Hz, 1H), 7.90-8.10 (m, 2H), 8.40 (s, 1H), 8.60 (s, 1H).

(4) 3-[({4-[(cyclohexyl{3-cyclopropyl-1-[5-(trifluoromethyl)pyridin-2-yl]-1H-pyrazol-4-yl}methyl)amino]phenyl}carbonyl)amino]propanoic acid Using cyclohexyl{3-cyclopropyl-1-[5-(trifluoromethyl)pyridin-2-yl]-1H-pyrazol-4-yl}methanol (0.50 g) synthesized above and ethyl 3-{[(4-aminophenyl)carbonyl]amino}propanoate (0.32 g) synthesized in Example 1(2) and in the same manner as in Example 1(7), the title object compound (0.15 g, 21%) was obtained as a white solid.
$^{1}$H NMR (300 MHz, CDCl$_3$) δ ppm 0.86-2.07 (m, 16H), 2.64 (t, J=5.5 Hz, 2H), 3.65 (q, J=5.9 Hz, 2H), 4.37 (d, J=6.4 Hz, 1H), 6.54-6.70 (m, 3H), 7.53 (d, J=8.3 Hz, 2H), 7.93 (s, 2H), 8.28 (s, 1H), 8.56 (s, 1H).

Example 10

3-[({4-[(cyclohexyl{3-cyclopropyl-1-[5-(trifluoromethyl)pyridin-2-yl]-1H-pyrazol-4-yl}methyl)amino]phenyl}carbonyl)(methyl)amino]propanoic acid

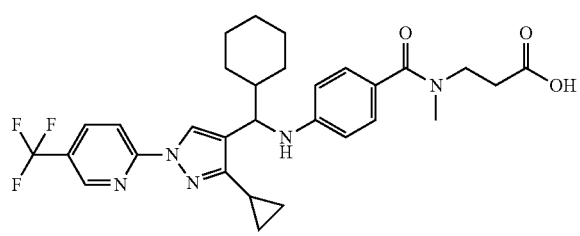 [SMILES: CN(CCC(=O)O)C(=O)c1ccc(NC(c2cn(-c3ccc(C(F)(F)F)cn3)nc2C2CC2)C2CCCCC2)cc1]

Using cyclohexyl{3-cyclopropyl-1-[5-(trifluoromethyl)pyridin-2-yl]-1H-pyrazol-4-yl}methanol (0.50 g) synthesized in Example 9(3) and ethyl 3-{[(4-aminophenyl)carbonyl](methyl)amino}propanoate (0.34 g) synthesized in Example 2(2) and in the same manner as in Example 1(7), the title object compound (0.19 g, 25%) was obtained as a white solid.
$^{1}$H NMR (300 MHz, CDCl$_3$) δ ppm 0.92-2.09 (m, 16H), 2.71 (t, J=6.2 Hz, 2H), 3.07 (s, 3H), 3.71 (t, J=6.4 Hz, 2H), 4.36 (d, J=6.4 Hz, 1H), 6.54 (d, J=8.7 Hz, 2H), 7.26 (d, J=8.7 Hz, 2H), 7.94 (s, 2H), 8.28 (s, 1H), 8.57 (s, 1H).

Example 11

3-[({4-[(cyclohexyl{3-(2-phenylethyl)-1-[5-(trifluoromethyl)pyridin-2-yl]-1H-pyrazol-4-yl}methyl)amino]phenyl}carbonyl)amino]propanoic acid

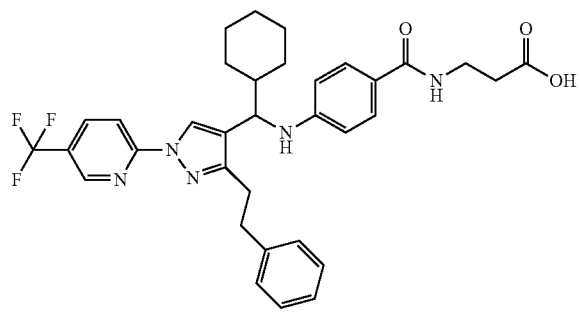 [SMILES: O=C(O)CCNC(=O)c1ccc(NC(c2cn(-c3ccc(C(F)(F)F)cn3)nc2CCc2ccccc2)C2CCCCC2)cc1]

(1) ethyl 3-(2-phenylethyl)-1-[5-(trifluoromethyl)pyridin-2-yl]-1H-pyrazole-4-carboxylate Using ethyl 3-oxo-5-phenylpentanoate (5.8 g), dimethylformamide dimethylacetal (3.6 mL) and hydrazine monohydrate (1.3 mL) and in the same manner as in Example 1(3), a crude product of ethyl 3-(2-phenylethyl)-1H-pyrazole-4-carboxylate was obtained. This was dissolved in dimethylformamide (30 ml), potassium carbonate (5.5 g) and 2-chloro-5-trifluoromethylpyridine (4.8 g) were added, and the mixture was stirred at 100° C. overnight. In the same manner as in Example 1(4), the title object compound (5.2 g, 50%) was obtained as a white solid.

¹H NMR (300 MHz, CDCl₃) δ ppm 1.39 (t, J=7.2 Hz, 3H), 3.00-3.15 (m, 2H), 3.22-3.39 (m, 2H), 4.34 (q, J=7.2 Hz, 2H), 7.15-7.38 (m, 10H), 7.99-8.17 (m, 2H), 8.69 (s, 1H), 9.01 (s, 1H).

(2) 3-(2-phenylethyl)-1-[5-(trifluoromethyl)pyridin-2-yl]-1H-pyrazole-4-carbaldehyde Ethyl 3-(2-phenylethyl)-1-[5-(trifluoromethyl)pyridin-2-yl]-1H-pyrazole-4-carboxylate (5.2 g) synthesized above was treated in the same manner as in Example 1(5) to give the title object compound (3.0 g, 65%) as a white solid. ¹H NMR (300 MHz, CDCl₃) δ ppm 2.98-3.17 (m, 2H), 3.22-3.41 (m, 2H), 7.11-7.47 (m, 5H), 7.99-8.22 (m, 2H), 8.71 (s, 1H), 9.04 (s, 1H), 9.99 (s, 1H).

(3) cyclohexyl{3-(2-phenylethyl)-1-[5-(trifluoromethyl)pyridin-2-yl]-1H-pyrazol-4-yl}methanol 3-(2-Phenylethyl)-1-[5-(trifluoromethyl)pyridin-2-yl]-1H-pyrazole-4-carbaldehyde (1.5 g) synthesized above was treated in the same manner as in Example 1(6) to give the title object compound (1.7 g, 95%) as a white solid.

¹H NMR (300 MHz, CDCl₃) δ ppm 0.83-2.02 (m, 12H), 2.92-3.23 (m, 4H), 4.28 (dd, J=7.3, 2.7 Hz, 1H), 7.15-7.40 (m, 5H), 7.93-8.13 (m, 2H), 8.42 (s, 1H), 8.64 (s, 1H).

(4) 3-[({4-[(cyclohexyl{3-(2-phenylethyl)-1-[5-(trifluoromethyl)pyridin-2-yl]-1H-pyrazol-4-yl}methyl)amino]phenyl}carbonyl)amino]propanoic acid Using cyclohexyl{3-(2-phenylethyl)-1-[5-(trifluoromethyl)pyridin-2-yl]-1H-pyrazol-4-yl}methanol (0.50 g) synthesized above and ethyl 3-{[(4-aminophenyl)carbonyl]amino}propanoate (0.28 g) synthesized in Example 1(2) and in the same manner as in Example 1(7), the title object compound (0.20 g, 28%) was obtained as a white solid.

¹H NMR (300 MHz, CDCl₃) δ ppm 0.84-1.97 (m, 11H), 2.45-2.64 (m, 2H), 2.87-3.18 (m, 4H), 3.49-3.67 (m, 2H), 4.16 (d, J=6.0 Hz, 1H), 6.41 (d, J=8.7 Hz, 2H), 6.61 (br. s., 1H), 7.15-7.34 (m, 5H), 7.49 (d, J=8.7 Hz, 2H), 7.87-8.10 (m, 2H), 8.31 (s, 1H), 8.57 (s, 1H).

Example 12

3-[({4-[(cyclohexyl{3-(2-phenylethyl)-1-[5-(trifluoromethyl)pyridin-2-yl]-1H-pyrazol-4-yl}methyl)amino]phenyl}carbonyl)(methyl)amino]propanoic acid

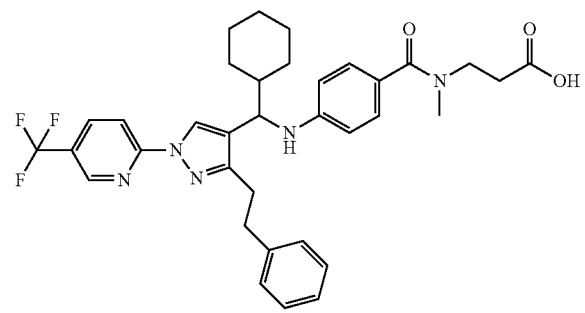 [SMILES: CN(CCC(=O)O)C(=O)c1ccc(NC(c2cn(-c3ccc(C(F)(F)F)cn3)nc2CCc2ccccc2)C2CCCCC2)cc1]

Using cyclohexyl{3-(2-phenylethyl)-1-[5-(trifluoromethyl)pyridin-2-yl]-1H-pyrazol-4-yl}methanol (0.50 g) synthesized in Example 11(3) and ethyl 3-{[(4-aminophenyl)carbonyl](methyl)amino}propanoate (0.35 g) synthesized in Example 2(2) and in the same manner as in Example 1(7), the title object compound (0.30 g, 41%) was obtained as a white solid.

¹H NMR (300 MHz, CDCl₃) δ ppm 0.93-2.01 (m, 11H), 2.59-2.74 (m, 2H), 2.89-3.20 (m, 7H), 3.71 (d, J=6.0 Hz, 2H), 4.18 (d, J=6.0 Hz, 1H), 6.43 (d, J=8.7 Hz, 2H), 7.16-7.37 (m, 5H), 7.90-8.13 (m, 2H), 8.32 (s, 1H), 8.60 (s, 1H).

Example 13

3-{[(4-{[{3-tert-butyl-1-[5-(trifluoromethyl)pyridin-2-yl]-1H-pyrazol-4-yl}(cyclohexyl)methyl]amino}phenyl)carbonyl]amino}propanoic acid

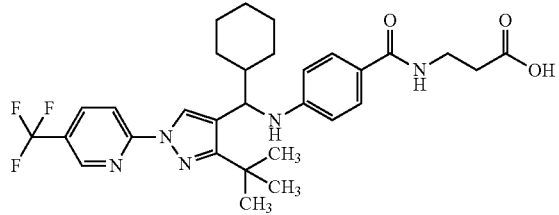 [SMILES: CC(C)(C)c1nn(-c2ccc(C(F)(F)F)cn2)cc1C(Nc1ccc(C(=O)NCCC(=O)O)cc1)C1CCCCC1]

(1) methyl 3-tert-butyl-1-[5-(trifluoromethyl)pyridin-2-yl]-1H-pyrazole-4-carboxylate Using ethyl 4,4-dimethyl-3-oxopentanoate (3.4 g), dimethylformamide dimethylacetal (2.8 mL) and hydrazine monohydrate (1.1 mL), and in the same manner as in Example 1(3), a crude product of methyl 3-tert-butyl-1H-pyrazole-4-carboxylate was obtained. This was dissolved in dimethylformamide (15 ml), potassium carbonate (1.2 g) and 2-chloro-5-trifluoromethylpyridine (1.7 g) were added, and the mixture was stirred at room temperature overnight. In the same manner as in Example 1(4), the title object compound (2.8 g, 43%) was obtained as a white solid.

¹H NMR (300 MHz, CDCl₃) δ ppm 1.38 (t, J=7.2 Hz, 3H), 1.49 (s, 9H), 4.32 (q, J=7.2 Hz, 2H), 7.98-8.21 (m, 2H), 8.68 (d, J=1.1 Hz, 1H), 9.03 (s, 1H).

(2) 3-tert-butyl-1-[5-(trifluoromethyl)pyridin-2-yl]-1H-pyrazole-4-carbaldehyde

Methyl 3-tert-butyl-1-[5-(trifluoromethyl)pyridin-2-yl]-1H-pyrazole-4-carboxylate (2.8 g) synthesized above was treated in the same manner as in Example 1(5) to give the title object compound (1.7 g, 93%) as a white solid.

¹H NMR (300 MHz, CDCl₃) δ ppm 1.49 (s, 9H), 7.98-8.21 (m, 2H), 8.68 (d, J=1.1 Hz, 1H), 9.09 (s, 1H), 10.11 (s, 1H).

(3) cyclohexyl{3-tert-butyl-1-[5-(trifluoromethyl)pyridin-2-yl]-1H-pyrazol-4-yl}methanol 3-Tert-butyl-1-[5-(trifluoromethyl)pyridin-2-yl]-1H-pyrazole-4-carbaldehyde (1.7 g) synthesized above was treated in the same manner as in Example 1(6) to give the title object compound (1.1 g, 49%) as a white solid.

¹H NMR (300 MHz, CDCl₃) δ ppm 0.79-2.20 (m, 12H), 1.43 (s, 9H), 4.65 (d, J=9.0 Hz, 1H), 7.91-8.15 (m, 2H), 8.52 (s, 1H), 8.62 (s, 1H).

(4) 3-{[(4-{[{3-tert-butyl-1-[5-(trifluoromethyl)pyridin-2-yl]-1H-pyrazol-4-yl}(cyclohexyl)methyl]amino}phenyl)carbonyl]amino}propanoic acid Using cyclohexyl{3-tert-butyl-1-[5-(trifluoromethyl)pyridin-2-yl]-1H-pyrazol-4-yl}methanol (0.53 g) synthesized above and ethyl 3-{[(4-aminophenyl)carbonyl]amino}propanoate (0.32 g) synthesized in Example 1(2) and in the same manner as in Example 1(7), the title object compound (0.12 g, 15%) was obtained as a white solid.

¹H NMR (300 MHz, CDCl₃) δ ppm 1.00-2.00 (m, 11H), 1.27 (s, 9H), 2.57-2.61 (m, 2H), 3.17-3.59 (m, 2H), 4.44 (br. s., 1H), 6.31-6.51 (m, 2H), 7.33-7.47 (m, 1H), 7.49-7.62 (m, 2H), 7.74-8.07 (m, 2H), 8.32-8.57 (m, 2H).

Example 14

3-{[(4-{[{3-tert-butyl-1-[5-(trifluoromethyl)pyridin-2-yl]-1H-pyrazol-4-yl}(cyclohexyl)methyl]amino}phenyl)carbonyl](methyl)amino}-propanoic acid

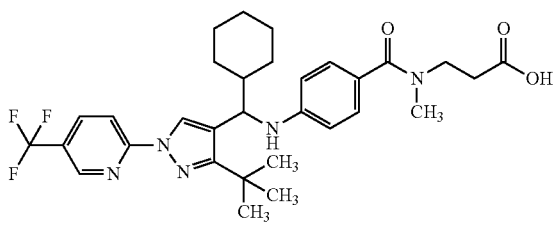 [SMILES: CN(CCC(=O)O)C(=O)c1ccc(NC(c2cn(-c3ccc(C(F)(F)F)cn3)nc2C(C)(C)C)C2CCCCC2)cc1]

Using cyclohexyl{3-tert-butyl-1-[5-(trifluoromethyl)pyridin-2-yl]-1H-pyrazol-4-yl}methanol (0.52 g) synthesized in Example 13(3) and ethyl 3-{[(4-aminophenyl)carbonyl](methyl)amino}propanoate (0.34 g) synthesized in Example 2(2) and in the same manner as in Example 1(7), the title object compound (0.13 g, 16%) was obtained as a white solid.

¹H NMR (300 MHz, CDCl₃) δ ppm 0.96-2.00 (m, 11H), 1.42 (s, 9H), 2.61-2.81 (m, 2H), 3.08 (s, 3H), 3.72 (t, J=6.4 Hz, 2H), 4.57 (d, J=6.1 Hz, 1H), 6.54 (d, J=8.7 Hz, 2H), 7.26 (d, J=8.7 Hz, 2H), 7.89-8.13 (m, 2H), 8.40 (s, 1H), 8.59 (s, 1H).

Example 15

3-({[4-({cyclohexyl[1-phenyl-3-(2-phenylethyl)-1H-pyrazol-4-yl]methyl}amino)phenyl]carbonyl}amino)propanoic acid

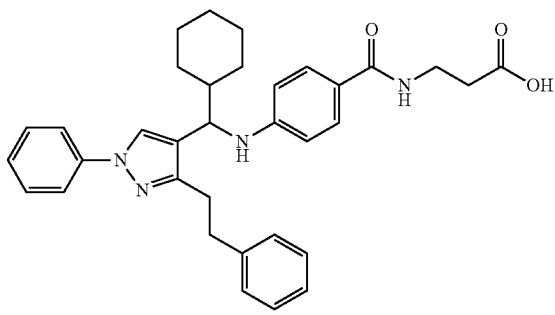 [SMILES: O=C(O)CCNC(=O)c1ccc(NC(c2cn(-c3ccccc3)nc2CCc2ccccc2)C2CCCCC2)cc1]

(1) ethyl 1-phenyl-3-(2-phenylethyl)-1H-pyrazole-4-carboxylate

A mixture of ethyl 3-oxo-5-phenylpentanoate (5.8 g) and dimethylformamide dimethylacetal (3.6 mL) was stirred at 100° C. overnight, and the mixture was allowed to cool to room temperature. To the reaction mixture were added ethanol (30 mL) and phenylhydrazine (2.9 g), and the mixture was further stirred at 100° C. for 8 hr. After allowing to cool, ethanol was evaporated under reduced pressure. Water was added to the residue, and the mixture was extracted with ethyl acetate. The extract was washed with brine, dried over magnesium sulfate and concentrated under reduced pressure. The residue was purified by silica gel column chromatography (ethyl acetate:hexane=1:10, volume ratio) to give the title object compound (7.1 g, 84%) as a yellow oil.

¹H NMR (300 MHz, CDCl₃) δ ppm 1.40 (t, J=7.2 Hz, 3H), 2.87 (dd, J=9.0, 6.6 Hz, 2H), 3.15-3.32 (m, 2H), 4.36 (q, J=7.2 Hz, 2H), 6.92-7.53 (m, J=7.5, 3.8, 3.8, 3.5 Hz, 10H), 8.05 (s, 1H).

(2) 1-phenyl-3-(2-phenylethyl)-1H-pyrazole-4-carbaldehyde

Ethyl 1-phenyl-3-(2-phenylethyl)-1H-pyrazole-4-carboxylate (7.1 g) synthesized above was treated in the same manner as in Example 1(5) to give the title object compound (4.6 g, 75%) as a white solid.

¹H NMR (300 MHz, CDCl₃) δ ppm 2.87 (t, J=7.8 Hz, 2H), 3.23 (t, J=7.6 Hz, 2H), 6.84-7.58 (m, 10H), 8.07 (s, 1H), 9.93 (s, 1H).

(3) cyclohexyl[1-phenyl-3-(2-phenylethyl)-1H-pyrazol-4-yl]methanol

1-Phenyl-3-(2-phenylethyl)-1H-pyrazole-4-carbaldehyde (2.6 g) synthesized above was treated in the same manner as in Example 1(6) to give the title object compound (2.9 g, 85%) as a white solid.

¹H NMR (300 MHz, CDCl₃) δ ppm 0.75-2.19 (m, 12H), 2.46-3.17 (m, 4H), 4.16 (dd, J=8.3, 2.7 Hz, 1H), 6.83-7.54 (m, 10H), 7.58 (s, 1H).

(4) 3-({[4-({cyclohexyl[1-phenyl-3-(2-phenylethyl)-1H-pyrazol-4-yl]methyl}amino)phenyl]carbonyl}amino)propanoic acid Using cyclohexyl[1-phenyl-3-(2-phenylethyl)-1H-pyrazol-4-yl]methanol (0.50 g) synthesized above and ethyl 3-{[(4-aminophenyl)carbonyl]amino}propanoate (0.33 g) synthesized in Example 1(2) and in the same manner as in Example 1(7), the title object compound (0.31 g, 41%) was obtained as a white solid.

¹H NMR (300 MHz, CDCl₃) δ ppm 0.94-2.03 (m, 11H), 2.40-2.56 (m, 2H), 2.67 (t, J=5.7 Hz, 2H), 2.91-3.07 (m, 2H), 3.68 (q, J=5.9 Hz, 2H), 4.20 (d, J=7.0 Hz, 1H), 6.52-6.58 (m, J=8.7 Hz, 3H), 6.82 (d, J=8.6 Hz, 2H), 7.12-7.22 (m, 4H), 7.35-7.65 (m, 11H).

Example 16

3-[{[4-({cyclohexyl[1-phenyl-3-(2-phenylethyl)-1H-pyrazol-4-yl]methyl}amino)phenyl]carbonyl}(methyl)amino]propanoic acid

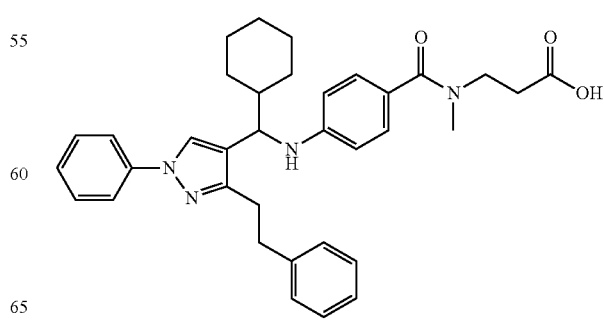

Using cyclohexyl[1-phenyl-3-(2-phenylethyl)-1H-pyrazol-4-yl]methanol (0.50 g) synthesized in Example 15(3) and ethyl 3-{[(4-aminophenyl)carbonyl](methyl)amino}propanoate (0.35 g) synthesized in Example 2(2) and in the same manner as in Example 1(7), the title object compound (0.37 g, 47%) was obtained as a white solid.

$^1$H NMR (300 MHz, CDCl$_3$) δ ppm 0.94-2.08 (m, 11H), 2.44-2.59 (m, 2H), 2.73 (d, J=6.0 Hz, 2H), 2.91-3.05 (m, 2H), 3.09 (s, 3H), 3.73 (t, J=6.4 Hz, 2H), 4.19 (d, J=6.8 Hz, 1H), 6.53 (d, J=8.7 Hz, 2H), 6.79-6.88 (m, 2H), 7.12-7.58 (m, 11H).

Example 17

3-{[(4-{[cyclohexyl(3-methyl-1-phenyl-1H-pyrazol-4-yl)methyl]amino}phenyl)carbonyl]amino}propanoic acid

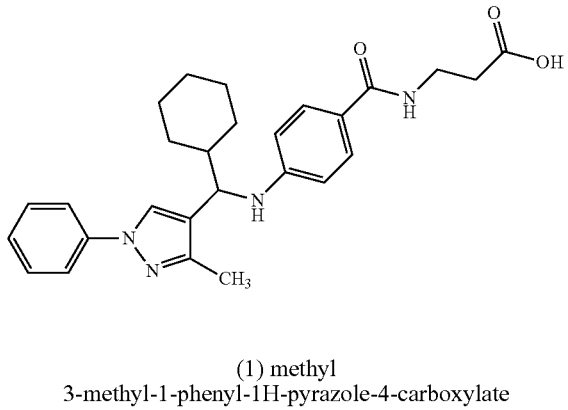

(1) methyl 3-methyl-1-phenyl-1H-pyrazole-4-carboxylate

Methyl 3-methyl-1H-pyrazole-4-carboxylate (14.4 g) synthesized in Example 1, (3) was dissolved in dimethylacetamide (200 mL), phenylboronic acid (25.0 g), copper acetate (36.4 g) and pyridine (32 mL) were added, and the mixture was stirred at room temperature overnight. The reaction mixture was filtered through celite, 1N hydrochloric acid (100 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=10:1, volume ratio) to give the title object compound (11.4 g, 53%) as a pale-yellow solid.

$^1$H NMR (300 MHz, CDCl$_3$) δ ppm 2.56 (s, 3H), 3.86 (s, 3H), 7.26-7.70 (m, 5H), 8.34 (s, 1H).

(2) 3-methyl-1-phenyl-1H-pyrazole-4-carbaldehyde

Methyl 3-methyl-1-phenyl-1H-pyrazole-4-carboxylate (11.4 g) synthesized above was treated in the same manner as in Example 1(5) to give the title object compound (3.8 g, 39%) as a pale-yellow solid.

$^1$H NMR (300 MHz, CDCl$_3$) δ ppm 2.59 (s, 3H), 7.27-7.72 (m, 5H), 8.34 (s, 1H), 10.00 (s, 1H).

(3) cyclohexyl(3-methyl-1-phenyl-1H-pyrazol-4-yl)methanol

3-Methyl-1-phenyl-1H-pyrazole-4-carbaldehyde (3.8 g) synthesized above was treated in the same manner as in Example 1(6) to give the title object compound (4.4 g, 79%) as a white solid.

$^1$H NMR (300 MHz, CDCl$_3$) δ ppm 0.80-2.20 (m, 11H), 2.34 (s, 3H), 3.61 (br s, 1H), 4.44 (d, J=7.2 Hz, 1H), 7.20-7.80 (m, 6H).

(4) 3-{[(4-{[cyclohexyl(3-methyl-1-phenyl-1H-pyrazol-4-yl)methyl]amino}phenyl)carbonyl]amino}propanoic acid Using cyclohexyl(3-methyl-1-phenyl-1H-pyrazol-4-yl)methanol (0.14 g) synthesized above and ethyl 3-{[(4-aminophenyl)carbonyl]amino}propanoate (0.15 g) synthesized in Example 1(2) and in the same manner as in Example 1(7), the title object compound (0.05 g, 31%) was obtained as a white solid.

$^1$H NMR (300 MHz, CDCl$_3$) δ ppm 1.04-2.21 (m, 12H), 2.36 (s, 3H), 2.65 (br. s., 2H), 3.67 (br. s., 2H), 4.20 (d, J=6.0 Hz, 1H), 6.49 (d, J=6.0 Hz, 2H), 6.55-6.71 (m, 1H), 7.14-7.74 (m, 8H).

Example 18

3-{[(4-{[cyclohexyl(3-methyl-1-phenyl-1H-pyrazol-4-yl)methyl]amino}phenyl)carbonyl](methyl)amino}propanoic acid

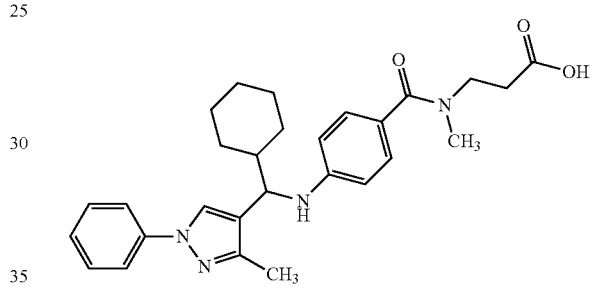

Using cyclohexyl(3-methyl-1-phenyl-1H-pyrazol-4-yl)methanol (0.14 g) synthesized in Example 17(3) and ethyl 3-{[(4-aminophenyl)carbonyl](methyl)amino}propanoate (0.15 g) synthesized in Example 2(2) and in the same manner as in Example 1(7), the title object compound (0.04 g, 23%) was obtained as a white solid.

$^1$H NMR (300 MHz, DMSO-d$_6$) δ ppm 0.87-2.10 (m, 12H), 2.25 (s, 3H), 2.47 (t, J=7.4 Hz, 2H), 2.89 (s, 3H), 3.51 (t, J=7.4 Hz, 2H), 4.16 (t, J=7.6 Hz, 1H), 6.22 (d, J=8.0 Hz, 1H), 6.58 (d, J=8.7 Hz, 2H), 7.10 (d, J=8.7 Hz, 2H), 7.22 (t, J=7.2 Hz, 1H), 7.43 (t, J=8.0 Hz, 1H).

Example 19

3-({[4-({[1-(4-chlorophenyl)-3-methyl-1H-pyrazol-4-yl](cyclohexyl)methyl}amino)phenyl]carbonyl}amino)propanoic acid

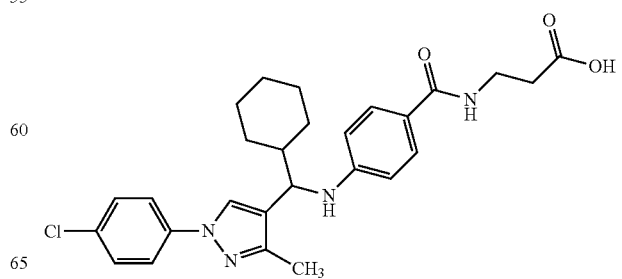

(1) methyl 1-(4-chlorophenyl)-3-methyl-1H-pyrazole-4-carboxylate

Using methyl 3-methyl-1H-pyrazole-4-carboxylate (6.25 g) synthesized in Example 1(3), 4-chlorophenylboronic acid (13.9 g), copper acetate (16.3 g) and pyridine (14.4 mL), and in the same manner as in Example 17(1), the title object compound (6.9 g, 62%) was obtained as a white solid.

$^1$H NMR (300 MHz, DMSO-$d_6$) δ ppm 2.54 (s, 3H), 3.85 (s, 3H), 7.43 (d, J=8.7 Hz, 2H), 7.62 (d, J=8.7 Hz, 2H), 8.31 (s, 1H).

(2) 1-(4-chlorophenyl)-3-methyl-1H-pyrazole-4-carbaldehyde

Methyl 1-(4-chlorophenyl)-3-methyl-1H-pyrazole-4-carboxylate (6.9 g) synthesized above was treated in the same manner as in Example 1(5) to give the title object compound (4.1 g, 68%) as a pale-yellow solid.

$^1$H NMR (300 MHz, CDCl$_3$) δ ppm 2.58 (s, 3H), 7.46 (d, J=9.0 Hz, 2H), 7.64 (d, J=9.0 Hz, 2H), 8.31 (s, 1H), 10.00 (s, 1H).

(3) [1-(4-chlorophenyl)-3-methyl-1H-pyrazol-4-yl](cyclohexyl)methanol 1-(4-Chlorophenyl)-3-methyl-1H-pyrazole-4-carbaldehyde (4.2 g) synthesized above was treated in the same manner as in Example 1(6) to give the title object compound (4.9 g, 85%) as a white solid.

$^1$H NMR (300 MHz, CDCl$_3$) δ ppm 0.88-2.00 (m, 11H), 2.32 (s, 3H), 3.59 (br. s., 1H), 4.43 (d, J=7.2 Hz, 1H), 7.38 (d, J=9.0 Hz, 2H), 7.58 (d, J=9.0 Hz, 2H), 7.76 (s, 1H).

(4) 3-({[4-({[1-(4-chlorophenyl)-3-methyl-1H-pyrazol-4-yl](cyclohexyl)methyl}amino)phenyl]carbonyl}amino)propanoic acid Using [1-(4-chlorophenyl)-3-methyl-1H-pyrazol-4-yl](cyclohexyl)methanol (0.46 g) synthesized above and ethyl 3-{[(4-aminophenyl)carbonyl]amino}propanoate (0.35 g) synthesized in Example 1(2) and in the same manner as in Example 1(7), the title object compound (0.42 g, 57%) was obtained as a white solid.

$^1$H NMR (300 MHz, DMSO-$d_6$) δ ppm 0.86-2.09 (m, 12H), 2.24 (s, 3H), 2.41 (t, J=7.1 Hz, 2H), 3.28-3.44 (m, 2H), 4.20 (t, J=7.7 Hz, 1H), 6.33 (d, J=7.9 Hz, 1H), 6.58 (d, J=8.9 Hz, 2H), 7.39-7.60 (m, 4H), 7.73 (d, J=9.0 Hz, 2H), 7.92-8.09 (m, 1H), 8.29 (s, 1H).

Example 20

3-[{[4-({[1-(4-chlorophenyl)-3-methyl-1H-pyrazol-4-yl](cyclohexyl)methyl}amino)phenyl]carbonyl}(methyl)amino]-propanoic acid

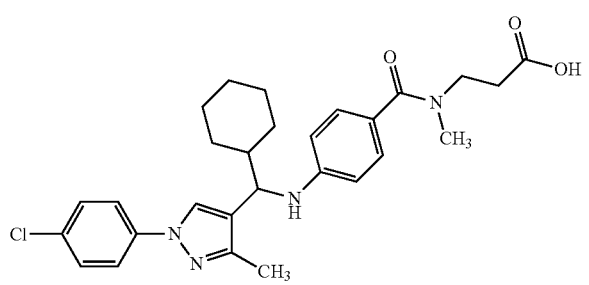 [SMILES: Cc1nn(-c2ccc(Cl)cc2)cc1C(Nc1ccc(C(=O)N(C)CCC(=O)O)cc1)C1CCCCC1]

Using [1-(4-chlorophenyl)-3-methyl-1H-pyrazol-4-yl](cyclohexyl)methanol (0.46 g) synthesized in Example 19(3) and ethyl 3-{[(4-aminophenyl)carbonyl](methyl)amino}propanoate (0.25 g) synthesized in Example 2(2) and in the same manner as in Example 1(7), the title object compound (0.41 g, 57%) was obtained as a white solid.

$^1$H NMR (300 MHz, DMSO-$d_6$) δ ppm 0.75-2.07 (m, 12H), 2.23 (s, 5H), 2.85 (br. s., 3H), 3.39-3.57 (m, 2H), 4.13 (br. s., 1H), 6.20 (d, J=7.0 Hz, 1H), 6.56 (d, J=8.5 Hz, 2H), 7.09 (d, J=8.5 Hz, 2H), 7.46 (d, J=8.7 Hz, 2H), 7.71 (d, J=8.7 Hz, 2H), 8.28 (s, 1H).

Example 21

3-({[4-({[1-(4-fluoro-2-methylphenyl)-3-methyl-1H-pyrazol-4-yl](cyclohexyl)methyl}amino)phenyl]carbonyl}amino)propanoic acid

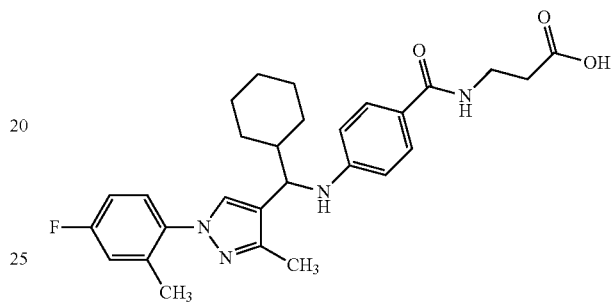

(1) methyl 1-(4-fluoro-2-methylphenyl)-3-methyl-1H-pyrazole-4-carboxylate

Using methyl 3-methyl-1H-pyrazole-4-carboxylate (6.25 g) synthesized in Example 1(3) and 4-fluoro-2-methylphenylboronic acid (13.9 g) and in the same manner as in Example 17(1), the title object compound (7.5 g, 68%) was obtained as a white solid.

$^1$H NMR (300 MHz, CDCl$_3$) δ ppm 2.26 (s, 3H), 2.54 (s, 3H), 3.85 (s, 3H), 6.80-7.35 (m, 3H), 7.97 (s, 1H).

(2) 1-(4-fluoro-2-methylphenyl)-3-methyl-1H-pyrazole-4-carbaldehyde

Methyl 1-(4-fluoro-2-methylphenyl)-3-methyl-1H-pyrazole-4-carboxylate (7.5 g) synthesized above was treated in the same manner as in Example 1(5) to give the title object compound (4.3 g, 83%) as a pale-yellow solid.

$^1$H NMR (300 MHz, CDCl$_3$) δ ppm 2.24 (s, 3H), 2.57 (s, 3H), 6.90-7.39 (m, 3H), 7.99 (s, 1H), 10.00 (s, 1H).

(3) cyclohexyl[1-(4-fluoro-2-methylphenyl)-3-methyl-1H-pyrazol-4-yl]methanol 1-(4-Fluoro-2-methylphenyl)-3-methyl-1H-pyrazole-4-carbaldehyde (4.3 g) synthesized above was treated in the same manner as in Example 1(6) to give the title object compound (6.1 g, 98%) as a white solid.

$^1$H NMR (300 MHz, CDCl$_3$) δ ppm 0.88-2.00 (m, 11H), 2.22 (s, 3H), 2.32 (s, 3H), 4.44 (dd, J=7.3, 3.3 Hz, 1H), 6.91-7.30 (m, 3H), 7.41 (s, 1H).

(4) 3-({[4-({[1-(4-fluoro-2-methylphenyl)-3-methyl-1H-pyrazol-4-yl](cyclohexyl)methyl}amino)phenyl]carbonyl}amino)propanoic acid Using cyclohexyl[1-(4-fluoro-2-methylphenyl)-3-methyl-1H-pyrazol-4-yl]methanol (0.50 g) synthesized above and ethyl 3-{[(4-aminophenyl)carbonyl]amino}propanoate (0.55 g) synthesized in Example 1(2) and in the same manner as in Example 1(7), the title object compound (0.52 g, 70%) was obtained as a white solid.

$^1$H NMR (300 MHz, DMSO-$d_6$) δ ppm 0.87-2.00 (m, 12H), 2.12 (s, 3H), 2.21 (s, 3H), 2.34 (t, J=7.1 Hz, 2H), 3.22-3.45 (m, 2H), 4.21 (t, J=7.7 Hz, 1H), 6.31 (d, J=8.1 Hz, 1H), 6.59 (d, J=8.9 Hz, 2H), 7.10-7.31 (m, 3H), 7.51 (d, J=8.7 Hz, 2H), 7.76 (s, 1H), 8.11 (s, 1H).

Example 22

3-[{[4-({[1-(4-fluoro-2-methylphenyl)-3-methyl-1H-pyrazol-4-yl](cyclohexyl)methyl}amino)phenyl]carbonyl}(methyl)amino]-propanoic acid

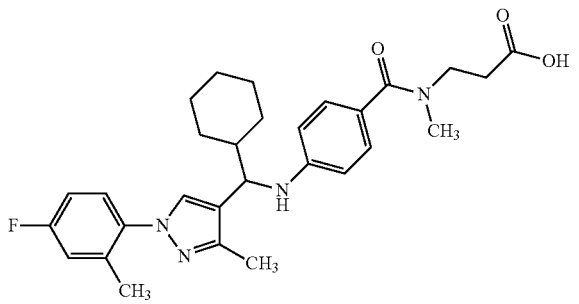 [SMILES: Cc1cc(F)ccc1-n1cc(C(Nc2ccc(C(=O)N(C)CCC(=O)O)cc2)C2CCCCC2)c(C)n1]

Using cyclohexyl[1-(4-fluoro-2-methylphenyl)-3-methyl-1H-pyrazol-4-yl]methanol (0.50 g) synthesized in Example 21(3) and ethyl 3-{[(4-aminophenyl)carbonyl](methyl)amino}propanoate (0.39 g) synthesized in Example 2(2) and in the same manner as in Example 1(7), the title object compound (0.48 g, 60%) was obtained as a white solid.

$^1$H NMR (300 MHz, DMSO-$d_6$) δ ppm 0.87-1.84 (m, 12H), 2.10 (s, 3H), 2.22 (s, 3H), 2.48-2.50 (m, 2H), 2.91 (s, 3H), 3.52 (m, 2H), 4.16 (d, J=9.0 Hz, 1H), 6.59 (d, J=8.7 Hz, 2H), 7.00-7.32 (m, 6H), 7.75 (s, 1H).

Example 23

3-({[4-({cyclohexyl[1-(4-methoxyphenyl)-3-methyl-1H-pyrazol-4-yl]methyl}amino)phenyl]carbonyl}amino)propanoic acid

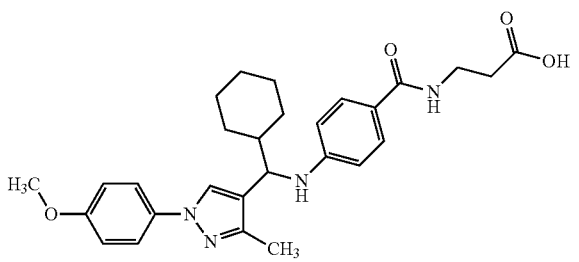 [SMILES: COc1ccc(-n2cc(C(Nc3ccc(C(=O)NCCC(=O)O)cc3)C3CCCCC3)c(C)n2)cc1]

(1) methyl 1-(4-methoxyphenyl)-3-methyl-1H-pyrazole-4-carboxylate

Using methyl 3-methyl-1H-pyrazole-4-carboxylate (5.7 g) synthesized in Example 1(3) and 4-methoxyphenylboronic acid (12.4 g) and in the same manner as in Example 17(1), the title object compound (6.5 g, 65%) was obtained as a white solid.

$^1$H NMR (300 MHz, CDCl$_3$) δ ppm 2.55 (s, 3H), 3.83 (s, 3H), 3.85 (s, 3H), 6.97 (d, J=9.0 Hz, 2H), 7.57 (d, J=9.0 Hz, 2H), 8.23 (s, 1H).

(2) 1-(4-methoxyphenyl)-3-methyl-1H-pyrazole-4-carbaldehyde

Methyl 1-(4-methoxyphenyl)-3-methyl-1H-pyrazole-4-carboxylate (6.6 g) synthesized above was treated in the same manner as in Example 1(5) to give the title object compound (4.1 g, 78%) as a pale-yellow solid.

$^1$H NMR (300 MHz, CDCl$_3$) δ ppm 2.58 (s, 3H), 3.86 (s, 3H), 6.99 (d, J=9.0 Hz, 2H), 7.59 (d, J=8.9 Hz, 2H), 8.24 (s, 1H), 9.98 (s, 1H).

(3) cyclohexyl[1-(4-methoxyphenyl)-3-methyl-1H-pyrazol-4-yl]methanol 1-(4-Methoxyphenyl)-3-methyl-1H-pyrazole-4-carbaldehyde (4.3 g) synthesized above was treated in the same manner as in Example 1(6) to give the title object compound (7.1 g, 98%) as a white solid.

$^1$H NMR (300 MHz, CDCl$_3$) δ ppm 0.88-1.97 (m, 11H), 2.33 (s, 3H), 3.59 (br. s., 1H), 3.83 (s, 3H), 4.43 (dd, J=7.3, 3.0 Hz, 1H), 6.94 (d, J=9.0 Hz, 2H), 7.53 (d, J=9.2 Hz, 2H), 7.70 (s, 1H).

(4) 3-({[4-({cyclohexyl[1-(4-methoxyphenyl)-3-methyl-1H-pyrazol-4-yl]methyl}amino)phenyl]carbonyl}amino)propanoic acid Using cyclohexyl[1-(4-methoxyphenyl)-3-methyl-1H-pyrazol-4-yl]methanol (0.68 g) synthesized above and ethyl 3-{[(4-aminophenyl)carbonyl]amino}propanoate (0.55 g) synthesized in Example 1(2) and in the same manner as in Example 1(7), the title object compound (0.44 g, 39%) was obtained as a white solid.

$^1$H NMR (300 MHz, DMSO-$d_6$) δ ppm 0.89-2.08 (m, 12H), 2.22 (s, 3H), 2.34-2.45 (m, 2H), 3.44-3.60 (m, 2H), 3.76 (s, 3H), 4.07-4.27 (m, 1H), 6.30 (d, J=9.0 Hz, 1H), 6.58 (d, J=8.9 Hz, 2H), 6.99 (d, J=9.2 Hz, 2H), 7.51 (d, J=8.9 Hz, 2H), 7.60 (d, J=9.2 Hz, 2H), 8.03 (br. s., 1H), 8.14 (s, 1H).

Example 24

3-[{[4-({cyclohexyl[1-(4-methoxyphenyl)-3-methyl-1H-pyrazol-4-yl]methyl}amino)phenyl]carbonyl}(methyl)amino]propanoic acid

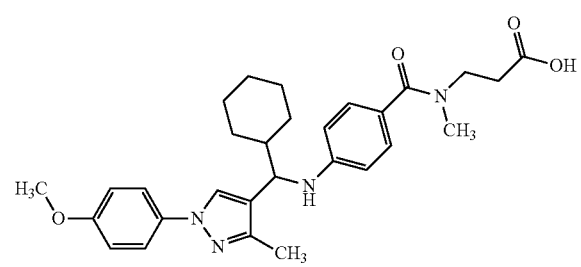 [SMILES: COc1ccc(-n2cc(C(Nc3ccc(C(=O)N(C)CCC(=O)O)cc3)C3CCCCC3)c(C)n2)cc1]

Using cyclohexyl[1-(4-methoxyphenyl)-3-methyl-1H-pyrazol-4-yl]methanol (0.68 g) synthesized in Example 23(3) and ethyl 3-{[(4-aminophenyl)carbonyl](methyl)amino}propanoate (0.42 g) synthesized in Example 2(2) and in the same manner as in Example 1(7), the title object compound (0.28 g, 24%) was obtained as a white solid.

$^1$H NMR (300 MHz, DMSO-$d_6$) δ ppm 0.87-2.10 (m, 12H), 2.23 (s, 3H), 2.45-2.50 (m, 2H), 2.90 (s, 3H), 3.44-3.60 (m, 2H), 3.77 (s, 3H), 4.13-4.15 (m, 1H), 6.21 (d, J=7.7 Hz, 1H), 6.58 (d, J=8.7 Hz, 2H), 6.99 (d, J=9.0 Hz, 2H), 7.10 (d, J=8.7 Hz, 2H), 7.60 (d, J=9.0 Hz, 2H), 8.14 (s, 1H).

Example 25

3-[({4-[(cyclohexyl{3-methyl-1-[4-(trifluoromethoxy)phenyl]-1H-pyrazol-4-yl}methyl)amino]phenyl}carbonyl)amino]propanoic acid

(1) methyl 3-methyl-1-[4-(trifluoromethoxy)phenyl]-1H-pyrazole-4-carboxylate

Using methyl 3-methyl-1H-pyrazole-4-carboxylate (6.8 g) synthesized in Example 1(3) and 4-trifluoromethoxyphenylboronic acid (20.0 g) and in the same manner as in Example 17(1), the title object compound (3.9 g, 27%) was obtained as a white solid.

$^1$H NMR (300 MHz, CDCl$_3$) δ ppm 2.55 (s, 3H), 3.86 (s, 3H), 7.32 (d, J=9.2 Hz, 2H), 7.71 (d, J=9.2 Hz, 2H), 8.32 (s, 1H).

(2) 3-methyl-1-[4-(trifluoromethoxy)phenyl]-1H-pyrazole-4-carbaldehyde

Methyl 3-methyl-1-[4-(trifluoromethoxy)phenyl]-1H-pyrazole-4-carboxylate (3.9 g) synthesized above was treated in the same manner as in Example 1(5) to give the title object compound (2.3 g, 66%) as a pale-yellow solid.

$^1$H NMR (300 MHz, CDCl$_3$) δ ppm 2.59 (s, 3H), 7.36 (d, J=9.0 Hz, 2H), 7.73 (d, J=9.0 Hz, 2H), 8.32 (s, 1H), 10.01 (s, 1H).

(3) cyclohexyl{3-methyl-1-[4-(trifluoromethoxy)phenyl]-1H-pyrazol-4-yl}methanol

3-Methyl-1-[4-(trifluoromethoxy)phenyl]-1H-pyrazole-4-carbaldehyde (2.6 g) synthesized above was treated in the same manner as in Example 1(6) to give the title object compound (2.2 g, 72%) as a pale-yellow solid.

$^1$H NMR (300 MHz, CDCl$_3$) δ ppm 0.89-1.91 (m, 11H), 2.33 (s, 3H), 4.44 (dd, J=7.2, 3.0 Hz, 1H), 7.26 (d, J=9.2 Hz, 2H), 7.66 (d, J=9.2 Hz, 2H), 7.77 (s, 1H).

(4) 3-[({4-[(cyclohexyl{3-methyl-1-[4-(trifluoromethoxy)phenyl]-1H-pyrazol-4-yl}methyl)amino]phenyl}carbonyl)amino]propanoic acid Using cyclohexyl{3-methyl-1-[4-(trifluoromethoxy)phenyl]-1H-pyrazol-4-yl}methanol (0.59 g) synthesized above and ethyl 3-{[(4-aminophenyl)carbonyl]amino}propanoate (0.55 g) synthesized in Example 1(2) and in the same manner as in Example 1(7), the title object compound (0.50 g, 55%) was obtained as a white solid.

$^1$H NMR (300 MHz, DMSO-d$_6$) δ ppm 0.85-2.11 (m, 11H), 2.24 (s, 3H), 2.39 (t, J=7.2 Hz, 2H), 3.30-3.43 (m, 2H), 4.20 (t, J=7.6 Hz, 1H), 6.34 (d, J=7.6 Hz, 1H), 6.58 (d, J=8.3 Hz, 2H), 7.34-7.61 (m, 4H), 7.82 (d, J=9.1 Hz, 2H), 8.02 (br. s., 1H).

Example 26

3-[({4-[(cyclohexyl{3-methyl-1-[4-(trifluoromethoxy)phenyl]-1H-pyrazol-4-yl}methyl)amino]phenyl}carbonyl)(methyl)amino]propanoic acid

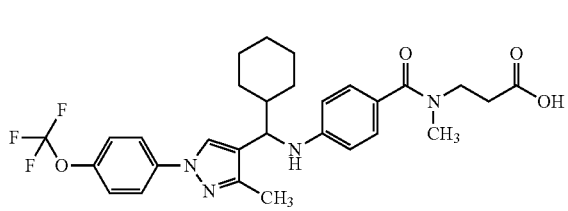 [SMILES: Cc1nn(-c2ccc(OC(F)(F)F)cc2)cc1C(Nc1ccc(C(=O)N(C)CCC(=O)O)cc1)C1CCCCC1]

Using cyclohexyl{3-methyl-1-[4-(trifluoromethoxy)phenyl]-1H-pyrazol-4-yl}methanol (0.97 g) synthesized in Example 25(3) and ethyl 3-{[(4-aminophenyl)carbonyl](methyl)amino}propanoate (0.63 g) synthesized in Example 2(2) and in the same manner as in Example 1(7), the title object compound (1.3 g, 63%) was obtained as a white solid.

$^1$H NMR (300 MHz, DMSO-d$_6$) δ ppm 0.89-2.06 (m, 11H), 2.24 (s, 3H), 2.40 (t, J=7.0 Hz, 2H), 3.28-3.45 (m, 5H), 4.20 (t, J=7.8 Hz, 1H), 6.34 (d, J=7.6 Hz, 1H), 6.58 (d, J=9.1 Hz, 2H), 7.35-7.57 (m, 4H), 7.82 (d, J=9.1 Hz, 2H), 8.01 (br s, 1H).

Example 27

3-[({4-[(cyclohexyl{3-methyl-1-[4-(trifluoromethyl)phenyl]-1H-pyrazol-4-yl}methyl)amino]phenyl}carbonyl)amino]propanoic acid

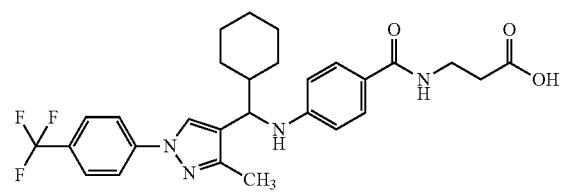 [SMILES: Cc1nn(-c2ccc(C(F)(F)F)cc2)cc1C(Nc1ccc(C(=O)NCCC(=O)O)cc1)C1CCCCC1]

(1) methyl 3-methyl-1-[4-(trifluoromethyl)phenyl]-1H-pyrazole-4-carboxylate

Using a crude product of methyl 3-methyl-1H-pyrazole-4-carboxylate (8.9 g) synthesized in Example 1(3) and 4-trifluoromethylphenylboronic acid (13.3 g) and in the same manner as in Example 17(1), the title object compound (2.0 g, 11%) was obtained as a white solid.

$^1$H NMR (300 MHz, CDCl$_3$) δ ppm 2.56 (s, 3H), 3.87 (s, 3H), 7.72 (d, J=9.2 Hz, 2H), 7.82 (d, J=9.2 Hz, 2H), 8.41 (s, 1H).

(2) 3-methyl-1-[4-(trifluoromethyl)phenyl]-1H-pyrazole-4-carbaldehyde

Methyl 3-methyl-1-[4-(trifluoromethyl)phenyl]-1H-pyrazole-4-carboxylate (2.0 g) synthesized above was treated in the same manner as in Example 1(5) to give the title object compound (0.6 g, 30%) as a pale-yellow solid.

$^1$H NMR (300 MHz, CDCl$_3$) δ ppm 2.56 (s, 3H), 7.72 (d, J=9.0 Hz, 2H), 7.82 (d, J=9.0 Hz, 2H), 8.40 (s, 1H), 9.98 (s, 1H).

(3) cyclohexyl{3-methyl-1-[4-(trifluoromethyl)phenyl]-1H-pyrazol-4-yl}methanol

3-Methyl-1-[4-(trifluoromethyl)phenyl]-1H-pyrazole-4-carbaldehyde (0.6 g) synthesized above was treated in the same manner as in Example 1(6) to give the title object compound (0.7 g, 93%) as a pale-yellow solid.

$^1$H NMR (300 MHz, CDCl$_3$) δ ppm 0.90-1.98 (m, 11H), 2.34 (s, 3H), 3.53-3.69 (m, 1H), 4.46 (d, J=7.0 Hz, 1H), 7.67 (d, J=9.0 Hz, 2H), 7.77 (d, J=9.0 Hz, 2H), 7.85 (s, 1H).

(4) 3-[({4-[(cyclohexyl{3-methyl-1-[4-(trifluoromethyl)phenyl]-1H-pyrazol-4-yl}methyl)amino]phenyl}carbonyl)amino]propanoic acid Using cyclohexyl{3-methyl-1-[4-(trifluoromethyl)phenyl]-1H-pyrazol-4-yl}methanol (0.36 g) synthesized above and ethyl 3-{[(4-aminophenyl)carbonyl]amino}propanoate (0.38 g) synthesized in Example 1(2) and in the same manner as in Example 1(7), the title object compound (77.5 mg, 7%) was obtained as a white solid.

$^1$H NMR (300 MHz, DMSO-d$_6$) δ ppm 0.90-2.12 (m, 11H), 2.26 (s, 3H), 2.41 (t, J=7.2 Hz, 2H), 3.23-3.44 (m, 2H), 4.22 (t, J=7.6 Hz, 1H), 6.36 (d, J=7.9 Hz, 1H), 6.60 (d, J=8.9 Hz, 2H), 7.52-7.80 (m, 4H), 7.93 (d, J=6.0 Hz, 2H), 7.97-8.10 (s, 1H).

Example 28

3-[({4-[(cyclohexyl{3-methyl-1-[4-(trifluoromethyl)phenyl]-1H-pyrazol-4-yl}methyl)amino]phenyl}carbonyl)(methyl)amino]propanoic acid

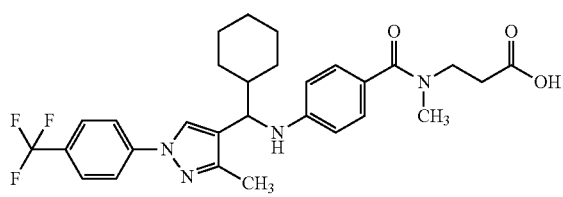 [SMILES: Cc1nn(-c2ccc(C(F)(F)F)cc2)cc1C(Nc1ccc(C(=O)N(C)CCC(=O)O)cc1)C1CCCCC1]

Using cyclohexyl{3-methyl-1-[4-(trifluoromethyl)phenyl]-1H-pyrazol-4-yl}methanol (0.36 g) synthesized in Example 27(3) and ethyl 3-{[(4-aminophenyl)carbonyl](methyl)amino}propanoate (0.40 g) synthesized in Example 2(2) and in the same manner as in Example 1(7), the title object compound (0.20 g, 35%) was obtained as a white solid.

$^1$H NMR (300 MHz, DMSO-d$_6$) δ ppm 0.81-2.10 (m, 11H), 2.28 (s, 3H), 2.42-2.50 (m, 2H), 2.90 (s, 3H), 3.52 (t, J=7.3 Hz, 2H), 4.18 (t, J=7.5 Hz, 1H), 6.26 (d, J=7.7 Hz, 1H), 6.59 (d, J=8.7 Hz, 2H), 7.11 (d, J=8.7 Hz, 2H), 7.80 (d, 2H), 7.94 (d, J=8.5 Hz, 2H), 8.43 (s, 1H).

Example 29

3-[({4-[(cyclohexyl{3-(methoxymethyl)-1-[5-(trifluoromethyl)pyridin-2-yl]-1H-pyrazol-4-yl}methyl)amino]phenyl}carbonyl)amino]propanoic acid

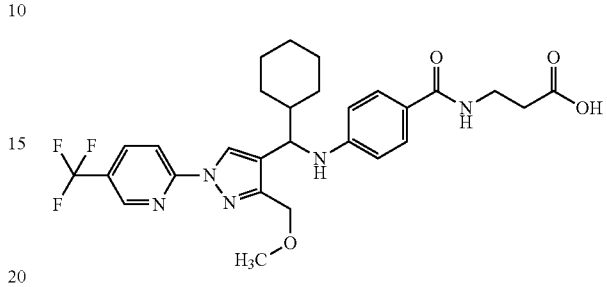

(1) methyl 3-(methoxymethyl)-1H-pyrazole-4-carboxylate

A mixture of methyl 4-methoxyacetoacetate (25.0 g) and dimethylformamide dimethylacetal (22.9 mL) was stirred at 100° C. for 2 hr, and the mixture was allowed to cool to room temperature. To the reaction mixture were added ethanol (250 mL) and hydrazine monohydrate (8.3 mL), and the mixture was heated under reflux for 12 hr. After allowing to cool, the reaction mixture was concentrated under reduced pressure, and water was added to the residue. The mixture was extracted with ethyl acetate to give a crude product (25.08 g) of methyl 3-methoxymethyl)-1H-pyrazole-4-carboxylate as a pale-yellow solid. The present compound was directly used for the next reaction.

$^1$H NMR (300 MHz, CDCl$_3$) δ ppm 3.51 (s, 3H), 3.84 (s, 3H), 4.85 (s, 2H), 7.99 (s, 1H).

(2) methyl 3-(methoxymethyl)-1-[5-(trifluoromethyl)pyridin-2-yl]-1H-pyrazole-4-carboxylate Using methyl 3-(methoxymethyl)-1H-pyrazole-4-carboxylate (7.4 g) synthesized above and 2-chloro-5-trifluoromethylpyridine (5.8 g) and in the same manner as in Example 1(4), the title object compound (5.2 g, 38%) was obtained as a white solid.

$^1$H NMR (300 MHz, CDCl$_3$) δ ppm 3.54 (s, 3H), 3.89 (s, 3H), 4.83 (s, 2H), 7.90-8.36 (m, 2H), 8.70 (s, 1H), 9.06 (s, 1H).

(3) 3-(methoxymethyl)-1-[5-(trifluoromethyl)pyridin-2-yl]-1H-pyrazole-4-carbaldehyde Methyl 3-(methoxymethyl)-1-[5-(trifluoromethyl)pyridin-2-yl]-1H-pyrazole-4-carboxylate (5.2 g) synthesized above was treated in the same manner as in Example 1(5) to give the title object compound (1.9 g, 40%) as a pale-yellow solid.

$^1$H NMR (300 MHz, CDCl$_3$) δ ppm 3.53 (s, 3H), 4.83 (s, 2H), 8.05-8.25 (m, 2H), 8.72 (s, 1H), 9.11 (s, 1H), 10.10 (s, 1H).

(4) cyclohexyl{3-(methoxymethyl)-1-[5-(trifluoromethyl)pyridin-2-yl]-1H-pyrazol-4-yl}methanol 3-(Methoxymethyl)-1-[5-(trifluoromethyl)pyridin-2-yl]-1H-pyrazole-4-carbaldehyde (1.9 g) synthesized above was treated in the same manner as in Example 1(6) to give the title object compound (2.4 g, 99%) as an oil.
$^1$H NMR (300 MHz, CDCl$_3$) δ ppm 0.90-2.25 (m, 11H), 3.02 (d, J=6.0 Hz, 1H), 3.46 (s, 3H), 4.43 (dd, J=7.7, 6.0 Hz, 1H), 4.52-4.69 (m, 2H), 7.93-8.11 (m, 2H), 8.44 (s, 1H), 8.65 (s, 1H).

(5) 3-[({4-[(cyclohexyl{3-(methoxymethyl)-1-[5-(trifluoromethyl)pyridin-2-yl]-1H-pyrazol-4-yl}methyl)amino]phenyl}carbonyl)amino]propanoic acid Using cyclohexyl{3-(methoxymethyl)-1-[5-(trifluoromethyl)pyridin-2-yl]-1H-pyrazol-4-yl}methanol (1.2 g) synthesized above and ethyl 3-{[(4-aminophenyl)carbonyl]amino}propanoate (0.94 g) synthesized in Example 1(2) and in the same manner as in Example 1(7), the title object compound (0.19 g, 10%) was obtained as a white solid.
$^1$H NMR (300 MHz, DMSO-d$_6$) δ ppm 1.90-2.10 (m, 11H), 2.40 (t, J=7.2 Hz, 2H), 3.24-3.45 (m, 5H), 4.28-4.71 (m, 3H), 6.37 (d, J=8.9 Hz, 1H), 6.64 (d, J=8.9 Hz, 2H), 7.51 (d, J=8.9 Hz, 2H), 8.00 (d, J=8.9 Hz, 2H), 8.33 (dd, J=9.0, 2.3 Hz, 1H).

Example 30

3-[({4-[(cyclohexyl{3-(methoxymethyl)-1-[5-(trifluoromethyl)pyridin-2-yl]-1H-pyrazol-4-yl}methyl)amino]phenyl}carbonyl)(methyl)amino]propanoic acid

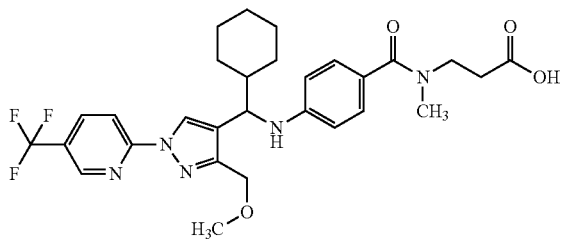 [SMILES: COCc1nn(-c2ccc(C(F)(F)F)cn2)cc1C(Nc1ccc(C(=O)N(C)CCC(=O)O)cc1)C1CCCCC1]

Using cyclohexyl{3-(methoxymethyl)-1-[5-(trifluoromethyl)pyridin-2-yl]-1H-pyrazol-4-yl}methanol (1.2 g) synthesized in Example 29(4) and ethyl 3-{[(4-aminophenyl)carbonyl](methyl)amino}propanoate (1.0 g) synthesized in Example 2(2) and in the same manner as in Example 1(7), the title object compound (0.17 g, 8%) was obtained as a white solid.
$^1$H NMR (300 MHz, DMSO-d$_6$) δ ppm 0.89-2.09 (m, 11H), 2.40-2.52 (m, 2H), 2.89 (s, 3H), 3.33 (s, 3H), 3.51 (t, J=7.3 Hz, 2H), 4.28-4.74 (m, 3H), 6.27 (d, J=8.7 Hz, 1H), 6.64 (d, J=8.7 Hz, 2H), 7.09 (d, J=8.7 Hz, 2H), 8.01 (d, J=8.9 Hz, 1H), 8.33 (dd, J=9.0, 2.3 Hz, 1H), 8.58 (s, 1H), 8.83 (s, 1H).

Example 31

3-{[(4-{[{1-[3-chloro-5-(trifluoromethyl)pyridin-2-yl]-3-methyl-1H-pyrazol-4-yl}(cyclohexyl)methyl]amino}phenyl)carbonyl]amino}propanoic acid

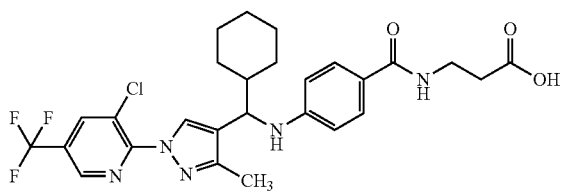 [SMILES: Cc1nn(-c2ncc(C(F)(F)F)cc2Cl)cc1C(Nc1ccc(C(=O)NCCC(=O)O)cc1)C1CCCCC1]

(1) methyl 1-[3-chloro-5-(trifluoromethyl)pyridin-2-yl]-3-methyl-1H-pyrazole-4-carboxylate Using methyl 3-methyl-1H-pyrazole-4-carboxylate (3.8 g) synthesized in Example 1(3) and 2,3-dichloro-5-trifluoromethylpyridine (5.8 g) and in the same manner as in Example 1(4), the title object compound (7.0 g, 78%) was obtained as a pale-yellow solid.
$^1$H NMR (300 MHz, CDCl$_3$) δ ppm 2.60 (s, 3H), 3.88 (s, 3H), 8.16 (d, J=1.5 Hz, 1H), 8.67-8.72 (m, 2H).

(2) 1-[3-chloro-5-(trifluoromethyl)pyridin-2-yl]-3-methyl-1H-pyrazole-4-carbaldehyde To a solution (150 mL) of methyl 1-[3-chloro-5-(trifluoromethyl)pyridin-2-yl]-3-methyl-1H-pyrazole-4-carboxylate (7.0 g) synthesized above in tetrahydrofuran was added dropwise diisobutylaluminum hydride (1.5M toluene solution, 58.4 mL) at 0° C. After stirring for 30 min, the reaction mixture was poured into 2N hydrochloric acid of 0° C., and the mixture was extracted with ethyl acetate. The extract was dried over magnesium sulfate, and the solvent was evaporated. The residue was treated in the same manner as in Example 1(5) to give the title object compound (1.7 g, 27%) as a pale-yellow solid.
$^1$H NMR (300 MHz, CDCl$_3$) δ ppm 2.63 (s, 3H), 8.19 (s, 1H), 8.70-8.73 (m, 2H), 10.07 (s, 1H).

(3){1-[3-chloro-5-(trifluoromethyl)pyridin-2-yl]-3-methyl-1H-pyrazol-4-yl}(cyclohexyl)methanol 1-[3-Chloro-5-(trifluoromethyl)pyridin-2-yl]-3-methyl-1H-pyrazole-4-carbaldehyde (1.7 g) synthesized above was treated in the same manner as in Example 1(6) to give the title object compound (1.5 g, 66%) as an oil.
$^1$H NMR (300 MHz, CDCl$_3$) δ ppm 0.94-2.02 (m, 11H), 2.39 (s, 3H), 4.47 (d, J=7.2 Hz, 1H), 8.05-8.14 (m, 1H), 8.18 (s, 1H), 8.66 (s, 2H).

(4) 3-{[(4-{[{1-[3-chloro-5-(trifluoromethyl)pyridin-2-yl]-3-methyl-1H-pyrazol-4-yl}(cyclohexyl)methyl]amino}phenyl)carbonyl]amino}propanoic acid Using {1-[3-chloro-5-(trifluoromethyl)pyridin-2-yl]-3-methyl-1H-pyrazol-4-yl}(cyclohexyl)methanol (0.74 g) synthesized above and ethyl 3-{[(4-aminophenyl)carbonyl]amino}propanoate (0.57 g) synthesized in Example 1(2) and in the same manner as in Example 1(7), the title object compound (0.11 g, 10%) was obtained as an amorphous pale-yellow solid.
$^1$H NMR (300 MHz, CDCl$_3$) δ ppm 0.91-1.98 (m, 11H), 2.37 (s, 3H), 2.50-2.72 (m, 2H), 3.44-3.75 (m, 2H), 4.24 (d, J=6.2 Hz, 1H), 6.51 (d, J=8.1 Hz, 2H), 6.66 (br. s., 1H), 6.89 (br. s., 1H), 7.52 (d, J=8.1 Hz, 2H), 7.98-8.20 (m, 2H), 8.60 (s, 1H).

Example 32

3-{[(4-{[{1-[3-chloro-5-(trifluoromethyl)pyridin-2-yl]-3-methyl-1H-pyrazol-4-yl}(cyclohexyl)methyl]amino}phenyl)carbonyl](methyl)amino}-propanoic acid

Using {1-[3-chloro-5-(trifluoromethyl)pyridin-2-yl]-3-methyl-1H-pyrazol-4-yl}(cyclohexyl)methanol (0.74 g) synthesized in Example 31(3) and ethyl 3-{[(4-aminophenyl)carbonyl](methyl)amino}propanoate (0.60 g) synthesized in Example 2(2) and in the same manner as in Example 1(7), the title object compound (54.4 mg, 5%) was obtained as an amorphous pale-yellow solid.

$^1$H NMR (300 MHz, CDCl$_3$) δ ppm 0.94-1.98 (m, 11H), 2.36 (s, 3H), 2.58-2.74 (m, 2H), 3.04 (s, 3H), 3.59-3.82 (m, 2H), 4.23 (d, J=6.0 Hz, 1H), 6.55 (d, J=8.5 Hz, 2H), 7.01 (br. s., 1H), 7.21 (d, J=8.5 Hz, 2H), 8.08 (s, 1H), 8.13 (s, 1H), 8.63 (s, 1H).

Example 33

3-[({4-[(cyclohexyl{3-(methoxymethyl)-1-[4-(trifluoromethoxy)phenyl]-1H-pyrazol-4-yl}methyl)amino]phenyl}carbonyl)amino]propanoic acid

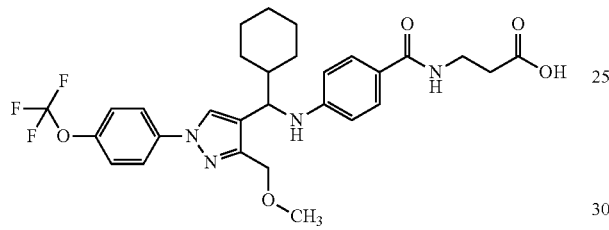

(1) methyl 3-(methoxymethyl)-1-[4-(trifluoromethoxy)phenyl]-1H-pyrazole-4-carboxylate Using methyl 4-methoxyacetoacetate (3.2 g), dimethylformamidedimethylacetal (2.9 mL) and 4-trifluoromethoxyphenylhydrazine hydrochloride (5.0 g) and in the same manner as in Example 15(1), the title object compound (3.4 g, 47%) was obtained as a white solid.

$^1$H NMR (300 MHz, CDCl$_3$) δ ppm 3.46 (s, 3H), 3.89 (s, 3H), 4.70 (s, 2H), 7.37 (d, J=9.0 Hz, 2H), 7.73 (d, J=9.0 Hz, 2H), 8.08 (s, 1H).

(2) 3-(methoxymethyl)-1-[4-(trifluoromethoxy)phenyl]-1H-pyrazole-4-carbaldehyde

Methyl 3-(methoxymethyl)-1-[4-(trifluoromethoxy)phenyl]-1H-pyrazole-4-carboxylate (3.4 g) synthesized above was treated in the same manner as in Example 1(5) to give the title object compound (2.9 g, 93%) as a pale-yellow solid.

$^1$H NMR (300 MHz, CDCl$_3$) δ ppm 3.41 (s, 3H), 4.70 (s, 2H), 7.37-8.08 (m, 5H), 10.00 (s, 1H).

(3) cyclohexyl{3-(methoxymethyl)-1-[4-(trifluoromethoxy)phenyl]-1H-pyrazol-4-yl}methanol 3-(Methoxymethyl)-1-[4-(trifluoromethoxy)phenyl]-1H-pyrazole-4-carbaldehyde (2.9 g) synthesized above was treated in the same manner as in Example 1(6) to give the title object compound (2.8 g, 77%) as a pale-yellow solid.

$^1$H NMR (300 MHz, CDCl$_3$) δ ppm 0.73-2.28 (m, 11H), 3.41 (s, 3H), 4.30-4.53 (m, 3H), 7.33 (d, J=8.5 Hz, 2H), 7.55-7.75 (m, 3H).

(4) 3-[({4-[(cyclohexyl{3-(methoxymethyl)-1-[4-(trifluoromethoxy)phenyl]-1H-pyrazol-4-yl}methyl)amino]phenyl}carbonyl)amino]propanoic acid Using cyclohexyl{3-(methoxymethyl)-1-[4-(trifluoromethoxy)phenyl]-1H-pyrazol-4-yl}methanol (0.75 g) synthesized above and ethyl 3-{[(4-aminophenyl)carbonyl]amino}propanoate (0.55 g) synthesized in Example 1(2) and in the same manner as in Example 1(7), the title object compound (0.43 g, 39%) was obtained as a colorless solid.

$^1$H NMR (300 MHz, DMSO-d$_6$) δ ppm 0.90-2.08 (m, 11H), 2.43 (t, J=7.1 Hz, 2H), 3.25-3.49 (m, 5H), 4.29-4.31 (m, 1H), 4.39-4.59 (m, 2H), 6.43 (d, J=8.5 Hz, 1H), 6.63 (d, J=8.9 Hz, 2H), 7.45-7.58 (m, 4H), 7.63-7.77 (m, 3H), 7.94-8.09 (m, 1H).

Example 34

3-[({4-[(cyclohexyl{3-(methoxymethyl)-1-[4-(trifluoromethoxy)phenyl]-1H-pyrazol-4-yl}methyl)amino]phenyl}carbonyl)(methyl)amino]propanoic acid

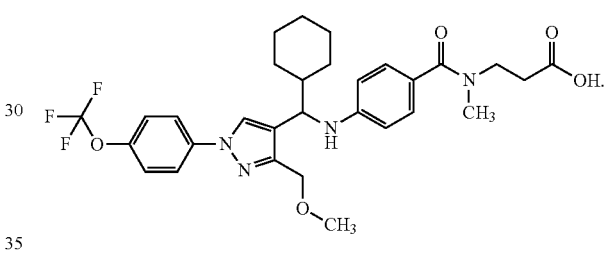

Using cyclohexyl{3-(methoxymethyl)-1-[4-(trifluoromethoxy)phenyl]-1H-pyrazol-4-yl}methanol (0.75 g) synthesized in Example 33(3) and ethyl 3-{[(4-aminophenyl)carbonyl](methyl)amino}propanoate (0.59 g) synthesized in Example 2(2) and in the same manner as in Example 1(7), the title object compound (0.42 g, 39%) was obtained as a colorless solid.

$^1$H NMR (300 MHz, DMSO-d$_6$) δ ppm 0.87-2.12 (m, 11H), 2.40-2.50 (m, 2H), 2.90 (s, 3H), 3.31 (s, 3H), 3.52 (t, J=7.2 Hz, 2H), 4.21-4.36 (m, 1H), 4.36-4.59 (m, 2H), 6.32 (d, J=8.7 Hz, 1H), 6.62 (d, J=8.7 Hz, 2H), 7.09 (d, J=8.5 Hz, 2H), 7.51 (d, J=8.5 Hz, 2H), 7.64-7.79 (m, 3H).

Example 35

3-({[4-({cyclohexyl[3-(methoxymethyl)-1-(4-methoxyphenyl)-1H-pyrazol-4-yl]methyl}amino)phenyl]carbonyl}amino)propanoic acid

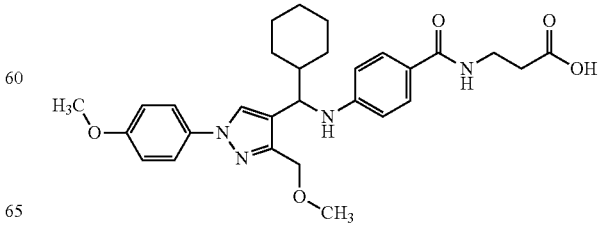

(1) methyl 3-(methoxymethyl)-1-(4-methoxyphenyl)-1H-pyrazole-4-carboxylate

Using methyl 4-methoxyacetoacetate (5.8 g), dimethylformamide dimethylacetal (5.4 mL) and 4-methoxyphenylhydrazine hydrochloride (7.0 g) and in the same manner as in Example 15(1), the title object compound (5.5 g, 50%) was obtained as a white solid.

$^1$H NMR (300 MHz, CDCl$_3$) δ ppm 3.42 (s, 3H), 3.87 (s, 3H), 3.88 (s, 3H), 4.64 (s, 2H), 7.00 (d, J=9.0 Hz, 2H), 7.53 (d, J=9.0 Hz, 2H), 8.05 (s, 1H).

(2) 3-(methoxymethyl)-1-(4-methoxyphenyl)-1H-pyrazole-4-carbaldehyde

Methyl 3-(methoxymethyl)-1-(4-methoxyphenyl)-1H-pyrazole-4-carboxylate (2.8 g) synthesized above was treated in the same manner as in Example 1(5) to give the title object compound (2.0 g, 83%) as a pale-yellow solid.

$^1$H NMR (300 MHz, CDCl$_3$) δ ppm 3.42 (s, 3H), 3.87 (s, 3H), 4.64 (s, 2H), 7.00-8.05 (m, 5H), 10.00 (s, 1H).

(3) cyclohexyl[3-(methoxymethyl)-1-(4-methoxyphenyl)-1H-pyrazol-4-yl]methanol 3-(Methoxymethyl)-1-(4-methoxyphenyl)-1H-pyrazole-4-carbaldehyde (2.0 g) synthesized above was treated in the same manner as in Example 1(6) to give the title object compound (2.1 g, 77%) as a white solid.

$^1$H NMR (300 MHz, CDCl$_3$) δ ppm 0.73-2.28 (m, 11H), 3.36 (s, 3H), 3.86 (s, 3H), 4.30-4.53 (m, 3H), 6.97 (d, J=8.9 Hz, 2H), 7.44 (d, J=8.9 Hz, 2H), 7.59 (s, 1H).

(4) 3-({[4-({cyclohexyl[3-(methoxymethyl)-1-(4-methoxyphenyl)-1H-pyrazol-4-yl]methyl}amino)phenyl]carbonyl}amino)propanoic acid Using cyclohexyl[3-(methoxymethyl)-1-(4-methoxyphenyl)-1H-pyrazol-4-yl]methanol (0.75 g) synthesized above and ethyl 3-{[(4-aminophenyl)carbonyl]amino}propanoate (0.54 g) synthesized in Example 1(2) and in the same manner as in Example 1(7), the title object compound (0.39 g, 33%) was obtained as a white solid.

$^1$H NMR (300 MHz, DMSO-d$_6$) δ ppm 0.89-2.11 (m, 11H), 2.44 (t, J=7.2 Hz, 2H), 3.32-3.46 (m, 2H), 3.80 (s, 3H), 4.22-4.56 (m, 3H), 6.40 (d, J=8.7 Hz, 1H), 6.62 (d, J=8.9 Hz, 2H), 7.04 (d, J=9.0 Hz, 2H), 7.36-7.55 (m, 4H), 7.57 (s, 1H), 8.01 (s, 1H).

Example 36

3-[{[4-({cyclohexyl[3-(methoxymethyl)-1-(4-methoxyphenyl)-1H-pyrazol-4-yl]methyl}amino)phenyl]carbonyl}(methyl)amino]propanoic acid

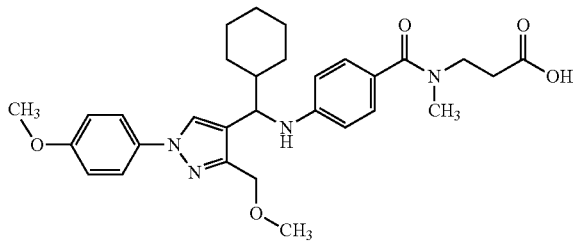 [SMILES: COCc1nn(-c2ccc(OC)cc2)cc1C(Nc1ccc(C(=O)N(C)CCC(=O)O)cc1)C1CCCCC1]

Using cyclohexyl[3-(methoxymethyl)-1-(4-methoxyphenyl)-1H-pyrazol-4-yl]methanol (0.75 g) synthesized in Example 35(3) and ethyl 3-{[(4-aminophenyl)carbonyl](methyl)amino}propanoate (0.57 g) synthesized in Example 2(2) and in the same manner as in Example 1(7), the title object compound (0.44 g, 36%) was obtained as a white solid.

$^1$H NMR (300 MHz, DMSO-d$_6$) δ ppm 0.90-2.12 (m, 11H), 2.42-2.50 (m, 2H), 2.91 (s, 3H), 3.26 (s, 3H), 3.52 (t, J=7.4 Hz, 2H), 3.80 (s, 3H), 4.14-4.54 (m, 3H), 6.29 (d, J=8.5 Hz, 1H), 6.62 (d, J=8.7 Hz, 2H), 6.97-7.19 (m, 4H), 7.44 (d, J=8.9 Hz, 2H), 7.58 (s, 1H).

Example 37

3-({[4-({cyclohexyl[3-(methoxymethyl)-1-phenyl-1H-pyrazol-4-yl]methyl}amino)phenyl]carbonyl}amino)propanoic acid

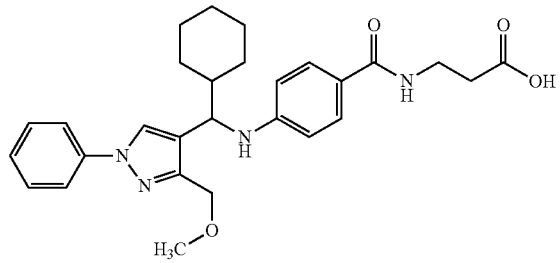 [SMILES: COCc1nn(-c2ccccc2)cc1C(Nc1ccc(C(=O)NCCC(=O)O)cc1)C1CCCCC1]

(1) methyl 3-(methoxymethyl)-1-phenyl-1H-pyrazole-4-carboxylate

Using methyl 4-methoxyacetoacetate (7.9 g), dimethylformamide dimethylacetal (7.2 mL) and phenylhydrazine hydrochloride (5.8 g) and in the same manner as in Example 15(1), the title object compound (7.3 g, 55%) was obtained as a pale-yellow solid.

$^1$H NMR (300 MHz, CDCl$_3$) δ ppm 3.44 (s, 3H), 3.89 (s, 3H), 4.68 (s, 2H), 7.30-7.70 (m, 5H), 8.08 (s, 1H).

(2) 3-(methoxymethyl)-1-phenyl-1H-pyrazole-4-carbaldehyde

Methyl 3-(methoxymethyl)-1-phenyl-1H-pyrazole-4-carboxylate (3.5 g) synthesized above was treated in the same manner as in Example 1(5) to give the title object compound (2.5 g, 82%) as a pale-yellow solid.

$^1$H NMR (300 MHz, CDCl$_3$) δ ppm 3.45 (s, 3H), 4.67 (s, 2H), 7.40-8.20 (m 6H), 10.08 (s, 1H).

(3) cyclohexyl[3-(methoxymethyl)-1-phenyl-1H-pyrazol-4-yl]methanol 3-(Methoxymethyl)-1-phenyl-1H-pyrazole-4-carbaldehyde (2.5 g) synthesized above was treated in the same manner as in Example 1(6) to give the title object compound (3.1 g, 75%) as a white solid.

$^1$H NMR (300 MHz, CDCl$_3$) δ ppm 0.73-2.40 (m, 11H), 3.38 (s, 3H), 4.40 (s, 2H), 4.42-4.55 (m, 1H), 7.27-7.70 (m, 6H).

(4) 3-({[4-({cyclohexyl[3-(methoxymethyl)-1-phenyl-1H-pyrazol-4-yl]methyl}amino)phenyl]carbonyl}amino)propanoic acid Using cyclohexyl[3-(methoxymethyl)-1-phenyl-1H-pyrazol-4-yl]methanol (0.50 g) synthesized above and ethyl 3-{[(4-aminophenyl)carbonyl]amino}propanoate (0.39 g) synthesized in Example 1(2) and in the same manner as in Example 1(7), the title object compound (0.37 g, 46%) was obtained as a white solid.
$^1$H NMR (300 MHz, CDCl$_3$) δ ppm 0.97-2.17 (m, 11H), 2.58-2.78 (m, 2H), 3.34 (s, 3H), 3.58-3.76 (m, 2H), 4.21-4.51 (m, 3H), 6.51-6.71 (m, 3H), 7.36-7.74 (m, 8H).

Example 38

3-[{[4-({cyclohexyl[3-(methoxymethyl)-1-phenyl-1H-pyrazol-4-yl]methyl}amino)phenyl]carbonyl}(methyl)amino]propanoic acid

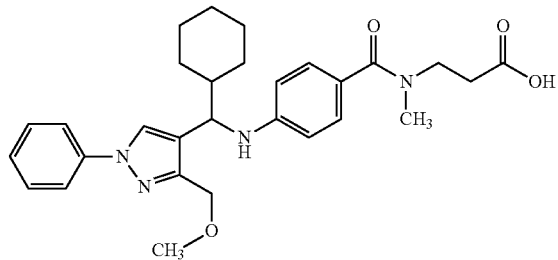 [SMILES: COCc1nn(-c2ccccc2)cc1C(Nc1ccc(C(=O)N(C)CCC(=O)O)cc1)C1CCCCC1]

Using cyclohexyl[3-(methoxymethyl)-1-phenyl-1H-pyrazol-4-yl]methanol (0.50 g) synthesized in Example 37(3) and ethyl 3-{[(4-aminophenyl)carbonyl](methyl)amino}propanoate (0.42 g) synthesized in Example 2(2) and in the same manner as in Example 1(7), the title object compound (0.33 g, 39%) was obtained as a white solid.
$^1$H NMR (300 MHz, CDCl$_3$) δ ppm 0.98-2.11 (m, 11H), 2.61-2.79 (m, 2H), 3.07 (s, 3H), 3.34 (s, 3H), 3.72 (t, J=6.5 Hz, 2H), 4.25-4.46 (m, 3H), 6.57 (d, J=8.5 Hz, 2H), 7.35-7.61 (m, 8H).

Example 39

3-[({4-[(cyclohexyl{3-ethyl-1-[4-(trifluoromethyl)phenyl]-1H-pyrazol-4-yl}methyl)amino]phenyl}carbonyl)amino]propanoic acid

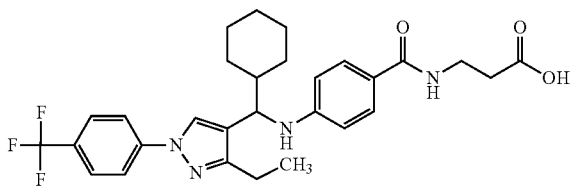 [SMILES: CCc1nn(-c2ccc(C(F)(F)F)cc2)cc1C(Nc1ccc(C(=O)NCCC(=O)O)cc1)C1CCCCC1]

(1) methyl 3-ethyl-1H-pyrazole-4-carboxylate

Using methyl 3-oxopentanoate (6.5 g) and in the same manner as in Example 1(3), the title object compound (7.0 g, 91%) was obtained as an oil.

$^1$H NMR (300 MHz, CDCl$_3$) δ ppm 1.32 (t, J=7.6 Hz, 3H), 3.02 (q, J=7.6 Hz, 2H), 3.84 (s, 3H), 7.96 (s, 1H), 11.28 (br. s., 1H).

(2) methyl 3-ethyl-1-[4-(trifluoromethyl)phenyl]-1H-pyrazole-4-carboxylate

Using methyl 3-ethyl-1H-pyrazole-4-carboxylate (4.6 g) synthesized above and in the same manner as in Example 17(1), the title object compound (6.0 g, 67%) was obtained as a white solid.
$^1$H NMR (300 MHz, CDCl$_3$) δ ppm 1.33 (t, J=7.4 Hz, 3H), 2.99 (q, J=7.5 Hz, 2H), 3.87 (s, 3H), 7.71-7.74 (m, 2H), 7.82-7.85 (m, 2H), 8.41 (s, 1H).

(3) 3-ethyl-1-[4-(trifluoromethyl)phenyl]-1H-pyrazole-4-carbaldehyde

Using methyl 3-ethyl-1-[4-(trifluoromethyl)phenyl]-1H-pyrazole-4-carboxylate (6.0 g) synthesized above and in the same manner as in Example 1(5), the title object compound (4.2 g, 78%) was obtained as a white solid.
$^1$H NMR (300 MHz, CDCl$_3$) δ ppm 1.37 (t, J=7.4 Hz, 3H), 3.00 (q, J=7.4 Hz, 2H), 7.74-7.77 (m, 2H), 7.84-7.87 (m, 2H), 8.42 (s, 1H), 10.03 (s, 1H).

(4) cyclohexyl{3-ethyl-1-[4-(trifluoromethyl)phenyl]-1H-pyrazol-4-yl}methanol

Using 3-ethyl-1-[4-(trifluoromethyl)phenyl]-1H-pyrazole-4-carbaldehyde (1.6 g) synthesized above and in the same manner as in Example 1(6), the title object compound (1.9 g, 91%) was obtained as a white solid.
$^1$H NMR (300 MHz, CDCl$_3$) δ ppm 0.86-1.43 (m, 8H), 1.52-1.90 (m, 5H), 2.05 (br.s, 1H), 2.72 (q, J=7.5 Hz, 2H), 4.46 (dd, J=7.2, 3.0 Hz, 1H), 7.60-7.71 (m, 2H), 7.71-7.82 (m, 2H), 7.86 (s, 1H).

(5) 3-({4-[(cyclohexyl{3-ethyl-1-[4-(trifluoromethyl)phenyl]-1H-pyrazol-4-yl}methyl)amino]benzoyl}amino)propanoic acid Using cyclohexyl{3-ethyl-1-[4-(trifluoromethyl)phenyl]-1H-pyrazol-4-yl}methanol (0.90 g) synthesized above and ethyl 3-{[(4-aminophenyl)carbonyl]amino}propanoate (0.75 g) synthesized in Example 1(2) and in the same manner as in Example 1(7), the title object compound (82 mg, 6%) was obtained as a white solid.
$^1$H NMR (300 MHz, CDCl$_3$) δ ppm 0.09-1.32 (m, 8H), 1.45-1.83 (m, 5H), 1.93-2.11 (m, 1H), 2.37 (t, J=7.0 Hz, 2H), 2.68 (qd, J=7.5, 4.0 Hz, 2H), 3.35 (q, J=5.7 Hz, 2H), 4.23 (t, J=7.8 Hz, 1H), 6.33 (d, J=7.9 Hz, 1H), 6.60 (d, J=8.7 Hz, 2H), 7.52 (d, J=8.9 Hz, 2H), 7.81 (d, J=8.7 Hz, 2H), 7.87-7.98 (m, 2H), 7.98-8.12 (m, 1H), 8.43 (s, 1H).

Example 40

3-[({4-[(cyclohexyl{3-ethyl-1-[4-(trifluoromethyl)phenyl]-1H-pyrazol-4-yl}methyl)amino]phenyl}carbonyl)(methyl)amino]propanoic acid

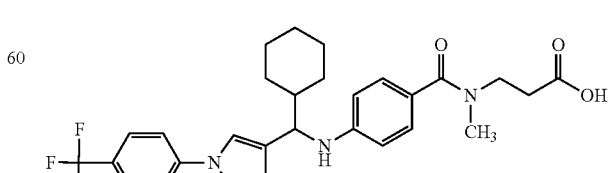

Using cyclohexyl{3-ethyl-1-[4-(trifluoromethyl)phenyl]-1H-pyrazol-4-yl}methanol (0.90 g) synthesized in Example 39(4) and ethyl 3-{[(4-aminophenyl)carbonyl](methyl)amino}propanoate (0.75 g) synthesized in Example 2(2) and in the same manner as in Example 1(7), the title object compound (85 mg, 6%) was obtained as a white solid.

$^1$H NMR (300 MHz, CDCl$_3$) δ ppm 0.88-1.24 (m, 8H), 1.46-1.80 (m, 5H), 1.92-2.09 (m, 1H), 2.46 (t, J=7.5 Hz, 2H), 2.68 (qd, J=7.5, 3.3 Hz, 2H), 2.98 (s, 3H), 3.50 (t, J=7.2 Hz, 2H), 4.20 (t, J=7.4 Hz, 1H), 6.22 (d, J=7.7 Hz, 1H), 6.60 (d, J=8.5 Hz, 2H), 7.10 (d, J=8.7 Hz, 2H), 7.81 (d, J=8.7 Hz, 2H), 7.86-8.05 (m, 2H), 8.43 (s, 1H).

Example 41

3-{[(4-{[(1-benzyl-3-methyl-1H-pyrazol-4-yl)(cyclohexyl)methyl]amino}phenyl)carbonyl]amino}propanoic acid

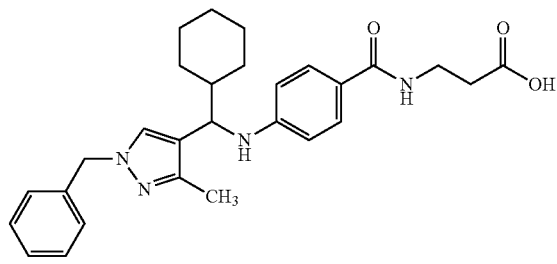 [SMILES: Cc1nn(Cc2ccccc2)cc1C(Nc1ccc(C(=O)NCCC(=O)O)cc1)C1CCCCC1]

(1) methyl 1-benzyl-3-methyl-1H-pyrazole-4-carboxylate

Methyl 3-methyl-1H-pyrazole-4-carboxylate (5.1 g) synthesized in Example 1(3) was dissolved in dimethylformamide (50 mL), potassium carbonate (5.3 g) and benzylbromide (4.6 mL) were added to at room temperature, and the mixture was stirred overnight. The reaction mixture was poured into water, and the mixture was extracted with diethyl ether. The extract was concentrated under reduced pressure, and the residue was purified by silica gel column chromatography (ethyl acetate:hexane=1:4, volume ratio) to give the title object compound (5.9 g, 71%) as an oil.

$^1$H NMR (300 MHz, CDCl$_3$) δ ppm 2.48 (s, 3H), 3.78 (s, 3H), 5.22 (s, 2H), 6.96-7.45 (m, 5H), 7.77 (s, 1H).

(2) 1-benzyl-3-methyl-1H-pyrazole-4-carbaldehyde

Using methyl 1-benzyl-3-methyl-1H-pyrazole-4-carboxylate (5.9 g) synthesized above and in the same manner as in Example 1(5), the title object compound (5.0 g, 96%) was obtained as an oil.

$^1$H NMR (300 MHz, CDCl$_3$) δ ppm 2.50 (s, 3H), 5.25 (s, 2H), 6.96-7.45 (m, 5H), 7.76 (s, 1H), 9.85 (s, 1H).

(3) (1-benzyl-3-methyl-1H-pyrazol-4-yl)(cyclohexyl)methanol

Using 1-benzyl-3-methyl-1H-pyrazole-4-carbaldehyde (5.0 g) synthesized above and in the same manner as in Example 1(6), the title object compound (3.3 g, 47%) was obtained as a white solid.

$^1$H NMR (300 MHz, CDCl$_3$) δ ppm 0.75-1.97 (m, 11H), 2.25 (s, 3H), 4.34 (d, J=7.4, 3.3 Hz, 1H), 5.20 (s, 2H), 7.00-7.50 (m, 6H).

(4) 3-{[(4-{[(1-benzyl-3-methyl-1H-pyrazol-4-yl)(cyclohexyl)methyl]amino}phenyl)carbonyl]amino}propanoic acid Using (1-benzyl-3-methyl-1H-pyrazol-4-yl)(cyclohexyl)methanol (1.0 g) synthesized above and ethyl 3-{[(4-aminophenyl)carbonyl]amino}propanoate (0.62 g) synthesized in Example 1(2) and in the same manner as in Example 1(7), the title object compound (28.6 mg, 4%) was obtained as a white solid.

$^1$H NMR (300 MHz, DMSO-d$_6$) δ ppm 0.77-2.01 (m, 11H), 2.12 (s, 3H), 2.38-2.46 (m, 2H), 3.35-3.44 (m, 2H), 3.99-4.21 (m, 1H), 5.11-5.19 (m, 2H), 6.25 (d, J=9.0 Hz, 1H), 6.52 (d, J=8.7 Hz, 2H), 7.04 (dd, J=7.5, 1.9 Hz, 2H), 7.25-7.60 (m, 6H), 7.99 (s, 1H).

Example 42

3-{[(4-{[(1-benzyl-3-methyl-1H-pyrazol-4-yl)(cyclohexyl)methyl]amino}phenyl)carbonyl](methyl)amino}-propanoic acid

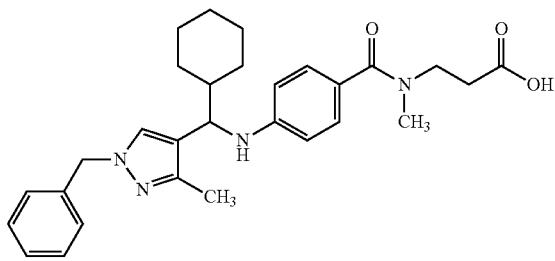 [SMILES: Cc1nn(Cc2ccccc2)cc1C(Nc1ccc(C(=O)N(C)CCC(=O)O)cc1)C1CCCCC1]

Using (1-benzyl-3-methyl-1H-pyrazol-4-yl)(cyclohexyl)methanol (0.65 g) synthesized in Example 41(3) and ethyl 3-{[(4-aminophenyl)carbonyl](methyl)amino}propanoate (0.65 g) synthesized in Example 2(2) and in the same manner as in Example 1(7), the title object compound (18.2 mg, 2%) was obtained as a white solid.

$^1$H NMR (300 MHz, DMSO-d$_6$ ppm 1.14-2.00 (br. s., 11H), 2.13 (s, 3H), 2.38-2.46 (m, 2H), 2.90 (s, 3H), 3.42-3.60 (m, 2H), 4.00-4.17 (m, 1H), 5.16 (s, 2H), 6.17 (d, J=6.0 Hz, 1H), 6.52 (d, J=8.5 Hz, 2H), 6.95-7.36 (m, 7H), 7.52 (s, 1H).

Example 43

3-({[4-({cyclohexyl[1-(1,1-dimethylpropyl)-3-methyl-1H-pyrazol-4-yl]methyl}amino)phenyl]carbonyl}amino)propanoic acid

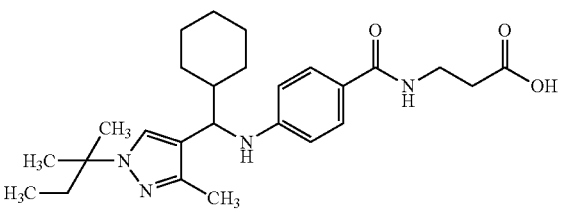 [SMILES: CCC(C)(C)n1cc(C(Nc2ccc(C(=O)NCCC(=O)O)cc2)C2CCCCC2)c(C)n1]

(1) methyl 1-(1,1-dimethylpropyl)-3-methyl-1H-pyrazole-4-carboxylate

Methyl 3-methyl-1H-pyrazole-4-carboxylate (10.8 g) synthesized in Example 1(3) was dissolved in acetonitrile (100 mL), 2-methyl-2-butene (16.3 mL) and p-toluenesulfonic acid monohydrate (4.4 g) were added, and the mixture was stirred in a sealed tube at 120° C. for 4 hr. The reaction mixture was poured into aqueous sodium hydrogen carbonate solution, and the mixture was extracted with ethyl acetate. The extract was concentrated under reduced pressure, and the residue was purified by silica gel column chromatography (ethyl acetate:hexane=1:4, volume ratio) to give the title object compound (4.6 g, 29%) as an oil.

$^1$H NMR (300 MHz, CDCl$_3$) δ ppm 0.68 (t, J=7.5 Hz, 3H), 1.53 (s, 6H), 1.88 (q, J=7.5 Hz, 2H), 2.46 (s, 3H), 3.80 (s, 3H), 7.90 (s, 1H).

(2) 1-(1,1-dimethylpropyl)-3-methyl-1H-pyrazole-4-carbaldehyde

Using methyl 1-(1,1-dimethylpropyl)-3-methyl-1H-pyrazole-4-carboxylate (4.6 g) synthesized above and in the same manner as in Example 1(5), the title object compound (3.0 g, 73%) was obtained as an oil.

$^1$H NMR (300 MHz, CDCl$_3$) δ ppm 0.68 (t, J=7.5 Hz, 3H), 1.53 (s, 6H), 1.88 (q, J=7.5 Hz, 2H), 2.46 (s, 3H), 7.90 (s, 1H), 9.85 (s, 1H).

(3) cyclohexyl[1-(1,1-dimethylpropyl)-3-methyl-1H-pyrazol-4-yl]methanol

Using 1-(1,1-dimethylpropyl)-3-methyl-1H-pyrazole-4-carbaldehyde (3.0 g) synthesized above and in the same manner as in Example 1(6), the title object compound (1.4 g, 32%) was obtained as a white solid.

$^1$H NMR (300 MHz, CDCl$_3$) δ ppm 0.67 (t, J=7.4 Hz, 3H), 0.88-2.00 (m, 13H), 1.52 (s, 6H), 2.24 (s, 3H), 3.61 (br. s., 1H), 4.34 (dd, J=7.6, 2.0 Hz, 1H), 7.34 (s, 1H).

(4) 3-({[4-({cyclohexyl[1-(1,1-dimethylpropyl)-3-methyl-1H-pyrazol-4-yl]methyl}amino)phenyl]carbonyl}amino)propanoic acid Using cyclohexyl[1-(1,1-dimethylpropyl)-3-methyl-1H-pyrazol-4-yl]methanol (1.0 g) synthesized above and ethyl 3-{[(4-aminophenyl)carbonyl]amino}propanoate (0.67 g) synthesized in Example 1(2) and in the same manner as in Example 1(7), the title object compound (0.41 g, 46%) was obtained as a white solid.

$^1$H NMR (300 MHz, CDCl$_3$) δ ppm 0.56 (t, J=7.6 Hz, 3H), 0.88-1.35 (m, 5H), 1.48 (s, 6H), 1.55-1.98 (m, 8H), 2.26 (s, 3H), 2.67 (t, J=5.9 Hz, 2H), 3.68 (q, J=5.8 Hz, 2H), 4.12 (d, J=6.1 Hz, 1H), 6.46 (d, J=8.7 Hz, 2H), 6.66 (t, J=6.2 Hz, 1H), 7.19 (s, 1H), 7.53 (d, J=9.1 Hz, 2H).

Example 44

3-({[4-({1-[3-cyclopropyl-1-(4-methoxyphenyl)-1H-pyrazol-4-yl]-3-methylbutyl}amino)phenyl]carbonyl}amino)propanoic acid

(1) methyl 3-cyclopropyl-1-(4-methoxyphenyl)-1H-pyrazole-4-carboxylate

Using methyl 3-cyclopropyl-3-oxopropanoate (3.7 g), dimethylformamide dimethylacetal (3.6 mL) and p-methoxyphenylhydrazine monohydrate (4.7 g) and in the same manner as in Example 15(1), the title object compound (5.9 g, 84%) was obtained as an oil.

$^1$H NMR (300 MHz, CDCl$_3$) δ ppm 0.60-1.01 (m, 4H), 1.86-2.01 (m, 1H), 3.85 (s, 3H), 3.87 (s, 3H), 6.98 (d, J=8.9 Hz, 2H), 7.41 (d, J=9.0 Hz, 2H), 7.98 (s, 1H).

(2) 3-cyclopropyl-1-(4-methoxyphenyl)-1H-pyrazole-4-carbaldehyde

Using methyl 3-cyclopropyl-1-(4-methoxyphenyl)-1H-pyrazole-4-carboxylate (5.9 g) synthesized above and in the same manner as in Example 1(5), the title object compound (3.6 g, 68%) was obtained as an oil.

$^1$H NMR (300 MHz, CDCl$_3$) δ ppm 0.73-1.10 (m, 4H), 1.87-2.07 (m, 1H), 3.88 (s, 3H), 7.01 (d, J=8.9 Hz, 2H), 7.44 (d, J=8.9 Hz, 2H), 8.03 (s, 1H), 10.03 (s, 1H).

(3) 1-[3-cyclopropyl-1-(4-methoxyphenyl)-1H-pyrazol-4-yl]-3-methylbutan-1-ol 3-Cyclopropyl-1-(4-methoxyphenyl)-1H-pyrazole-4-carbaldehyde (1.8 g) synthesized above was dissolved in tetrahydrofuran (10 mL), isobutylmagnesium bromide (1M tetrahydrofuran solution, 12 mL) was added dropwise at 0° C. In the same manner as in Example 1(6), the title object compound (1.8 g, 82%) was obtained as a white solid.

$^1$H NMR (300 MHz, CDCl$_3$) δ ppm 0.36-0.91 (m, 5H), 0.99 (d, J=6.4 Hz, 6H), 1.48-1.97 (m, 3H), 3.86 (s, 3H), 4.89-5.05 (m, 1H), 6.96 (d, J=9.0 Hz, 2H), 7.42 (d, J=9.0 Hz, 2H), 7.60 (s, 1H).

(4) 3-({[4-({1-[3-cyclopropyl-1-(4-methoxyphenyl)-1H-pyrazol-4-yl]-3-methylbutyl}amino)phenyl]carbonyl}amino)propanoic acid Using 1-[3-cyclopropyl-1-(4-methoxyphenyl)-1H-pyrazol-4-yl]-3-methylbutan-1-ol (0.5 g) synthesized above and ethyl 3-{[(4-aminophenyl)carbonyl]amino}propanoate (0.31 g) synthesized in Example 1(2) and in the same manner as in Example 1(7), the title object compound (23 mg, 3%) was obtained as a white solid.

$^1$H NMR (300 MHz, CDCl$_3$) δ ppm 0.42-0.84 (m, 4H), 0.99 (dd, J=13.8, 5.7 Hz, 6H), 1.60-1.80 (m, 4H), 2.60-2.65 (m., 2H), 3.64-3.66 (m., 2H), 3.84 (s, 3H), 4.69 (s, 1H), 6.55 (d, J=8.5 Hz, 2H), 6.70 (br. s., 1H), 6.94 (d, J=8.8 Hz, 2H), 7.39 (d, J=8.8 Hz, 2H), 7.50 (s, 1H), 7.58 (d, J=8.5 Hz, 2H).

Example 45

3-[{[4-({1-[3-cyclopropyl-1-(4-methoxyphenyl)-1H-pyrazol-4-yl]-3-methylbutyl}amino)phenyl]carbonyl}(methyl)amino]propanoic acid

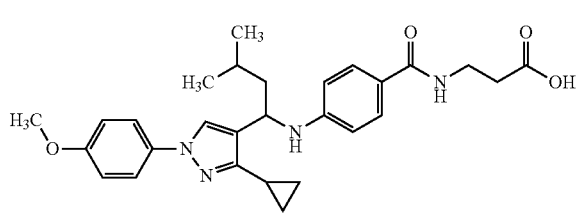 [SMILES: COc1ccc(-n2cc(C(CC(C)C)Nc3ccc(C(=O)NCCC(=O)O)cc3)c(C3CC3)n2)cc1]

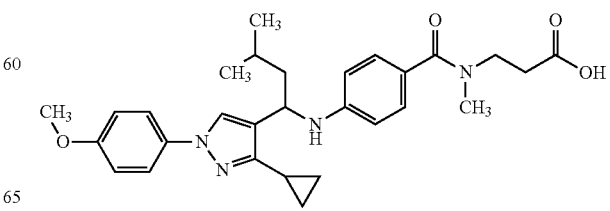

Using 1-[3-cyclopropyl-1-(4-methoxyphenyl)-1H-pyrazol-4-yl]-3-methylbutan-1-ol (0.5 g) synthesized in Example 44(3) and ethyl 3-{[(4-aminophenyl)carbonyl](methyl)amino}propanoate (0.33 g) synthesized in Example 2(2) and in the same manner as in Example 1(7), the title object compound (80 mg, 9%) was obtained as a white solid.

$^1$H NMR (300 MHz, CDCl$_3$) δ ppm 0.34-0.90 (m, 4H), 0.99 (dd, J=14.0, 4.8 Hz, 6H), 1.70-2.00 (m, 4H), 2.71 (br. s., 2H), 3.10 (s, 3H), 3.74 (s, 2H), 3.85 (s, 3H), 4.68 (br. s., 1H), 6.55 (d, J=8.7 Hz, 2H), 6.95 (dd, J=8.7, 1.3 Hz, 2H), 7.31-7.40 (m, 4H), 7.50 (s, 1H).

Example 46

3-({[4-({cyclohexyl[3-cyclopropyl-1-(4-methoxyphenyl)-1H-pyrazol-4-yl]methyl}amino)phenyl]carbonyl}amino)propanoic acid

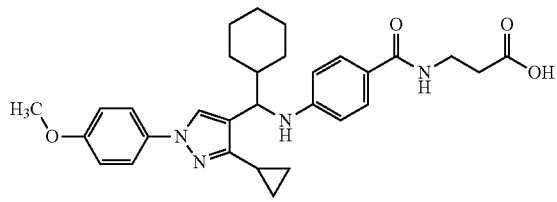 [SMILES: COc1ccc(-n2cc(C(Nc3ccc(C(=O)NCCC(=O)O)cc3)C3CCCCC3)c(C3CC3)n2)cc1]

(1) cyclohexyl[3-cyclopropyl-1-(4-methoxyphenyl)-1H-pyrazol-4-yl]methanol

Using 3-cyclopropyl-1-(4-methoxyphenyl)-1H-pyrazole-4-carbaldehyde (1.8 g) synthesized in Example 44(2) and in the same manner as in Example 1(6), the title object compound (2.1 mg, 85%) was obtained as a white solid.

$^1$H NMR (300 MHz, CDCl$_3$) δ ppm 0.29-2.27 (m, 16H), 3.86 (s, 3H), 4.57 (dd, J=8.1, 4.0 Hz, 1H), 6.96 (d, J=9.0 Hz, 2H), 7.42 (d, J=8.9 Hz, 2H), 7.59 (s, 1H).

(2) 3-({[4-({cyclohexyl[3-cyclopropyl-1-(4-methoxyphenyl)-1H-pyrazol-4-yl]methyl}amino)phenyl]carbonyl}amino)propanoic acid Using cyclohexyl[3-cyclopropyl-1-(4-methoxyphenyl)-1H-pyrazol-4-yl]methanol (0.5 g) synthesized above and ethyl 3-{[(4-aminophenyl)carbonyl]amino}propanoate (0.36 g) synthesized in Example 1(2) and in the same manner as in Example 1(7), the title object compound (43 mg, 5%) was obtained as a white solid.

$^1$H NMR (300 MHz, CDCl$_3$) δ ppm 0.30-2.20 (m., 16H), 2.65 (br. s., 2H), 3.66 (br. s., 2H), 3.85 (s, 3H), 4.45 (d, J=7.2 Hz, 1H), 6.55 (d, J=8.9 Hz, 2H), 6.60-6.69 (m, 1H), 6.94 (d, J=9.0 Hz, 2H), 7.38 (d, J=9.0 Hz, 2H), 7.47 (s, 1H), 7.56 (d, J=8.9 Hz, 2H).

Example 47

3-[{[4-({cyclohexyl[3-cyclopropyl-1-(4-methoxyphenyl)-1H-pyrazol-4-yl]methyl}amino)phenyl]carbonyl}(methyl)amino]propanoic acid

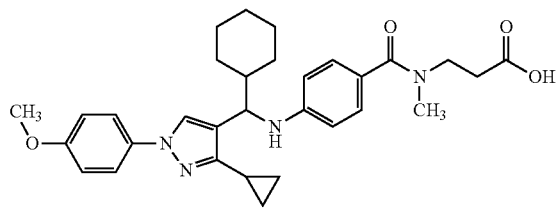 [SMILES: COc1ccc(-n2cc(C(Nc3ccc(C(=O)N(C)CCC(=O)O)cc3)C3CCCCC3)c(C3CC3)n2)cc1]

Using cyclohexyl[3-cyclopropyl-1-(4-methoxyphenyl)-1H-pyrazol-4-yl]methanol (0.5 g) synthesized in Example 46(1) and ethyl 3-{[(4-aminophenyl)carbonyl](methyl)amino}propanoate (0.38 g) synthesized in Example 2(2) and in the same manner as in Example 1(7), the title object compound (0.11 g, 14%) was obtained as a white solid.

$^1$H NMR (300 MHz, CDCl$_3$) δ ppm 0.31-2.00 (m, 16H), 2.70-2.74 (m, 2H), 3.10 (s, 3H), 3.74 (t, J=6.5 Hz, 2H), 3.85 (s, 3H), 4.45 (d, J=6.8 Hz, 1H), 6.55 (d, J=8.7 Hz, 2H), 6.95 (d, J=9.0 Hz, 2H), 7.30-7.42 (m, 4H), 7.47 (s, 1H).

Example 48

3-({[4-({1-[3-ethyl-1-(4-methoxyphenyl)-1H-pyrazol-4-yl]-3-methylbutyl}amino)phenyl]carbonyl}amino)propanoic acid

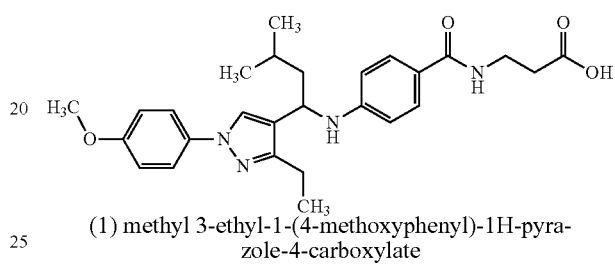

(1) methyl 3-ethyl-1-(4-methoxyphenyl)-1H-pyrazole-4-carboxylate

Using methyl 3-oxopentanoate (3.3 g), dimethylformamide dimethylacetal (3.6 mL) and p-methoxyphenylhydrazine monohydrate (4.7 g) and in the same manner as in Example 15(1), the title object compound (6.0 g, 84%) was obtained as an oil.

$^1$H NMR (300 MHz, CDCl$_3$) δ ppm 1.14 (t, J=7.5 Hz, 3H), 2.92 (q, J=7.3 Hz, 2H), 3.86 (s, 3H), 3.87 (s, 3H), 7.00 (d, J=9.0 Hz, 2H), 7.31 (d, J=9.0 Hz, 2H), 7.99 (s, 1H).

(2)-3-ethyl-1-(4-methoxyphenyl)-1H-pyrazole-4-carbaldehyde

Using methyl 3-ethyl-1-(4-methoxyphenyl)-1H-pyrazole-4-carboxylate (6.0 g) synthesized above and in the same manner as in Example 1(5), the title object compound (4.0 g, 76%) was obtained as a white solid.

$^1$H NMR (300 MHz, CDCl$_3$) δ ppm 1.18 (t, J=7.5 Hz, 3H), 2.92 (q, J=7.5 Hz, 2H), 3.88 (s, 3H), 6.91-7.08 (m, 2H), 7.12-7.22 (m, 2H), 7.33 (d, J=9.0 Hz, 2H), 8.03 (s, 1H), 9.97 (s, 1H).

(3) 1-[3-ethyl-1-(4-methoxyphenyl)-1H-pyrazol-4-yl]-3-methylbutan-1-ol

Using 3-ethyl-1-(4-methoxyphenyl)-1H-pyrazole-4-carbaldehyde (2.1 g) synthesized above and in the same manner as in Example 1(6), the title object compound (1.2 g, 47%) was obtained as a white solid.

$^1$H NMR (300 MHz, CDCl$_3$) δ ppm 0.98 (6H, d, J=6.4 Hz), 1.06 (3H, t, J=7.6 Hz), 1.50 (1H, d, J=4.3 Hz), 1.59-1.96 (3H, m), 2.70 (2H, q, J=7.5 Hz), 3.86 (3H, s), 4.77 (1H, dt, J=8.1, 5.1 Hz), 6.97 (2H, d, J=8.9 Hz), 7.31 (2H, d, J=8.9 Hz), 7.60 (1H, s).

(4) 3-({[4-({1-[3-ethyl-1-(4-methoxyphenyl)-1H-pyrazol-4-yl]-3-methylbutyl}amino)phenyl]carbonyl}amino)propanoic acid Using in 1-[3-ethyl-1-(4-methoxyphenyl)-1H-pyrazol-4-yl]-3-methylbutan-1-ol (0.5 g) synthesized above and ethyl 3-{[(4-aminophenyl)carbonyl]amino}propanoate (0.41 g) synthesized in Example 1(2) and in the same manner as in Example 1(7), the title object compound (0.2 g, 25%) was obtained as a white solid.

¹H NMR (300 MHz, CDCl₃) δ ppm 0.93-1.20 (m, 9H), 1.70-1.90 (m, 3H), 2.63 (d, J=6.0 Hz, 4H), 3.67 (d, J=5.5 Hz, 2H), 3.84 (s, 3H), 4.48 (t, J=6.8 Hz, 1H), 6.58 (d, J=8.1 Hz, 2H), 6.65-6.80 (m, 1H), 6.95 (d, J=8.9 Hz, 2H), 7.25-7.79 (m, 5H).

Example 49

3-[{[4-({1-[3-ethyl-1-(4-methoxyphenyl)-1H-pyrazol-4-yl]-3-methylbutyl}amino)phenyl]carbonyl}(methyl)amino]propanoic acid

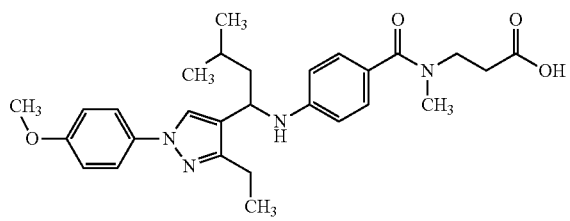 [SMILES: CCc1nn(-c2ccc(OC)cc2)cc1C(CC(C)C)Nc1ccc(C(=O)N(C)CCC(=O)O)cc1]

Using 1-[3-ethyl-1-(4-methoxyphenyl)-1H-pyrazol-4-yl]-3-methylbutan-1-ol (0.5 g) synthesized in Example 48(3) and ethyl 3-{[(4-aminophenyl)carbonyl](methyl)amino}propanoate (0.44 g) synthesized in Example 2(2) and in the same manner as in Example 1(7), the title object compound (0.1 g, 12%) was obtained as a white solid.

¹H NMR (300 MHz, CDCl₃) δ ppm 0.90-1.09 (m, 9H), 1.70-1.80 (m, 3H), 2.59-2.81 (m, 4H), 3.11 (s, 3H), 3.74 (t, J=6.5 Hz, 2H), 3.86 (s, 3H), 4.41-4.57 (m, 1H), 6.55 (d, J=8.7 Hz, 2H), 6.97 (d, J=8.9 Hz, 2H), 7.25-7.36 (m, 4H), 7.53 (s, 1H).

Example 50

3-({[4-({cyclohexyl[3-ethyl-1-(4-methoxyphenyl)-1H-pyrazol-4-yl]methyl}amino)phenyl]carbonyl}amino)propanoic acid

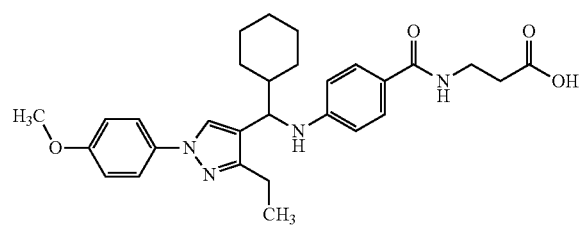 [SMILES: CCc1nn(-c2ccc(OC)cc2)cc1C(Nc1ccc(C(=O)NCCC(=O)O)cc1)C1CCCCC1]

(1) cyclohexyl[3-ethyl-1-(4-methoxyphenyl)-1H-pyrazol-4-yl]methanol

Using 3-ethyl-1-(4-methoxyphenyl)-1H-pyrazole-4-carbaldehyde (2.1 g) synthesized in Example 48(2) and in the same manner as in Example 1(6), the title object compound (1.9 g, 65%) was obtained as a white solid.

¹H NMR (300 MHz, CDCl₃) δ ppm 0.82-2.18 (m., 12H), 2.66 (q, J=7.6 Hz, 2H), 3.86 (s, 3H), 4.34 (dd, J=8.2, 3.7 Hz, 1H), 6.97 (d, J=9.0 Hz, 2H), 7.32 (d, J=9.0 Hz, 2H), 7.57 (s, 1H).

(2) 3-({[4-({cyclohexyl[3-ethyl-1-(4-methoxyphenyl)-1H-pyrazol-4-yl]methyl}amino)phenyl]carbonyl}amino)propanoic acid Using cyclohexyl[3-ethyl-1-(4-methoxyphenyl)-1H-pyrazol-4-yl]methanol (0.5 g) synthesized above and ethyl 3-{[(4-aminophenyl)carbonyl]amino}propanoate (0.38 g) synthesized in Example 1(2) and in the same manner as in Example 1(7), the title object compound (0.35 mg, 43%) was obtained as a white solid.

¹H NMR (300 MHz, CDCl₃) δ ppm 0.93 (t, J=7.5 Hz, 3H), 1.02-2.07 (m, 11H), 2.64 (t, J=7.3 Hz, 4H), 3.58-3.74 (m, 2H), 3.84 (s, 3H), 4.20 (d, J=7.0 Hz, 1H), 6.54 (d, J=8.7 Hz, 2H), 6.61-6.72 (m, 1H), 6.95 (d, J=9.0 Hz, 2H), 7.25-7.55 (m, 5H).

Example 51

3-[{[4-({cyclohexyl[3-ethyl-1-(4-methoxyphenyl)-1H-pyrazol-4-yl]methyl}amino)phenyl]carbonyl}(methyl)amino]propanoic acid

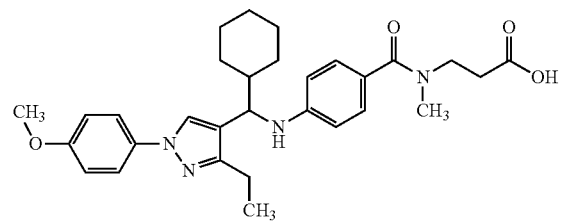 [SMILES: CCc1nn(-c2ccc(OC)cc2)cc1C(Nc1ccc(C(=O)N(C)CCC(=O)O)cc1)C1CCCCC1]

Using cyclohexyl[3-ethyl-1-(4-methoxyphenyl)-1H-pyrazol-4-yl]methanol (0.5 g) synthesized in Example 50(1) and ethyl 3-{[(4-aminophenyl)carbonyl](methyl)amino}propanoate (0.40 g) synthesized in Example 2(2) and in the same manner as in Example 1(7), the title object compound (0.15 mg, 18%) was obtained as a white solid.

¹H NMR (300 MHz, CDCl₃) δ ppm 0.94 (t, J=7.5 Hz, 3H), 1.01-2.11 (m, 12H), 2.56-2.83 (m, 4H), 3.09 (s, 3H), 3.73 (t, J=6.4 Hz, 2H), 3.85 (s, 3H), 4.19 (d, J=6.8 Hz, 1H), 6.54 (d, J=8.7 Hz, 2H), 6.96 (d, J=8.9 Hz, 2H), 7.27-7.37 (m, 4H), 7.48 (s, 1H).

Example 52

3-({[4-({cyclohexyl[1-(4-methoxyphenyl)-3-(1-methylethyl)-1H-pyrazol-4-yl]methyl}amino)phenyl]carbonyl}amino)propanoic acid

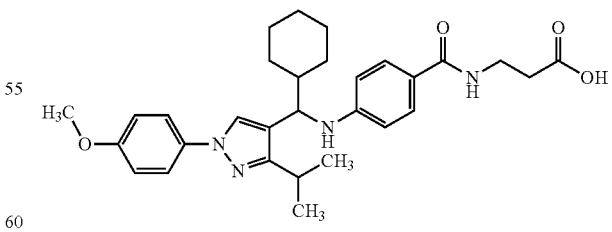

(1) methyl 1-(4-methoxyphenyl)-3-(1-methylethyl)-1H-pyrazole-4-carboxylate

Using methyl 4-methyl-3-oxopentanoate (3.6 g), dimethylformamide dimethylacetal (3.5 mL) and p-methoxyphenylhydrazine monohydrochloride (4.5 g) and in the same manner as in Example 15(1), the title object compound (3.5 g, 51%) was obtained as a pale-yellow solid.

$^1$H NMR (300 MHz, CDCl$_3$) δ ppm 1.37 (d, J=6.0 Hz, 6H), 3.20-3.40 (m, 1H), 3.86 (s, 3H), 3.90 (s, 3H), 6.98 (d, J=9.0 Hz, 2H), 7.27 (d, J=9.0 Hz, 2H), 7.29 (s, 1H), 7.99 (s, 1H).

(2) 1-(4-methoxyphenyl)-3-(1-methylethyl)-1H-pyrazole-4-carbaldehyde

Using methyl 1-(4-methoxyphenyl)-3-(1-methylethyl)-1H-pyrazole-4-carboxylate (3.5 g) synthesized above and in the same manner as in Example 1(5), the title object compound (2.6 g, 84%) was obtained as a pale-yellow solid.

$^1$H NMR (300 MHz, CDCl$_3$) δ ppm 1.37 (d, J=7.0 Hz, 6H), 3.12-3.25 (m, 1H), 3.88 (s, 3H), 7.01 (d, J=9.0 Hz, 2H), 7.29 (d, J=9.0 Hz, 2H), 8.05 (s, 1H), 10.06 (s, 1H).

(3) cyclohexyl[1-(4-methoxyphenyl)-3-(1-methylethyl)-1H-pyrazol-4-yl]methanol Using 1-(4-methoxyphenyl)-3-(1-methylethyl)-1H-pyrazole-4-carbaldehyde (1.3 g) synthesized above and in the same manner as in Example 1(6), the title object compound (1.4 g, 84%) was obtained as a white solid.

$^1$H NMR (300 MHz, CDCl$_3$) δ ppm 0.81-2.21 (m., 18H), 3.08 (quint, J=7.2 Hz, 1H), 3.86 (s, 3H), 4.52 (dd, 3=8.7, 3.8 Hz, 1H), 6.96 (d, J=9.0 Hz, 2H), 7.27 (d, J=9.0 Hz, 2H), 7.59 (s, 1H).

(4) 3-({[4-({cyclohexyl[1-(4-methoxyphenyl)-3-(1-methylethyl)-1H-pyrazol-4-yl]methyl}amino)phenyl]carbonyl}amino)propanoic acid Using cyclohexyl[1-(4-methoxyphenyl)-3-(1-methylethyl)-1H-pyrazol-4-yl]methanol (0.70 g) synthesized above and ethyl 3-{[(4-aminophenyl)carbonyl]amino}propanoate (0.52 g) synthesized in Example 1(2) and in the same manner as in Example 1(7), the title object compound (0.34 g, 30%) was obtained as a white solid.

$^1$H NMR (300 MHz, CDCl$_3$) δ ppm 1.10 (d, J=7.2 Hz, 3H), 1.18 (d, J=7.2 Hz, 3H), 1.20-2.06 (m, 12H), 2.64 (t, J=5.5 Hz, 2H), 3.10 (quint, J=7.3 Hz, 1H), 3.66 (q, J=5.8 Hz, 2H), 3.85 (s, 3H), 4.37 (d, J=7.2 Hz, 1H), 6.57 (d, J=8.7 Hz, 2H), 6.61-6.74 (m, 1H), 6.94 (d, J=8.7 Hz, 2H), 7.20-7.58 (m, 5H).

Example 53

3-[{[4-({cyclohexyl[1-(4-methoxyphenyl)-3-(1-methylethyl)-1H-pyrazol-4-yl]methyl}amino)phenyl]carbonyl}(methyl)amino]propanoic acid

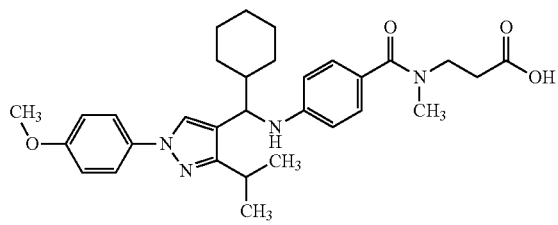 [SMILES: COc1ccc(-n2cc(C(Nc3ccc(C(=O)N(C)CCC(=O)O)cc3)C3CCCCC3)c(C(C)C)n2)cc1]

Using cyclohexyl[1-(4-methoxyphenyl)-3-(1-methylethyl)-1H-pyrazol-4-yl]methanol (0.70 g) synthesized in Example 52(3) and ethyl 3-{[(4-aminophenyl)carbonyl](methyl)amino}propanoate (0.55 g) synthesized in Example 2(2) and in the same manner as in Example 1(7), the title object compound (0.28 g, 24%) was obtained as a white solid.

$^1$H NMR (300 MHz, CDCl$_3$) δ ppm 1.11 (d, J=6.8 Hz, 3H), 1.19 (d, J=7.2 Hz, 3H), 1.20-2.13 (m, 11H), 2.72 (t, J=6.1 Hz, 2H), 3.03-3.23 (m, 4H), 3.73 (t, J=6.6 Hz, 2H), 3.85 (s, 3H), 4.36 (d, J=7.2 Hz, 1H), 6.55 (d, J=8.3 Hz, 2H), 6.95 (d, J=9.1 Hz, 2H), 7.21-7.35 (m, 4H), 7.50 (s, 1H).

Example 54

3-({[4-({1-[1-(4-methoxyphenyl)-3-(1-methylethyl)-1H-pyrazol-4-yl]-3-methylbutyl}amino)phenyl]carbonyl}amino)propanoic acid

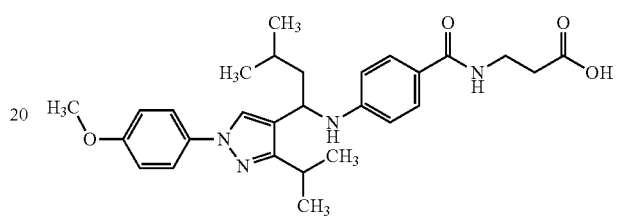

(1) 1-[1-(4-methoxyphenyl)-3-(1-methylethyl)-1H-pyrazol-4-yl]-3-methylbutan-1-ol Using 1-(4-methoxyphenyl)-3-(1-methylethyl)-1H-pyrazole-4-carbaldehyde (1.3 g) synthesized in Example 52(2) and in the same manner as in Example 1(6), the title object compound (1.6 g, 98%) was obtained as a white solid.

$^1$H NMR (300 MHz, CDCl$_3$) δ ppm 0.99 (d, J=5.7 Hz, 6H), 1.28 (dd, J=17.0, 7.2 Hz, 6H), 1.75-1.98 (m, 2H), 2.99-3.19 (m, 1H), 3.86 (s, 3H), 4.96 (dd, J=8.4, 4.4 Hz, 1H), 6.97 (d, J=8.9 Hz, 2H), 7.26 (d, J=9.0 Hz, 2H), 7.62 (s, 1H).

(2) 3-({[4-({1-[1-(4-methoxyphenyl)-3-(1-methylethyl)-1H-pyrazol-4-yl]-3-methylbutyl}amino)phenyl]carbonyl}amino)propanoic acid Using 1-[1-(4-methoxyphenyl)-3-(1-methylethyl)-1H-pyrazol-4-yl]-3-methylbutan-1-ol (0.57 g) synthesized above and ethyl 3-{[(4-aminophenyl)carbonyl]amino}propanoate (0.45 g) synthesized in Example 1(2) and in the same manner as in Example 1(7), the title object compound (28.0 mg, 3%) was obtained as a white solid.

$^1$H NMR (300 MHz, CDCl$_3$) δ ppm 0.97 (d, J=6.4 Hz, 3H), 1.02 (d, J=6.4 Hz, 3H), 1.11-1.98 (m, 9H), 2.67 (t, J=5.7 Hz, 2H), 2.98-3.19 (m, 1H), 3.68 (t, J=6.0 Hz, 2H), 3.85 (s, 3H), 4.66 (d, J=9.0 Hz, 1H), 6.51-6.77 (m, 3H), 6.95 (d, J=8.9 Hz, 2H), 7.26-7.59 (m, 5H).

Example 55

3-[{[4-({1-[1-(4-methoxyphenyl)-3-(1-methylethyl)-1H-pyrazol-4-yl]-3-methylbutyl}amino)phenyl]carbonyl}(methyl)amino]propanoic acid

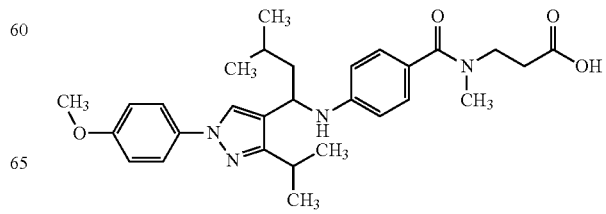

Using 1-[(1-(4-methoxyphenyl)-3-(1-methylethyl)-1H-pyrazol-4-yl]-3-methylbutan-1-ol (0.57 g) synthesized in Example 54(1) and ethyl 3-{[(4-aminophenyl)carbonyl](methyl)amino}propanoate (0.48 g) synthesized in Example 2(2) and in the same manner as in Example 1(7), the title object compound (8.0 mg, 1%) was obtained as a white solid.

$^1$H NMR (300 MHz, CDCl$_3$) δ ppm 0.97 (d, J=6.6 Hz, 3H), 1.02 (d, J=6.4 Hz, 3H), 1.11-2.01 (m, 9H), 2.72 (br. s., J=6.0 Hz, 2H), 2.96-3.24 (m, 4H), 3.74 (br. s., J=6.0 Hz, 2H), 3.86 (s, 3H), 4.63 (d, J=6.0 Hz, 1H), 6.50-6.70 (m, 2H), 6.96 (d, J=8.9 Hz, 2H), 7.21-7.38 (m, 4H), 7.59 (br. s., 1H).

Example 56

3-[({4-[(cyclohexyl{1-ethyl-3-[4-(trifluoromethyl)phenyl]-1H-pyrazol-5-yl}methyl)amino]phenyl}carbonyl)amino]propanoic acid

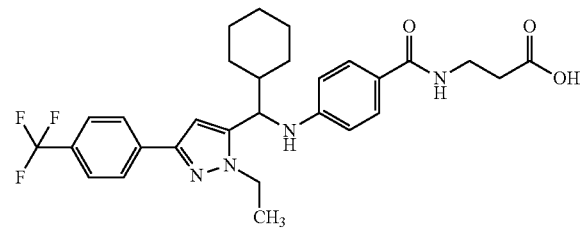 [SMILES: CCn1nc(-c2ccc(C(F)(F)F)cc2)cc1C(Nc1ccc(C(=O)NCCC(=O)O)cc1)C1CCCCC1]

(1) ethyl 1-ethyl-3-[4-(trifluoromethyl)phenyl]-1H-pyrazole-5-carboxylate

1-[4-(Trifluoromethyl)phenyl]ethanone (12.0 g) was dissolved in ethanol (100 mL), sodium hydride (60%, oily, 2.8 g) was carefully added under ice-cooling. After stirring for 5 min, diethyl oxalate (8.7 mL) was added, and the mixture was stirred at room temperature overnight. The precipitate (18.6 g) was collected, and to 7.3 g thereof were added ethanol (16 mL), 6N hydrochloric acid (4.3 mL) and ethylhydrazine (1.6 g), and the mixture was stirred at room temperature overnight. The solvent was evaporated under reduced pressure, and the residue was extracted with ethyl acetate. The extract was washed with brine, dried over magnesium sulfate, and concentrated under reduced pressure. The residue was purified by silica gel column chromatography (ethyl acetate:hexane=1:4, volume ratio) to give the title object compound (5.7 g, 78%) as an oil.

$^1$H NMR (300 MHz, CDCl$_3$) δ ppm 1.42 (t, J=7.2 Hz, 3H), 1.50 (t, J=7.2 Hz, 3H), 4.39 (q, J=7.2 Hz, 2H), 4.66 (q, J=7.2 Hz, 2H), 7.17 (s, 1H), 7.65 (d, J=8.1 Hz, 2H), 7.92 (d, J=8.1 Hz, 2H).

(2) 1-ethyl-3-[4-(trifluoromethyl)phenyl]-1H-pyrazole-5-carbaldehyde

Using ethyl 1-ethyl-3-[4-(trifluoromethyl)phenyl]-1H-pyrazole-5-carboxylate (5.7 g) synthesized above and in the same manner as in Example 1(5), the title object compound (3.2 g, 68%) was obtained as a white solid.

$^1$H NMR (300 MHz, CDCl$_3$) δ ppm 1.48 (t, J=7.2 Hz, 3H), 4.25 (q, J=7.2 Hz, 2H), 6.85 (s, 1H), 7.54 (d, J=8.0 Hz, 2H), 7.77 (d, J=8.0 Hz, 2H), 10.01 (s, 1H).

(3) cyclohexyl{1-ethyl-3-[4-(trifluoromethyl)phenyl]-1H-pyrazol-5-yl}methanol

Using 1-ethyl-3-[4-(trifluoromethyl)phenyl]-1H-pyrazole-5-carbaldehyde (2.28 g) synthesized above and in the same manner as in Example 1(6), the title object compound (1.2 g, 41%) was obtained as a white solid.

$^1$H NMR (300 MHz, CDCl$_3$) δ ppm 0.92-2.00 (m, 11H), 1.39 (t, J=7.2 Hz, 3H), 2.27 (d, J=4.7 Hz, 1H), 4.00-4.25 (m, 2H), 4.53 (dd, J=6.4, 4.7 Hz, 1H), 6.23 (s, 1H), 7.53 (d, J=7.9 Hz, 2H), 7.72 (d, J=7.9 Hz, 2H).

(4) 3-[({4-[(cyclohexyl{1-ethyl-3-[4-(trifluoromethyl)phenyl]-1H-pyrazol-5-yl}methyl)amino]phenyl}carbonyl)amino]propanoic acid Using cyclohexyl{1-ethyl-3-[4-(trifluoromethyl)phenyl]-1H-pyrazol-5-yl}methanol (0.6 g) synthesized above and ethyl 3-{[(4-aminophenyl)carbonyl]amino}propanoate (0.42 g) synthesized in Example 1(2) and in the same manner as in Example 1(7), the title object compound (0.18 g, 20%) was obtained as a white solid.

$^1$H NMR (300 MHz, CDCl$_3$) δ ppm 0.97-1.27 (m, 11H), 1.33 (t, J=7.3 Hz, 3H), 2.68 (t, J=5.5 Hz, 2H), 3.59-3.80 (m, 2H), 4.11 (q, J=7.2 Hz, 2H), 4.39 (d, J=6.8 Hz, 1H), 6.16 (s, 1H), 6.64 (d, J=8.7 Hz, 2H), 6.70-6.83 (m, 1H), 7.48 (d, J=8.1 Hz, 2H), 7.58 (d, J=8.7 Hz, 2H), 7.69 (d, J=8.1 Hz, 2H).

Example 57

3-[({4-[(cyclohexyl{1-ethyl-3-[4-(trifluoromethyl)phenyl]-1H-pyrazol-5-yl}methyl)amino]phenyl}carbonyl)(methyl)amino]propanoic acid

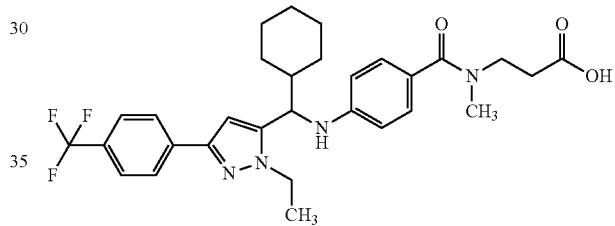

Using cyclohexyl{1-ethyl-3-[4-(trifluoromethyl)phenyl]-1H-pyrazol-5-yl}methanol (0.6 g) synthesized in Example 56(3) and ethyl 3-{[(4-aminophenyl)carbonyl](methyl)amino}propanoate (0.48 g) synthesized in Example 2(2) and in the same manner as in Example 1(7), the title object compound (0.19 g, 19%) was obtained as a white solid.

$^1$H NMR (300 MHz, CDCl$_3$) δ ppm 0.92-2.00 (m, 11H), 1.35 (t, J=7.2 Hz, 3H), 2.62-2.78 (m, 2H), 3.09 (s, 3H), 3.75 (t, J=6.6 Hz, 2H), 4.15 (q, J=7.2 Hz, 2H), 4.39 (d, J=6.6 Hz, 1H), 6.18 (s, 1H), 6.61 (d, J=8.7 Hz, 2H), 7.25 (d, J=8.7 Hz, 2H), 7.50 (d, J=8.1 Hz, 2H), 7.70 (d, J=8.1 Hz, 2H).

Example 58

3-[({4-[(cyclohexyl{1-ethyl-3-[4-(trifluoromethoxy)phenyl]-1H-pyrazol-5-yl}methyl)amino]phenyl}carbonyl)(methyl)amino]propanoic acid

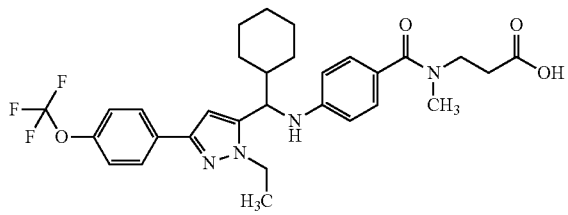 [SMILES: CCn1nc(-c2ccc(OC(F)(F)F)cc2)cc1C(Nc1ccc(C(=O)N(C)CCC(=O)O)cc1)C1CCCCC1]

(1) ethyl 1-ethyl-3-[4-(trifluoromethoxy)phenyl]-1H-pyrazole-5-carboxylate

Using 1-[4-(trifluoromethoxy)phenyl]ethanone (13.0 g), sodium hydride (60%, oily, 2.8 g), diethyl oxalate (8.7 mL) and ethylhydrazine (4.2 g) and in the same manner as in Example 56(1), the title object compound (19.4 g, 92%) was obtained as an oil.

$^1$H NMR (300 MHz, CDCl$_3$) δ ppm 1.34-1.53 (m, 6H), 4.24 (d, J=7.2 Hz, 2H), 4.23 (q, J=7.2 Hz, 2H), 4.43 (q, J=7.2 Hz, 2H), 4.45 (d, J=7.2 Hz, 2H), 6.82 (s, 1H), 7.33 (d, J=9.0 Hz, 2H), 7.44 (d, J=9.0 Hz, 2H).

(2) 1-ethyl-3-[4-(trifluoromethoxy)phenyl]-1H-pyrazole-5-carbaldehyde

Using ethyl 1-ethyl-3-[4-(trifluoromethoxy)phenyl]-1H-pyrazole-5-carboxylate (5.0 g) synthesized above and in the same manner as in Example 1(5), the title object compound (4.9 g, 38%) was obtained as a white solid.

$^1$H NMR (300 MHz, CDCl$_3$) δ ppm 1.48 (t, J=7.3 Hz, 3H), 4.23 (q, J=7.3 Hz, 2H), 6.80 (s, 1H), 7.30-7.58 (m, 4H), 10.00 (s, 1H).

(3) cyclohexyl{1-ethyl-3-[4-(trifluoromethoxy)phenyl]-1H-pyrazol-5-yl}methanol

Using 1-ethyl-3-[4-(trifluoromethoxy)phenyl]-1H-pyrazole-5-carbaldehyde (2.5 g) synthesized above and in the same manner as in Example 1(6), the title object compound (1.7 g, 54%) was obtained as a white solid.

$^1$H NMR (300 MHz, CDCl$_3$) δ ppm 1.26-2.00 (m, 11H), 1.39 (t, J=7.2 Hz, 3H), 4.12 (d, J=7.2 Hz, 2H), 4.52 (d, J=6.4 Hz, 1H), 6.18 (s, 1H), 7.30 (d, J=8.7 Hz, 2H), 7.43 (d, J=8.7 Hz, 2H).

(4) 3-[({4-[(cyclohexyl{1-ethyl-3-[4-(trifluoromethoxy)phenyl]-1H-pyrazol-5-yl}methyl)amino]phenyl}carbonyl)(methyl)amino]propanoic acid Using cyclohexyl{1-ethyl-3-[4-(trifluoromethoxy)phenyl]-1H-pyrazol-5-yl}methanol, (0.39 g) synthesized above and ethyl 3-{[(4-aminophenyl)carbonyl](methyl)amino}propanoate (0.32 g) synthesized in Example 2(2) and in the same manner as in Example 1(7), the title object compound (0.06 g, 11%) was obtained as a white solid.

$^1$H NMR (300 MHz, CDCl$_3$) δ ppm 0.99-2.00 (m, 11H), 1.36 (t, J=7.2 Hz, 3H), 2.74 (t, J=6.2 Hz, 2H), 3.10 (s, 3H), 3.74 (t, J=6.2 Hz, 2H), 4.12 (q, J=7.2 Hz, 2H), 4.37 (d, J=6.4 Hz, 1H), 6.10 (s, 1H), 6.63 (d, J=8.7 Hz, 2H), 7.26-7.46 (m, 6H).

Example 59

3-[({4-[(1-{1-ethyl-3-[4-(trifluoromethoxy)phenyl]-1H-pyrazol-5-yl}-3-methylbutyl)amino]phenyl}carbonyl)(methyl)amino]propanoic acid

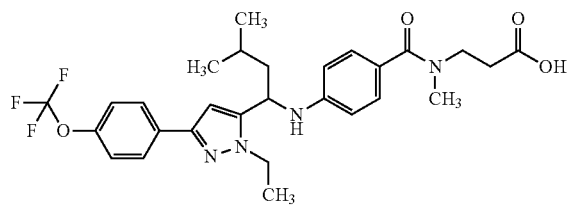 [SMILES: CCn1nc(-c2ccc(OC(F)(F)F)cc2)cc1C(CC(C)C)Nc1ccc(C(=O)N(C)CCC(=O)O)cc1]

(1) 1-{1-ethyl-3-[4-(trifluoromethoxy)phenyl]-1H-pyrazol-5-yl}-3-methylbutan-1-ol 1-Ethyl-3-[4-(trifluoromethoxy)phenyl]-1H-pyrazole-5-carbaldehyde (2.5 g) synthesized in Example 58(2) was dissolved in tetrahydrofuran (20 mL), and 1M isobutylmagnesium bromide tetrahydrofuran solution (12 mL) was added dropwise at 0° C. In the same manner as in Example 1(6), the title object compound (0.9 g, 31%) was obtained as an oil.

$^1$H NMR (300 MHz, CDCl$_3$) δ ppm 0.98 (d, J=6.4 Hz, 6H), 1.39 (t, J=7.2 Hz, 3H), 1.56-1.98 (m, 3H), 2.21 (d, J=4.3 Hz, 1H), 4.10-4.30 (q, J=7.2 Hz, 2H), 4.86 (ddd, J=8.9, 4.7, 4.3 Hz, 1H), 6.22 (s, 1H), 7.32-7.50 (m, 4H).

(2) 3-[({4-[(1-{1-ethyl-3-[4-(trifluoromethoxy)phenyl]-1H-pyrazol-5-yl}-3-methylbutyl)amino]phenyl}carbonyl)(methyl)amino]propanoic acid Using 1-{1-ethyl-3-[4-(trifluoromethoxy)phenyl]-1H-pyrazol-5-yl}-3-methylbutan-1-ol (0.39 g) synthesized above and ethyl 3-{[(4-aminophenyl)carbonyl](methyl)amino}propanoate (0.28 g) synthesized in Example 2(2) and in the same manner as in Example 1(7), the title object compound (0.02 g, 4%) was obtained as a white solid.

$^1$H NMR (300 MHz, CDCl$_3$) δ ppm 0.97 (dd, J=19.1, 6.2 Hz, 6H), 1.34 (t, J=7.2 Hz, 3H), 1.55-1.97 (m, 3H), 2.70 (br. s., 2H), 3.07 (s, 3H), 3.73 (br. s., 2H), 4.10 (q, J=7.2 Hz, 2H), 4.61 (t, J=6.8 Hz, 1H), 6.17 (s, 1H), 6.67 (d, J=8.0 Hz, 2H), 7.34-7.49 (m, 6H).

Example 60

3-{[(4-{[{3-(benzyloxy)-1-[4-(trifluoromethoxy)phenyl]-1H-pyrazol-4-yl}(cyclohexyl)methyl]amino}phenyl)carbonyl]amino}propanoic acid

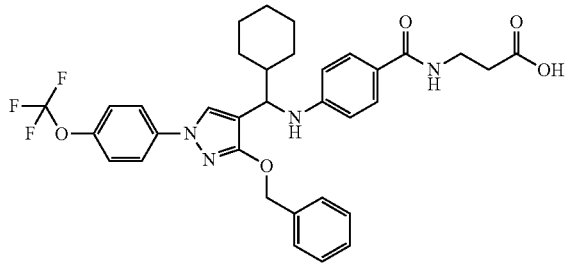 [SMILES: O=C(O)CCNC(=O)c1ccc(NC(c2cn(-c3ccc(OC(F)(F)F)cc3)nc2OCc2ccccc2)C2CCCCC2)cc1]

(1) 3-(benzyloxy)-1-[4-(trifluoromethoxy)phenyl]-1H-pyrazole-4-carbaldehyde

Using ethyl 3-(benzyloxy)-1-[4-(trifluoromethoxy)phenyl]-1H-pyrazole-4-carboxylate (3.1 g) synthesized in the method described in EP1394154 and in the same manner as in Example 1(5), the title object compound (2.1 g, 75%) was obtained as a white solid.

$^1$H NMR (300 MHz, CDCl$_3$) δ ppm 5.50 (s, 2H), 7.27-7.70 (m, 9H), 8.24 (s, 1H), 10.00 (s, 1H).

(2) {3-(benzyloxy)-1-[4-(trifluoromethoxy)phenyl]-1H-pyrazol-4-yl}(cyclohexyl)methanol Using 3-(benzyloxy)-1-[4-(trifluoromethoxy)phenyl]-1H-pyrazole-4-carbaldehyde (2.1 g) synthesized above and in the same manner as in Example 1(6), the title object compound (1.9 g, 76%) was obtained as a white solid.
$^1$H NMR (300 MHz, CDCl$_3$) δ ppm 0.92-2.00 (m, 12H), 4.44 (dd, J=6.8, 5.3 Hz, 1H), 5.36 (s, 2H), 7.26-7.51 (m, 9H), 7.66 (s, 1H).

(3) 3-{[(4-{[{3-(benzyloxy)-1-[4-(trifluoromethoxy)phenyl]-1H-pyrazol-4-yl}(cyclohexyl)methyl]amino}phenyl)carbonyl]amino}propanoic acid Using {3-(benzyloxy)-1-[4-(trifluoromethoxy)phenyl]-1H-pyrazol-4-yl}(cyclohexyl)methanol (0.50 g) synthesized above and ethyl 3-{[(4-aminophenyl)carbonyl]amino}propanoate (0.26 g) synthesized in Example 1(2) and in the same manner as in Example 1(7), the title object compound (0.39 g, 56%) was obtained as a white solid.
$^1$H NMR (300 MHz, CDCl$_3$) δ ppm 0.78-2.00 (m, 11H), 2.12-2.42 (m, 2H), 3.30-3.57 (m, 2H), 4.14 (d, J=7.0 Hz, 1H), 5.31 (s, 2H), 6.41 (d, J=8.5 Hz, 2H), 6.77 (br. s., 1H), 7.12 (d, J=9.0 Hz, 2H), 7.29-7.67 (m, 10H).

Example 61

3-{[(4-{[{3-(benzyloxy)-1-[4-(trifluoromethoxy)phenyl]-1H-pyrazol-4-yl}(cyclohexyl)methyl]amino}phenyl)carbonyl](methyl)amino}-propanoic acid

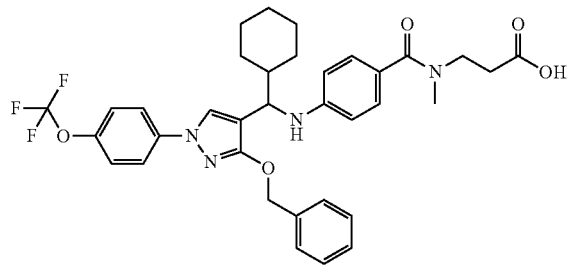 [SMILES: CN(CCC(=O)O)C(=O)c1ccc(NC(c2cn(-c3ccc(OC(F)(F)F)cc3)nc2OCc2ccccc2)C2CCCCC2)cc1]

Using {3-(benzyloxy)-1-[4-(trifluoromethoxy)phenyl]-1H-pyrazol-4-yl}(cyclohexyl)methanol (0.50 g) synthesized in Example 60(2) and ethyl 3-{[(4-aminophenyl)carbonyl](methyl)amino}propanoate (0.28 g) synthesized in Example 2(2) and in the same manner as in Example 1(7), the title object compound (0.37 g, 52%) was obtained as a white solid.
$^1$H NMR (300 MHz, CDCl$_3$) δ ppm 0.87-2.05 (m, 11H), 2.52 (t, J=6.0 Hz, 2H), 2.96 (s, 3H), 3.50-3.78 (m, 2H), 4.20 (d, J=6.8 Hz, 1H), 5.25-5.46 (m, 2H), 6.47 (d, J=8.7 Hz, 2H), 7.12-7.62 (m, 12H).

Example 62

3-[({4-[(cyclohexyl{3-methoxy-1-[4-(trifluoromethoxy)phenyl]-1H-pyrazol-4-yl}methyl)amino]phenyl}carbonyl)amino]propanoic acid

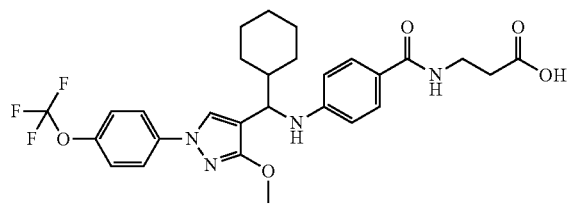 [SMILES: COc1nn(-c2ccc(OC(F)(F)F)cc2)cc1C(Nc1ccc(C(=O)NCCC(=O)O)cc1)C1CCCCC1]

(1) 3-methoxy-1-[4-(trifluoromethoxy)phenyl]-1H-pyrazole-4-carbaldehyde

Using ethyl 3-methoxy-1-[4-(trifluoromethoxy)phenyl]-1H-pyrazole-4-carboxylate (4.8 g) synthesized in the method described in WO2007/89031 and in the same manner as in Example 1(5), the title object compound (1.0 g, 35%) was obtained as a white solid.
$^1$H NMR (30.0 MHz, CDCl$_3$) δ ppm 4.10 (s, 3H), 7.33 (d, J=9.1 Hz, 2H), 7.69 (d, J=9.1 Hz, 2H), 8.23 (s, 1H), 9.87 (s, 1H).

(2) cyclohexyl{3-methoxy-1-[4-(trifluoromethoxy)phenyl]-1H-pyrazol-4-yl}methanol Using 3-methoxy-1-[4-(trifluoromethoxy)phenyl]-1H-pyrazole-4-carbaldehyde (1.0 g) synthesized above and in the same manner as in Example 1(6), the title object compound (1.5 g, 75%) was obtained as a white solid.
$^1$H NMR (300 MHz, CDCl$_3$) δ ppm 0.90-2.02 (m, 11H), 3.62 (br. s., 1H), 4.00 (s, 3H), 4.40 (dd, J=7.0, 4.7 Hz, 1H), 7.24-7.62 (m, 4H), 7.64 (s, 1H).

(3) ethyl 3-methoxy-1-[4-(trifluoromethoxy)phenyl]-1H-pyrazole-4-carboxylate

Using cyclohexyl{3-methoxy-1-[4-(trifluoromethoxy)phenyl]-1H-pyrazol-4-yl}methanol (0.75 g) synthesized above and ethyl 3-{[(4-aminophenyl)carbonyl]amino}propanoate (0.47 g) synthesized in Example 1(2) and in the same manner as in Example 1(7), the title object compound (0.10 g, 9%) was obtained as a white solid.
$^1$H NMR (300 MHz, CDCl$_3$) δ ppm 0.88-2.00 (m, 11H), 2.58 (t., J=6.0 Hz, 2H), 3.54-3.68 (m, 2H), 4.00 (s, 3H), 4.20 (d, J=6.6 Hz, 1H), 6.52 (d, J=8.7 Hz, 2H), 6.56-6.68 (m, 1H), 7.20 (d, J=8.3 Hz, 2H), 7.48-7.59 (m, 5H).

Example 63

3-[({4-[(cyclohexyl{3-methoxy-1-[4-(trifluoromethoxy)phenyl]-1H-pyrazol-4-yl}methyl)amino]phenyl}carbonyl)(methyl)amino]propanoic acid

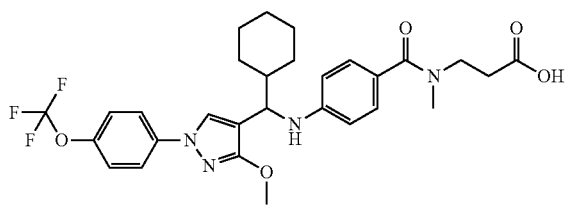 [SMILES: COc1nn(-c2ccc(OC(F)(F)F)cc2)cc1C(Nc1ccc(C(=O)N(C)CCC(=O)O)cc1)C1CCCCC1]

Using cyclohexyl{3-methoxy-1-[4-(trifluoromethoxy)phenyl]-1H-pyrazol-4-yl}methanol (0.75 g) synthesized in Example 62(2) and ethyl 3-{[(4-aminophenyl)carbonyl](methyl)amino}propanoate (0.50 g) synthesized in Example 2(2) and in the same manner as in Example 1(7), the title object compound (0.13 g, 12%) was obtained as a white solid.
$^1$H NMR (300 MHz, CDCl$_3$) δ ppm 0.90-2.02 (m, 11H), 2.68 (t, J=6.2 Hz, 2H), 3.05 (s, 3H), 3.71 (t, J=6.4 Hz, 2H), 4.01 (s, 3H), 4.19 (d, J=6.6 Hz, 1H), 6.53 (d, J=8.7 Hz, 2H), 7.17-7.28 (m, 4H), 7.47-7.61 (m, 3H).

Example 64

3-[({4-[(cyclohexyl{3-(1-methylethoxy)-1-[4-(trifluoromethoxy)phenyl]-1H-pyrazol-4-yl}methyl)amino]phenyl}carbonyl)amino]propanoic acid

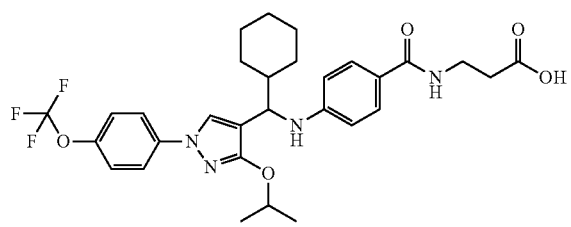 [SMILES: CC(C)Oc1nn(-c2ccc(OC(F)(F)F)cc2)cc1C(Nc1ccc(C(=O)NCCC(=O)O)cc1)C1CCCCC1]

(1) 3-(1-methylethoxy)-1-[4-(trifluoromethoxy)phenyl]-1H-pyrazole-4-carbaldehyde Using ethyl 3-(1-methylethoxy)-1-[4-(trifluoromethoxy)phenyl]-1H-pyrazole-4-carboxylate (1.3 g) synthesized in the method described in WO2007/89031 and in the same manner as in Example 1(5), the title object compound (0.43 g, 37%) was obtained as an oil.

$^1$H NMR (300 MHz, CDCl$_3$) δ ppm 1.33 (d, J=6.2 Hz, 6H), 5.20 (quint, J=6.2 Hz, 1H), 7.03-7.76 (m, 4H), 7.98 (s, 1H), 9.78 (s, 1H).

(2) cyclohexyl{3-(1-methylethoxy)-1-[4-(trifluoromethoxy)phenyl]-1H-pyrazol-4-yl}methanol Using 3-(1-methylethoxy)-1-[4-(trifluoromethoxy)phenyl]-1H-pyrazole-4-carbaldehyde (0.43 g) synthesized above and in the same manner as in Example 1(6), the title object compound (0.40 g, 74%) was obtained as an oil.

$^1$H NMR (300 MHz, CDCl$_3$) δ ppm 1.47-2.20 (m, 17H), 3.61 (br, s. 1H), 4.20-4.40 (m, 2H), 7.28 (d, J=8.7 Hz, 2H), 7.57 (s, 1H), 7.74 (d, J=8.7 Hz, 2H).

(3) 3-[({4-[(cyclohexyl{3-(1-methylethoxy)-1-[4-(trifluoromethoxy)phenyl]-1H-pyrazol-4-yl}methyl)amino]phenyl}carbonyl)amino]propanoic acid Using cyclohexyl{3-(1-methylethoxy)-1-[4-(trifluoromethoxy)phenyl]-1H-pyrazol-4-yl}methanol (0.20 g) synthesized above and ethyl 3-{[(4-aminophenyl)carbonyl]amino}propanoate (0.12 g) synthesized in Example 1(2) and in the same manner as in Example 1(7), the title object compound (0.11 g, 36%) was obtained as a white solid.

$^1$H NMR (300 MHz, CDCl$_3$) δ ppm 1.00-2.08 (m, 11H), 1.11-1.18 (m, 6H), 2.50-2.66 (m, 2H), 3.54-3.70 (m, 2H), 4.11-4.30 (m, 2H), 6.57 (d, J=8.7 Hz, 2H), 6.69 (br. s., 1H), 7.26 (d, J=8.7 Hz, 2H), 7.46 (s, 1H), 7.57 (d, J=8.7 Hz, 2H).

Example 65

3-[({4-[(cyclohexyl{3-(1-methylethoxy)-1-[4-(trifluoromethoxy)phenyl]-1H-pyrazol-4-yl}methyl)amino]phenyl}carbonyl)(methyl)amino]propanoic acid

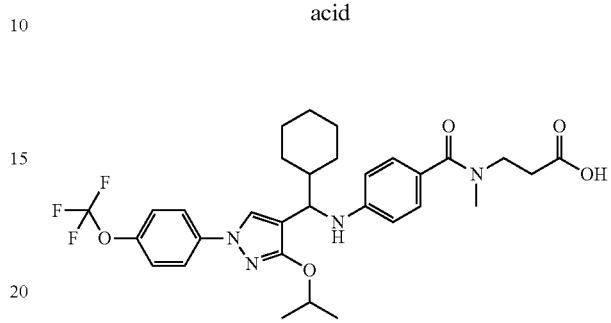

Using cyclohexyl{3-(1-methylethoxy)-1-[4-(trifluoromethoxy)phenyl]-1H-pyrazol-4-yl}methanol (0.20 g) synthesized in Example 64(2) and ethyl 3-{[(4-aminophenyl)carbonyl](methyl)amino}propanoate (0.13 g) synthesized in Example 2(2) and in the same manner as in Example 1(7), the title object compound (0.11 g, 36%) was obtained as a white solid.

$^1$H NMR (300 MHz, CDCl$_3$) δ ppm 0.97-2.00 (m, 11H), 1.12-1.19 (m, 6H), 2.53-2.70 (m, 2H), 3.05 (s, 3H), 3.63-3.78 (m, 2H), 4.13-4.29 (m, 2H), 6.57 (d, J=8.9 Hz, 2H), 7.27-7.32 (m, 4H), 7.46 (s, 1H), 7.72 (d, J=8.9 Hz, 2H).

Example 66

3-({[4-({[3-(benzyloxy)-1-phenyl-1H-pyrazol-4-yl](cyclohexyl)methyl}amino)phenyl]carbonyl}amino)propanoic acid

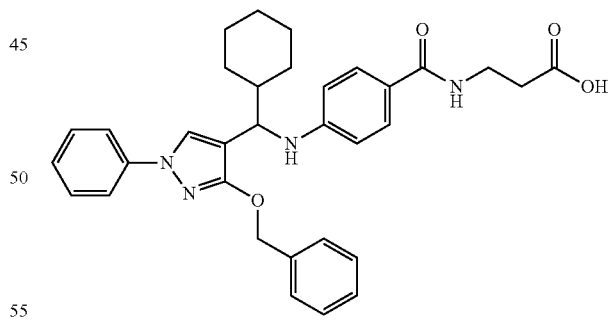

(1) 3-(benzyloxy)-1-phenyl-1H-pyrazole-4-carbaldehyde

Using ethyl 3-(benzyloxy)-1-phenyl-1H-pyrazole-4-carboxylate (1.8 g) synthesized in the method described in EP1394154 and in the same manner as in Example 1(5), the title object compound (1.4 g, 90%) was obtained as an oil.

$^1$H NMR (300 MHz, CDCl$_3$) δ ppm 5.50 (s, 2H), 7.29-7.78 (m, 10H), 8.26 (s, 1H), 9.98 (s, 1H).

(2) [3-(benzyloxy)-1-phenyl-1H-pyrazol-4-yl](cyclohexyl)methanol

Using 3-(benzyloxy)-1-phenyl-1H-pyrazole-4-carbaldehyde (1.4 g) synthesized above and in the same manner as in Example 1(6), the title object compound (1.6 g, 91%) was obtained as an oil.

$^1$H NMR (300 MHz, CDCl$_3$) δ ppm 1.58-2.20 (m, 12H), 4.44 (dd, J=7.2, 5.3 Hz, 1H), 5.37 (s, 2H), 7.10-7.62 (m, 10H), 7.69 (s, 1H).

(3) 3-({[4-({[3-(benzyloxy)-1-phenyl-1H-pyrazol-4-yl](cyclohexyl)methyl}amino)phenyl]carbonyl}amino)propanoic acid Using [3-(benzyloxy)-1-phenyl-1H-pyrazol-4-yl](cyclohexyl)methanol (0.79 g) synthesized above and ethyl 3-{[(4-aminophenyl)carbonyl]amino}propanoate (0.51 g) synthesized in Example 1(2) and in the same manner as in Example 1(7), the title object compound (0.51 g, 43%) was obtained as a white solid.

$^1$H NMR (300 MHz, CDCl$_3$) δ ppm 0.84-1.97 (m, 11H), 2.30-2.48 (m, 2H), 3.37-3.58 (m, 2H), 4.18 (d, J=6.6 Hz, 1H), 5.24-5.42 (m, 2H), 6.44 (d, J=8.7 Hz, 2H), 6.66 (br. s., 1H), 7.02-7.63 (m, 13H).

Example 67

3-[{[4-({[3-(benzyloxy)-1-phenyl-1H-pyrazol-4-yl](cyclohexyl)methyl}amino)phenyl]carbonyl}(methyl)amino]-propanoic acid

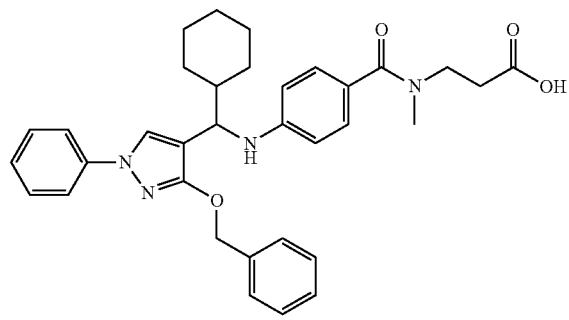 [SMILES: CN(CCC(=O)O)C(=O)c1ccc(NC(c2cn(-c3ccccc3)nc2OCc2ccccc2)C2CCCCC2)cc1]

Using [3-(benzyloxy)-1-phenyl-1H-pyrazol-4-yl](cyclohexyl)methanol (0.79 g) synthesized in Example 66(2) and ethyl 3-{[(4-aminophenyl)carbonyl](methyl)amino}propanoate synthesized in Example 2(2) and in the same manner as in Example 1(7), the title object compound (0.68 g, 55%) was obtained as a white solid.

$^1$H NMR (300 MHz, CDCl$_3$) δ ppm 0.91-2.01 (m, 11H), 2.71 (d, J=6.0 Hz, 1H), 3.06 (s, 3H), 3.71 (t, J=6.4 Hz, 2H), 4.23 (d, J=6.6 Hz, 1H), 5.28-5.47 (m, 2H), 6.50 (d, J=8.7 Hz, 2H), 7.10-7.64 (m, 13H).

Example 68

3-({[4-({cyclohexyl[1-(4-methoxyphenyl)-3-(morpholin-4-ylmethyl)-1H-pyrazol-4-yl]methyl}amino)phenyl]carbonyl}amino)propanoic acid

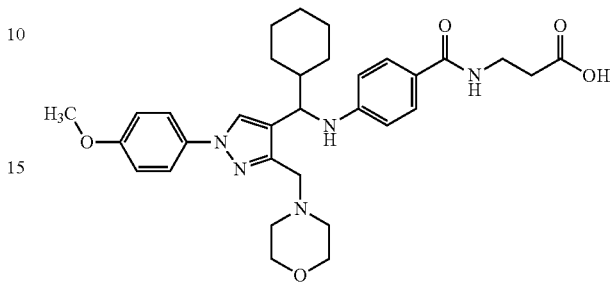

(1) methyl 4-(morpholin-4-yl)-3-oxobutanoate

To a solution (300 mL) of methyl 4-chloro-3-oxobutanoate (27.1 g) in tetrahydrofuran was added morpholine (34.5 g) under ice-cooling. The ice bath was removed, and the reaction mixture was stirred at room temperature for 2 hr. The solvent was evaporated under reduced pressure, 1N hydrochloric acid (100 mL) was added, and the mixture was extracted with diethyl ether. The extract was washed with saturated brine, dried over magnesium sulfate, and concentrated under reduced pressure. The residue was purified by silica gel column chromatography (ethyl acetate:hexane=1:10, volume ratio) to give the title object compound (12.8 g, 35%) as a yellow oil.

$^1$H NMR (300 MHz, CDCl$_3$) δ ppm 2.37-2.55 (m, 4H), 3.26 (s, 2H), 3.52 (s, 2H), 3.70-3.76 (m, 4H), 3.74 (s, 3H).

(2) methyl 1-(4-methoxyphenyl)-3-(morpholin-4-ylmethyl)-1H-pyrazole-4-carboxylate To methyl 4-(morpholin-4-yl)-3-oxobutanoate (7.0 g) synthesized in the above-mentioned (1) was added dimethylformamide-dimethylacetal (4.9 mL), and the mixture was stirred at 100° C. for 2 hr. The reaction mixture was allowed to cool to room temperature, ethanol (200 mL) and 4-methoxyphenylhydrazine hydrochloride (6.3 g) were added, and the mixture was stirred at 100° C. for 3 hr. The mixture was allowed to cool to room temperature and the solvent was evaporated under reduced pressure. Water was added to the residue and the mixture was extracted with ethyl acetate. The extract was concentrated, and the residue was purified by silica gel column chromatography (ethyl acetate:hexane=1:2, volume ratio) to give the title object compound (10.6 g, 93%) as a yellow oil.

$^1$H NMR (300 MHz, CDCl$_3$) δ ppm 2.44-2.50 (m, 4H), 3.60-3.65 (m, 4H), 3.75 (s, 2H), 3.86 (s, 3H), 3.87 (s, 3H), 6.97 (d, J=9.1 Hz, 2H), 7.68 (d, J=9.1 Hz, 2H), 8.03 (s, 1H).

(3) 1-(4-methoxyphenyl)-3-(morpholin-4-ylmethyl)-1H-pyrazole-4-carbaldehyde

A solution (20 mL) of methyl 1-(4-methoxyphenyl)-3-(morpholin-4-ylmethyl)-1H-pyrazole-4-carboxylate (11.3 g)

synthesized in the above-mentioned (2) in tetrahydrofuran was added to an ice-cooled solution (80 mL) of lithium aluminum hydride (1.4 g) in tetrahydrofuran. The ice bath was removed, and the reaction mixture was stirred at room temperature for 1 hr. The mixture was ice-cooled again, and water (3.7 mL), 1N aqueous sodium hydroxide solution (18.5 mL) and water (3.7 mL) were successively added dropwise to quench the reaction. The residue was filtered through celite, and the filtrate was concentrated under reduced pressure to give a crude product (8.5 g) of 1-(4-methoxyphenyl)-3-(morpholin-4-ylmethyl)-1H-pyrazole-4-methanol as a pale-yellow oil. This was dissolved in toluene (150 mL), manganese dioxide (15 g) was added, and the mixture was heated for 30 min with a Dean-Stark trap. The reaction mixture was allowed to cool to room temperature, and manganese dioxide was collected by filtration. The solvent was evaporated under reduced pressure to give the title object compound (7.2 g, 70%) as a yellow oil.

$^1$H NMR (300 MHz, CDCl$_3$) δ ppm 2.44-2.50 (m, 4H), 3.60-3.65 (m, 4H), 3.72 (s, 2H), 3.88 (s, 3H), 6.99 (d, J=9.1 Hz, 2H), 7.60 (d, J=9.1 Hz, 2H), 8.08 (s, 1H), 10.10 (s, 1H).

(4) cyclohexyl[1-(4-methoxyphenyl)-3-(morpholin-4-ylmethyl)-1H-pyrazol-4-yl]methanol To a solution (15 mL) of 1-(4-methoxyphenyl)-3-(morpholin-4-ylmethyl)-1H-pyrazole-4-carbaldehyde (2.0 g) synthesized in the above-mentioned (3) in tetrahydrofuran was added dropwise cyclohexylmagnesium bromide (10 mL, 1M tetrahydrofuran solution) under ice-cooling. After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (1.3 g, 51%) as a pale-yellow oil.

$^1$H NMR (300 MHz, CDCl$_3$) δ ppm 0.92-2.20 (m, 11H), 2.24-2.50 (m, 4H), 3.47 (d, J=12.0 Hz, 1H), 3.58-3.73 (m, 5H), 3.87 (s, 3H), 4.43 (d, J=6.6 Hz, 1H), 6.10 (s, 1H), 6.98 (d, J=8.9 Hz, 2H), 7.26 (d, J=8.9 Hz, 2H), 7.49 (s, 1H).

(5) 3-({[4-({cyclohexyl[1-(4-methoxyphenyl)-3-(morpholin-4-ylmethyl)-1H-pyrazol-4-yl]methyl}amino)phenyl]carbonyl}amino)propanoic acid To a solution (15 mL) of cyclohexyl[1-(4-methoxyphenyl)-3-(morpholin-4-ylmethyl)-1H-pyrazol-4-yl]methanol (0.65 g) synthesized in the above-mentioned (4) in tetrahydrofuran was added thionyl chloride (0.37 mL) at room temperature. The reaction mixture was stirred at room temperature for 30 min and ice-cooled, and saturated aqueous sodium hydrogen carbonate solution (15 mL) was carefully poured. The reaction mixture was stirred for 10 min, and the mixture was extracted to with ethyl acetate. The extract was washed with saturated brine, dried over magnesium sulfate, and concentrated under reduced pressure. The residue was dissolved in dimethylacetamide (15 mL), sodium iodide (0.37 g), sodium carbonate (0.27 g) and ethyl 3-{[(4-aminophenyl)carbonyl]amino}propanoate (0.39 g) synthesized in Example 1(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-({[4-({cyclohexyl[1-(4-methoxyphenyl)-3-(morpholin-4-ylmethyl)-1H-pyrazol-4-yl]methyl}amino)phenyl]carbonyl}amino)propanoate (0.35 g) as a pale-yellow oil. This was dissolved in ethanol (2 mL), 1N aqueous sodium hydroxide solution (1.5 mL) was added at room temperature, and the mixture was stirred at room temperature for 0.5 hr. Ethanol was evaporated under reduced pressure, and 1N hydrochloric acid (1.5 mL) was added to the residue. The precipitate was washed with water to give the title object compound (0.22 g, 22%) as a colorless solid.

$^1$H NMR (300 MHz, CDCl$_3$) δ ppm 0.92-2.00 (m, 11H), 2.24-2.50 (m, 4H), 2.66 (br s., 2H), 3.44 (s, 2H), 3.58-3.73 (m, 6H), 3.85 (s, 3H), 4.47 (d, J=7.2 Hz, 1H), 6.47-6.79 (m, 3H), 6.94 (d, J=8.7 Hz, 2H), 7.26-7.30 (m, 2H), 7.50-7.60 (m, 3H).

Example 69

3-[{[4-({cyclohexyl[1-(4-methoxyphenyl)-3-(morpholin-4-ylmethyl)-1H-pyrazol-4-yl]methyl}amino)phenyl]carbonyl}(methyl)amino]propanoic acid

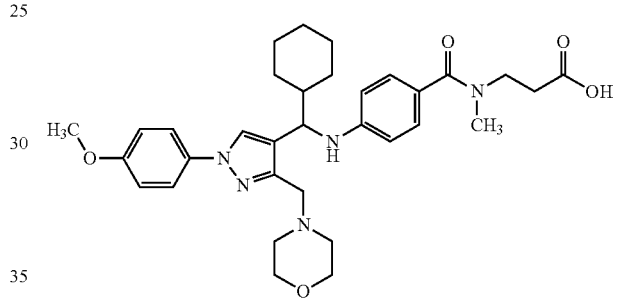

To a solution (15 mL) of cyclohexyl[1-(4-methoxyphenyl)-3-(morpholin-4-ylmethyl)-1H-pyrazol-4-yl]methanol (0.65 g) synthesized in Example 68(4) in tetrahydrofuran was added at room temperature thionyl chloride (0.37 mL). The reaction mixture was stirred at room temperature for 30 min and ice-cooled, and saturated aqueous sodium hydrogen carbonate solution (15 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15 mL), sodium iodide (0.37 g), sodium carbonate (0.27 g) and ethyl 3-{[(4-aminophenyl)carbonyl](methyl)amino}propanoate (0.42 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(4-methoxyphenyl)-3-(morpholin-4-ylmethyl)-1H-pyrazol-4-yl]methyl}amino)phenyl]carbonyl}(methyl)amino]propanoate (0.38 g) as a pale-yellow oil. This was dissolved in ethanol (2 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.12 g, 12%) as a colorless solid.

$^1$H NMR (300 MHz, CDCl$_3$) δ ppm 0.89-2.10 (m, 11H), 2.50-2.75 (m, 6H), 3.07 (s, 3H), 3.50-3.85 (m, 6H), 3.88 (s, 3H), 4.17-4.25 (m, 2H), 4.70-4.78 (m, 1H), 6.83 (d, J=8.7 Hz, 2H), 7.02 (d, J=9.0 Hz, 2H), 7.19-7.35 (m, 4H), 7.77 (s, 1H).

Example 70

3-[{[4-({cyclohexyl[1-(3-methoxyphenyl)-3-methyl-1H-pyrazol-4-yl]methyl}amino)phenyl]carbonyl}(methyl)amino]propanoic acid

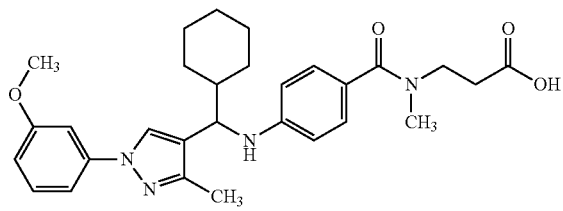 [SMILES: COc1cccc(-n2cc(C(Nc3ccc(C(=O)N(C)CCC(=O)O)cc3)C3CCCCC3)c(C)n2)c1]

(1) methyl 1-(3-methoxyphenyl)-3-methyl-1H-pyrazole-4-carboxylate

Methyl 3-methyl-1H-pyrazole-4-carboxylate (4.6 g) synthesized in Example 1(3) was dissolved in N,N-dimethylacetamide (50 mL), 3-methoxyphenylboronic acid (10.0 g), copper acetate (12.0 g) and pyridine (10.6 mL) were added, and the mixture was stirred at room temperature overnight. The reaction mixture was filtered through celite, 1N hydrochloric acid (100 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (3.9 g, 48%) as a pale-yellow oil.

$^1$H NMR (300 MHz, CDCl$_3$) δ ppm 2.56 (s, 3H), 3.86 (s, 3H), 3.87 (s, 3H), 6.80-8.33 (m, 5H).

(2) 1-(3-methoxyphenyl)-3-methyl-1H-pyrazole-4-carbaldehyde

A solution (20 mL) of methyl 1-(3-methoxyphenyl)-3-methyl-1H-pyrazole-4-carboxylate (3.9 g) synthesized in the above-mentioned (1) in tetrahydrofuran was added to an ice-cooled solution (80 mL) of lithium aluminum hydride (0.6 g) in tetrahydrofuran. The ice bath was removed, and the reaction mixture was stirred at room temperature for 1 hr. The mixture was ice-cooled again, and water (1.6 mL), 1N aqueous sodium hydroxide solution (7.8 mL) and water (1.6 mL) were successively added dropwise to quench the reaction. The residue was filtered through celite, and the filtrate was concentrated under reduced pressure to give a crude product (1.9 g) of 1-(3-methoxyphenyl)-3-methyl-1H-pyrazole-4-methanol as a pale-yellow oil. This was dissolved in toluene (30 mL), manganese dioxide (3.0 g) was added, and the mixture was heated for 30 min with a Dean-Stark trap. The reaction mixture was allowed to cool to room temperature, and manganese dioxide was collected by filtration. The solvent was evaporated under reduced pressure to give the title object compound (1.2 g, 64%) as a colorless solid.

$^1$H NMR (300 MHz, CDCl$_3$) δ ppm 2.59 (s, 3H), 3.88 (s, 3H), 6.80-7.40 (m, 4H), 8.32 (s, 1H), 10.00 (s, 1H).

(3) cyclohexyl[1-(3-methoxyphenyl)-3-methyl-1H-pyrazol-4-yl]methanol

To a solution (15 mL) of in 1-(3-methoxyphenyl)-3-methyl-1H-pyrazole-4-carbaldehyde (0.62 g) synthesized in the above-mentioned (2) in tetrahydrofuran under ice-cooling was added dropwise cyclohexylmagnesium bromide (4.3 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.60 g, 70%) as a pale-yellow oil.

$^1$H NMR (300 MHz, CDCl$_3$) δ ppm 0.90-2.10 (m, 12H), 2.34 (s, 3H), 3.87 (s, 3H), 4.43 (d, J=7.2 Hz, 1H), 6.70-7.40 (m, 4H), 7.78 (s, 1H).

(4) 3-[{[4-({cyclohexyl[1-(3-methoxyphenyl)-3-methyl-1H-pyrazol-4-yl]methyl}amino)phenyl]carbonyl}(methyl)amino]propanoic acid To a solution (3 mL) of cyclohexyl[1-(3-methoxyphenyl)-3-methyl-1H-pyrazol-4-yl]methanol (0.30 g) synthesized in the above-mentioned (3) in tetrahydrofuran was added at room temperature thionyl chloride (0.11 mL). The reaction mixture was stirred at room temperature for 30 min and ice-cooled, and saturated aqueous sodium hydrogen carbonate solution (5 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5 mL), sodium iodide (0.23 g), sodium carbonate (0.16 g) and ethyl 3-{[(4-aminophenyl)carbonyl](methyl)amino}propanoate (0.25 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(3-methoxyphenyl)-3-methyl-1H-pyrazol-4-yl]methyl}amino)phenyl]carbonyl}(methyl)amino]propanoate (0.38 g) as a pale-yellow oil. This was dissolved in ethanol (3 mL), 1N aqueous sodium hydroxide solution (1.5 mL) was added at room temperature, and the mixture was stirred at room temperature for 0.5 hr. Ethanol was evaporated under reduced pressure, and 1N hydrochloric acid (1.5 mL) was added to the residue. The precipitate was washed with water to give the title object compound (0.17 g, 34%) as a colorless solid.

$^1$H NMR (300 MHz, CDCl$_3$) δ ppm 0.96-2.03 (m, 11H), 2.35 (s, 3H), 2.70 (t, J=6.2 Hz, 2H), 3.06 (s, 3H), 3.71 (t, J=6.2 Hz, 2H), 3.85 (s, 3H), 4.19 (d, J=6.1 Hz, 1H), 6.50 (d, J=8.0 Hz, 2H), 6.76 (dd, J=7.8, 2.1 Hz, 1H), 7.09-7.37 (m, 5H), 7.67 (br. s., 1H).

Example 71

3-[{[4-({[1-(3-chlorophenyl)-3-methyl-1H-pyrazol-4-yl](cyclohexyl)methyl}amino)phenyl]carbonyl}(methyl)amino]-propanoic acid

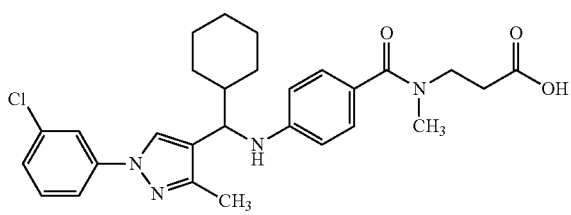 [SMILES: Cc1nn(-c2cccc(Cl)c2)cc1C(Nc1ccc(C(=O)N(C)CCC(=O)O)cc1)C1CCCCC1]

(1) methyl 1-(3-chlorophenyl)-3-methyl-1H-pyrazole-4-carboxylate

Methyl 3-methyl-1H-pyrazole-4-carboxylate (1.6 g) synthesized in Example 1(3) was dissolved in N,N-dimethylacetamide (30 mL), 3-chlorophenylboronic acid (3.58 g), copper acetate (5.0 g) and pyridine (4.0 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (1.9 g, 67%) as a pale-yellow oil.

$^1$H NMR (300 MHz, CDCl$_3$) δ ppm 2.55 (s, 3H), 3.86 (s, 3H), 3.87 (s, 3H), 6.70-8.35 (m, 5H).

(2) 1-(3-chlorophenyl)-3-methyl-1H-pyrazole-4-carbaldehyde

A solution (20 mL) of methyl 1-(3-chlorophenyl)-3-methyl-1H-pyrazole-4-carboxylate (1.9 g) synthesized in the above-mentioned (1) in tetrahydrofuran was added to an ice-cooled solution (80 mL) of lithium aluminide hydride (0.29 g) in tetrahydrofuran. The ice bath was removed, and the reaction mixture was stirred at room temperature for 1 hr. The mixture was ice-cooled again, and water (0.80 mL), 1N aqueous sodium hydroxide solution (4.0 mL) and water (0.80 mL) were successively added dropwise to quench the reaction. The residue was filtered through celite, and the filtrate was concentrated under reduced pressure to give a crude product (0.65 g) of 1-(3-chlorophenyl)-3-methyl-1H-pyrazole-4-methanol as a pale-yellow oil. This was dissolved in toluene (30 mL), manganese dioxide (2.0 g) was added, and the mixture was heated for 30 min with a Dean-Stark trap. The reaction mixture was allowed to cool to room temperature, and manganese dioxide was collected by filtration. The solvent was evaporated under reduced pressure to give the title object compound (0.35 g, 23%) as a colorless solid.

$^1$H NMR (300 MHz, CDCl$_3$) δ ppm 2.59 (s, 3H), 3.88 (s, 3H), 7.20-7.80 (m, 4H), 8.34 (s, 1H), 10.00 (s, 1H).

(3) cyclohexyl[1-(3-chlorophenyl)-3-methyl-1H-pyrazol-4-yl]methanol

To a solution (5 mL) of 1-(3-chlorophenyl)-3-methyl-1H-pyrazole-4-carbaldehyde (0.35 g) synthesized in the above-mentioned (2) in tetrahydrofuran under ice-cooling was added dropwise cyclohexylmagnesium bromide (2.4 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.25 g, 51%) as a pale-yellow oil.

$^1$H NMR (300 MHz, CDCl$_3$) δ ppm 0.91-1.97 (m, 12H), 2.33 (s, 3H), 4.44 (d, J=7.2 Hz, 1H), 7.20-7.78 (m, 5H).

(4) 3-[{[4-({cyclohexyl[1-(3-chlorophenyl)-3-methyl-1H-pyrazol-4-yl]methyl}amino)phenyl]carbonyl}(methyl)amino]propanoic acid To a solution (3 mL) of cyclohexyl[1-(3-chlorophenyl)-3-methyl-1H-pyrazol-4-yl]methanol (0.25 g) synthesized in the above-mentioned (3) in tetrahydrofuran was added at room temperature thionyl chloride (0.10 mL). The reaction mixture was stirred at room temperature for 30 min and ice-cooled, and saturated aqueous sodium hydrogen carbonate solution (5 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5 mL), sodium iodide (0.19 g), sodium carbonate (0.13 g) and ethyl 3-{[(4-aminophenyl)carbonyl](methyl)amino}propanoate (0.20 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(3-chlorophenyl)-3-methyl-1H-pyrazol-4-yl]methyl}amino)phenyl]carbonyl}(methyl)amino]propanoate (0.35 g) as a pale-yellow oil. This was dissolved in ethanol (3 mL), 1N aqueous sodium hydroxide solution (1.5 mL) was added at room temperature, and the mixture was stirred at room temperature for 0.5 hr. Ethanol was evaporated under reduced pressure, and 1N hydrochloric acid (1.5 mL) was added to the residue. The precipitate was washed with water to give the title object compound (0.24 g, 58%) as a colorless solid.

$^1$H NMR (300 MHz, CDCl$_3$) δ ppm 0.91-2.07 (m, 11H), 2.36 (s, 3H), 2.71 (t, J=6.4 Hz, 2H), 3.07 (s, 3H), 3.72 (t, J=6.4 Hz, 2H), 4.19 (d, J=6.1 Hz, 1H), 6.48 (d, J=8.7 Hz, 2H), 7.12-7.73 (m, 7H).

Example 72

3-[{[4-({[1-(2-methoxyphenyl)-3-methyl-1H-pyrazol-4-yl](cyclohexyl)methyl}amino)phenyl]carbonyl}(methyl)amino]-propanoic acid

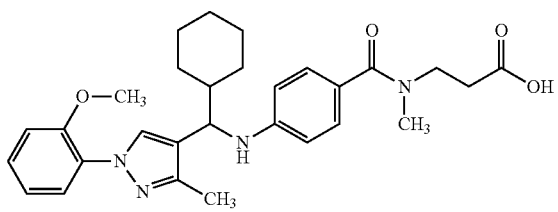 [SMILES: COc1ccccc1-n1cc(C(Nc2ccc(C(=O)N(C)CCC(=O)O)cc2)C2CCCCC2)c(C)n1]

(1) methyl 1-(2-methoxyphenyl)-3-methyl-1H-pyrazole-4-carboxylate

Methyl 3-methyl-1H-pyrazole-4-carboxylate (7.3 g) synthesized in Example 1(3) was dissolved in N,N-dimethylacetamide (150 mL), 2-methoxyphenylboronic acid (15.9 g), copper acetate (18.2 g) and pyridine (16.2 mL) were added, and the mixture was stirred at room temperature overnight. The reaction mixture was filtered through celite, 1N hydrochloric acid (100 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (10.3 g, 80%) as a pale-yellow oil.

$^1$H NMR (300 MHz, CDCl$_3$) δ ppm 2.55 (s, 3H), 3.85 (s, 3H), 6.80-8.50 (m, 5H).

(2) 1-(2-methoxyphenyl)-3-methyl-1H-pyrazole-4-carbaldehyde

A solution (50 mL) of methyl 1-(2-methoxyphenyl)-3-methyl-1H-pyrazole-4-carboxylate (10.3 g) synthesized in the above-mentioned (1) in tetrahydrofuran was added to an ice-cooled solution (350 mL) of lithium aluminum hydride (1.6 g) in tetrahydrofuran. The ice bath was removed, and the reaction mixture was stirred at room temperature for 1 hr. The mixture was ice-cooled again, and water (4.2 mL), 1N aqueous sodium hydroxide solution (21.0 mL) and water (4.2 mL) were successively added dropwise to quench the reaction. The residue was filtered through celite, and the filtrate was concentrated under reduced pressure to give a crude product (2.5 g) of 1-(2-methoxyphenyl)-3-methyl-1H-pyrazole-4-methanol as a pale-yellow oil. This was dissolved in toluene (50 mL), manganese dioxide (1.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (2.2 g, 87%) as a colorless solid.

$^1$H NMR (300 MHz, CDCl$_3$) δ ppm 2.58 (s, 3H), 3.92 (s, 3H), 7.00-7.80 (m, 4H), 8.50 (s, 1H), 9.99 (s, 1H).

(3) cyclohexyl[1-(2-methoxyphenyl)-3-methyl-1H-pyrazol-4-yl]methanol

To a solution (15 mL) of 1-(2-methoxyphenyl)-3-methyl-1H-pyrazole-4-carbaldehyde (1.5 g) synthesized in the above-mentioned (2) in tetrahydrofuran was added dropwise under ice-cooling cyclohexylmagnesium bromide (11.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate: hexane=1:2, volume ratio) to give the title object compound (1.1 g, 53%) as a pale-yellow oil.

$^1$H NMR (300 MHz, CDCl$_3$) δ ppm 0.90-2.10 (m, 12H), 2.34 (s, 3H), 3.87 (s, 3H), 4.43 (dd, J=7.6, 3.0 Hz, 1H), 7.00-7.75 (m, 4H), 7.92 (s, 1H).

(4) 3-[{[4-({cyclohexyl[1-(2-methoxyphenyl)-3-methyl-1H-pyrazol-4-yl]methyl}amino)phenyl]carbonyl}(methyl)amino]propanoic acid To a solution (5 mL) of cyclohexyl[1-(2-methoxyphenyl)-3-methyl-1H-pyrazol-4-yl]methanol (0.40 g) synthesized in the above-mentioned (3) in tetrahydrofuran was added at room temperature thionyl chloride (0.15 mL). The reaction mixture was stirred at room temperature for 30 min and ice-cooled, and saturated aqueous sodium hydrogen carbonate solution (5 mL) was carefully poured. The reaction mixture was stirred for 10% min, and the mixture was extracted with ethyl acetate. The extract was washed with saturated brine, dried over magnesium sulfate, and concentrated under reduced pressure. The residue was dissolved in dimethylacetamide (5.0 mL), sodium iodide (0.30 g), sodium carbonate (0.21 g) and ethyl 3-{[(4-aminophenyl)carbonyl](methyl)amino}propanoate (0.33 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate: hexane=1:1, volume ratio) to give ethyl 3-[{[4-({cyclohexyl[1-(2-methoxyphenyl)-3-methyl-1H-pyrazol-4-yl]methyl}amino)phenyl]carbonyl}(methyl)amino]propanoate (0.10 g) as a pale-yellow oil. This was dissolved in ethanol (1.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.04 g, 6%) as a colorless solid.

$^1$H NMR (300 MHz, CDCl$_3$) δ ppm 0.83-1.97 (m, 11H), 2.26 (s, 3H), 2.69 (br. s., 2H), 3.03 (s, 3H), 3.62-3.78 (m, 2H), 3.82 (s, 3H), 4.20 (d, J=6.6 Hz, 1H), 6.93-7.70 (m, 9H).

Example 73

3-[{[4-({[1-(2-chlorophenyl)-3-methyl-1H-pyrazol-4-yl](cyclohexyl)methyl}amino)phenyl]carbonyl}(methyl)amino]-propanoic acid

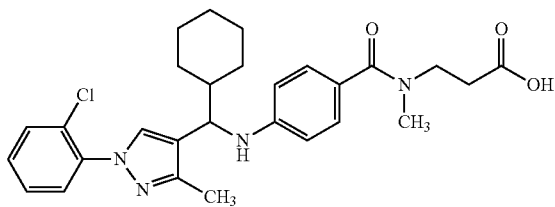 [SMILES: Cc1nn(-c2ccccc2Cl)cc1C(Nc1ccc(C(=O)N(C)CCC(=O)O)cc1)C1CCCCC1]

(1) methyl 1-(2-chlorophenyl)-3-methyl-1H-pyrazole-4-carboxylate

Methyl 3-methyl-1H-pyrazole-4-carboxylate (4.5 g) synthesized in Example 1(3) was dissolved in N,N-dimethylacetamide (100 mL), 2-chlorophenylboronic acid (10.0 g), copper acetate (11.7 g) and pyridine (10.4 mL) were added, and the mixture was stirred at room temperature overnight. The reaction mixture was filtered through celite, 1N hydrochloric acid (100 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (2.0 g, 25%) as a pale-yellow oil.

$^1$H NMR (300 MHz, CDCl$_3$) δ ppm 2.55 (s, 3H), 3.85 (s, 3H), 6.79-7.40 (m, 5H).

(2) 1-(2-chlorophenyl)-3-methyl-1H-pyrazole-4-carbaldehyde

A solution (20 mL) of methyl 1-(2-chlorophenyl)-3-methyl-1H-pyrazole-4-carboxylate (2.0 g) synthesized in the above-mentioned (1) in tetrahydrofuran was added to an ice-cooled solution (20 mL) of lithium aluminum hydride (0.30 g) in tetrahydrofuran. The ice bath was removed, and the reaction mixture was stirred at room temperature for 1 hr. The mixture was ice-cooled again, and water (0.80 mL), 1N aqueous sodium hydroxide solution (4.0 mL) and water (0.80 mL) were successively added dropwise to quench the reaction. The residue was filtered through celite, and the filtrate was concentrated under reduced pressure to give a crude product (0.36 g) of 1-(2-chlorophenyl)-3-methyl-1H-pyrazole-4-methanol as a pale-yellow oil. This was dissolved in toluene (10 mL), manganese dioxide (2.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (0.27 g, 15%) as a colorless solid.
$^1$H NMR (300 MHz, CDCl$_3$) δ ppm 2.59 (s, 3H), 7.00-7.70 (m, 4H), 8.32 (s, 1H), 10.02 (s, 1H).

(3) cyclohexyl[1-(2-chlorophenyl)-3-methyl-1H-pyrazol-4-yl]methanol

To a solution (5 mL) of 1-(2-chlorophenyl)-3-methyl-1H-pyrazole-4-carbaldehyde (0.27 g) synthesized in the above-mentioned (2) in tetrahydrofuran was added dropwise under ice-cooling cyclohexylmagnesium bromide (2.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate: hexane=1:2, volume ratio) to give the title object compound (0.29 g, 79%) as a pale-yellow oil.
$^1$H NMR (300 MHz, CDCl$_3$) δ ppm 0.90-2.20 (m, 12H), 2.35 (s, 3H), 4.45 (d, J=7.2 Hz, 1H), 7.20-7.60 (m, 4H), 7.76 (s, 1H).

(4) 3-[{[4-({cyclohexyl[1-(2-chlorophenyl)-3-methyl-1H-pyrazol-4-yl]methyl}amino)phenyl]carbonyl}(methyl)amino]propanoic acid To a solution (5 mL) of cyclohexyl[1-(2-chlorophenyl)-3-methyl-1H-pyrazol-4-yl]methanol (0.29 g) synthesized in the above-mentioned (3) in tetrahydrofuran was added at room temperature thionyl chloride (0.11 mL). The reaction mixture was stirred at room temperature for 30 min and ice-cooled, and saturated aqueous sodium hydrogen carbonate solution (3 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5.0 mL), sodium iodide (0.21 g), sodium carbonate (0.15 g) and ethyl 3-{[(4-aminophenyl)carbonyl](methyl)amino}propanoate (0.24 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(2-chlorophenyl)-3-methyl-1H-pyrazol-4-yl]methyl}amino)phenyl]carbonyl}(methyl)amino]propanoate (0.24 g) as a pale-yellow oil. This was dissolved in ethanol (2.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.18 g, 37%) as a colorless solid.
$^1$H NMR (300 MHz, CDCl$_3$) δ ppm 0.94-2.08 (m, 11H), 2.34 (s, 3H), 2.65-2.80 (m, 2H), 3.08 (s, 3H), 3.73 (br. s., 2H), 4.23 (d, J=6.1 Hz, 1H), 6.54 (br. s., 2H), 7.29-7.79 (m, 7H).

Example 74

3-[{[4-({cyclohexyl[1-(4-methoxyphenyl)-4-methyl-1H-pyrazol-3-yl]methyl}amino)phenyl]carbonyl}(methyl)amino]propanoic acid

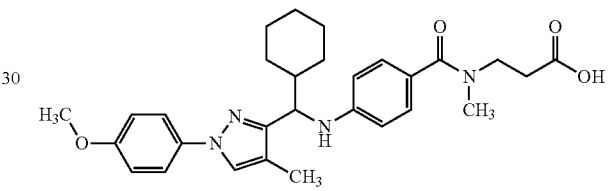

(1) ethyl 1-(4-methoxyphenyl)-4-methyl-1H-pyrazole-3-carboxylate

Ethyl 4-methyl-1H-pyrazole-3-carboxylate (2.58 g) was dissolved in N,N-dimethylacetamide (50 mL), 4-methoxyphenylboronic acid (5.0 g), copper acetate (6.0°g) and pyridine (5.3 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (2.7 g, 66%) as a pale-yellow oil.
$^1$H NMR (300 MHz, CDCl$_3$) δ ppm 1.21 (t, J=7.2 Hz, 3H), 2.33 (s, 3H), 3.85 (s, 3H), 4.22 (q, J=7.2 Hz, 2H), 6.94 (d, J=9.0 Hz, 2H), 7.28 (d, J=9.0 Hz, 2H), 7.50 (s, 1H).

(2) 1-(4-methoxyphenyl)-4-methyl-1H-pyrazole-3-carbaldehyde

A solution (10 mL) of ethyl 1-(4-methoxyphenyl)-4-methyl-1H-pyrazole-3-carboxylate (2.7 g) synthesized in the above-mentioned (1) in tetrahydrofuran was added to an ice-cooled solution (20 mL) of lithium aluminum hydride (0.40 g) in tetrahydrofuran. The ice bath was removed, and the reaction mixture was stirred at room temperature for 1 hr. The mixture was ice-cooled again, and water (1.0 mL), 1N aqueous sodium hydroxide solution (5.0 mL) and water (1.0 mL) were successively added dropwise to quench the reaction.

The residue was filtered through celite, and the filtrate was concentrated under reduced pressure to give a crude product (1.38 g) of 1-(4-methoxyphenyl)-4-methyl-1H-pyrazole-3-methanol as a pale-yellow oil. This was dissolved in toluene (30 mL), manganese dioxide (2.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (0.96 g, 43%) as a yellow solid.

$^1$H NMR (300 MHz, CDCl$_3$) δ ppm 2.41 (s, 3H), 3.87 (s, 3H), 7.01 (d, J=8.7 Hz, 2H), 7.38 (d, J=8.7 Hz, 2H), 7.55 (s, 1H), 9.88 (s, 1H).

(3) cyclohexyl[1-(4-methoxyphenyl)-4-methyl-1H-pyrazol-3-yl]methanol

To a solution (10 mL) of 1-(4-methoxyphenyl)-4-methyl-1H-pyrazole-3-carbaldehyde (0.96 g) synthesized in the above-mentioned (2) in tetrahydrofuran was added dropwise under ice-cooling cyclohexylmagnesium bromide (6.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.70 g, 53%) as a pale-yellow oil.

$^1$H NMR (300 MHz, CDCl$_3$) δ ppm 0.61-1.87 (m, 12H), 2.19 (s, 3H), 3.86 (s, 3H), 4.34 (dd, J=9.7, 4.4 Hz, 1H), 6.95 (d, J=9.0 Hz, 2H), 7.32 (d, J=9.0 Hz, 2H), 7.41 (s, 1H).

(4) 3-[{[4-({cyclohexyl[1-(4-methoxyphenyl)-4-methyl-1H-pyrazol-3-yl]methyl}amino)phenyl]carbonyl}(methyl)amino]propanoic acid To a solution (5 mL) of cyclohexyl[1-(4-methoxyphenyl)-4-methyl-1H-pyrazol-3-yl]methanol (0.40 g) synthesized in the above-mentioned (3) in tetrahydrofuran was added at room temperature thionyl chloride (0.15 mL). The reaction mixture was stirred at room temperature for 30 min and ice-cooled, and saturated aqueous sodium hydrogen carbonate solution (3 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.30 g), sodium carbonate (0.21 g) and ethyl 3-{[(4-aminophenyl)carbonyl](methyl)amino}propanoate (0.34 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(4-methoxyphenyl)-4-methyl-1H-pyrazol-3-yl]methyl}amino)phenyl]carbonyl}(methyl)amino]propanoate (0.06 g) as a pale-yellow oil. This was dissolved in ethanol (1.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.04 g, 6%) as a pale-yellow solid.

$^1$H NMR (300 MHz, CDCl$_3$) δ ppm 0.84-2.07 (m, 11H), 2.18 (s, 3H), 2.71 (br. s., 2H), 3.08 (s, 3H), 3.72 (t, J=6.4 Hz, 2H), 3.88 (s, 3H), 4.24 (d, J=9.1 Hz, 1H), 6.30 (d, J=8.7 Hz, 2H), 6.94 (d, J=8.7 Hz, 2H), 7.10-7.26 (m, 4H), 7.37 (s, 1H).

Example 75

3-[{[4-({cyclohexyl[1-(3-methoxyphenyl)-4-methyl-1H-pyrazol-3-yl]methyl}amino)phenyl]carbonyl}(methyl)amino]propanoic acid

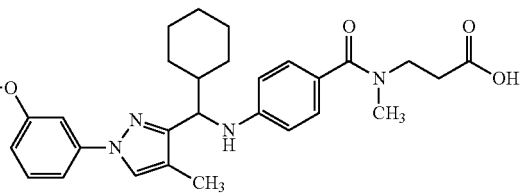

(1) ethyl 1-(3-methoxyphenyl)-4-methyl-1H-pyrazole-3-carboxylate

Ethyl 4-methyl-1H-pyrazole-3-carboxylate (2.58 g) was dissolved in N,N-dimethylacetamide (50 mL), 3-methoxyphenylboronic acid (5.0 g), copper acetate (6.0 g) and pyridine (5.3 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (1.9 g, 46%) as a pale-yellow oil.

$^1$H NMR (300 MHz, CDCl$_3$) δ ppm 1.43 (t, J=7.2 Hz, 3H), 2.37 (s, 3H), 3.87 (s, 3H), 4.43 (q, J=7.2 Hz, 2H), 6.94-7.50 (m, 5H).

(2) 1-(3-methoxyphenyl)-4-methyl-1H-pyrazole-3-carbaldehyde

A solution (5 mL) of ethyl 1-(3-methoxyphenyl)-4-methyl-1H-pyrazole-3-carboxylate (1.9 g) synthesized in the above-mentioned (1) in tetrahydrofuran was added to an ice-cooled solution (20 mL) of lithium aluminum hydride (0.29 g) in tetrahydrofuran. The ice bath was removed, and the reaction mixture was stirred at room temperature for 1 hr. The mixture was ice-cooled again, and water (0.76 mL), 1N aqueous sodium hydroxide solution (3.8 mL) and water (0.76 mL) were successively added dropwise to quench the reaction. The residue was filtered through celite, and the filtrate was concentrated under reduced pressure to give a crude product (0.99 g) of 1-(3-methoxyphenyl)-4-methyl-1H-pyrazole-3-methanol as a pale-yellow oil. This was dissolved in toluene (15 mL), manganese dioxide (0.32 g) was added, and the mixture was heated under reflux with a Dean-Stark trap for 1 hr. The reaction mixture was allowed to cool to room temperature, and manganese dioxide was collected by filtration. The filtrate was concentrated under reduced pressure to give the title object compound (0.84 g, 54%) as a yellow solid.

¹H NMR (300 MHz, CDCl₃) δ ppm 2.39 (s, 3H), 3.89 (s, 3H), 6.80-7.45 (m, 4H), 7.74 (s, 1H), 10.13 (s, 1H).

(3) cyclohexyl[1-(3-methoxyphenyl)-4-methyl-1H-pyrazol-3-yl]methanol

To a solution (10 mL) of 1-(3-methoxyphenyl)-4-methyl-1H-pyrazole-3-carbaldehyde (0.84 g) synthesized in the above-mentioned (2) in tetrahydrofuran was added dropwise under ice-cooling cyclohexylmagnesium bromide (7.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.62 g, 52%) as a pale-yellow oil.

¹H NMR (300 MHz, CDCl₃) δ ppm 0.99-2.00 (m, 12H), 2.12 (s, 3H), 3.86 (s, 3H), 4.52 (t, J=6.6 Hz, 1H), 6.75-7.32 (m, 4H), 7.64 (s, 1H).

(4) 3-[{[4-({cyclohexyl[1-(3-methoxyphenyl)-4-methyl-1H-pyrazol-3-yl]methyl}amino)phenyl]carbonyl}(methyl)amino]propanoic acid To a solution (5 mL) of cyclohexyl[1-(3-methoxyphenyl)-4-methyl-1H-pyrazol-3-yl]methanol (0.52 g) synthesized in the above-mentioned (3) in tetrahydrofuran was added at room temperature thionyl chloride (0.19 mL). The reaction mixture was stirred at room temperature for 30 min and ice-cooled, and saturated aqueous sodium hydrogen carbonate solution (3 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.39 g), sodium carbonate (0.28 g) and ethyl 3-{[(4-aminophenyl)carbonyl](methyl)amino}propanoate (0.38 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(3-methoxyphenyl)-4-methyl-1H-pyrazol-3-yl]methyl}amino)phenyl]carbonyl}(methyl)amino]propanoate (0.16 g) as a pale-yellow oil. This was dissolved in ethanol (2.0 mL), 1N aqueous sodium hydroxide solution (1.5 mL) was added at room temperature, and the mixture was stirred at room temperature for 0.5 hr. Ethanol was evaporated under reduced pressure, and 1N hydrochloric acid (1.5 mL) was added to the residue. The precipitate was washed with water to give the title object compound (0.09 g, 11%) as a pale-yellow solid.

¹H NMR (300 MHz, CDCl₃) δ ppm 0.97-2.06 (m, 11H), 2.09 (s, 3H), 2.73 (t, J=6.2 Hz, 2H), 3.08 (s, 3H), 3.72 (t, J=6.2 Hz, 2H), 3.87 (s, 3H), 4.40 (d, J=7.2 Hz, 1H), 6.62 (d, J=8.7 Hz, 2H), 6.78 (dd, J=7.8, 2.1 Hz, 1H), 7.10-7.50 (m, 5H), 7.57 (s, 1H).

Example 76

3-[{[4-({cyclohexyl[3-(methoxymethyl)-1-(3-methoxyphenyl)-1H-pyrazol-4-yl]methyl}amino)phenyl]carbonyl}(methyl)amino]propanoic acid

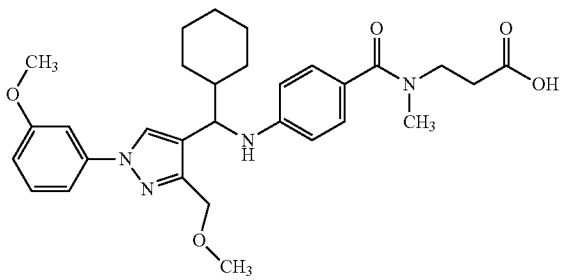 [SMILES: COCc1nn(-c2cccc(OC)c2)cc1C(Nc1ccc(C(=O)N(C)CCC(=O)O)cc1)C1CCCCC1]

(1) methyl 3-(methoxymethyl)-1-(3-methoxyphenyl)-1H-pyrazole-4-carboxylate

To a solution of methyl 3-(methoxymethyl)-1H-pyrazole-4-carboxylate (2.8 g) synthesized in Example 29 (1) in N,N-dimethylacetamide (50 mL) were added 3-methoxyphenylboronic acid (5.0 g), copper acetate (6.0 g) and pyridine (5.3 mL), and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (1.1 g, 23%) as a pale-yellow oil.

¹H NMR (300 MHz, CDCl₃) δ ppm 3.51 (s, 3H), 3.87 (s, 3H), 3.92 (s, 3H), 4.80 (s, 2H), 7.29-7.93 (m, 4H), 8.37 (s, 1H).

(2) 3-(methoxymethyl)-1-(3-methoxyphenyl)-1H-pyrazole-4-carbaldehyde

A solution (5 mL) of methyl 3-(methoxymethyl)-1-(3-methoxyphenyl)-1H-pyrazole-4-carboxylate (1.1 g) synthesized in the above-mentioned (1) in tetrahydrofuran was added to an ice-cooled solution (10 mL) of lithium aluminum hydride (0.25 g) in tetrahydrofuran. The ice bath was removed, and the reaction mixture was stirred at room temperature for 1 hr. The mixture was ice-cooled again, and water (0.38 mL), 1N aqueous sodium hydroxide solution (1.9 mL) and water (0.38 mL) were successively added dropwise to quench the reaction. The residue was filtered through celite, and the filtrate was concentrated under reduced pressure to give a crude product (0.68 g) of 3-(methoxymethyl)-1-(3-methoxyphenyl)-1H-pyrazole-4-methanol as a pale-yellow oil. This was dissolved in toluene (15 mL), manganese dioxide (1.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (0.30 g, 32%) as a yellow oil.

$^1$H NMR (300 MHz, CDCl$_3$) δ ppm 3.50 (s, 3H), 3.88 (s, 3H), 4.80 (s, 2H), 6.91 (dd, J=8.3, 1.5 Hz, 1H), 7.16-7.49 (m, 3H), 8.40 (s, 1H), 10.07 (s, 1H).

(3) cyclohexyl[3-(methoxymethyl)-1-(3-methoxyphenyl)-1H-pyrazol-4-yl]methanol

To a solution (5 mL) of 3-(methoxymethyl)-1-(3-methoxyphenyl)-1H-pyrazole-4-carbaldehyde (0.30 g) synthesized in the above-mentioned (2) in tetrahydrofuran was added dropwise under ice-cooling cyclohexylmagnesium bromide (2.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.40 g, quantitative) as a pale-yellow oil.

$^1$H NMR (300 MHz, CDCl$_3$) δ ppm 0.89-2.21 (m, 11H), 3.04 (br.s, 1H), 3.44 (s, 3H), 3.87 (s, 3H), 4.41 (d, J=7.7 Hz, 1H), 4.61 (d, J=3.6 Hz, 2H), 6.82 (ddd, J=8.1, 2.5, 0.8 Hz, 1H), 7.14-7.40 (m, 3H), 7.77 (s, 1H).

(4) 3-[{[4-({cyclohexyl[3-(methoxymethyl)-1-(3-methoxyphenyl)-1H-pyrazol-4-yl]methyl}amino)phenyl]carbonyl}(methyl)amino]propanoic acid To a solution (5 mL) of cyclohexyl[3-(methoxymethyl)-1-(3-methoxyphenyl)-1H-pyrazol-4-yl]methanol (0.40 g) synthesized in the above-mentioned (3) in tetrahydrofuran was added at room temperature thionyl chloride (0.14 mL). The reaction mixture was stirred at room temperature for 30 min and ice-cooled, and saturated aqueous sodium hydrogen carbonate solution (3 mL) was carefully poured. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5.0 mL), sodium iodide (0.23 g), sodium carbonate (0.18 g) and ethyl 3-{[(4-aminophenyl)carbonyl](methyl)amino}propanoate (0.25 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[3-(methoxymethyl)-1-(3-methoxyphenyl)-1H-pyrazol-4-yl]methyl}amino)phenyl]carbonyl}(methyl)amino]propanoate (0.11 g) as a pale-yellow oil. This was dissolved in ethanol (3.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.07 g, 10%) as a colorless solid.

$^1$H NMR (300 MHz, CDCl$_3$) δ ppm 0.94-2.12 (m, 11H), 2.73 (t, J=6.5 Hz, 2H), 3.07 (s, 3H), 3.41 (s, 3H), 3.72 (t, J=6.5 Hz, 2H), 3.85 (s, 3H), 4.34 (d, J=7.2 Hz, 1H), 4.57 (s, 2H), 6.57 (d, J=8.7 Hz, 2H), 6.79 (dt, J=8.2, 1.3 Hz, 1H), 7.11-7.38 (m, 5H), 7.72 (s, 1H).

Example 77

3-[{[4-({cyclohexyl[1-(2-methoxyphenyl)-4-methyl-1H-pyrazol-3-yl]methyl}amino)phenyl]carbonyl}(methyl)amino]propanoic acid

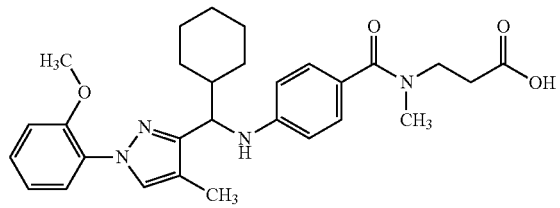 [SMILES: COc1ccccc1-n1cc(C)c(C(Nc2ccc(C(=O)N(C)CCC(=O)O)cc2)C2CCCCC2)n1]

(1) ethyl 1-(2-methoxyphenyl)-4-methyl-1H-pyrazole-3-carboxylate

Ethyl 4-methyl-1H-pyrazole-3-carboxylate (4.0 g) was dissolved in N,N-dimethylacetamide (30 mL), 2-methoxyphenylboronic acid (7.9 g), copper acetate (9.5 g) and pyridine (8.4 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (1.6 g, 25%) as a pale-yellow oil.

$^1$H NMR (300 MHz, CDCl$_3$) δ ppm 1.41 (t, J=7.2 Hz, 3H), 2.37 (s, 3H), 3.87 (s, 3H), 4.43 (q, J=7.2 Hz, 2H), 7.00-7.45 (m, 4H), 7.78 (s, 1H).

(2) 1-(2-methoxyphenyl)-4-methyl-1H-pyrazole-3-carbaldehyde

A solution (5 mL) of ethyl 1-(2-methoxyphenyl)-4-methyl-1H-pyrazole-3-carboxylate (1.6 g) synthesized in the above-mentioned (1) in tetrahydrofuran was added to an ice-cooled solution (10 mL) of lithium aluminum hydride (0.50 g) in tetrahydrofuran. The ice bath was removed, and the reaction mixture was stirred at room temperature for 1 hr, ice-cooled again, and water (1.3 mL), 1N aqueous sodium hydroxide solution (6.5 mL) and water (1.3 mL) were successively added dropwise to quench the reaction. The residue was filtered through celite, and the filtrate was concentrated under reduced pressure to give a crude product (0.79 g) of 1-(2-methoxyphenyl)-4-methyl-1H-pyrazole-3-methanol as a pale-yellow oil. This was dissolved in toluene (20 mL), manganese dioxide (2.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (0.97 g, 70%) as a yellow solid.

$^1$H NMR (300 MHz, CDCl$_3$) δ ppm 2.39 (s, 3H), 3.90 (s, 3H), 7.00-7.45 (m, 3H), 7.64-7.84 (m, 2H), 10.13 (s, 1H).

(3) cyclohexyl[1-(2-methoxyphenyl)-4-methyl-1H-pyrazol-3-yl]methanol

To a solution (10 mL) of 1-(2-methoxyphenyl)-4-methyl-1H-pyrazole-3-carbaldehyde (0.97 g) synthesized in the above-mentioned (2) in tetrahydrofuran was added dropwise under ice-cooling cyclohexylmagnesium bromide (5.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.56 g, 40%) as a pale-yellow oil.

$^1$H NMR (300 MHz, CDCl$_3$) δ ppm 0.99-2.00 (m, 12H), 2.12 (s, 3H), 3.86 (s, 3H), 4.52 (t, J=6.6 Hz, 1H), 6.75-7.32 (m, 4H), 7.64 (s, 1H).

(4) 3-[{[4-({cyclohexyl[1-(3-methoxyphenyl)-4-methyl-1H-pyrazol-3-yl]methyl}amino)phenyl]carbonyl}(methyl)amino]propanoic acid To a solution (5 mL) of cyclohexyl[1-(2-methoxyphenyl)-4-methyl-1H-pyrazol-3-yl]methanol (0.45 g) synthesized in the above-mentioned (3) in tetrahydrofuran was added thionyl chloride (0.17 mL) at room temperature. The reaction mixture was stirred at room temperature for 30 min, ice-cooled, and saturated aqueous sodium hydrogen carbonate solution (3 mL) was carefully added. The reaction mixture was stirred for 10% min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.33 g), sodium carbonate (0.24 g) and ethyl 3-{[(4-aminophenyl)carbonyl](methyl)amino}propanoate (0.38 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(2-methoxyphenyl)-4-methyl-1H-pyrazol-3-yl]methyl}amino)phenyl]carbonyl}(methyl)amino]propanoate (0.09 g) as a pale-yellow oil. This was dissolved in ethanol (2.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.06 g, 8%) as a pale-yellow solid.

$^1$H NMR (300 MHz, CDCl$_3$) δ ppm 0.98-2.07 (m, 11H), 2.10 (s, 3H), 2.73 (t, J=6.2 Hz, 2H), 3.09 (s, 3H), 3.72 (t, J=6.2 Hz, 2H), 3.86 (s, 3H), 4.41 (d, J=7.2 Hz, 1H), 6.62 (d, J=8.3 Hz, 2H), 6.96-7.37 (m, 5H), 7.63 (d, J=8.0 Hz, 1H), 7.70 (s, 1H).

Example 78

3-[{[4-({cyclohexyl[3-ethyl-1-(3-methoxyphenyl)-1H-pyrazol-4-yl]methyl}amino)phenyl]carbonyl}(methyl)amino]propanoic acid

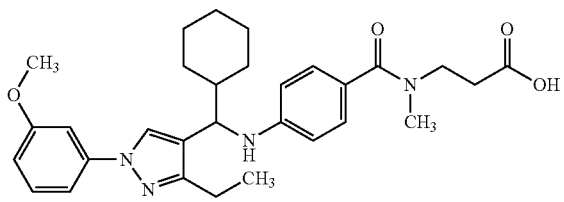 [SMILES: CCc1nn(-c2cccc(OC)c2)cc1C(Nc1ccc(C(=O)N(C)CCC(=O)O)cc1)C1CCCCC1]

(1) methyl 3-ethyl-1-(3-methoxyphenyl)-1H-pyrazole-4-carboxylate

Methyl 3-ethyl-1H-pyrazole-4-carboxylate (2.5 g) synthesized in Example 39(1) was dissolved in N,N-dimethylacetamide (50 mL), 3-methoxyphenylboronic acid (5.0 g), copper acetate (6.0 g) and pyridine (5.3 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (2.3 g, 54%) as a pale-yellow oil.

$^1$H NMR (300 MHz, CDCl$_3$) δ ppm 1.32 (t, J=7.5 Hz, 3H), 2.98 (q, J=7.5 Hz, 2H), 3.86 (s, 3H), 3.87 (s, 3H), 6.86 (ddd, J=8.2, 2.5, 0.9 Hz, 1H), 7.16-7.46 (m, 3H), 8.32 (s, 1H).

(2) 3-ethyl-1-(3-methoxyphenyl)-1H-pyrazole-4-carbaldehyde

A solution (5 mL) of methyl 3-ethyl-1-(3-methoxyphenyl)-1H-pyrazole-4-carboxylate (2.3 g) synthesized in the above-mentioned (1) in tetrahydrofuran was added to an ice-cooled solution (15 mL) of lithium aluminum hydride (0.34 g) in tetrahydrofuran. The ice bath was removed, and the reaction mixture was stirred at room temperature for 1 hr, ice-cooled again, and water (0.88 mL), 1N aqueous sodium hydroxide solution (4.4 mL), water (0.88 mL) were successively added dropwise to quench the reaction. The residue was filtered through celite, and the filtrate was concentrated under reduced pressure to give a crude product (2.3 g) of 3-ethyl-1-(3-methoxyphenyl)-1H-pyrazole-4-methanol as a pale-yellow oil. This was dissolved in toluene (50 mL), manganese dioxide (4.0 g) was added, and the mixture was heated under reflux with a Dean-Stark trap for 1 hr. The reaction mixture was allowed to cool to room temperature, manganese dioxide was collected by filtration, and the solvent was evaporated under reduced pressure to give the title object compound (1.9 g, 94%) as a yellow solid.

$^1$H NMR (300 MHz, CDCl$_3$) δ ppm 1.35 (t, J=7.6 Hz, 3H), 2.99 (q, J=7.6 Hz, 2H), 3.88 (s, 3H), 6.89 (dd, J=8.3, 1.5 Hz, 1H), 7.11-7.50 (m, 3H), 8.33 (s, 1H), 10.00 (s, 1H).

(3) cyclohexyl[3-ethyl-1-(3-methoxyphenyl)-1H-pyrazol-4-yl]methanol

To a solution (20 mL) of 3-ethyl-1-(3-methoxyphenyl)-1H-pyrazole-4-carbaldehyde (1.9 g) synthesized in the above-mentioned (2) in tetrahydrofuran was added dropwise under ice-cooling cyclohexylmagnesium bromide (12.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure to give a crude product (2.6 g, quantitative) of the title object compound as a pale-yellow oil.

¹H NMR (300 MHz, CDCl₃) δ ppm 0.86-1.98 (m, 14H), 2.71 (q, J=7.5 Hz, 2H), 3.60 (br, s., 1H), 3.87 (s, 3H), 4.44 (d, J=7.3 Hz, 1H), 6.78 (ddd, J=8.1, 2.4, 0.9 Hz, 1H), 7.14-7.38 (m, 3H), 7.78 (s, 1H).

(4) 3-[{[4-({cyclohexyl[3-ethyl-1-(3-methoxyphenyl)-1H-pyrazol-4-yl]methyl}amino)phenyl]carbonyl}(methyl)amino]propanoic acid To a solution (5 mL) of cyclohexyl[3-ethyl-1-(3-methoxyphenyl)-1H-pyrazol-4-yl]methanol (0.31 g) synthesized in the above-mentioned (3) in tetrahydrofuran was added thionyl chloride (0.13 mL) at room temperature. The reaction mixture was stirred at room temperature for 30 min, ice-cooled, and saturated aqueous sodium hydrogen carbonate solution (3 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved indimethylacetamide (10.0 mL), sodium iodide (0.23 g), sodium carbonate (0.15 g) and ethyl 3-{[(4-aminophenyl)carbonyl](methyl)amino}propanoate (0.25 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[3-ethyl-1-(3-methoxyphenyl)-1H-pyrazol-4-yl]methyl}amino)phenyl]carbonyl}(methyl)amino]propanoate (0.16 g) as a pale-yellow oil. This was dissolved in ethanol (3.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.12 g, 23%) as a pale-yellow solid.

¹H NMR (300 MHz, CDCl₃) δ ppm 0.98-2.07 (m, 14H), 2.62-2.81 (m, 4H), 3.07 (s, 3H), 3.72 (t, J=6.0 Hz, 2H), 3.85 (s, 3H), 4.22 (d, J=5.8 Hz, 1H), 6.51 (d, J=8.5 Hz, 2H), 6.76 (dt, J=8.2, 1.2 Hz, 1H), 7.10-7.37 (m, 5H), 7.65 (s, 1H).

Example 79

3-[{[4-({cyclohexyl[1-(3-methoxyphenyl)-3-(1-methylethyl)-1H-pyrazol-4-yl]methyl}amino)phenyl]carbonyl}(methyl)amino]propanoic acid

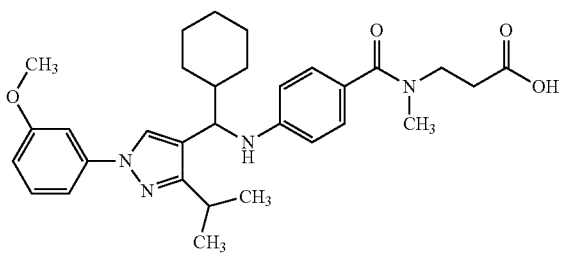 [SMILES: COc1cccc(-n2cc(C(Nc3ccc(C(=O)N(C)CCC(=O)O)cc3)C3CCCCC3)c(C(C)C)n2)c1]

(1) methyl 1-(3-methoxyphenyl)-3-(propan-2-yl)-1H-pyrazole-4-carboxylate

Methyl 3-(1-methylethyl)-1H-pyrazole-4-carboxylate (2.8 g) synthesized in Example 7(1) was dissolved in N,N-dimethylacetamide (50 mL), 3-methoxyphenylboronic acid (5.0 g), copper acetate (6.0 g) and pyridine (5.3 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (3.4 g, 75%) as a pale-yellow oil.

¹H NMR (300 MHz, CDCl₃) δ ppm 1.36 (d, J=7.0 Hz, 6H), 3.56-3.59 (m, 1H), 3.85 (s, 3H), 3.87 (s, 3H), 6.85 (ddd, J=8.1, 2.5, 1.0 Hz, 1H), 7.18-7.45 (m, 3H), 8.31 (s, 1H).

(2) 1-(3-methoxyphenyl)-3-(propan-2-yl)-1H-pyrazole-4-carbaldehyde

A solution (15 mL) of methyl 1-(3-methoxyphenyl)-3-(propan-2-yl)-1H-pyrazole-4-carboxylate (3.4 g) synthesized in the above-mentioned (1) in tetrahydrofuran was added to an ice-cooled solution (35 mL) of lithium aluminum hydride (0.48 g) in tetrahydrofuran. The ice bath was removed, and the reaction mixture was stirred at room temperature for 1 hr, ice-cooled again, and water (1.25 mL), 1N aqueous sodium hydroxide solution (6.3 mL), water (1.25 mL) were successively added dropwise to quench the reaction. The residue was filtered through celite, and the filtrate was concentrated under reduced pressure to give a crude product (2.7 g) of 1-(3-methoxyphenyl)-3-(propan-2-yl)-1H-pyrazole-4-methanol as a pale-yellow oil. This was dissolved in toluene (50 mL), manganese dioxide (3.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (2.6 g, 84%) as a yellow solid.

¹H NMR (300 MHz, CDCl₃) δ ppm 1.39 (d, J=6.8 Hz, 6H), 3.48-3.52 (m, 1H), 3.88 (s, 3H), 6.88 (dd, J=7.8, 2.1 Hz, 1H), 7.09-7.45 (m, 3H), 8.33 (s, 1H), 10.02 (s, 1H).

(3) cyclohexyl[1-(3-methoxyphenyl)-3-(propan-2-yl)-1H-pyrazol-4-yl]methanol

To a solution (20 mL) of 1-(3-methoxyphenyl)-3-(propan-2-yl)-1H-pyrazole-4-carbaldehyde (2.6 g) synthesized in the above-mentioned (2) in tetrahydrofuran was added dropwise cyclohexylmagnesium bromide (15.0 mL, 1M tetrahydrofuran solution) under ice-cooling. After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure to give a crude product (2.6 g, 75%) of the title object compound as a pale-yellow oil.

¹H NMR (300 MHz, CDCl₃) δ ppm 0.90-2.15 (m, 17H), 3.00-3.20 (m, 1H), 3.86 (s, 3H), 4.46 (d, J=7.6 Hz, 1H), 6.63-7.48 (m, 4H), 7.77 (s, 1H).

(4) 3-[{[4-({cyclohexyl[1-(3-methoxyphenyl)-3-(1-methylethyl)-1H-pyrazol-4-yl]methyl}amino)phenyl]carbonyl}(methyl)amino]propanoic acid To a solution (5 mL) of cyclohexyl[1-(3-methoxyphenyl)-3-(propan-2-yl)-1H-pyrazol-4-yl]methanol (0.45 g) synthesized in the above-mentioned (3) in tetrahydrofuran was added thionyl chloride (0.18 mL) at room temperature. The reaction mixture was stirred at room temperature for 30 min, ice-cooled, and saturated aqueous sodium hydrogen carbonate solution (5 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.30 g), sodium carbonate (0.21 g) and ethyl 3-{[(4-aminophenyl)carbonyl](methyl)amino}propanoate (0.34 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate: hexane=1:1, volume ratio) to give ethyl 3-[{[4-({cyclohexyl[1-(3-methoxyphenyl)-3-(1-methylethyl)-1H-pyrazol-4-yl]methyl}amino)phenyl]carbonyl}(methyl)amino]propanoate (0.37 g) as a pale-yellow oil. This was dissolved in ethanol (5.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.28 g, 38%) as a pale-yellow solid.

¹H NMR (300 MHz, CDCl₃) δ ppm 0.95-1.27 (m, 11H), 1.30-1.40 (m, 6H), 2.73 (d, J=6.0 Hz, 2H), 2.94-3.17 (m, 4H), 3.73 (d, J=6.0 Hz, 2H), 3.85 (s, 3H), 4.26 (d, J=6.0 Hz, 1H), 6.52 (d, J=8.7 Hz, 2H), 6.75 (ddd, J=8.2, 2.5, 0.9 Hz, 1H), 7.10-7.32 (m, 5H), 7.62 (s, 1H).

Example 80

3-[({4-[{cyclohexyl[3-ethyl-1-(3-methoxyphenyl)-1H-pyrazol-4-yl]methyl}(methyl)amino]phenyl}carbonyl)(methyl)amino]-propanoic acid

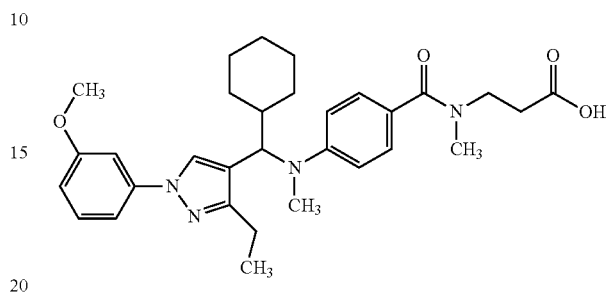

To a solution of ethyl 3-[{[4-({cyclohexyl[3-ethyl-1-(3-methoxyphenyl)-1H-pyrazol-4-yl]methyl}amino)phenyl]carbonyl}(methyl)amino]propanoate (1.1 g) synthesized in Example 78(4) in N,N-dimethylacetamide (5 mL) was added sodium hydride (0.16 g) under ice-cooling and, after stirring for 30 min, methyl iodide (0.37 mL) was added. The ice bath was removed, the reaction mixture was stirred at room temperature overnight, saturated aqueous ammonium chloride solution was added and the mixture was extracted with diethyl ether. The extract was washed with brine to give ethyl 3-[({4-[{cyclohexyl[3-ethyl-1-(3-methoxyphenyl)-1H-pyrazol-4-yl]methyl}(methyl)amino]phenyl}carbonyl)(methyl)amino]propanoate (0.23 g, 75%) as a pale-yellow oil. This was dissolved in ethanol (3.0 mL), 1N aqueous sodium hydroxide solution (1.5 mL) was added at room temperature, and the mixture was stirred at room temperature for 0.5 hr. Ethanol was evaporated under reduced pressure, 1N hydrochloric acid (1.5 mL) was added to the residue, and the mixture was extracted with ethyl acetate. The extract was washed with water, dried over magnesium sulfate, and concentrated under reduced pressure. The residue was purified by silica gel column chromatography (ethyl acetate:hexane=10:1, volume ratio) to give the title object compound (0.10 g, 10%) as a pale-yellow solid.

¹H NMR (300 MHz, CDCl₃) δ ppm 0.94-1.99 (m, 14H), 2.17 (s, 3H), 2.72 (q, J=7.4 Hz, 2H), 2.76-2.90 (m, 2H), 3.07 (s, 3H), 3.75-3.85 (m, 5H), 4.22 (d, J=5.3 Hz, 1H), 6.50 (d, J=8.7 Hz, 2H), 6.76 (d, J=8.3 Hz, 1H), 7.07-7.43 (m, 5H), 7.65 (s, 1H).

Example 81

3-[{[4-({cyclohexyl[1-(3,5-dimethoxyphenyl)-3-methyl-1H-pyrazol-4-yl]methyl}amino)phenyl]carbonyl}(methyl)amino]propanoic acid

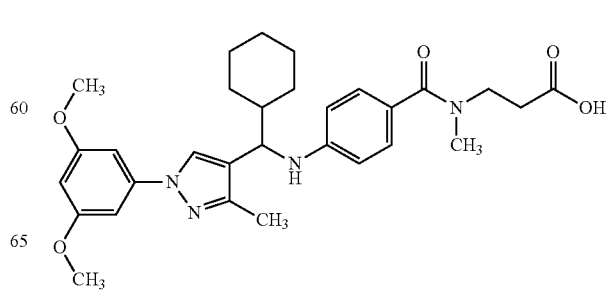

(1) methyl 1-(3,5-dimethoxyphenyl)-3-methyl-1H-pyrazole-4-carboxylate

Methyl 3-methyl-1H-pyrazole-4-carboxylate (3.9 g) synthesized in Example 1(3) was dissolved in N,N-dimethylacetamide (50 mL), 3,5-dimethoxyphenylboronic acid (10.0 g), copper acetate (10.0 g) and pyridine (8.9 mL) were added, and the mixture was stirred at room temperature overnight. The reaction mixture was filtered through celite, 1N hydrochloric acid (50 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (3.0 g, 40%) as a pale-yellow oil.

$^1$H NMR (300 MHz, CDCl$_3$) δ ppm 2.55 (s, 3H), 3.85 (s, 6H), 6.41 (t, J=2.3 Hz, 1H), 6.83 (d, J=2.3 Hz, 2H), 8.30 (s, 1H).

(2) 1-(3,5-dimethoxyphenyl)-3-methyl-1H-pyrazole-4-carbaldehyde

A solution (15 mL) of methyl 1-(3,5-dimethoxyphenyl)-3-methyl-1H-pyrazole-4-carboxylate (3.0 g) synthesized in the above-mentioned (1) in tetrahydrofuran was added to an ice-cooled solution (35 mL) of lithium aluminum hydride (0.42 g) in tetrahydrofuran. The ice bath was removed, and the reaction mixture was stirred at room temperature for 1 hr, ice-cooled again, and water (1.1 mL), 1N aqueous sodium hydroxide solution (5.5 mL), water (1.1 mL) were successively added dropwise to quench the reaction. The residue was filtered through celite, and the filtrate was concentrated under reduced pressure to give a crude product (2.7 g) of 1-(3,5-dimethoxyphenyl)-3-methyl-1H-pyrazole-4-methanol as a pale-yellow oil. This was dissolved in toluene (30 mL), manganese dioxide (2.0 g) was added, and the mixture was heated under reflux with a Dean-Stark trap for 1 hr. The reaction mixture was allowed to cool to room temperature, manganese dioxide was collected by filtration, and the solvent was evaporated under reduced pressure to give the title object compound (2.0 g, 74%) as a yellow solid.

$^1$H NMR (300 MHz, CDCl$_3$) δ ppm 2.55 (s, 3H), 3.85 (s, 6H), 6.44 (s, 1H), 6.82-6.84 (m, 2H), 8.30 (s, 1H), 9.98 (s, 1H).

(3) cyclohexyl[1-(3,5-dimethoxyphenyl)-3-methyl-1H-pyrazol-4-yl]methanol

To a solution (10 mL) of 1-(3,5-dimethoxyphenyl)-3-methyl-1H-pyrazole-4-carbaldehyde (2.0 g) synthesized in the above-mentioned (2) in tetrahydrofuran was added dropwise cyclohexylmagnesium bromide (15.0 mL, 1M tetrahydrofuran solution) under ice-cooling. After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (2.6 g, 40%) as a pale-yellow oil.

$^1$H NMR (300 MHz, CDCl$_3$) δ ppm 0.89-2.00 (m, 12H), 2.33 (s, 3H), 3.84 (s, 6H), 4.40-4.45 (m, 1H), 6.34 (t, J=2.1 Hz, 1H), 6.81 (d, J=2.3 Hz, 2H), 7.76 (s, 1H).

(4) 3-[{[4-({cyclohexyl[1-(3,5-dimethoxyphenyl)-3-methyl-1H-pyrazol-4-yl]methyl}amino)phenyl]carbonyl}(methyl)amino]propanoic acid To a solution (20 mL) of cyclohexyl[1-(3,5-dimethoxyphenyl)-3-methyl-1H-pyrazol-4-yl]methanol (1.0 g) synthesized in the above-mentioned (3) in tetrahydrofuran was added thionyl chloride (0.40 mL) at room temperature. The reaction mixture was stirred at room temperature for 30 min, ice-cooled, and saturated aqueous sodium hydrogen carbonate solution (15 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15.0 mL), sodium iodide (0.67 g), sodium carbonate (0.45 g) and ethyl 3-{[(4-aminophenyl)carbonyl](methyl)amino}propanoate (0.75 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(3,5-dimethoxyphenyl)-3-methyl-1H-pyrazol-4-yl]methyl}amino)phenyl]carbonyl}(methyl)amino]propanoate (0.74 g) as a pale-yellow oil. This was dissolved in ethanol (5.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.46 g, 29%) as a colorless solid.

$^1$H NMR (300 MHz, CDCl$_3$) δ ppm 0.91-2.02 (m, 11H), 2.35 (s, 3H), 2.70 (br. s., 2H), 3.06 (s, 3H), 3.71 (t, J=6.4 Hz, 2H), 3.82 (s, 6H), 4.18 (d, J=5.8 Hz, 1H), 6.32 (t, J=2.2 Hz, 1H), 6.49 (d, J=8.7 Hz, 2H), 6.77 (s, 2H), 7.26 (d, 2H), 7.64 (s, 1H).

Example 82

3-({[4-({cyclohexyl[1-(3,5-dimethoxyphenyl)-3-methyl-1H-pyrazol-4-yl]methyl}amino)phenyl}carbonyl]amino)propanoic acid

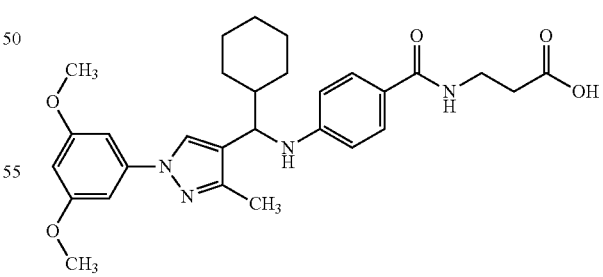

To a solution (20 mL) of cyclohexyl[1-(3,5-dimethoxyphenyl)-3-methyl-1H-pyrazol-4-yl]methanol (1.0 g) synthesized in Example 81(3) in tetrahydrofuran was added at room temperature thionyl chloride (0.40 mL). The reaction mixture was stirred at room temperature for 30 min and ice-cooled, and saturated aqueous sodium hydrogen carbonate solution (15 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15.0 mL), sodium iodide (0.67 g), sodium carbonate (0.45 g) and ethyl 3-{[(4-aminophenyl)carbonyl]amino}propanoate (0.70 g) synthesized in Example 1(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-({[4-({cyclohexyl[1-(3,5-dimethoxyphenyl)-3-methyl-1H-pyrazol-4-yl]methyl}amino)phenyl]carbonyl}amino)propanoate (1.3 g) as a pale-yellow oil. This was dissolved in ethanol (5.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.65 g, 42%) as a colorless solid.

$^1$H NMR (300 MHz, CDCl$_3$) δ ppm 0.96-1.98 (m, 11H), 2.35 (s, 3H), 2.65 (t, J=6.0 Hz, 2H), 3.66 (d, J=6.0 Hz, 2H), 3.80 (s, 6H), 4.20 (d, J=6.0 Hz, 1H), 6.31 (t, J=2.2 Hz, 1H), 6.49 (d, J=8.7 Hz, 2H), 6.60 (d, J=6.0 Hz, 1H), 6.75 (s, 2H), 7.53 (d, J=8.9 Hz, 2H), 7.62 (s, 1H).

Example 83

3-[{[4-({cyclohexyl[1-(3-ethoxyphenyl)-3-ethyl-1H-pyrazol-4-yl]methyl}amino)phenyl]carbonyl}(methyl)amino]propanoic acid

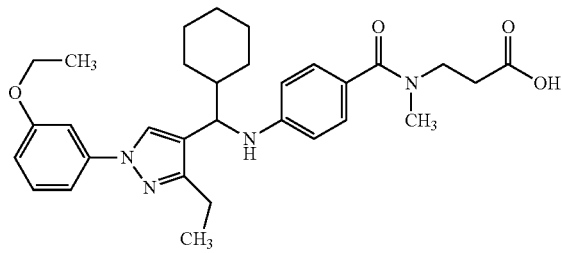 [SMILES: CCOc1cccc(-n2cc(C(Nc3ccc(C(=O)N(C)CCC(=O)O)cc3)C3CCCCC3)c(CC)n2)c1]

(1) methyl 1-(3-ethoxyphenyl)-3-ethyl-1H-pyrazole-4-carboxylate

Methyl 3-ethyl-1H-pyrazole-4-carboxylate (6.9 g) synthesized in Example 39(1) was dissolved in N,N-dimethylacetamide (150 mL), 3-ethoxyphenylboronic acid (15.0 g), copper acetate (16.4 g) and pyridine (14.5 mL) were added, and the mixture was stirred at room temperature overnight. The reaction mixture was filtered through celite, 1N hydrochloric acid (70 mL) was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:2, volume ratio) to give the title object compound (4.4 g, 36%) as a pale-yellow oil.

$^1$H NMR (300 MHz, CDCl$_3$) δ ppm 1.32 (t, J=7.5 Hz, 3H), 1.44 (t, J=7.0 Hz, 3H), 2.98 (q, J=7.5 Hz, 2H), 3.85 (s, 3H), 4.10 (q, J=7.0 Hz, 2H), 6.84 (dd, J=8.2, 1.6 Hz, 1H), 7.14-7.43 (m, 3H), 8.31 (s, 1H).

(2) 1-(3-ethoxyphenyl)-3-ethyl-1H-pyrazole-4-carbaldehyde

A solution (15 mL) of methyl 1-(3-ethoxyphenyl)-3-ethyl-1H-pyrazole-4-carboxylate (4.4 g) synthesized in the above-mentioned (1) in tetrahydrofuran was added to an ice-cooled solution (35 mL) of lithium aluminum hydride (0.61 g) in tetrahydrofuran. The ice bath was removed, and the reaction mixture was stirred at room temperature for 1 hr, the mixture was ice-cooled again, and water (1.6 mL), 1N aqueous sodium hydroxide solution (8.0 mL) and water (1.6 mL) were successively added dropwise to quench the reaction. The residue was filtered through celite, and the filtrate was concentrated under reduced pressure to give a crude product (3.5 g) of 1-(3-ethoxyphenyl)-3-ethyl-1H-pyrazole-4-methanol as a pale-yellow oil. This was dissolved in toluene (100 mL), manganese dioxide (4.0 g) was added, and the mixture was heated under reflux with a Dean-Stark trap for 1 hr. The reaction mixture was allowed to cool to room temperature, manganese dioxide was collected by filtration, and the solvent was evaporated under reduced pressure to give the title object compound (3.4 g, 87%) as a yellow solid.

$^1$H NMR (300 MHz, CDCl$_3$) δ ppm 1.29-1.50 (m, 6H), 2.99 (q, J=7.5 Hz, 2H), 4.11 (q, J=7.0 Hz, 2H), 6.88 (ddd, J=8.2, 2.4, 0.8 Hz, 1H), 7.15-7.45 (m, 3H), 8.32 (s, 1H), 10.00 (s, 1H).

(3) cyclohexyl[1-(3-ethoxyphenyl)-3-ethyl-1H-pyrazol-4-yl]methanol

To a solution (20 mL) of 1-(3-ethoxyphenyl)-3-ethyl-1H-pyrazole-4-carbaldehyde (1.7 g) synthesized in the above-mentioned (2) in tetrahydrofuran was added dropwise under ice-cooling cyclohexylmagnesium bromide (12.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate: hexane=1:2, volume ratio) to give the title object compound (2.2 g, 96%) as a pale-yellow oil.

$^1$H NMR (300 MHz, CDCl$_3$) δ ppm 0.79-1.97 (m, 18H), 2.71 (q, J=7.5 Hz, 2H), 4.07-4.21 (m, 2H), 4.44 (dd, J=7.3, 2.6 Hz, 1H), 6.77 (dd, J=7.9, 2.1 Hz, 1H), 7.13-7.37 (m, 3H), 7.78 (s, 1H).

(4) 3-[{[4-({cyclohexyl[1-(3-ethoxyphenyl)-3-ethyl-1H-pyrazol-4-yl]methyl}amino)phenyl]carbonyl}(methyl)amino]propanoic acid To a solution (10 mL) of cyclohexyl[1-(3-ethoxyphenyl)-3-ethyl-1H-pyrazol-4-yl]methanol (0.60 g) synthesized in the above-mentioned (3) in tetrahydrofuran was added at room temperature thionyl chloride (0.24 mL). The reaction mixture was stirred at room temperature for 30 min and ice-cooled, and saturated aqueous sodium hydrogen carbonate solution (15 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.27 g), sodium carbonate (0.29 g) and ethyl 3-{[(4-aminophenyl)carbonyl](methyl)amino}propanoate (0.45 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(3-ethoxyphenyl)-3-ethyl-1H-pyrazol-4-yl]methyl}amino)phenyl]carbonyl}(methyl)amino]propanoate (0.7 g) as a pale-yellow oil. This was dissolved in ethanol (3.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.66 g, 69%) as a colorless solid.

$^1$H NMR (300 MHz, CDCl$_3$) δ ppm 0.90-2.30 (m, 17H), 2.60-2.75 (m, 4H), 3.06 (s, 3H), 3.72 (t, J=6.4 Hz, 1H), 4.08 (q, J=6.9 Hz, 2H), 4.22 (d, J=5.7 Hz, 1H), 6.50 (d, J=8.7 Hz, 2H), 6.74 (dd, J=8.7, 1.9 Hz, 1H), 7.09-7.34 (m, 5H), 7.64 (s, 1H).

Example 84

3-({[4-({cyclohexyl[1-(3-ethoxyphenyl)-3-ethyl-1H-pyrazol-4-yl]methyl}amino)phenyl]carbonyl}amino)propanoic acid

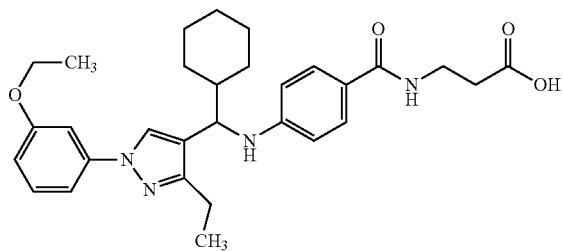 [SMILES: CCOc1cccc(-n2cc(C(Nc3ccc(C(=O)NCCC(=O)O)cc3)C3CCCCC3)c(CC)n2)c1]

To a solution (10 of cyclohexyl[1-(3-ethoxyphenyl)-3-ethyl-1H-pyrazol-4-yl]methanol (0.60 g) synthesized in Example 83(3) in tetrahydrofuran was added at room temperature thionyl chloride (0.24 mL). The reaction mixture was stirred at room temperature for 30 min and ice-cooled, and saturated aqueous sodium hydrogen carbonate solution (15 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.27 g), sodium carbonate (0.29 g) and ethyl 3-{[(4-aminophenyl)carbonyl]amino}propanoate (0.43 g) synthesized in Example 1(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-({[4-({cyclohexyl[1-(3-ethoxyphenyl)-3-ethyl-1H-pyrazol-4-yl]methyl}amino)phenyl]carbonyl}amino)propanoate (0.6 g) as a pale-yellow oil. This was dissolved in ethanol (3.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.59 g, 63%) as a colorless solid.

$^1$H NMR (300 MHz, CDCl$_3$) δ ppm 0.97-2.00 (m, 17H), 2.56-2.81 (m, 4H), 3.64 (q, J=5.8 Hz, 2H), 4.06 (q, J=7.0 Hz, 2H), 4.24 (d, J=6.0 Hz, 1H), 6.50 (d, J=8.7 Hz, 2H), 6.54-6.62 (m, 1H), 6.73 (dd, J=7.7, 2.1 Hz, 1H), 7.07-7.32 (m, 3H), 7.53 (d, J=8.9 Hz, 2H), 7.63 (s, 1H).

Example 85

3-[{[4-({1-[1-(3-ethoxyphenyl)-3-ethyl-1H-pyrazol-4-yl]-3-methylbutyl}amino)phenyl]carbonyl}(methyl)amino]propanoic acid

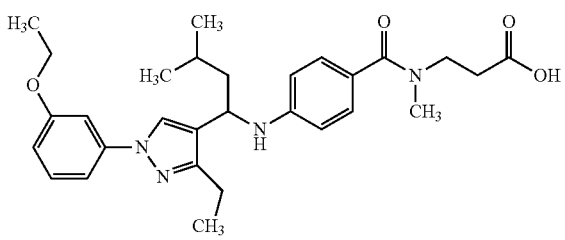 [SMILES: CCOc1cccc(-n2cc(C(CC(C)C)Nc3ccc(C(=O)N(C)CCC(=O)O)cc3)c(CC)n2)c1]

(1) 1-[1-(3-ethoxyphenyl)-3-ethyl-1H-pyrazol-4-yl]-3-methylbutan-1-ol

To a solution (20 mL) of 1-(3-ethoxyphenyl)-3-ethyl-1H-pyrazole-4-carbaldehyde (1.7 g) synthesized in Example 83(2) in tetrahydrofuran was added dropwise under ice-cooling, isobutylmagnesium bromide (12.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (1.4 g, 67%) as a pale-yellow oil.

$^1$H NMR (300 MHz, CDCl$_3$) δ ppm 0.98 (dd, J=6.4, 2.4 Hz, 6H), 1.18-1.90 (m, 9H), 2.75 (q, J=7.6 Hz, 2H), 4.09 (q, J=7.0 Hz, 2H), 4.81 (d, J=3.6 Hz, 1H), 6.77 (ddd, J=8.1, 2.4, 0.9 Hz, 1H), 7.11-7.38 (m, 3H), 7.79 (s, 1H).

(2) 3-[{[4-({1-[1-(3-ethoxyphenyl)-3-ethyl-1H-pyrazol-4-yl]-3-methylbutyl}amino)phenyl]carbonyl}(methyl)amino]propanoic acid To a solution (10 mL) of 1-[1-(3-ethoxyphenyl)-3-ethyl-1H-pyrazol-4-yl]-3-methylbutan-1-ol (0.71 g) synthesized in the above-mentioned (1) in tetrahydrofuran was added at room temperature thionyl chloride (0.39 mL). The reaction mixture was stirred at room temperature for 30 min and ice-cooled, and saturated aqueous sodium hydrogen carbonate solution (15 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15.0 mL), sodium iodide (0.53 g), sodium carbonate (0.35 g) and ethyl 3-{[(4-aminophenyl)carbonyl](methyl)amino}propanoate (0.59 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({1-[1-(3-ethoxyphenyl)-3-ethyl-1H-pyrazol-4-yl]-3-methylbutyl}amino)phenyl]carbonyl}(methyl)amino]propanoate (0.55 g) as a pale-yellow oil. This was dissolved in ethanol (3.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.46 g, 39%) as a colorless solid.

$^1$H NMR (300 MHz, CDCl$_3$) δ ppm 0.89-2.00 (m, 15H), 2.56-2.82 (m, 4H), 3.06 (s, 3H), 3.72 (t, J=6.2 Hz, 2H), 4.08 (q, J=6.8 Hz, 2H), 4.46 (t, J=6.8 Hz, 1H), 6.55 (d, J=7.2 Hz, 2H), 6.75 (dd, J=8.0, 1.5 Hz, 1H), 7.05-7.38 (m, 5H), 7.72 (br. s., 1H).

Example 86

3-({[4-({1-[1-(3-ethoxyphenyl)-3-ethyl-1H-pyrazol-4-yl]-3-methylbutyl}amino)phenyl]carbonyl}amino)propanoic acid

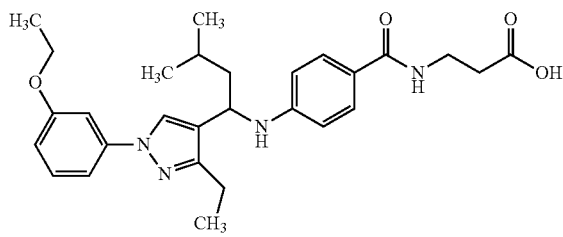 [SMILES: CCOc1cccc(-n2cc(C(CC(C)C)Nc3ccc(C(=O)NCCC(=O)O)cc3)c(CC)n2)c1]

To a solution (10 mL) of 1-[1-(3-ethoxyphenyl)-3-ethyl-1H-pyrazol-4-yl]-3-methylbutan-1-ol (0.71 g) synthesized in Example 85(1) in tetrahydrofuran was added at room temperature thionyl chloride (0.39 mL). The reaction mixture was stirred at room temperature for 30 min and ice-cooled, and saturated aqueous sodium hydrogen carbonate solution (15 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15.0 mL), sodium iodide (0.53 g), sodium carbonate (0.35 g) and ethyl 3-{[(4-aminophenyl)carbonyl]amino}propanoate (0.55 g) synthesized in Example 1(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-({[4-({1-[1-(3-ethoxyphenyl)-3-ethyl-1H-pyrazol-4-yl]-3-methylbutyl}amino)phenyl]carbonyl}amino)propanoate (0.56 g) as a pale-yellow oil. This was dissolved in ethanol (3.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.54 g, 47%) as a colorless solid.

$^1$H NMR (300 MHz, CDCl$_3$) δ ppm 0.84-1.10 (m, 6H), 1.32 (t, J=7.6 Hz, 3H), 1.41 (t, J=7.0 Hz, 3H), 1.57-1.87 (m, 3H), 2.58-2.80 (m, 4H), 3.67 (q, J=5.9 Hz, 2H), 4.07 (q, J=6.8 Hz, 2H), 4.48 (t, J=6.6 Hz, 1H), 4.75 (br. s., 1H), 6.53 (d, J=8.7 Hz, 2H), 6.66 (t, J=5.9 Hz, 1H), 6.74 (dd, J=8.1, 1.7 Hz, 1H), 7.07-7.33 (m, 3H), 7.57 (d, J=8.7 Hz, 2H), 7.68 (s, 1H).

Example 87

3-[{[4-({cyclohexyl[1-(3,5-difluorophenyl)-3-ethyl-1H-pyrazol-4-yl]methyl}amino)phenyl]carbonyl}(methyl)amino]propanoic acid

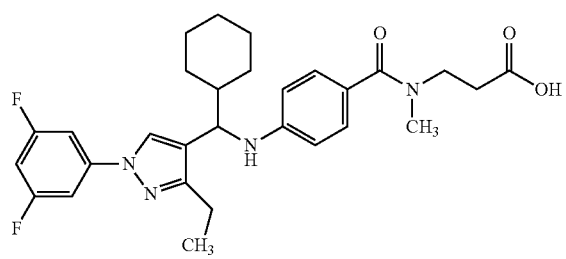 [SMILES: CCc1nn(-c2cc(F)cc(F)c2)cc1C(Nc1ccc(C(=O)N(C)CCC(=O)O)cc1)C1CCCCC1]

(1) methyl 1-(3,5-difluorophenyl)-3-ethyl-1H-pyrazole-4-carboxylate

A mixture of methyl 3-oxopentanoate (5.2 g) and dimethylformamide dimethylacetal (5.6 mL) was stirred at 100° C. overnight, and the mixture was allowed to cool to room temperature. Ethanol (100 mL) and 3,5-difluorophenylhydrazine hydrochloride (7.9 g) were added to the reaction mixture, and the mixture was further stirred at 100° C. for 15 hr. After allowing to cool, ethanol was evaporated under reduced pressure, water was added to the residue, and the mixture was extracted with ethyl acetate. The extract was washed with brine, dried over magnesium sulfate, and concentrated under reduced pressure. The residue was purified by silica gel column chromatography (ethyl acetate:hexane=1:10, volume ratio) to give the title object compound (6.5 g, 62%) as a yellow oil.

$^1$H NMR (300 MHz, CDCl$_3$) δ ppm 1.21 (t, J=7.4 Hz, 3H), 3.03 (q, J=7.4 Hz, 2H), 3.87 (s, 3H), 6.87-7.11 (m, 3H), 8.02 (s, 1H).

(2) 1-(3,5-difluorophenyl)-3-ethyl-1H-pyrazole-4-carbaldehyde

A solution (35 mL) of methyl 1 (3,5-difluorophenyl)-3-ethyl-1H-pyrazole-4-carboxylate (6.5 g) synthesized in the above-mentioned (1) in tetrahydrofuran was added to an ice-cooled solution (65 mL) of lithium aluminum hydride (0.94 g) in tetrahydrofuran. The ice bath was removed, and the reaction mixture was stirred at room temperature for 1 hr. The mixture was ice-cooled again, and water (2.5 mL), 1N aqueous sodium hydroxide solution (12.5 mL) and water (2.5 mL) were successively added dropwise to quench the reaction. The residue was filtered through celite, and the filtrate was concentrated under reduced pressure to give a crude product (3.3 g) of 1-(3,5-difluorophenyl)-3-ethyl-1H-pyrazole-4-methanol as a pale-yellow oil. This was dissolved in toluene (100 mL), manganese dioxide (6.0 g) was added, and the mixture was heated under reflux with a Dean-Stark trap for 1 hr. The reaction mixture was allowed to cool to room temperature, manganese dioxide was collected by filtration, and the solvent was evaporated under reduced pressure to give the title object compound (3.1 g, 51%) as a yellow solid.

$^1$H NMR (300 MHz, CDCl$_3$) δ ppm 1.25 (t, J=7.6 Hz, 3H), 3.03 (q, J=7.6 Hz, 2H), 6.85-7.11 (m, 3H), 8.07 (s, 1H), 9.99 (s, 1H).

(3) cyclohexyl[1-(3,5-difluorophenyl)-3-ethyl-1H-pyrazol-4-yl]methanol

To a solution (10 mL) of 1-(3,5-difluorophenyl)-3-ethyl-1H-pyrazole-4-carbaldehyde (1.5 g) synthesized in the above-mentioned (2) in tetrahydrofuran was added dropwise under ice-cooling cyclohexylmagnesium bromide (12.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (1.9 g, quantitative) as a pale-yellow oil.

$^1$H NMR (300 MHz, CDCl$_3$) δ ppm 1.26 (t, J=7.2 Hz, 3H), 1.32-2.14 (m, 12H), 2.78 (q, J=7.2 Hz, 2H), 4.35 (dd, J=8.2, 2.9 Hz, 1H), 6.80-7.12 (m, 3H), 7.62 (s, 1H).

(4) 3-[{[4-({cyclohexyl[1-(3,5-difluorophenyl)-3-ethyl-1H-pyrazol-4-yl]methyl}amino)phenyl]carbonyl}(methyl)amino]propanoic acid To a solution (15 mL) of cyclohexyl[1-(3,5-difluorophenyl)-3-methyl-1H-pyrazol-4-yl]methanol (0.96 g) synthesized in the above-mentioned (3) in tetrahydrofuran was added at room temperature thionyl chloride (0.40 mL). The reaction mixture was stirred at room temperature for 30 min and ice-cooled, and saturated aqueous sodium hydrogen carbonate solution (10 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15.0 mL), sodium iodide (0.68 g), sodium carbonate (0.48 g) and ethyl 3-{[(4-aminophenyl)carbonyl](methyl)amino}propanoate (0.75 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[1-(3,5-difluorophenyl)-3-ethyl-1H-pyrazol-4-yl]methyl}amino)phenyl]carbonyl}(methyl)amino]propanoate (0.90 g) as a pale-yellow oil. This was dissolved in ethanol (3.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.70 g, 44%) as a colorless solid.

$^1$H NMR (300 MHz, CDCl$_3$) δ ppm 0.94-2.08 (m, 14H), 2.59-2.89 (m, 4H), 3.08 (s, 3H), 3.73 (t, J=6.5 Hz, 2H), 4.19 (d, J=6.8 Hz, 1H), 6.53 (d, J=8.5 Hz, 2H), 6.77-7.30 (m, 5H), 7.52 (s, 1H).

Example 88

3-({[4-({cyclohexyl[1-(3,5-difluorophenyl)-3-ethyl-1H-pyrazol-4-yl]methyl}amino)phenyl]carbonyl}amino)propanoic acid

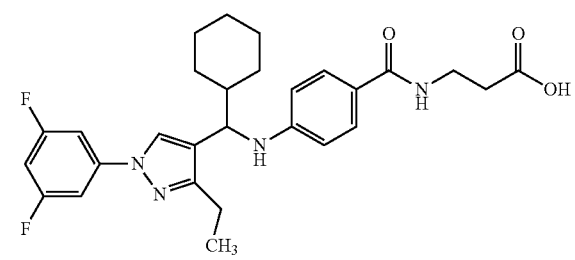 [SMILES: CCc1nn(-c2cc(F)cc(F)c2)cc1C(Nc1ccc(C(=O)NCCC(=O)O)cc1)C1CCCCC1]

To a solution (15 mL) of cyclohexyl[1-(3,5-difluorophenyl)-3-ethyl-1H-pyrazol-4-yl]methanol (0.96 g) synthesized in Example 87(3) in tetrahydrofuran was added at room temperature thionyl chloride (0.40 mL). The reaction mixture was stirred at room temperature for 30 min and ice-cooled, and saturated aqueous sodium hydrogen carbonate solution (10 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15.0 mL), sodium iodide (0.68 g), sodium carbonate (0.48 g) and ethyl 3-{[(4-aminophenyl)carbonyl]amino}propanoate (0.70 g) synthesized in Example 1(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-({[4-({cyclohexyl[1-(3,5-difluorophenyl)-3-ethyl-1H-pyrazol-4-yl]methyl}amino)phenyl]carbonyl}amino)propanoate (0.80 g) as a pale-yellow oil. This was dissolved in ethanol (3.0 mL), 1N aqueous sodium hydroxide solution (3.0 mL) was added at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.50 g, 33%) as a colorless solid.

$^1$H NMR (300 MHz, CDCl$_3$) δ ppm 1.02 (t, J=7.5 Hz, 3H), 1.06-2.08 (m, 11H), 2.65 (t, J=5.7 Hz, 2H), 2.78 (q, J=7.5 Hz, 2H), 3.67 (q, J=7.0 Hz, 2H), 4.20 (d, J=6.8 Hz, 1H), 6.52 (d, J=8.7 Hz, 2H), 6.57-6.68 (m, 1H), 6.77-7.10 (m, 3H), 7.51 (s, 1H), 7.55 (d, J=8.7 Hz, 2H).

Example 89

3-[({4-[(cyclohexyl{3-(methoxymethyl)-1-[4-(trifluoromethyl)pyridin-2-yl]-1H-pyrazol-4-yl}methyl)amino]phenyl}carbonyl)(methyl)amino]propanoic acid

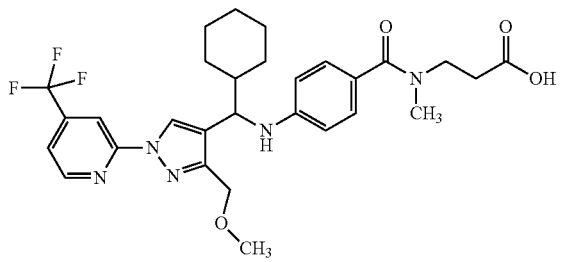 [SMILES: COCc1nn(-c2cccc(C(F)(F)F)n2)cc1C(Nc1ccc(C(=O)N(C)CCC(=O)O)cc1)C1CCCCC1]

(1) methyl 3-(methoxymethyl)-1-[4-(trifluoromethyl)pyridin-2-yl]-1H-pyrazole-4-carboxylate To a solution of methyl 3-(methoxymethyl)-1H-pyrazole-4-carboxylate (1.8 g) synthesized in Example 29(1) in N,N-dimethylformamide (20 mL) were added 2-chloro-4-trifluoromethylpyridine (2.0 g) and potassium carbonate (2.3 g), and the mixture was stirred at 100° C. overnight. The reaction mixture was allowed to cool to room temperature and filtered through celite, water was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (0.62 g, 18%) as a pale-yellow oil.
$^1$H NMR (300 MHz, CDCl$_3$) δ ppm 3.54 (s, 3H), 3.89 (s, 3H), 4.83 (s, 2H), 7.47 (dd, J=5.1, 0.9 Hz, 1H), 8.31 (s, 1H), 8.61 (d, J=5.1 Hz, 1H), 9.04 (s, 1H).

(2) 3-(methoxymethyl)-1-[4-(trifluoromethyl)pyridin-2-yl]-1H-pyrazole-4-carbaldehyde A solution (2 mL) of methyl 3-(methoxymethyl)-1-[4-(trifluoromethyl)pyridin-2-yl]-1H-pyrazole-4-carboxylate (0.62 g) synthesized in the above-mentioned (1) in tetrahydrofuran was added to an ice-cooled solution (5 mL) of lithium aluminum hydride (0.10 g) in tetrahydrofuran. The ice bath was removed, and the reaction mixture was stirred at room temperature for 1 hr. The mixture was ice-cooled again, and water (0.2 mL), 1N aqueous sodium hydroxide solution (1.0 mL) and water (0.2 mL) were successively added dropwise to quench the reaction. The residue was filtered through celite, and the filtrate was concentrated under reduced pressure to give a crude product (0.53 g) of 3-(methoxymethyl)-1-[4-(trifluoromethyl)pyridin-2-yl]-1H-pyrazole-4-methanol as a pale-yellow oil. This was dissolved in toluene (30 mL), manganese dioxide (2.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (0.59 g, quantitative) as a yellow oil.
$^1$H NMR (300 MHz, CDCl$_3$) δ ppm 3.53 (s, 3H), 4.83 (s, 2H), 7.50 (d, J=4.9 Hz, 1H), 8.31 (s, 1H), 8.63 (d, J=5.1 Hz, 1H), 9.09 (s, 1H), 10.10 (s, 1H).

(3) cyclohexyl{3-(methoxymethyl)-1-[4-(trifluoromethyl)pyridin-2-yl]-1H-pyrazol-4-yl}methanol To a solution (10 mL) of 3-(methoxymethyl)-1-[4-(trifluoromethyl)pyridin-2-yl]-1H-pyrazole-4-carbaldehyde (0.59 g) synthesized in the above-mentioned (2) in tetrahydrofuran was added dropwise under ice-cooling cyclohexylmagnesium bromide (4.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:4, volume ratio) to give the title object compound (0.23 g, 30%) as a pale-yellow oil.
$^1$H NMR (300 MHz, CDCl$_3$) δ ppm 0.94-1.96 (m, 12H), 3.45 (s, 3H), 4.43 (d, J=7.7 Hz, 1H), 4.58-4.65 (m, 2H), 7.38 (d, J=0.9 Hz, 1H), 8.15-8.60 (m, 3H).

(4) 3-[({4-[(cyclohexyl{3-(methoxymethyl)-1-[4-(trifluoromethyl)pyridin-2-yl]-1H-pyrazol-4-yl}methyl)amino]phenyl}carbonyl)(methyl)amino]propanoic acid To a solution (5 mL) of cyclohexyl{3-(methoxymethyl)-1-[4-(trifluoromethyl)pyridin-2-yl]-1H-pyrazol-4-yl}methanol (0.23 g) synthesized in the above-mentioned (3) in tetrahydrofuran was added at room temperature thionyl chloride (0.10 mL). The reaction mixture was stirred at room temperature for 30 min and ice-cooled, and saturated aqueous sodium hydrogen carbonate solution (5 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5.0 mL), sodium iodide (0.14 g), sodium carbonate (0.10 g) and ethyl 3-{[(4-aminophenyl)carbonyl](methyl)amino}propanoate (0.17 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[({4-[(cyclohexyl{3-(methoxymethyl)-1-[4-(trifluoromethyl)pyridin-2-yl]-1H-pyrazol-4-yl}methyl)amino]phenyl}carbonyl)(methyl)amino]propanoate (0.10 g) as a pale-yellow oil. This was dissolved in ethanol (1.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.04 g, 10%) as a pale-yellow solid.
$^1$H NMR (300 MHz, CDCl$_3$) δ ppm 0.95-2.18 (m, 11H), 2.70 (t, J=6.3 Hz, 2H), 3.06 (s, 3H), 3.42 (s, 3H), 3.71 (t, J=6.3 Hz, 2H), 4.36 (d, J=7.2 Hz, 1H), 4.57 (d, J=2.1 Hz, 2H), 6.56

(d, J=8.7 Hz, 2H), 7.24 (d, J=8.7 Hz, 2H), 7.37 (d, J=5.3 Hz, 1H), 8.16 (s, 1H), 8.36 (s, 1H), 8.53 (d, J=5.3 Hz, 1H).

Example 90

3-[({4-[(cyclohexyl{3-(methoxymethyl)-1-[6-(trifluoromethyl)pyridin-2-yl]-1H-pyrazol-4-yl}methyl)amino]phenyl}carbonyl)(methyl)amino]propanoic acid

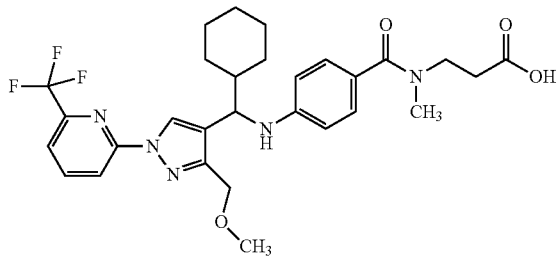

(1) methyl 3-(methoxymethyl)-1-[6-(trifluoromethyl)pyridin-2-yl]-1H-pyrazole-4-carboxylate To a solution of methyl 3-(methoxymethyl)-1H-pyrazole-4-carboxylate (5.1 g) synthesized in Example 29(1) in N,N-dimethylformamide (70 mL) were added 2-chloro-6-trifluoromethylpyridine (5.0 g) and potassium carbonate (6.2 g), and the mixture was stirred at 100° C. overnight. The reaction mixture was allowed to cool to room temperature and filtered through celite, water was added to the filtrate, and the mixture was extracted with diethyl ether. The extract was washed with brine, dried over magnesium sulfate, and concentrated under reduced pressure. The residue was purified by silica gel column chromatography (ethyl acetate:hexane=1:4, volume ratio) to give the title object compound (6.5 g, 69%) as colorless crystals.
$^1$H NMR (300 MHz, CDCl$_3$) δ ppm 3.54 (s, 3H), 3.89 (s, 3H), 4.83 (s, 2H), 7.62 (d, J=7.2 Hz, 1H), 8.00-8.02 (m, 1H), 8.25-8.30 (m, 1H), 9.06 (s, 1H).

(2) 3-(methoxymethyl)-1-[6-(trifluoromethyl)pyridin-2-yl]-1H-pyrazole-4-carbaldehyde A solution (10 mL) of methyl 3-(methoxymethyl)-1-[6-(trifluoromethyl)pyridin-2-yl]-1H-pyrazole-4-carboxylate (6.5 g) synthesized in the above-mentioned (1) in tetrahydrofuran was added to an ice-cooled solution (25 mL) of lithium aluminum hydride (0.79 g) in tetrahydrofuran. The ice bath was removed, and the reaction mixture was stirred at room temperature for 1 hr. The mixture was ice-cooled again, and water (2.0 mL), 1N aqueous sodium hydroxide solution (10.0 mL) and water (2.0 mL) were successively added dropwise to quench the reaction. The residue was filtered through celite, and the filtrate was concentrated under reduced pressure to give a crude product (6.0 g) of 3-(methoxymethyl)-1-[6-(trifluoromethyl)pyridin-2-yl]-1H-pyrazole-4-methanol as a pale-yellow oil. This was dissolved in toluene (100 mL), manganese dioxide (3.0 g) was added, and the mixture was heated under reflux with a Dean-Stark trap for 1 hr. The reaction mixture was allowed to cool to room temperature, and manganese dioxide was collected by filtration. The solvent was evaporated under reduced pressure to give the title object compound (5.3 g, 90%) as a yellow oil.
$^1$H NMR (300 MHz, CDCl$_3$) δ ppm 3.53 (s, 3H), 4.83 (s, 2H), 7.66 (d, J=7.5 Hz, 1H), 8.05-8.08 (m, 1H), 8.27 (d, J=8.3 Hz, 1H), 9.13 (s, 1H), 10.10 (s, 1H).

(3) cyclohexyl{3-(methoxymethyl)-1-[6-(trifluoromethyl)pyridin-2-yl]-1H-pyrazol-4-yl}methanol To a solution (100 mL) of 3-(methoxymethyl)-1-[6-(trifluoromethyl)pyridin-2-yl]-1H-pyrazole-4-carbaldehyde (5.3 g) synthesized in the above-mentioned (2) in tetrahydrofuran was added dropwise under ice-cooling cyclohexylmagnesium bromide (25.0 mL, 1M tetrahydrofuran solution). After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (4.6 g, 67%) as a pale-yellow oil.
$^1$H NMR (300 MHz, CDCl$_3$) δ ppm 0.94-2.22 (m, 11H), 2.95 (d, J=6.0 Hz, 1H), 3.45 (s, 3H), 4.44 (dd, J=7.7, 6.0 Hz, 1H), 4.50-4.65 (m, 2H), 7.53 (d, J=7.0 Hz, 1H), 7.93-8.00 (m, 1H), 8.14 (d, J=8.3 Hz, 1H), 8.45 (s, 1H).

(4) 3-[({4-[(cyclohexyl{3-(methoxymethyl)-1-[6-(trifluoromethyl)pyridin-2-yl]-1H-pyrazol-4-yl}methyl)amino]phenyl}carbonyl)(methyl)amino]propanoic acid To a solution (5 mL) of cyclohexyl{3-(methoxymethyl)-1-[6-(trifluoromethyl)pyridin-2-yl]-1H-pyrazol-4-yl}methanol (0.50 g) synthesized in the above-mentioned (3) in tetrahydrofuran was added at room temperature thionyl chloride (0.15 mL). The reaction mixture was stirred at room temperature for 30 min and ice-cooled, and saturated aqueous sodium hydrogen carbonate solution (5 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5.0 mL), sodium iodide (0.37 g), sodium carbonate (0.26 g) and ethyl 3-{[(4-aminophenyl)carbonyl](methyl)amino}propanoate (0.34 g) synthesized in Example 2(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[({4-[(cyclohexyl{3-(methoxymethyl)-1-[6-(trifluoromethyl)pyridin-2-yl]-1H-pyrazol-4-yl}methyl)amino]phenyl}carbonyl)(methyl)amino]propanoate (0.08 g) as a pale-yellow oil. This was dissolved in ethanol (3.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.06 g, 7%) as a colorless solid.
$^1$H NMR (300 MHz, CDCl$_3$) δ ppm 0.92-2.19 (m, 11H), 2.73 (br. s., 2H), 3.08 (s, 3H), 3.41 (s, 3H), 3.72 (t, J=6.2 Hz, 2H), 4.36 (d, J=8.0 Hz, 1H), 4.57 (d, J=2.1 Hz, 2H), 6.58 (d, J=8.7 Hz, 2H), 7.20-7.30 (m, 2H), 7.51-8.12 (m, 3H), 8.40 (s, 1H).

Example 91

3-[({4-[(cyclohexyl{3-(methoxymethyl)-1-[6-(trifluoromethyl)pyridin-2-yl]-1H-pyrazol-4-yl}methyl)amino]phenyl}carbonyl)amino]propanoic acid

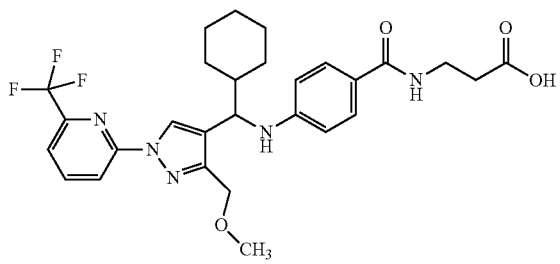 [SMILES: COCc1nn(-c2cccc(C(F)(F)F)n2)cc1C(Nc1ccc(C(=O)NCCC(=O)O)cc1)C1CCCCC1]

To a solution (5 mL) of cyclohexyl{3-(methoxymethyl)-1-[6-(trifluoromethyl)pyridin-2-yl]-1H-pyrazol-4-yl}methanol (0.50 g) synthesized in Example 90(3) in tetrahydrofuran was added at room temperature thionyl chloride (0.15 mL). The reaction mixture was stirred at room temperature for 30 min and ice-cooled, and saturated aqueous sodium hydrogen carbonate solution (5 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5.0 mL), sodium iodide (0.37 g), sodium carbonate (0.26 g) and ethyl 3-{[(4-aminophenyl)carbonyl]amino}propanoate (0.32 g) synthesized in Example 1(2) were added, and the mixture was stirred at 70° C. for 12 hr. After allowing to cool, water was added to the reaction mixture and the mixture was extracted with ethyl acetate. The extract was concentrated under reduced pressure, and the residue was purified by silica gel column chromatography (ethyl acetate: hexane=1:1, volume ratio) to give ethyl 3-[({4-[(cyclohexyl{3-(methoxymethyl)-1-[6-(trifluoromethyl)pyridin-2-yl]-1H-pyrazol-4-yl}methyl)amino]phenyl}carbonyl)amino]propanoate (0.07 g) as a pale-yellow oil. This was dissolved in ethanol (3.0 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.06 g, 8%) as a colorless solid.

$^1$H NMR (300 MHz, CDCl$_3$) δ ppm 0.87-2.17 (m, 11H), 2.67 (t, J=5.7 Hz, 2H), 3.41 (s, 3H), 3.56-3.77 (m, 2H), 4.38 (d, J=7.6 Hz, 1H), 4.56 (d, J=2.3 Hz, 2H), 6.47-6.71 (m, 3H), 7.46-8.11 (m, 5H), 8.40 (s, 1H).

Example 92

3-({[4-({cyclohexyl[1-(3-ethoxyphenyl)-3-ethyl-1H-pyrazol-4-yl]methyl}amino)phenyl]carbonyl}amino)-2-methylpropanoic acid

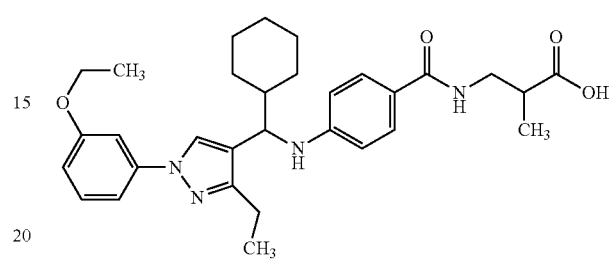

(1) methyl 4-({cyclohexyl[1-(3-ethoxyphenyl)-3-ethyl-1H-pyrazol-4-yl]methyl}amino)benzoate To a solution (5 mL) of cyclohexyl[1-(3-ethoxyphenyl)-3-ethyl-1H-pyrazol-4-yl]methanol (0.64 g) synthesized in Example 83(3) in tetrahydrofuran was added at room temperature thionyl chloride (0.22 mL). The reaction mixture was stirred at room temperature for 30 min and ice-cooled, and saturated aqueous sodium hydrogen carbonate solution (10 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10.0 mL), sodium iodide (0.44 g), sodium carbonate (0.30 g) and methyl 4-aminobenzoate (0.35 g) were added, and the mixture was stirred at 70° C. overnight. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (0.34 g, 38%) as a pale-yellow oil.

$^1$H NMR (300 MHz, CDCl$_3$) δ ppm 0.76-1.85 (m, 17H), 2.63-2.82 (m, 2H), 3.82 (s, 3H), 4.02-4.11 (m, 2H), 4.27 (br. s., 1H), 6.51 (d, J=8.9 Hz, 2H), 6.75 (dd, J=2.4, 0.9 Hz, 1H), 7.09-7.26 (m, 3H), 7.64 (s, 1H), 7.80 (d, J=8.9 Hz, 2H).

(2) 4-({cyclohexyl[1-(3-ethoxyphenyl)-3-ethyl-1H-pyrazol-4-yl]methyl}amino)benzoic acid To a solution of methyl 4-({cyclohexyl[1-(3-ethoxyphenyl)-3-ethyl-1H-pyrazol-4-yl]methyl}amino)benzoate (0.34 g) synthesized in the above-mentioned (1) in ethanol (6.0 mL) was added 1N aqueous sodium hydroxide solution (6.0 mL), and the mixture was stirred at 60° C. for 6 hr. Ethanol was evaporated under reduced pressure, and 1N hydrochloric acid (8.0 mL) was added to the residue, and the mixture was extracted with ethyl acetate. The extract was washed with saturated brine, dried over magnesium sulfate, and concentrated under reduced pressure to give a crude product (0.33 g, quantitative) of the title object compound as a yellow oil.

$^1$H NMR (300 MHz, CDCl$_3$) δ ppm 0.92-2.00 (m, 17H), 2.72 (q, J=7.5 Hz, 2H), 3.99-4.11 (m, 2H), 4.28 (d, J=5.8 Hz, 1H), 6.52 (d, J=8.9 Hz, 2H), 6.74 (ddd, J=8.1, 2.5, 0.8 Hz, 1H), 7.10-7.25 (m, 3H), 7.65 (s, 1H), 7.84 (d, J=8.9 Hz, 2H).

(3) 3-({[4-({cyclohexyl[1-(3-ethoxyphenyl)-3-ethyl-1H-pyrazol-4-yl]methyl}amino)phenyl]carbonyl}amino)-2-methylpropanoic acid 4-({Cyclohexyl[1-(3-ethoxyphenyl)-3-ethyl-1H-pyrazol-4-yl]methyl}amino)benzoic acid (0.18 g) synthesized in the above-mentioned (2) was dissolved in N,N-dimethylformamide (3 mL), 1-ethyl-3-(3-dimethylaminopropyl)carbodiimide hydrochloride (0.11 g), 1-hydroxybenzotriazole.monohydrate (0.09 g) and methyl 3-amino-2-methylpropanoate (0.07 g) were added at room temperature, and the mixture was stirred overnight. Water was added to the reaction mixture, and the mixture was extracted with diethyl ether. The extract was concentrated under reduced pressure, and the residue was purified by silica gel column chromatography (ethyl acetate:hexane=1:1, volume ratio) to give methyl 3-({[4-({cyclohexyl[1-(3-ethoxyphenyl)-3-ethyl-1H-pyrazol-4-yl]methyl}amino)phenyl]carbonyl}amino)-2-methylpropanoate (0.03 g) as a yellow oil. This was dissolved in ethanol (2.0 mL), 1N aqueous sodium hydroxide solution (0.5 mL) was added at room temperature, and the mixture was stirred at room temperature for 0.5 hr. Ethanol was evaporated under reduced pressure, and 1N hydrochloric acid (0.5 mL) was added to the residue. The precipitate was washed with water to give the title object compound (0.02 g, 9%) as a colorless solid.
$^1$H NMR (300 MHz, CDCl$_3$) δ ppm 0.96-2.00 (m, 20H), 2.62-2.91 (m, 3H), 3.59-3.75 (m, 2H), 4.07 (q, J=6.8 Hz, 2H), 4.24 (d, J=6.0 Hz, 1H), 6.43-6.59 (m, 3H), 6.74 (dd, J=8.1, 2.4 Hz, 1H), 7.08-7.66 (m, 6H).

Example 93

2-[({[4-({cyclohexyl[1-(3-ethoxyphenyl)-3-ethyl-1H-pyrazol-4-yl]methyl}amino)phenyl]carbonyl}amino)methyl]-2-ethylbutanoic acid

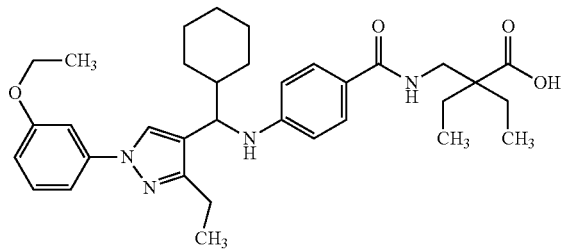 [SMILES: CCOc1cccc(-n2cc(C(Nc3ccc(C(=O)NCC(CC)(CC)C(=O)O)cc3)C3CCCCC3)c(CC)n2)c1]

4-({Cyclohexyl[1-(3-ethoxyphenyl)-3-ethyl-1H-pyrazol-4-yl]methyl}amino)benzoic acid (0.18 g) synthesized in Example 92(2) was dissolved in N,N-dimethylformamide (3 mL), 1-ethyl-3-(3-dimethylaminopropyl)carbodiimide hydrochloride (0.11 g), 1-hydroxybenzotriazole.monohydrate (0.09 g), ethyl 2-(aminomethyl)-2-ethylbutanoate hydrochloride (0.12 g) and triethylamine (0.09 mL) were added at room temperature, and the mixture was stirred overnight. Water was added to the reaction mixture, and the mixture was extracted with ethyl acetate. The extract was concentrated under reduced pressure, and the residue was purified by silica gel column chromatography (ethyl acetate:hexane=1:2, volume ratio) to give ethyl 2-[({[4-({cyclohexyl[1-(3-ethoxyphenyl)-3-ethyl-1H-pyrazol-4-yl]methyl}amino)phenyl]carbonyl}amino)methyl]-2-ethylbutanoate (0.18 g) as a yellow oil. This was dissolved in ethanol (2.0 mL), 1N aqueous sodium hydroxide solution (2.0 mL) was added at room temperature, and the mixture was stirred at 60° C. overnight. Ethanol was evaporated under reduced pressure, and 1N hydrochloric acid (2.0 mL) was added to the residue. The precipitate was washed with water to give the title object compound (0.17 g, 74%) as a colorless solid.
$^1$H NMR (300 MHz, CDCl$_3$) δ ppm 0.91 (t, J=7.4 Hz, 6H), 1.00-1.99 (m, 21H), 2.72 (q, J=7.5 Hz, 2H), 3.62 (d, J=6.2 Hz, 2H), 4.07 (q, J=7.0 Hz, 2H), 4.24 (d, J=6.0 Hz, 1H), 6.38-6.47 (m, 1H), 6.51 (d, J=8.9 Hz, 2H), 6.73 (ddd, J=7.1, 1.5, 1.2 Hz, 1H), 7.09-7.24 (m, 3H), 7.54 (d, J=8.9 Hz, 2H), 7.63 (s, 1H).

Example A1

3-{[(4-{[1-benzothiophen-3-yl(cyclohexyl)methyl]amino}phenyl)carbonyl]amino}propanoic acid

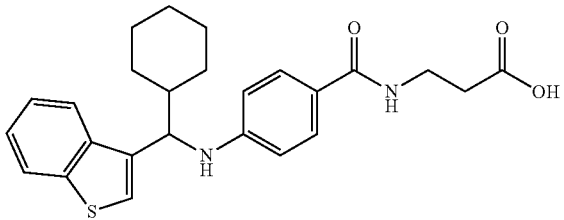 [SMILES: O=C(O)CCNC(=O)c1ccc(NC(c2csc3ccccc23)C2CCCCC2)cc1]

(1) 1-benzothiophen-3-yl(cyclohexyl)methanol

To a solution (40 mL) of 1-benzothiophene-3-carbaldehyde (2.25 g) in tetrahydrofuran was added dropwise 1.0M cyclohexylmagnesium bromide tetrahydrofuran solution (20.9 mL) at 0° C., and the mixture was stirred for 1.5 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=3:17, volume ratio) to give the title object compound (2.37 g, 69%) as an orange oil.
$^1$H NMR (300 MHz, CDCl$_3$) δ ppm 1.00-1.31 (m, 5H), 1.43-1.52 (m, 1H), 1.60-1.73 (m, 2H), 1.74-1.83 (m, 1H), 1.83-1.96 (m, 2H), 1.97-2.05 (m, 1H), 4.83 (dd, J=6.8, 3.2 Hz, 1H), 7.30-7.40 (m, 3H), 7.82-7.93 (m, 2H).

(2) 3-[chloro(cyclohexyl)methyl]-1-benzothiophene

To a solution of 1-benzothiophen-3-yl(cyclohexyl)methanol (2.32 g) synthesized above in toluene (25 mL) was added dropwise thionyl chloride (824 μL), and the mixture was stirred at room temperature for 4 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (2.42 g, 97%) as an orange oil.
$^1$H NMR (300 MHz, CDCl$_3$) δ ppm 0.95-1.34 (m, 5H), 1.46-1.56 (m, 1H), 1.60-1.72 (m, 2H), 1.76-1.86 (m, 1H), 2.10-2.28 (m, 2H), 5.03 (d, J=8.1 Hz, 1H), 7.32-7.43 (m, 3H), 7.82-7.93 (m, 2H).

(3) 4-{[1-benzothiophen-3-yl(cyclohexyl)methyl]amino}benzoic acid

To a mixture of 3-[chloro(cyclohexyl)methyl]-1-benzothiophene (2.42 g) synthesized above, methyl 4-aminobenzoate (2.77 g), sodium iodide (2.74 g) and N,N-dimethylacetamide (50 mL) was added sodium carbonate (1.94 g), and the mixture was stirred under argon atmosphere at 100° C. overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:3, volume ratio) to give a pale-yellow oil. To a mixture of the obtained oil, tetrahydrofuran (20 mL) and ethanol (20 mL) was added 1N aqueous sodium hydroxide solution (20 mL), and the mixture was stirred overnight with heating under reflux. The reaction mixture was concentrated under reduced pressure, and the residue was dissolved in water (40 mL), and 1N hydrochloric acid (20 mL) was added at 0° C. The resulting precipitate was collected by filtration to give the title object compound (1.80 g, 54%) as a white solid.

$^1$H NMR (300 MHz, CDCl$_3$) δ ppm 1.02-1.35 (m, 5H), 1.60-2.03 (m, 6H), 4.69 (d, J=5.7 Hz, 1H), 6.43-6.53 (m, 2H), 7.22 (s, 1H), 7.32-7.47 (m, 2H), 7.73-7.91 (m, 4H).

(4) 3-{[(4-{[1-benzothiophen-3-yl(cyclohexyl)methyl]amino}phenyl)carbonyl]amino}propanoic acid To a mixture of 4-{[1-benzothiophen-3-yl(cyclohexyl)methyl]amino}benzoic acid (250 mg) synthesized above, β-alanine ethyl ester hydrochloride (126 mg), 1-hydroxybenzotriazole.monohydrate (126 mg), triethylamine (114 μL) and N,N-dimethylformamide (10 mL) was added 1-ethyl-3-(3-dimethylaminopropyl)carbodiimide hydrochloride (157 mg), and the mixture was stirred at room temperature for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:1, volume ratio) to give a pale-yellow oil. To a mixture of the obtained oil, tetrahydrofuran (5 mL) and ethanol (5 mL) was added 1N aqueous sodium hydroxide solution (1 mL), and the mixture was stirred at room temperature for 2 hr. The reaction mixture was concentrated under reduced pressure, and the residue was dissolved in water (10 mL), and 1N hydrochloric acid (1 mL) was added at 0° C. The resulting precipitate was collected by filtration to give the title object compound (201 mg, 67%) as a white solid.

$^1$H NMR (300 MHz, CDCl$_3$) δ ppm 1.00-1.32 (m, 5H), 1.57-1.81 (m, 4H), 1.81-1.99 (m, 2H), 2.57 (t, J=5.7 Hz, 2H), 3.53-3.63 (m, 2H), 4.63 (d, J=5.7 Hz, 1H), 6.42 (d, J=8.7 Hz, 2H), 6.62 (t, J=6.1 Hz, 1H), 7.18 (s, 1H), 7.31-7.46 (m, 4H), 7.80-7.89 (m, 2H).

Example A2

3-{[(4-{[1-benzothiophen-3-yl(cyclohexyl)methyl]amino}phenyl)carbonyl](methyl)amino}-propanoic acid

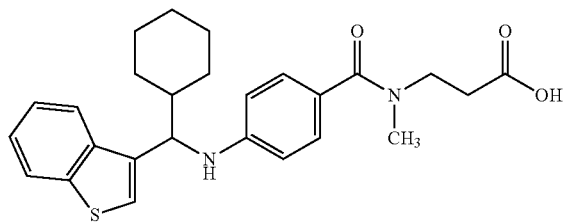 [SMILES: CN(CCC(=O)O)C(=O)c1ccc(NC(c2csc3ccccc23)C2CCCCC2)cc1]

Using 4-{[1-benzothiophen-3-yl(cyclohexyl)methyl]amino}benzoic acid (250 mg) synthesized in Example A1(3) and ethyl 3-(methylamino)propanoate (108 mg) and in the same manner as in Example A1(4), the title object compound (220 mg, 71%) was obtained as a white solid.

$^1$H NMR (300 MHz, CDCl$_3$) δ ppm 1.02-1.34 (m, 5H), 1.61-1.83 (m, 4H), 1.83-2.00 (m, 2H), 2.67 (t, J=6.4 Hz, 2H), 3.02 (s, 3H), 3.69 (t, J=6.4 Hz, 2H), 4.64 (d, J=5.7 Hz, 1H), 6.45 (d, J=8.7 Hz, 2H), 7.19 (d, J=8.7 Hz, 2H), 7.21 (s, 1H), 7.33-7.45 (m, 2H), 7.82-7.91 (m, 2H).

Example A3

3-{[(4-{[cyclohexyl(1-methyl-1H-benzimidazol-2-yl)methyl]amino}phenyl)carbonyl]amino}propanoic acid

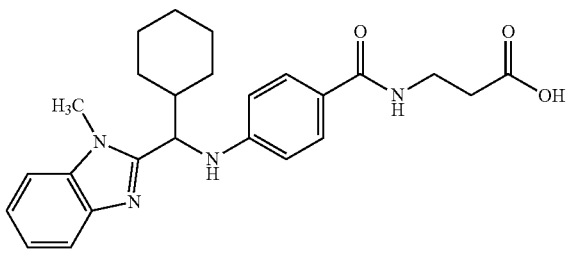 [SMILES: Cn1c(C(Nc2ccc(C(=O)NCCC(=O)O)cc2)C2CCCCC2)nc2ccccc21]

(1) cyclohexyl(1-methyl-1H-benzimidazol-2-yl)methanol

Using 1-methyl-1H-benzoimidazole-2-carbaldehyde (1.03 g) and in the same manner as in Example A1(1), the title object compound (0.58 g, 37%) was obtained as a brown oil.

$^1$H NMR (300 MHz, CDCl$_3$) δ ppm 1.05-1.30 (m, 5H), 1.36-1.46 (m, 1H), 1.58-2.03 (m, 5H), 3.77 (s, 3H), 4.65 (d, J=7.2 Hz, 1H), 7.20-7.30 (m, 3H), 7.65-7.73 (m, 1H).

(2) 2-[chloro(cyclohexyl)methyl]-1-methyl-1H-benzoimidazole

Using cyclohexyl(1-methyl-1H-benzimidazol-2-yl)methanol (0.58 g) synthesized above and in the same manner as in Example A1(2), the title object compound (605 mg, 97%) was obtained as a brown solid.

$^1$H NMR (300 MHz, CDCl$_3$) δ ppm 0.91-1.45 (m, 5H), 1.50-1.60 (m, 1H), 1.62-1.75 (m, 2H), 1.81-1.92 (m, 1H), 2.33-2.49 (m, 2H), 3.87 (s, 3H), 4.88 (d, J=9.9 Hz, 1H), 7.24-7.38 (m, 3H), 7.74-7.79 (m, 1H).

(3) 4-{[cyclohexyl(1-methyl-1H-benzimidazol-2-yl)methyl]amino}benzoic acid

Using 2-[chloro(cyclohexyl)methyl]-1-methyl-1H-benzoimidazole (605 mg) synthesized above and in the same manner as in Example A1(3), the title object compound (87.0 mg, 10%) was obtained as a white solid.

$^1$H NMR (300 MHz, CDCl$_3$) δ ppm 1.04-1.32 (m, 5H), 1.39-1.51 (m, 1H), 1.60-1.84 (m, 3H), 2.03-2.20 (m, 2H), 3.90 (s, 3H), 4.63-4.72 (m, 1H), 5.90-6.04 (m, 1H), 6.69 (d, J=8.7 Hz, 2H), 7.25-7.39 (m, 3H), 7.73-7.81 (m, 1H), 7.88 (d, J=8.7 Hz, 2H).

(4) 3-{[(4-{[cyclohexyl(1-methyl-1H-benzimidazol-2-yl)methyl]amino}phenyl)carbonyl]amino}propanoic acid Using 4-{[cyclohexyl(1-methyl-1H-benzimidazol-2-yl)methyl]amino}benzoic acid (78.3 mg) synthesized above and in the same manner as in Example A1(4), the title object compound (39.5 mg, 42%) was obtained as a white solid.

$^1$H NMR (300 MHz, CDCl$_3$) δ ppm 0.98-1.40 (m, 6H), 1.59-1.71 (m, 2H), 1.71-1.84 (m, 1H), 1.92-2.08 (m, 1H), 2.13-2.26 (m, 1H), 2.71 (t, J=5.3 Hz, 2H), 3.71-3.83 (m, 2H), 3.93 (s, 3H), 4.59-4.71 (m, 1H), 6.74 (d, J=8.7 Hz, 2H), 7.20-7.40 (m, 4H), 7.59-7.70 (m, 3H).

Example A4

3-{[(4-{[1-benzofuran-2-yl(cyclohexyl)methyl]amino}phenyl)carbonyl](methyl)amino}-propanoic acid $^1$H NMR (300 MHz, CDCl$_3$) δ ppm 0.98-1.38 (m, 5H), 1.50-1.86 (m, 4H), 2.08-2.23 (m, 2H), 4.78 (d, J=8.1 Hz, 1H), 6.66 (s, 1H), 7.12-7.32 (m, 2H), 7.45-7.56 (m, 2H).

(3) 4-{[1-benzofuran-2-yl(cyclohexyl)methyl]amino}benzoic acid

Using 2-[chloro(cyclohexyl)methyl]-1-benzofuran (1.17 g) synthesized above and in the same manner as in Example A1(3), the title object compound (523 mg, 32%) was obtained as a pale-brown solid.

$^1$H NMR (300 MHz, CDCl$_3$) δ ppm 1.05-1.38 (m, 5H), 1.57-1.86 (m, 4H), 1.88-2.03 (m, 2H), 4.41-4.50 (m, 1H), 4.52-4.62 (m, 1H), 6.53 (s, 1H), 6.60 (d, J=8.9 Hz, 2H), 7.14-7.25 (m, 2H), 7.41-7.50 (m, 2H), 7.85 (d, J=8.9 Hz, 2H).

(4) 3-{[(4-{[1-benzofuran-2-yl(cyclohexyl)methyl]amino}phenyl)carbonyl](methyl)amino}-propanoic acid Using 4-{[1-benzofuran-2-yl(cyclohexyl)methyl]amino}benzoic acid (250 mg) synthesized above and ethyl 3-(methylamino)propanoate (113 mg) and in the same manner as in Example A1(4), the title object compound (226 mg, 73%) was obtained as a pale-red solid.

$^1$H NMR (300 MHz, DMSO-d$_6$) δ ppm 0.98-1.29 (m, 5H), 1.39-1.50 (m, 1H), 1.55-1.7.8 (m, 3H), 1.83-2.03 (m, 2H), 2.43-2.54 (m, 2H), 2.89 (s, 3H), 3.51 (t, J=7.3 Hz, 2H), 4.38-4.49 (m, 1H), 6.46 (d, J=8.1 Hz, 1H), 6.67 (d, J=8.7 Hz, 2H), 6.75 (s, 1H), 7.11 (d, J=8.7 Hz, 2H), 7.14-7.26 (m, 2H), 7.47-7.57 (m, 2H).

Example A5

3-{[(4-{[1-benzothiophen-2-yl(cyclohexyl)methyl]amino}phenyl)carbonyl](methyl)amino}-propanoic acid

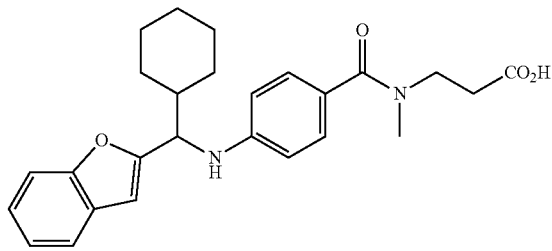 [SMILES: CN(CCC(=O)O)C(=O)c1ccc(NC(c2cc3ccccc3o2)C2CCCCC2)cc1]

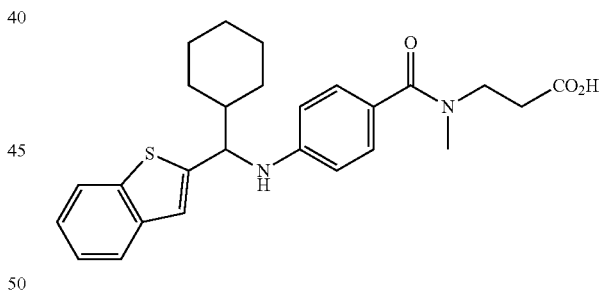

(1) 1-benzofuran-2-yl(cyclohexyl)methanol

Using 1-benzofuran-2-carbaldehyde (2.52 g) and in the same manner as in Example A1(1), the title object compound (2.38 g, 60%) was obtained as a yellow oil.

$^1$H NMR (300 MHz, CDCl$_3$) δ ppm 1.00-1.36 (m, 5H), 1.49-1.59 (m, 1H), 1.61-2.03 (m, 6H), 4.50-4.57 (m, 1H), 6.60 (s, 1H), 7.16-7.29 (m, 2H), 7.43-7.47 (m, 1H), 7.50-7.55 (m, 1H).

(2) 2-[chloro(cyclohexyl)methyl]-1-benzofuran

Using 1-benzofuran-2-yl(cyclohexyl)methanol (1.20 g) synthesized above and in the same manner as in Example A1(2), the title object compound (1.17 g, 90%) was obtained as a yellow oil.

(1) 1-benzothiophen-2-yl(cyclohexyl)methanol

Using 1-benzothiophene-2-carbaldehyde (2.00 g) and in the same manner as in Example A1(1), the title object compound (1.93 g, 64%) was obtained as a yellow solid.

$^1$H NMR (300 MHz, CDCl$_3$) δ ppm 0.96-1.35 (m, 5H), 1.50-1.84 (m, 5H), 1.99-2.10 (m, 2H), 4.70 (dd, J=7.2, 3.9 Hz, 1H), 7.15 (s, 1H), 7.24-7.36 (m, 2H), 7.67-7.73 (m, 1H), 7.77-7.83 (m, 1H).

(2) 2-[chloro(cyclohexyl)methyl]-1-benzothiophene

Using 1-benzothiophen-2-yl(cyclohexyl)methanol (1.93 g) synthesized above and in the same manner as in Example A1(2), the title object compound (1.94 g, 94%) was obtained as a brown solid.

¹H NMR (300 MHz, CDCl₃) δ ppm 0.98-1.38 (m, 5H), 1.50-2.01 (m, 5H), 2.15-2.25 (m, 1H), 4.97 (d, J=7.8 Hz, 1H), 7.21 (s, 1H), 7.26-7.37 (m, 2H), 7.66-7.73 (m, 1H), 7.74-7.82 (m, 1H).

(3) 4-{[1-benzothiophen-2-yl(cyclohexyl)methyl]amino}benzoic acid

Using 2-[chloro(cyclohexyl)methyl]-1-benzothiophene (1.93 g) synthesized above and in the same manner as in Example A1(3), the title object compound (719 mg, 27%) was obtained as a white solid.

¹H NMR (300 MHz, CDCl₃) δ ppm 1.06-1.37 (m, 5H), 1.61-1.90 (m, 5H), 1.91-2.04 (m, 1H), 4.51-4.67 (m, 1H), 6.61 (d, J=8.8 Hz, 2H), 7.16 (s, 1H), 7.21-7.36 (m, 2H), 7.67 (d, J=7.0 Hz, 1H), 7.74 (d, J=7.9 Hz, 1H), 7.84 (d, J=8.8 Hz, 2H).

(4) 3-{[(4-{[1-benzothiophen-2-yl(cyclohexyl)methyl]amino}phenyl)carbonyl](methyl)amino}-propanoic acid Using 4-{[1-benzothiophen-2-yl(cyclohexyl)methyl]amino}benzoic acid (250 mg) synthesized above and ethyl 3-(methylamino)propanoate (108 mg) and in the same manner as in Example A1(4), the title object compound (277 mg, 90%) was obtained as a white solid.

¹H NMR (300 MHz, DMSO-d₆) δ ppm 1.06-1.36 (m, 5H), 1.62-1.87 (m, 5H), 1.91-2.01 (m, 1H), 2.65 (t, J=6.4 Hz, 2H), 3.01 (s, 3H), 3.69 (t, J=6.4 Hz, 2H), 4.49 (d, J=6.2 Hz, 1H), 6.58 (d, J=8.7 Hz, 2H), 7.15 (s, 1H), 7.18-7.35 (m, 4H), 7.64-7.70 (m, 1H), 7.71-7.76 (m, 1H).

Example A6

3-{[(4-{[1-benzothiophen-2-yl(cyclohexyl)methyl]amino}phenyl)carbonyl]amino}propanoic acid

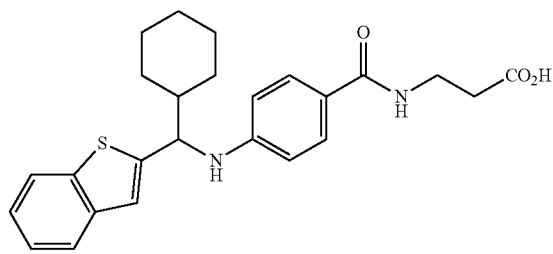 [SMILES: O=C(O)CCNC(=O)c1ccc(NC(c2cc3ccccc3s2)C2CCCCC2)cc1]

Using 4-{[1-benzothiophen-2-yl(cyclohexyl)methyl]amino}benzoic acid (250 mg) synthesized in Example A5(3) and in the same manner as in Example A1(4), the title object compound (275 mg, 92%) was obtained as a white solid.

¹H NMR (300 MHz, CDCl₃) δ ppm 1.06-1.35 (m, 5H), 1.61-1.87 (m, 5H), 1.89-2.01 (m, 1H), 2.60 (t, J=5.7 Hz, 2H), 3.55-3.67 (m, 2H), 4.50 (d, J=6.2 Hz, 1H), 6.53-6.64 (m, 3H), 7.14 (s, 1H), 7.19-7.34 (m, 2H), 7.50 (d, J=8.7 Hz, 2H), 7.66 (d, J=7.3 Hz, 1H), 7.72 (d, J=7.9 Hz, 1H).

Example A7

3-{[(4-{[cyclohexyl(1-methyl-1H-indazol-3-yl)methyl]amino}phenyl)carbonyl](methyl)amino}propanoic acid

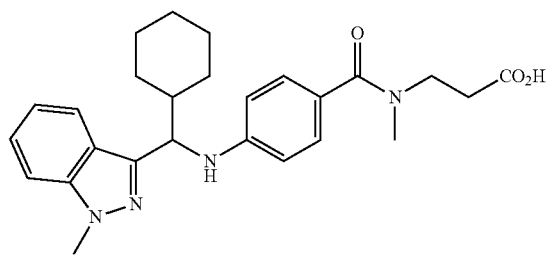 [SMILES: CN(CCC(=O)O)C(=O)c1ccc(NC(c2nn(C)c3ccccc23)C2CCCCC2)cc1]

(1) cyclohexyl(1-methyl-1H-indazol-3-yl)methanol

Using 1-methyl-1H-indazole-3-carbaldehyde (1.00 g) and in the same manner as in Example A1(1), the title object compound (799 mg, 52%) was obtained as a pale-yellow oil.

¹H NMR (300 MHz, CDCl₃) δ ppm 1.03-1.37 (m, 5H), 1.45-1.54 (m, 1H), 1.60-1.82 (m, 3H), 1.84-2.03 (m, 2H), 2.37-2.43 (m, 1H), 4.02 (s, 3H), 4.83-4.89 (m, 1H), 7.09-7.16 (m, 1H), 7.31-7.41 (m, 2H), 7.80 (d, J=8.1 Hz, 1H).

(2) 3-[chloro(cyclohexyl)methyl]-1-methyl-1H-indazole

Using cyclohexyl(1-methyl-1H-indazol-3-yl)methanol (799 mg) synthesized above and in the same manner as in Example A1(2), the title object compound (818 mg, 95%) was obtained as a yellow oil.

¹H NMR (300 MHz, CDCl₃) δ ppm 0.92-1.38 (m, 5H), 1.40-1.50 (m, 1H), 1.59-1.70 (m, 2H), 1.77-1.87 (m, 1H), 2.18-2.40 (m, 2H), 4.03 (s, 3H), 5.06 (d, J=8.7 Hz, 1H), 7.12-7.19 (m, 1H), 7.32-7.42 (m, 2H), 7.87 (d, J=8.1 Hz, 1H).

(3) 3-{[(4-{[cyclohexyl(1-methyl-1H-indazol-3-yl)methyl]amino}phenyl)carbonyl](methyl)amino}propanoic acid To a mixture of 3-[chloro(cyclohexyl)methyl]-1-methyl-1H-indazole (465 mg) synthesized above, ethyl 3-{[(4-aminophenyl)carbonyl](methyl)amino}propanoate (531 mg) synthesized in Example 2(2), sodium iodide (531 mg) and N,N-dimethylacetamide (10 mL) was added sodium carbonate (375 mg), and the mixture was stirred under argon atmosphere at 100° C. overnight. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate: hexane=3:2, volume ratio) to give a white solid. To a mixture of the obtained solid, tetrahydrofuran (5 mL) and ethanol (5 mL) was added 1N aqueous sodium hydroxide solution (2.00 mL), and the mixture was stirred at room temperature for 3 hr. The reaction mixture was concentrated under reduced pressure, and the residue was dissolved in water (10 mL), and 1N hydrochloric acid (2.00 mL) was added at 0° C. The resulting precipitate was collected by filtration to give the title object compound (356 mg, 45%) as a white solid.

$^1$H NMR (300 MHz, CDCl$_3$) δ ppm 0.97-1.34 (m, 5H), 1.47-1.82 (m, 4H), 1.89-2.10 (m, 2H), 2.66 (t, J=6.5 Hz, 2H), 3.03 (s, 3H), 3.69 (t, J=6.5 Hz, 2H), 4.01 (s, 3H), 4.70 (d, J=7.0 Hz, 1H), 6.60 (d, J=8.6 Hz, 2H), 7.06-7.14 (m, 1H), 7.20 (d, J=8.6 Hz, 2H), 7.29-7.40 (m, 2H), 7.74 (d, J=8.1 Hz, 1H).

Example A8

3-{[(4-{[cyclohexyl(2-methyl-1-benzothiophen-3-yl)methyl]amino}phenyl)carbonyl]amino}propanoic acid

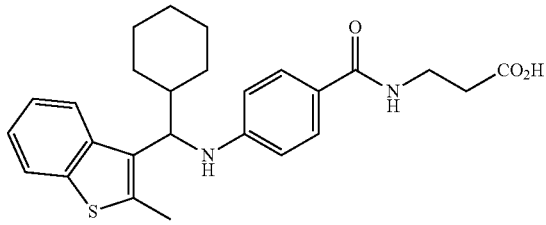 [SMILES: Cc1sc2ccccc2c1C(Nc1ccc(C(=O)NCCC(=O)O)cc1)C1CCCCC1]

(1) 3-bromo-2-methyl-1-benzothiophene

To a solution (50 mL) of 2-methyl-1-benzothiophene (5.00 g) in acetic acid was added dropwise bromine (1.90 mL) at 0° C., and the mixture was stirred at room temperature overnight. The reaction mixture was concentrated under reduced pressure, saturated aqueous sodium hydrogen carbonate solution was added to the residue, and the mixture was extracted with ethyl acetate. The extract was washed with saturated brine, dried over magnesium sulfate, and concentrated under reduced pressure. The residue was purified by silica gel column chromatography (ethyl acetate:hexane=1:1, volume ratio) to give the title object compound (8.02 g, quantitative) as a brown oil.

$^1$H NMR (300 MHz, CDCl$_3$) δ ppm 2.56 (s, 3H), 7.28-7.36 (m, 1H), 7.36-7.44 (m, 1H), 7.67-7.75 (m, 2H).

(2) cyclohexyl(2-methyl-1-benzothiophen-3-yl)methanol

3-Bromo-2-methyl-1-benzothiophene (2.00 g) synthesized above was dissolved in tetrahydrofuran (40 mL), 1.6M n-butyllithium hexane solution (6.63 mL) was added dropwise at −78° C. The mixture was stirred under a nitrogen atmosphere for 10 min, cyclohexanecarbaldehyde (2.50 mL) was added, and the mixture was stirred −78° C. for 30 min and at room temperature for 30 min. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=3:17, volume ratio) to give the title object compound (1.95 g, 85%) as a yellow oil.

$^1$H NMR (300 MHz, CDCl$_3$) δ ppm 0.95-1.42 (m, 5H), 1.51-1.70 (m, 2H), 1.71-1.92 (m, 3H), 1.97-2.13 (m, 1H), 2.24-2.35 (m, 1H), 2.54 (s, 3H), 4.74 (dd, J=9.1, 2.2 Hz, 1H), 7.21-7.35 (m, 2H), 7.71-7.77 (m, 1H), 7.97-8.05 (m, 1H).

(3) 3-[chloro(cyclohexyl)methyl]-2-methyl-1-benzothiophene

Using cyclohexyl(2-methyl-1-benzothiophen-3-yl)methanol (1.95 g) synthesized above and in the same manner as in Example A1(2), the title object compound (1.98 g, 95%) was obtained as a brown oil.

$^1$H NMR (300 MHz, CDCl$_3$) δ ppm 0.70-0.85 (m, 1H), 0.96-1.40 (m, 4H), 1.49-1.91 (m, 4H), 2.24-2.32 (m, 1H), 2.46-2.58 (m, 4H), 4.94 (d, J=10.5 Hz, 1H), 7.23-7.36 (m, 2H), 7.70-7.75 (m, 1H), 7.99 (d, J=7.5 Hz, 1H).

(4) 4-{[cyclohexyl(2-methyl-1-benzothiophen-3-yl)methyl]amino}benzoic acid

Using 3-[chloro(cyclohexyl)methyl]-2-methyl-1-benzothiophene (1.98 g) synthesized above and in the same manner as in Example A1(3), the title object compound (1.69 g, 63%) was obtained as a white solid.

$^1$H NMR (300 MHz, CDCl$_3$) δ ppm 0.96-1.34 (m, 5H), 1.39-1.51 (m, 1H), 1.62-1.71 (m, 2H), 1.78-1.89 (m, 1H), 1.93-2.08 (m, 1H), 2.09-2.20 (m, 1H), 2.58 (s, 3H), 4.56 (d, J=8.5 Hz, 1H), 6.46 (d, J=9.0 Hz, 2H), 7.21-7.36 (m, 2H), 7.69-7.84 (m, 4H).

(5) 3-{[(4-{[cyclohexyl(2-methyl-1-benzothiophen-3-yl)methyl]amino}phenyl)carbonyl]amino}propanoic acid Using 4-{[cyclohexyl(2-methyl-1-benzothiophen-3-yl)methyl]amino}benzoic acid (300 mg) synthesized above and in the same manner as in Example A1(4), the title object compound (323 mg, 91%) was obtained as a white solid.

$^1$H NMR (300 MHz, CDCl$_3$) δ ppm 0.94-1.34 (m, 5H), 1.40-1.51 (m, 1H), 1.61-1.72 (m, 2H), 1.78-1.88 (m, 1H), 1.92-2.07 (m, 1H), 2.09-2.20 (m, 1H), 2.53-2.65 (m, 5H), 3.54-3.65 (m, 2H), 4.52 (d, J=8.7 Hz, 1H), 6.39-6.55 (m, 3H), 7.20-7.34 (m, 2H), 7.39-7.48 (m, 2H), 7.72 (d, J=8.0 Hz, 1H), 7.81 (d, J=7.6 Hz, 1H).

Example A9

3-{[(4-{[cyclohexyl(2-methyl-1-benzothiophen-3-yl)methyl]amino}phenyl)carbonyl](methyl)amino}propanoic acid

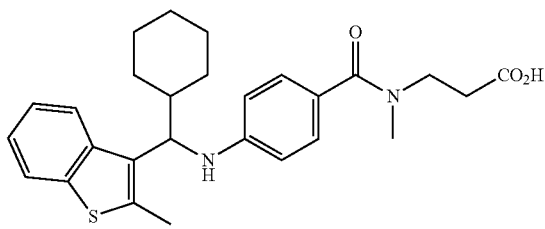 [SMILES: Cc1sc2ccccc2c1C(Nc1ccc(C(=O)N(C)CCC(=O)O)cc1)C1CCCCC1]

Using 4-{[cyclohexyl(2-methyl-1-benzothiophen-3-yl)methyl]amino}benzoic acid (300 mg) synthesized in Example A8(4) and ethyl 3-(methylamino)propanoate (124 mg) and in the same manner as in Example A1(4), the title object compound (312 mg, 85%) was obtained as a white solid.

$^1$H NMR (300 MHz, CDCl$_3$) δ ppm 0.95-1.35 (m, 5H), 1.39-1.50 (m, 1H), 1.61-1.73 (m, 2H), 1.78-1.88 (m, 1H), 1.91-2.06 (m, 1H), 2.09-2.20 (m, 1H), 2.57 (s, 3H), 2.58-2.67

(m, 2H), 2.99 (s, 3H), 3.67 (t, J=6.4 Hz, 1H), 4.50 (d, J=8.7 Hz, 1H), 6.44 (d, J=8.5 Hz, 2H), 7.17 (d, J=8.5 Hz, 1H), 7.21-7.35 (m, 2H), 7.73 (d, J=7.2 Hz, 1H), 7.83 (d, J=7.6 Hz, 1H).

Example A10

3-{[(4-{[cyclohexyl(3-methyl-1-benzothiophen-2-yl)methyl]amino}phenyl)carbonyl]amino}propanoic acid

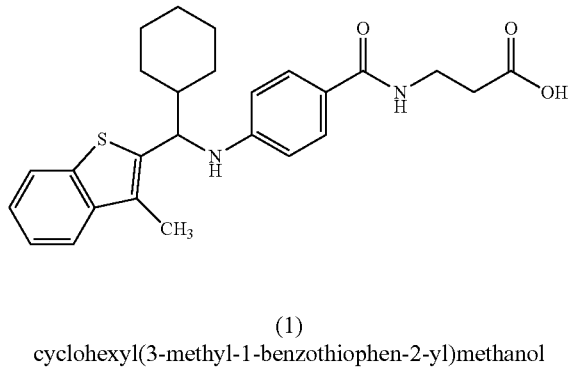

(1) cyclohexyl(3-methyl-1-benzothiophen-2-yl)methanol

Using 3-methyl-1-benzothiophene-2-carbaldehyde (2.00 g) and in the same manner as in Example A1(1), the title object compound (1.65 g, 56%) was obtained as a yellow oil.

$^1$H NMR (300 MHz, CDCl$_3$) δ ppm 0.85-1.36 (m, 5H), 1.41-1.52 (m, 1H), 1.60-1.86 (m, 4H), 2.01 (d, J=3.3 Hz, 1H), 2.14-2.24 (m, 1H), 2.37 (s, 3H), 4.83 (dd, J=8.1, 3.3 Hz, 1H), 7.27-7.39 (m, 2H), 7.62-7.67 (m, 1H), 7.77-7.82 (m, 1H).

(2) 2-[chloro(cyclohexyl)methyl]-3-methyl-1-benzothiophene

Using cyclohexyl(3-methyl-1-benzothiophen-2-yl)methanol (1.65 g) synthesized above and in the same manner as in Example A1(2), the title object compound (1.68 g, 95%) was obtained as a yellow oil.

$^1$H NMR (300 MHz, CDCl$_3$) δ ppm 0.84-0.99 (m, 1H), 1.04-1.39 (m, 4H), 1.56-1.71 (m, 3H), 1.77-1.88 (m, 1H), 1.88-2.03 (m, 1H), 2.32-2.45 (m, 4H), 5.09 (d, J=9.6 Hz, 1H), 7.29-7.39 (m, 2H), 7.62-7.67 (m, 1H), 7.75-7.80 (m, 1H).

(3) 4-{[cyclohexyl(3-methyl-1-benzothiophen-2-yl)methyl]amino}benzoic acid

Using 2-[chloro(cyclohexyl)methyl]-3-methyl-1-benzothiophene (1.68 g) synthesized above and in the same manner as in Example A1(3), the title object compound (1.63 g, 71%) was obtained as a yellow solid.

$^1$H NMR (300 MHz, CDCl$_3$) δ ppm 1.00-1.34 (m, 5H), 1.53-1.87 (m, 5H), 2.03-2.16 (m, 1H), 2.44 (s, 3H), 4.54-4.63 (m, 1H), 6.46 (d, J=8.6 Hz, 2H), 7.21-7.29 (m, 1H), 7.30-7.38 (m, 1H), 7.63 (d, J=7.9 Hz, 1H), 7.69 (d, J=7.7 Hz, 1H), 7.75 (d, J=8.6 Hz, 2H).

(4) 3-{[(4-{[cyclohexyl(3-methyl-1-benzothiophen-2-yl)methyl]amino}phenyl)carbonyl]amino}propanoic acid Using 4-{[cyclohexyl(3-methyl-1-benzothiophen-2-yl)methyl]amino}benzoic acid (300 mg) synthesized above and in the same manner as in Example A1(4), the title object compound (275 mg, 77%) was obtained as a white solid.

$^1$H NMR (300 MHz, CDCl$_3$) δ ppm 1.01-1.34 (m, 5H), 1.53-1.85 (m, 5H), 2.03-2.14 (m, 1H), 2.44 (s, 3H), 2.53 (t, J=5.6 Hz, 2H), 3.50-3.61 (m, 2H), 4.54 (d, J=7.7 Hz, 1H), 6.48 (d, J=8.8 Hz, 2H), 6.58 (t, J=5.9 Hz, 1H), 7.20-7.27 (m, 1H), 7.29-7.37 (m, 1H), 7.46 (d, J=8.8 Hz, 2H), 7.62 (d, J=7.5 Hz, 1H), 7.67 (d, J=7.5 Hz, 1H).

Example A11

3-({[4-({cyclohexyl[5-(trifluoromethyl)-1-benzothiophen-2-yl]methyl}amino)phenyl]carbonyl}amino)propanoic acid

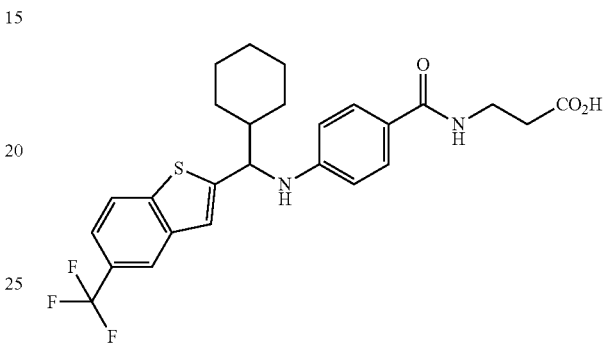

(1) 5-(trifluoromethyl)-1-benzothiophene-2-carbaldehyde

To a solution (40 mL) of methyl 5-(trifluoromethyl)-1-benzothiophene-2-carboxylate (2.00 g) in tetrahydrofuran was added lithium aluminum hydride (292 mg) at 0° C., and the mixture was stirred for 1 hr. Water (300 μL) was added to quench the reaction, 1N aqueous sodium hydroxide solution (300 μL) was added, and the mixture was stirred at room temperature for 3 hr. The resulting insoluble material was filtered off, and the filtrate was concentrated under reduced pressure to give a white solid. To a solution of the obtained solid in tetrahydrofuran (40 mL) was added active manganese dioxide (9.00 g), and the mixture was stirred overnight at room temperature. Manganese dioxide was filtered off, and the filtrate was concentrated under reduced pressure to give the title object compound (1.15 g, 65%) as a brown solid.

$^1$H NMR (300 MHz, CDCl$_3$) δ ppm 7.69-7.75 (m, 1H), 8.00-8.06 (m, 1H), 8.11 (s, 1H), 8.21-8.25 (m, 1H), 10.14 (s, 1H).

(2) cyclohexyl[5-(trifluoromethyl)-1-benzothiophen-2-yl]methanol

Using 5-(trifluoromethyl)-1-benzothiophene-2-carbaldehyde (1.15 g) synthesized above and in the same manner as in Example A1(1), the title object compound (860 mg, 55%) was obtained as a pale-yellow solid.

$^1$H NMR (300 MHz, CDCl$_3$) δ ppm 0.98-1.35 (m, 5H), 1.50-1.59 (m, 1H), 1.62-1.85 (m, 4H), 1.95-2.06 (m, 1H), 2.12-2.18 (m, 1H), 4.75 (d, J=7.2 Hz, 1H), 7.22 (s, 1H), 7.48-7.53 (m, 1H), 7.87-7.92 (m, 1H), 7.97 (s, 1H).

(3) 2-[chloro(cyclohexyl)methyl]-5-(trifluoromethyl)-1-benzothiophene

To a solution of cyclohexyl[5-(trifluoromethyl)-1-benzothiophen-2-yl]methanol (860 mg) synthesized above in toluene (20 mL) was added thionyl chloride (239 μL), and the mixture was stirred at 100° C. for 1 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (806 mg, 89%) as a pale-brown oil.

$^1$H NMR (300 MHz, CDCl$_3$) δ ppm 0.99-1.37 (m, 5H), 1.58-2.01 (m, 5H), 2.13-2.23 (m, 1H), 4.97 (d, J=7.8 Hz, 1H), 7.29 (s, 1H), 7.51-7.56 (m, 1H), 7.86-7.91 (m, 1H), 7.96-7.99 (m, 1H).

(4) 4-({cyclohexyl[5-(trifluoromethyl)-1-benzothiophen-2-yl]methyl}amino)benzoic acid Using 2-[chloro(cyclohexyl)methyl]-5-(trifluoromethyl)-1-benzothiophene (806 mg) synthesized above and in the same manner as in Example A1(3), the title object compound (68.7 mg, 7%) was obtained as a pale-yellow oil.

$^1$H NMR (300 MHz, CDCl$_3$) δ ppm 1.07-1.37 (m, 5H), 1.62-1.89 (m, 5H), 1.90-2.00 (m, 1H), 4.58 (d, J=6.3 Hz, 1H), 6.59 (d, J=8.7 Hz, 2H), 7.25 (s, 1H), 7.45-7.50 (m, 1H), 7.82 (d, J=8.4 Hz, 1H), 7.84 (d, J=8.7 Hz, 2H), 7.93-7.96 (m, 1H).

(5) 3-({[4-({cyclohexyl[5-(trifluoromethyl)-1-benzothiophen-2-yl]methyl}amino)phenyl]carbonyl}amino)propanoic acid Using 4-({cyclohexyl[5-(trifluoromethyl)-1-benzothiophen-2-yl]methyl}amino)benzoic acid (68.7 mg) synthesized above and in the same manner as in Example A1(4), the title object compound (57.8 mg, 73%) was obtained as a white solid.

$^1$H NMR (300 MHz, CDCl$_3$) δ ppm 1.02-1.36 (m, 5H), 1.59-1.87 (m, 5H), 1.88-1.99 (m, 1H), 2.58 (t, J=5.3 Hz, 2H), 3.54-3.66 (m, 2H), 4.51 (d, J=6.4 Hz, 1H), 6.56 (d, J=8.3 Hz, 2H), 6.63 (t, J=5.7 Hz, 1H), 7.22 (s, 1H), 7.43-7.49 (m, 1H), 7.51 (d, J=8.3 Hz, 2H), 7.80 (d, J=8.7 Hz, 1H), 7.93 (s, 1H).

Example A12

3-({[4-({cyclohexyl[6-(trifluoromethyl)-1-benzothiophen-2-yl]methyl}amino)phenyl]carbonyl}amino)propanoic acid

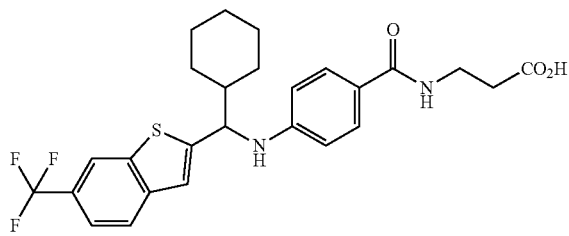 [SMILES: O=C(O)CCNC(=O)c1ccc(NC(c2cc3ccc(C(F)(F)F)cc3s2)C2CCCCC2)cc1]

(1) 6-(trifluoromethyl)-1-benzothiophene-2-carbaldehyde

Using methyl 6-(trifluoromethyl)-1-benzothiophene-2-carboxylate (2.07 g) and in the same manner as in Example A11(1), the title object compound (1.38 g, 75%) was obtained as a brown solid.

$^1$H NMR (300 MHz, CDCl$_3$) δ ppm 7.63-7.69 (m, 1H), 8.06 (d, J=8.4 Hz, 1H), 8.08 (s, 1H), 8.18-8.22 (m, 1H), 10.15 (s, 1H).

(2) cyclohexyl[6-(trifluoromethyl)-1-benzothiophen-2-yl]methanol

Using 6-(trifluoromethyl)-1-benzothiophene-2-carbaldehyde (1.38 g) synthesized above and in the same manner as in Example A1(1), the title object compound (668 mg, 35%) was obtained as a yellow solid.

$^1$H NMR (300 MHz, CDCl$_3$) δ ppm 0.99-1.35 (m, 5H), 1.50-1.60 (m, 1H), 1.62-1.84 (m, 4H), 1.94-2.04 (m, 1H), 2.15-2.20 (m, 1H), 4.76 (dd, J=6.9, 3.6 Hz, 1H), 7.21 (s, 1H), 7.52-7.58 (m, 1H), 7.79 (d, J=8.1 Hz, 1H), 8.06-8.10 (m, 1H).

(3) 2-[chloro(cyclohexyl)methyl]-6-(trifluoromethyl)-1-benzothiophene cyclohexyl[6-(trifluoromethyl)-1-benzothiophen-2-yl]methanol (668 mg) synthesized above and in the same manner as in Example A11(3), the title object compound (659 mg, 93%) was obtained as a brown oil.

$^1$H NMR (300 MHz, CDCl$_3$) δ ppm 1.00-1.37 (m, 5H), 1.58-1.86 (m, 4H), 1.88-2.01 (m, 1H), 2.12-2.22 (m, 1H), 4.97 (d, J=7.8 Hz, 1H), 7.28 (s, 1H), 7.53-7.58 (m, 1H), 7.80 (d, J=8.4 Hz, 1H), 8.05-8.08 (m, 1H).

(4) 4-({cyclohexyl[6-(trifluoromethyl)-1-benzothiophen-2-yl]methyl}amino)benzoic acid Using 2-[chloro(cyclohexyl)methyl]-6-(trifluoromethyl)-1-benzothiophene (659 mg) synthesized above and in the same manner as in Example A1(3), the title object compound (82.5 mg, 10%) was obtained as a brown oil.

$^1$H NMR (300 MHz, CDCl$_3$) δ ppm 1.02-1.37 (m, 5H), 1.62-1.88 (m, 5H), 1.90-1.99 (m, 1H), 4.58 (d, J=6.3 Hz, 1H), 6.59 (d, J=8.7 Hz, 2H), 7.23 (s, 1H), 7.50-7.55 (m, 1H), 7.76 (d, J=8.4 Hz, 1H), 7.84 (d, J=8.7 Hz, 2H), 7.99-8.02 (m, 1H).

(5) 3-({[4-{(cyclohexyl[6-(trifluoromethyl)-1-benzothiophen-2-yl]methyl}amino)phenyl]carbonyl}amino)propanoic acid Using 4-({cyclohexyl[6-(trifluoromethyl)-1-benzothiophen-2-yl]methyl}amino)benzoic acid (82.5 mg) synthesized above and in the same manner as in Example A1(4), the title object compound (54.0 mg, 56%) was obtained as a white solid.

$^1$H NMR (300 MHz, CDCl$_3$) δ ppm 1.03-1.35 (m, 5H), 1.58-1.87 (m, 5H), 1.88-1.99 (m, 1H), 2.53-2.63 (m, 2H), 3.54-3.66 (m, 2H), 4.52 (d, J=6.1 Hz, 1H), 6.56 (d, J=8.7 Hz, 2H), 6.58-6.66 (m, 1H), 7.20 (s, 1H), 7.46-7.55 (m, 3H), 7.73 (d, J=8.3 Hz, 1H), 7.98 (s, 1H).

Example A13

3-{[(4-{[cyclohexyl(3-methyl-1-benzothiophen-2-yl)methyl]amino}phenyl)carbonyl](methyl)amino}propanoic acid

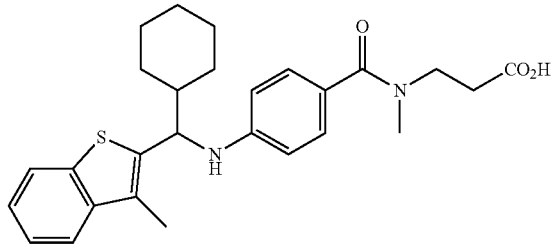 [SMILES: Cc1c(C(Nc2ccc(C(=O)N(C)CCC(=O)O)cc2)C2CCCCC2)sc2ccccc12]

Using 4-{[cyclohexyl(3-methyl-1-benzothiophen-2-yl)methyl]amino}benzoic acid (300 mg) synthesized in Example A10(3) and ethyl 3-(methylamino)propanoate (124 mg) and in the same manner as in Example A1(4), the title object compound (269 mg, 73%) was obtained as a white solid.

$^1$H NMR (300 MHz, CDCl$_3$) δ ppm 1.02-1.34 (m, 5H), 1.53-1.87 (m, 5H), 2.05-2.16 (m, 1H), 2.45 (s, 3H), 2.59 (t, J=6.4 Hz, 2H), 2.97 (s, 3H), 3.65 (t, J=6.4 Hz, 2H), 4.53 (d, J=7.5 Hz, 1H), 6.50 (d, J=8.7 Hz, 2H), 7.18 (d, J=8.7 Hz, 2H), 7.22-7.29 (m, 1H), 7.30-7.38 (m, 1H), 7.63 (d, J=7.5 Hz, 1H), 7.70 (d, J=7.7 Hz, 1H).

Example A14

3-{[(4-{[cyclohexyl(1-phenyl-1H-indazol-3-yl)methyl]amino}phenyl)carbonyl]amino}propanoic acid

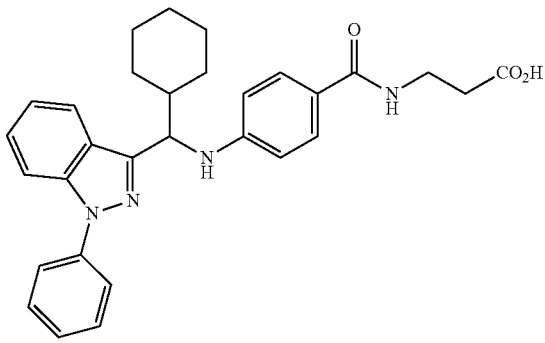 [SMILES: O=C(O)CCNC(=O)c1ccc(NC(c2nn(-c3ccccc3)c3ccccc23)C2CCCCC2)cc1]

(1) methyl 1-phenyl-1H-indazole-3-carboxylate

To a mixture of methyl 1H-indazole-3-carboxylate (3.44 g), phenylboronic acid (4.76 g), pyridine (2.84 mL) and N,N-dimethylformamide (70 mL) was added copper (II) acetate (5.32 g), and the mixture was stirred at 30° C. overnight. The insoluble material was filtered off, saturated aqueous ammonium chloride solution was added, and the mixture was extracted with ethyl acetate. The extract was washed with saturated sodium hydrogen carbonate and saturated brine, dried over magnesium sulfate, and concentrated under reduced pressure. The residue was purified by silica gel column chromatography (ethyl acetate:hexane=1:4, volume ratio) to give the title object compound (1.58 g, 32%) as a pale-yellow oil.

$^1$H NMR (300 MHz, CDCl$_3$) δ ppm 4.07 (s, 3H), 7.35-7.60 (m, 5H), 7.70-7.77 (m, 3H), 8.30-8.35 (m, 1H).

(2) 1-phenyl-1H-indazole-3-carbaldehyde

To a solution (40 mL) of methyl 1-phenyl-1H-indazole-3-carboxylate (2.25 g) synthesized above in tetrahydrofuran was added dropwise 1.5M diisobutylaluminum hydride toluene solution (26.7 mL) at 0° C., and the mixture was stirred for 1 hr. 1N Hydrochloric acid was added to quench the reaction, and the mixture was extracted with ethyl acetate. The extract was washed with 1N hydrochloric acid and saturated brine, dried over magnesium sulfate, and concentrated under reduced pressure to give a colorless oil. To a solution of the obtained oil in tetrahydrofuran (40 mL) was added active manganese dioxide (8.00 g), and the mixture was stirred at 50° C. for 5 hr. Active manganese dioxide (1.00 g) was additionally added, and the mixture was stirred at 50° C. for 1 hr. Manganese dioxide was filtered off, and the filtrate was concentrated under reduced pressure. The residue was purified by silica gel column chromatography (ethyl acetate:hexane=3:17, volume ratio) to give the title object compound (926 mg, 47%) as a pale-yellow oil.

$^1$H NMR (300 MHz, CDCl$_3$) δ ppm 7.39-7.47 (m, 1H), 7.47-7.55 (m, 2H), 7.57-7.64 (m, 2H), 7.72-7.80 (m, 3H), 8.37-8.42 (m, 1H), 10.34 (s, 1H).

(3) cyclohexyl(1-phenyl-1H-indazol-3-yl)methanol

Using 1-phenyl-1H-indazole-3-carbaldehyde (926 mg) synthesized above and in the same manner as in Example A1(1), the title object compound (716 mg, 56%) was obtained as a pale-yellow oil.

$^1$H NMR (300 MHz, CDCl$_3$) δ ppm 1.11-1.31 (m, 5H), 1.51-1.84 (m, 4H), 1.94-2.08 (m, 2H), 2.52 (d, J=4.5 Hz, 1H), 4.93-5.00 (m, 1H), 7.18-7.25 (m, 1H), 7.31-7.38 (m, 1H), 7.39-7.45 (m, 1H), 7.49-7.56 (m, 2H), 7.68-7.74 (m, 3H), 7.87-7.92 (m, 1H).

(4) 3-[chloro(cyclohexyl)methyl]-1-phenyl-1H-indazole

To a mixture of cyclohexyl(1-phenyl-1H-indazol-3-yl)methanol (716 mg) synthesized above, pyridine (284 μL) and toluene (20 mL) was added thionyl chloride (256 μL), and the mixture was stirred at room temperature for 2 hr. Saturated aqueous sodium hydrogen carbonate solution was added to quench the reaction, and the mixture was extracted with ethyl acetate. The extract was washed with saturated brine, dried over magnesium sulfate, and concentrated under reduced pressure to give the title object compound (767 mg, quantitative) as a pale-yellow oil.

$^1$H NMR (300 MHz, CDCl$_3$) δ ppm 0.99-1.38 (m, 5H), 1.46-1.55 (m, 1H), 1.60-1.72 (m, 2H), 1.80-1.90 (m, 1H), 2.24-2.44 (m, 2H), 5.15 (d, J=9.0 Hz, 1H), 7.21-7.27 (m, 1H), 7.32-7.39 (m, 1H), 7.40-7.46 (m, 1H), 7.49-7.56 (m, 2H), 7.67-7.74 (m, 3H), 7.96-8.00 (m, 1H).

(5) 3-{[(4-{[cyclohexyl(1-phenyl-1H-indazol-3-yl)methyl]amino}phenyl)carbonyl]amino}propanoic acid Using 3-[chloro(cyclohexyl)methyl]-1-phenyl-1H-indazole (370 mg) synthesized above and ethyl 3-{[(4-aminophenyl)carbonyl]amino}propanoate (269 mg) synthesized in Example 1(2) and in the same manner as in Example A7(3), the title object compound (79.1 mg, 14%) was obtained as a pale-yellow solid.

$^1$H NMR (300 MHz, CDCl$_3$) δ ppm 1.01-1.36 (m, 5H), 1.54-1.84 (m, 4H), 1.98-2.13 (m, 2H), 2.52-2.64 (m, 2H), 3.53-3.66 (m, 2H), 4.81 (d, J=6.8 Hz, 1H), 6.52-6.71 (m, 3H), 7.16 (t, J=7.6 Hz, 1H), 7.29-7.42 (m, 2H), 7.45-7.56 (m, 4H), 7.62-7.71 (m, 3H), 7.81 (d, J=8.3 Hz, 1H).

Example A15

3-{[(4-{[cyclohexyl(1-phenyl-1H-indazol-3-yl)methyl]amino}phenyl)carbonyl](methyl)amino}propanoic acid

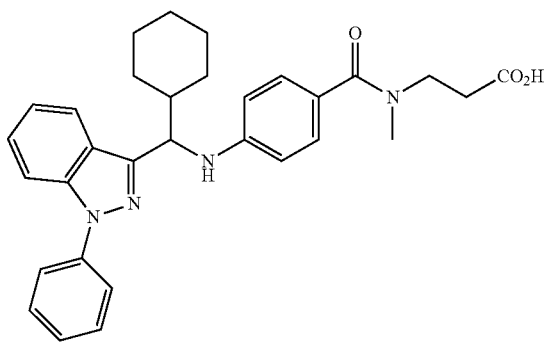 [SMILES: CN(CCC(=O)O)C(=O)c1ccc(NC(c2nn(-c3ccccc3)c3ccccc23)C2CCCCC2)cc1]

Using 3-[chloro(cyclohexyl)methyl]-1-phenyl-1H-indazole (397 mg) synthesized in Example A14(4) and ethyl 3-{[(4-aminophenyl)carbonyl](methyl)amino}propanoate (305 mg) synthesized in Example 2(2) and in the same manner as in Example A7(3), the title object compound (76.9 mg, 12%) was obtained as a pale-yellow solid.

$^1$H NMR (300 MHz, CDCl$_3$) δ ppm 1.04-1.35 (m, 5H), 1.54-1.84 (m, 4H), 1.98-2.13 (m, 2H), 2.56-2.67 (m, 2H), 2.99 (s, 3H), 3.67 (t, J=6.1 Hz, 2H), 4.80 (d, J=6.4 Hz, 1H), 6.66 (d, J=8.7 Hz, 2H), 7.13-7.18 (m, 1H), 7.21 (d, J=8.7 Hz, 2H), 7.30-7.42 (m, 2H), 7.52 (t, J=7.8 Hz, 2H), 7.64-7.72 (m, 2H), 7.82 (d, J=8.3 Hz, 1H).

Example A16

3-{[(4-{[cyclohexyl(3-methyl-1-benzofuran-2-yl)methyl]amino}phenyl)carbonyl](methyl)amino}propanoic acid

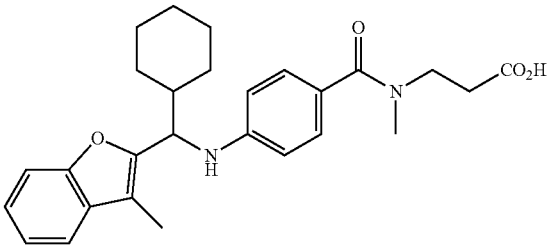 [SMILES: Cc1c(C(Nc2ccc(C(=O)N(C)CCC(=O)O)cc2)C2CCCCC2)oc2ccccc12]

(1) 3-methyl-1-benzofuran-2-carbaldehyde

To a solution (40 mL) of ethyl 3-methyl-1-benzofuran-2-carboxylate (2.00 g) in tetrahydrofuran was added dropwise 1.5M diisobutylaluminum hydride toluene solution (19.6 mL) at 0° C., and the mixture was stirred for 2 hr. 1N Hydrochloric acid was added to quench the reaction, and the mixture was extracted with ethyl acetate. The extract was washed with saturated brine, dried over magnesium sulfate, and concentrated under reduced pressure to give a white solid. To a solution (40 mL) of the obtained solid in dichloromethane was added Dess-Martin periodinane (4.96 g) at 0° C., and the mixture was stirred at room temperature overnight. Saturated sodium sulfite aqueous solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (ethyl acetate:hexane=1:9, volume ratio) to give the title object compound (753 mg, 48%) as a white solid.

$^1$H NMR (300 MHz, CDCl$_3$) δ ppm 2.63 (s, 3H), 7.30-7.37 (m, 1H), 7.48-7.58 (m, 2H), 7.67-7.71 (m, 1H), 10.03 (s, 1H).

(2) cyclohexyl(3-methyl-1-benzofuran-2-yl)methanol

Using 3-methyl-1-benzofuran-2-carbaldehyde (753 mg) synthesized above and in the same manner as in Example A1(1), the title object compound (843 mg, 73%) was obtained as a pale-yellow oil.

$^1$H NMR (300 MHz, CDCl$_3$) δ ppm 0.85-1.03 (m, 1H), 1.03-1.34 (m, 4H), 1.34-1.44 (m, 1H), 1.60-1.71 (m, 2H), 1.75-1.99 (m, 3H), 2.10-2.20 (m, 1H), 2.23 (s, 3H), 4.49-4.56 (m, 1H), 7.18-7.29 (m, 2H), 7.39-7.49 (m, 2H).

(3) 2-[chloro(cyclohexyl)methyl]-3-methyl-1-benzofuran

To a mixture of cyclohexyl(3-methyl-1-benzofuran-2-yl)methanol (843 mg) synthesized above and toluene (20 mL) was added thionyl chloride (256 μL), and the mixture was stirred at room temperature for 2.5 hr and at 50° C. for 1.5 hr. Saturated aqueous sodium hydrogen carbonate solution was added to quench the reaction, and the mixture was extracted with ethyl acetate. The extract was washed with saturated brine, dried over magnesium sulfate, and concentrated under reduced pressure to give the title object compound (862 mg, 95%) as a yellow oil.

$^1$H NMR (300 MHz, CDCl$_3$) δ ppm 0.84-0.98 (m, 1H), 1.00-1.37 (m, 4H), 1.42-1.53 (m, 1H), 1.57-1.77 (m, 2H), 1.77-1.88 (m, 1H), 2.12-2.28 (m, 4H), 2.08-2.38 (m, 1H), 4.82 (d, J=9.6 Hz, 1H), 7.14-7.33 (m, 2H), 7.43-7.50 (m, 2H).

(4) 3-{[(4-{[cyclohexyl(3-methyl-1-benzofuran-2-yl)methyl]amino}phenyl)carbonyl](methyl)amino}propanoic acid Using 2-[chloro(cyclohexyl)methyl]-3-methyl-1-benzofuran (429 mg) synthesized above and ethyl 3-{[(4-aminophenyl)carbonyl](methyl)amino}propanoate (408 mg) synthesized in Example 2(2) and in the same manner as in Example A7(3), the title object compound (247 mg, 34%) was obtained as a white solid.

$^1$H NMR (300 MHz, CDCl$_3$) δ ppm 0.94-1.37 (m, 5H), 1.47-1.58 (m, 1H), 1.60-1.73 (m, 2H), 1.73-1.83 (m, 1H), 1.84-1.98 (m, 1H), 2.03-2.15 (m, 1H), 2.25 (s, 3H), 2.59-2.69

(m, 2H), 3.01 (s, 2H), 3.68 (t, J=6.5 Hz, 2H), 4.38 (d, J=7.9 Hz, 1H), 6.56 (d, J=8.7 Hz, 2H), 7.16-7.27 (m, 4H), 7.35-7.40 (m, 1H), 7.41-7.45 (m, 1H).

Example A17

3-{[(4-{[cyclohexyl(3-methyl-1-benzofuran-2-yl)methyl]amino}phenyl)carbonyl]amino}propanoic acid

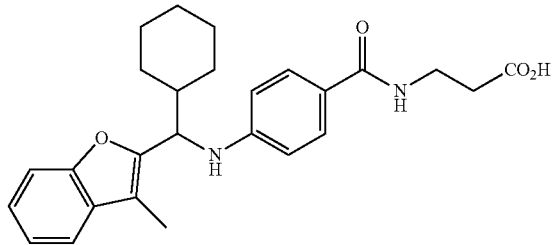 [SMILES: Cc1c(C(Nc2ccc(C(=O)NCCC(=O)O)cc2)C2CCCCC2)oc2ccccc12]

Using 2-[chloro(cyclohexyl)methyl]-3-methyl-1-benzofuran (433 mg) synthesized in Example A16(3) and ethyl 3-{[(4-aminophenyl)carbonyl]amino}propanoate (390 mg) synthesized in Example 1(2) and in the same manner as in Example A7(3), the title object compound (268 mg, 37%) was obtained as a white solid.

$^1$H NMR (300 MHz, CDCl$_3$) δ ppm 0.93-1.37 (m, 5H), 1.46-1.59 (m, 1H), 1.59-1.74 (m, 2H), 1.74-1.84 (m, 1H), 1.84-1.99 (m, 1H), 2.02-2.13 (m, 1H), 2.25 (s, 3H), 2.55-2.66 (m, 2H), 3.57-3.68 (m, 2H), 4.40 (d, J=8.1 Hz, 1H), 6.51-6.65 (m, 3H), 7.14-7.25 (m, 2H), 7.34-7.39 (m, 1H), 7.39-7.45 (m, 1H), 7.52 (d, J=8.9 Hz, 2H).

Example A18

3-{[(4-{[cyclohexyl(1-cyclohexyl-1H-indazol-3-yl)methyl]amino}phenyl)carbonyl](methyl)amino}propanoic acid

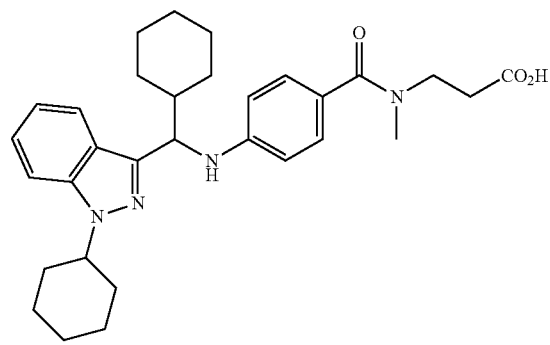 [SMILES: CN(CCC(=O)O)C(=O)c1ccc(NC(c2nn(C3CCCCC3)c3ccccc23)C2CCCCC2)cc1]

(1) methyl 1-cyclohexyl-1H-indazole-3-carboxylate

To a mixture of methyl 1H-indazole-3-carboxylate (5.00 g), cyclohexanol (9.00 mL), triphenylphosphine (14.9 g) and tetrahydrofuran (100 mL) was added 40% diethyl azodicarboxylate toluene solution (25.6 mL), and the mixture was stirred overnight at room temperature. The reaction mixture was concentrated under reduced pressure, diethyl ether was added to the residue, and the mixture was stirred at 0° C. The precipitate was filtered off, and the filtrate was concentrated under reduced pressure. The residue was purified by silica gel column chromatography (ethyl acetate:hexane=1:9, volume ratio) to give the title object compound (6.84 g, 93%) as a pale-red oil.

$^1$H NMR (300 MHz, CDCl$_3$) δ ppm 1.25-1.43 (m, 1H), 1.45-1.62 (m, 2H), 1.72-1.82 (m, 1H), 1.90-2.00 (m, 2H), 2.01-2.16 (m, 4H), 4.03 (s, 3H), 5.50-5.62 (m, 1H), 7.24-7.37 (m, 2H), 7.78-7.83 (m, 1H), 7.99-8.04 (m, 1H).

(2) 1-cyclohexyl-1H-indazole-3-carbaldehyde

Using methyl 1-cyclohexyl-1H-indazole-3-carboxylate (3.08 g) synthesized above and in the same manner as in Example A14(2), the title object compound (1.98 g, 73%) was obtained as a pale-yellow oil.

$^1$H NMR (300 MHz, CDCl$_3$) δ ppm 1.31-1.43 (m, 1H), 1.45-1.63 (m, 2H), 1.74-1.84 (m, 1H), 1.92-2.02 (m, 2H), 2.06-2.18 (m, 4H), 5.24-5.36 (m, 1H), 7.33-7.43 (m, 2H), 7.83-7.90 (m, 1H), 7.98-8.05 (m, 1H), 10.32 (s, 1H).

(3) cyclohexyl(1-cyclohexyl-1H-indazol-3-yl)methanol

Using 1-cyclohexyl-1H-indazole-3-carbaldehyde (980 mg) synthesized above and in the same manner as in Example A1(1), the title object compound (984 mg, 73%) was obtained as a white solid.

$^1$H NMR (300 MHz, CDCl$_3$) δ ppm 0.82-1.00 (m, 1H), 1.05-2.07 (m, 17H), 2.07-2.33 (m, 4H), 4.48-4.62 (m, 1H), 4.93 (dd, J=13.9, 3.6 Hz, 1H), 6.99-7.07 (m, 1H), 7.20-7.28 (m, 1H), 7.65-7.73 (m, 2H).

(4) 3-[chloro(cyclohexyl)methyl]-1-cyclohexyl-1H-indazole

Using cyclohexyl(1-cyclohexyl-1H-indazol-3-yl)methanol (934 mg) synthesized above and in the same manner as in Example A14(4), the title object compound (1.05 g, quantitative) was obtained as a pale-yellow solid.

$^1$H NMR (300 MHz, CDCl$_3$) δ ppm 0.75-0.89 (m, 1H), 1.06-2.08 (m, 16H), 2.09-2.38 (m, 3H), 2.45-2.56 (m, 1H), 4.41-4.54 (m, 1H), 5.09 (d, J=10.5 Hz, 1H), 7.04-7.11 (m, 1H), 7.21-7.29 (m, 1H), 7.66-7.72 (m, 2H).

(5) 3-{[(4-{[cyclohexyl(1-cyclohexyl-1H-indazol-3-yl)methyl]amino}phenyl)carbonyl]methyl)amino}propanoic acid Using 3-[chloro(cyclohexyl)methyl]-1-cyclohexyl-1H-indazole (400 mg) synthesized above and ethyl 3-{[(4-aminophenyl)carbonyl](methyl)amino}propanoate (303 mg) synthesized in Example 2(2) and in the same manner as in Example A7(3), the title object compound (451 mg, 72%) was obtained as a white solid.

$^1$H NMR (300 MHz, CDCl$_3$) δ ppm 0.92-1.50 (m, 9H), 1.61-2.04 (m, 9H), 2.06-2.29 (m, 3H), 2.57-2.69 (m, 2H), 2.99 (s, 3H), 3.67 (t, J=6.2 Hz, 2H), 4.43-4.57 (m, 1H), 4.72

(d, J=8.3 Hz, 1H), 6.47 (d, J=8.7 Hz, 2H), 6.99-7.06 (m, 1H), 7.17 (d, J=8.7 Hz, 2H), 7.20-7.29 (m, 1H), 7.65-7.73 (m, 4H).

Example A19

3-{[(4-{[cyclohexyl(1-cyclohexyl-1H-indazol-3-yl)methyl]amino}phenyl)carbonyl]amino}propanoic acid

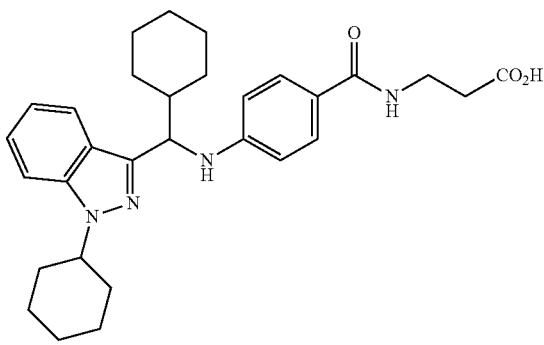 [SMILES: O=C(O)CCNC(=O)c1ccc(NC(c2nn(C3CCCCC3)c3ccccc23)C2CCCCC2)cc1]

Using 3-[chloro(cyclohexyl)methyl]-1-cyclohexyl-1H-indazole (400 mg) synthesized in Example A18(4) and ethyl 3-{[(4-aminophenyl)carbonyl]amino}propanoate (286 mg) synthesized in Example 1(2) and in the same manner as in Example A7(3), the title object compound (441 mg, 72%) was obtained as a white solid.

$^1$H NMR (300 MHz, CDCl$_3$) δ ppm 0.93-1.48 (m, 9H), 1.61-2.04 (m, 9H), 2.03-2.29 (m, 3H), 2.61 (t, J=5.7 Hz, 2H), 3.54-3.69 (m, 2H), 4.43-4.55 (m, 1H), 4.74 (d, J=8.3 Hz, 1H), 6.46 (d, J=8.7 Hz, 2H), 6.67 (t, J=5.8 Hz, 1H), 6.97-7.06 (m, 1H), 7.18-7.29 (m, 1H), 7.46 (d, J=8.7 Hz, 2H), 7.68 (d, J=9.4 Hz, 2H).

Example A20

3-{[(4-{[cyclohexyl(7-methoxy-1-benzofuran-2-yl)methyl]amino}phenyl)carbonyl]amino}propanoic acid

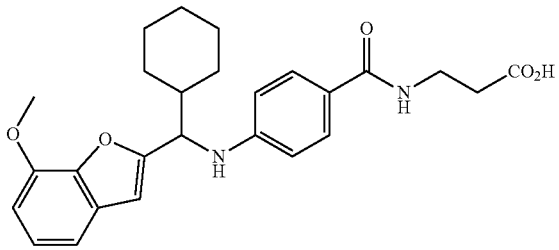 [SMILES: COc1cccc2cc(C(Nc3ccc(C(=O)NCCC(=O)O)cc3)C3CCCCC3)oc12]

(1) 7-methoxy-1-benzofuran-2-carbaldehyde

Using ethyl 7-methoxy-1-benzofuran-2-carboxylate (2.00 g) and in the same manner as in Example A14(2), the title object compound (950 mg, 59%) was obtained as a brown oil.

$^1$H NMR (300 MHz, CDCl$_3$) δ ppm 4.04 (s, 3H), 6.96-7.00 (m, 1H), 7.22-7.34 (m, 2H), 7.54 (s, 1H), 9.90 (s, 1H).

(2) cyclohexyl(7-methoxy-1-benzofuran-2-yl)methanol

Using 7-methoxy-1-benzofuran-2-carbaldehyde (950 mg) synthesized above and in the same manner as in Example A1(1), the title object compound (790 mg, 56%) was obtained as a yellow oil.

$^1$H NMR (300 MHz, CDCl$_3$) δ ppm 1.02-1.34 (m, 5H), 1.49-1.60 (m, 1H), 1.60-1.83 (m, 3H), 1.84-2.02 (m, 3H), 4.00 (s, 3H), 4.53-4.59 (m, 1H), 6.60 (s, 1H), 6.74-6.81 (m, 1H), 7.09-7.17 (m, 2H).

(3) 2-[chloro(cyclohexyl)methyl]-7-methoxy-1-benzofuran

Using cyclohexyl(7-methoxy-1-benzofuran-2-yl)methanol (790 mg) synthesized above and in the same manner as in Example A1(2), the title object compound (823 mg, 97%) was obtained as a yellow oil.

$^1$H NMR (300 MHz, CDCl$_3$) δ ppm 1.02-1.37 (m, 5H), 1.55-1.84 (m, 4H), 2.06-2.25 (m, 2H), 4.01 (s, 3H), 4.81 (d, J=7.8 Hz, 1H), 6.67 (s, 1H), 6.75-6.83 (m, 1H), 7.10-7.18 (m, 2H).

(4) 3-{[(4-{[cyclohexyl(7-methoxy-1-benzofuran-2-yl)methyl]amino}phenyl)carbonyl]amino}propanoic acid Using 2-[chloro(cyclohexyl)methyl]-7-methoxy-1-benzofuran (422 mg) synthesized above and ethyl 3-{[(4-aminophenyl)carbonyl]amino}propanoate (357 mg) synthesized in Example 1(2) and in the same manner as in Example A7(3), the title object compound (64.3 mg, 9%) was obtained as a pale-yellow solid.

$^1$H NMR (300 MHz, CDCl$_3$) δ ppm 1.02-1.34 (m, 5H), 1.54-1.82 (m, 4H), 1.87-2.07 (m, 2H), 2.64 (t, J=5.6 Hz, 2H), 3.59-3.69 (m, 2H), 4.00 (s, 3H), 4.43 (d, J=6.4 Hz, 1H), 6.50 (s, 1H), 6.53-6.61 (m, 3H), 6.75 (dd, J=7.5, 1.3 Hz, 1H), 7.02-7.13 (m, 2H), 7.53 (d, J=8.7 Hz, 2H).

Example A21

3-{[(4-{[cyclohexyl(7-methoxy-1-benzofuran-2-yl)methyl]amino}phenyl)carbonyl](methyl)amino}propanoic acid

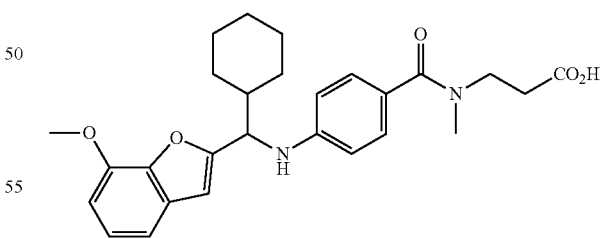

Using 2-[chloro(cyclohexyl)methyl]-7-methoxy-1-benzofuran (401 mg) synthesized in Example A20(3) and ethyl 3-{[(4-aminophenyl)carbonyl](methyl)amino}propanoate (360 mg) synthesized in Example 2(2) and in the same manner as in Example A7(3), the title object compound (48.7 mg, 7%) was obtained as a white solid.

$^1$H NMR (300 MHz, CDCl$_3$) δ ppm 1.03-1.34 (m, 5H), 1.54-1.82 (m, 4H), 1.88-2.08 (m, 2H), 2.68 (t, J=6.4 Hz, 2H), 3.04 (s, 3H), 3.71 (t, J=6.4 Hz, 2H), 4.01 (s, 3H), 4.42 (d, J=6.6 Hz, 1H), 6.51 (s, 1H), 6.57 (d, J=8.7 Hz, 2H), 6.76 (dd, J=7.3, 1.5 Hz, 1H), 7.04-7.15 (m, 2H), 7.24 (d, J=8.7 Hz, 2H).

Example A22

3-{[(4-{[cyclohexyl(5-methoxy-1-benzofuran-2-yl)methyl]amino}phenyl)carbonyl]amino}propanoic acid

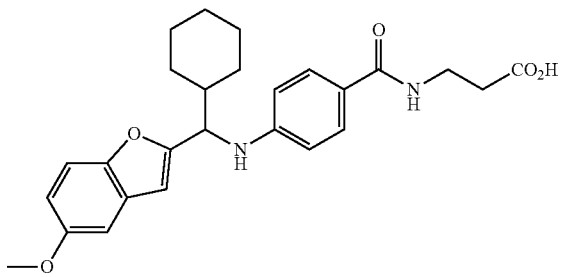 [SMILES: COc1ccc2oc(C(Nc3ccc(C(=O)NCCC(=O)O)cc3)C3CCCCC3)cc2c1]

(1) 5-methoxy-1-benzofuran-2-carbaldehyde

Using ethyl 5-methoxy-1-benzofuran-2-carboxylate (2.00 g) and in the same manner as in Example A14(2), the title object compound (914 mg, 57%) was obtained as a brown solid.
$^1$H NMR (300 MHz, CDCl$_3$) δ ppm 3.86 (s, 3H), 7.10-7.16 (m, 2H), 7.46-7.52 (m, 2H), 9.82 (s, 1H).

(2) cyclohexyl(5-methoxy-1-benzofuran-2-yl)methanol

Using 5-methoxy-1-benzofuran-2-carbaldehyde (914 mg) synthesized above and in the same manner as in Example A1(1), the title object compound (702 mg, 52%) was obtained as a brown oil.
$^1$H NMR (300 MHz, CDCl$_3$) δ ppm 0.98-1.35 (m, 5H), 1.47-1.58 (m, 1H), 1.60-2.02 (m, 6H), 3.83 (s, 3H), 4.47-4.53 (m, 1H), 6.54 (s, 1H), 6.85 (dd, J=8.7, 2.7 Hz, 1H), 6.99 (d, J=2.7 Hz, 1H), 7.33 (d, J=8.7 Hz, 1H).

(3) 2-[chloro(cyclohexyl)methyl]-5-methoxy-1-benzofuran

Using cyclohexyl(5-methoxy-1-benzofuran-2-yl)methanol (702 mg) synthesized above and in the same manner as in Example A1(2), the title object compound (722 mg, 96%) was obtained as a brown oil.
$^1$H NMR (300 MHz, CDCl$_3$) δ ppm 0.98-1.38 (m, 5H), 1.51-1.86 (m, 4H), 2.06-2.21 (m, 2H), 3.83 (s, 3H), 4.75 (d, J=8.1 Hz, 1H), 6.59-6.61 (m, 1H), 6.88 (dd, J=8.9, 2.4 Hz, 1H), 6.97 (d, J=2.4 Hz, 1H), 7.33-7.38 (m, 1H).

(4) 3-{[(4-{[cyclohexyl(5-methoxy-1-benzofuran-2-yl)methyl]amino}phenyl)carbonyl]amino}propanoic acid To a mixture of 2-[chloro(cyclohexyl)methyl]-5-methoxy-1-benzofuran (360 mg) synthesized above, ethyl 3-{[(4-aminophenyl)carbonyl]amino}propanoate (305 mg) synthesized in Example 1(2), sodium iodide (291 mg) and N,N-dimethylacetamide (10 mL) was added sodium carbonate (206 mg), and the mixture was stirred at 80° C. overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=11:9, volume ratio) to give a yellow oil. To a mixture of the obtained oil, tetrahydrofuran (2.5 and ethanol (2.5 mL) was added 1N aqueous sodium hydroxide solution (1 mL), and the mixture was stirred at room temperature for 4 hr. The reaction mixture was concentrated under reduced pressure, the residue was dissolved in water (5 mL), and 1N hydrochloric acid (1 mL) was added at 0° C. The resulting precipitate was collected by filtration to give the title object compound (96.0 mg, 17%) as a yellow solid.
$^1$H NMR (300 MHz, CDCl$_3$) δ ppm 1.02-1.35 (m, 5H), 1.54-1.84 (m, 4H), 1.85-2.01 (m, 2H), 2.60-2.69 (m, 2H), 3.59-3.70 (m, 2H), 3.80 (s, 3H), 4.38 (d, J=6.4 Hz, 1H), 6.44 (s, 1H), 6.53-6.62 (m, 3H), 6.82 (dd, J=9.1, 2.7 Hz, 1H), 6.92 (d, J=2.7 Hz, 1H), 7.30 (d, J=9.1 Hz, 1H), 7.54 (d, J=8.7 Hz, 2H).

Example A23

3-{[(4-{[3-methyl-1-(3-methyl-1-benzofuran-2-yl)butyl]amino}phenyl)carbonyl]amino}propanoic acid

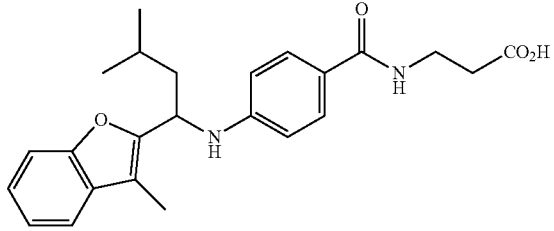

(1) N-methoxy-N,3-dimethyl-1-benzofuran-2-carboxamide

To a mixture of 3-methyl-1-benzofuran-2-carboxylic acid (15.0 g), N,O-dimethylhydroxyamine hydrochloride (9.95 g), 1-hydroxybenzotriazole-monohydrate (15.6 g), triethylamine (14.2 mL) and N,N-dimethylformamide (150 mL) was added 1-ethyl-3-(3-dimethylaminopropyl)carbodiimide hydrochloride (19.6 g), and the mixture was stirred overnight at room temperature. In addition, N,O-dimethylhydroxyamine hydrochloride (4.16 g), 1-hydroxybenzotriazole-monohydrate (6.52 g), triethylamine (5.94 mL) and 1-ethyl-3-(3-dimethylaminopropyl)carbodiimide hydrochloride (8.17 g) were added, and the mixture was stirred at room temperature for 4 hr. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (ethyl acetate:hexane=3:7, volume ratio) to give the title object compound (16.2 g, 87%) as a colorless oil.
$^1$H NMR (300 MHz, CDCl$_3$) δ ppm 2.51 (s, 3H), 3.39 (s, 3H), 3.87 (s, 3H), 7.25-7.32 (m, 1H), 7.37-7.50 (m, 2H), 7.58-7.63 (m, 1H).

(2) 3-methyl-1-(3-methyl-1-benzofuran-2-yl)butan-1-one

To a solution (20 mL) of N-methoxy-N,3-dimethyl-1-benzofuran-2-carboxamide (1.00 g) synthesized above in tetrahydrofuran was added dropwise a 1.0M solution (6.84 mL) of isobutylmagnesium bromide in tetrahydrofuran at 0° C., and the mixture was stirred for 1 hr. In addition, 1.0M isobutylmagnesium bromide tetrahydrofuran solution (6.84 mL) was added, and the mixture was stirred at 0° C. for 1 hr then at room temperature for 2 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate: hexane=1:9, volume ratio) to give the title object compound (873 mg, 89%) as a colorless oil.

$^1$H NMR (300 MHz, CDCl$_3$) δ ppm 1.02 (d, J=6.9 Hz, 6H), 2.26-2.41 (m, 1H), 2.61 (s, 3H), 2.87 (d, J=6.9 Hz, 2H), 7.26-7.33 (m, 1H), 7.42-7.53 (m, 2H), 7.62-7.67 (m, 1H).

(3) methyl 4-{[3-methyl-1-(3-methyl-1-benzofuran-2-yl)butyl]amino}benzoate

To a mixture of 3-methyl-1-(3-methyl-1-benzofuran-2-yl)butan-1-one (200 mg) synthesized above, methyl 4-aminobenzoate (140 mg), triethylamine (1.03 mL) and dichloromethane (5 mL) was added titanium (IV) chloride (122 μL) at 0° C., and the mixture was stirred at room temperature overnight. Saturated aqueous sodium hydrogen carbonate solution was added to quench the reaction, and the mixture was extracted with ethyl acetate. The extract was washed with saturated brine, dried over magnesium sulfate, and concentrated under reduced pressure to give a dark brown solid. To a mixture of the obtained solid, acetic acid (1 mL), methanol (5 mL) and tetrahydrofuran (5 mL) was added sodium cyanoborohydride (175 mg) by small portions, and the mixture was stirred at room temperature for 1 hr. Saturated aqueous sodium hydrogen carbonate solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (254 mg, 78%) as a pale-yellow solid.

$^1$H NMR (300 MHz, CDCl$_3$) δ ppm 0.92 (d, J=6.6 Hz, 3H), 1.01 (d, J=6.6 Hz, 3H), 1.49-1.64 (m, 1H), 1.79-1.96 (m, 2H), 2.29 (s, 3H), 3.81 (s, 3H), 4.48 (d, J=7.8 Hz, 1H), 4.70-4.80 (m, 1H), 6.58 (d, J=8.9 Hz, 2H), 7.16-7.26 (m, 2H), 7.34-7.39 (m, 1H), 7.41-7.45 (m, 1H), 7.80 (d, J=8.9 Hz, 2H).

(4) 4-{[3-methyl-1-(3-methyl-1-benzofuran-2-yl)butyl]amino}benzoic acid

To a mixture of methyl 4-{[3-methyl-1-(3-methyl-1-benzofuran-2-yl)butyl]amino}benzoate (1.38 g) synthesized above, tetrahydrofuran (20 mL) and ethanol (20 mL) was added 1N aqueous sodium hydroxide solution (20 mL), and the mixture was stirred with heating under reflux overnight. In addition, 1N aqueous sodium hydroxide solution (20 mL) was added, and the mixture was stirred with heating under reflux for 3 hr. The reaction mixture was concentrated under reduced pressure, 1N hydrochloric acid (40 mL) was added to the residue, and the mixture was extracted with ethyl acetate. The extract was washed with water and saturated brine, dried over magnesium sulfate, and concentrated under reduced pressure. The residue was washed with diisopropyl ether to give the title object compound (1.06 g, 80%) as a white solid.

$^1$H NMR (300 MHz, CDCl$_3$) δ ppm 0.92 (d, J=6.6 Hz, 3H), 1.01 (d, J=6.6 Hz, 3H), 1.49-1.64 (m, 1H), 1.79-1.97 (m, 2H), 2.30 (s, 3H), 4.77 (t, J=7.5 Hz, 1H), 6.59 (d, J=9.0 Hz, 2H), 7.16-7.28 (m, 2H), 7.35-7.40 (m, 1H), 7.42-7.47 (m, 1H), 7.86 (d, J=9.0 Hz, 2H).

(5) 3-{[(4-{[3-methyl-1-(3-methyl-1-benzofuran-2-yl)butyl]amino}phenyl)carbonyl]amino}propanoic acid Using 4-{[3-methyl-1-(3-methyl-1-benzofuran-2-yl)butyl]amino}benzoic acid (300 mg) synthesized above and in the same manner as in Example A1(4), the title object compound (289 mg, 80%) was obtained as a white solid.

$^1$H NMR (300 MHz, CDCl$_3$) δ ppm 0.91 (d, J=6.6 Hz, 3H), 1.00 (d, J=6.6 Hz, 3H), 1.48-1.64 (m, 1H), 1.78-1.94 (m, 2H), 2.28 (s, 3H), 2.64 (t, J=5.5 Hz, 2H), 3.60-3.69 (m, 2H), 4.73 (t, J=7.5 Hz, 1H), 6.54-6.65 (m, 3H), 7.15-7.26 (m, 2H), 7.34-7.39 (m, 1H), 7.40-7.45 (m, 1H), 7.54 (d, J=8.7 Hz, 2H).

Example A24

3-{methyl[(4-{[3-methyl-1-(3-methyl-1-benzofuran-2-yl)butyl]amino}phenyl)carbonyl]amino}propanoic acid

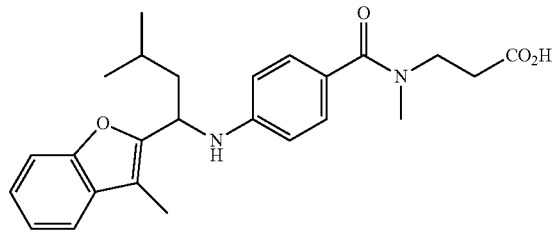 [SMILES: Cc1c(C(CC(C)C)Nc2ccc(C(=O)N(C)CCC(=O)O)cc2)oc2ccccc12]

Using 4-{[3-methyl-1-(3-methyl-1-benzofuran-2-yl)butyl]amino}benzoic acid (300 mg) synthesized in Example A23(4) and ethyl 3-(methylamino)propanoate (140 mg) and in the same manner as in Example A1(4), the title object compound (221 mg, 59%) was obtained as a white solid.

$^1$H NMR (300 MHz, CDCl$_3$) δ ppm 0.91 (d, J=6.6 Hz, 3H), 1.00 (d, J=6.6 Hz, 3H), 1.48-1.64 (m, 1H), 1.81-1.92 (m, 2H), 2.29 (s, 3H), 2.61-2.71 (m, 2H), 3.03 (s, 3H), 3.70 (t, J=6.4

Hz, 2H), 4.71 (t, J=7.5 Hz, 1H), 6.58 (d, J=8.5 Hz, 2H), 7.16-7.29 (m, 6H), 7.35-7.40 (m, 1H), 7.41-7.46 (m, 1H).

Example A25

3-{[(4-{[cyclohexyl(5-methoxy-1-benzofuran-2-yl)methyl]amino}phenyl)carbonyl](methyl)amino}propanoic acid

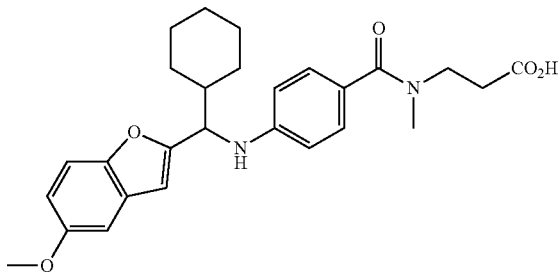 [SMILES: COc1ccc2oc(C(Nc3ccc(C(=O)N(C)CCC(=O)O)cc3)C3CCCCC3)cc2c1]

Using 2-[chloro(cyclohexyl)methyl]-5-methoxy-1-benzofuran (361 mg) synthesized in Example A22(3) and ethyl 3-{[(4-aminophenyl)carbonyl](methyl)amino}propanoate (325 mg) synthesized in Example 2(2) and in the same manner as in Example A22(4), the title object compound (87.0 mg, 14%) was obtained as a white solid.

$^1$H NMR (300 MHz, CDCl$_3$) δ ppm 1.02-1.36 (m, 5H), 1.55-1.84 (m, 4H), 1.86-2.01 (m, 2H), 2.61-2.74 (m, 2H), 3.04 (s, 3H), 3.71 (t, J=6.2 Hz, 2H), 3.81 (s, 3H), 4.36 (d, J=6.1 Hz, 1H), 6.45 (s, 1H), 6.57 (d, J=8.7 Hz, 2H), 6.83 (dd, J=8.9, 2.5 Hz, 1H), 6.94 (d, J=2.5 Hz, 1H), 7.21-7.29 (m, 2H), 7.31 (d, J=8.9 Hz, 1H).

Example A26

3-{[(4-{[cyclohexyl(2-ethyl-1-benzofuran-3-yl)methyl]amino}phenyl)carbonyl](methyl)amino}propanoic acid

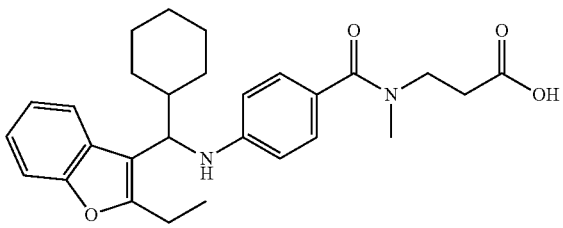 [SMILES: CCc1oc2ccccc2c1C(Nc1ccc(C(=O)N(C)CCC(=O)O)cc1)C1CCCCC1]

(1) cyclohexyl(2-ethyl-1-benzofuran-3-yl)methanol

Using 2-ethyl-1-benzofuran-3-carbaldehyde (1.20 g) and in the same manner as in Example A1(1), the title object compound (1.76 g, 99%) was obtained as a yellow oil.

$^1$H NMR (300 MHz, CDCl$_3$) δ ppm 0.79-0.94 (m, 1H), 1.01-1.19 (m, 3H), 1.20-1.34 (m, 4H), 1.37-1.46 (m, 1H), 1.57-1.70 (m, 2H), 1.77-2.02 (m, 3H), 2.17-2.27 (m, 1H), 2.70-2.85 (m, 2H), 4.54 (dd, J=8.7, 2.7 Hz, 1H), 7.14-7.24 (m, 2H), 7.37-7.41 (m, 1H), 7.60-7.65 (m, 1H).

(2) 3-[chloro(cyclohexyl)methyl]-2-ethyl-1-benzofuran

Using cyclohexyl(2-ethyl-1-benzofuran-3-yl)methanol (763 mg) synthesized above and in the same manner as in Example A1(2), the title object compound (765 mg, 94%) was obtained as a pale-yellow oil.

$^1$H NMR (300 MHz, CDCl$_3$) δ ppm 0.75-0.89 (m, 1H), 1.00-1.39 (m, 7H), 1.43-1.53 (m, 1H), 1.58-1.69 (m, 2H), 1.78-1.89 (m, 1H), 2.12-2.26 (m, 1H), 2.35-2.46 (m, 1H), 2.70-2.85 (m, 2H), 4.78 (d, J=9.9 Hz, 1H), 7.14-7.28 (m, 2H), 7.37-7.42 (m, 1H), 7.67-7.72 (m, 1H).

(3) 3-{[(4-{[cyclohexyl(2-ethyl-1-benzofuran-3-yl)methyl]amino}phenyl)carbonyl](methyl)amino}propanoic acid Using 3-[chloro(cyclohexyl)methyl]-2-ethyl-1-benzofuran (300 mg) synthesized above and ethyl 3-{[(4-aminophenyl)carbonyl](methyl)amino}propanoate (270 mg) synthesized in Example 2(2) and in the same manner as in Example A22(4), the title object compound (287 mg, 57%) was obtained as a white solid.

$^1$H NMR (300 MHz, CDCl$_3$) δ ppm 0.87-1.23 (m, 5H), 1.28 (t, J=7.5 Hz, 3H), 1.55-1.75 (m, 3H), 1.75-1.98 (m, 2H), 2.04-2.15 (m, 1H), 2.61-2.71 (m, 2H), 2.75-2.90 (m, 2H), 3.02 (s, 3H), 3.69 (t, J=6.4 Hz, 2H), 4.30 (d, J=7.9 Hz, 1H), 6.49 (d, J=8.7 Hz, 2H), 7.12-7.24 (m, 4H), 7.35-7.41 (m, 1H), 7.53-7.59 (m, 1H).

Example A27

3-{[(4-{[cyclohexyl(5-methoxy-3-methyl-1-benzofuran-2-yl)methyl]amino}phenyl)carbonyl](methyl)amino}propanoic acid

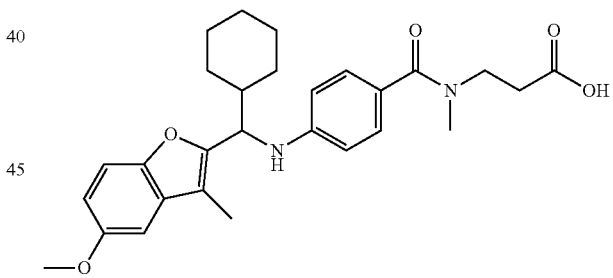

(1) methyl 5-methoxy-3-methyl-1-benzofuran-2-carboxylate

To a mixture of 1-(2-hydroxy-5-methoxyphenyl)ethanone (5.00 g), methyl bromoacetate (3.13 mL) and N,N-dimethylformamide (50 mL) was added potassium carbonate (12.5 g), and the mixture was stirred overnight at room temperature. Water was added to quench the reaction, and the reaction mixture was extracted with ethyl acetate. The extract was washed with saturated brine, dried over magnesium sulfate, and concentrated under reduced pressure to give a brown oil. To a solution (50 mL) of the obtained oil in methanol was added sodium methoxide (1.63 g), and the mixture was stirred with heating under reflux for 3 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (1.25 g, 19%) as a white solid.

$^1$H NMR (300 MHz, CDCl$_3$) δ ppm 2.57 (s, 3H), 3.87 (s, 3H), 3.97 (s, 3H), 6.99 (d, J=2.6 Hz, 1H), 7.06 (dd, J=9.0, 2.6 Hz, 1H), 7.42 (d, J=9.0 Hz, 1H).

(2)
5-methoxy-3-methyl-1-benzofuran-2-carbaldehyde

To a solution (100 mL) of methyl 5-methoxy-3-methyl-1-benzofuran-2-carboxylate (5.00 g) in tetrahydrofuran was added lithium aluminum hydride (862 mg) at 0° C., and the mixture was stirred for 1.5 hr. Water (860 µL) was added to quench the reaction, 1N aqueous sodium hydroxide solution (860 µL) was added, and the mixture was stirred at room temperature for 1 hr. The resulting insoluble material was filtered off, and the filtrate was concentrated under reduced pressure to give a pale-yellow solid. To a solution of the obtained solid in tetrahydrofuran (80 mL) was added active manganese dioxide (21.2 g), and the mixture was stirred at 50° C. overnight. Manganese dioxide was filtered off, and the filtrate was concentrated under reduced pressure to give the title object compound (3.41 g, 79%) as a brown solid.

$^1$H NMR (300 MHz, CDCl$_3$) δ ppm 2.60 (s, 3H), 3.88 (s, 3H), 7.03 (d, J=2.5 Hz, 1H), 7.14 (dd, J=9.0, 2.5 Hz, 1H), 7.44 (d, J=9.0 Hz, 1H), 10.00 (s, 1H).

(3) cyclohexyl(5-methoxy-3-methyl-1-benzofuran-2-yl)methanol

Using 5-methoxy-3-methyl-1-benzofuran-2-carbaldehyde (1.50 g) synthesized above as in Example A1(1), the title object compound (1.54 g, 71%) was obtained as a yellow oil.

$^1$H NMR (300 MHz, CDCl$_3$) δ ppm 0.84-0.99 (m, 1H), 1.00-1.33 (m, 4H), 1.33-1.44 (m, 1H), 1.60-1.70 (m, 2H), 1.74-1.99 (m, 3H), 2.09-2.22 (m, 4H), 3.85 (s, 3H), 4.50 (dd, J=8.6, 6.5 Hz, 1H), 6.86 (dd, J=8.7, 2.6 Hz, 1H), 6.91 (d, J=2.6 Hz, 1H), 7.30 (d, J=8.7 Hz, 1H).

(4) 2-[chloro(cyclohexyl)methyl]-5-methoxy-3-methyl-1-benzofuran

Using cyclohexyl(5-methoxy-3-methyl-1-benzofuran-2-yl)methanol (754 mg) synthesized above and in the same manner as in Example A1(2), the title object compound (795 mg, 99%) was obtained as a brown oil.

$^1$H NMR (300 MHz, CDCl$_3$) δ ppm 0.83-0.97 (m, 1H), 1.00-1.40 (m, 4H), 1.42-1.52 (m, 1H), 1.60-1.70 (m, 2H), 1.77-1.87 (m, 1H), 2.10-2.38 (m, 5H), 3.85 (s, 3H), 4.80 (d, J=9.6 Hz, 1H), 6.86-6.91 (m, 2H), 7.31-7.36 (m, 1H).

(5) 3-{[(4-{[cyclohexyl(5-methoxy-3-methyl-1-benzofuran-2-yl)methyl]amino}phenyl)carbonyl](methyl)amino}propanoic acid Using 2-[chloro(cyclohexyl)methyl]-5-methoxy-3-methyl-1-benzofuran (395 mg) synthesized above and ethyl 3-{[(4-aminophenyl)carbonyl](methyl)amino}propanoate (338 mg) synthesized in Example 2(2) and in the same manner as in Example A22(4), the title object compound (305 mg, 47%) was obtained as a white solid.

$^1$H NMR (300 MHz, CDCl$_3$) δ ppm 0.93-1.37 (m, 5H), 1.47-1.57 (m, 1H), 1.60-1.96 (m, 4H), 2.03-2.13 (m, 1H), 2.23 (s, 3H), 2.65 (t, J=6.4 Hz, 2H), 3.02 (s, 3H), 3.69 (t, J=6.4 Hz, 2H), 3.83 (s, 3H), 4.36 (d, J=8.0 Hz, 1H), 6.55 (d, J=8.7 Hz, 2H), 6.82 (dd, J=8.9, 2.4 Hz, 1H), 6.88 (d, J=2.4 Hz, 1H), 7.19-7.29 (m, 3H).

Example A28

3-{[(4-{[cyclohexyl(6-methoxy-1-benzofuran-2-yl)methyl]amino}phenyl)carbonyl](methyl)amino}propanoic acid

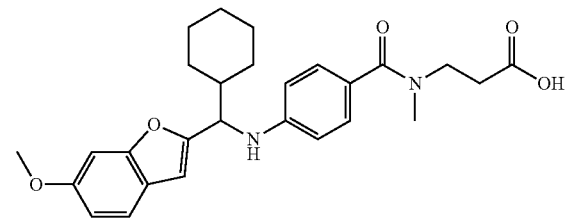

(1) 6-methoxy-1-benzofuran-2-carbonitrile

To a mixture of 2-hydroxy-4-methoxybenzaldehyde (10.0 g), bromoacetonitrile (5.04 mL) and acetone (100 mL) was added potassium carbonate (18.1 g), and the mixture was stirred at room temperature for 3 hr. The insoluble material was filtered off, and the filtrate was concentrated under reduced pressure to give a pale-brown solid. To a solution (100 mL) of the obtained solid in N,N-dimethylformamide was added 1,8-diazabicyclo[5.4.0]undec-7-ene (9.83 mL), and the mixture was stirred at 140° C. for 1.5 hr. The reaction mixture was concentrated under reduced pressure, 1N hydrochloric acid was added, and the mixture was extracted with ethyl acetate. The extract was washed with saturated brine, dried over magnesium sulfate, and concentrated under reduced pressure. Ethyl acetate was added to the residue, the insoluble material was filtered off, and the filtrate was concentrated under reduced pressure. The residue was purified by silica gel column chromatography (ethyl acetate:hexane=3:17, volume ratio) to give the title object compound (5.32 g, 47%) as a yellow solid.

$^1$H NMR (300 MHz, CDCl$_3$) δ ppm 3.88 (s, 3H), 6.96-7.04 (m, 2H), 7.39 (d, J=0.9 Hz, 1H), 7.52 (d, J=8.5 Hz, 1H).

(2)
cyclohexyl(6-methoxy-1-benzofuran-2-yl)methanone

To a solution (20 mL) of 6-methoxy-1-benzofuran-2-carbonitrile (1.00 g) synthesized above in tetrahydrofuran was added 1.0M cyclohexylmagnesium bromide tetrahydrofuran solution (11.5 mL), and the mixture was stirred at 50° C. overnight, and stirred with heating under reflux for 1 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:9, volume ratio) to give the title object compound (584 mg, 39%) as a yellow solid.

$^1$H NMR (300 MHz, CDCl$_3$) δ ppm 1.20-1.64 (m, 5H), 1.69-1.79 (m, 1H), 1.81-1.98 (m, 4H), 3.09-3.21 (m, 1H), 3.87 (s, 3H), 6.93 (dd, J=8.4, 2.1 Hz, 1H), 7.03-7.06 (m, 1H), 7.44-7.46 (m, 1H), 7.54 (d, J=8.4 Hz, 1H).

(3) methyl 4-{[cyclohexyl(6-methoxy-1-benzofuran-2-yl)methyl]amino}benzoate

Using cyclohexyl(6-methoxy-1-benzofuran-2-yl)methanone (584 mg) synthesized above and in the same manner as in Example A23(3), the title object compound (682 mg, 77%) was obtained as a brown oil.

$^1$H NMR (300 MHz, CDCl$_3$) δ ppm 1.03-1.36 (m, 5H), 1.56-1.84 (m, 4H), 1.86-2.00 (m, 2H), 3.81 (s, 3H), 3.83 (s, 3H), 4.35-4.57 (m, 2H), 6.44 (s, 1H), 6.58 (d, J=8.9 Hz, 1H), 6.81 (dd, J=8.6, 2.3 Hz, 1H), 6.97 (d, J=2.3 Hz, 1H), 7.31 (d, J=8.6 Hz, 1H), 7.80 (d, J=8.9 Hz, 2H).

(4) 4-{[cyclohexyl(6-methoxy-1-benzofuran-2-yl)methyl]amino}benzoic acid

Using methyl 4-{[cyclohexyl(6-methoxy-1-benzofuran-2-yl)methyl]amino}benzoate (682 mg) synthesized above and in the same manner as in Example A23(4), the title object compound (633 mg, 96%) was obtained as a yellow solid.

$^1$H NMR (300 MHz, CDCl$_3$) δ ppm 1.02-1.37 (m, 5H), 1.56-1.86 (m, 4H), 1.86-2.01 (m, 2H), 3.83 (s, 3H), 4.36-4.46 (m, 1H), 4.48-4.65 (m, 1H), 6.45 (s, 1H), 6.60 (d, J=8.9 Hz, 2H), 6.82 (dd, J=8.6, 2.3 Hz, 1H), 6.98 (d, J=2.3 Hz, 1H), 7.33 (d, J=8.6 Hz, 1H), 7.86 (d, J=8.9 Hz, 2H).

(5) 3-{[(4-{[cyclohexyl(6-methoxy-1-benzofuran-2-yl)methyl]amino}phenyl)carbonyl](methyl)amino}propanoic acid Using 4-{[cyclohexyl(6-methoxy-1-benzofuran-2-yl)methyl]amino}benzoic acid (300 mg) synthesized above and ethyl 3-(methylamino)propanoate (125 mg) and in the same manner as in Example A1(4), the title object compound (201 mg, 55%) was obtained as a white solid.

$^1$H NMR (300 MHz, CDCl$_3$) δ ppm 1.03-1.36 (m, 5H), 1.55-1.84 (m, 4H), 1.85-2.00 (m, 2H), 2.67 (t, J=6.5 Hz, 2H), 3.03 (s, 3H), 3.70 (t, J=6.5 Hz, 2H), 3.83 (s, 3H), 4.35 (d, J=6.6 Hz, 1H), 6.44 (s, 1H), 6.57 (d, J=8.7 Hz, 2H), 6.82 (dd, J=8.5, 2.2 Hz, 1H), 6.98 (d, J=2.2 Hz, 1H), 7.22-7.28 (m, 2H), 7.32 (d, J=8.5 Hz, 1H).

Example A29

3-{[(4-{[cyclohexyl(2-ethyl-1-benzofuran-3-yl)methyl]amino}phenyl)carbonyl]amino}propanoic acid

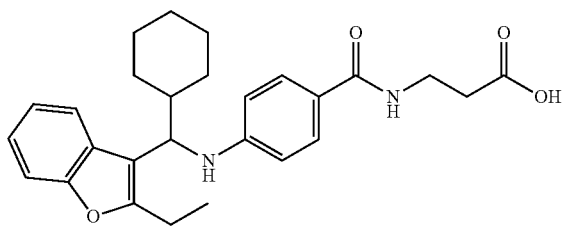 [SMILES: CCc1oc2ccccc2c1C(Nc1ccc(C(=O)NCCC(=O)O)cc1)C1CCCCC1]

Using 3-[chloro(cyclohexyl)methyl]-2-ethyl-1-benzofuran (300 mg) synthesized in Example A26(2) and ethyl 3-{[(4-aminophenyl)carbonyl]amino}propanoate (255 mg) synthesized in Example 1(2) and in the same manner as in Example A22(4), the title object compound (374 mg, 77%) was obtained as a pale-brown solid.

$^1$H NMR (300 MHz, CDCl$_3$) δ ppm 0.92-1.23 (m, 5H), 1.27 (t, J=7.5 Hz, 3H), 1.55-1.74 (m, 3H), 1.76-1.97 (m, 2H), 2.04-2.15 (m, 1H), 2.56-2.66 (m, 2H), 2.71-2.92 (m, 2H), 3.56-3.66 (m, 2H), 4.31 (d, J=7.9 Hz, 1H), 6.48 (d, J=8.7 Hz, 2H), 6.52-6.62 (m, 1H), 7.11-7.22 (m, 2H), 7.34-7.40 (m, 1H), 7.47 (d, J=8.7 Hz, 2H), 7.52-7.57 (m, 1H).

Example A30

3-{[(4-{[cyclohexyl(5-methoxy-3-methyl-1-benzofuran-2-yl)methyl]amino}phenyl)carbonyl]amino}propanoic acid

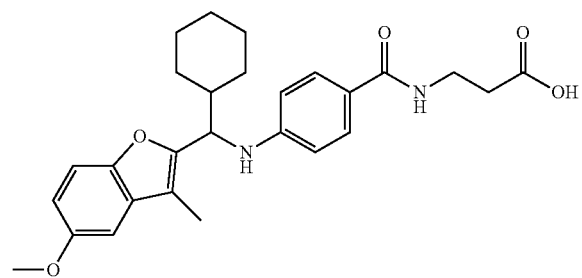 [SMILES: COc1ccc2oc(C(Nc3ccc(C(=O)NCCC(=O)O)cc3)C3CCCCC3)c(C)c2c1]

Using 2-[chloro(cyclohexyl)methyl]-5-methoxy-3-methyl-1-benzofuran (395 mg) synthesized in Example A27(4) and ethyl 3-{[(4-aminophenyl)carbonyl]amino}propanoate (319 mg) synthesized in Example 1(2) and in the same manner as in Example A22(4), the title object compound (413 mg, 66%) was obtained as a white solid.

$^1$H NMR (300 MHz, CDCl$_3$) δ ppm 0.92-1.36 (m, 5H), 1.46-1.58 (m, 1H), 1.60-1.97 (m, 4H), 2.01-2.13 (m, 1H), 2.22 (s, 3H), 2.61 (t, J=5.9 Hz, 2H), 3.57-3.67 (m, 2H), 3.82 (s, 3H), 4.37 (d, J=8.0 Hz, 1H), 6.55 (d, J=8.7 Hz, 2H), 6.61 (t, J=6.1 Hz, 1H), 6.81 (dd, J=9.1, 2.7 Hz, 1H), 6.87 (d, J=2.3 Hz, 1H), 7.21-7.28 (m, 1H), 7.52 (d, J=8.7 Hz, 2H).

Example A31

3-{[(4-{[1-(3-ethyl-1-benzofuran-2-yl)-3-methylbutyl]amino}phenyl)carbonyl](methyl)amino}propanoic acid

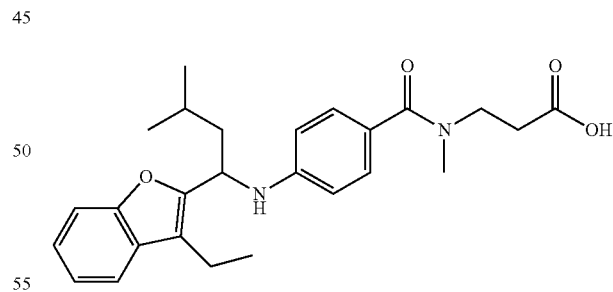

(1) methyl 3-ethyl-1-benzofuran-2-carboxylate

To a mixture of 1-(2-hydroxyphenyl)propan-1-one (10.0 g), methyl bromoacetate (5.11 mL) and acetone (100 mL) was added potassium carbonate (18.4 g), and the mixture was stirred overnight at room temperature. The insoluble material was filtered off, and the filtrate was concentrated under reduced pressure. The residue was purified by silica gel column chromatography (ethyl acetate:hexane=1:4, volume ratio) to give a colorless oil. To a solution (150 mL) of the obtained oil in N,N-dimethylformamide was added 1,8-diazabicyclo[5.4.0]undec-7-ene (8.12 mL), and the mixture was stirred at 120° C. for 2 hr. 1N Hydrochloric acid was added to quench the reaction, and the mixture was extracted with ethyl acetate. The extract was washed with saturated brine, dried over magnesium sulfate, and concentrated under reduced pressure. Ethyl acetate was added to the residue, the insoluble material was filtered off, and the filtrate was concentrated under reduced pressure. The residue was purified by silica gel column chromatography (ethyl acetate:hexane=1:9, volume ratio) to give the title object compound (7.14 g, 52%) as a white solid.

$^1$H NMR (300 MHz, CDCl$_3$) δ ppm 1.31 (t, J=7.5 Hz, 4H), 3.12 (q, J=7.5 Hz, 2H), 3.99 (s, 3H), 7.27-7.34 (m, 1H), 7.41-7.49 (m, 1H), 7.53-7.58 (m, 1H), 7.65-7.70 (m, 1H).

(2) 3-ethyl-1-benzofuran-2-carbaldehyde

Using methyl 3-ethyl-1-benzofuran-2-carboxylate (3.00 g) synthesized above and in the same manner as in Example A27(2), the title object compound (2.27 g, 90%) was obtained as a brown oil.

$^1$H NMR (300 MHz, CDCl$_3$) δ ppm 1.40 (t, J=7.6 Hz, 3H), 3.12 (q, J=7.6 Hz, 2H), 7.30-7.37 (m, 1H), 7.48-7.60 (m, 2H), 7.71-7.76 (m, 1H), 10.04 (s, 1H).

(3) 1-(3-ethyl-1-benzofuran-2-yl)-3-methylbutan-1-ol

To a solution (50 mL) of 3-ethyl-1-benzofuran-2-carbaldehyde (2.27 g) synthesized above in tetrahydrofuran was added dropwise 1.0M isobutylmagnesium bromide tetrahydrofuran solution (19.5 mL) at 0° C., and the mixture was stirred for 1 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=3:17, volume ratio) to give the title object compound (1.55 g, 51%) as a yellow oil.

$^1$H NMR (300 MHz, CDCl$_3$) δ ppm 0.94 (d, J=6.6 Hz, 3H), 0.96 (d, J=6.6 Hz, 3H), 1.28 (t, J=7.5 Hz, 3H), 1.56-1.73 (m, 1H), 1.74-1.86 (m, 2H), 1.88-1.99 (m, 1H), 2.74 (q, J=7.5 Hz, 2H), 4.91-4.99 (m, 1H), 7.18-7.31 (m, 2H), 7.41-7.47 (m, 1H), 7.50-7.56 (m, 1H).

(4) 2-(1-chloro-3-methylbutyl)-3-ethyl-1-benzofuran

Using 1-(3-ethyl-1-benzofuran-2-yl)-3-methylbutan-1-ol (1.00 g) synthesized above and in the same manner as in Example A1(2), the title object compound (1.03 g, 96%) was obtained as a yellow oil.

$^1$H NMR (300 MHz, CDCl$_3$) δ ppm 0.92-0.97 (m, 6H), 1.29 (t, J=7.5 Hz, 3H), 1.60-1.75 (m, 1H), 2.14-2.21 (m, 2H), 2.73 (q, J=7.5 Hz, 2H), 5.22 (t, J=8.0 Hz, 1H), 7.19-7.33 (m, 2H), 7.41-7.48 (m, 1H), 7.51-7.55 (m, 1H).

(5) 3-{[(4-{[1-(3-ethyl-1-benzofuran-2-yl)-3-methylbutyl]amino}phenyl)carbonyl](methyl)amino}propanoic acid Using 2-(1-chloro-3-methylbutyl)-3-ethyl-1-benzofuran (300 mg) synthesized above and ethyl 3-{[(4-aminophenyl)carbonyl](methyl)amino}propanoate (300 mg) synthesized in Example 2(2) and in the same manner as in Example A22(4), the title object compound (97.4 mg, 19%) was obtained as a yellow solid.

$^1$H NMR (300 MHz, CDCl$_3$) δ ppm 0.92 (d, J=6.6 Hz, 3H), 1.00 (d, J=6.4 Hz, 3H), 1.27 (t, J=7.6 Hz, 3H), 1.51-1.69 (m, 1H), 1.82-1.89 (m, 2H), 2.60-2.70 (m, 2H), 2.77 (q, J=7.6 Hz, 2H), 3.02 (s, 3H), 3.69 (t, J=6.4 Hz, 2H), 4.72 (t, J=7.5 Hz, 1H), 6.58 (d, J=8.7 Hz, 2H), 7.15-7.28 (m, 4H), 7.36-7.42 (m, 1H), 7.47-7.52 (m, 1H).

Example A32

3-{methyl[(4-{[3-methyl-1-(3-methyl-1-benzothiophen-2-yl)butyl]amino}phenyl)carbonyl]amino}propanoic acid

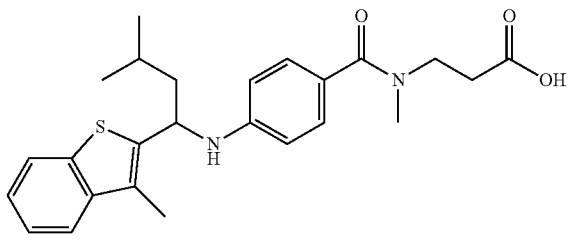 [SMILES: Cc1c(C(CC(C)C)Nc2ccc(C(=O)N(C)CCC(=O)O)cc2)sc2ccccc12]

(1) 3-methyl-1-(3-methyl-1-benzothiophen-2-yl)butan-1-one

To a mixture of 3-methyl-1-benzothiophene (5.00 g), isovaleryl chloride (4.52 mL) and nitromethane (50 mL) was added aluminum (III) chloride (8.98 g) at 0° C., and the mixture was stirred at 0° C. for 30 min then at room temperature for 4 hr. The reaction mixture was poured into ice-cooled water, and the mixture was extracted with ethyl acetate. The extract was washed with 1N hydrochloric acid and saturated brine, dried over magnesium sulfate, and concentrated under reduced pressure. The residue was purified by silica gel column chromatography (ethyl acetate:hexane=1:19, volume ratio) to give the title object compound (7.72 g, 99%) as a yellow oil.

$^1$H NMR (300 MHz, CDCl$_3$) δ ppm 1.03 (d, J=6.8 Hz, 6H), 2.28-2.43 (m, 1H), 2.77 (s, 3H), 2.80 (d, J=7.0 Hz, 2H), 7.39-7.53 (m, 2H), 7.81-7.90 (m, 2H).

(2) methyl 4-{[3-methyl-1-(3-methyl-1-benzothiophen-2-yl)butyl]amino}benzoate

Using 3-methyl-1-(3-methyl-1-benzothiophen-2-yl)butan-1-one (1.00 g) synthesized above and in the same manner as in Example A23(3), the title object compound (923 mg, 58%) was obtained as a pale-brown solid.

$^1$H NMR (300 MHz, CDCl$_3$) δ ppm 0.98 (d, J=6.0 Hz, 3H), 1.02 (d, J=6.0 Hz, 3H), 1.68-1.81 (m, 2H), 1.81-1.95 (m, 1H), 2.47 (s, 3H), 3.80 (s, 3H), 4.40-4.47 (m, 1H), 4.86-4.95 (m, 1H), 6.54 (d, J=8.1 Hz, 2H), 7.23-7.30 (m, 1H), 7.32-7.39 (m, 1H), 7.62-7.67 (m, 2H), 7.69-7.74 (m, 1H), 7.79 (d, J=8.1 Hz, 2H).

(3) 4-{[3-methyl-1-(3-methyl-1-benzothiophen-2-yl)butyl]amino}benzoic acid

Using methyl 4-{[3-methyl-1-(3-methyl-1-benzothiophen-2-yl)butyl]amino}benzoate (923 mg) synthesized above and in the same manner as in Example A23(4), the title object compound (817 mg, 92%) was obtained as a pale-brown solid.

$^1$H NMR (300 MHz, CDCl$_3$) δ ppm 0.98 (d, J=6.2 Hz, 3H), 1.02 (d, J=6.2 Hz, 3H), 1.67-1.96 (m, 3H), 2.47 (s, 3H), 4.88-4.96 (m, 1H), 6.55 (d, J=8.9 Hz, 2H), 7.23-7.30 (m, 1H), 7.32-7.39 (m, 1H), 7.62-7.68 (m, 1H), 7.69-7.74 (m, 1H), 7.84 (d, J=8.9 Hz, 2H).

(4) 3-{methyl[(4-{[3-methyl-1-(3-methyl-1-benzothiophen-2-yl)butyl]amino}phenyl)carbonyl]amino}propanoic acid Using 4-{[3-methyl-1-(3-methyl-1-benzothiophen-2-yl)butyl]amino}benzoic acid (300 mg) synthesized above and ethyl 3-(methylamino)propanoate (134 mg) and in the same manner as in Example A1(4), the title object compound (218 mg, 59%) was obtained as a white solid.

$^1$H NMR (300 MHz, CDCl$_3$) δ ppm 0.98 (d, J=6.2 Hz, 3H), 1.02 (d, J=6.2 Hz, 3H), 1.66-1.94 (m, 3H), 2.46 (s, 3H), 2.62-2.72 (m, 2H), 3.02 (s, 3H), 3.70 (t, J=6.4 Hz, 2H), 4.82-4.89 (m, 1H), 6.54 (d, J=8.7 Hz, 2H), 7.20-7.31 (m, 3H), 7.32-7.39 (m, 1H), 7.65 (d, J=7.9 Hz, 1H), 7.72 (d, J=7.3 Hz, 1H).

Example A33

3-{[(4-{[3-methyl-1-(3-methyl-1-benzothiophen-2-yl)butyl]amino}phenyl)carbonyl]amino}propanoic acid

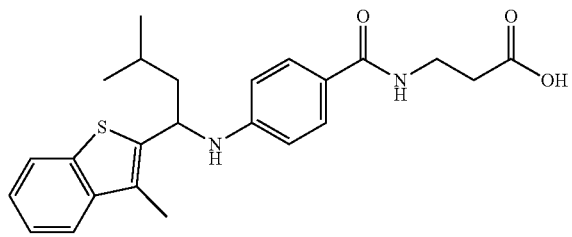 [SMILES: Cc1c(C(CC(C)C)Nc2ccc(C(=O)NCCC(=O)O)cc2)sc2ccccc12]

Using 4-{[3-methyl-1-(3-methyl-1-benzothiophen-2-yl)butyl]amino}benzoic acid (300 mg) synthesized in Example A32(3) and in the same manner as in Example A1(4), the title object compound (316 mg, 88%) was obtained as a white solid.

$^1$H NMR (300 MHz, CDCl$_3$) δ ppm 0.97 (d, J=6.0 Hz, 3H), 1.01 (d, J=6.2 Hz, 3H), 1.66-1.94 (m, 3H), 2.46 (s, 3H), 2.61 (t, J=5.7 Hz, 2H), 3.57-3.67 (m, 2H), 4.83-4.91 (m, 1H), 6.50-6.62 (m, 3H), 7.22-7.29 (m, 1H), 7.31-7.38 (m, 1H), 7.51 (d, J=8.7 Hz, 2H), 7.64 (d, J=7.5 Hz, 1H), 7.70 (d, J=7.9 Hz, 1H).

Example A34

3-{[(4-{[1-(3-ethyl-1-benzofuran-2-yl)-3-methylbutyl]amino}phenyl)carbonyl]amino}propanoic acid

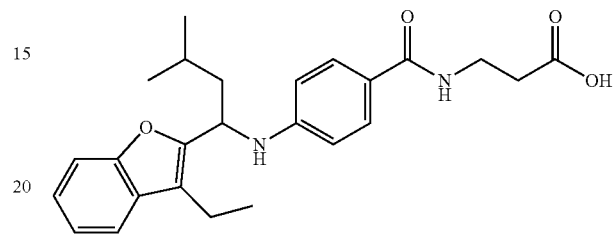

Using 2-(1-chloro-3-methylbutyl)-3-ethyl-1-benzofuran (300 mg) synthesized in Example A31(4) and ethyl 3-{[(4-aminophenyl)carbonyl]amino}propanoate (283 mg) synthesized in Example 1(2) and in the same manner as in Example A22(4), the title object compound (162 mg, 32%) was obtained as a pale-brown solid.

$^1$H NMR (300 MHz, CDCl$_3$) δ ppm 0.91 (d, J=6.6 Hz, 3H), 1.00 (d, J=6.6 Hz, 3H), 1.27 (t, J=7.5 Hz, 3H), 1.51-1.68 (m, 1H), 1.81-1.90 (m, 2H), 2.58-2.68 (m, 2H), 2.76 (q, J=7.5 Hz, 2H), 3.58-3.68 (m, 2H), 4.73 (t, J=7.5 Hz, 1H), 6.54-6.63 (m, 3H), 7.14-7.26 (m, 2H), 7.35-7.40 (m, 1H), 7.46-7.51 (m, 1H), 7.54 (d, J=8.7 Hz, 2H).

Example A35

3-{[(4-{[cyclohexyl(6-methoxy-1-benzofuran-2-yl)methyl]amino}phenyl)carbonyl]amino}propanoic acid

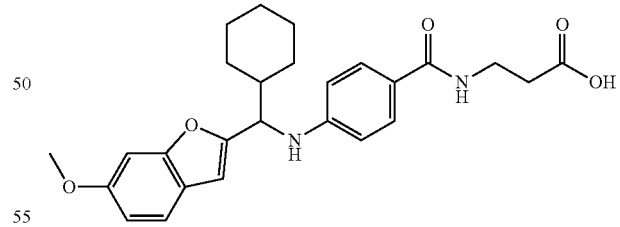

Using 4-{[cyclohexyl(6-methoxy-1-benzofuran-2-yl)methyl]amino}benzoic acid (102 mg) synthesized in Example A28(4) and in the same manner as in Example A1(4), the title object compound (40.0 mg, 33%) was obtained as a pale-red solid.

$^1$H NMR (300 MHz, CDCl$_3$) δ ppm 1.00-1.35 (m, 5H), 1.54-1.84 (m, 4H), 1.84-1.99 (m, 2H), 2.55-2.68 (m, 2H), 3.56-3.69 (m, 2H), 3.82 (s, 3H), 4.36 (d, J=6.4 Hz, 1H), 6.42

(s, 1H), 6.51-6.66 (m, 3H), 6.81 (dd, J=8.5, 2.1 Hz, 1H), 6.97 (d, J=2.1 Hz, 1H), 7.31 (d, J=8.5 Hz, 1H), 7.53 (d, J=8.3 Hz, 2H).

Example A36

3-{[(6-{[3-methyl-1-(3-methyl-1-benzothiophen-2-yl)butyl]amino}pyridin-3-yl)carbonyl]amino}propanoic acid

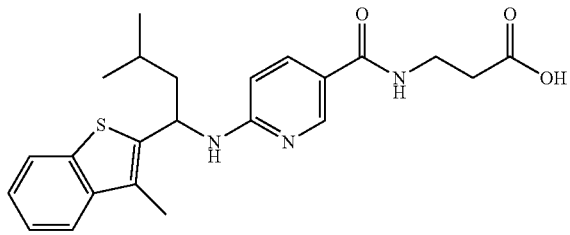 [SMILES: Cc1c(C(CC(C)C)Nc2ccc(C(=O)NCCC(=O)O)cn2)sc2ccccc12]

(1) methyl 6-{[3-methyl-1-(3-methyl-1-benzothiophen-2-yl)butyl]amino}pyridine-3-carboxylate To a mixture of 3-methyl-1-(3-methyl-1-benzothiophen-2-yl)butan-1-one (1.00 g) synthesized in Example A32(1), methyl 6-aminopyridine-3-carboxylate (654 mg), triethylamine (4.79 mL) and dichloromethane (20 mL) was added titanium (IV) chloride (566 μL) at 0° C., and the mixture was stirred overnight at room temperature. Saturated aqueous sodium hydrogen carbonate solution was added to quench the reaction, and the mixture was extracted with ethyl acetate. The extract was washed with saturated brine, dried over magnesium sulfate, and concentrated under reduced pressure to give a dark brown solid. To a mixture of the obtained solid, acetic acid (2 mL) and tetrahydrofuran (20 mL) was added sodium cyanoborohydride (540 mg), and the mixture was stirred at room temperature for 2 hr. Saturated aqueous sodium hydrogen carbonate solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give a pale-brown solid. To a mixture of the obtained solid, trifluoroacetic acid (1.00 mL) and ethanol (10 mL) was added sodium cyanoborohydride (251 mg), and the mixture was stirred at room temperature for 1 hr. In addition, sodium cyanoborohydride (251 mg) was added, and the mixture was stirred at room temperature for 30 min then at 50° C. for 1 hr. Saturated aqueous sodium hydrogen carbonate solution was added to quench the reaction, and the mixture was extracted with ethyl acetate. The extract was washed with saturated brine, dried over magnesium sulfate, and concentrated under reduced pressure to give the title object compound (743 mg, 47%) as a pale-yellow solid.

$^1$H NMR (300 MHz, CDCl$_3$) δ ppm 0.98 (d, J=6.3 Hz, 3H), 1.01 (d, J=6.3 Hz, 3H), 1.64-1.96 (m, 3H), 2.48 (s, 3H), 3.83 (s, 3H), 5.25-5.40 (m, 2H), 6.28 (d, J=8.7 Hz, 1H), 7.24-7.39 (m, 2H), 7.61-7.66 (m, 1H), 7.71-7.76 (m, 1H), 7.91 (dd, J=8.7, 2.0 Hz, 1H), 8.73 (d, J=2.0 Hz, 1H).

(2) 6-{[3-methyl-1-(3-methyl-1-benzothiophen-2-yl)butyl]amino}pyridine-3-carboxylic acid Using methyl 6-{[3-methyl-1-(3-methyl-1-benzothiophen-2-yl)butyl]amino}pyridine-3-carboxylate (743 mg) synthesized above and in the same manner as in Example A23(4), the title object compound (236 mg, 33%) was obtained as a white solid.

$^1$H NMR (300 MHz, CDCl$_3$) δ ppm 0.90-0.99 (m, 6H), 1.58-1.78 (m, 2H), 1.81-1.95 (m, 1H), 2.44 (s, 3H), 5.51-5.64 (m, 1H), 6.53 (d, J=8.7 Hz, 1H), 7.24-7.38 (m, 2H), 7.67 (d, J=8.1 Hz, 1H), 7.73-7.92 (m, 3H), 8.50 (d, J=2.4 Hz, 1H), 12.29 (br s, 1H).

(3) 3-{[(6-{[3-methyl-1-(3-methyl-1-benzothiophen-2-yl)butyl]amino}pyridin-3-yl)carbonyl]amino}propanoic acid Using 6-{[3-methyl-1-(3-methyl-1-benzothiophen-2-yl)butyl]amino}pyridine-3-carboxylic acid (115 mg) synthesized above and in the same manner as in Example A1(4), the title object compound (112 mg, 81%) was obtained as a white solid.

$^1$H NMR (300 MHz, CDCl$_3$) δ ppm 0.98 (d, J=6.0 Hz, 3H), 1.03 (d, J=6.2 Hz, 3H), 1.71-1.85 (m, 2H), 1.95-2.11 (m, 1H), 2.49 (s, 3H), 2.57-2.67 (m, 2H), 3.67-3.79 (m, 2H), 4.86-4.98 (m, 1H), 6.48 (d, J=9.2 Hz, 1H), 7.24-7.33 (m, 1H), 7.33-7.41 (m, 1H), 7.61-7.75 (m, 3H), 8.10-8.20 (m, 2H), 8.87-8.97 (m, 1H).

Example A37

3-{[(4-{[cyclohexyl(5-fluoro-3-methyl-1-benzofuran-2-yl)methyl]amino}phenyl)carbonyl](methyl)amino}propanoic acid

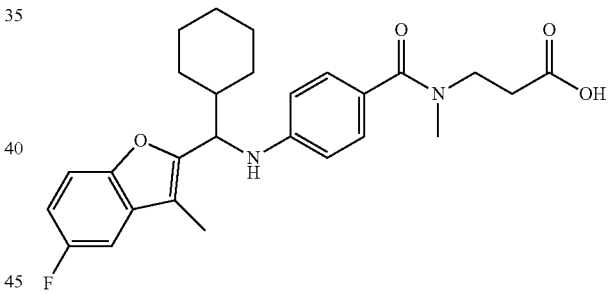

(1) 5-fluoro-N-methoxy-N,3-dimethyl-1-benzofuran-2-carboxamide

To a mixture of 1-(5-fluoro-2-hydroxyphenyl)ethanone (10.0 g), 2-chloro-N-methoxy-N-methylacetamide (9.82 g), sodium iodide (19.5 g) and N,N-dimethylformamide (200 mL) was added potassium carbonate (18.0 g), and the mixture was stirred at 80° C. overnight. 1N Hydrochloric acid was added to quench the reaction, and the mixture was extracted with ethyl acetate. The extract was washed with saturated brine, dried over magnesium sulfate, and concentrated under reduced pressure to give a brown solid. To a solution (200 mL) of the obtained solid in N,N-dimethylformamide was added 1,8-diazabicyclo[5.4.0]undec-7-ene (9.71 mL), and the mixture was stirred at 120° C. for 4 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:3, volume ratio) to give the title object compound (4.37 g, 28%) as a brown oil.

¹H NMR (300 MHz, CDCl₃) δ ppm 2.47 (s, 3H), 3.38 (s, 3H), 3.86 (s, 3H), 6.98-7.16 (m, 1H), 7.21-7.27 (m, 1H), 7.37-7.43 (m, 1H).

(2) cyclohexyl(5-fluoro-3-methyl-1-benzofuran-2-yl)methanol

To a solution (80 mL) of 5-fluoro-N-methoxy-N,3-dimethyl-1-benzofuran-2-carboxamide (4.37 g) synthesized above in tetrahydrofuran was added dropwise 1.5M diisobutylaluminum hydride toluene solution (24.5 mL) at 0° C., and the mixture was stirred for 1 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=1:9, volume ratio) to give a pale-brown solid. To a solution (50 mL) of the obtained solid in tetrahydrofuran was added dropwise 1.0M cyclohexylmagnesium bromide tetrahydrofuran solution (21.8 mL) at 0° C., and the mixture was stirred for 1 hr. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (ethyl acetate:hexane=3:17, volume ratio) to give the title object compound (1.32 g, 27%) as a pale-yellow oil.

¹H NMR (300 MHz, CDCl₃) δ ppm 0.85-1.43 (m, 6H), 1.61-1.71 (m, 2H), 1.75-1.98 (m, 3H), 2.09-2.21 (m, 4H), 4.51 (dd, J=8.4, 6.0 Hz, 1H), 6.92-7.00 (m, 1H), 7.08-7.13 (m, 1H), 7.30-7.36 (m, 1H).

(3) 2-[chloro(cyclohexyl)methyl]-5-fluoro-3-methyl-1-benzofuran

Using cyclohexyl(5-fluoro-3-methyl-1-benzofuran-2-yl)methanol (1.01 g) synthesized above and in the same manner as in Example A11(3), the title object compound (900 mg, 83%) was obtained as a pale-yellow oil.

¹H NMR (300 MHz, CDCl₃) δ ppm 0.83-1.40 (m, 5H), 1.40-1.50 (m, 1H), 1.60-1.72 (m, 2H), 1.77-1.88 (m, 1H), 2.10-2.25 (m, 4H), 2.28-2.38 (m, 1H), 4.79 (d, J=9.6 Hz, 1H), 6.96-7.04 (m, 1H), 7.09-7.14 (m, 1H), 7.34-7.39 (m, 1H).

(4) 3-{[(4-{[cyclohexyl(5-fluoro-3-methyl-1-benzofuran-2-yl)methyl]amino}phenyl)carbonyl](methyl)amino}propanoic acid Using 2-[chloro(cyclohexyl)methyl]-5-fluoro-3-methyl-1-benzofuran (400 mg) synthesized above and ethyl 3-{[(4-aminophenyl)carbonyl](methyl)amino}propanoate (355 mg) synthesized in Example 2(2) and in the same manner as in Example A22(4), the title object compound (303 mg, 46%) was obtained as a pale-yellow solid.

¹H NMR (300 MHz, CDCl₃) δ ppm 0.92-1.37 (m, 5H), 1.45-1.56 (m, 1H), 1.60-1.97 (m, 4H), 2.03-2.14 (m, 1H), 2.22 (s, 3H), 2.64 (t, J=6.5 Hz, 2H), 3.02 (s, 3H), 3.69 (t, J=6.5 Hz, 2H), 4.36 (d, J=7.9 Hz, 1H), 6.55 (d, J=8.7 Hz, 2H), 6.88-6.97 (m, 1H), 7.07 (dd, J=8.5, 2.6 Hz, 1H), 7.23 (d, J=8.7 Hz, 2H), 7.25-7.31 (m, 1H).

Example A38

3-{methyl[(6-{[3-methyl-1-(3-methyl-1-benzothiophen-2-yl)butyl]amino}pyridin-3-yl)carbonyl]amino}propanoic acid

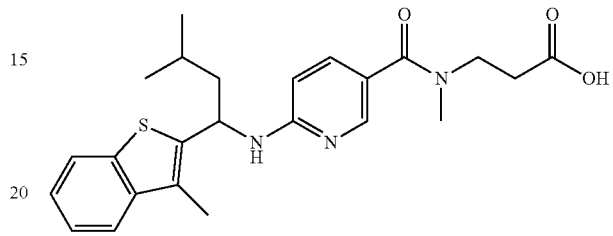

Using 6-{[3-methyl-1-(3-methyl-1-benzothiophen-2-yl)butyl]amino}pyridine-3-carboxylic acid (121 mg) synthesized in Example A36(2) and ethyl 3-(methylamino)propanoate (67.2 mg) and in the same manner as in Example A1(4), the title object compound (115 mg, 77%) was obtained as a white solid.

¹H NMR (300 MHz, CDCl₃) δ ppm 0.97 (d, J=6.2 Hz, 3H), 1.01 (d, J=6.4 Hz, 3H), 1.67-1.86 (m, 2H), 1.93-2.08 (m, 1H), 2.47 (s, 3H), 2.62-2.71 (m, 2H), 3.08 (s, 3H), 3.67-3.84 (m, 2H), 4.84-4.95 (m, 1H), 6.35 (d, J=8.9 Hz, 1H), 7.24-7.31 (m, 1H), 7.32-7.39 (m, 1H), 7.51-7.59 (m, 1H), 7.64 (d, J=7.7 Hz, 1H), 7.73 (d, J=7.7 Hz, 1H), 8.05-8.17 (m, 1H).

Example A39

3-{[(4-{[cyclohexyl(5-fluoro-3-methyl-1-benzofuran-2-yl)methyl]amino}phenyl)carbonyl]amino}propanoic acid

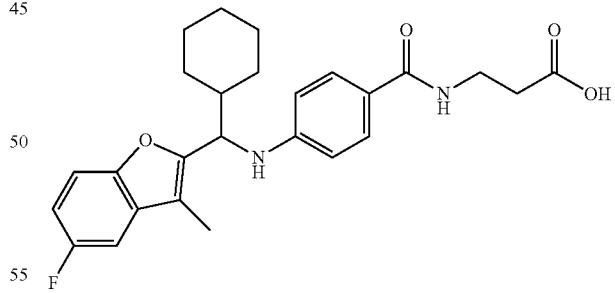

Using 2-[chloro(cyclohexyl)methyl]-5-fluoro-3-methyl-1-benzofuran (400 mg) synthesized in Example A37(3) and ethyl 3-{[(4-aminophenyl)carbonyl]amino}propanoate (336 mg) synthesized in Example 1(2) and in the same manner as in Example A22(4), the title object compound (321 mg, 50%) was obtained as a pale-brown solid.

¹H NMR (300 MHz, CDCl₃) δ ppm 0.91-1.36 (m, 5H), 1.43-1.56 (m, 1H), 1.59-1.95 (m, 4H), 2.00-2.12 (m, 1H), 2.20 (s, 3H), 2.59 (t, J=5.7 Hz, 2H), 3.55-3.67 (m, 2H), 4.37 (d, J=8.1 Hz, 1H), 6.54 (d, J=8.8 Hz, 2H), 6.71 (t, J=6.0 Hz, 1H), 6.87-6.95 (m, 1H), 7.05 (dd, J=8.5, 2.4 Hz, 1H), 7.21-7.30 (m, 1H), 7.52 (d, J=8.8 Hz, 2H).

Example A40

3-[{[4-({cyclohexyl[6-(trifluoromethyl)imidazo[1,2-a]pyridin-2-yl]methyl}amino) phenyl]carbonyl}(methyl)amino]propanoic acid

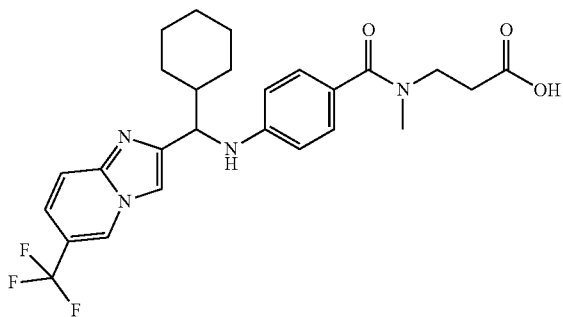 [SMILES: CN(CCC(=O)O)C(=O)c1ccc(NC(c2cn3cc(C(F)(F)F)ccc3n2)C2CCCCC2)cc1]

(1) 6-(trifluoromethyl)imidazo[1,2-a]pyridine-2-carbaldehyde

To a solution of 5-(Trifluoromethyl)pyridin-2-amine (12.9 g) was dissolved in dimethoxyethane (150 mL) was added 1,1,3-trichloroacetone (12.7 mL) at room temperature, and the mixture was stirred overnight. The precipitated solid was collected, and suspended in ethanol (50 mL), and the mixture was heated under reflux for 3 hr. After allowing to cool to room temperature, the solvent was evaporated under reduced pressure, saturated aqueous sodium hydrogen carbonate was added to the residue, and the mixture was extracted with ethyl acetate-tetrahydrofuran (1:1, volume ratio). The extract was washed with saturated brine, dried over magnesium sulfate, and concentrated under reduced pressure. The residue was purified by silica gel column chromatography (ethyl acetate:hexane=1:2, volume ratio) to give 2-(dichloromethyl)-6-(trifluoromethyl)imidazo[1,2-a]pyridine (10.3 g) as a white solid. The obtained solid was suspended in a mixed solvent of water (100 mL) and tetrahydrofuran (20 mL), and calcium carbonate (8.0 g) was added to the mixture at room temperature, and the mixture was stirred at 100° C. for 1 hr. The mixture was allowed to cool to room temperature, the insoluble material was filtered off, and the filtrate was extracted with ethyl acetate. The extract was dried over magnesium sulfate, and concentrated under reduced pressure to give a white solid. The residue was washed with diisopropyl ether to give the title object compound (7.3 g, 43%) as white crystals.

$^1$H NMR (300 MHz, CDCl$_3$) δ ppm 7.43 (d, J=9.8 Hz, 1H), 7.82 (d, J=9.8 Hz, 1H), 8.26 (s, 1H), 8.58 (s, 1H), 10.19 (s, 1H).

(2) cyclohexyl[6-(trifluoromethyl)imidazo[1,2-a]pyridin-2-yl]methanol

To a solution of 6-(trifluoromethyl)imidazo[1,2-a]pyridine-2-carbaldehyde (2.1 g) synthesized above in tetrahydrofuran (40 mL) was added dropwise cyclohexylmagnesium bromide (1M tetrahydrofuran solution, 15 mL) at 0° C. After stirring at 0° C. for 1 hr, aqueous ammonium chloride solution was added. The mixture was extracted with ethyl acetate, and the solvent was evaporated under reduced pressure. The precipitate was washed with ethanol-diisopropyl ether to give the title object compound (0.9 g, 30%) as a colorless solid.

$^1$H NMR (300 MHz, CDCl$_3$) δ ppm 1.01-1.96 (m, 11H), 2.43 (d, J=6.1 Hz, 1H), 4.66 (t, J=5.9 Hz, 1H), 7.31 (d, J=9.8 Hz, 1H), 7.59 (s, 1H), 7.66 (d, J=9.8 Hz, 1H), 8.46 (s, 1H).

(3) 3-[{[4-({cyclohexyl[6-(trifluoromethyl)imidazo[1,2-a]pyridin-2-yl]methyl}amino)phenyl]carbonyl}(methyl)amino]propanoic acid Using cyclohexyl[6-(trifluoromethyl)imidazo[1,2-a]pyridin-2-yl]methanol (1.1 g) synthesized above and ethyl 3-{[(4-aminophenyl)carbonyl](methyl)amino}propanoate (0.94 g) synthesized in Example 2(2) and in the same manner as in Example 4, the title object compound (3.0 mg, 2%) was obtained as an oil.

$^1$H NMR (300 MHz, CDCl$_3$) δ ppm 0.98-2.16 (m, 11H), 2.50-2.75 (m, 2H), 3.06 (s, 3H), 3.10-3.25 (br s, 1H), 3.61-3.82 (m, 2H), 4.43 (d, J=6.0 Hz, 1H), 6.54 (d, J=9.0 Hz, 2H), 7.16 (d, J=9.0 Hz, 2H), 7.45 (d, J=9.0 Hz, 1H), 7.63 (s, 1H), 7.84 (d, J=9.0 Hz, 1H), 8.53 (s, 1H).

Example A41

3-{[(4-{[cyclohexyl(3-methyl-1-benzofuran-2-yl)methyl]amino}phenyl)carbonyl](methyl)amino}propanoic acid

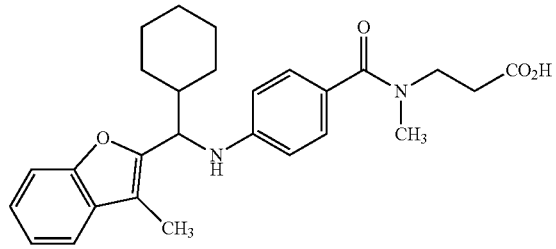 [SMILES: Cc1c(C(Nc2ccc(C(=O)N(C)CCC(=O)O)cc2)C2CCCCC2)oc2ccccc12]

Ethyl 3-{[(4-{[cyclohexyl(3-methyl-1-benzofuran-2-yl)methyl]amino}phenyl)carbonyl](methyl)amino}propanoate (9.85 g) synthesized in Example A16 was fractionated by high performance liquid chromatography (column: CHIRALPAK AD (50 mm ID×500 mL, manufactured by Daicel Chemical Industries, Ltd., mobile phase:hexane/ethanol (500/500), flow rate: 60 mL/min, column temperature: room temperature). The fraction containing an optically active form having a shorter retention time under the abovementioned high performance liquid chromatography conditions was concentrated to give an amorphous form (4.85 g, 99.9% ee). To a mixture of the obtained amorphous form, ethanol (20 mL) and tetrahydrofuran (20 mL) was added 1N lithium hydroxide (22 mL), and the mixture was stirred at room temperature for 1 hr and concentrated under reduced pressure. The residue was dissolved in water (20 mL), and 1N hydrochloric acid (20 mL) was added at 0° C. The resulting precipitate was collected by filtration to give the title object compound (4.41 g, 97%, 99.9% ee) as a white solid. The obtained white solid (50 mg) was crystallized from ethanol/water to give ethanol-containing crystals (41 mg). The ethanol-containing crystals (35 mg) were recrystallized from diethyl ether to give colorless crystal (18 mg) free of solvent.

$^1$H NMR (300 MHz, DMSO-d$_6$) δ ppm 0.97-1.28 (m, 5H) 1.30-1.39 (m, 1H) 1.52-1.81 (m, 3H) 1.81-2.00 (m, 1H) 2.03-

2.18 (m, 1H) 2.26 (s, 3H) 2.40-2.49 (m, 2H) 2.88 (s, 3H) 3.50 (t, J=7.38 Hz, 2H) 4.41 (t, J=8.33 Hz, 1H) 6.48 (d, J=7.95 Hz, 1H) 6.60 (d, J=8.71 Hz, 2H) 7.09 (d, J=8.33 Hz, 2H) 7.14-7.29 (m, 2H) 7.36-7.55 (m, 2H) 12.27 (brs, 1H).

Example A42

3-{[(4-{[cyclohexyl(3-methyl-1-benzofuran-2-yl)methyl]amino}phenyl)carbonyl]methyl)amino}propanoic acid

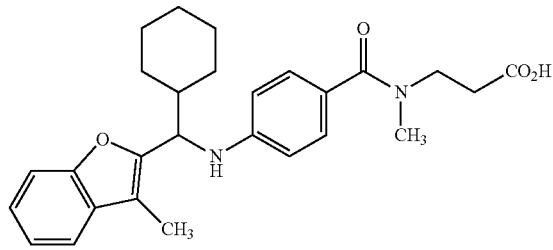 [SMILES: Cc1c(C(Nc2ccc(C(=O)N(C)CCC(=O)O)cc2)C2CCCCC2)oc2ccccc12]

Ethyl 3-{[(4-{[cyclohexyl(3-methyl-1-benzofuran-2-yl)methyl]amino}phenyl)carbonyl](methyl)amino}propanoate (9.85 g) synthesized in Example A16 was fractionated by high performance liquid chromatography (column: CHIRALPAK AD (50 mm ID×500 mL, manufactured by Daicel Chemical Industries, Ltd., mobile phase: hexane/ethanol (500/500), flow rate: 60 mL/min, column temperature: room temperature). The fraction containing an optically active form having a longer retention time under the above-mentioned high performance liquid chromatography conditions was concentrated to give an amorphous form (4.81 g, 99.9% ee). To a mixture of the obtained amorphous form, ethanol (20 mL) and tetrahydrofuran (20 mL) was added 1N lithium hydroxide aqueous solution (22 mL), and the mixture was stirred at room temperature for 1 hr and concentrated under reduced pressure. The residue was dissolved in water (20 mL), and 1N hydrochloric acid (20 mL) was added at 0° C. The resulting precipitate was collected by filtration to give the title object compound (4.43 g, 98%, 99.9% ee) as a white solid.

$^1$H NMR (300 MHz, DMSO-$d_6$) δ ppm 0.97-1.28 (m, 5H) 1.30-1.39 (m, 1H) 1.52-1.81 (m, 3H) 1.81-2.00 (m, 1H) 2.03-2.18 (m, 1H) 2.26 (s, 3H) 2.40-2.49 (m, 2H) 2.88 (s, 3H) 3.50 (t, J=7.38 Hz, 2H) 4.41 (t, J=8.33 Hz, 1H) 6.48 (d, J=7.95 Hz, 1H) 6.60 (d, J=8.71 Hz, 2H) 7.09 (d, J=8.33 Hz, 2H) 7.14-7.29 (m, 2H) 7.36-7.55 (m, 2H) 12.27 (brs, 1H).

Example A43

3-{[(4-{[cyclohexyl(5-methoxy-3-methyl-1-benzofuran-2-yl)methyl]amino}phenyl)carbonyl](methyl)amino}propanoic acid

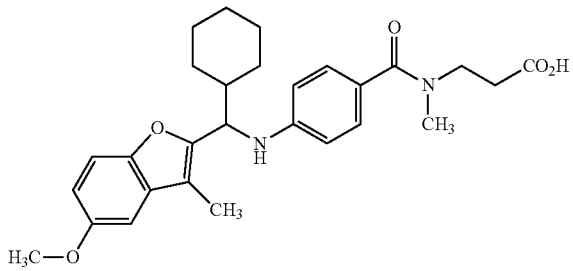

(1) 4-{[cyclohexyl(5-methoxy-3-methyl-1-benzofuran-2-yl)methyl]amino}benzoic acid To a mixture of 2-[chloro(cyclohexyl)methyl]-5-methoxy-3-methyl-1-benzofuran (748 mg) synthesized in Example A27(4), methyl 4-aminobenzoate (385 mg), sodium iodide (764 mg) and N,N-dimethylformamide (15 mL) was added sodium carbonate (541 mg), and the mixture was stirred at 80° C. overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (25% ethyl acetate/hexane) to give a yellow oil. To a mixture of the obtained oil, tetrahydrofuran (20 mL) and ethanol (20 mL) was added 1N aqueous sodium hydroxide solution (20 mL), and the mixture was stirred with heating under reflux for 5 hr, and concentrated under reduced pressure. The residue was dissolved in water (40 mL), and 1N hydrochloric acid (20 mL) was added at 0° C. The resulting precipitate was collected by filtration to give the title object compound (745 mg, 74%) as a pale-brown solid.

$^1$H NMR (300 MHz, CDCl$_3$) δ ppm 0.92-1.37 (m, 5H), 1.47-1.58 (m, 1H), 1.61-1.98 (m, 4H), 2.02-2.12 (m, 1H), 2.24 (s, 3H), 3.83 (s, 3H), 4.42 (d, J=7.9 Hz, 1H), 6.57 (d, J=8.9 Hz, 2H), 6.83 (dd, J=8.8, 2.5 Hz, 1H), 6.88 (d, J=2.5 Hz, 1H), 7.26 (d, J=8.8 Hz, 1H), 7.85 (d, J=8.9 Hz, 2H).

(2) ethyl 3-{[(4-{[cyclohexyl(5-methoxy-3-methyl-1-benzofuran-2-yl)methyl]amino}phenyl)carbonyl](methyl)amino}propanoate To a mixture of 4-{[cyclohexyl(5-methoxy-3-methyl-1-benzofuran-2-yl)methyl]amino}benzoic acid (745 mg) synthesized above, ethyl 3-(methylamino)propanoate (298 mg), 1-hydroxybenzotriazole monohydrate (348 mg), triethylamine (633 μL) and N,N-dimethylformamide (10 mL) was added 1-ethyl-3-(3-dimethylaminopropyl)carbodiimide hydrochloride (435 mg), and the mixture was stirred at room temperature for overnight then at 50° C. for 3 hr. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (55% ethyl acetate/hexane) to give the title object compound (801 mg, 84%) as a pale-brown solid.

$^1$H NMR (300 MHz, CDCl$_3$) δ ppm 0.93-1.35 (m, 8H), 1.47-1.60 (m, 1H), 1.60-1.97 (m, 4H), 2.02-2.14 (m, 1H), 2.22 (s, 3H), 2.61 (t, J=7.0 Hz, 2H), 3.01 (s, 3H), 3.70 (t, J=7.0 Hz, 2H), 3.84 (s, 3H), 4.07-4.17 (m, 2H), 4.30-4.40 (m, 2H), 6.56 (d, J=8.7 Hz, 2H), 6.82 (dd, J=8.9, 2.6 Hz, 1H), 6.88 (d, J=2.6 Hz, 1H), 7.18-7.30 (m, 3H).

(3) 3-{[(4-{[cyclohexyl(5-methoxy-3-methyl-1-benzofuran-2-yl)methyl]amino}phenyl)carbonyl](methyl)amino}propanoic acid Ethyl 3-{[(4-{[cyclohexyl(5-methoxy-3-methyl-1-benzofuran-2-yl)methyl]amino}phenyl)carbonyl](methyl)amino}propanoate (795 mg) synthesized above was fractionated by high performance liquid chromatography (column: CHIRALPAK AD (50 mm ID×500 mL, manufactured by Daicel Chemical Industries, Ltd., mobile phase: hexane/ethanol (400/600), flow rate: 60 mL/min, column temperature: 30° C.). The fraction containing an optically active form having a shorter retention time under the above-mentioned high performance liquid chromatography conditions was concentrated to give an amorphous form (413 mg, 99.9% ee). To a mixture of the obtained amorphous form, ethanol (5 mL) and tetrahydrofuran (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (355 mg, 47%, 99.9% ee) as a white solid.

¹H NMR (300 MHz, CDCl₃) δ ppm 0.93-1.37 (m, 5H), 1.47-1.57 (m, 1H), 1.60-1.96 (m, 4H), 2.03-2.13 (m, 1H), 2.23 (s, 3H), 2.65 (t, J=6.4 Hz, 2H), 3.02 (s, 3H), 3.69 (t, J=6.4 Hz, 2H), 3.83 (s, 3H), 4.36 (d, J=8.0 Hz, 1H), 6.55 (d, J=8.7 Hz, 2H), 6.82 (dd, J=8.9, 2.4 Hz, 1H), 6.88 (d, J=2.4 Hz, 1H), 7.19-7.29 (m, 3H).

Example A44

3-{[(4-{[cyclohexyl(5-methoxy-3-methyl-1-benzofuran-2-yl)methyl]amino}phenyl)carbonyl](methyl)amino}propanoic acid

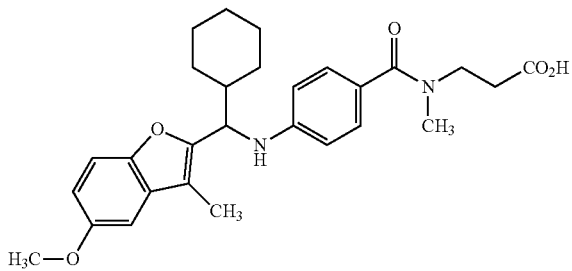

Ethyl 3-{[(4-{[cyclohexyl(5-methoxy-3-methyl-1-benzofuran-2-yl)methyl]amino}phenyl)carbonyl](methyl)amino}propanoate (795 mg) synthesized in Example A43(2) was fractionated by high performance liquid chromatography (column: CHIRALPAK AD (50 mm ID×500 mL, manufactured by Daicel Chemical Industries, Ltd., mobile phase: hexane/ethanol (400/600), flow rate: 60 mL/min, column temperature: 30° C.). The fraction containing an optically active form having a longer retention time under the above-mentioned high performance liquid chromatography conditions was concentrated to give an amorphous form (418 mg, 99.9% ee). To a mixture of the obtained amorphous form, ethanol (5 mL) and tetrahydrofuran (5 mL) was added 1N aqueous sodium hydroxide solution (2.00 mL), and the mixture was stirred at room temperature for 1.5 hr, and concentrated under reduced pressure. The residue was dissolved in water (10 mL), and 1N hydrochloric acid (2.00 mL) was added at 0° C. The resulting precipitate was collected by filtration to give the title object compound (354 mg, 47%, 99.9% ee) as a white solid.

¹H NMR (300 MHz, CDCl₃) δ ppm 0.93-1.37 (m, 5H), 1.47-1.57 (m, 1H), 1.60-1.96 (m, 4H), 2.03-2.13 (m, 1H), 2.23 (s, 3H), 2.65 (t, J=6.4 Hz, 2H), 3.02 (s, 3H), 3.69 (t, J=6.4 Hz, 2H), 3.83 (s, 3H), 4.36 (d, J=8.0 Hz, 1H), 6.55 (d, J=8.7 Hz, 2H), 6.82 (dd, J=8.9, 2.4 Hz, 1H), 6.88 (d, J=2.4 Hz, 1H), 7.19-7.29 (m, 3H).

Example A45

3-{[(4-{[cyclohexyl(5-fluoro-3-methyl-1-benzofuran-2-yl)methyl]amino}phenyl)carbonyl](methyl)amino}propanoic acid

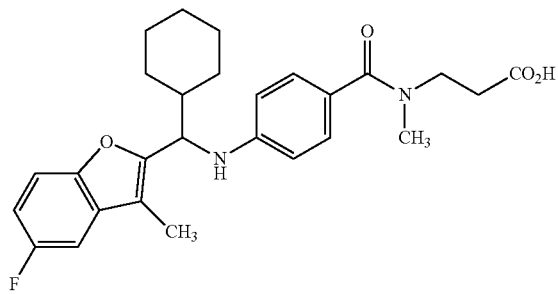 [SMILES: Cc1c(C(Nc2ccc(C(=O)N(C)CCC(=O)O)cc2)C2CCCCC2)oc2ccc(F)cc12]

(1) 4-{[cyclohexyl(5-fluoro-3-methyl-1-benzofuran-2-yl)methyl]amino}benzoic acid To a mixture of 2-[chloro(cyclohexyl)methyl]-5-fluoro-3-methyl-1-benzofuran (1.44 g) synthesized in Example A37 (3), methyl 4-aminobenzoate (776 mg), sodium iodide (1.54 g) and N,N-dimethylformamide (30 mL) was added sodium carbonate (1.09 g), and the mixture was stirred at 80° C. overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give a yellow solid. To a mixture of the obtained solid, tetrahydrofuran (20 mL) and ethanol (20 mL) was added 1N aqueous sodium hydroxide solution (20 mL), and the mixture was stirred overnight with heating under reflux, and concentrated under reduced pressure. The residue was dissolved in water (40 mL), and 1N hydrochloric acid (20 mL) was added at 0° C. The resulting precipitate was collected by filtration to give the title object compound (1.06 g, 54%) as a yellow solid.

¹H NMR (300 MHz, CDCl₃) δ ppm 0.92-1.37 (m, 5H), 1.46-1.58 (m, 1H), 1.60-1.99 (m, 4H), 2.02-2.13 (m, 1H), 2.23 (s, 3H), 4.43 (d, J=8.0 Hz, 1H), 4.51-4.73 (m, 1H), 6.57 (d, J=8.7 Hz, 2H), 6.87-6.98 (m, 1H), 7.04-7.11 (m, 1H), 7.24-7.32 (m, 1H), 7.85 (d, J=8.7 Hz, 2H).

(2) ethyl 3-{[(4-{[cyclohexyl(5-fluoro-3-methyl-1-benzofuran-2-yl)methyl]amino}phenyl)carbonyl](methyl)amino}propanoate To a mixture of 4-{[cyclohexyl(5-fluoro-3-methyl-1-benzofuran-2-yl)methyl]amino}benzoic acid (1.06 g) synthesized above, ethyl 3-(methylamino)propanoate (438 mg), 1-hydroxybenzotriazole monohydrate (512 mg), triethylamine (930 μL) and N,N-dimethylformamide (20 mL) was added 1-ethyl-3-(3-dimethylaminopropyl)carbodiimide hydrochloride (640 mg), and the mixture was stirred at room temperature for 1.5 hr. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (55% ethyl acetate/hexane) to give the title object compound (564 mg, 41%) as a white solid.

¹H NMR (300 MHz, CDCl₃) δ ppm 0.93-1.37 (m, 8H), 1.46-1.56 (m, 1H), 1.61-1.98 (m, 4H), 2.03-2.14 (m, 1H), 2.22 (s, 3H), 2.61 (t, J=7.0 Hz, 2H), 3.01 (s, 3H), 3.70 (t, J=7.0 Hz, 2H), 4.06-4.17 (m, 2H), 4.28-4.41 (m, 2H), 6.56 (d, J=8.7 Hz, 2H), 6.88-6.97 (m, 1H), 7.04-7.09 (m, 1H), 7.22 (d, J=8.7 Hz, 2H), 7.25-7.31 (m, 1H).

(3) 3-{[(4-{[cyclohexyl(5-fluoro-3-methyl-1-benzofuran-2-yl)methyl]amino}phenyl)carbonyl](methyl)amino}propanoic acid Ethyl 3-{[(4-{[cyclohexyl (5-fluoro-3-methyl-1-benzofuran-2-yl)methyl]amino}phenyl) carbonyl](methyl)amino}propanoate (564 mg) synthesized above was fractionated by high performance liquid chromatography (column: CHIRALPAK AD (50 mm ID×500 mL, manufactured by Daicel Chemical Industries, Ltd., mobile phase: hexane/ethanol (400/600), flow rate: 60 mL/min, column temperature: 30° C.). The fraction containing an optically active form having a shorter retention time under the above-mentioned high performance liquid chromatography conditions was concentrated to give an amorphous form (274 mg, 99.9% ee). To a mixture of the obtained amorphous form, ethanol (5 mL) and tetrahydrofuran (5 mL) was added 1N aqueous sodium hydroxide solution (1.00 mL), and the mixture was stirred at room temperature for 1.5 hr, and concentrated under reduced pressure. The residue was dissolved in water (10 mL), and 1N hydrochloric acid (1.00 mL) was added at 0° C. The resulting precipitate was collected by filtration to give the title object compound (249 mg, 47%, 99.9% ee) as a white solid.

$^1$H NMR (300 MHz, CDCl$_3$) δ ppm 0.92-1.37 (m, 5H), 1.45-1.56 (m, 1H), 1.60-1.97 (m, 4H), 2.03-2.14 (m, 1H), 2.22 (s, 3H), 2.64 (t, J=6.5 Hz, 2H), 3.02 (s, 3H), 3.69 (t, J=6.5 Hz, 2H), 4.36 (d, J=7.9 Hz, 1H), 6.55 (d, J=8.7 Hz, 2H), 6.88-6.97 (m, 1H), 7.07 (dd, J=8.5, 2.6 Hz, 1H), 7.23 (d, J=8.7 Hz, 2H), 7.25-7.31 (m, 1H).

Example A46

3-{[(4-{[cyclohexyl(5-fluoro-3-methyl-1-benzofuran-2-yl)methyl]amino}phenyl)carbonyl](methyl)amino}propanoic acid

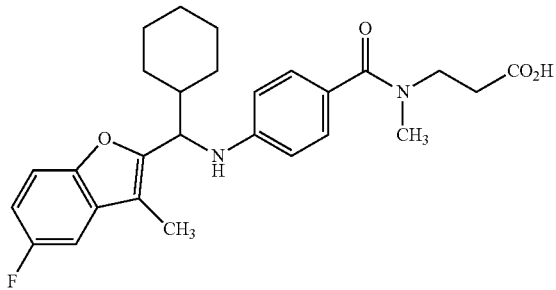

Ethyl 3-{[(4-{[cyclohexyl(5-fluoro-3-methyl-1-benzofuran-2-yl)methyl]amino}phenyl)carbonyl](methyl)amino}propanoate (564 mg) synthesized in Example A45(2) was fractionated by high performance liquid chromatography (column: CHIRALPAK AD (50 mm ID×500 mL, manufactured by Daicel Chemical Industries, Ltd., mobile phase: hexane/ethanol (400/600), flow rate: 60 mL/min, column temperature: 30° C.). The fraction containing an optically active form having a longer retention time under the above-mentioned high performance liquid chromatography conditions was concentrated to give an amorphous form (273 mg, 99.9% ee). To a mixture of the obtained amorphous form, methanol (5 mL) and tetrahydrofuran (5 mL) was added 1N aqueous sodium hydroxide solution (1.00 mL), and the mixture was stirred at room temperature for 1.5 hr, and concentrated under reduced pressure. The residue was dissolved in water (10 mL), and 1N hydrochloric acid (1.00 mL) was added at 0° C. The resulting precipitate was collected by filtration to give the title object compound (248 mg, 47%, 99.9% ee) as a white solid.

$^1$H NMR (300 MHz, CDCl$_3$) δ ppm 0.92-1.37 (m, 5H), 1.45-1.56 (m, 1H), 1.60-1.97 (m, 4H), 2.03-2.14 (m, 1H), 2.22 (s, 3H), 2.64 (t, J=6.5 Hz, 2H), 3.02 (s, 3H), 3.69 (t, J=6.5 Hz, 2H), 4.36 (d, J=7.9 Hz, 1H), 6.55 (d, J=8.7 Hz, 2H), 6.88-6.97 (m, 1H), 7.07 (dd, J=8.5, 2.6 Hz, 1H), 7.23 (d, J=8.7 Hz, 2H), 7.25-7.31 (m, 1H).

Example A47

3-({[4-({cyclohexyl[5-fluoro-3-(methoxymethyl)-1-benzofuran-2-yl]methyl}amino)phenyl]carbonyl}amino)propanoic acid

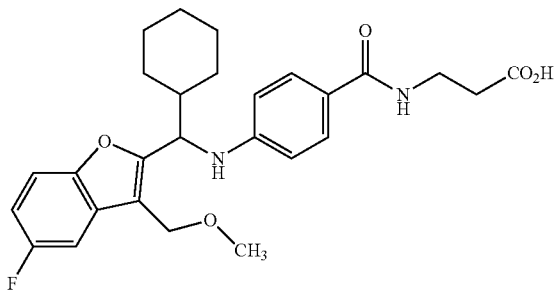 [SMILES: COCc1c(C(Nc2ccc(C(=O)NCCC(=O)O)cc2)C2CCCCC2)oc2ccc(F)cc12]

(1) methyl 5-fluoro-3-methyl-1-benzofuran-2-carboxylate

To a mixture of 1-(5-fluoro-2-hydroxyphenyl)ethanone (100 g), methyl bromoacetate (67.6 mL) and N,N-dimethylformamide (500 mL) was added potassium carbonate (135 g), and the mixture was stirred at 50° C. for 2 hr. The insoluble material was filtered off, 1,8-diazabicyclo[5.4.0]undec-7-ene (97.1 mL) was added, and the mixture was stirred at 120° C. for 30 min. 1N Hydrochloric acid was added to the reaction mixture at 0° C., and the resulting precipitate was collected by filtration to give the title object compound (77.9 g, 58%) as a white solid.

$^1$H NMR (300 MHz, CDCl$_3$) δ ppm 2.56 (s, 3H), 3.99 (s, 3H), 7.14-7.22 (m, 1H), 7.24-7.30 (m, 1H), 7.45-7.51 (m, 1H).

(2) methyl 3-(bromomethyl)-5-fluoro-1-benzofuran-2-carboxylate

To a solution (150 mL) of methyl 5-fluoro-3-methyl-1-benzofuran-2-carboxylate (15.4 g) synthesized above in acetonitrile were added N-bromosuccinimide (19.8 g) and 2,2'-azobis(isobutyronitrile) (1.21 g), and the mixture was stirred under argon atmosphere at 50° C. for 2.5 days. The reaction mixture was concentrated under reduced pressure, and the residue was purified by silica gel column chromatography (20-30% ethyl acetate/hexane) to give a white solid. The obtained solid was washed with hexane to give the title object compound (15.1 g, 71%) as a white solid.

$^1$H NMR (300 MHz, CDCl$_3$) δ ppm 4.02 (s, 3H), 4.96 (s, 2H), 7.18-7.27 (m, 1H), 7.41-7.47 (m, 1H), 7.49-7.55 (m, 1H).

(3) methyl 5-fluoro-3-(methoxymethyl)-1-benzofuran-2-carboxylate

To a solution (50 mL) of methyl 3-(bromomethyl)-5-fluoro-1-benzofuran-2-carboxylate (5.87 g) synthesized above in methanol was added 28% solution (8.33 mL) of sodium methoxide in methanol, and the mixture was stirred with heating under reflux for 3 hr. 1N Hydrochloric acid was added to the reaction mixture, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give the title object compound (3.04 g, 63%) as a white solid.

$^1$H NMR (300 MHz, CDCl$_3$) δ ppm 3.44 (s, 3H), 3.99 (s, 3H), 4.99 (s, 2H), 7.18 (td, J=9.1, 2.7 Hz, 1H), 7.46-7.52 (m, 1H), 7.53-7.58 (m, 1H).

(4) 5-fluoro-3-(methoxymethyl)-1-benzofuran-2-carbaldehyde

To a mixture of methyl 5-fluoro-3-(methoxymethyl)-1-benzofuran-2-carboxylate (5.01 g) synthesized above, calcium chloride (4.66 g), ethanol (50 mL) and tetrahydrofuran (50 mL) was added at 0° C. sodium borohydride (3.18 g), and the mixture was stirred at room temperature for 3 hr. Saturated aqueous ammonium chloride solution was added to quench the reaction, the organic solvent was evaporated in an evaporator, and the residue was extracted with ethyl acetate. The extract was washed with saturated brine, dried over magnesium sulfate, and concentrated under reduced pressure to give a colorless oil. To a mixture of the obtained oil, 4-methylmorpholine N-oxide (3.69 g) and acetonitrile (50 mL) was added tetrapropylammonium perruthenate (738 mg) at 0° C., and the mixture was stirred for 1.5 hr and concentrated under reduced pressure. The residue was purified by silica gel column chromatography (0-20% ethyl acetate/hexane) to give the title object compound (2.33 g, 53%) as a pale-yellow solid.

$^1$H NMR (300 MHz, CDCl$_3$) δ ppm 3.49 (s, 3H), 4.94 (s, 2H), 7.21-7.29 (m, 1H), 7.47-7.54 (m, 2H), 10.08 (s, 1H).

(5) cyclohexyl[5-fluoro-3-(methoxymethyl)-1-benzofuran-2-yl]methanone

To a solution (20 mL) of 5-fluoro-3-(methoxymethyl)-1-benzofuran-2-carbaldehyde (1.07 g) synthesized above in tetrahydrofuran was added a 1.0M solution (7.71 mL) of cyclohexylmagnesium bromide in tetrahydrofuran at 0° C., and the mixture was stirred for 1 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (10-50% ethyl acetate/hexane) to give a pale-yellow oil. To a mixture of the obtained oil, 4-methylmorpholine N-oxide (841 mg) and acetonitrile (20 mL) was added tetrapropylammonium perruthenate (126 mg), and the mixture was stirred at room temperature for 1.5 hr and concentrated under reduced pressure. The residue was purified by silica gel column chromatography (0-20% ethyl acetate/hexane) to give the title object compound (857 mg, 57%) as a colorless oil.

$^1$H NMR (300 MHz, CDCl$_3$) δ ppm 1.15-1.55 (m, 5H), 1.69-1.80 (m, 1H), 1.80-2.02 (m, 4H), 3.25-3.39 (m, 1H), 3.44 (s, 3H), 5.00 (s, 2H), 7.15-7.23 (m, 1H), 7.43-7.49 (m, 1H), 7.57-7.62 (m, 1H).

(6) methyl 4-({cyclohexyl[5-fluoro-3-(methoxymethyl)-1-benzofuran-2-yl]methyl}amino)benzoate To a mixture of cyclohexyl[5-fluoro-3-(methoxymethyl)-1-benzofuran-2-yl]methanone (857 mg) synthesized above, methyl 4-aminobenzoate (491 mg), triethylamine (3.29 mL) and methylene chloride (10 mL) was added titanium (IV) chloride (388 μL), and the mixture was stirred under argon atmosphere at room temperature overnight. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (847 μL) and sodium cyanoborohydride (371 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (454 mg, 36%) as a pale-brown oil $^1$H NMR (300 MHz, CDCl$_3$) δ ppm 0.97-1.36 (m, 5H), 1.43-1.54 (m, 1H), 1.60-1.99 (m, 4H), 2.00-2.11 (m, 1H), 3.37 (s, 3H), 3.81 (s, 3H), 4.48-4.64 (m, 4H), 6.60 (d, J=8.8 Hz, 2H), 6.90-6.99 (m, 1H), 7.17-7.23 (m, 1H), 7.28-7.34 (m, 1H), 7.79 (d, J=8.8 Hz, 2H).

(7) 4-({cyclohexyl[5-fluoro-3-(methoxymethyl)-1-benzofuran-2-yl]methyl}amino)benzoic acid To a mixture of methyl 4-({cyclohexyl[5-fluoro-3-(methoxymethyl)-1-benzofuran-2-yl]methyl}amino)benzoate (454 mg) synthesized above, tetrahydrofuran (10 mL) and ethanol (10 mL) was added 1N aqueous sodium hydroxide solution (10.0 mL), and the mixture was stirred overnight with heating under reflux, and concentrated under reduced pressure. The residue was dissolved in water (20 mL), and 1N hydrochloric acid (10.0 mL) was added at 0° C. The resulting precipitate was collected by filtration to give the title object compound (423 mg, 96%) as a white solid.

$^1$H NMR (300 MHz, CDCl$_3$) δ ppm 0.96-1.36 (m, 5H), 1.40-1.55 (m, 1H), 1.60-1.99 (m, 4H), 1.99-2.13 (m, 1H), 3.38 (s, 3H), 4.49-4.77 (m, 4H), 6.61 (d, J=8.8 Hz, 2H), 6.90-6.99 (m, 1H), 7.17-7.23 (m, 1H), 7.28-7.35 (m, 1H), 7.84 (d, J=8.8 Hz, 2H).

(8) ethyl 3-({[4-({cyclohexyl[5-fluoro-3-(methoxymethyl)-1-benzofuran-2-yl]methyl}amino)phenyl]carbonyl}amino)propanoate To a mixture of 4-({cyclohexyl[5-fluoro-3-(methoxymethyl)-1-benzofuran-2-yl]methyl}amino)benzoic acid (200 mg) synthesized above, β-alanine ethyl ester hydrochloride (112 mg), 1-hydroxybenzotriazole monohydrate (112 mg), triethylamine (203 μL) and N,N-dimethylformamide (10 mL) was added 1-ethyl-3-(3-dimethylaminopropyl)carbodiimide hydrochloride (140 mg), and the mixture was stirred at room temperature overnight. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (207 mg, 83%) as a pale-yellow oil.

$^1$H NMR (300 MHz, CDCl$_3$) δ ppm 0.95-1.36 (m, 8H), 1.42-1.54 (m, 1H), 1.60-1.97 (m, 4H), 2.01-2.13 (m, 1H), 2.58 (t, J=5.8 Hz, 2H), 3.37 (s, 3H), 3.61-3.70 (m, 2H), 4.13 (q, J=7.1 Hz, 2H), 4.46-4.62 (m, 4H), 6.56-6.65 (m, 3H), 6.90-6.99 (m, 1H), 7.17-7.23 (m, 1H), 7.27-7.33 (m, 1H), 7.54 (d, J=8.8 Hz, 2H).

(9) 3-({[4-({cyclohexyl[5-fluoro-3-(methoxymethyl)-1-benzofuran-2-yl]methyl}amino)phenyl]carbonyl}amino)propanoic acid To a mixture of ethyl 3-({[4-({cyclohexyl[5-fluoro-3-(methoxymethyl)-1-benzofuran-2-yl]methyl}amino)phenyl]

carbonyl}amino)propanoate (207 mg) synthesized above, tetrahydrofuran (5 mL) and ethanol (5 mL) was added 1N aqueous sodium hydroxide solution (1.00 mL), and the mixture was stirred at room temperature for 5 hr and concentrated under reduced pressure. The residue was dissolved in water (10 mL), and 1N hydrochloric acid (1.00 mL) was added at 0° C. The resulting precipitate was collected by filtration to give the title object compound (186 mg, 95%) as a white solid.

$^1$H NMR (300 MHz, CDCl$_3$) δ ppm 0.95-1.35 (m, 5H), 1.41-1.53 (m, 1H), 1.60-1.97 (m, 4H), 2.00-2.11 (m, 1H), 2.63 (t, J=5.7 Hz, 2H), 3.37 (s, 3H), 3.59-3.68 (m, 2H), 4.50 (d, J=8.1 Hz, 1H), 4.54 (d, J=12.2 Hz, 1H), 4.59 (d, J=12.2 Hz, 1H), 6.55-6.66 (m, 3H), 6.90-6.99 (m, 1H), 7.16-7.23 (m, 1H), 7.27-7.34 (m, 1H), 7.53 (d, J=8.9 Hz, 2H).

Example A48

3-[{[4-({cyclohexyl[5-fluoro-3-(methoxymethyl)-1-benzofuran-2-yl]methyl}amino)phenyl]carbonyl}(methyl)amino]propanoic acid

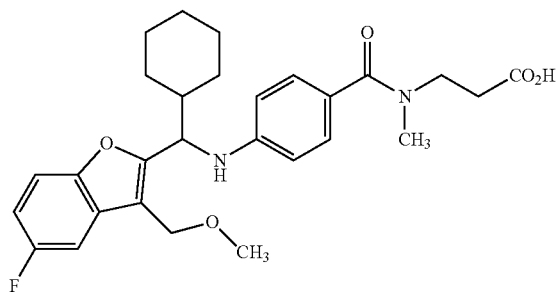 [SMILES: COCc1c(C(Nc2ccc(C(=O)N(C)CCC(=O)O)cc2)C2CCCCC2)oc2ccc(F)cc12]

(1) ethyl 3-[{[4-({cyclohexyl[5-fluoro-3-(methoxymethyl)-1-benzofuran-2-yl]methyl}amino)phenyl]carbonyl}(methyl)amino]propanoate To a mixture of 4-({cyclohexyl[5-fluoro-3-(methoxymethyl)-1-benzofuran-2-yl]methyl}amino)benzoic acid (200 mg) synthesized in Example A47(7), ethyl 3-(methylamino)propanoate (95.6 mg), 1-hydroxybenzotriazole monohydrate (112 mg), triethylamine (203 μL) and N,N-dimethylformamide (10 mL) was added 1-ethyl-3-(3-dimethylaminopropyl)carbodiimide hydrochloride (140 mg), and the mixture was stirred at room temperature overnight. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (197 mg, 77%) as a pale-yellow oil.

$^1$H NMR (300 MHz, CDCl$_3$) δ ppm 0.96-1.36 (m, 8H), 1.42-1.53 (m, 1H), 1.59-1.97 (m, 4H), 2.02-2.13 (m, 1H), 2.61 (t, J=7.0 Hz, 2H), 3.00 (s, 3H), 3.36 (s, 3H), 3.70 (t, J=7.0 Hz, 2H), 4.11 (q, J=7.1 Hz, 2H), 4.35-4.51 (m, 2H), 4.54 (d, J=12.3 Hz, 1H), 4.59 (d, J=12.3 Hz, 1H), 6.59 (d, J=8.5 Hz, 2H), 6.90-6.99 (m, 1H), 7.17-7.24 (m, 3H), 7.28-7.34 (m, 1H).

(2) 3-[{[4-({cyclohexyl[5-fluoro-3-(methoxymethyl)-1-benzofuran-2-yl]methyl}amino)phenyl]carbonyl}(methyl)amino]propanoic acid To a mixture of ethyl 3-[{[4-({cyclohexyl[5-fluoro-3-(methoxymethyl)-1-benzofuran-2-yl]methyl}amino)phenyl]carbonyl}(methyl)amino]propanoate (197 mg) synthesized above, tetrahydrofuran (5 mL) and ethanol (5 mL) was added 1N aqueous sodium hydroxide solution (1.00 mL), and the mixture was stirred at room temperature for 7 hr, and concentrated under reduced pressure. The residue was dissolved in water (10 mL), and 1N hydrochloric acid (1.00 mL) was added at 0° C. The resulting precipitate was collected by filtration to give the title object compound (161 mg, 87%) as a pale-yellow solid.

$^1$H NMR (300 MHz, CDCl$_3$) δ ppm 0.95-1.36 (m, 5H), 1.41-1.53 (m, 1H), 1.59-1.97 (m, 4H), 2.01-2.13 (m, 1H), 2.54-2.70 (m, 2H), 3.01 (s, 3H), 3.37 (s, 3H), 3.68 (t, J=6.6 Hz, 2H), 4.47 (d, J=7.9 Hz, 1H), 4.55 (d, J=12.2 Hz, 1H), 4.60 (d, J=12.2 Hz, 1H), 6.59 (d, J=8.5 Hz, 2H), 6.89-7.00 (m, 1H), 7.17-7.25 (m, 3H), 7.28-7.35 (m, 1H).

Example A49

3-[{[4-({cyclohexyl[5-fluoro-3-(methoxymethyl)-1-benzofuran-2-yl]methyl}amino)phenyl]carbonyl}(methyl)amino]propanoic acid

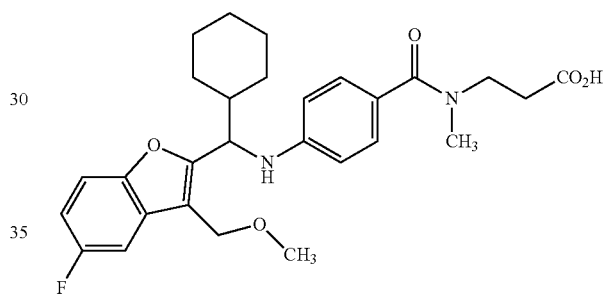

Ethyl 3-[{[4-({cyclohexyl[5-fluoro-3-(methoxymethyl)-1-benzofuran-2-yl]methyl}amino)phenyl]carbonyl}(methyl)amino]propanoate (1.20 g) synthesized in Example A48 (1) was fractionated by high performance liquid chromatography (column: CHIRALPAK AD (50 mm ID×500 mL, manufactured by Daicel Chemical Industries, Ltd., mobile phase: hexane/ethanol (200/800), flow rate: 60 mL/min, column temperature: 30° C.). The fraction containing an optically active form having a shorter retention time under the above-mentioned high performance liquid chromatography conditions was concentrated to give an amorphous form (470 mg, 99.9% ee). To a mixture of the obtained amorphous form, ethanol (5 mL) and tetrahydrofuran (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (433 mg, 38%, 99.9% ee) as a white solid.

$^1$H NMR (300 MHz, CDCl$_3$) δ ppm 0.95-1.36 (m, 5H), 1.41-1.53 (m, 1H), 1.59-1.97 (m, 4H), 2.01-2.13 (m, 1H), 2.54-2.70 (m, 2H), 3.01 (s, 3H), 3.37 (s, 3H), 3.68 (t, J=6.6 Hz, 2H), 4.47 (d, J=7.9 Hz, 1H), 4.55 (d, J=12.2 Hz, 1H), 4.60

(d, J=12.2 Hz, 1H), 6.59 (d, J=8.5 Hz, 2H), 6.89-7.00 (m, 1H), 7.17-7.25 (m, 3H), 7.28-7.35 (m, 1H).

Example A50

3-[{[4-({cyclohexyl[5-fluoro-3-(methoxymethyl)-1-benzofuran-2-yl]methyl}amino)phenyl]carbonyl}(methyl)amino]propanoic acid

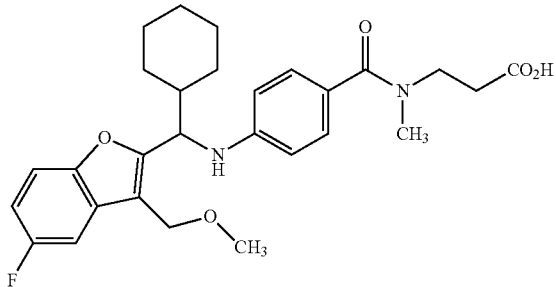 [SMILES: COCc1c(C(Nc2ccc(C(=O)N(C)CCC(=O)O)cc2)C2CCCCC2)oc2ccc(F)cc12]

Ethyl 3-[{[4-({cyclohexyl[5-fluoro-3-(methoxymethyl)-1-benzofuran-2-yl]methyl}amino)phenyl]carbonyl}(methyl)amino]propanoate (1.20 g) synthesized in Example A48 (1) was fractionated by high performance liquid chromatography (column: CHIRALPAK AD (50 mm ID×500 mL, manufactured by Daicel Chemical Industries, Ltd., mobile phase: hexane/ethanol (200/800), flow rate: 60 mL/min, column temperature: 30° C.). The fraction containing an optically active form having a longer retention time under the above-mentioned high performance liquid chromatography conditions was concentrated to give an amorphous form (465 mg, 99.9% ee). To a mixture of the obtained amorphous form, ethanol (5 mL) and tetrahydrofuran (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (415 mg, 37%, 99.9% ee) as a white solid.

$^1$H NMR (300 MHz, CDCl$_3$) δ ppm 0.95-1.36 (m, 5H), 1.41-1.53 (m, 1H), 1.59-1.97 (m, 4H), 2.01-2.13 (m, 1H), 2.54-2.70 (m, 2H), 3.01 (s, 3H), 3.37 (s, 3H), 3.68 (t, J=6.6 Hz, 2H), 4.47 (d, J=7.9 Hz, 1H), 4.55 (d, J=12.2 Hz, 1H), 4.60 (d, J=12.2 Hz, 1H), 6.59 (d, J=8.5 Hz, 2H), 6.89-7.00 (m, 1H), 7.17-7.25 (m, 3H), 7.28-7.35 (m, 1H).

Example A51

3-{[(6-{[cyclohexyl(5-fluoro-3-methyl-1-benzofuran-2-yl)methyl]amino}pyridin-3-yl)carbonyl]amino}propanoic acid

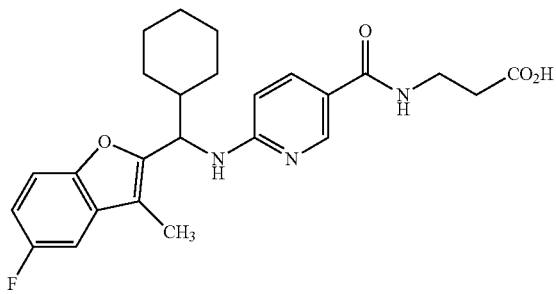 [SMILES: Cc1c(C(Nc2ccc(C(=O)NCCC(=O)O)cn2)C2CCCCC2)oc2ccc(F)cc12]

(1) 2-bromo-1-cyclohexylethanone

To a solution (50 mL) of 1-cyclohexylethanone (25.0 g) in methanol was added bromine (10.1 mL) at 0° C., and the mixture was stirred at room temperature for 30 min. Saturated sodium sulfite aqueous solution was added to quench the reaction, and the mixture was extracted with ethyl acetate. The extract was washed with saturated brine, dried over magnesium sulfate, and concentrated under reduced pressure. The residue was purified by silica gel column chromatography (0-10% ethyl acetate/hexane) to give the title object compound (25.8 g, 63%) as a colorless oil.

$^1$H NMR (300 MHz, CDCl$_3$) δ ppm 1.10-1.50 (m, 5H), 1.62-1.73 (m, 1H), 1.75-1.94 (m, 4H), 2.64-2.79 (m, 1H), 3.97 (s, 2H).

(2) cyclohexyl(5-fluoro-3-methyl-1-benzofuran-2-yl)methanone

To a mixture of 5'-fluoro-2'-hydroxyacetophenone (5.00 g), 2-bromo-1-cyclohexylethanone (7.98 g) synthesized above and N,N-dimethylformamide (50 mL) was added potassium carbonate (13.4 g), and the mixture was stirred at room temperature overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (0-20% ethyl acetate/hexane) to give the title object compound (5.38 g, 64%) as a pale-yellow solid.

$^1$H NMR (300 MHz, CDCl$_3$) δ ppm 1.19-1.57 (m, 5H), 1.70-2.01 (m, 5H), 2.56 (s, 3H), 3.25-3.36 (m, 1H), 7.15-7.23 (m, 1H), 7.24-7.30 (m, 1H), 7.42-7.48 (m, 1H).

(3) methyl 6-{[cyclohexyl(5-fluoro-3-methyl-1-benzofuran-2-yl)methyl]amino}pyridine-3-carboxylate To a mixture of cyclohexyl(5-fluoro-3-methyl-1-benzofuran-2-yl)methanone (3.00 g) synthesized above, methyl 6-aminopyridine-3-carboxylate (1.93 g), triethylamine (12.8 mL) and methylene chloride (40 mL) was added a 1.0M solution (13.8 mL) of titanium (IV) chloride in methylene chloride at 0° C., and the mixture was stirred under an argon atmosphere at room temperature for 1.5 days. Saturated aqueous sodium hydrogen carbonate solution was added to quench the reaction, methylene chloride was removed by an evaporator, and the residue was extracted with ethyl acetate. The extract was washed with saturated brine, dried over magnesium sulfate, and concentrated under reduced pressure to give a dark brown oil. To a mixture of the obtained oil, ethanol (40 mL) and tetrahydrofuran (20 mL) were added acetic acid (3.29 mL) and sodium cyanoborohydride (3.61 g), and the mixture was stirred at room temperature for 3 hr. Saturated aqueous sodium hydrogen carbonate solution was added to quench the reaction, the organic solvent was removed by an evaporator, and the residue was extracted with ethyl acetate. The extract was washed with saturated brine, dried over magnesium sulfate, and concentrated under reduced pressure. The residue was purified by silica gel column chromatography (0-30% ethyl acetate/hexane) to give the title object compound (547 mg, 12%) as a pale-brown solid.

$^1$H NMR (300 MHz, CDCl$_3$) δ ppm 0.82-1.35 (m, 5H), 1.44-1.55 (m, 1H), 1.56-1.86 (m, 3H), 1.85-2.10 (m, 2H), 2.24 (s, 3H), 3.83 (s, 3H), 5.02-5.14 (m, 1H), 5.42 (d, J=8.2 Hz, 1H), 6.33 (d, J=8.8 Hz, 1H), 6.88-6.97 (m, 1H), 7.04-7.10 (m, 1H), 7.26-7.32 (m, 1H), 7.90 (dd, J=8.8, 2.4 Hz, 1H), 8.72 (d, J=2.4 Hz, 1H).

(4) 6-{[cyclohexyl(5-fluoro-3-methyl-1-benzofuran-2-yl)methyl]amino}pyridine-3-carboxylic acid To a mixture of methyl 6-{[cyclohexyl(5-fluoro-3-methyl-1-benzofuran-2-yl)methyl]amino}pyridine-3-carboxylate (547 mg) synthesized above, ethanol (10 mL) and tetrahydrofuran (10 mL) was added 1N aqueous sodium hydroxide solution (10 mL), and the mixture was stirred overnight with heating under reflux. In addition, 1N aqueous sodium hydroxide solution (5.00 mL) was added, and the mixture was stirred with heating under reflux for 5 hr, and concentrated under reduced pressure. The residue was dissolved in water (20 mL), and 1N hydrochloric acid (15 mL) was added at 0° C. The resulting precipitate was collected by filtration, and the obtained pale-brown solid was dissolved in ethyl acetate. The solution was washed with saturated brine, dried over magnesium sulfate, and concentrated under reduced pressure to give the title object compound (478 mg, 90%) as a pale-brown solid.

$^1$H NMR (300 MHz, CDCl$_3$) δ ppm 0.98-1.41 (m, 5H), 1.48-1.84 (m, 4H), 2.01-2.18 (m, 2H), 2.23 (s, 3H), 4.47-4.65 (m, 1H), 6.34 (d, J=8.8 Hz, 1H), 6.87-6.97 (m, 1H), 7.03-7.10 (m, 1H), 7.26-7.33 (m, 1H), 8.08 (d, J=8.8 Hz, 1H), 8.70-8.74 (m, 1H).

(5) ethyl 3-{[(6-{[cyclohexyl(5-fluoro-3-methyl-1-benzofuran-2-yl)methyl]amino}pyridin-3-yl)carbonyl]amino}propanoate To a mixture of 6-{[cyclohexyl(5-fluoro-3-methyl-1-benzofuran-2-yl)methyl]amino}pyridine-3-carboxylic acid (300 mg) synthesized above, β-alanine ethyl ester hydrochloride (181 mg), 1-hydroxybenzotriazole monohydrate (181 mg), triethylamine (328 μL) and N,N-dimethylformamide (10 mL) was added 1-ethyl-3-(3-dimethylaminopropyl)carbodiimide hydrochloride (226 mg), and the mixture was stirred at room temperature overnight. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (366 mg, 97%) as a pale-brown oil.

$^1$H NMR (300 MHz, CDCl$_3$) δ ppm 0.93-1.36 (m, 8H), 1.43-1.55 (m, 1H), 1.57-1.85 (m, 3H), 1.85-2.08 (m, 2H), 2.24 (s, 3H), 2.60 (t, J=5.9 Hz, 2H), 3.62-3.72 (m, 2H), 4.15 (q, J=7.1 Hz, 2H), 5.01-5.12 (m, 1H), 5.25 (d, J=8.8 Hz, 1H), 6.35 (d, J=8.8 Hz, 1H), 6.65 (t, J=6.0 Hz, 1H), 6.88-6.97 (m, 1H), 7.03-7.10 (m, 1H), 7.23-7.31 (m, 1H), 7.75 (dd, J=8.8, 2.5 Hz, 1H), 8.48 (d, J=2.5 Hz, 1H).

(6) 3-{[(6-{[cyclohexyl(5-fluoro-3-methyl-1-benzofuran-2-yl)methyl]amino}pyridin-3-yl)carbonyl]amino}propanoic acid To a mixture of ethyl 3-{[(6-{[cyclohexyl(5-fluoro-3-methyl-1-benzofuran-2-yl)methyl]amino}pyridin-3-yl)carbonyl]amino}propanoate (366 mg) synthesized above, tetrahydrofuran (5 mL) and ethanol (5 mL) was added 1N aqueous sodium hydroxide solution (1.00 mL), and the mixture was stirred at room temperature overnight, and concentrated under reduced pressure. The residue was dissolved in water (10 mL), and 1N hydrochloric acid (1.00 mL) was added at 0° C. The resulting precipitate was collected by filtration to give the title object compound (287 mg, 83%) as a white solid.

$^1$H NMR (300 MHz, CDCl$_3$) δ ppm 0.84-1.41 (m, 5H), 1.44-1.55 (m, 1H), 1.59-1.84 (m, 3H), 1.97-2.15 (m, 2H), 2.23 (s, 3H), 2.55-2.69 (m, 2H), 3.65-3.78 (m, 2H), 4.46 (t, J=7.8 Hz, 1H), 6.48 (d, J=9.1 Hz, 1H), 6.89-6.99 (m, 1H), 7.04-7.11 (m, 1H), 7.27-7.35 (m, 1H), 7.51-7.61 (m, 1H), 8.13 (dd, J=9.1, 2.1 Hz, 1H), 8.22 (d, J=2.1 Hz, 1H), 8.25-8.41 (m, 1H).

Example A52

3-{[(6-{[cyclohexyl(5-fluoro-3-methyl-1-benzofuran-2-yl)methyl]amino}pyridin-3-yl)carbonyl](methyl)amino}propanoic acid

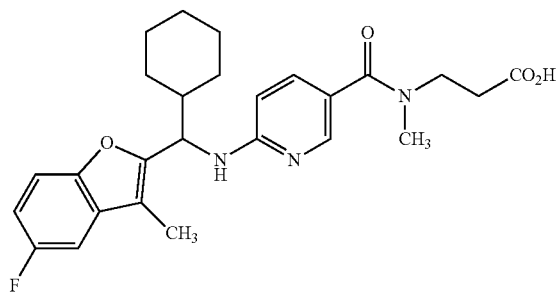 [SMILES: Cc1c(C(Nc2ccc(C(=O)N(C)CCC(=O)O)cn2)C2CCCCC2)oc2ccc(F)cc12]

(1) ethyl 3-{[(6-{[cyclohexyl(5-fluoro-3-methyl-1-benzofuran-2-yl)methyl]amino}pyridin-3-yl)carbonyl](methyl)amino}propanoate To a mixture of 6-{[cyclohexyl(5-fluoro-3-methyl-1-benzofuran-2-yl)methyl]amino}pyridine-3-carboxylic acid (294 mg) synthesized in Example A51(4), ethyl 3-(methylamino)propanoate (151 mg), 1-hydroxybenzotriazole monohydrate (176 mg), triethylamine (322 μL) and N,N-dimethylformamide (10 mL) was added 1-ethyl-3-(3-dimethylaminopropyl)carbodiimide hydrochloride (221 mg), and the mixture was stirred at room temperature overnight. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (236 mg, 62%) as a pale-brown solid.

$^1$H NMR (300 MHz, CDCl$_3$) δ ppm 0.94-1.34 (m, 8H), 1.45-1.57 (m, 1H), 1.58-1.83 (m, 3H), 1.84-2.09 (m, 2H), 2.23 (s, 3H), 2.63 (t, J=7.0 Hz, 2H), 3.05 (s, 3H), 3.72 (t, J=7.0 Hz, 2H), 4.03-4.17 (m, 2H), 4.97-5.07 (m, 1H), 5.08-5.18 (m, 1H), 6.34 (d, J=8.6 Hz, 1H), 6.88-6.97 (m, 1H), 7.04-7.10 (m, 1H), 7.23-7.31 (m, 1H), 7.46 (dd, J=8.6, 2.1 Hz, 1H), 8.18 (d, J=2.1 Hz, 1H).

(2) 3-{[(6-{[cyclohexyl(5-fluoro-3-methyl-1-benzofuran-2-yl)methyl]amino}pyridin-3-yl)carbonyl](methyl)amino}propanoic acid To a mixture of ethyl 3-{[(6-{[cyclohexyl(5-fluoro-3-methyl-1-benzofuran-2-yl)methyl]amino}pyridin-3-yl)carbonyl](methyl)amino}propanoate (236 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), 1N hydrochloric acid (1.00 mL) was added at 0° C., and the mixture was extracted with ethyl acetate. The extract was washed with saturated brine, dried over magnesium sulfate, and concentrated under reduced pressure to give a pale-yellow solid. The obtained solid was recrystallized from ethyl acetate/hexane to give the title object compound (143 mg, 64%) as colorless crystals.

$^1$H NMR (300 MHz, CDCl$_3$) δ ppm 0.84-1.37 (m, 5H), 1.38-1.53 (m, 1H), 1.55-1.82 (m, 3H), 1.87-2.12 (m, 2H), 2.20 (s, 3H), 2.48-2.68 (m, 2H), 2.99 (br s, 3H), 3.59-3.79 (m, 2H), 4.54-4.76 (m, 1H), 6.34 (d, J=8.8 Hz, 1H), 6.86-6.97 (m, 1H), 7.01-7.09 (m, 1H), 7.23-7.34 (m, 1H), 7.51 (d, J=8.8 Hz, 1H), 8.11 (br s, 1H).

Example A53

3-{[(6-{[cyclohexyl(5-fluoro-3-methyl-1-benzofuran-2-yl)methyl]amino}pyridin-3-yl)carbonyl](methyl)amino}propanoic acid

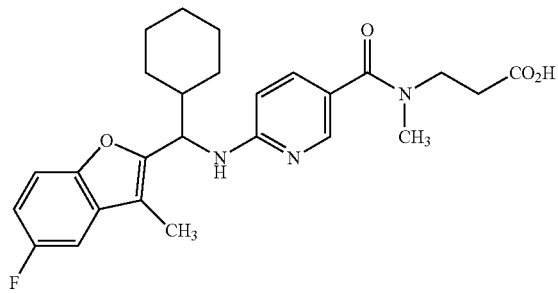 [SMILES: Cc1c(C(Nc2ccc(C(=O)N(C)CCC(=O)O)cn2)C2CCCCC2)oc2ccc(F)cc12]

Ethyl 3-{[(6-{[cyclohexyl(5-fluoro-3-methyl-1-benzofuran-2-yl)methyl]amino}pyridin-3-yl)carbonyl](methyl)amino}propanoate (4.06 g) synthesized in Example A52(1) was fractionated by high performance liquid chromatography (column: CHIRALPAK AD (50 mm ID×500 mL, manufactured by Daicel Chemical Industries, Ltd., mobile phase: hexane/2-propanol (700/300-200/800), flow rate: 60 mL/min-50 mL/min, column temperature: room temperature). The fraction containing an optically active form having a shorter retention time under the above-mentioned high performance liquid chromatography conditions was concentrated to give an amorphous form (1.94 g, 99.9% ee). To a mixture of the obtained amorphous form, ethanol (10 mL) and tetrahydrofuran (10 mL) was added 1N lithium hydroxide aqueous solution (8 mL), and the mixture was stirred at room temperature for 1 hr and concentrated under reduced pressure. The residue was dissolved in water (10 mL), and 1N hydrochloric acid (8 mL) was added at 0° C. The resulting precipitate was collected by filtration to give the title object compound (1.81 g, 95%, 99.9% ee) as a white solid.

$^1$H NMR (300 MHz, DMSO-d$_6$) δ ppm 0.89-1.28 (m, 5H) 1.34 (d, J=12.12 Hz, 1H) 1.49-1.80 (m, 3H) 1.80-2.08 (m, 2H) 2.23 (s, 3H) 2.50-2.54 (m, 2H) 2.92 (s, 3H) 3.53 (t, J=7.38 Hz, 2H) 5.15 (t, J=8.90 Hz, 1H) 6.56 (d, J=8.71 Hz, 1H) 7.05 (td, J=9.28, 2.65 Hz, 1H) 7.31 (dd, J=8.71, 2.65 Hz, 1H) 7.36-7.56 (m, 2H) 8.04 (d, J=2.27 Hz, 1H) 12.22 (brs, 1H).

Example A54

3-{[(6-{[cyclohexyl(5-fluoro-3-methyl-1-benzofuran-2-yl)methyl]amino}pyridin-3-yl)carbonyl](methyl)amino}propanoic acid

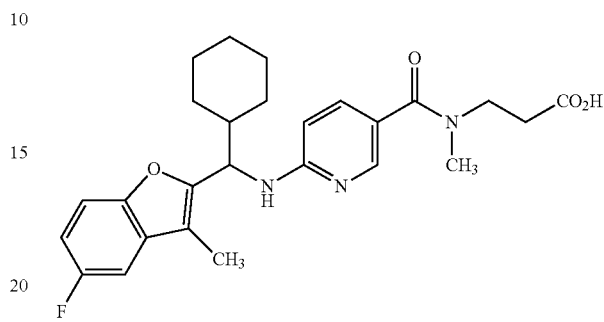

Ethyl 3-{[(6-{[cyclohexyl(5-fluoro-3-methyl-1-benzofuran-2-yl)methyl]amino}pyridin-3-yl)carbonyl](methyl)amino}propanoate (4.06 g) synthesized in Example A52(1) was fractionated by high performance liquid chromatography (column: CHIRALPAK AD (50 mm ID×500 mmL, manufactured by Daicel Chemical Industries, Ltd., mobile phase: hexane/2-propanol (700/300-200/800), flow rate: 60 mL/min, column temperature: room temperature). The fraction containing an optically active form having a longer retention time under the above-mentioned high performance liquid chromatography conditions was concentrated to give an amorphous form (1.96 g, 99.9% ee). To a mixture of the obtained amorphous form, ethanol (10 mL) and tetrahydrofuran (10 mL) was added 1N lithium hydroxide aqueous solution (8 mL), and the mixture was stirred at room temperature for 1 hr and concentrated under reduced pressure. The residue was dissolved in water (10 mL), and 1N hydrochloric acid (8 mL) was added at 0° C. The resulting precipitate was collected by filtration to give the title object compound (1.80 g, 99%, 99.9% ee) as a white solid.

$^1$H NMR (300 MHz, DMSO-d$_6$) δ ppm 0.89-1.28 (m, 5H) 1.34 (d, J=12.12 Hz, 1H) 1.49-1.80 (m, 3H) 1.80-2.08 (m, 2H) 2.23 (s, 3H) 2.50-2.54 (m, 2H) 2.92 (s, 3H) 3.53 (t, J=7.38 Hz, 2H) 5.15 (t, J=8.90 Hz, 1H) 6.56 (d, J=8.71 Hz, 1H) 7.05 (td, J=9.28, 2.65 Hz, 1H) 7.31 (dd, J=8.71, 2.65 Hz, 1H) 7.36-7.56 (m, 2H) 8.04 (d, J=2.27 Hz, 1H) 12.22 (brs, 1H).

Example A55

3-{[(5-{[cyclohexyl(5-fluoro-3-methyl-1-benzofuran-2-yl)methyl]amino}pyridin-2-yl)carbonyl]amino}propanoic acid

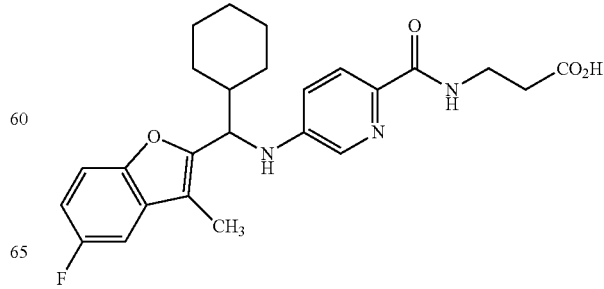

(1) methyl 5-{[cyclohexyl(5-fluoro-3-methyl-1-benzofuran-2-yl)methyl]amino}pyridine-2-carboxylate To a solution (15 mL) of cyclohexyl(5-fluoro-3-methyl-1-benzofuran-2-yl)methanol (1.50 g) synthesized in Example A37(2) in toluene was added thionyl chloride (625 μL), and the mixture was stirred at room temperature for 3 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give a brown oil. To a mixture of the obtained oil, methyl 5-aminopyridine-2-carboxylate (957 mg), sodium iodide (1.71 g) and N,N-dimethylformamide (15 mL) was added sodium carbonate (1.21 g), and the mixture was stirred at 80° C. overnight. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (10-50% ethyl acetate/hexane) to give the title object compound (909 mg, 40%) as a pale-brown solid.

$^1$H NMR (300 MHz, CDCl$_3$) δ ppm 0.94-1.37 (m, 5H), 1.46-1.57 (m, 1H), 1.60-2.00 (m, 4H), 2.02-2.14 (m, 1H), 2.23 (s, 3H), 3.90 (s, 3H), 4.39 (t, J=8.2 Hz, 1H), 4.70 (d, J=8.2 Hz, 1H), 6.84 (dd, J=8.6, 3.0 Hz, 1H), 6.89-6.97 (m, 1H), 7.04-7.10 (m, 1H), 7.22-7.30 (m, 1H), 7.88 (d, J=8.6 Hz, 1H), 8.08 (d, J=3.0 Hz, 1H).

(2) 5-{[cyclohexyl(5-fluoro-3-methyl-1-benzofuran-2-yl)methyl]amino}pyridine-2-carboxylic acid To a mixture of methyl 5-{[cyclohexyl(5-fluoro-3-methyl-1-benzofuran-2-yl)methyl]amino}pyridine-2-carboxylate (909 mg) synthesized above, ethanol (20 mL) and tetrahydrofuran (20 mL) was added 1N aqueous sodium hydroxide solution (20 mL), and the mixture was stirred with heating under reflux for 5 hr, and concentrated under reduced pressure. 1N Hydrochloric acid (20 mL) was added to the residue, and the mixture was extracted with ethyl acetate. The extract was washed with saturated brine, dried over magnesium sulfate, and concentrated under reduced pressure. The residue was washed with hexane to give the title object compound (751 mg, 86%) as a pale-brown solid.

$^1$H NMR (300 MHz, CDCl$_3$) δ ppm 0.94-1.39 (m, 5H), 1.46-1.60 (m, 1H), 1.62-2.02 (m, 4H), 2.02-2.15 (m, 1H), 2.25 (s, 3H), 4.41 (t, J=7.9 Hz, 1H), 4.72-4.83 (m, 1H), 6.90-7.00 (m, 2H), 7.07-7.13 (m, 1H), 7.24-7.33 (m, 1H), 7.91-7.98 (m, 2H).

(3) ethyl 3-{[(5-{[cyclohexyl(5-fluoro-3-methyl-1-benzofuran-2-yl)methyl]amino}pyridin-2-yl)carbonyl]amino}propanoate To a mixture of 5-{[cyclohexyl(5-fluoro-3-methyl-1-benzofuran-2-yl)methyl]amino}pyridine-2-carboxylic acid (300 mg) synthesized above, β-alanine ethyl ester hydrochloride (181 mg), 1-hydroxybenzotriazole monohydrate (181 mg), triethylamine (328 μL) and N,N-dimethylformamide (10 mL) was added 1-ethyl-3-(3-dimethylaminopropyl)carbodiimide hydrochloride (226 mg), and the mixture was stirred at room temperature overnight. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (361 mg, 96%) as a pale-yellow oil.

$^1$H NMR (300 MHz, CDCl$_3$) δ ppm 0.94-1.39 (m, 8H), 1.46-2.00 (m, 5H), 2.03-2.14 (m, 1H), 2.24 (s, 3H), 2.60 (t, J=6.2 Hz, 2H), 3.64-3.72 (m, 2H), 4.15 (q, J=7.1 Hz, 2H), 4.34-4.42 (m, 1H), 4.45-4.52 (m, 1H), 6.86-6.98 (m, 2H), 7.05-7.10 (m, 1H), 7.24-7.30 (m, 1H), 7.87-7.93 (m, 2H), 8.06-8.13 (m, 1H).

(4) 3-{[(5-{[cyclohexyl(5-fluoro-3-methyl-1-benzofuran-2-yl)methyl]amino}pyridin-2-yl)carbonyl]amino}propanoic acid To a mixture of ethyl 3-{[(5-{[cyclohexyl(5-fluoro-3-methyl-1-benzofuran-2-yl)methyl]amino}pyridin-2-yl)carbonyl]amino}propanoate (361 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (324 mg, 95%) as a white solid.

$^1$H NMR (300 MHz, CDCl$_3$) δ ppm 0.93-1.36 (m, 5H), 1.45-1.56 (m, 1H), 1.61-2.00 (m, 4H), 2.01-2.12 (m, 1H), 2.22 (s, 3H), 2.65 (t, J=6.1 Hz, 2H), 3.64-3.75 (m, 2H), 4.37 (d, J=8.0 Hz, 1H), 6.85-6.99 (m, 2H), 7.03-7.10 (m, 1H), 7.23-7.30 (m, 1H), 7.86-7.94 (m, 2H), 8.14 (t, J=6.2 Hz, 1H).

Example A56

3-{[(5-{[cyclohexyl(5-fluoro-3-methyl-1-benzofuran-2-yl)methyl]amino}pyridin-2-yl)carbonyl](methyl)amino}propanoic acid

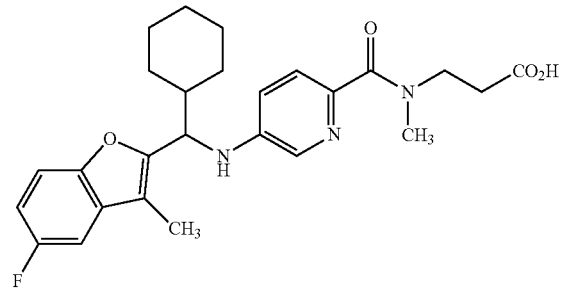

(1) ethyl 3-{[(5-{[cyclohexyl(5-fluoro-3-methyl-1-benzofuran-2-yl)methyl]amino}pyridin-2-yl)carbonyl](methyl)amino}propanoate To a mixture of 5-{[cyclohexyl(5-fluoro-3-methyl-1-benzofuran-2-yl)methyl]amino}pyridine-2-carboxylic acid (300 mg) synthesized in Example A55(2), ethyl 3-(methylamino)propanoate (155 mg), 1-hydroxybenzotriazole monohydrate (181 mg), triethylamine (328 μL) and N,N-dimethylformamide (10 mL) was added 1-ethyl-3-(3-dimethylaminopropyl)carbodiimide hydrochloride (226 mg), and the mixture was stirred at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (20-60% ethyl acetate/hexane) to give the title object compound (318 mg, 82%) as a pale-yellow oil.

$^1$H NMR (300 MHz, CDCl$_3$) δ ppm 0.93-1.38 (m, 8H), 1.46-1.57 (m, 1H), 1.60-1.99 (m, 4H), 2.03-2.16 (m, 1H), 2.22 (s, 3H), 2.63-2.78 (m, 2H), 3.00-3.21 (m, 3H), 3.69-3.87 (m, 2H), 4.01-4.19 (m, 2H), 4.32-4.40 (m, 1H), 4.41-4.49 (m, 1H), 6.84-6.98 (m, 2H), 7.04-7.11 (m, 1H), 7.24-7.31 (m, 1H), 7.44-7.59 (m, 1H), 7.88-7.95 (m, 1H).

(2) 3-{[(5-{[cyclohexyl(5-fluoro-3-methyl-1-benzofuran-2-yl)methyl]amino}pyridin-2-yl)carbonyl](methyl)amino}propanoic acid To a mixture of ethyl 3-{[(5-{[cyclohexyl(5-fluoro-3-methyl-1-benzofuran-2-yl)methyl]amino}pyridin-2-yl)carbonyl](methyl)amino}propanoate (318 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (262 mg, 87%) as a white solid.

$^1$H NMR (300 MHz, CDCl$_3$) δ ppm 0.93-1.37 (m, 5H), 1.46-1.56 (m, 1H), 1.60-1.99 (m, 4H), 2.03-2.13 (m, 1H), 2.23 (s, 3H), 2.68-2.89 (m, 2H), 3.09 (br s, 3H), 3.77 (t, J=6.8 Hz, 2H), 4.36 (d, J=8.3 Hz, 1H), 6.87-6.99 (m, 2H), 7.05-7.11 (m, 1H), 7.24-7.32 (m, 1H), 7.48-7.66 (m, 1H), 7.90-8.00 (m, 1H).

Example A57

3-{[(5-{[cyclohexyl(5-fluoro-3-methyl-1-benzofuran-2-yl)methyl]amino}pyridin-2-yl)carbonyl]methyl)amino}propanoic acid

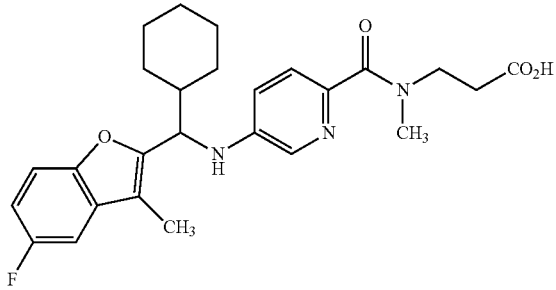 [SMILES: Cc1c(C(Nc2ccc(C(=O)N(C)CCC(=O)O)nc2)C2CCCCC2)oc2ccc(F)cc12]

Ethyl 3-{[(5-{[cyclohexyl(5-fluoro-3-methyl-1-benzofuran-2-yl)methyl]amino}pyridin-2-yl)carbonyl](methyl)amino}propanoate (5.83 g) synthesized in Example A56(1) was fractionated by high performance liquid chromatography (column: CHIRALPAK AD (50 mm ID×500 mL, manufactured by Daicel Chemical Industries, Ltd., mobile phase: hexane/ethanol (500/500), flow rate: 60 mL/min, column temperature: room temperature). The fraction containing an optically active form having a shorter retention time under the above-mentioned high performance liquid chromatography conditions was concentrated to give an amorphous form (2.90 g, 99.9% ee). To a mixture of the obtained amorphous form, ethanol (10 mL) and tetrahydrofuran (10 mL) was added 1N lithium hydroxide aqueous solution (12 mL), and the mixture was stirred at room temperature for 1 hr, and concentrated under reduced pressure. The residue was dissolved in water (30 mL), and 1N hydrochloric acid (12 mL) was added at 0° C. The resulting precipitate was collected by filtration to give the title object compound (2.67 g, 99%, 99.9% ee) as a white solid.

$^1$H NMR (300 MHz, DMSO-d$_6$) δ ppm 0.98-1.29 (m, 5H) 1.30-1.39 (m, 1H) 1.63 (brs, 2H) 1.75 (d, J=11.36 Hz, 1H) 1.82-2.00 (m, 1H) 2.09 (d, J=11.74 Hz, 1H) 2.25 (s, 3H) 2.53-2.66 (m, 2H) 2.88-3.03 (m, 3H) 3.32 (br s, 2H) 4.51 (t, J=8.33 Hz, 1H) 6.80 (d, J=8.33 Hz, 1H) 6.96 (dd, J=8.71, 2.65 Hz, 1H) 7.05 (td, J=9.28, 2.65 Hz, 1H) 7.26-7.39 (m, 2H) 7.47 (dd, J=8.90, 3.98 Hz, 1H) 7.95 (d, J=2.27 Hz, 1H) 12.26 (br s, 1H).

Example A58

3-{[(5-{[cyclohexyl(5-fluoro-3-methyl-1-benzofuran-2-yl)methyl]amino}pyridin-2-yl)carbonyl]methyl)amino}propanoic acid

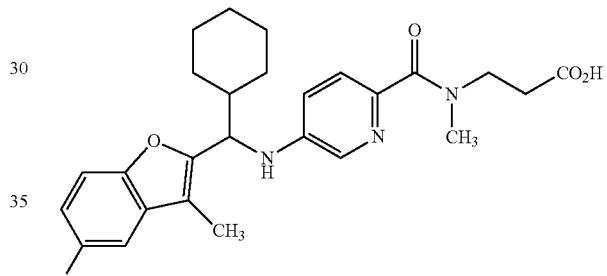

Ethyl 3-{[(5-{[cyclohexyl(5-fluoro-3-methyl-1-benzofuran-2-yl)methyl]amino}pyridin-2-yl)carbonyl](methyl)amino}propanoate (5.83 g) synthesized in Example A56(1) was fractionated by high performance liquid chromatography (column: CHIRALPAK AD (50 mm ID×500 mL, manufactured by Daicel Chemical Industries, Ltd., mobile phase: hexane/ethanol (500/500), flow rate: 60 mL/min, column temperature: room temperature). The fraction containing an optically active form having a longer retention time under the above-mentioned high performance liquid chromatography conditions was concentrated to give an amorphous form (2.82 g, 99.9% ee). To a mixture of the obtained amorphous form, ethanol (10 mL) and tetrahydrofuran (10 mL) was added 1N lithium hydroxide aqueous solution (12 mL), and the mixture was stirred at room temperature for 1 hr and concentrated under reduced pressure. The residue was dissolved in water (30 mL), and 1N hydrochloric acid (12 mL) was added at 0° C. The resulting precipitate was collected by filtration to give the title object compound (2.64 g, 97%, 99.9% ee) as a white solid.

$^1$H NMR (300 MHz, DMSO-d$_6$) δ ppm 0.98-1.29 (m, 5H) 1.30-1.39 (m, 1H) 1.63 (brs, 2H) 1.75 (d, J=11.36 Hz, 1H) 1.82-2.00 (m, 1H) 2.09 (d, J=11.74 Hz, 1H) 2.25 (s, 3H) 2.53-2.66 (m, 2H) 2.88-3.03 (m, 3H) 3.32 (br s, 2H) 4.51 (t, J=8.33 Hz, 1H) 6.80 (d, J=8.33 Hz, 1H) 6.96 (dd, J=8.71, 2.65

Hz, 1H) 7.05 (td, J=9.28, 2.65 Hz, 1H) 7.26-7.39 (m, 2H) 7.47 (dd, J=8.90, 3.98 Hz, 1H) 7.95 (d, J=2.27 Hz, 1H) 12.26 (br s, 1H).

Example A59

3-{[(5-{[cyclohexyl(3-methyl-1-benzothiophen-2-yl)methyl]amino}pyridin-2-yl)carbonyl](methyl)amino}propanoic acid

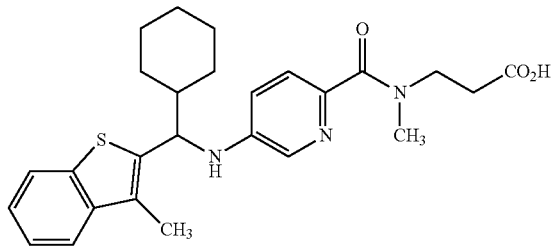

(1) methyl 5-{[cyclohexyl(3-methyl-1-benzothiophen-2-yl)methyl]amino}pyridine-2-carboxylate To a mixture of 2-[chloro(cyclohexyl)methyl]-3-methyl-1-benzothiophene (664 mg) synthesized in Example A10(2), methyl 5-aminopyridine-2-carboxylate (362 mg), sodium iodide (714 mg) and N,N-dimethylformamide (10 mL) was added sodium carbonate (505 mg), and the mixture was stirred at 80° C. overnight. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (460 mg, 49%) as a pale-yellow solid.

$^1$H NMR (300 MHz, CDCl$_3$) δ ppm 1.03-1.37 (m, 5H), 1.54-1.88 (m, 5H), 2.07-2.18 (m, 1H), 2.47 (s, 3H), 3.88 (s, 3H), 4.54-4.68 (m, 2H), 6.78 (dd, J=8.6, 2.7 Hz, 1H), 7.22-7.30 (m, 1H), 7.31-7.38 (m, 1H), 7.63 (d, J=8.0 Hz, 1H), 7.68 (d, J=8.0 Hz, 1H), 7.84 (d, J=8.6 Hz, 1H), 8.05 (d, J=2.7 Hz, 1H).

(2) 5-{[cyclohexyl(3-methyl-1-benzothiophen-2-yl)methyl]amino}pyridine-2-carboxylic acid To a mixture of methyl 5-{[cyclohexyl(3-methyl-1-benzothiophen-2-yl)methyl]amino}pyridine-2-carboxylate (460 mg) synthesized above, ethanol (5 mL) and tetrahydrofuran (5 mL) was added 1N aqueous sodium hydroxide solution (5.00 mL), and the mixture was stirred overnight with heating under reflux, and concentrated under reduced pressure. The residue was dissolved in water (10 mL), 1N hydrochloric acid (5.00 mL) was added at 0° C., and the mixture was extracted with ethyl acetate. The extract was washed with saturated brine, dried over magnesium sulfate, and concentrated under reduced pressure to give the title object compound (452 mg, quantitative) as a pale-brown solid.

$^1$H NMR (300 MHz, CDCl$_3$) δ ppm 1.03-1.38 (m, 5H), 1.56-1.90 (m, 5H), 2.08-2.18 (m, 1H), 2.50 (s, 3H), 4.56-4.64 (m, 1H), 4.68-4.77 (m, 1H), 6.88 (dd, J=8.7, 2.6 Hz, 1H), 7.25-7.33 (m, 1H), 7.34-7.41 (m, 1H), 7.66 (d, J=7.4 Hz, 1H), 7.71 (d, J=7.7 Hz, 1H), 7.86-7.93 (m, 2H).

(3) ethyl 3-{[(5-{[cyclohexyl(3-methyl-1-benzothiophen-2-yl)methyl]amino}pyridin-2-yl)carbonyl](methyl)amino}propanoate To a mixture of 5-{[cyclohexyl(3-methyl-1-benzothiophen-2-yl)methyl]amino}pyridine-2-carboxylic acid (200 mg) synthesized above, ethyl 3-(methylamino)propanoate (104 mg), 1-hydroxybenzotriazole monohydrate (121 mg), triethylamine (220 μL) and N,N-dimethylformamide (10 mL) was added 1-ethyl-3-(3-dimethylaminopropyl)carbodiimide hydrochloride (151 mg), and the mixture was stirred at room temperature for 4 hr. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (141 mg, 54%) as a white solid.

$^1$H NMR (300 MHz, CDCl$_3$) δ ppm 1.03-1.35 (m, 8H), 1.55-1.88 (m, 5H), 2.06-2.17 (m, 1H), 2.46 (s, 3H), 2.61-2.76 (m, 2H), 2.98-3.18 (m, 3H), 3.69-3.87 (m, 2H), 3.98-4.18 (m, 2H), 4.39 (d, J=6.0 Hz, 1H), 4.51-4.58 (m, 1H), 6.81 (dd, J=8.5, 2.7 Hz, 1H), 7.23-7.30 (m, 1H), 7.31-7.38 (m, 1H), 7.39-7.55 (m, 1H), 7.63 (d, J=7.4 Hz, 1H), 7.70 (d, J=7.7 Hz, 1H), 7.84-7.91 (m, 1H).

(4) 3-{[(5-{[cyclohexyl(3-methyl-1-benzothiophen-2-yl)methyl]amino}pyridin-2-yl)carbonyl](methyl)amino}propanoic acid To a mixture of ethyl 3-{[(5-{[cyclohexyl(3-methyl-1-benzothiophen-2-yl)methyl]amino}pyridin-2-yl)carbonyl](methyl)amino}propanoate (141 mg) synthesized above, tetrahydrofuran (5 mL) and ethanol (5 mL) was added 1N aqueous sodium hydroxide solution (1.00 mL), and the mixture was stirred at room temperature for 30 min and concentrated under reduced pressure. The residue was dissolved in water (10 mL), and 1N hydrochloric acid (1.00 mL) was added at 0° C. The resulting precipitate was collected by filtration to give the title object compound (112 mg, 84%) as a white solid.

$^1$H NMR (300 MHz, CDCl$_3$) δ ppm 1.01-1.37 (m, 5H), 1.54-1.89 (m, 5H), 2.06-2.18 (m, 1H), 2.47 (s, 3H), 2.73-2.90 (m, 2H), 3.08 (br s, 3H), 3.76 (t, J=6.4 Hz, 2H), 4.55 (d, J=8.0 Hz, 1H), 6.83-6.93 (m, 1H), 7.23-7.33 (m, 1H), 7.33-7.41 (m, 1H), 7.47-7.63 (m, 1H), 7.65 (d, J=7.6 Hz, 1H), 7.71 (d, J=7.6 Hz, 1H), 7.85-7.94 (m, 1H).

Example A60

3-{[(5-{[cyclohexyl(3-methyl-1-benzothiophen-2-yl)methyl]amino}pyridin-2-yl)carbonyl](methyl)amino}propanoic acid

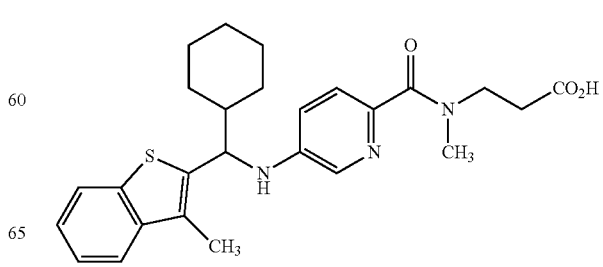

Ethyl 3-{[(5-{[cyclohexyl(3-methyl-1-benzothiophen-2-yl)methyl]amino}pyridin-2-yl)carbonyl](methyl)amino}propanoate (9.31 g) synthesized in Example A59(3) was fractionated by high performance liquid chromatography (column: CHIRALPAK AD (50 mm ID×500 mL, manufactured by Daicel Chemical Industries, Ltd., mobile phase: hexane/2-propanol (700/300-200/800), flow rate: 60 mL/min-50 mL/min, column temperature: room temperature). The fraction containing an optically active form having a shorter retention time under the above-mentioned high performance liquid chromatography conditions was concentrated to give an amorphous form (4.67 g, 99.9% ee). To a mixture of the obtained amorphous form, ethanol (20 mL) and tetrahydrofuran (20 mL) was added 1N lithium hydroxide aqueous solution (20 mL), and the mixture was stirred at room temperature for 1 hr and concentrated under reduced pressure. The residue was dissolved in water (20 mL), and 1N hydrochloric acid (20 mL) was added at 0° C. The resulting precipitate was collected by filtration to give the title object compound (4.17 g, 99%, 99.9% ee) as a white solid.

$^1$H NMR (300 MHz, DMSO-$d_6$) δ ppm 1.00-1.32 (m, 5H) 1.37-1.51 (m, 1H) 1.52-1.84 (m, 4H) 2.07-2.20 (m, 1H) 2.46 (s, 3H) 2.50-2.57 (m, 2H) 2.87-3.01 (m, 3H) 3.27-3.36 (m, 5H) 3.43-3.68 (m, 2H) 4.63 (t, J=7.38 Hz, 1H) 6.87 (d, J=6.82 Hz, 2H) 7.19-7.41 (m, 3H) 7.69 (d, J=7.19 Hz, 1H) 7.79 (d, J=7.57 Hz, 1H) 7.89 (d, J=2.65 Hz, 1H) 12.16 (brs, 1H).

Example A61

3-{[(5-{[cyclohexyl(3-methyl-1-benzothiophen-2-yl)methyl]amino}pyridin-2-yl)carbonyl](methyl)amino}propanoic acid

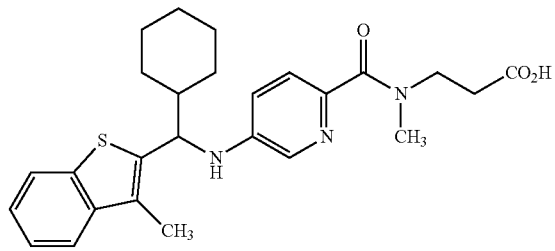

Ethyl 3-{[(5-{[cyclohexyl(3-methyl-1-benzothiophen-2-yl)methyl]amino}pyridin-2-yl)carbonyl](methyl)amino}propanoate (9.31 g) synthesized in Example A59(3) was fractionated by high performance liquid chromatography (column: CHIRALPAK AD (50 mm ID×500 mL, manufactured by Daicel Chemical Industries, Ltd., mobile phase: hexane/2-propanol (700/300-200/800), flow rate: 60 mL/min-50 mL/min, column temperature: room temperature). The fraction containing an optically active form having a longer retention time under the above-mentioned high performance liquid chromatography conditions was concentrated to give an amorphous form (4.52 g, 99.9% ee). To a mixture of the obtained amorphous form, ethanol (20 mL) and tetrahydrofuran (20 mL) was added 1N lithium hydroxide aqueous solution (20 mL), and the mixture was stirred at room temperature for 1 hr and concentrated under reduced pressure. The residue was dissolved in water (20 mL), and 1N hydrochloric acid (20 mL) was added at 0° C. The resulting precipitate was collected by filtration to give the title object compound (4.12 g, 98%, 99.9% ee) as a white solid.

$^1$H NMR (300 MHz, DMSO-$d_6$) δ ppm 1.00-1.32 (m, 5H) 1.37-1.51 (m, 1H) 1.52-1.84 (m, 4H) 2.07-2.20 (m, 1H) 2.46 (s, 3H) 2.50-2.57 (m, 2H) 2.87-3.01 (m, 3H) 3.27-3.36 (m, 5H) 3.43-3.68 (m, 2H) 4.63 (t, J=7.38 Hz, 1H) 6.87 (d, J=6.82 Hz, 2H) 7.19-7.41 (m, 3H) 7.69 (d, J=7.19 Hz, 1H) 7.79 (d, J=7.57 Hz, 1H) 7.89 (d, J=2.65 Hz, 1H) 12.16 (brs, 1H).

Example A62

3-{[(5-{[cyclohexyl(3-methyl-1-benzothiophen-2-yl)methyl]amino}pyridin-2-yl)carbonyl]amino}propanoic acid

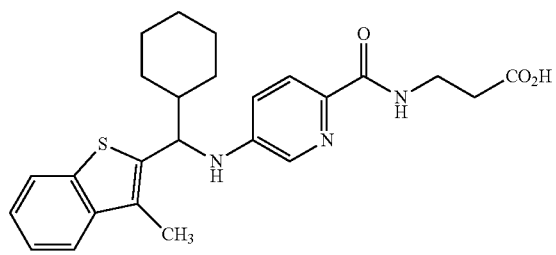 [SMILES: Cc1c(C(Nc2ccc(C(=O)NCCC(=O)O)nc2)C2CCCCC2)sc2ccccc12]

(1) ethyl 3-{[(5-{[cyclohexyl(3-methyl-1-benzothiophen-2-yl)methyl]amino}pyridin-2-yl)carbonyl]amino}propanoate To a mixture of 5-{[cyclohexyl(3-methyl-1-benzothiophen-2-yl)methyl]amino}pyridine-2-carboxylic acid (247 mg) synthesized in Example A59(2), β-alanine ethyl ester hydrochloride (149 mg), 1-hydroxybenzotriazole monohydrate (149 mg), triethylamine (270 μL) and N,N-dimethylformamide (10 mL) was added 1-ethyl-3-(3-dimethylaminopropyl)carbodiimide hydrochloride (186 mg), and the mixture was stirred at room temperature overnight. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (274 mg, 88%) as a colorless oil.

$^1$H NMR (300 MHz, CDCl$_3$) δ ppm 1.02-1.35 (m, 8H), 1.54-1.88 (m, 5H), 2.06-2.18 (m, 1H), 2.47 (s, 3H), 2.58 (t, J=6.3 Hz, 2H), 3.61-3.71 (m, 2H), 4.13 (q, J=7.1 Hz, 2H), 4.48-4.60 (m, 2H), 6.80-6.87 (m, 1H), 7.22-7.30 (m, 1H), 7.31-7.38 (m, 1H), 7.64 (d, J=7.4 Hz, 1H), 7.69 (d, J=8.0 Hz, 1H), 7.83-7.88 (m, 2H), 8.07 (t, J=6.3 Hz, 1H).

(2) 3-{[(5-{[cyclohexyl(3-methyl-1-benzothiophen-2-yl)methyl]amino}pyridin-2-yl)carbonyl]amino}propanoic acid To a mixture of ethyl 3-{[(5-{[cyclohexyl(3-methyl-1-benzothiophen-2-yl)methyl]amino}pyridin-2-yl)carbonyl]amino}propanoate (274 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), and 1N hydrochloric acid (1.00 mL) was added at 0° C. The resulting precipitate was collected by filtration to give the title object compound (235 mg, 91%) as a white solid.

¹H NMR (300 MHz, CDCl₃) δ ppm 1.02-1.36 (m, 5H), 1.54-1.89 (m, 5H), 2.06-2.18 (m, 1H), 2.47 (s, 3H), 2.64 (t, J=6.0 Hz, 2H), 3.61-3.73 (m, 2H), 4.56 (d, J=7.9 Hz, 1H), 6.84 (dd, J=8.5, 2.4 Hz, 1H), 7.22-7.31 (m, 1H), 7.31-7.40 (m, 1H), 7.64 (d, J=7.9 Hz, 1H), 7.69 (d, J=7.9 Hz, 1H), 7.82-7.91 (m, 2H), 8.11 (t, J=6.0 Hz, 1H).

Example A63

3-{[(4-{[cyclopentyl(3-methyl-1-benzothiophen-2-yl)methyl]amino}phenyl)carbonyl]amino}propanoic acid

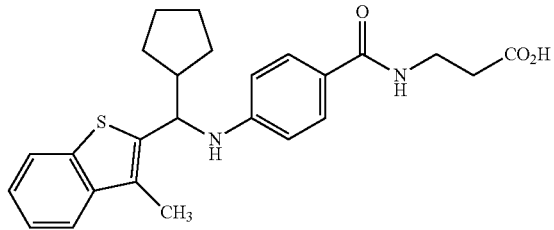 [SMILES: Cc1c(C(Nc2ccc(C(=O)NCCC(=O)O)cc2)C2CCCC2)sc2ccccc12]

(1) cyclopentyl(3-methyl-1-benzothiophen-2-yl)methanone

To a mixture of 3-methyl-1-benzothiophene (1.00 g), cyclopentanecarbonyl chloride (903 µL) and nitromethane (10 mL) was added aluminum chloride (1.35 g) at 0° C., and the mixture was stirred for 1.5 hr. Water was added to quench the reaction, and the reaction mixture was extracted with ethyl acetate. The extract was washed with saturated brine, dried over magnesium sulfate, and concentrated under reduced pressure. The residue was purified by NH-silica gel column chromatography (ethyl acetate) to give the title object compound (1.54 g, 93%) as a pale-brown oil.

¹H NMR (300 MHz, CDCl₃) δ ppm 1.60-1.84 (m, 4H), 1.92-2.03 (m, 4H), 2.78 (s, 3H), 3.48-3.60 (m, 1H), 7.40-7.52 (m, 2H), 7.81-7.91 (m, 2H).

(2) methyl 4-{[cyclopentyl(3-methyl-1-benzothiophen-2-yl)methyl]amino}benzoate

To a mixture of cyclopentyl(3-methyl-1-benzothiophen-2-yl)methanone (1.54 g) synthesized above, methyl 4-aminobenzoate (1.05 g), triethylamine (7.02 mL) and methylene chloride (30 mL) was added titanium (IV) chloride (829 µL), and the mixture was stirred under argon atmosphere at room temperature for 3 days. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (30 mL) of the obtained oil in tetrahydrofuran were added acetic acid (721 µL) and sodium cyanoborohydride (792 mg), and the mixture was stirred at room temperature for 1 hr. Saturated aqueous sodium hydrogen carbonate solution was evaporated to quench the reaction, the organic solvent was evaporated in an evaporator, and the residue was extracted with ethyl acetate. The extract was washed with saturated brine, dried over magnesium sulfate, and concentrated under reduced pressure. The residue was purified by silica gel column chromatography (0-30% ethyl acetate/hexane) to give the title object compound (1.56 g, 65%) as an orange solid.

¹H NMR (300 MHz, CDCl₃) δ ppm 1.30-1.44 (m, 1H), 1.45-1.82 (m, 6H), 1.90-2.06 (m, 1H), 2.28-2.46 (m, 1H), 2.50 (s, 3H), 3.79 (s, 3H), 4.47-4.56 (m, 1H), 4.62 (d, J=9.1 Hz, 1H), 6.51 (d, J=9.1 Hz, 2H), 7.22-7.29 (m, 1H), 7.31-7.37 (m, 1H), 7.61-7.66 (m, 1H), 7.67-7.72 (m, 1H), 7.76 (d, J=9.1 Hz, 2H).

(3) 4-{[cyclopentyl(3-methyl-1-benzothiophen-2-yl)methyl]amino}benzoic acid

To a mixture of methyl 4-{[cyclopentyl(3-methyl-1-benzothiophen-2-yl)methyl]amino}benzoate (1.56 g) synthesized above, tetrahydrofuran (20 mL) and ethanol (20 mL) was added 1N aqueous sodium hydroxide solution (20.0 mL), and the mixture was stirred with heating under reflux for 4 hr, and concentrated under reduced pressure. The residue was dissolved in water (40 mL), and 1N hydrochloric acid (20.0 mL) was added at 0° C. The resulting precipitate was collected by filtration, and the obtained pale-brown solid was dissolved in ethyl acetate. The solution was washed with saturated brine, dried over magnesium sulfate, and concentrated under reduced pressure to give the title object compound (1.42 g, 95%) as a pale-brown solid.

¹H NMR (300 MHz, CDCl₃) δ ppm 1.30-1.45 (m, 1H), 1.45-1.82 (m, 6H), 1.90-2.05 (m, 1H), 2.27-2.45 (m, 1H), 2.50 (s, 3H), 4.63 (d, J=9.1 Hz, 1H), 6.52 (d, J=8.8 Hz, 2H), 7.22-7.29 (m, 1H), 7.31-7.38 (m, 1H), 7.61-7.66 (m, 1H), 7.67-7.71 (m, 1H), 7.80 (d, J=8.8 Hz, 2H).

(4) ethyl 3-{[(4-{[cyclopentyl(3-methyl-1-benzothiophen-2-yl)methyl]amino}phenyl)carbonyl]amino}propanoate To a mixture of 4-{[cyclopentyl(3-methyl-1-benzothiophen-2-yl)methyl]amino}benzoic acid (300 mg) synthesized above, β-alanine ethyl ester hydrochloride (189 mg), 1-hydroxybenzotriazole monohydrate (188 mg), triethylamine (343 µL) and N,N-dimethylformamide (10 mL) was added 1-ethyl-3-(3-dimethylaminopropyl)carbodiimide hydrochloride (236 mg), and the mixture was stirred at room temperature for 5 hr. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (331 mg, 87%) as a pale-brown oil.

¹H NMR (300 MHz, CDCl₃) δ ppm 1.23 (t, J=7.1 Hz, 3H), 1.30-1.45 (m, 1H), 1.45-1.81 (m, 6H), 1.90-2.07 (m, 1H), 2.27-2.47 (m, 1H), 2.50 (s, 3H), 2.56 (t, J=5.8 Hz, 2H), 3.59-3.68 (m, 2H), 4.12 (q, J=7.1 Hz, 2H), 4.42 (d, J=5.7 Hz, 1H), 4.60 (dd, J=9.1, 5.7 Hz, 1H), 6.48-6.60 (m, 3H), 7.21-7.29 (m, 1H), 7.30-7.37 (m, 1H), 7.50 (d, J=8.8 Hz, 2H), 7.61-7.65 (m, 1H), 7.66-7.72 (m, 1H).

(5) 3-{[(4-{[cyclopentyl(3-methyl-1-benzothiophen-2-yl)methyl]amino}phenyl)carbonyl]amino}propanoic acid To a mixture of ethyl 3-{[(4-{[cyclopentyl(3-methyl-1-benzothiophen-2-yl)methyl]amino}phenyl)carbonyl]amino}propanoate (331 mg) synthesized above, tetrahydrofuran (5 mL) and ethanol (5 mL) was added 1N aqueous sodium hydroxide solution (2.00 mL), and the mixture was stirred at room temperature for 1.5 hr, and concentrated under reduced pressure. The residue was dissolved in water (10 mL), and 1N hydrochloric acid (2.00 mL) was added at 0° C. The resulting precipitate was collected by filtration to give the title object compound (276 mg, 89%) as a white solid.

$^1$H NMR (300 MHz, CDCl$_3$) δ ppm 1.28-1.43 (m, 1H), 1.44-1.80 (m, 6H), 1.89-2.03 (m, 1H), 2.25-2.43 (m, 1H), 2.48 (s, 3H), 2.56 (t, J=5.3 Hz, 2H), 3.52-3.63 (m, 2H), 4.58 (d, J=9.0 Hz, 1H), 6.45-6.60 (m, 3H), 7.20-7.28 (m, 1H), 7.29-7.37 (m, 1H), 7.46 (d, J=8.3 Hz, 2H), 7.62 (d, J=7.5 Hz, 1H), 7.68 (d, J=7.9 Hz, 1H).

Example A64

3-{[(4-{[cyclopentyl(3-methyl-1-benzothiophen-2-yl)methyl]amino}phenyl)carbonyl](methyl)amino}propanoic acid

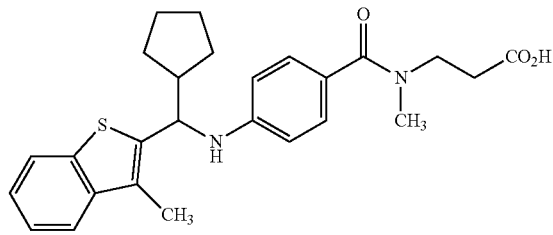 [SMILES: Cc1c(C(Nc2ccc(C(=O)N(C)CCC(=O)O)cc2)C2CCCC2)sc2ccccc12]

(1) ethyl 3-{[(4-{[cyclopentyl(3-methyl-1-benzothiophen-2-yl)methyl]amino}phenyl)carbonyl](methyl)amino}propanoate To a mixture of 4-{[cyclopentyl(3-methyl-1-benzothiophen-2-yl)methyl]amino}benzoic acid (300 mg) synthesized in Example A63(3), ethyl 3-(methylamino)propanoate (161 mg), 1-hydroxybenzotriazole monohydrate (188 mg), triethylamine (343 μL) and N,N-dimethylformamide (10 mL) was added 1-ethyl-3-(3-dimethylaminopropyl)carbodiimide hydrochloride (236 mg), and the mixture was stirred at room temperature for 5 hr. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (228 mg, 58%) as a pale-brown oil.

$^1$H NMR (300 MHz, CDCl$_3$) δ ppm 1.21 (t, J=7.2 Hz, 3H), 1.31-1.44 (m, 1H), 1.45-1.83 (m, 6H), 1.89-2.04 (m, 1.H), 2.28-2.43 (m, 1H), 2.49 (s, 3H), 2.59 (t, J=7.1 Hz, 2H), 2.98 (s, 3H), 3.68 (t, J=7.1 Hz, 2H), 4.09 (q, J=7.2 Hz, 2H), 4.27-4.33 (m, 1H), 4.53-4.61 (m, 1H), 6.51 (d, J=8.5 Hz, 2H), 7.17 (d, J=8.5 Hz, 2H), 7.22-7.29 (m, 1H), 7.31-7.38 (m, 1H), 7.61-7.66 (m, 1H), 7.68-7.73 (m, 1H).

(2) 3-{[(4-{[cyclopentyl(3-methyl-1-benzothiophen-2-yl)methyl]amino}phenyl)carbonyl](methyl)amino}propanoic acid To a mixture of ethyl 3-{[(4-{[cyclopentyl(3-methyl-1-benzothiophen-2-yl)methyl]amino}phenyl)carbonyl](methyl)amino}propanoate (228 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration to give the title object compound (198 mg, 92%) as a white solid.

$^1$H NMR (300 MHz, CDCl$_3$) δ ppm 1.28-1.44 (m, 1H), 1.44-1.79 (m, 6H), 1.89-2.04 (m, 1H), 2.26-2.43 (m, 1H), 2.49 (s, 3H), 2.62 (t, J=6.2 Hz, 2H), 2.98 (s, 3H), 3.66 (t, J=6.2 Hz, 2H), 4.57 (d, J=9.0 Hz, 1H), 6.51 (d, J=8.5 Hz, 2H), 7.20 (d, J=8.5 Hz, 2H), 7.23-7.30 (m, 1H), 7.31-7.38 (m, 1H), 7.64 (d, J=7.5 Hz, 1H), 7.71 (d, J=7.5 Hz, 1H).

Example A65

3-{[(4-{[cyclopentyl(3-methyl-1-benzothiophen-2-yl)methyl]amino}phenyl)carbonyl](methyl)amino}propanoic acid

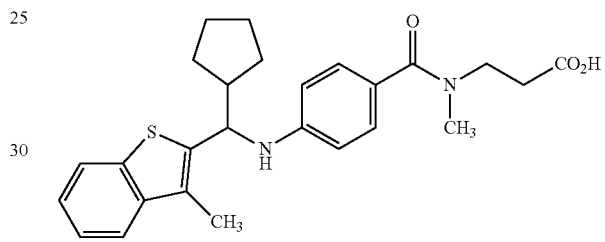

Ethyl 3-{[(4-{[cyclopentyl(3-methyl-1-benzothiophen-2-yl)methyl]amino}phenyl)carbonyl](methyl)amino}propanoate (19.7 g) synthesized in Example A64(1) was fractionated by high performance liquid chromatography (column: CHIRALPAK AD (50 mm ID×500 mL, manufactured by Daicel Chemical Industries, Ltd., mobile phase: hexane/ethanol (500/500), flow rate: 60 mL/min, column temperature: room temperature). The fraction containing an optically active form having a shorter retention time under the above-mentioned high performance liquid chromatography conditions was concentrated to give an amorphous form (8.75 g, 99.9% ee). To a mixture of the obtained amorphous form, ethanol (100 mL) and tetrahydrofuran (100 mL) was added 1N aqueous sodium hydroxide solution (30 mL), and the mixture was stirred at room temperature for 5 hr and concentrated under reduced pressure. The residue was dissolved in water (200 mL), and 1N hydrochloric acid (30 mL) was added at 0° C., and the mixture was extracted with ethyl acetate. The extract was washed with saturated brine, dried over magnesium sulfate, and concentrated under reduced pressure to give the title object compound (7.54 g, 41%, 99.9% ee) as a white solid. The obtained solid was recrystallized from ethanol/water to give colorless crystals.

$^1$H NMR (300 MHz, CDCl$_3$) δ ppm 1.28-1.44 (m, 1H), 1.44-1.79 (m, 6H), 1.89-2.04 (m, 1H), 2.26-2.43 (m, 1H), 2.49 (s, 3H), 2.62 (t, J=6.2 Hz, 2H), 2.98 (s, 3H), 3.66 (t, J=6.2 Hz, 2H), 4.57 (d, J=9.0 Hz, 1H), 6.51 (d, J=8.5 Hz, 2H), 7.20

(d, J=8.5 Hz, 2H), 7.23-7.30 (m, 1H), 7.31-7.38 (m, 1H), 7.64 (d, J=7.5 Hz, 1H), 7.71 (d, J=7.5 Hz, 1H).

Example A66

3-{[(4-{[cyclopentyl(3-methyl-1-benzothiophen-2-yl)methyl]amino}phenyl)carbonyl](methyl)amino}propanoic acid

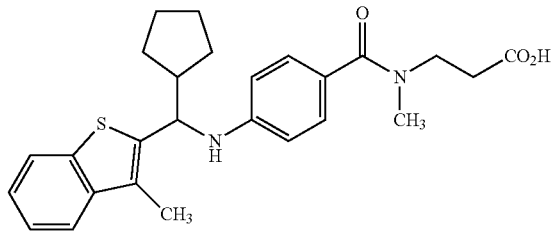 [SMILES: Cc1c(C(Nc2ccc(C(=O)N(C)CCC(=O)O)cc2)C2CCCC2)sc2ccccc12]

Ethyl 3-{[(4-{[cyclopentyl(3-methyl-1-benzothiophen-2-yl)methyl]amino}phenyl)carbonyl](methyl)amino}propanoate (19.7 g) synthesized in Example A64(1) was fractionated by high performance liquid chromatography (column: CHIRALPAK AD (50 mm ID×500 mL, manufactured by Daicel Chemical Industries, Ltd., mobile phase: hexane/ethanol (500/500), flow rate: 60 mL/min, column temperature: room temperature). The fraction containing an optically active form having a longer retention time under the above-mentioned high performance liquid chromatography conditions was concentrated to give an amorphous form (8.95 g, 99.9% ee). To a mixture of the obtained amorphous form, ethanol (100 mL) and tetrahydrofuran (100 mL) was added 1N aqueous sodium hydroxide solution (30 mL), and the mixture was stirred at room temperature for 3 hr and concentrated under reduced pressure. The residue was dissolved in water (200 mL), and 1N hydrochloric acid (35 mL) was added at 0° C., and the mixture was extracted with ethyl acetate. The extract was washed with saturated brine, dried over magnesium sulfate, and concentrated under reduced pressure to give the title object compound (8.06 g, 43%, 99.9% ee) as a white solid.

$^1$H NMR (300 MHz, CDCl$_3$) δ ppm 1.28-1.44 (m, 1H), 1.44-1.79 (m, 6H), 1.89-2.04 (m, 1H), 2.26-2.43 (m, 1H), 2.49 (s, 3H), 2.62 (t, J=6.2 Hz, 2H), 2.98 (s, 3H), 3.66 (t, J=6.2 Hz, 2H), 4.57 (d, J=9.0 Hz, 1H), 6.51 (d, J=8.5 Hz, 2H), 7.20 (d, J=8.5 Hz, 2H), 7.23-7:30 (m, 1H), 7.31-7.38 (m, 1H), 7.64 (d, J=7.5 Hz, 1H), 7.71 (d, J=7.5 Hz, 1H).

Example A67

Ethyl 3-{[(4-{[cyclopentyl(5-fluoro-3-methyl-1-benzofuran-2-yl)methyl]amino}phenyl)carbonyl](methyl)amino}propanoate

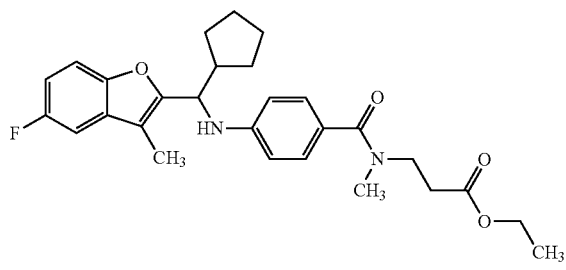 [SMILES: CCOC(=O)CCN(C)C(=O)c1ccc(NC(c2oc3ccc(F)cc3c2C)C2CCCC2)cc1]

(1) (2-acetyl-4-fluorophenoxy)acetic acid

A solution of 5'-fluoro-2'-hydroxyacetophenone (25.0 g), methyl bromoacetate (27.2 g), potassium carbonate (33.6 g) in N,N-dimethylformamide (250 mL) was stirred at room temperature for 1.5 hr. The insoluble material was filtered off, 1N hydrochloric acid was added to the filtrate, and the mixture was extracted with ethyl acetate. The extract was washed with saturated brine, dried over magnesium sulfate, and concentrated under reduced pressure to give a brown oil. Tetrahydrofuran (300 mL), ethanol (300 mL) and 1N aqueous sodium hydroxide solution (300 mL) were added to the obtained oil, and the mixture was stirred at room temperature for 30 min. The solvent was concentrated under reduced pressure, 1N hydrochloric acid (300 mL) was added, and the resulting crystals were collected by filtration. The crystals were dissolved in ethyl acetate, dried over magnesium sulfate, and concentrated under reduced pressure to give the title compound (23.7 g, 69%) as a white solid.

$^1$H NMR (300 MHz, CDCl$_3$) δ ppm 2.68 (s, 3H), 4.75 (s, 2H), 6.86-7.03 (m, 1H), 7.13-7.30 (m, 1H), 7.43-7.60 (m, 1H).

(2) 5-fluoro-3-methyl-1-benzofuran

A mixture of (2-acetyl-4-fluorophenoxy)acetic acid (22.94 g) synthesized above, sodium acetate (44.38 g) and acetic anhydride (200 mL) was stirred at 110° C. for 15 hr. The reaction mixture was cooled to room temperature, water was added and the mixture was extracted with ethyl acetate. The organic layer was washed with saturated aqueous sodium hydrogen carbonate solution and saturated brine, and dried over anhydrous magnesium sulfate. After filtration, the filtrate was concentrated. The residue was subjected to silica gel column chromatography (NH silica, hexane) to give the title compound (14.73 g, 91%) as a yellow oil.

$^1$H NMR (300 MHz, CDCl$_3$) δ ppm 2.20 (s, 3H), 6.91-7.03 (m, 1H), 7.15 (dd, J=8.3, 2.7 Hz, 1H), 7.35 (dd, J=8.7, 4.2 Hz, 1H), 7.42 (s, 1H).

(3) cyclopentyl(5-fluoro-3-methyl-1-benzofuran-2-yl)methanone

To a solution of 5-fluoro-3-methyl-1-benzofuran (2.0 g) synthesized above, cyclopentanecarbonylchloride (1.94 g) in nitromethane (40 mL) was added aluminum chloride (anhydrous) (2.66 g) at 0° C., and the mixture was stirred for 3 hr. Water was added to the reaction mixture and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-95:5, v/v) to give the title compound (2.11 g, 64%) as a colorless amorphous form.

$^1$H NMR (300 MHz, CDCl$_3$) δ ppm 1.67-2.09 (m, 8H), 2.57 (s, 3H), 3.64-3.91 (m, 1H), 7.10-7.23 (m, 1H), 7.25-7.31 (m, 1H), 7.38-7.53 (m, 1H).

(4) cyclopentyl(5-fluoro-3-methyl-1-benzofuran-2-yl)methanol

Cyclopentyl(5-fluoro-3-methyl-1-benzofuran-2-yl) methanone (27.15 g) synthesized above was dissolved in a mixed solvent of methanol (40 mL)-tetrahydrofuran (240 mL), and sodium tetrahydroborate (90%, 5.5 g) was added at 0° C. The reaction mixture was stirred at 0° C. for 2 hr. Water was added to the reaction mixture and the mixture was extracted with ethyl acetate. The organic layer was washed with saturated brine, and dried over anhydrous magnesium sulfate. After filtration, the filtrate was concentrated to give the title compound (29.26 g, 100%) as a yellow oil.

$^1$H NMR (300 MHz, CDCl$_3$) δ ppm 1.04-1.20 (m, 1H), 1.42-1.77 (m, 6H), 1.92-2.02 (m, 2H), 2.21 (s, 3H), 2.42-2.60 (m, 1H), 4.56 (dd, J=9.3, 5.9 Hz, 1H), 6.97 (td, J=9.1, 2.7 Hz, 1H), 7.11 (dd, J=8.7, 2.7 Hz, 1H), 7.33 (dd, J=8.9, 4.0 Hz, 1H).

(5) ethyl 3-{[(4-{[cyclopentyl(5-fluoro-3-methyl-1-benzofuran-2-yl)methyl]amino}phenyl)carbonyl](methyl)amino}propanoate To a solution of cyclopentyl(5-fluoro-3-methyl-1-benzofuran-2-yl)methanol (27.31 g) obtained above in tetrahydrofuran (200 mL) was added thionyl chloride (12.0 mL) at room temperature. The reaction mixture was stirred at room temperature for 2 hr. To the reaction mixture was added aqueous sodium hydrogen carbonate solution ice-cooled to 0° C., and the mixture was extracted with ethyl acetate. The organic layer was washed with saturated brine, and dried over anhydrous magnesium sulfate. After filtration, the filtrate was concentrated, ethyl 3-{[(4aminophenyl)carbonyl](methyl)amino}propanoate (28.90 g) obtained in Example 2(2), sodium iodide (16.48 g), sodium carbonate (23.3 g) and N,N-dimethylacetamide (200 mL) were added to the obtained residue, and the mixture was stirred at 80° C. for 18 hr. Water was added to the reaction mixture and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (17.88 g, 34%) as a yellow amorphous.

Example A68

3-{[(4-{[cyclopentyl(5-fluoro-3-methyl-1-benzofuran-2-yl)methyl]amino}phenyl)carbonyl](methyl)amino}propanoic acid

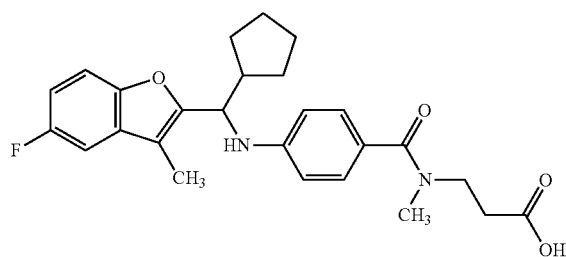 [SMILES: Cc1c(C(Nc2ccc(C(=O)N(C)CCC(=O)O)cc2)C2CCCC2)oc2ccc(F)cc12]

Ethyl 3-{[(4-{[cyclopentyl(5-fluoro-3-methyl-1-benzofuran-2-yl)methyl]amino}phenyl)carbonyl](methyl)amino}propanoate (460 mg) obtained in Example A67(5) was dissolved in ethanol (1.9 mL) and tetrahydrofuran (1.9 mL), 1N aqueous sodium hydroxide solution (1.9 mL) was added, and the mixture was stirred at room temperature for 1 hr. The solvent was evaporated under reduced pressure. Water (6 mL) was added, and the mixture was neutralized with 1N hydrochloric acid under ice-cooling and stirred for 1 hr. The resulting precipitate was collected by filtration and dried to give the title compound (352 mg, 81%) as a colorless solid.

$^1$H NMR (300 MHz, CDCl$_3$) δ ppm 1.23-1.74 (m, B H), 1.90-2.08 (m, 1H), 2.24 (s, 3H), 2.47 (d, J=8.0 Hz, 1H), 2.60-2.70 (m, 2H), 3.01 (s, 3H), 3.69 (t, J=6.6 Hz, 2H), 4.36 (d, J=9.1 Hz, 1H), 6.55 (d, J=8.7 Hz, 2H), 6.86-6.97 (m, 1H), 7.07 (dd, J=8.7, 2.7 Hz, 1H), 7.18-7.31 (m, 3H).

Example A69

3-{[(4-{[cyclopentyl(5-fluoro-3-methyl-1-benzofuran-2-yl)methyl]amino}phenyl)carbonyl]methyl)amino}propanoic acid

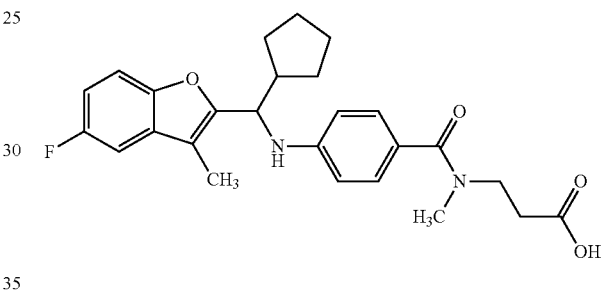

Ethyl 3-{[(4-{[cyclopentyl(5-fluoro-3-methyl-1-benzofuran-2-yl)methyl]amino}phenyl)carbonyl](methyl)amino}propanoate (4.18 g) obtained in Example A67(5) was dissolved in hexane-ethanol (1:1, volume ratio), subjected to HPLC using CHIRALPAK AD (50 mm ID×500 mL, manufactured by Daicel Chemical Industries, Ltd.), and eluted with hexane-ethanol (1:1, volume ratio) as a mobile phase at 30° C. and at a flow rate 60 mL/min. The resulting fraction containing an optically active form having a shorter retention time was concentrated to give an amorphous form (2.07 g, 99.9% ee). The obtained amorphous form was dissolved in ethanol (9 mL) and tetrahydrofuran (9 mL), 1N aqueous sodium hydroxide solution (8.6 mL) was added, and the mixture was stirred at room temperature for 30 min. The solvent was evaporated under reduced pressure, water (15 mL) was added, and the mixture was under ice-cooling neutralized with 1N hydrochloric acid (8.6 mL), and stirred for 1 hr. The resulting precipitate was collected by filtration, and dried to give the title compound (1.81 g, 93%, 99.9% ee) as a colorless amorphous form. The obtained colorless amorphous (150 mg) was crystallized from 2-propanol/water to give colorless 2-propanol-containing crystals (140 mg). In addition, the colorless amorphous (773 mg) obtained above was crystallized from ethanol/water to give ethanol-containing crystals (756 mg). The ethanol-containing crystals (756 mg) were recrystallized from diethyl ether to give colorless crystals (553 mg) free of solvent.

$^1$H NMR (300 MHz, CDCl$_3$) δ ppm 1.15-1.72 (m, 7H), 1.86-2.09 (m, 1H), 2.24 (s, 3H), 2.40-2.53 (m, 1H), 2.62 (t, J=6.2 Hz, 2H), 3.00 (s, 3H), 3.68 (t, J=6.6 Hz, 2H), 4.36 (d, J=9.0 Hz, 1H), 6.54 (d, J=8.7 Hz, 2H), 6.91 (td, J=8.9, 2.6 Hz, 1H), 7.06 (dd, J=8.7, 2.6 Hz, 1H), 7.19-7.30 (m, 3H).

Example A70

3-{[(4-{[cyclopentyl(5-fluoro-3-methyl-1-benzofuran-2-yl)methyl]amino}phenyl)carbonyl](methyl)amino}propanoic acid

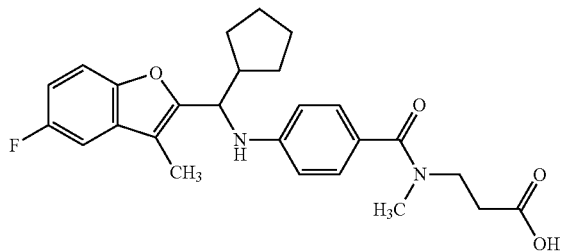 [SMILES: Cc1c(C(Nc2ccc(C(=O)N(C)CCC(=O)O)cc2)C2CCCC2)oc2ccc(F)cc12]

Ethyl 3-{[(4-{[cyclopentyl(5-fluoro-3-methyl-1-benzofuran-2-yl)methyl]amino}phenyl)carbonyl](methyl)amino}propanoate (4.18 g) obtained in Example A67(5) was dissolved in hexane-ethanol (1:1, volume ratio), subjected to HPLC using CHIRALPAK AD (50 mm ID×500 mL, manufactured by Daicel Chemical Industries, Ltd.), and eluted with hexane-ethanol (1:1, volume ratio) as a mobile phase at 30° C. and at a flow rate 60 mL/min. The resulting fraction containing an optically active form having a longer retention time was concentrated to give an amorphous form (2.04 g, 99.9% ee). The obtained amorphous form (2.04 g) was dissolved in ethanol (9 mL) and tetrahydrofuran (9 mL), 1N aqueous sodium hydroxide solution (8.5 mL) was added, and the mixture was stirred at room temperature for 30 min. The solvent was evaporated under reduced pressure, water (15 mL) was added, and the mixture was neutralized with 1N hydrochloric acid (8.5 mL) under ice-cooling, and stirred for 1 hr. The resulting precipitate was collected by filtration, and dried to give the title compound (1.88 g, 98%, 99.9% ee) as a colorless amorphous form.

$^1$H NMR (300 MHz, CDCl$_3$) δ ppm 1.23-1.75 (m, 7H), 1.86-2.03 (m, 1H), 2.25 (s, 3H), 2.39-2.54 (m, 1H), 2.63 (t, J=6.4 Hz, 2H), 3.01 (s, 3H), 3.69 (t, J=6.6 Hz, 2H), 4.36 (d, J=9.1 Hz, 1H), 4.48 (br. s., 1H), 6.55 (d, J=8.7 Hz, 2H), 6.92 (td, J=8.9, 2.7 Hz, 1H), 7.07 (dd, J=8.5, 2.5 Hz, 1H), 7.16-7.32 (m, 3H).

Example A71 ethyl 3-{[(4-{[2-ethyl-1-(5-fluoro-3-methyl-1-benzofuran-2-yl)butyl]amino}phenyl)carbonyl]methyl)amino}propanoate

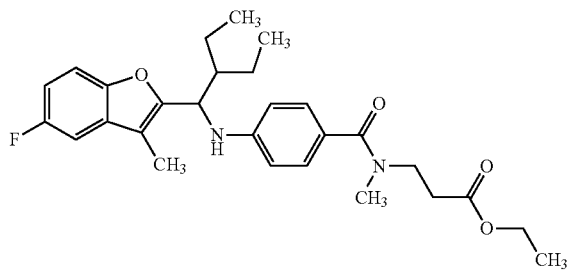 [SMILES: CCOC(=O)CCN(C)C(=O)c1ccc(NC(c2oc3ccc(F)cc3c2C)C2CCCC2)cc1]

(1) 2-ethyl-1-(5-fluoro-3-methyl-1-benzofuran-2-yl)butan-1-one

To a solution of 5-fluoro-3-methyl-1-benzofuran (12.0 g) synthesized in Example A67(2), 2-ethylbutyrylchloride (9.58 g) in nitromethane (240 mL) was added aluminum chloride (anhydrous) (12.94 g) at 0° C., and the mixture was stirred for 1.5 hr. Water was added to the reaction mixture and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-90:10, v/v) to give the title compound (15.02 g, 93%) as a yellow oil.

$^1$H NMR (300 MHz, CDCl$_3$) δ ppm 0.91 (t, J=7.6 Hz, 6H), 1.59-1.67 (m, 2H), 1.75-1.91 (m, 2H), 2.58 (s, 3H), 3.26-3.42 (m, 1H), 7.11-7.35 (m, 2H), 7.40-7.55 (m, 1H).

(2) 2-ethyl-1-(5-fluoro-3-methyl-1-benzofuran-2-yl)butan-1-ol

2-Ethyl-1-(5-fluoro-3-methyl-1-benzofuran-2-yl)butan-1-one (15.0 g) synthesized above was dissolved in a mixed solvent of methanol (50 mL)-tetrahydrofuran (250 mL), and sodium tetrahydroborate (90%, 5.1 g) was added at 0° C. The reaction mixture was stirred at 0° C. for 1.5 hr. Water was added to the reaction mixture, and the mixture was extracted with ethyl acetate. The organic layer was washed with saturated brine, and dried over anhydrous magnesium sulfate. After filtration, the filtrate was concentrated to give the title compound (16.17 g, 100%) as a colorless oil.

$^1$H NMR (300 MHz, CDCl$_3$) δ ppm 0.75-0.86 (m, 3H), 0.95 (t, J=7.6 Hz, 3H), 1.10-1.35 (m, 2H), 1.66-1.94 (m, 3H), 2.21 (s, 3H), 4.66-4.81 (m, 1H), 6.90-7.02 (m, 1H), 7.11 (dd, J=8.7, 2.7 Hz, 1H), 7.30-7.40 (m, 1H).

(3) methyl 4-{[2-ethyl-1-(5-fluoro-3-methyl-1-benzofuran-2-yl)butyl]amino}benzoate To a solution of 2-ethyl-1-(5-fluoro-3-methyl-1-benzofuran-2-yl)butan-1-ol (1.00 g) synthesized above in tetrahydrofuran (10 mL) was added thionyl chloride (320 μL), and the mixture was stirred at room temperature for 3.5 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give a yellow oil (1.11 g). A solution of this yellow oil (1.11 g), methyl 4-aminobenzoate (638 mg), sodium iodide (1.20 g) and sodium carbonate (852 mg) in N,N-dimethylformamide (10 mL) was stirred at 100° C. for 20 hr. Water was added to quench the reaction, and the mixture was extracted with ethyl acetate. The extract was washed with saturated brine, dried over magnesium sulfate, and concentrated under reduced pressure. The residue was purified by silica gel column chromatography (hexane-ethyl acetate 90:10, v/v) to give the title compound (790 mg, 52%) as a yellow oil.

$^1$H NMR (300 MHz, CDCl$_3$) δ ppm 0.95 (t, J=7.5 Hz, 6H), 1.62-1.73 (m, 2H), 1.84-1.94 (m, 2H), 2.23 (s, 3H), 3.81 (s, 3H), 4.46-4.52 (m, 1H), 4.56-4.65 (m, 1H), 4.68-4.76 (m, 1H), 6.54-6.61 (m, 2H), 6.85-7.00 (m, 1H), 7.04-7.15 (m, 1H), 7.29-7.37 (m, 1H), 7.80 (d, J=9.0 Hz, 2H).

(4) 4-{[2-ethyl-1-(5-fluoro-3-methyl-1-benzofuran-2-yl)butyl]amino}benzoic acid

To a mixture of methyl 4-{[2-ethyl-1-(5-fluoro-3-methyl-1-benzofuran-2-yl)butyl]amino}benzoate (709 mg) synthesized above, tetrahydrofuran (6 mL) and ethanol (6 mL) was added 1N aqueous sodium hydroxide solution (3.7 mL), and the mixture was heated under reflux for 14 hr. 1N Aqueous sodium hydroxide solution (4.0 mL) was added, and the mixture was further stirred with heating under reflux for 2 hr. 8N Aqueous sodium hydroxide solution (2.0 mL) and ethanol (2 mL) were added to the mixture, and the mixture was further stirred with heating under reflux for 1 hr. The reaction mixture was concentrated under reduced pressure, 8N aqueous sodium hydroxide solution (4.0 mL), ethanol (4 mL) and tetrahydrofuran (4 mL) were added, and the mixture was further stirred with heating under reflux for 1 hr. The reaction mixture was allowed to cool to room temperature, 1N hydrochloric acid was added, and the mixture was extracted with ethyl acetate. The extract was washed with saturated brine, dried over magnesium sulfate, and concentrated under reduced pressure. The residue was purified by silica gel column chromatography (hexane-ethyl acetate 100:0-70:30, v/v) to give the title compound (412 mg, 61%) as a colorless amorphous form.

$^1$H NMR (300 MHz, CDCl$_3$) δ ppm 0.80-1.02 (m, 6H), 1.32-1.72 (m, 4H), 1.83-1.97 (m, 1H), 2.23 (s, 3H), 4.51-4.71 (m, 2H), 6.57 (d, J=8.7 Hz, 2H), 6.87-6.98 (m, 1H), 7.07 (dd, J=8.3, 2.7 Hz, 1H), 7.27-7.35 (m, 1H), 7.86 (d, J=8.7 Hz, 2H).

(5) ethyl 3-{[(4-{[2-ethyl-1-(5-fluoro-3-methyl-1-benzofuran-2-yl)butyl]amino}phenyl)carbonyl]methyl)amino}propanoate A mixture of 4-{[2-ethyl-1-(5-fluoro-3-methyl-1-benzofuran-2-yl)butyl]amino}benzoic acid (10.77 g) synthesized above, ethyl 3-(methylamino)propanoate (4.59 g), 1-hydroxybenzotriazole-monohydrate (5.34 g), triethylamine (3.53 g), 1-ethyl-3-(3-dimethylaminopropyl)carbodiimide hydrochloride (6.69 g) and N,N-dimethylformamide (100 mL) was stirred at room temperature for 14 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (hexane-ethyl acetate 100:0-0:100, v/v) to give the title compound (9.83 g, 70%) as a yellow amorphous.

$^1$H NMR (300 MHz, CDCl$_3$) δ ppm 0.80-0.88 (m, 3H), 0.95 (t, J=7.3 Hz, 3H), 1.19-1.25 (m, 5H), 1.33-1.54 (m, 2H), 1.87 (dt, J=7.3, 4.9 Hz, 1H), 2.22 (s, 3H), 2.61 (t, J=7.0 Hz, 2H), 3.01 (s, 3H), 3.70 (t, J=7.2 Hz, 2H), 4.11 (q, J=6.9 Hz, 2H), 4.28 (d, J=8.7 Hz, 1H), 4.56 (t, J=8.3 Hz, 1H), 6.56 (d, J=8.7 Hz, 2H), 6.92 (td, J=9.0, 2.6 Hz, 1H), 7.06 (dd, J=8.3, 2.6 Hz, 1H), 7.22 (d, J=8.7 Hz, 2H), 7.25-7.31 (m, 1H).

Example A72

3-{[(4-{[2-ethyl-1-(5-fluoro-3-methyl-1-benzofuran-2-yl)butyl]amino}phenyl)carbonyl](methyl)amino}propanoic acid

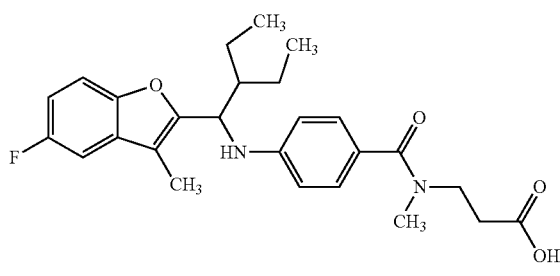 [SMILES: CCC(CC)C(Nc1ccc(C(=O)N(C)CCC(=O)O)cc1)c1oc2ccc(F)cc2c1C]

To a mixture of ethyl 3-{[(4-{[2-ethyl-1-(5-fluoro-3-methyl-1-benzofuran-2-yl)butyl]amino}phenyl)carbonyl]methyl)amino}propanoate (132 mg) obtained in Example A71 (5) in tetrahydrofuran (1 mL) and ethanol (1 mL) was added 1N aqueous sodium hydroxide solution (0.54 mL), and the mixture was stirred at room temperature for 1 hr. The reaction mixture was concentrated under reduced pressure, and the residue was dissolved in water (4 mL), and 1N hydrochloric acid (0.54 mL) was added at 0° C. The mixture was stirred at 0° C. for 1 hr, and the resulting precipitate was collected by filtration to give the title compound (103 mg, 70%) as a colorless amorphous form.

$^1$H NMR (300 MHz, CDCl$_3$) δ ppm 0.79-1.01 (m, 6H), 1.12-1.90 (m, 6H), 2.21 (s, 3H), 2.58-2.69 (m, 2H), 3.00 (s, 3H), 3.66 (d, 2H), 4.56 (d, J=8.0 Hz, 1H), 6.55 (d, J=8.3 Hz, 2H), 6.92 (td, J=8.9, 2.7 Hz, 1H), 7.06 (dd, J=8.3, 2.7 Hz, 1H), 7.19-7.36 (m, 3H).

Example A73

3-{[(4-{[2-ethyl-1-(5-fluoro-3-methyl-1-benzofuran-2-yl)butyl]amino}phenyl)carbonyl](methyl)amino}propanoic acid

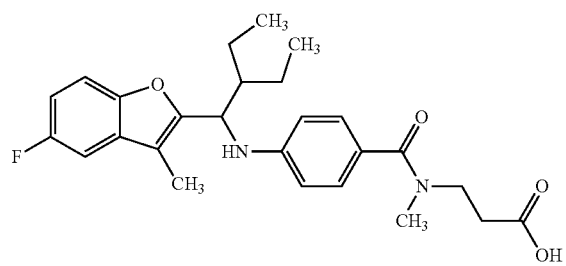 [SMILES: CCC(CC)C(Nc1ccc(C(=O)N(C)CCC(=O)O)cc1)c1oc2ccc(F)cc2c1C]

Ethyl 3-{[(4-{[2-ethyl-1-(5-fluoro-3-methyl-1-benzofuran-2-yl)butyl]amino}phenyl)carbonyl](methyl)amino}propanoate (9.18 g) obtained in Example A71(5) was dissolved in hexane-ethanol (1:1, volume ratio), subjected to HPLC using CHIRALPAK AD (50 mm ID×500 mL, manufactured by Daicel Chemical Industries, Ltd.), and eluted with hexane-ethanol (1:1, volume ratio) as a mobile phase at room temperature and at a flow rate 60 mL/min. The resulting fraction containing an optically active form having a shorter retention time was concentrated to give an amorphous form (4.56 g, 99.9% ee). The obtained amorphous form (4.56 g) was dissolved in ethanol (19 mL) and tetrahydrofuran (19 mL), 1N aqueous sodium hydroxide solution (18.6 mL) was added, and the mixture was stirred at room temperature for 20 min. The solvent was evaporated under reduced pressure. Water (30 mL) was added, and the mixture was neutralized with 1N hydrochloric acid (18.6 mL) under ice-cooling and stirred for 20 min. The resulting precipitate was collected by filtration, and dried to give the title compound (3.63 g, 86%, 99.9% ee) as a colorless amorphous form. The obtained colorless amorphous (1.0 g) was crystallized from 2-propanol/water to give colorless crystals (927 mg).

$^1$H NMR (300 MHz, CDCl$_3$) δ ppm 0.85 (t, J=7.3 Hz, 3H), 0.94 (t, J=7.5 Hz, 3H), 1.11-1.72 (m, 4H), 1.77-1.92 (m, 1H), 2.22 (s, 3H), 2.65 (t, J=6.6 Hz, 2H), 3.02 (s, 3H), 3.69 (t, J=6.8 Hz, 2H), 4.56 (d, J=7.9 Hz, 1H), 6.55 (d, J=8.7 Hz, 2H), 6.92 (td, J=9.0, 2.6 Hz, 1H), 7.06 (dd, J=8.5, 2.4 Hz, 1H), 7.18-7.39 (m, 3H).

Example A74

3-{[(4-{[2-ethyl-1-(5-fluoro-3-methyl-1-benzofuran-2-yl)butyl]amino}phenyl)carbonyl](methyl)amino}propanoic acid

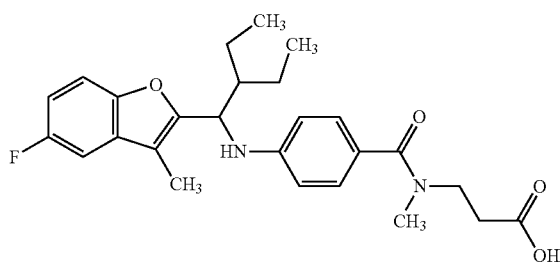 [SMILES: CCC(CC)C(Nc1ccc(C(=O)N(C)CCC(=O)O)cc1)c1oc2ccc(F)cc2c1C]

Ethyl 3-{[(4-{[2-ethyl-1-(5-fluoro-3-methyl-1-benzofuran-2-yl)butyl]amino}phenyl)carbonyl](methyl)amino}propanoate (9.18 g) obtained in Example A71(5) was dissolved in hexane-ethanol (1:1, volume ratio), subjected to HPLC using CHIRALPAK AD (50 mm ID×500 mL, manufactured by Daicel Chemical Industries, Ltd.), and eluted with hexane-ethanol (1:1, volume ratio) as a mobile phase at room temperature and at a flow rate 60 mL/min. The resulting fraction containing an optically active form having a longer retention time was concentrated to give an amorphous form (4.67 g, 99.9% ee). The obtained amorphous form (4.67 g) was dissolved in ethanol (20 mL) and tetrahydrofuran (20 mL), 1N aqueous sodium hydroxide solution (19.4 mL) was added, and the mixture was stirred at room temperature for 20 min. The solvent was evaporated under reduced pressure. Water (30 mL) was added, and the mixture was neutralized with 1N hydrochloric acid under ice-cooling and stirred for 20 min. The resulting precipitate was collected by filtration, and dried to give the title compound (4.21 g, 96%, 99.9% ee).

$^1$H NMR (300 MHz, CDCl$_3$) δ ppm 0.80-0.89 (m, 3H), 0.94 (t, J=7.5 Hz, 3H), 1.16-1.71 (m, 4H), 1.74-1.91 (m, 1H), 2.22 (s, 3H), 2.62 (t, J=6.2 Hz, 2H), 3.01 (s, 3H), 3.61-3.76 (m, 2H), 4.56 (d, J=7.9 Hz, 1H), 6.55 (d, J=8.7 Hz, 2H), 6.92 (td, J=9.0, 2.6 Hz, 1H), 7.06 (dd, J=8.5, 2.4 Hz, 1H), 7.16-7.31 (m, 3H).

Example A75 ethyl 3-[{[4-({1-[5-(cyclopropylmethoxy)-3-methyl-1-benzofuran-2-yl]-2-methylpropyl}amino)phenyl]carbonyl}(methyl)amino]propanoate

(1) 1-bromo-3-methylbutan-2-one

To a solution of 3-methyl-2-butanone (43.0 g) in methanol (300 mL) was added dropwise bromine (80 g) over 20 min while cooling in an ice bath. The ice bath was removed, and the mixture was stirred at room temperature for 40 min. Water (450 mL) was added to the reaction mixture, and the mixture was stirred for 20 min. The reaction mixture was extracted twice with diethyl ether (500 mL). The extract was washed with water (400 mL), 10% aqueous potassium carbonate solution (400 mL) and saturated brine (200 mL), dried over magnesium sulfate, and concentrated under reduced pressure to give the title compound (55.9 g) as a yellow oil.

$^1$H NMR (300 MHz, CDCl$_3$) δ ppm 1.17 (d, J=6.8 Hz, 6H), 2.88-3.05 (m, 1H), 3.98 (s, 2H).

(2) 1-[5-(cyclopropylmethoxy)-3-methyl-1-benzofuran-2-yl]-2-methylpropan-1-one A solution of 2',5'-dihydroxyacetophenone (25.0 g), bromomethylcyclopropane (24.43 g), potassium carbonate (27.2 g) in acetonitrile (400 mL) was stirred with heating under reflux for 2.5 hr. Bromomethylcyclopropane (4.4 g) was added to the mixture, and the mixture was further stirred with heating under reflux for 14 hr. The reaction mixture was cooled to room temperature, the insoluble material was filtered off, and the filtrate was concentrated under reduced pressure. The residue was purified by silica gel column chromatography (hexane-ethyl acetate 100:0-10:90, v/v) to give 1-[5-(cyclopropylmethoxy)-2-hydroxyphenyl]ethanone (35.5 g) as a yellow oil at purity 70%. A solution of the obtained 1-[5-(cyclopropylmethoxy)-2-hydroxyphenyl]ethanone (35.5 g), 1-bromo-3-methylbutan-2-one (35.5 g) synthesized above and potassium carbonate (66.3 g) in N,N-dimethylformamide (350 mL) was stirred at room temperature for 1 hr. Water was added to the reaction mixture, and the mixture was extracted with ethyl acetate. The extract was washed with saturated brine, dried over magnesium sulfate, and concentrated under reduced pressure. 1,8-Diazabicyclo[5.4.0]undec-7-ene (22.5 mL) and N,N-dimethylformamide (300 mL) were added to the obtained residue, and the mixture was stirred at 100° C. for 30 min. The reaction mixture was cooled to room temperature, 1N hydrochloric acid (300 mL) was added, and the mixture was extracted with ethyl acetate. The extract was washed with saturated brine, dried over magnesium sulfate, and concentrated under reduced pressure. The residue was purified by silica gel column chromatography (hexane-ethyl acetate 100:0-90:10, v/v) to give the title compound (19.91 g, 45%) as a colorless solid.

$^1$H NMR (300 MHz, CDCl$_3$) δ ppm 0.29-0.50 (m, 2H), 0.61-0.73 (m, 2H), 1.01-1.46 (m, 7H), 2.57 (s, 3H), 3.44-3.68

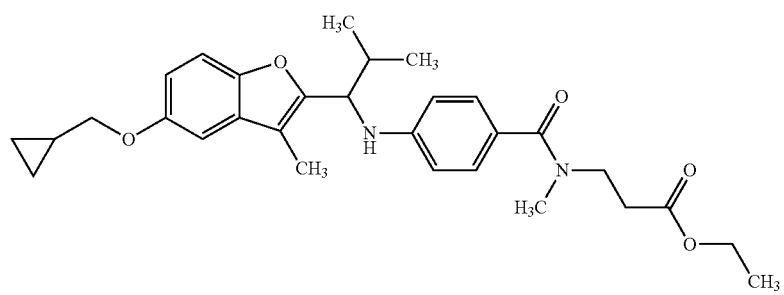 [SMILES: CCOC(=O)CCN(C)C(=O)c1ccc(NC(c2oc3ccc(OCC4CC4)cc3c2C)C(C)C)cc1]

(m, 1H), 3.86 (d, J=7.2 Hz, 2H), 7.00 (d, J=2.3 Hz, 1H), 7.11 (dd, J=9.0, 2.6 Hz, 1H), 7.39 (d, J=9.0 Hz, 1H).

(3) 1-[5-(cyclopropylmethoxy)-3-methyl-1-benzofuran-2-yl]-2-methylpropan-1-ol 1-[5-(Cyclopropylmethoxy)-3-methyl-1-benzofuran-2-yl]-2-methylpropan-1-one (19.91 g) synthesized above was dissolved in mixed solvent of methanol (40 mL)-tetrahydrofuran (200 mL), and sodium tetrahydroborate (90%, 5.53 g) was added at 0° C. The reaction mixture was stirred at 0° C. for 30 min. Water was added to the reaction mixture and the mixture was extracted with ethyl acetate. The organic layer was washed with saturated brine, and dried over anhydrous magnesium sulfate. After filtration, the filtrate was concentrated to give the title compound (22.74 g, 100%) as a colorless oil.

$^1$H NMR (300 MHz, CDCl$_3$) δ ppm 0.32-0.42 (m, 2H), 0.60-0.71 (m, 2H), 0.81 (d, 3H), 1.12 (d, J=6.4 Hz, 3H), 1.26-1.36 (m, 1H), 1.99 (d, J=6.0 Hz, 1H), 2.17-2.28 (m, 4H), 3.84 (d, 2H), 4.45 (dd, J=8.3, 6.4 Hz, 1H), 6.84-6.96 (m, 2H), 7.29 (d, J=8.7 Hz, 1H).

(4) ethyl 3-[{[4-({1-[5-(cyclopropylmethoxy)-3-methyl-1-benzofuran-2-yl]-2-methylpropyl}amino)phenyl]carbonyl}(methyl)amino]propanoate To a solution of 1-[5-(cyclopropylmethoxy)-3-methyl-1-benzofuran-2-yl]-2-methylpropan-1-ol (22.74 g) obtained above in tetrahydrofuran (200 mL) was added thionyl chloride (6.4 mL) at room temperature. The reaction mixture was stirred at room temperature for 1.5 hr. To the reaction mixture was added ice-cooled to 0° C. aqueous sodium hydrogen carbonate solution, and the mixture was extracted with ethyl acetate. The organic layer was washed with saturated brine, and dried over anhydrous magnesium sulfate. After filtration, the filtrate was concentrated, ethyl 3-{[(4-aminophenyl)carbonyl](methyl)amino}propanoate (19.2 g) obtained in Example 2(2), sodium iodide (21.9 g), sodium carbonate (15.4 g) and N,N-dimethylacetamide (200 mL) were added to the obtained residue, and the mixture was stirred at 80° C. for 1.5 hr. Water was added to the reaction mixture and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (18.34 g, 50%) as a yellow amorphous.

$^1$H NMR (300 MHz, CDCl$_3$) δ ppm 0.29-0.40 (m, 2H), 0.58-0.70 (m, 2H), 0.91 (d, J=6.8 Hz, 3H), 1.12 (d, J=6.8 Hz, 3H), 1.19-1.33 (m, 4H), 2.17-2.28 (m, 4H), 2.61 (t, J=6.8 Hz, 2H), 3.01 (s, 3H), 3.70 (t, J=7.2 Hz, 2H), 3.82 (d, J=7.2 Hz, 2H), 4.05-4.16 (m, 2H), 4.27-4.38 (m, 2H), 6.57 (d, J=9.0 Hz, 2H), 6.78-6.91 (m, 2H), 7.17-7.25 (m, 3H).

Example A76

3-[{[4-({1-[5-(cyclopropylmethoxy)-3-methyl-1-benzofuran-2-yl]-2-methylpropyl}amino)phenyl]carbonyl}(methyl)amino]propanoic acid

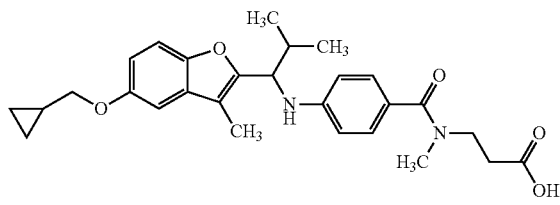 [SMILES: Cc1c(C(Nc2ccc(C(=O)N(C)CCC(=O)O)cc2)C(C)C)oc2ccc(OCC3CC3)cc12]

To a mixture of ethyl 3-[{[4-({1-[5-(cyclopropylmethoxy)-3-methyl-1-benzofuran-2-yl]-2-methylpropyl}amino)phenyl]carbonyl}(methyl)amino]propanoate (667 mg) obtained in Example A75(4) in tetrahydrofuran (3 mL) and ethanol (3 mL) was added 1N aqueous sodium hydroxide solution (2.6 mL), and the mixture was stirred at room temperature for 30 min. The reaction mixture was concentrated under reduced pressure, the residue was dissolved in water (4 mL), and 1N hydrochloric acid (2.6 mL) was added at 0° C. The mixture was stirred at 0° C. for 30 min, and the resulting precipitate was collected by filtration to give the title compound (509 mg, 81%) as a colorless amorphous form.

$^1$H NMR (300 MHz, CDCl$_3$) δ ppm 0.28-0.40 (m, 2H), 0.58-0.71 (m, 2H), 0.91 (d, J=6.8 Hz, 3H), 1.11 (d, J=6.8 Hz, 3H), 1.23-1.34 (m, 1H), 2.17-2.28 (m, 4H), 2.64 (t, J=6.4 Hz, 2H), 3.02 (s, 3H), 3.69 (t, J=6.4 Hz, 2H), 3.82 (d, J=7.2 Hz, 2H), 4.31 (d, J=8.0 Hz, 1H), 6.56 (d, J=8.7 Hz, 2H), 6.78-6.91 (m, 2H), 7.19-7.25 (m, 3H).

Example A77

3-[{[4-({1-[5-(cyclopropylmethoxy)-3-methyl-1-benzofuran-2-yl]-2-methylpropyl}amino)phenyl]carbonyl}(methyl)amino]propanoic acid

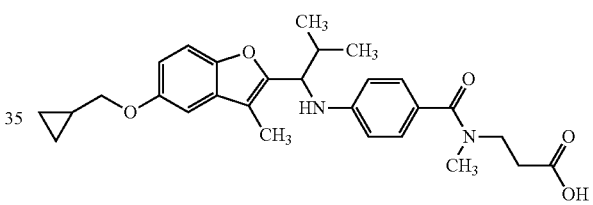

Ethyl 3-[{[4-({1-[5-(cyclopropylmethoxy)-3-methyl-1-benzofuran-2-yl]-2-methylpropyl}amino)phenyl]carbonyl}(methyl)amino]propanoate (18.23 g) obtained in Example A75(4) was dissolved in hexane-ethanol (1:1, volume ratio), subjected to HPLC using CHIRALPAK AD (50 mm ID×500 mL, manufactured by Daicel Chemical Industries, Ltd.), and eluted with hexane-ethanol (1:1-1:4, volume ratio) as a mobile phase at room temperature and at a flow rate 60-50 mL/min. The resulting fraction containing an optically active form having a shorter retention time was concentrated to give an amorphous form (9.08 g, 99.9% ee). The obtained amorphous form (4.72 g) was dissolved in ethanol (19 mL) and tetrahydrofuran (19 mL), 1N aqueous sodium hydroxide solution (18.6 mL) was added, and the mixture was stirred at room temperature for 20 min. The solvent was evaporated under reduced pressure. Water (40 mL) was added, and the mixture was neutralized with 1N hydrochloric acid (18.6 mL) under ice-cooling and stirred for 20 min. The resulting precipitate was collected by filtration, and dried to give the title compound (4.27 g, 96%, 99.9% ee) as a colorless amorphous form.

$^1$H NMR (300 MHz, CDCl$_3$) δ ppm 0.31-0.38 (m, 2H), 0.58-0.68 (m, 2H), 0.90 (d, J=6.8 Hz, 3H), 1.12 (d, J=6.4 Hz, 3H), 1.28 (s, 1H), 2.17-2.29 (m, 4H), 2.63 (t, J=6.4 Hz, 2H), 3.01 (s, 3H), 3.69 (t, J=6.4 Hz, 2H), 3.82 (d, J=6.8 Hz, 2H), 4.31 (d, J=7.5 Hz, 1H), 6.56 (d, J=8.7 Hz, 2H), 6.78-6.89 (m, 2H), 7.19-7.27 (m, 3H).

Example A78

3-[{[4-({1-[5-(cyclopropylmethoxy)-3-methyl-1-benzofuran-2-yl]-2-methylpropyl}amino)phenyl]carbonyl}(methyl)amino]propanoic acid

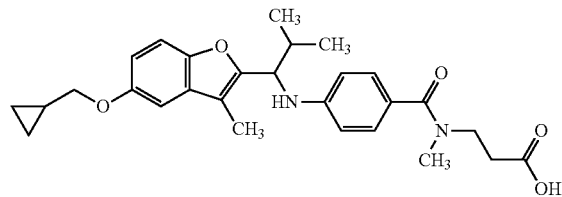 [SMILES: Cc1c(C(Nc2ccc(C(=O)N(C)CCC(=O)O)cc2)C(C)C)oc2ccc(OCC3CC3)cc12]

Ethyl 3-[{[4-({1-[5-(cyclopropylmethoxy)-3-methyl-1-benzofuran-2-yl]-2-methylpropyl}amino)phenyl]carbonyl}(methyl)amino]propanoate (18.23 g) obtained in Example A75(4) was dissolved in hexane-ethanol (1:1, volume ratio), subjected to HPLC using CHIRALPAK AD (50 mm ID×500 mL, manufactured by Daicel Chemical Industries, Ltd.), and eluted with hexane-ethanol (1:1-1:4, volume ratio) as a mobile phase at room temperature and at a flow rate 60-50 mL/min. The resulting fraction containing an optically active form having a longer retention time was concentrated to give an amorphous form (9.08 g, 99.9% ee). The obtained amorphous form (4.73 g) was dissolved in ethanol (19 mL) and tetrahydrofuran (19 mL), 1N aqueous sodium hydroxide solution (18.7 mL) was added, and the mixture was stirred at room temperature for 20 min. The solvent was evaporated under reduced pressure. Water (40 mL) was added, and the mixture was neutralized with 1N hydrochloric acid (18.7 mL) under ice-cooling and stirred for 30 min. The resulting precipitate was collected by filtration, and dried to give the title compound (4.02 g, 90%, 98.8% ee) as a colorless amorphous form. The obtained colorless amorphous (500 mg) was dissolved in ethyl acetate, and the mixture was washed with water and saturated brine. The organic layer was dried over anhydrous magnesium sulfate. After filtration, the filtrate was concentrated to give a colorless amorphous. The obtained colorless amorphous was crystallized from ethyl acetate/hexane to give colorless crystals (401 mg). In addition, an amorphous product (60 mg) obtained by partitioning was crystallized from diethyl ether/hexane to give colorless crystals (45 mg).

$^1$H NMR (300 MHz, CDCl$_3$) δ ppm 0.27-0.42 (m, 2H), 0.56-0.66 (m, 2H), 0.91 (d, J=6.8 Hz, 3H), 1.12 (d, J=6.8 Hz, 3H), 1.28 (s, 1H), 2.18-2.28 (m, 4H), 2.66 (t, J=6.4 Hz, 2H), 3.03 (s, 3H), 3.70 (t, J=6.6 Hz, 2H), 3.82 (d, J=7.2 Hz, 2H), 4.31 (d, J=7.5 Hz, 1H), 6.56 (d, J=8.7 Hz, 2H), 6.73-6.89 (m, 2H), 7.19-7.25 (m, 3H).

Example A79

3-[{[4-({cyclohexyl[5-(2-methoxyethoxy)-3-methyl-1-benzofuran-2-yl]methyl}amino)phenyl]carbonyl}(methyl)amino]propanoic acid

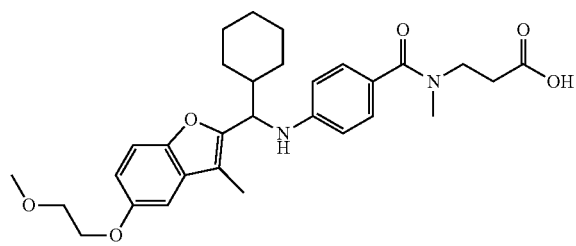 [SMILES: COCCOc1ccc2oc(C(Nc3ccc(C(=O)N(C)CCC(=O)O)cc3)C3CCCCC3)c(C)c2c1]

(1) 1-[2-hydroxy-5-(2-methoxyethoxy)phenyl]ethanone

To a solution (250 mL) of 1-(2,5-dihydroxyphenyl)ethanone (11.0 g) in acetonitrile were added 2-methoxyethylbromide (19.6 mL) and potassium carbonate (12.0 g) at room temperature, and the mixture was heated under reflux for 15 hr. The reaction mixture was allowed to cool to room temperature and filtered through celite, and the filtrate was concentrated under reduced pressure. Saturated aqueous ammonium chloride solution was added to the residue, and the mixture was extracted with ethyl acetate. The extract was washed with saturated brine, dried over magnesium sulfate, and concentrated under reduced pressure. The residue was purified by silica gel column chromatography (ethyl acetate:hexane=1:10, volume ratio) to give the title object compound (7.6 g, 50%) as a pale-yellow oil.

$^1$H NMR (300 MHz, CDCl$_3$) δ ppm 2.61 (s, 3H), 3.46 (s, 3H), 3.66-4.21 (m, 4H), 6.92 (d, J=9.0 Hz, 1H), 7.15 (d, J=9.0 Hz, 1H), 7.22-7.26 (m, 1H), 11.84 (s, 1H).

(2) cyclohexyl[5-(2-methoxyethoxy)-3-methyl-1-benzofuran-2-yl]methanone

1-[2-Hydroxy-5-(2-methoxyethoxy)phenyl]ethanone (7.0 g) synthesized in the above-mentioned (1) was dissolved in N,N-dimethylformamide (140 mL). Potassium carbonate (13.8 g) and 2-bromo-1-cyclohexylethanone (8.9 g) synthesized in Example A51(1) were added to the reaction mixture at room temperature, and the mixture was stirred for 15 hr. The reaction mixture was filtered through celite, water (200 mL) was added, and the mixture was extracted with diethyl ether (100 mL×2). The extract was washed with saturated brine, dried over magnesium sulfate, and concentrated under reduced pressure. The residue was dissolved in N,N-dimethylformamide solution (100 mL), DBU (5.3 mL) was added at room temperature, and the mixture was stirred at 100° C. for 1 hr. The reaction mixture was allowed to cool to room temperature, 1N hydrochloric acid (100 mL) was added, and the mixture was extracted with diethyl ether (100 mL×2). The extract was washed with water, saturated aqueous sodium hydrogen carbonate solution and saturated brine, dried over magnesium sulfate, and concentrated under reduced pressure. The residue was purified by silica gel column chromatography (ethyl acetate:hexane=1:20, volume ratio) to give the title object compound (10.3 g, 98%) as a pale-yellow oil.

$^1$H NMR (300 MHz, CDCl$_3$) δ ppm 1.32-2.00 (m, 11H), 2.56 (s, 3H), 3.30 (d, J=3.4 Hz, 1H), 3.48 (s, 3H), 3.75-3.85 (m, 2H), 4.15-4.25 (m, 2H), 7.04 (d, J=2.5 Hz, 1H), 7.13 (dd, J=8.9, 2.5 Hz, 1H), 7.40 (d, J=8.9 Hz, 1H).

(3) cyclohexyl[5-(2-methoxyethoxy)-3-methyl-1-benzofuran-2-yl]methanol

Cyclohexyl[5-(2-methoxyethoxy)-3-methyl-1-benzofuran-2-yl]methanone (10.3 g) synthesized in the above-mentioned (2) was dissolved in a mixed solvent of tetrahydrofuran (180 mL) and methanol (20 mL). The reaction mixture was ice-cooled, and sodium borohydride (90%, 2.7 g) was added, and the reaction mixture was stirred at room temperature for 2 hr. The reaction mixture was ice-cooled again, water (10 mL) and 1N hydrochloric acid (100 mL) were carefully added, and the mixture was extracted with ethyl acetate. The extract was washed with saturated brine, dried over magnesium sulfate, and concentrated under reduced pressure to give a crude product (10.3 g) of the title object compound as a pale-yellow oil.

$^1$H NMR (300 MHz, CDCl$_3$) δ ppm 1.15-2.02 (m, 11H), 2.56 (s, 3H), 3.48 (s, 3H), 3.73-3.87 (m, 2H), 4.14-4.26 (m, 2H), 4.44-4.46 (m, 1H), 7.04 (d, J=2.6 Hz, 1H), 7.13 (dd, J=9.0, 2.6 Hz, 1H), 7.40 (d, J=9.0 Hz, 1H).

(4) ethyl 3-[{[4-({cyclohexyl[5-(2-methoxyethoxy)-3-methyl-1-benzofuran-2-yl]methyl}amino)phenyl]carbonyl}(methyl)amino]propanoate To a solution (200 mL) of cyclohexyl[5-(2-methoxyethoxy)-3-methyl-1-benzofuran-2-yl]methanol (10.3 g) synthesized in the above-mentioned (3) in tetrahydrofuran was added thionyl chloride (4.7 mL) at room temperature. The reaction mixture was stirred at room temperature for 30 min and ice-cooled, and saturated aqueous sodium hydrogen carbonate solution (100 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (150 mL), sodium iodide (8.0 g), sodium carbonate (5.3 g) and ethyl 3-{[(4-aminophenyl)carbonyl](methyl)amino}propanoate (8.9 g) synthesized in Example 2(2) were added, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate: hexane=1:1, volume ratio) to give the title object compound (8.5 g, 43%) as a yellow oil.

$^1$H NMR (300 MHz, CDCl$_3$) δ ppm 0.92-2.14 (m, 14H), 2.21 (s, 3H), 2.61 (t, J=6.8 Hz, 2H), 3.01 (s, 3H), 3.46 (s, 3H), 3.60-3.81 (m, 4H), 4.01-4.21 (m, 4H), 4.27-4.46 (m, 2H), 6.56 (d, J=8.3 Hz, 2H), 6.76-6.95 (m, 2H), 7.14-7.25 (m, 3H).

(5) 3-[{[4-({cyclohexyl[5-(2-methoxyethoxy)-3-methyl-1-benzofuran-2-yl]methyl}amino)phenyl]carbonyl}(methyl)amino]propanoic acid Ethyl 3-[{[4-({cyclohexyl[5-(2-methoxyethoxy)-3-methyl-1-benzofuran-2-yl]methyl}amino)phenyl]carbonyl}(methyl)amino]propanoate (5.4 g) synthesized in the above-mentioned (4) was dissolved in ethanol (150 mL), 1N aqueous sodium hydroxide solution (15 mL) was added at room temperature, and the mixture was stirred at 50° C. for 0.5 hr. Ethanol was evaporated under reduced pressure, 1N hydrochloric acid (20 mL) was added to the residue, and the mixture was extracted with diethyl ether. The extract was concentrated under reduced pressure, and the residue was purified by silica gel column chromatography (ethyl acetate: hexane=1:1, volume ratio) to give the title object compound (3.0 g, 59%) as a white solid.

$^1$H NMR (300 MHz, CDCl$_3$) δ ppm 0.92-2.14 (m, 12H), 2.21 (s, 3H), 2.66 (t, J=6.1 Hz, 2H), 3.03 (s, 3H), 3.46 (s, 3H), 3.60-3.81 (m, 4H), 4.01-4.21 (m, 4H), 4.35 (d, J=7.8 Hz, 2H), 6.55 (d, J=8.7 Hz, 2H), 6.76-6.95 (m, 2H), 7.14-7.25 (m, 3H).

Example A80

3-[{[4-({cyclohexyl[5-(2-methoxyethoxy)-3-methyl-1-benzofuran-2-yl]methyl}amino)phenyl]carbonyl}(methyl)amino]propanoic acid

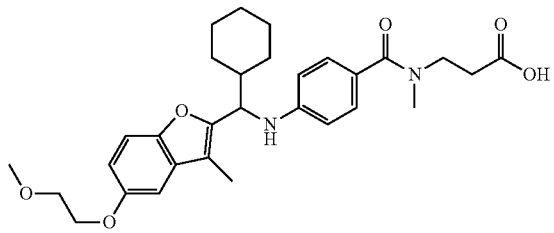 [SMILES: COCCOc1ccc2oc(C(Nc3ccc(C(=O)N(C)CCC(=O)O)cc3)C3CCCCC3)c(C)c2c1]

(1) 3-[{[4-({cyclohexyl[5-(2-methoxyethoxy)-3-methyl-1-benzofuran-2-yl]methyl}amino)phenyl]carbonyl}(methyl)amino]propanoic acid 3-[{[4-({Cyclohexyl[5-(2-methoxyethoxy)-3-methyl-1-benzofuran-2-yl]methyl}amino)phenyl]carbonyl}(methyl)amino]propanoic acid (3.0 g) synthesized in Example A79(5) was fractionated by high performance liquid chromatography (column: CHIRALPAK AD (5 mm i.d.×500 mL, manufactured by Daicel Chemical Industries, Ltd., mobile phase: hexane/2-propanol/trifluoroacetic acid (500/500/1), flow rate: 60 mL/min, column temperature: 30° C.). To the fraction containing an optically active form having a shorter retention time under the above-mentioned high performance liquid chromatography conditions was added triethylamine (10 mL) and the mixture was concentrated to give a triethylamine salt (3.7 g) of the title object compound. 1N Hydrochloric acid (30 mL) was added thereto, and the mixture was extracted with diethyl ether. The extract was washed with water and saturated brine, dried over magnesium sulfate and concentrated under reduced pressure to give the title object compound (1.49 g, 99.9% ee) as a white solid.

$^1$H NMR (300 MHz, CDCl$_3$) δ ppm 0.92-2.14 (m, 12H), 2.21 (s, 3H), 2.66 (t, J=6.1 Hz, 2H), 3.03 (s, 3H), 3.46 (s, 3H), 3.60-3.81 (m, 4H), 4.01-4.21 (m, 4H), 4.35 (d, J=7.8 Hz, 2H), 6.55 (d, J=8.7 Hz, 2H), 6.76-6.95 (m, 2H), 7.14-7.25 (m, 3H).

Example A81

3-[{[4-({cyclohexyl[5-(2-methoxyethoxy)-3-methyl-1-benzofuran-2-yl]methyl}amino)phenyl]carbonyl}(methyl)amino]propanoic acid

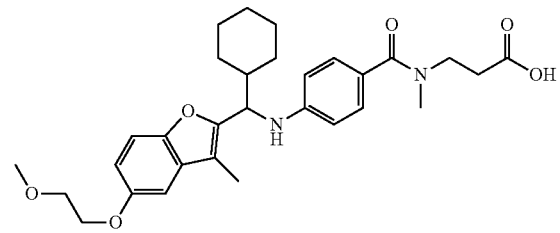 [SMILES: COCCOc1ccc2oc(C(Nc3ccc(C(=O)N(C)CCC(=O)O)cc3)C3CCCCC3)c(C)c2c1]

3-[{[4-({Cyclohexyl[5-(2-methoxyethoxy)-3-methyl-1-benzofuran-2-yl]methyl}amino)phenyl]carbonyl}(methyl)amino]propanoic acid (3.0 g) synthesized in Example A79(5) was fractionated by high performance liquid chromatography (column: CHIRALPAK AD (50 mm i.d.×500 mL, manufactured by Daicel Chemical Industries, Ltd., mobile phase: hexane/2-propanol/trifluoroacetic acid (500/500/1), flow rate: 60 mL/min, column temperature: 30° C.). To the fraction containing an optically active form having a longer retention time under the above-mentioned high performance liquid chromatography conditions was added triethylamine (30 mL), and the mixture was concentrated to give a triethylamine salt (9.2 g) of the title object compound. 1N Hydrochloric acid (30 mL) was added thereto, and the mixture was extracted with diethyl ether. The extract was washed with water and saturated brine, dried over magnesium sulfate and concentrated under reduced pressure to give the title object compound (1.50 g, 99.9% ee) as a white solid.

$^1$H NMR (300 MHz, CDCl$_3$) δ ppm 0.92-2.14 (m, 12H), 2.21 (s, 3H), 2.66 (t, J=6.1 Hz, 2H), 3.03 (s, 3H), 3.46 (s, 3H), 3.60-3.81 (m, 4H), 4.01-4.21 (m, 4H), 4.35 (d, J=7.8 Hz, 2H), 6.55 (d, J=8.7 Hz, 2H), 6.76-6.95 (m, 2H), 7.14-7.25 (m, 3H).

Example A82

3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid

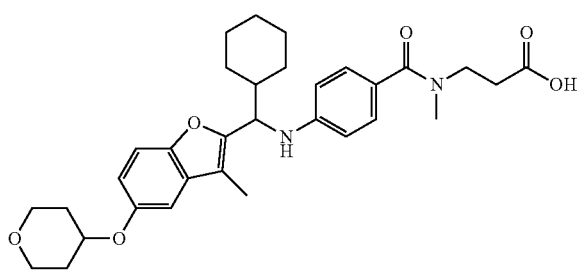 [SMILES: Cc1c(C(Nc2ccc(C(=O)N(C)CCC(=O)O)cc2)C2CCCCC2)oc2ccc(OC3CCOCC3)cc12]

(1) 1-[5-(benzyloxy)-2-hydroxyphenyl]ethanone

To a solution (400 mL) of 1-(2,5-dihydroxyphenyl)ethanone (25.0 g) in acetonitrile were added benzylbromide (19.6 mL) and potassium carbonate (25.0 g) at room temperature, and the mixture was heated under reflux for 2 hr. The reaction mixture was allowed to cool to room temperature, filtered through celite, and the filtrate was concentrated under reduced pressure. Saturated aqueous ammonium chloride solution was added to the residue, and the mixture was extracted with ethyl acetate. The extract was washed with saturated brine, dried over magnesium sulfate, and concentrated under reduced pressure to give a solid. The obtained solid was washed with ethanol-isopropyl ether to give the title object compound (31.0 g, 80%) as a yellow-green solid.

$^1$H NMR (300 MHz, CDCl$_3$) δ ppm 2.58 (s, 3H), 5.05 (s, 2H), 7.11-7.53 (m, 8H), 11.85 (s, 1H).

(2) [5-(benzyloxy)-3-methyl-1-benzofuran-2-yl](cyclohexyl)methanone

To a solution (500 mL) of 1-[5-(benzyloxy)-2-hydroxyphenyl]ethanone (29.5 g) synthesized in the above-mentioned (1) in N,N-dimethylformamide were added potassium carbonate (41.4 g) and 2-bromo-1-cyclohexylethanone (25.0 g) synthesized in Example A51(1) at room temperature, and the mixture was stirred at 60° C. for 15 hr. The reaction mixture was allowed to cool to room temperature, filtered through celite. Water was added to the filtrate, and the mixture was extracted with diethyl ether. The extract was washed with saturated brine, dried over magnesium sulfate, and concentrated under reduced pressure to give a solid. The obtained solid was washed with ethanol-isopropyl ether to give the title object compound (18.0 g, 43%) as a pale-yellow solid.

$^1$H NMR (300 MHz, CDCl$_3$) δ ppm 1.17-2.10 (m, 10H), 2.56 (s, 3H), 3.17-3.43 (m, 1H), 5.12 (s, 2H), 7.04-7.21 (m, 2H), 7.30-7.51 (m, 6H).

(3) cyclohexyl(5-hydroxy-3-methyl-1-benzofuran-2-yl)methanone

[5-(Benzyloxy)-3-methyl-1-benzofuran-2-yl](cyclohexyl)methanone (7.3 g) synthesized in the above-mentioned (2) was dissolved in a ethanol (150 mL) and tetrahydrofuran (30 mL), and palladium carbon-ethylenediamine complex (1.0 g) was added at room temperature. The reaction mixture was stirred at 60° C. for 3 hr under hydrogen atmosphere (1 atm), allowed to cool to room temperature, and the catalyst was filtered. The filtrate was concentrated under reduced pressure to give a crude product (5.2 g, quantitative) of the title object compound as a colorless solid.

$^1$H NMR (300 MHz, CDCl$_3$) δ ppm 1.21-2.03 (m, 10H), 2.54 (s, 3H), 3.22-3.38 (m, 1H), 4.78 (br. s., 1H), 6.96-7.05 (m, 2H), 7.38 (d, J=9.5 Hz, 1H).

(4) cyclohexyl[3-methyl-5-(tetrahydro-2H-pyran-4-yloxy)-1-benzofuran-2-yl]methanone Cyclohexyl(5-hydroxy-3-methyl-1-benzofuran-2-yl)methanone (5.2 g) synthesized in the above-mentioned (3) was dissolved in dimethylformamide (100 mL), and potassium phosphate (7.4 g) and tetrahydro-2H-pyran-4-yl 4-methylbenzenesulfonate (9.0 g) synthesized by the method of EP-A-1367058 were added to the mixture at room temperature, and the mixture was stirred at 80° C. overnight. The reaction mixture was allowed to cool to room temperature, water (150 mL) was added and the mixture was extracted with diethyl ether (100 mL×2). The extract was concentrated under reduced pressure, and the residue was purified by silica gel column chromatography (ethyl acetate:hexane=1:10, volume ratio) to give the title object compound (7.1 g, 99%) as a pale-yellow solid.

$^1$H NMR (300 MHz, CDCl$_3$) δ ppm 1.35-2.10 (m, 14H), 2.56 (s, 3H), 3.24-3.38 (m, 1H), 3.50-3.65 (m, 2H), 3.95-4.07 (m, 2H), 4.50 (tt, J=7.8, 3.9 Hz, 1H), 7.04-7.16 (m, 2H), 7.42 (d, J=8.7 Hz, 1H).

(5) cyclohexyl[3-methyl-5-(tetrahydro-2H-pyran-4-yloxy)-1-benzofuran-2-yl]methanol Cyclohexyl[3-methyl-5-(tetrahydro-2H-pyran-4-yloxy)-1-benzofuran-2-yl]methanone (7.1 g) synthesized in the above-mentioned (4) was dissolved in tetrahydrofuran (200 mL) and methanol (20 mL), and sodium borohydride (90%, 1.6 g) was added under ice-cooling. The ice bath was removed, and the reaction mixture was stirred at room temperature for 2 hr. The reaction mixture was ice-cooled again, water (10 mL) and 1N hydrochloric acid (100 mL) were added carefully, and the mixture was extracted with ethyl acetate. The extract was washed with saturated brine, dried over magnesium sulfate, and concentrated under reduced pressure to give a crude product (6.7 g, 98%) of the title object compound as a pale-yellow oil.

$^1$H NMR (300 MHz, CDCl$_3$) δ ppm 0.82-2.14 (m, 15H), 2.18 (s, 3H), 3.57 (ddd, J=11.6, 8.4, 3.4 Hz, 2H), 3.93-4.06 (m, 2H), 4.36-4.59 (m, 2H), 6.89 (dd, J=8.7, 2.3 Hz, 1H), 6.97 (d, J=2.3 Hz, 1H), 7.31 (d, J=8.7 Hz, 1H).

(6) ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate Cyclohexyl[3-methyl-5-(tetrahydro-2H-pyran-4-yloxy)-1-benzofuran-2-yl]methanol (6.7 g) synthesized in the above-mentioned (5) was dissolved in tetrahydrofuran (120 mL), and thionyl chloride (2.6 mL) was added at room temperature. The reaction mixture was stirred at room temperature for 30 min then ice-cooled, and saturated aqueous sodium hydrogen carbonate solution (100 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (100 mL), sodium iodide (5.3 g), sodium carbonate (3.5 g) and ethyl 3-{[(4-aminophenyl)carbonyl](methyl)amino}propanoate (4.9 g) synthesized in Example 2(2) were added, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (6.1 g, 54%) as a yellow oil.

$^1$H NMR (300 MHz, CDCl$_3$) δ ppm 1.00-2.10 (m, 18H), 2.21 (s, 3H), 2.61 (t, J=7.0 Hz, 2H), 3.01 (s, 3H), 3.55 (ddd, J=11.7, 8.5, 3.2 Hz, 2H), 3.70 (t, J=7.0 Hz, 2H), 3.90-4.05 (m, 2H), 4.27-4.52 (m, 4H), 6.56 (d, J=8.7 Hz, 2H), 6.77-6.96 (m, 2H), 7.15-7.25 (m, 3H).

(7) 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid Ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate (0.6 g) synthesized in the above-mentioned (6) was dissolved in ethanol (20 mL), 1N aqueous sodium hydroxide solution (3 mL) was added at room temperature, and the mixture was stirred at room temperature for 12 hr. Ethanol was evaporated under reduced pressure, 1N hydrochloric acid (3 mL) was added to the residue, and the mixture was extracted with ethyl acetate. The extract was washed with saturated brine, dried over magnesium sulfate, and concentrated under reduced pressure. The residue was recrystallized from acetone to give the title object compound (0.5 g, 77%) as colorless crystals.

$^1$H NMR (300 MHz, CDCl$_3$) δ ppm 0.85-2.14 (m, 15H), 2.21 (s, 3H), 2.67 (t, J=6.2 Hz, 2H), 3.03 (s, 3H), 3.56 (ddd, J=11.6, 8.4, 3.0 Hz, 2H), 3.69 (t, J=6.6 Hz, 2H), 3.88-4.08 (m, 2H), 4.27-4.53 (m, 2H), 6.55 (d, J=8.7 Hz, 2H), 6.78-6.99 (m, 2H), 7.17-7.26 (m, 3H).

Example A83

3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid

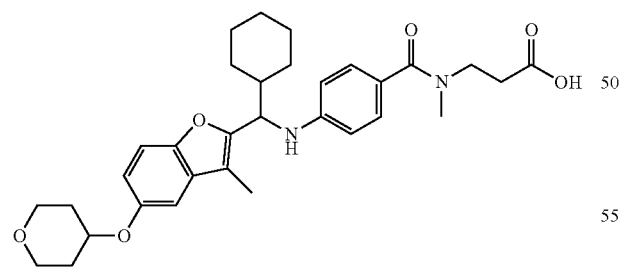

(1) ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate Ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate (4.0 g) synthesized in Example A82(6) was fractionated by high performance liquid chromatography (column: CHIRALPAK AD (50 mm i.d.× 500 mL, manufactured by Daicel Chemical Industries, Ltd., mobile phase: hexane/ethanol (200/800), flow rate: 60 mL/min, column temperature: 30° C.). The fraction containing an optically active form having a shorter retention time under the above-mentioned high performance liquid chromatography conditions was concentrated to give the title object compound (1.8 g, 99.9% ee).

$^1$H NMR (300 MHz, CDCl$_3$) δ ppm 1.00-2.10 (m, 18H), 2.21 (s, 3H), 2.61 (t, J=7.0 Hz, 2H), 3.01 (s, 3H), 3.55 (ddd, J=11.7, 8.5, 3.2 Hz, 2H), 3.70 (t, J=7.0 Hz, 2H), 3.90-4.05 (m, 2H), 4.27-4.52 (m, 4H), 6.56 (d, J=8.7 Hz, 2H), 6.77-6.96 (m, 2H), 7.15-7.25 (m, 3H).

(2) 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid Ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate (1.8 g) optically resolved in the above-mentioned (1) was dissolved in ethanol (20 mL), 1N aqueous sodium hydroxide solution (5 mL) was added at room temperature, and the mixture was stirred at 50° C. for 0.5 hr. Ethanol was evaporated under reduced pressure, 1N hydrochloric acid (5 mL) was added to the residue, and the mixture was extracted with ethyl acetate. The extract was washed with saturated brine, dried over magnesium sulfate, and concentrated under reduced pressure. The residue was recrystallized from acetone to give the title object compound (1.6 g, 95%, 99.9% ee) as colorless crystals.

$^1$H NMR (300 MHz, CDCl$_3$) δ ppm 0.85-2.14 (m, 15H), 2.21 (s, 3H), 2.67 (t, J=6.2 Hz, 2H), 3.03 (s, 3H), 3.56 (ddd, J=11.6, 8.4, 3.0 Hz, 2H), 3.69 (t, J=6.6 Hz, 2H), 3.88-4.08 (m, 2H), 4.27-4.53 (m, 2H), 6.55 (d, J=8.7 Hz, 2H), 6.78-6.99 (m, 2H), 7.17-7.26 (m, 3H).

Example A84

3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid

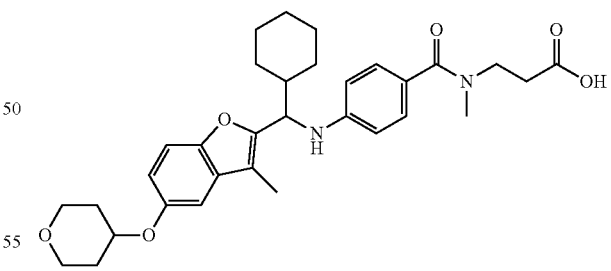

(1) ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate Ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate (4.0 g) synthesized in Example A82(6) was fractionated by high performance liquid chromatography (column: CHIRALPAK AD (50 mm i.d.× 500 mL, manufactured by Daicel Chemical Industries, Ltd., mobile phase: hexane/ethanol (200/800), flow rate: 60 mL/min, column temperature: 30° C.). The fraction containing an optically active form having a longer retention time under the above-mentioned high performance liquid chromatography conditions was concentrated to give the title object compound (1.8 g, 99.9% ee).

$^1$H NMR (300 MHz, CDCl$_3$) δ ppm 1.00-2.10 (m, 18H), 2.21 (s, 3H), 2.61 (t, J=7.0 Hz, 2H), 3.01 (s, 3H), 3.55 (ddd, J=11.7, 8.5, 3.2 Hz, 2H), 3.70 (t, J=7.0 Hz, 2H), 3.90-4.05 (m, 2H), 4.27-4.52 (m, 4H), 6.56 (d, J=8.7 Hz, 2H), 6.77-6.96 (m, 2H), 7.15-7.25 (m, 3H).

(2) 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoic acid Ethyl 3-[{[4-({cyclohexyl[3-methyl-5-(tetrahydro-2H-pyran-4-yloxy)-1-benzofuran-2-yl]methyl}amino)phenyl]carbonyl}(methyl)amino]propanoate (1.8 g) optically resolved in the above-mentioned (1) was dissolved in ethanol (20 mL), 1N aqueous sodium hydroxide solution (5 mL) was added at room temperature, and the mixture was stirred at 50° C. for 0.5 hr. Ethanol was evaporated under reduced pressure, 1N hydrochloric acid (5 mL) was added to the residue, and the mixture was extracted with ethyl acetate. The extract was washed with saturated brine, dried over magnesium sulfate, and concentrated under reduced pressure. The residue was recrystallized from acetone to give the title object compound (1.5 g, 88%, 99.9% ee) as colorless crystals.

$^1$H NMR (300 MHz, CDCl$_3$) δ ppm 0.85-2.14 (m, 15H), 2.21 (s, 3H), 2.67 (t, J=6.2 Hz, 2H), 3.03 (s, 3H), 3.56 (ddd, J=11.6, 8.4, 3.0 Hz, 2H), 3.69 (t, J=6.6 Hz, 2H), 3.88-4.08 (m, 2H), 4.27-4.53 (m, 2H), 6.55 (d, J=8.7 Hz, 2H), 6.78-6.99 (m, 2H), 7.17-7.26 (m, 3H).

Example A85

3-[{[4-({1-[5-(benzyloxy)-3-methyl-1-benzofuran-2-yl]-2-methylpropyl}amino)phenyl]carbonyl}(methyl)amino]propanoic acid

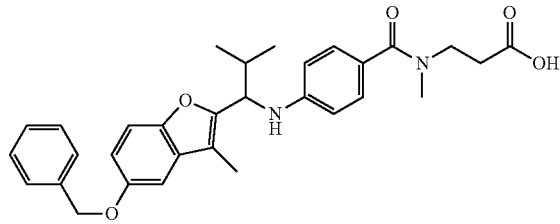 [SMILES: Cc1c(C(Nc2ccc(C(=O)N(C)CCC(=O)O)cc2)C(C)C)oc2ccc(OCc3ccccc3)cc12]

(1) 1-[5-(benzyloxy)-3-methyl-1-benzofuran-2-yl]-2-methylpropan-1-one

To a solution (200 mL) of 1-[5-(benzyloxy)-2-hydroxyphenyl]ethanone (16.1 g) synthesized in Example A82(1) in N,N-dimethylformamide were added at room temperature potassium carbonate (27.6 g) and 1-bromo-3-methylbutan-2-one (14.3 g) synthesized in Example A75(1), and the mixture was stirred for 15 hr. The reaction mixture was filtered through celite, water (200 mL) was added and the mixture was extracted with diethyl ether (100 mL×2). The extract was washed with saturated brine, dried over magnesium sulfate, and concentrated under reduced pressure. The residue was dissolved in N,N-dimethylformamide (100 mL), and DBU (9.9 mL) was added at room temperature. The reaction mixture was stirred at 100° C. for 1 hr. The reaction mixture was allowed to cool to room temperature, 1N hydrochloric acid (150 mL) was added, and the mixture was extracted with diethyl ether (100 mL×2). The extract was washed with water, saturated aqueous sodium hydrogen carbonate solution and saturated brine, dried over magnesium sulfate, and concentrated under reduced pressure. The residue was recrystallized from ethanol-diisopropyl ether to give the title object compound (11.7 g, 57%) as pale-yellow crystals.

$^1$H NMR (300 MHz, CDCl$_3$) δ ppm 1.23 (d, J=6.8 Hz, 6H), 2.57 (s, 3H), 3.57 (dt, J=13.8, 6.8 Hz, 1H), 5.12 (s, 2H), 7.11 (d, J=2.6 Hz, 1H), 7.13-7.21 (m, 1H), 7.30-7.55 (m, 6H).

(2) 1-[5-(benzyloxy)-3-methyl-1-benzofuran-2-yl]-2-methylpropan-1-ol

1-[5-(Benzyloxy)-3-methyl-1-benzofuran-2-yl]-2-methylpropan-1-one (11.7 g) synthesized in the above-mentioned (1) was dissolved in a tetrahydrofuran (150 mL) and methanol (15 mL), and sodium borohydride (90%, 3.0 g) was added under ice-cooling. The ice bath was removed, the reaction mixture was stirred at room temperature for 2 hr. The mixture was ice-cooled again, water (10 mL) and 1N hydrochloric acid (100 mL) were carefully added, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (11.3 g, quantitative) as a pale-yellow oil.

$^1$H NMR (300 MHz, CDCl$_3$) δ ppm 0.82 (d, J=6.8 Hz, 3H), 1.12 (d, J=6.8 Hz, 3H), 1.55 (d, J=2.6 Hz, 1H), 2.11-2.34 (m, 4H), 4.46 (dd, J=8.3, 6.0 Hz, 1H), 5.10 (s, 2H), 6.82-7.08 (m, 2H), 7.28-7.55 (m, 6H).

(3) ethyl 3-[{[4-({1-[5-(benzyloxy)-3-methyl-1-benzofuran-2-yl]-2-methylpropyl}amino)phenyl]carbonyl}(methyl)amino]propanoate 1-[5-(Benzyloxy)-3-methyl-1-benzofuran-2-yl]-2-methylpropan-1-ol (10.2 g) synthesized in the above-mentioned (2) was dissolved in tetrahydrofuran (150 mL), and thionyl chloride (4.3 mL) was added at room temperature. The reaction mixture was stirred at room temperature for 30 min then ice-cooled, and saturated aqueous sodium hydrogen carbonate solution (100 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (200 mL), sodium iodide (7.4 g), sodium carbonate (5.0 g) and ethyl 3-{[(4-aminophenyl)carbonyl](methyl)amino}propanoate (8.2 g) synthesized in Example 2(2) were added, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (6.3 g, 35%) as a yellow oil.

$^1$H NMR (300 MHz, CDCl$_3$) δ ppm 0.91 (d, J=6.8 Hz, 3H), 1.12 (d, J=6.8 Hz, 3H), 1.23 (t, J=7.2 Hz, 3H), 2.13-2.33 (m, 4H), 2.61 (t, J=7.2 Hz, 2H), 3.01 (s, 3H), 3.71 (t, J=7.2 Hz, 2H), 4.12 (q, J=7.2 Hz, 2H), 4.25-4.46 (m, 2H), 5.09 (s, 2H), 6.57 (d, J=8.7 Hz, 2H), 6.81-7.02 (m, 2H), 7.15-7.25 (m, 3H), 7.30-7.59 (m, 5H).

(4) 3-[{[4-({1-[5-(benzyloxy)-3-methyl-1-benzofuran-2-yl]-2-methylpropyl}amino)phenyl]carbonyl}(methyl)amino]propanoic acid Ethyl 3-[{[4-({1-[5-(benzyloxy)-3-methyl-1-benzofuran-2-yl]-2-methylpropyl}amino)phenyl]carbonyl}(methyl)amino]propanoate (0.38 g) synthesized in the above-mentioned (3) was dissolved in ethanol (5 mL), 1N aqueous sodium hydroxide solution (1.5 mL) was added at room temperature, and the mixture was stirred at room temperature for 0.5 hr. Ethanol was evaporated under reduced pressure, 1N hydrochloric acid (1.5 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.28 g, 79%) as a colorless solid.

¹H NMR (300 MHz, CDCl₃) δ ppm 0.91 (d, J=6.8 Hz, 3H), 1.12 (d, J=6.8 Hz, 3H), 2.18-2.30 (m, 4H), 2.66 (t, J=6.2 Hz, 2H), 3.03 (s, 3H), 3.69 (t, J=6.2 Hz, 2H), 4.32 (d, J=7.5 Hz, 1H), 5.08 (s, 2H), 6.56 (d, J=8.7 Hz, 2H), 6.83-7.02 (m, 2H), 7.17-7.26 (m, 3H), 7.30-7.53 (m, 5H).

Example A86

3-[{[4-({1-[5-(benzyloxy)-3-methyl-1-benzofuran-2-yl]-2-methylpropyl}amino)phenyl]carbonyl}(methyl)amino]propanoic acid

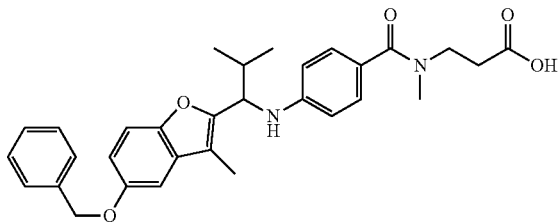 [SMILES: Cc1c(C(Nc2ccc(C(=O)N(C)CCC(=O)O)cc2)C(C)C)oc2ccc(OCc3ccccc3)cc12]

(1) ethyl 3-[{[4-({1-[5-(benzyloxy)-3-methyl-1-benzofuran-2-yl]-2-methylpropyl}amino)phenyl]carbonyl}(methyl)amino]propanoate Ethyl 3-[{[4-({1-[5-(benzyloxy)-3-methyl-1-benzofuran-2-yl]-2-methylpropyl}amino)phenyl]carbonyl}(methyl)amino]propanoate (3.0 g) synthesized in Example A85(3) was fractionated by high performance liquid chromatography (column: CHIRALPAK AD (50 mm i.d.×500 mL, manufactured by Daicel Chemical Industries, Ltd., mobile phase: hexane/ethanol (200/800), flow rate: 60 mL/min, column temperature: 30° C.). The fraction containing an optically active form having a longer retention time under the above-mentioned high performance liquid chromatography conditions was concentrated to give the title object compound (1.23 g, 99.9% ee).

¹H NMR (300 MHz, CDCl₃) δ ppm 0.91 (d, J=6.8 Hz, 3H), 1.12 (d, J=6.8 Hz, 3H), 1.23 (t, J=7.2 Hz, 3H), 2.13-2.33 (m, 4H), 2.61 (t, J=7.2 Hz, 2H), 3.01 (s, 3H), 3.71 (t, J=7.2 Hz, 2H), 4.12 (q, J=7.2 Hz, 2H), 4.25-4.46 (m, 2H), 5.09 (s, 2H), 6.57 (d, J=8.7 Hz, 2H), 6.81-7.02 (m, 2H), 7.15-7.25 (m, 3H), 7.30-7.59 (m, 5H).

(2) 3-[{[4-({1-[5-(benzyloxy)-3-methyl-1-benzofuran-2-yl]-2-methylpropyl}amino)phenyl]carbonyl}(methyl)amino]propanoic acid Ethyl 3-[{[4-({1-[5-(benzyloxy)-3-methyl-1-benzofuran-2-yl]-2-methylpropyl}amino)phenyl]carbonyl}(methyl)amino]propanoate (1.23 g) optically resolved in the above-mentioned (1) was dissolved in ethanol (15 mL), 1N aqueous sodium hydroxide solution (4 mL) was added at room temperature, and the mixture was stirred at 50° C. for 0.5 hr. Ethanol was evaporated under reduced pressure, 1N hydrochloric acid (4 mL) was added to the residue, and the mixture was extracted with ethyl acetate. The extract was washed with saturated brine, dried over magnesium sulfate, and concentrated under reduced pressure. The residue was washed with ethanol-water to give the title object compound (1.22 g, 95%, 99.9% ee) as a colorless solid.

¹H NMR (300 MHz, CDCl₃) δ ppm 0.91 (d, J=6.8 Hz, 3H), 1.12 (d, J=6.8 Hz, 3H), 2.18-2.30 (m, 4H), 2.66 (t, J=6.2 Hz, 2H), 3.03 (s, 3H), 3.69 (t, J=6.2 Hz, 2H), 4.32 (d, J=7.5 Hz, 1H), 5.08 (s, 2H), 6.56 (d, J=8.7 Hz, 2H), 6.83-7.02 (m, 2H), 7.17-7.26 (m, 3H), 7.30-7.53 (m, 5H).

Example A87

3-[{[4-({1-[5-(benzyloxy)-3-methyl-1-benzofuran-2-yl]-2-methylpropyl}amino)phenyl]carbonyl}(methyl)amino]propanoic acid

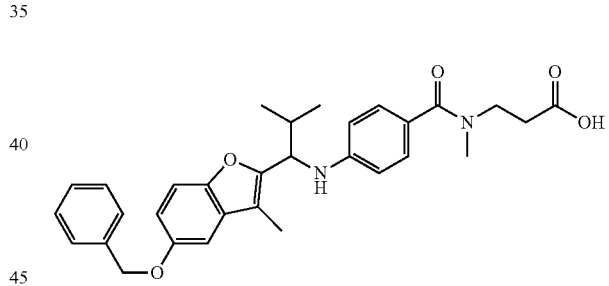

(1) ethyl 3-[{[4-({1-[5-(benzyloxy)-3-methyl-1-benzofuran-2-yl]-2-methylpropyl}amino)phenyl]carbonyl}(methyl)amino]propanoate Ethyl 3-[{[4-({1-[5-(benzyloxy)-3-methyl-1-benzofuran-2-yl]-2-methylpropyl}amino)phenyl]carbonyl}(methyl)amino]propanoate (3.0 g) synthesized in Example A85(3) was fractionated by high performance liquid chromatography (column: CHIRALPAK AD (50 mm i.d.×500 mL, manufactured by Daicel Chemical Industries, Ltd., mobile phase: hexane/ethanol (200/800), flow rate: 60 mL/min, column temperature: 30° C.). The fraction containing an optically active form having a shorter retention time under the above-mentioned high performance liquid chromatography conditions was concentrated to give the title object compound (1.25 g, 99.9% ee).

¹H NMR (300 MHz, CDCl₃) δ ppm 0.91 (d, J=6.8 Hz, 3H), 1.12 (d, J=6.8 Hz, 3H), 1.23 (t, J=7.2 Hz, 3H), 2.13-2.33 (m, 4H), 2.61 (t, J=7.2 Hz, 2H), 3.01 (s, 3H), 3.71 (t, J=7.2 Hz, 2H), 4.12 (q, J=7.2 Hz, 2H), 4.25-4.46 (m, 2H), 5.09 (s, 2H), 6.57 (d, J=8.7 Hz, 2H), 6.81-7.02 (m, 2H), 7.15-7.25 (m, 3H), 7.30-7.59 (m, 5H).

(2) 3-[{[4-({1-[5-(benzyloxy)-3-methyl-1-benzofuran-2-yl]-2-methylpropyl}amino)phenyl]carbonyl}(methyl)amino]propanoic acid Ethyl 3-[{[4-({1-[5-(benzyloxy)-3-methyl-1-benzofuran-2-yl]-2-methylpropyl}amino)phenyl]carbonyl}(methyl)amino]propanoate (1.25 g) optically resolved in the above-mentioned (1) was dissolved in ethanol (15 mL), 1N aqueous sodium hydroxide solution (4 mL) was added at room temperature, and the mixture was stirred at 50° C. for 0.5 hr. Ethanol was evaporated under reduced pressure, 1N hydrochloric acid (4 mL) was added to the residue, and the mixture was extracted with ethyl acetate. The extract was washed with saturated brine, dried over magnesium sulfate, and concentrated under reduced pressure. The residue was washed with ethanol-water to give the title object compound (1.08 g, 93%, 99.9% ee) as a colorless solid.

$^1$H NMR (300 MHz, CDCl$_3$) δ ppm 0.91 (d, J=6.8 Hz, 3H), 1.12 (d, J=6.8 Hz, 3H), 2.18-2.30 (m, 4H), 2.66 (t, J=6.2 Hz, 2H), 3.03 (s, 3H), 3.69 (t, J=6.2 Hz, 2H), 4.32 (d, J=7.5 Hz, 1H), 5.08 (s, 2H), 6.56 (d, J=8.7 Hz, 2H), 6.83-7.02 (m, 2H), 7.17-7.26 (m, 3H), 7.30-7.53 (m, 5H).

Example A88

3-{[(4-{[(5-chloro-3-methyl-1-benzofuran-2-yl)(cyclohexyl)methyl]amino}phenyl)carbonyl]amino}propanoic acid

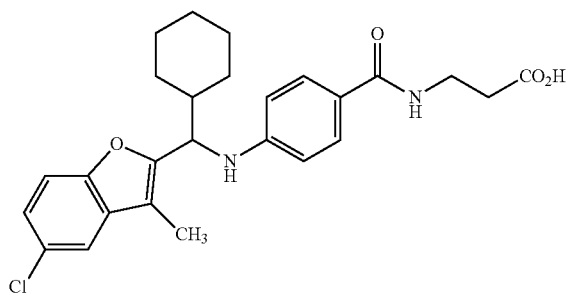 [SMILES: Cc1c(C(Nc2ccc(C(=O)NCCC(=O)O)cc2)C2CCCCC2)oc2ccc(Cl)cc12]

(1) 5-chloro-N-methoxy-N,3-dimethyl-1-benzofuran-2-carboxamide

To a solution (50 mL) of 1-(5-chloro-2-hydroxyphenyl)ethanone (5.00 g) in tetrahydrofuran were added potassium carbonate (8.10 g), sodium iodide (8.78 g) and 2-chloro-N-methoxy-N-methylacetamide (4.43 g), and the mixture was stirred overnight with heating under reflux. Insoluble material was filtered off, and the filtrate was concentrated under reduced pressure to give a white solid. To a solution (50 mL) of the obtained solid in N,N-dimethylformamide was added 1,8-diazabicyclo[5.4.0]undec-7-ene (4.38 mL), and the mixture was stirred at 120° C. for 2 hr. The reaction mixture was cooled to room temperature, 1N hydrochloric acid was added, and the mixture was extracted with ethyl acetate. The extract was washed with saturated brine, dried over magnesium sulfate, and concentrated under reduced pressure. The residue was purified by silica gel column chromatography (30% ethyl acetate/hexane) to give the title object compound (2.15 g, 29%) as a brown solid.

$^1$H NMR (300 MHz, CDCl$_3$) δ ppm 2.47 (s, 3H), 3.38 (s, 3H), 3.86 (s, 3H), 7.35 (dd, J=8.9, 1.8 Hz, 1H), 7.40 (dd, J=8.9, 0.6 Hz, 1H), 7.57 (dd, J=1.8, 0.6 Hz, 1H).

(2) 5-chloro-3-methyl-1-benzofuran-2-carbaldehyde

To a solution (40 mL) of 5-chloro-N-methoxy-N,3-dimethyl-1-benzofuran-2-carboxamide (2.15 g) synthesized above in tetrahydrofuran was added lithium aluminum hydride (322 mg) at 0° C., and the mixture was stirred for 1 hr. Water (320 μL) was added to quench the reaction, 1N aqueous sodium hydroxide solution (320 μL) was added, and the mixture was stirred at room temperature for 1 hr. The resulting insoluble material was filtered off, and the filtrate was concentrated under reduced pressure. The residue was purified by silica gel column chromatography (tetrahydrofuran) to give a pale-yellow solid. The obtained solid was washed with diisopropyl ether to give the title object compound (1.21 g, 73%) as a pale-yellow solid.

$^1$H NMR (300 MHz, CDCl$_3$) δ ppm 2.60 (s, 3H), 7.43-7.51 (m, 2H), 7.65-7.67 (m, 1H), 10.02 (s, 1H).

(3) (5-chloro-3-methyl-1-benzofuran-2-yl)(cyclohexyl)methanol

To a solution (10 mL) of 5-chloro-3-methyl-1-benzofuran-2-carbaldehyde (600 mg) synthesized above in tetrahydrofuran was added a 1.0M solution (4.62 mL) of cyclohexylmagnesium bromide in tetrahydrofuran at 0° C., and the mixture was stirred for 1 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (15% ethyl acetate/hexane) to give the title object compound (518 mg, 60%) as a pale-yellow oil.

$^1$H NMR (300 MHz, CDCl$_3$) δ ppm 0.85-1.41 (m, 6H), 1.61-1.71 (m, 2H), 1.75-1.98 (m, 3H), 2.09-2.18 (m, 1H), 2.19 (s, 3H), 4.52 (dd, J=8.4, 6.0 Hz, 1H), 7.20 (dd, J=8.4, 2.1 Hz, 1H), 7.33 (dd, J=8.4, 0.6 Hz, 1H), 7.42 (dd, J=2.1, 0.6 Hz, 1H).

(4) 5-chloro-2-[chloro(cyclohexyl)methyl]-3-methyl-1-benzofuran

To a solution (10 mL) of (5-chloro-3-methyl-1-benzofuran-2-yl)(cyclohexyl)methanol (518 mg) synthesized above in toluene was added thionyl chloride (163 μL), and the mixture was stirred at 100° C. for 1 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (553 mg, quantitative) as a pale-yellow oil.

$^1$H NMR (300 MHz, CDCl$_3$) δ ppm 0.83-1.48 (m, 6H), 1.60-1.71 (m, 2H), 1.77-1.87 (m, 1H), 2.10-2.24 (m, 4H), 2.27-2.37 (m, 1H), 4.78 (d, J=9.6 Hz, 1H), 7.20-7.26 (m, 1H), 7.34-7.38 (m, 1H), 7.42-7.44 (m, 1H).

(5) 3-{[(4-{[(5-chloro-3-methyl-1-benzofuran-2-yl)(cyclohexyl)methyl]amino}phenyl)carbonyl]amino}propanoic acid A mixture of 5-chloro-2-[chloro(cyclohexyl)methyl]-3-methyl-1-benzofuran (270 mg) synthesized above, ethyl 3-{[(4-aminophenyl)carbonyl]amino}propanoate (215 mg) synthesized in Example 1(2), sodium iodide (204 mg), sodium carbonate (144 mg) and N,N-dimethylformamide (10 mL) was stirred overnight at 80° C. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give a pale-yellow oil. To a mixture of the obtained oil, tetrahydrofuran (5 mL) and ethanol (5 mL) 1N aqueous sodium hydroxide solution (1.00 mL) was added, and the mixture was stirred at room temperature for 2 hr, and the reaction mixture was concentrated under reduced pressure. The residue was dissolved in water (10 mL), and 1N hydrochloric acid (1.00 mL) was added at 0° C. The resulting precipitate was collected by filtration to give the title object compound (132 mg, 31%) as a yellow solid.

$^1$H NMR (300 MHz, CDCl$_3$) δ ppm 0.92-1.35 (m, 5H), 1.44-1.55 (m, 1H), 1.60-1.96 (m, 4H), 2.01-2.12 (m, 1H), 2.20 (s, 3H), 2.54-2.67 (m, 2H), 3.56-3.68 (m, 2H), 4.37 (d, J=7.9 Hz, 1H), 6.50-6.66 (m, 3H), 7.12-7.18 (m, 1H), 7.23-7.30 (m, 1H), 7.37 (d, J=1.9 Hz, 1H), 7.52 (d, J=8.7 Hz, 2H).

Example A89

3-{[(4-{[(5-chloro-3-methyl-1-benzofuran-2-yl)(cyclohexyl)methyl]amino}phenyl)carbonyl]methyl)amino}-propanoic acid

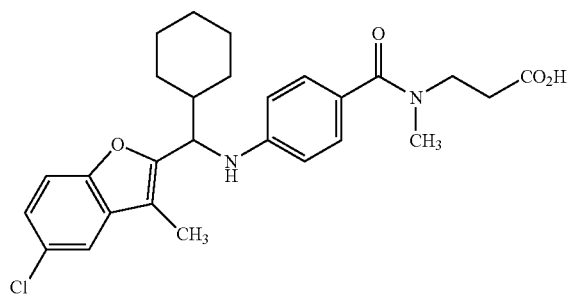 [SMILES: Cc1c(C(Nc2ccc(C(=O)N(C)CCC(=O)O)cc2)C2CCCCC2)oc2ccc(Cl)cc12]

A mixture of 5-chloro-2-[chloro(cyclohexyl)methyl]-3-methyl-1-benzofuran (283 mg) synthesized in Example A88 (4), ethyl 3-{[(4-aminophenyl)carbonyl](methyl)amino}propanoate (238 mg) synthesized in Example 2(2), sodium iodide (214 mg), sodium carbonate (152 mg) and N,N-dimethylformamide (10 mL) was stirred overnight at 80° C. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (40% ethyl acetate/hexane) to give a pale-yellow oil. To a mixture of the obtained oil, tetrahydrofuran (5 mL) and ethanol (5 mL) 1N aqueous sodium hydroxide solution (1.00 mL) was added, and the mixture was stirred at room temperature for 1.5 hr, and concentrated under reduced pressure. The residue was dissolved in water (10 mL), and 1N hydrochloric acid (1.00 mL) was added at 0° C. The resulting precipitate was collected by filtration to give the title object compound (113 mg, 25%) as a yellow solid.

$^1$H NMR (300 MHz, CDCl$_3$) δ ppm 0.93-1.38 (m, 5H), 1.45-1.56 (m, 1H), 1.61-1.97 (m, 4H), 2.02-2.13 (m, 1H), 2.21 (s, 3H), 2.60-2.69 (m, 2H), 3.01 (s, 3H), 3.68 (t, J=6.2 Hz, 2H), 4.36 (d, J=7.9 Hz, 1H), 6.54 (d, J=8.7 Hz, 2H), 7.13-7.19 (m, 1H), 7.20-7.31 (m, 3H), 7.38 (d, J=1.9 Hz, 1H).

Example A90

3-{[(4-{[cyclohexyl(3,5-dimethyl-1-benzofuran-2-yl)methyl]amino}phenyl)carbonyl]amino}propanoic acid

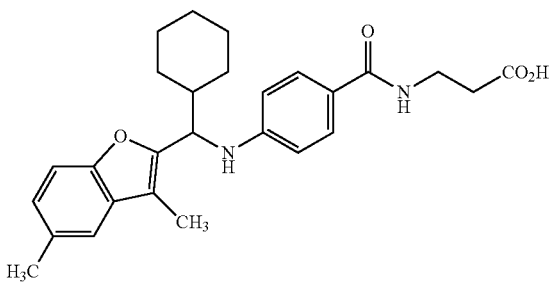 [SMILES: Cc1ccc2oc(C(Nc3ccc(C(=O)NCCC(=O)O)cc3)C3CCCCC3)c(C)c2c1]

(1) N-methoxy-N,3,5-trimethyl-1-benzofuran-2-carboxamide

To a solution (50 mL) of 1-(2-hydroxy-5-methylphenyl)ethanone (5.00 g) in N,N-dimethylformamide were added potassium carbonate (9.20 g), sodium iodide (9.98 g) and 2-chloro-N-methoxy-N-methylacetamide (5.04 g), and the mixture was stirred at 50° C. for 5 hr then at 80° C. overnight. The insoluble material was filtered off, 1,8-diazabicyclo[5.4.0]undec-7-ene (5.00 mL) was added to the filtrate and the mixture was stirred at 120° C. for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (3.78 g, 49%) as a brown oil.

$^1$H NMR (300 MHz, CDCl$_3$) δ 2.47 (s, 3H), 2.49 (s, 3H), 3.38 (s, 3H), 3.86 (s, 3H), 7.19-7.24 (m, 1H), 7.32-7.34 (m, 1H), 7.35-7.39 (m, 1H).

(2) 3,5-dimethyl-1-benzofuran-2-carbaldehyde

To a solution (50 mL) of N-methoxy-N,3,5-trimethyl-1-benzofuran-2-carboxamide (3.78 g) synthesized above in tetrahydrofuran was added lithium aluminum hydride (307 mg) at −78° C., and the mixture was stirred for 2 hr. Water (350 µL) was added to quench the reaction, 1N aqueous sodium hydroxide solution (700 µL) was added, and the mixture was stirred at room temperature for 1 hr. The resulting insoluble material was filtered off, and the filtrate was concentrated under reduced pressure. The residue was washed with hexane to give the title object compound (2.08 g, 74%) as a yellow solid.

$^1$H NMR (300 MHz, CDCl$_3$) δ ppm 2.48 (s, 3H), 2.60 (s, 3H), 7.30-7.35 (m, 1H), 7.40-7.47 (m, 2H), 10.01 (s, 1H).

(3) cyclohexyl(3,5-dimethyl-1-benzofuran-2-yl)methanol

To a solution (20 mL) of 3,5-dimethyl-1-benzofuran-2-carbaldehyde (1.00 g) synthesized above in tetrahydrofuran was added a 1.0M solution (8.61 mL) of cyclohexylmagnesium bromide in tetrahydrofuran at 0° C., and the mixture was stirred for 1 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (25% ethyl acetate/hexane) to give the title object compound (1.13 g, 76%) as a pale-yellow solid.

$^1$H NMR (300 MHz, CDCl$_3$) δ ppm 0.83-0.99 (m, 1H), 1.00-1.44 (m, 5H), 1.58-1.70 (m, 2H), 1.74-1.98 (m, 3H), 2.09-2.22 (m, 4H), 2.45 (s, 3H), 4.51 (dd, J=8.5, 5.9 Hz, 1H), 7.03-7.11 (m, 1H), 7.23-7.33 (m, 2H).

(4) 2-[chloro(cyclohexyl)methyl]-3,5-dimethyl-1-benzofuran

To a solution (20 mL) of cyclohexyl(3,5-dimethyl-1-benzofuran-2-yl)methanol (1.13 g) synthesized above in toluene pyridine (424 μL) and thionyl chloride (382 μL) were added, and the mixture was stirred at room temperature for 5 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give the title object compound (1.12 g, 93%) as a yellow oil.

$^1$H NMR (300 MHz, CDCl$_3$) δ ppm 0.82-0.97 (m, 1H), 1.00-1.40 (m, 4H), 1.41-1.51 (m, 1H), 1.59-1.70 (m, 2H), 1.76-1.87 (m, 1H), 2.11-2.25 (m, 4H), 2.28-2.38 (m, 1H), 2.44 (s, 3H), 4.80 (d, J=9.3 Hz, 1H), 7.07-7.12 (m, 1H), 7.23-7.26 (m, 1H), 7.32 (d, J=8.4 Hz, 1H).

(5) 3-{[(4-{[cyclohexyl(3,5-dimethyl-1-benzofuran-2-yl)methyl]amino}phenyl)carbonyl]amino}propanoic acid A mixture of 2-[chloro(cyclohexyl)methyl]-3,5-dimethyl-1-benzofuran (400 mg) synthesized above, ethyl 3-{[(4-aminophenyl)carbonyl]amino}propanoate (343 mg) synthesized in Example 1(2), sodium iodide (327 mg), sodium carbonate (231 mg) and N,N-dimethylformamide (10 mL) was stirred at 80° C. for 5 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (45% ethyl acetate/hexane) to give a yellow oil. To a mixture of the obtained oil, tetrahydrofuran (5 mL) and ethanol (5 mL) 1N aqueous sodium hydroxide solution (2.00 mL) were added, and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (436 mg, 67%) as a white solid.

$^1$H NMR (300 MHz, CDCl$_3$) δ ppm 0.93-1.36 (m, 5H), 1.47-1.58 (m, 1H), 1.59-1.97 (m, 4H), 2.02-2.12 (m, 1H), 2.22 (s, 3H), 2.42 (s, 3H), 2.61-2.69 (m, 2H), 3.60-3.70 (m, 2H), 4.38 (d, J=8.0 Hz, 1H), 6.49-6.60 (m, 3H), 7.00-7.06 (m, 1H), 7.19-7.24 (m, 2H), 7.52 (d, J=7.6 Hz, 2H).

Example A91

3-{[(4-{[cyclohexyl(3,5-dimethyl-1-benzofuran-2-yl)methyl]amino}phenyl)carbonyl](methyl)amino}propanoic acid

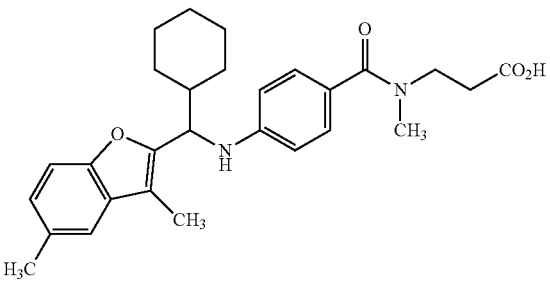 [SMILES: Cc1ccc2oc(C(Nc3ccc(C(=O)N(C)CCC(=O)O)cc3)C3CCCCC3)c(C)c2c1]

(1) ethyl 3-{[(4-{[cyclohexyl(3,5-dimethyl-1-benzofuran-2-yl)methyl]amino}phenyl)carbonyl](methyl)amino}propanoate A mixture of 2-[chloro(cyclohexyl)methyl]-3,5-dimethyl-1-benzofuran (400 mg) synthesized in Example A90(4), ethyl 3-{[(4-aminophenyl)carbonyl](methyl)amino}propanoate (363 mg) synthesized in Example 2(2), sodium iodide (327 mg), sodium carbonate (231 mg) and N,N-dimethylformamide (10 mL) was stirred at 80° C. for 5 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (45% ethyl acetate/hexane) to give the title object compound (471 mg, 66%) as a yellow oil.

$^1$H NMR (300 MHz, CDCl$_3$) δ ppm 0.94-1.36 (m, 8H), 1.48-1.59 (m, 1H), 1.60-1.96 (m, 4H), 2.03-2.13 (m, 1H), 2.22 (s, 3H), 2.42 (s, 3H), 2.57-2.65 (m, 2H), 3.01 (s, 3H), 3.70 (t, J=7.1 Hz, 2H), 4.07-4.17 (m, 2H), 4.32-4.40 (m, 2H), 6.56 (d, J=8.7 Hz, 2H), 7.03 (dd, J=8.3, 1.3 Hz, 1H), 7.17-7.24 (m, 4H).

(2) 3-{[(4-{[cyclohexyl(3,5-dimethyl-1-benzofuran-2-yl)methyl]amino}phenyl)carbonyl](methyl)amino}propanoic acid To a mixture of ethyl 3-{[(4-{[cyclohexyl(3,5-dimethyl-1-benzofuran-2-yl)methyl]amino}phenyl)carbonyl](methyl)amino}propanoate (471 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 μL), and 1N hydrochloric acid (2.00 mL) was added at 0° C. The resulting precipitate was collected by filtration to give the title object compound (407 mg, 92%) as a white solid.

$^1$H NMR (300 MHz, CDCl$_3$) δ ppm 0.93-1.37 (m, 5H), 1.47-1.58 (m, 1H), 1.60-1.97 (m, 4H), 2.02-2.14 (m, 1H), 2.23 (s, 3H), 2.42 (s, 3H), 2.62-2.73 (m, 2H), 3.04 (s, 3H), 3.70 (t, J=6.4 Hz, 2H), 4.37 (d, J=8.0 Hz, 1H), 6.56 (d, J=8.7 Hz, 2H), 7.00-7.06 (m, 1H), 7.19-7.28 (m, 4H).

Example A92

3-{[(4-{[1-(5-methoxy-3-methyl-1-benzofuran-2-yl)-3-methylbutyl]amino}phenyl)carbonyl]amino}propanoic acid

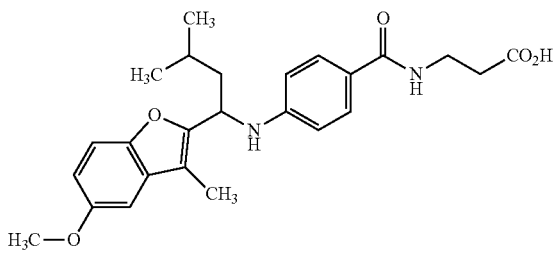 [SMILES: COc1ccc2oc(C(CC(C)C)Nc3ccc(C(=O)NCCC(=O)O)cc3)c(C)c2c1]

(1) 1-(5-methoxy-3-methyl-1-benzofuran-2-yl)-3-methylbutan-1-ol

To a solution (4.0 mL) of 5-methoxy-3-methyl-1-benzofuran-2-carbaldehyde (1.91 g) synthesized in Example A27(2) in tetrahydrofuran was added a solution (15.0 mL) of 1.0M isobutylmagnesium bromide in tetrahydrofuran at 0° C., and the mixture was stirred for 1 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (1.53 g, 62%) as a yellow oil.
$^1$H NMR (300 MHz, CDCl$_3$) δ ppm 0.93 (d, J=6.6 Hz, 3H), 0.95 (d, J=6.6 Hz, 3H), 1.54-1.69 (m, 1H), 1.74-1.96 (m, 3H), 2.23 (s, 3H), 3.85 (s, 3H), 4.88-4.97 (m, 1H), 6.86 (dd, J=8.6, 2.7 Hz, 1H), 6.91 (d, J=2.7 Hz, 1H), 7.30 (d, J=8.6 Hz, 1H).

(2) 2-(1-chloro-3-methylbutyl)-5-methoxy-3-methyl-1-benzofuran

To a solution (10 mL) of 1-(5-methoxy-3-methyl-1-benzofuran-2-yl)-3-methylbutan-1-ol (761 mg) synthesized above in toluene were added pyridine (297 μL) and thionyl chloride (268 μL), and the mixture was stirred at room temperature for 3 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give the title object compound (769 mg, 94%) as a brown oil.
$^1$H NMR (300 MHz, CDCl$_3$) δ ppm 0.91-0.96 (m, 3H), 1.12 (d, J=6.8 Hz, 3H), 1.58-1.75 (m, 1H), 2.15 (d, J=7.9 Hz, 2H), 2.24 (s, 3H), 3.86 (s, 3H), 5.20 (t, J=7.8 Hz, 1H), 6.86-6.93 (m, 2H), 7.34 (d, J=9.4 Hz, 1H).

(3) ethyl 3-{[(4-{[1-(5-methoxy-3-methyl-1-benzofuran-2-yl)-3-methylbutyl]amino}phenyl)carbonyl]amino}propanoate A mixture of 2-(1-chloro-3-methylbutyl)-5-methoxy-3-methyl-1-benzofuran (380 mg) synthesized above, ethyl 3-{[(4-aminophenyl)carbonyl]amino}propanoate (350 mg) synthesized in Example 1(2), sodium iodide (443 mg), sodium carbonate (314 mg) and N,N-dimethylformamide (10 mL) was stirred at 80° C. for 5 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (50% ethyl acetate/hexane) to give the title object compound (266 mg, 40%) as a yellow oil.
$^1$H NMR (300 MHz, CDCl$_3$) δ ppm 0.91 (d, J=6.8 Hz, 3H), 1.00 (d, J=6.8 Hz, 3H), 1.20-1.30 (m, 3H), 1.49-1.64 (m, 1H), 1.79-1.91 (m, 2H), 2.26 (s, 3H), 2.59 (t, J=5.9 Hz, 2H), 3.62-3.71 (m, 2H), 3.83 (s, 3H), 4.07-4.21 (m, 2H), 4.30-4.44 (m, 1H), 4.70 (t, J=7.4 Hz, 1H), 6.56-6.63 (m, 3H), 6.80-6.85 (m, 1H), 6.88 (d, J=2.3 Hz, 1H), 7.25 (d, J=8.7 Hz, 1H), 7.56 (d, J=8.7 Hz, 2H).

(4) 3-{[(4-{[1-(5-methoxy-3-methyl-1-benzofuran-2-yl)-3-methylbutyl]amino}phenyl)carbonyl]amino}propanoic acid To a mixture of ethyl 3-{[(4-{[1-(5-methoxy-3-methyl-1-benzofuran-2-yl)-3-methylbutyl]amino}phenyl)carbonyl]amino}propanoate (266 mg) synthesized above, tetrahydrofuran (5 mL) and ethanol (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (216 mg, 86%) as a white solid.
$^1$H NMR (300 MHz, CDCl$_3$) δ ppm 0.90 (d, J=6.4 Hz, 3H), 0.99 (d, J=6.4 Hz, 3H), 1.48-1.64 (m, 1H), 1.76-1.93 (m, 2H), 2.25 (s, 3H), 2.63 (t, J=5.7 Hz, 2H), 3.59-3.69 (m, 2H), 3.83 (s, 3H), 4.70 (t, J=7.4 Hz, 1H), 6.54-6.65 (m, 3H), 6.78-6.85 (m, 1H), 6.87 (d, J=2.7 Hz, 1H), 7.20-7.30 (m, 1H), 7.53 (d, J=8.7 Hz, 2H).

Example A93

3-{[(4-{[1-(5-methoxy-3-methyl-1-benzofuran-2-yl)-3-methylbutyl]amino}phenyl)carbonyl](methyl)amino}propanoic acid

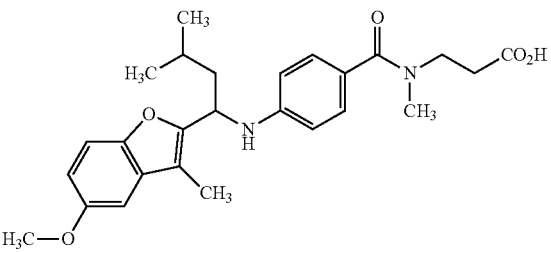 [SMILES: COc1ccc2oc(C(CC(C)C)Nc3ccc(C(=O)N(C)CCC(=O)O)cc3)c(C)c2c1]

(1) ethyl 3-{[(4-{[1-(5-methoxy-3-methyl-1-benzofuran-2-yl)-3-methylbutyl]amino}phenyl)carbonyl](methyl)amino}propanoate A mixture of 2-(1-chloro-3-methylbutyl)-5-methoxy-3-methyl-1-benzofuran (380 mg) synthesized in Example A92 (2), ethyl 3-{[(4-aminophenyl)carbonyl](methyl)amino}propanoate (370 mg) synthesized in Example 2(2), sodium iodide (443 mg), sodium carbonate (314 mg) and N,N-dimethylformamide (10 mL) was stirred at 80° C. for 5 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (60% ethyl acetate/hexane) to give the title object compound (350 mg, 51%) as a yellow oil.

$^1$H NMR (300 MHz, CDCl$_3$) δ ppm 0.91 (d, J=6.4 Hz, 3H), 1.00 (d, J=6.8 Hz, 3H), 1.19-1.30 (m, 3H), 1.49-1.64 (m, 1H), 1.80-1.89 (m, 2H), 2.26 (s, 3H), 2.61 (t, J=7.0 Hz, 2H), 3.01 (s, 3H), 3.71 (t, J=7.0 Hz, 2H), 3.84 (s, 3H), 4.07-4.17 (m, 2H), 4.68 (t, J=7.4 Hz, 1H), 6.58 (d, J=8.7 Hz, 2H), 6.80-6.86 (m, 1H), 6.88 (d, J=2.3 Hz, 1H), 7.23 (d, J=8.7 Hz, 2H), 7.26 (d, J=8.7 Hz, 1H).

(2) 3-{[(4-{[1-(5-methoxy-3-methyl-1-benzofuran-2-yl)-3-methylbutyl]amino}phenyl)carbonyl](methyl)amino}propanoic acid To a mixture of ethyl 3-{[(4-{[1-(5-methoxy-3-methyl-1-benzofuran-2-yl)-3-methylbutyl]amino}phenyl)carbonyl](methyl)amino}propanoate (350 mg) synthesized above, tetrahydrofuran (5 mL) and ethanol (5 mL) was added 1N aqueous sodium hydroxide solution (2.00 mL), and the mixture was stirred at room temperature for 5 hr, and concentrated under reduced pressure. The residue was dissolved in water (10 mL), and 1N hydrochloric acid (2.00 mL) was added at 0° C. The resulting precipitate was collected by filtration to give the title object compound (308 mg, 94%) as a white solid.

$^1$H NMR (300 MHz, CDCl$_3$) δ ppm 0.91 (d, J=6.4 Hz, 3H), 1.00 (d, J=6.4 Hz, 3H), 1.48-1.65 (m, 1H), 1.81-1.89 (m, 2H), 2.26 (s, 3H), 2.65-2.75 (m, 2H), 3.05 (s, 3H), 3.71 (t, J=6.4 Hz, 2H), 3.84 (s, 3H), 4.69 (t, J=7.4 Hz, 1H), 6.58 (d, J=8.7 Hz, 2H), 6.80-6.86 (m, 1H), 6.88 (d, J=2.3 Hz, 1H), 7.23-7.30 (m, 3H).

Example A94

3-{[(4-{[1-(3-methyl-1-benzofuran-2-yl)-2-phenoxyethyl]amino}phenyl)carbonyl]amino}propanoic acid

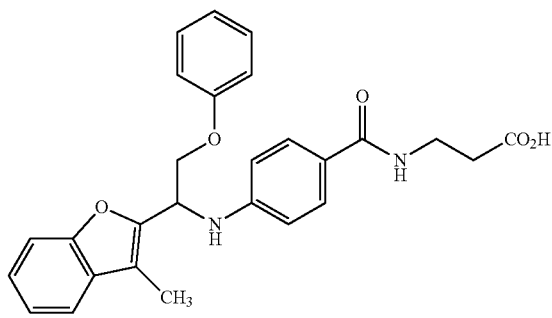 [SMILES: Cc1c(C(COc2ccccc2)Nc2ccc(C(=O)NCCC(=O)O)cc2)oc2ccccc12]

(1) 1-(3-methyl-1-benzofuran-2-yl)-2-phenoxyethanone

To a mixture of 2-bromo-1-(3-methyl-1-benzofuran-2-yl)ethanone (1.00 g), phenol (446 mg) and N,N-dimethylformamide (20 mL) was added potassium carbonate (655 mg), and the mixture was stirred overnight at room temperature. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (10% ethyl acetate/hexane) to give the title object compound (697 mg, 66%) as a yellow solid.

$^1$H NMR (300 MHz, CDCl$_3$) δ ppm 2.65 (s, 3H), 5.36 (s, 2H), 6.81-6.86 (m, 1H), 6.98-7.06 (m, 2H), 7.20-7.39 (m, 3H), 7.51-7.57 (m, 2H), 7.67-7.73 (m, 1H).

(2) methyl 4-{[1-(3-methyl-1-benzofuran-2-yl)-2-phenoxyethyl]amino}benzoate

To a mixture of 1-(3-methyl-1-benzofuran-2-yl)-2-phenoxyethanone (697 mg) synthesized above, methyl 4-aminobenzoate (399 mg), triethylamine (2.93 mL) and methylene chloride (10 mL) was added titanium (IV) chloride (344 μL) at 0° C. under argon atmosphere, and the mixture was stirred overnight at room temperature. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (2 mL) and sodium cyanoborohydride (329 mg), and the mixture was stirred at room temperature for 15 min. Trifluoroacetic acid (2 mL) was added to the reaction mixture, and the mixture was further stirred at room temperature for 3 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (25% ethyl acetate/hexane) to give the title object compound (279 mg, 27%) as a yellow solid.

$^1$H NMR (300 MHz, CDCl$_3$) δ ppm 2.29 (s, 3H), 3.83 (s, 3H), 4.32-4.44 (m, 2H), 4.91 (d, J=6.6 Hz, 1H), 5.08-5.16 (m, 1H), 6.66 (d, J=8.9 Hz, 1H), 6.81-6.99 (m, 3H), 7.18-7.31 (m, 4H), 7.38-7.48 (m, 2H), 7.84 (d, J=8.9 Hz, 2H).

(3) 4-{[1-(3-methyl-1-benzofuran-2-yl)-2-phenoxyethyl]amino}benzoic acid

To a mixture of methyl 4-{[1-(3-methyl-1-benzofuran-2-yl)-2-phenoxyethyl]amino}benzoate (279 mg) synthesized above, tetrahydrofuran (5 mL) and ethanol (5 mL) was added 1N aqueous sodium hydroxide solution (5.00 mL), and the mixture was stirred overnight with heating under reflux, and concentrated under reduced pressure. The residue was dissolved in water (10 mL), and 1N hydrochloric acid (5.00 mL) was added at 0° C. The resulting precipitate was collected by filtration to give the title object compound (220 mg, 82%) as a white solid.

$^1$H NMR (300 MHz, CDCl$_3$) δ ppm 2.30 (s, 3H), 4.32-4.46 (m, 2H), 4.92-5.03 (m, 1H), 5.09-5.20 (m, 1H), 6.69 (d, J=9.1 Hz, 2H), 6.90 (d, J=7.6 Hz, 2H), 6.93-7.01 (m, 1H), 7.19-7.34 (m, 4H), 7.38-7.51 (m, 2H), 7.90 (d, J=8.7 Hz, 2H).

(4) ethyl 3-{[(4-{[1-(3-methyl-1-benzofuran-2-yl)-2-phenoxyethyl]amino}phenyl)carbonyl]amino}propanoate To a mixture of 4-{[1-(3-methyl-1-benzofuran-2-yl)-2-phenoxyethyl]amino}benzoic acid (100 mg) synthesized above, β-alanine ethyl ester hydrochloride (59.4 mg), 1-hydroxybenzotriazole monohydrate (59.3 mg), triethylamine (72 μL) and N,N-dimethylformamide (10 mL) was added 1-ethyl-3-(3-dimethylaminopropyl)carbodiimide hydrochloride (74.2 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (45% ethyl acetate/hexane) to give the title object compound (63.0 mg, 50%) as a pale-yellow oil.

$^1$H NMR (300 MHz, CDCl$_3$) δ ppm 1.25 (t, J=7.2 Hz, 3H), 2.29 (s, 3H), 2.59 (t, J=5.8 Hz, 2H), 3.62-3.72 (m, 2H), 4.14 (q, J=7.2 Hz, 2H), 4.31-4.44 (m, 2H), 4.78-4.88 (m, 1H), 5.06-5.15 (m, 1H), 6.60-6.71 (m, 3H), 6.89 (dd, J=8.8, 1.0 Hz, 2H), 6.93-7.00 (m, 1H), 7.18-7.31 (m, 4H), 7.38-7.49 (m, 2H), 7.59 (d, J=8.9 Hz, 2H).

(5) 3-{[(4-{[1-(3-methyl-1-benzofuran-2-yl)-2-phenoxyethyl]amino}phenyl)carbonyl]amino}propanoic acid To a mixture of ethyl 3-{[(4-{[1-(3-methyl-1-benzofuran-2-yl)-2-phenoxyethyl]amino}phenyl)carbonyl] amino}propanoate (63.0 mg) synthesized above, tetrahydrofuran (5 mL) and ethanol (5 mL) was added 1N aqueous sodium hydroxide solution (1.00 mL), and the mixture was stirred at room temperature for 1 hr, and concentrated under reduced pressure. The residue was dissolved in water (10 mL), and 1N hydrochloric acid (1.00 mL) was added at 0° C. The resulting precipitate was collected by filtration to give the title object compound (57.5 mg, 97%) as a pale-brown solid.

$^1$H NMR (300 MHz, CDCl$_3$) δ ppm 2.29 (s, 3H), 2.68 (t, J=5.9 Hz, 2H), 3.63-3.72 (m, 2H), 4.32-4.44 (m, 2H), 5.10 (t, J=6.1 Hz, 1H), 6.58 (t, J=5.7 Hz, 1H), 6.67 (d, J=8.7 Hz, 2H), 6.87-6.92 (m, 2H), 6.93-7.00 (m, 1H), 7.18-7.31 (m, 4H), 7.38-7.43 (m, 1H), 7.44-7.49 (m, 1H), 7.58 (d, J=8.7 Hz, 2H).

Example A95

3-{methyl[(4-{[1-(3-methyl-1-benzofuran-2-yl)-2-phenoxyethyl]amino}phenyl)carbonyl]amino}propanoic acid

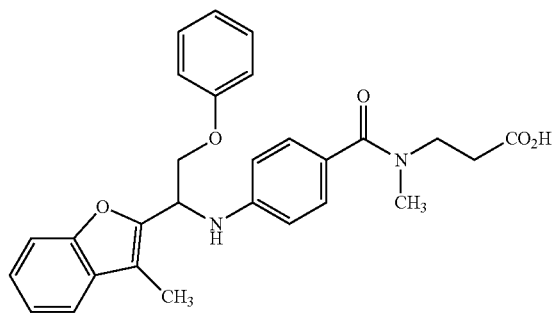 [SMILES: Cc1c(C(COc2ccccc2)Nc2ccc(C(=O)N(C)CCC(=O)O)cc2)oc2ccccc12]

(1) ethyl 3-{methyl[(4-{[1-(3-methyl-1-benzofuran-2-yl)-2-phenoxyethyl]amino}phenyl)carbonyl]amino}propanoate To a mixture of 4-{[1-(3-methyl-1-benzofuran-2-yl)-2-phenoxyethyl]amino}benzoic acid (100 mg) synthesized in Example A94(3), ethyl 3-(methylamino)propanoate (50.8 mg), 1-hydroxybenzotriazole monohydrate (59.3 mg), triethylamine (54 μL) and N,N-dimethylformamide (10 mL) 1-ethyl-3-(3-dimethylaminopropyl)carbodiimide hydrochloride (74.2 mg) was added, and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (82.5 mg, 64%) as a yellow oil.

$^1$H NMR (300 MHz, CDCl$_3$) δ ppm 1.23 (t, J=7.2 Hz, 3H), 2.29 (s, 3H), 2.57-2.67 (m, 2H), 3.02 (s, 3H), 3.72 (t, J=7.1 Hz, 2H), 4.12 (q, J=7.2 Hz, 2H), 4.30-4.44 (m, 2H), 5.08 (t, J=6.0 Hz, 1H), 6.66 (d, J=8.7 Hz, 2H), 6.90 (dd, J=8.7, 0.9 Hz, 2H), 6.93-7.01 (m, 1H), 7.19-7.32 (m, 6H), 7.38-7.50 (m, 2H).

(2) 3-{methyl[(4-{[1-(3-methyl-1-benzofuran-2-yl)-2-phenoxyethyl]amino}phenyl)carbonyl] amino}propanoic acid To a mixture of ethyl 3-{methyl[(4-{[1-(3-methyl-1-benzofuran-2-yl)-2-phenoxyethyl]amino}phenyl)carbonyl] amino}propanoate (82.5 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), and 1N hydrochloric acid (1.00 mL) was added at 0° C. The resulting precipitate was collected by filtration to give the title object compound (54.8 mg, 70%) as a white solid.

$^1$H NMR (300 MHz, CDCl$_3$) δ ppm 2.29 (s, 3H), 2.61-2.72 (m, 2H), 3.04 (s, 3H), 3.71 (t, J=6.6 Hz, 2H), 4.30-4.42 (m, 2H), 5.08 (t, J=6.1 Hz, 1H), 6.66 (d, J=8.7 Hz, 2H), 6.86-6.92 (m, 2H), 6.92-7.00 (m, 1H), 7.18-7.31 (m, 6H), 7.38-7.43 (m, 1H), 7.44-7.49 (m, 1H).

Example A96

3-{[(4-{[cyclohexyl(6-fluoro-3-methyl-1-benzofuran-2-yl)methyl]amino}phenyl)carbonyl] amino}propanoic acid

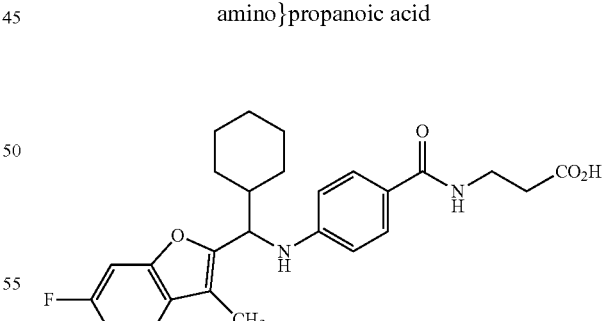

(1)-6-fluoro-N-methoxy-N,3-dimethyl-1-benzofuran-2-carboxamide

To a solution (50 mL) of 1-(4-fluoro-2-hydroxyphenyl) ethanone (5.00 g) in N,N-dimethylformamide were added 2-chloro-N-methoxy-N-methylacetamide (4.90 g), sodium iodide (9.71 g) and potassium carbonate (8.96 g), and the mixture was stirred overnight at 80° C. The reaction mixture was cooled to room temperature, the insoluble material was filtered off. 1,8-diazabicyclo[5.4.0]undec-7-ene (4.85 mL) was added to the filtrate, and the mixture was stirred at 120° C. for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (25% ethyl acetate/hexane) to give the title object compound (3.65 g, 47%) as a pale-brown oil $^1$H NMR (300 MHz, CDCl$_3$) δ 2.50 (s, 3H), 3.38 (s, 3H), 3.87 (s, 3H), 7.01-7.11 (m, 1H), 7.18 (dd, J=8.8, 1.9 Hz, 1H), 7.54 (dd, J=8.8, 5.5 Hz, 1H).

(2) 6-fluoro-3-methyl-1-benzofuran-2-carbaldehyde

To a solution (50 mL) of 6-fluoro-N-methoxy-N,3-dimethyl-1-benzofuran-2-carboxamide (3.65 g) synthesized above in tetrahydrofuran was added lithium aluminum hydride (292 mg) at 0° C., and the mixture was stirred for 1 hr. Water (300 μL) was added to quench the reaction, 1N aqueous sodium hydroxide solution (600 μL) was added, and the mixture was stirred at room temperature for 1 hr. The resulting insoluble material was filtered off, and the filtrate was concentrated under reduced pressure. The residue was purified by silica gel column chromatography (20% ethyl acetate/hexane) to give the title object compound (1.88 g, 69%) as a pale-yellow solid.

$^1$H NMR (300 MHz, CDCl$_3$) δ ppm 2.62 (s, 3H), 7.07-7.15 (m, 1H), 7.22-7.28 (m, 1H), 7.65 (dd, J=8.8, 5.4 Hz, 1H), 9.99 (s, 1H).

(3) cyclohexyl(6-fluoro-3-methyl-1-benzofuran-2-yl) methanol

To a solution (20 mL) of 6-fluoro-3-methyl-1-benzofuran-2-carbaldehyde (940 mg) synthesized above in tetrahydrofuran was added a 1.0M solution (7.92 mL) of cyclohexylmagnesium bromide in tetrahydrofuran at 0° C., and the mixture was stirred for 1 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (15% ethyl acetate/hexane) to give the title object compound (931 mg, 67%) as a pale-yellow oil.

$^1$H NMR (300 MHz, CDCl$_3$) δ ppm 0.85-1.00 (m, 1H), 1.00-1.44 (m, 5H), 1.60-1.71 (m, 2H), 1.76-1.99 (m, 3H), 2.10-2.23 (m, 4H), 4.50 (dd, J=8.3, 6.1 Hz, 1H), 6.94-7.02 (m, 1H), 7.10-7.17 (m, 1H), 7.34-7.40 (m, 1H).

(4) 2-[chloro(cyclohexyl)methyl]-6-fluoro-3-methyl-1-benzofuran

To a solution (20 mL) of cyclohexyl(6-fluoro-3-methyl-1-benzofuran-2-yl)methanol (931 mg) synthesized above in toluene was added thionyl chloride (311 μL), and the mixture was stirred at 100° C. for 1 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (945 mg, 95%) as a yellow oil.

$^1$H NMR (300 MHz, CDCl$_3$) δ ppm 0.82-0.98 (m, 1H), 0.99-1.52 (m, 5H), 1.60-1.72 (m, 2H), 1.76-1.89 (m, 1H), 2.11-2.25 (m, 4H), 2.26-2.39 (m, 1H), 4.79 (d, J=9.6 Hz, 1H), 6.96-7.04 (m, 1H), 7.15-7.20 (m, 1H), 7.35-7.41 (m, 1H).

(5) 4-{[cyclohexyl(6-fluoro-3-methyl-1-benzofuran-2-yl)methyl]amino}benzoic acid To a mixture of 2-[chloro(cyclohexyl)methyl]-6-fluoro-3-methyl-1-benzofuran (945 mg) synthesized above, methyl 4-aminobenzoate (508 mg), sodium iodide (1.01 g) and N,N-dimethylformamide (10 mL) was added sodium carbonate (712 mg), and the mixture was stirred at 80° C. overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give a yellow solid. To a mixture of the obtained solid, tetrahydrofuran (20 mL) and ethanol (20 mL) was added 1N aqueous sodium hydroxide solution (10.0 mL), and the mixture was stirred overnight with heating under reflux, and concentrated under reduced pressure. The residue was dissolved in water (40 mL), and 1N hydrochloric acid (10.0 mL) was added at 0° C. The resulting precipitate was collected by filtration to give the title object compound (722 mg, 56%) as a brown solid.

$^1$H NMR (300 MHz, CDCl$_3$) δ ppm 0.92-1.38 (m, 5H), 1.46-1.57 (m, 1H), 1.61-1.98 (m, 4H), 2.02-2.13 (m, 1H), 2.25 (s, 3H), 4.40 (d, J=7.9 Hz, 1H), 4.51-4.74 (m, 1H), 6.57 (d, J=8.8 Hz, 2H), 6.91-7.00 (m, 1H), 7.06-7.12 (m, 1H), 7.29-7.36 (m, 1H), 7.85 (d, J=8.8 Hz, 2H).

(6) ethyl 3-{[(4-{[cyclohexyl(6-fluoro-3-methyl-1-benzofuran-2-yl)methyl]amino}phenyl)carbonyl] amino}propanoate To a mixture of 4-{[cyclohexyl(6-fluoro-3-methyl-1-benzofuran-2-yl)methyl]amino}benzoic acid (350 mg) synthesized above, β-alanine ethyl ester hydrochloride (212 mg), 1-hydroxybenzotriazole monohydrate (211 mg), triethylamine (383 μL) and N,N-dimethylformamide (10 mL) was added 1-ethyl-3-(3-dimethylaminopropyl)carbodiimide hydrochloride (265 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (403 mg, 91%) as a pale-yellow oil.

$^1$H NMR (300 MHz, CDCl$_3$) δ ppm 0.94-1.39 (m, 8H), 1.46-1.57 (m, 1H), 1.62-1.97 (m, 4H), 2.03-2.14 (m, 1H), 2.24 (s, 3H), 2.58 (t, J=5.9 Hz, 2H), 3.61-3.70 (m, 2H), 4.14 (q, J=7.2 Hz, 2H), 4.32-4.47 (m, 2H), 6.54-6.63 (m, 3H), 6.90-7.00 (m, 1H), 7.05-7.12 (m, 1H), 7.28-7.35 (m, 1H), 7.55 (d, J=8.9 Hz, 2H).

(7) 3-{[(4-{[cyclohexyl(6-fluoro-3-methyl-1-benzofuran-2-yl)methyl]amino}phenyl)carbonyl] amino}propanoic acid To a mixture of ethyl 3-{[(4-{[cyclohexyl(6-fluoro-3-methyl-1-benzofuran-2-yl)methyl]amino}phenyl)carbonyl] amino}propanoate (403 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration to give the title object compound (355 mg, 93%) as a white solid.

$^1$H NMR (300 MHz, CDCl$_3$) δ ppm 0.92-1.37 (m, 5H), 1.44-1.56 (m, 1H), 1.60-1.96 (m, 4H), 2.00-2.12 (m, 1H), 2.22 (s, 3H), 2.53-2.66 (m, 2H), 3.54-3.67 (m, 2H), 4.35 (d, J=8.3 Hz, 1H), 6.48-6.64 (m, 3H), 6.89-6.99 (m, 1H), 7.03-7.11 (m, 1H), 7.27-7.34 (m, 1H), 7.52 (d, J=8.7 Hz, 2H).

Example A97

3-{[(4-{[cyclohexyl(6-fluoro-3-methyl-1-benzofuran-2-yl)methyl]amino}phenyl)carbonyl]methyl)amino}propanoic acid

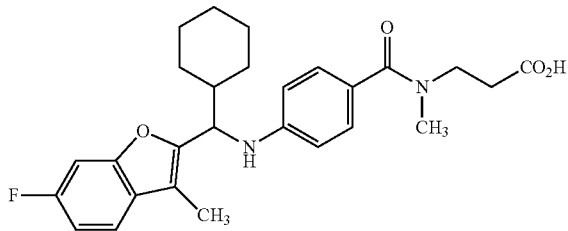 [SMILES: Cc1c(C(Nc2ccc(C(=O)N(C)CCC(=O)O)cc2)C2CCCCC2)oc2cc(F)ccc12]

(1) ethyl 3-{[(4-{[cyclohexyl(6-fluoro-3-methyl-1-benzofuran-2-yl)methyl]amino}phenyl)carbonyl](methyl)amino}propanoate To a mixture of 4-{[cyclohexyl(6-fluoro-3-methyl-1-benzofuran-2-yl)methyl]amino}benzoic acid (350 mg) synthesized in Example A96(5), ethyl 3-(methylamino)propanoate (181 mg), 1-hydroxybenzotriazole monohydrate (211 mg), triethylamine (383 µL) and N,N-dimethylformamide (10 mL) was added 1-ethyl-3-(3-dimethylaminopropyl)carbodiimide hydrochloride (265 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (432 mg, 95%) as a yellow oil.

$^1$H NMR (300 MHz, CDCl$_3$) δ ppm 0.93-1.37 (m, 8H), 1.46-1.56 (m, 1H), 1.60-1.96 (m, 4H), 2.02-2.14 (m, 1H), 2.23 (s, 3H), 2.61 (t, J=6.9 Hz, 2H), 3.01 (s, 3H), 3.70 (t, J=6.9 Hz, 2H), 4.07-4.17 (m, 2H), 4.27-4.39 (m, 2H), 6.56 (d, J=8.7 Hz, 2H), 6.91-7.00 (m, 1H), 7.06-7.12 (m, 1H), 7.21 (d, J=8.7 Hz, 2H), 7.28-7.35 (m, 1H).

(2) 3-{[(4-{[cyclohexyl(6-fluoro-3-methyl-1-benzofuran-2-yl)methyl]amino}phenyl)carbonyl]methyl)amino}propanoic acid To a mixture of ethyl 3-{[(4-{[cyclohexyl(6-fluoro-3-methyl-1-benzofuran-2-yl)methyl]amino}phenyl)carbonyl](methyl)amino}propanoate (432 mg) synthesized above, tetrahydrofuran (10 mL) and ethanol (10 mL) was added 1N aqueous sodium hydroxide solution (2.00 mL), and the mixture was stirred at room temperature for 4 hr, and concentrated under reduced pressure. The residue was dissolved in water (10 mL), and 1N hydrochloric acid (2.00 mL) was added at 0° C. The resulting precipitate was collected by filtration to give the title object compound (367 mg, 90%) as a pale-red solid.

$^1$H NMR (300 MHz, CDCl$_3$) δ ppm 0.93-1.37 (m, 5H), 1.46-1.57 (m, 1H), 1.61-1.96 (m, 4H), 2.03-2.14 (m, 1H), 2.23 (s, 3H), 2.67 (t, J=6.4 Hz, 2H), 3.04 (s, 3H), 3.70 (t, J=6.4 Hz, 2H), 4.35 (d, J=8.0 Hz, 1H), 6.56 (d, J=8.7 Hz, 2H), 6.91-7.00 (m, 1H), 7.06-7.12 (m, 1H), 7.21-7.28 (m, 2H), 7.29-7.36 (m, 1H).

Example A98

3-{[(4-{[(5-cyano-3-methyl-1-benzofuran-2-yl)(cyclohexyl)methyl]amino}phenyl)carbonyl]amino}propanoic acid

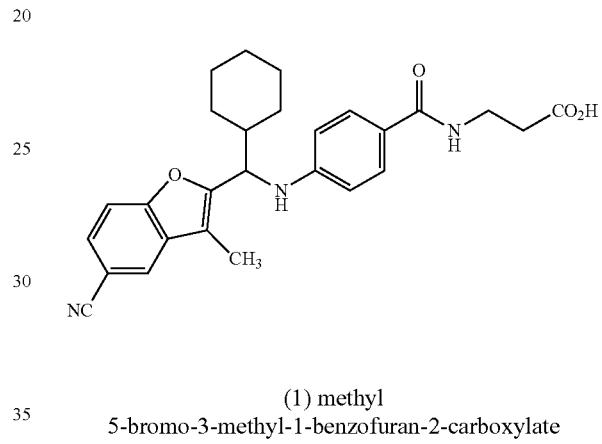

(1) methyl 5-bromo-3-methyl-1-benzofuran-2-carboxylate

To a solution (100 mL) of 1-(5-bromo-2-hydroxyphenyl)ethanone (10.0 g) in N,N-dimethylformamide were added methyl bromoacetate (4.85 mL) and potassium carbonate (12.9 g), and the mixture was stirred overnight at room temperature. The insoluble material was filtered off, 1,8-diazabicyclo[5.4.0]undec-7-ene (6.95 mL) was added to the filtrate, and the mixture was stirred at 120° C. for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (10% ethyl acetate/hexane) to give the title object compound (6.06 g, 48%) as a pale-brown solid.

$^1$H NMR (300 MHz, CDCl$_3$) δ ppm 2.56 (s, 3H), 3.99 (s, 3H), 7.39-7.44 (m, 1H), 7.51-7.56 (m, 1H), 7.76 (d, J=1.9 Hz, 1H).

(2) methyl 5-cyano-3-methyl-1-benzofuran-2-carboxylate

To a mixture of methyl 5-bromo-3-methyl-1-benzofuran-2-carboxylate (6.06 g) synthesized above, zinc cyanide (2.64 g) and N,N-dimethylformamide (60 mL) was added tetrakis(triphenylphosphine)palladium (0) (1.31 g), and the mixture was deaerated and stirred under argon atmosphere at 80° C. overnight. Water was added to quench the reaction, and the mixture was extracted with ethyl acetate. The extract was washed with saturated brine, dried over magnesium sulfate, and concentrated under reduced pressure. The residue was washed with diisopropyl ether to give the title object compound (4.20 g, 87%) as a pale-brown solid.

$^1$H NMR (300 MHz, CDCl$_3$) δ ppm 2.61 (s, 3H), 4.01 (s, 3H), 7.61-7.66 (m, 1H), 7.69-7.74 (m, 1H), 8.00 (d, J=0.9 Hz, 1H).

(3) 5-cyano-3-methyl-1-benzofuran-2-carboxylic acid

To a mixture of methyl 5-cyano-3-methyl-1-benzofuran-2-carboxylate (4.20 g) synthesized above, tetrahydrofuran (80 mL), water (20 mL) and methanol (20 mL) was added lithium hydroxide monohydrate (1.64 g), and the mixture was stirred overnight at room temperature, and concentrated under reduced pressure. 1N Hydrochloric acid was added to the residue, and the mixture was extracted with ethyl acetate. The extract was washed with saturated brine, dried over magnesium sulfate, and concentrated under reduced pressure. The residue was washed with diisopropyl ether to give the title object compound (3.58 g, 91%) as a pale-brown solid.

$^1$H NMR (300 MHz, DMSO-d$_6$) δ ppm 2.55 (s, 3H), 7.85-7.89 (m, 1H), 7.91-7.95 (m, 1H), 8.44-8.47 (m, 1H), 13.76 (br s, 1H).

(4) 2-formyl-3-methyl-1-benzofuran-5-carbonitrile

To 5-cyano-3-methyl-1-benzofuran-2-carboxylic acid (2.58 g) synthesized above in tetrahydrofuran (30 mL) were added oxalyl chloride (1.32 mL) and several drops of N,N-dimethylformamide, and the mixture was stirred at room temperature for 5 hr. The reaction mixture was concentrated under reduced pressure, and the residue was washed with diisopropyl ether to give a pale-brown solid. To a solution (50 mL) of the obtained solid in tetrahydrofuran was added a 1.1M solution (12.0 mL) of lithium tri(isobutoxy)aluminum hydride in tetrahydrofuran at −78° C., and the mixture was stirred at −78° C. for 1.5 hr then at 0° C. for 3 hr. 1N Hydrochloric acid was added to quench the reaction, and the mixture was extracted with ethyl acetate. The extract was washed with saturated brine, dried over magnesium sulfate, and concentrated under reduced pressure to give a pale-brown solid. To a solution (40 mL) of the obtained solid in tetrahydrofuran was added active manganese dioxide (10.0 g), and the mixture was stirred at 50° C. overnight. Manganese dioxide was filtered off, and the filtrate was concentrated under reduced pressure. The residue was washed with diisopropyl ether to give the title object compound (1.49 g, 63%) as a white solid.

$^1$H NMR (300 MHz, CDCl$_3$) δ ppm 2.65 (s, 3H), 7.65 (d, J=8.7 Hz, 1H), 7.77 (dd, J=8.7, 1.5 Hz, 1H), 8.05-8.08 (m, 1H), 10.08 (s, 1H).

(5) 2-[cyclohexyl(hydroxy)methyl]-3-methyl-1-benzofuran-5-carbonitrile

To a solution (30 mL) of 2-formyl-3-methyl-1-benzofuran-5-carbonitrile (1.49 g) synthesized above in tetrahydrofuran was added a 1.0M solution (12.1 mL) of cyclohexylmagnesium bromide in tetrahydrofuran at 0° C., and the mixture was stirred for 1 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (25% ethyl acetate/hexane), and then purified by NH silica gel column chromatography (ethyl acetate) to give the title object compound (922 mg, 43%) as a pale-yellow solid.

$^1$H NMR (300 MHz, CDCl$_3$) δ ppm 0.84-1.43 (m, 6H), 1.48-1.99 (m, 5H), 2.03-2.19 (m, 1H), 2.24 (s, 3H), 4.56 (dd, J=8.4, 5.4 Hz, 1H), 7.47-7.51 (m, 1H), 7.52-7.57 (m, 1H), 7.78-7.81 (m, 1H).

(6) 2-[chloro(cyclohexyl)methyl]-3-methyl-1-benzofuran-5-carbonitrile

To a solution (10 mL) of 2-[cyclohexyl(hydroxy)methyl]-3-methyl-1-benzofuran-5-carbonitrile (922 mg) synthesized above in toluene was added thionyl chloride (374 μL), and the mixture was stirred at 100° C. for 1 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (868 mg, 88%) as a pale-yellow solid.

$^1$H NMR (300 MHz, CDCl$_3$) δ ppm 0.85-1.55 (m, 6H), 1.62-1.74 (m, 2H), 1.79-1.90 (m, 1H), 2.10-2.22 (m, 1H), 2.26 (s, 3H), 2.28-2.39 (m, 1H), 4.80 (d, J=9.6 Hz, 1H), 7.51-7.55 (m, 1H), 7.56-7.61 (m, 1H), 7.81-7.83 (m, 1H).

(7) 4-{[(5-cyano-3-methyl-1-benzofuran-2-yl)(cyclohexyl)methyl]amino}benzoic acid To a mixture of 2-[chloro(cyclohexyl)methyl]-3-methyl-1-benzofuran-5-carbonitrile (868 mg) synthesized above, methyl 4-aminobenzoate (546 mg), sodium iodide (902 mg) and N,N-dimethylformamide (10 mL) was added sodium carbonate (638 mg), and the mixture was stirred at 80° C. overnight. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (30% ethyl acetate/hexane) to give a pale-brown solid. To a mixture of the obtained solid, tetrahydrofuran (20 mL), water (8 mL) and ethanol (10 mL) was added 1N lithium hydroxide aqueous solution (3.38 mL), and the mixture was stirred overnight with heating under reflux, and concentrated under reduced pressure. The residue was dissolved in water (40 mL), and 1N hydrochloric acid (3.50 mL) was added at 0° C. The resulting precipitate was collected by filtration to give the title object compound (621 mg, 53%) as a white solid.

$^1$H NMR (300 MHz, CDCl$_3$) δ ppm 0.90-1.41 (m, 5H), 1.44-1.56 (m, 1H), 1.62-2.01 (m, 4H), 2.03-2.14 (m, 1H), 2.28 (s, 3H), 4.40-4.51 (m, 1H), 4.52-4.67 (m, 1H), 6.56 (d, J=8.8 Hz, 2H), 7.41-7.46 (m, 1H), 7.49-7.54 (m, 1H), 7.75-7.77 (m, 1H), 7.85 (d, J=8.8 Hz, 2H).

(8) ethyl 3-{[(4-{[(5-cyano-3-methyl-1-benzofuran-2-yl)(cyclohexyl)methyl]amino}phenyl)carbonyl]amino}propanoate To a mixture of 4-{[(5-cyano-3-methyl-1-benzofuran-2-yl)(cyclohexyl)methyl]amino}benzoic acid (250 mg) synthesized above, β-alanine ethyl ester hydrochloride (148 mg), 1-hydroxybenzotriazole monohydrate (148 mg), triethylamine (269 μL) and N,N-dimethylformamide (10 mL) was added 1-ethyl-3-(3-dimethylaminopropyl)carbodiimide hydrochloride (185 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (195 mg, 62%) as a colorless oil.

$^1$H NMR (300 MHz, CDCl$_3$) δ ppm 0.95-1.38 (m, 8H), 1.45-1.63 (m, 3H), 1.63-1.99 (m, 2H), 2.03-2.15 (m, 1H), 2.27 (s, 3H), 2.54-2.61 (m, 2H), 3.61-3.70 (m, 2H), 4.14 (q, J=7.2 Hz, 2H), 4.39-4.46 (m, 1H), 6.53-6.64 (m, 3H), 7.41-7.45 (m, 1H), 7.48-7.53 (m, 1H), 7.55 (d, J=8.7 Hz, 2H), 7.76 (d, J=1.5 Hz, 1H).

(9) 3-{[(4-{[(5-cyano-3-methyl-1-benzofuran-2-yl)(cyclohexyl)methyl]amino}phenyl)carbonyl]amino}propanoic acid To a mixture of ethyl 3-{[(4-{[(5-cyano-3-methyl-1-benzofuran-2-yl)(cyclohexyl)methyl]amino}phenyl)carbonyl]amino}propanoate (195 mg) synthesized above, tetrahydrofuran (5 mL) and ethanol (5 mL) was added 1N lithium hydroxide aqueous solution (800 μL), and the mixture was stirred at room temperature for 5 hr, and concentrated under reduced pressure. The residue was dissolved in water (10 mL), and 1N hydrochloric acid (800 μL) was added at 0° C. The resulting precipitate was collected by filtration to give the title object compound (168 mg, 92%) as a white solid.

$^1$H NMR (300 MHz, CDCl$_3$) δ ppm 0.94-1.37 (m, 5H), 1.43-1.54 (m, 1H), 1.62-1.98 (m, 4H), 2.03-2.14 (m, 1H), 2.26 (s, 3H), 2.57-2.67 (m, 2H), 3.54-3.70 (m, 2H), 4.42 (d, J=8.1 Hz, 1H), 6.51-6.65 (m, 3H), 7.39-7.44 (m, 1H), 7.45-7.56 (m, 3H), 7.74 (d, J=1.1 Hz, 1H).

Example A99

3-{[(4-{[(5-cyano-3-methyl-1-benzofuran-2-yl)(cyclohexyl)methyl]amino}phenyl)carbonyl](methyl)amino}-propanoic acid

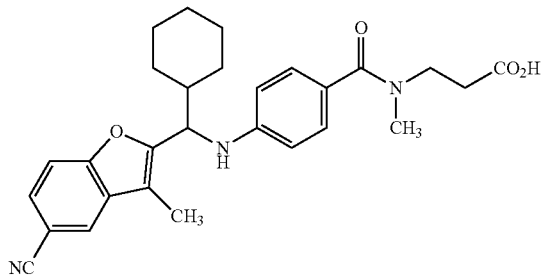 [SMILES: Cc1c(C(Nc2ccc(C(=O)N(C)CCC(=O)O)cc2)C2CCCCC2)oc2ccc(C#N)cc12]

(1) ethyl 3-{[(4-{[(5-cyano-3-methyl-1-benzofuran-2-yl)(cyclohexyl)methyl]amino}phenyl)carbonyl](methyl)amino}-propanoate To a mixture of 4-{[(5-cyano-3-methyl-1-benzofuran-2-yl)(cyclohexyl)methyl]amino}benzoic acid (250 mg) synthesized in Example A98(7), ethyl 3-(methylamino)propanoate (127 mg), 1-hydroxybenzotriazole monohydrate (148 mg), triethylamine (269 μL) and N,N-dimethylformamide (10 mL) was added 1-ethyl-3-(3-dimethylaminopropyl)carbodiimide hydrochloride (185 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (193 mg, 60%) as a colorless oil.

$^1$H NMR (300 MHz, CDCl$_3$) δ ppm 0.95-1.38 (m, 8H), 1.44-1.54 (m, 1H), 1.62-1.98 (m, 4H), 2.05-2.15 (m, 1H), 2.27 (s, 3H), 2.55-2.66 (m, 2H), 3.00 (s, 3H), 3.70 (t, J=7.1 Hz, 2H), 4.11 (q, J=7.0 Hz, 2H), 4.26-4.33 (m, 1H), 4.40 (t, J=7.9 Hz, 1H), 6.55 (d, J=8.6 Hz, 2H), 7.21 (d, J=8.6 Hz, 2H), 7.40-7.46 (m, 1H), 7.48-7.54 (m, 1H), 7.76 (d, J=1.5 Hz, 1H).

(2) 3-{[(4-{[(5-cyano-3-methyl-1-benzofuran-2-yl)(cyclohexyl)methyl]amino}phenyl)carbonyl](methyl)amino}-propanoic acid To a mixture of ethyl 3-{[(4-{[(5-cyano-3-methyl-1-benzofuran-2-yl)(cyclohexyl)methyl]amino}phenyl)carbonyl](methyl)amino}-propanoate (193 mg) synthesized above, tetrahydrofuran (5 mL) and ethanol (5 mL) was added 1N lithium hydroxide aqueous solution (770 μL), and the mixture was stirred at room temperature for 3 hr, and concentrated under reduced pressure. The residue was dissolved in water (10 mL), and 1N hydrochloric acid (770 μL) was added at 0° C. The resulting precipitate was collected by filtration to give the title object compound (163 mg, 90%) as a white solid.

$^1$H NMR (300 MHz, CDCl$_3$) δ ppm 0.94-1.37 (m, 5H), 1.44-1.54 (m, 1H), 1.62-1.98 (m, 4H), 2.04-2.15 (m, 1H), 2.27 (s, 3H), 2.61-2.70 (m, 2H), 3.03 (s, 3H), 3.69 (t, J=6.5 Hz, 2H), 4.40 (d, J=7.9 Hz, 1H), 6.55 (d, J=8.9 Hz, 2H), 7.24 (d, J=8.9 Hz, 2H), 7.40-7.46 (m, 1H), 7.48-7.53 (m, 1H), 7.76 (d, J=1.1 Hz, 1H).

Example A100

3-{[(4-{[1-(5-chloro-3-methyl-1-benzofuran-2-yl)-3-methylbutyl]amino}phenyl)carbonyl]amino}propanoic acid

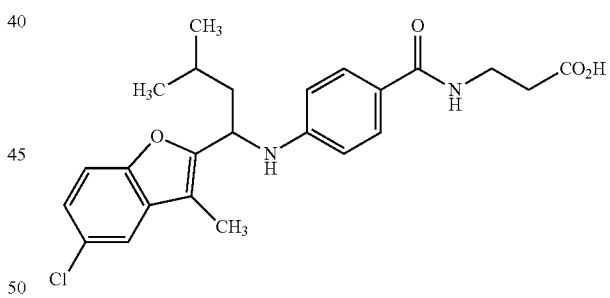

(1) 1-(5-chloro-3-methyl-1-benzofuran-2-yl)-3-methylbutan-1-ol

To a solution (20 mL) of 5-chloro-3-methyl-1-benzofuran-2-carbaldehyde (1.00 g) synthesized in Example A88(2) in tetrahydrofuran was added a 1.0M solution (10.3 mL) of isobutylmagnesium bromide in tetrahydrofuran at 0° C., and the mixture was stirred for 1 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (650 mg, 50%) as a colorless oil.

¹H NMR (300 MHz, CDCl₃) δ ppm 0.91-0.98 (m, 6H), 1.53-1.70 (m, 1H), 1.71-1.97 (m, 3H), 2.22 (s, 3H), 4.89-4.98 (m, 1H), 7.19-7.23 (m, 1H), 7.31-7.35 (m, 1H), 7.43 (d, J=2.2 Hz, 1H).

(2) 5-chloro-2-(1-chloro-3-methylbutyl)-3-methyl-1-benzofuran

To a solution (10 mL) of 1-(5-chloro-3-methyl-1-benzofuran-2-yl)-3-methylbutan-1-ol (650 mg) synthesized above in toluene was added thionyl chloride (225 μL), and the mixture was stirred at 50° C. for 2 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (668 mg, 96%) as a pale-yellow oil.

¹H NMR (300 MHz, CDCl₃) δ ppm 0.93 (d, J=2.5 Hz, 3H), 0.95 (d, J=2.7 Hz, 3H), 1.58-1.74 (m, 1H), 2.06-2.21 (m, 2H), 2.23 (s, 3H), 5.17 (t, J=8.0 Hz, 1H), 7.22-7.27 (m, 1H), 7.34-7.38 (m, 1H), 7.44 (d, J=2.2 Hz, 1H).

(3) 4-{[1-(5-chloro-3-methyl-1-benzofuran-2-yl)-3-methylbutyl]amino}benzoic acid To a mixture of 5-chloro-2-(1-chloro-3-methylbutyl)-3-methyl-1-benzofuran (668 mg) synthesized above, methyl 4-aminobenzoate (410 mg), sodium iodide (737 mg) and N,N-dimethylformamide (10 mL) was added sodium carbonate (521 mg) and the mixture was stirred at 80° C. for 8 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (15% ethyl acetate/hexane) to give a yellow oil. To a mixture of the obtained oil, tetrahydrofuran (10 mL) and ethanol (10 mL) was added 1N aqueous sodium hydroxide solution (10.0 mL), and the mixture was stirred with heating under reflux for 8 hr, and concentrated under reduced pressure. The residue was dissolved in water (20 mL), and 1N hydrochloric acid (10.0 mL) was added at 0° C. The resulting precipitate was collected by filtration to give the title object compound (394 mg, 43%) as a pale-yellow solid.

¹H NMR (300 MHz, CDCl₃) δ ppm 0.92 (d, J=6.6 Hz, 3H), 1.01 (d, J=6.6 Hz, 3H), 1.47-1.65 (m, 1H), 1.87 (t, J=7.4 Hz, 2H), 2.27 (s, 3H), 4.75 (t, J=7.4 Hz, 1H), 6.58 (d, J=8.7 Hz, 2H), 7.16-7.21 (m, 1H), 7.27-7.31 (m, 1H), 7.40 (d, J=2.1 Hz, 1H), 7.86 (d, J=8.7 Hz, 2H).

(4) ethyl 3-{[(4-{[1-(5-chloro-3-methyl-1-benzofuran-2-yl)-3-methylbutyl]amino}phenyl)carbonyl]amino}propanoate To a mixture of 4-{[1-(5-chloro-3-methyl-1-benzofuran-2-yl)-3-methylbutyl]amino}benzoic acid (180 mg) synthesized above, β-alanine ethyl ester hydrochloride (112 mg), 1-hydroxybenzotriazole monohydrate (111 mg), triethylamine (202 μL) and N,N-dimethylformamide (10 mL) was added 1-ethyl-3-(3-dimethylaminopropyl)carbodiimide hydrochloride (139 mg) and the mixture was stirred at room temperature for 2.5 days. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (196 mg, 86%) as a colorless oil.

¹H NMR (300 MHz, CDCl₃) δ ppm 0.91 (d, J=6.3 Hz, 3H), 1.00 (d, J=6.6 Hz, 3H), 1.25 (t, J=7.1 Hz, 3H), 1.48-1.64 (m, 1H), 1.85 (t, J=7.3 Hz, 2H), 2.25 (s, 3H), 2.55-2.62 (m, 2H), 3.61-3.69 (m, 2H), 4.13 (q, J=7.1 Hz, 2H), 4.30-4.39 (m, 1H), 4.65-4.76 (m, 1H), 6.53-6.65 (m, 3H), 7.13-7.19 (m, 1H), 7.23-7.29 (m, 1H), 7.38 (d, J=2.2 Hz, 1H), 7.55 (d, J=8.8 Hz, 2H).

(5) 3-{[(4-{[1-(5-chloro-3-methyl-1-benzofuran-2-yl)-3-methylbutyl]amino}phenyl)carbonyl]amino}propanoic acid To a mixture of ethyl 3-{[(4-{[1-(5-chloro-3-methyl-1-benzofuran-2-yl)-3-methylbutyl]amino}phenyl)carbonyl]amino}propanoate (196 mg) synthesized above, tetrahydrofuran (5 mL) and ethanol (5 mL) was added 1N aqueous sodium hydroxide solution (1.50 mL), and the mixture was stirred at room temperature for 2 hr, and concentrated under reduced pressure. The residue was dissolved in water (10 mL), and 1N hydrochloric acid (1.50 mL) was added at 0° C. The resulting precipitate was collected by filtration to give the title object compound (170 mg, 92%) as a white solid.

¹H NMR (300 MHz, CDCl₃) δ ppm 0.91 (d, J=6.8 Hz, 3H), 1.00 (d, J=6.4 Hz, 3H), 1.48-1.63 (m, 1H), 1.85 (t, J=7.5 Hz, 2H), 2.24 (s, 3H), 2.64 (t, J=5.9 Hz, 2H), 3.60-3.69 (m, 2H), 4.70 (t, J=7.5 Hz, 1H), 6.57 (d, J=8.7 Hz, 2H), 6.62 (t, J=6.1 Hz, 1H), 7.14-7.19 (m, 1H), 7.24-7.29 (m, 1H), 7.38 (d, J=1.9 Hz, 1H), 7.54 (d, J=8.7 Hz, 2H).

Example A101

3-{[(4-{[1-(5-chloro-3-methyl-1-benzofuran-2-yl)-3-methylbutyl]amino}phenyl)carbonyl](methyl)amino}propanoic acid

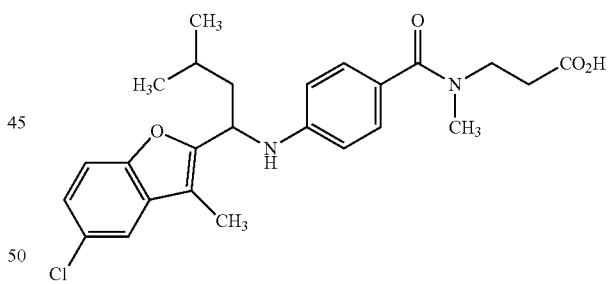

(1) ethyl 3-{[(4-{[1-(5-chloro-3-methyl-1-benzofuran-2-yl)-3-methylbutyl]amino}phenyl)carbonyl](methyl)amino}propanoate To a mixture of 4-{[1-(5-chloro-3-methyl-1-benzofuran-2-yl)-3-methylbutyl]amino}benzoic acid (180 mg) synthesized in Example A100(3), ethyl 3-(methylamino)propanoate (95.2 mg), 1-hydroxybenzotriazole monohydrate (111 mg), triethylamine (202 μL) and N,N-dimethylformamide (10 mL) was added 1-ethyl-3-(3-dimethylaminopropyl)carbodiimide hydrochloride (139 mg), and the mixture was stirred at room temperature for 2.5 days. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (55% ethyl acetate/hexane) to give the title object compound (199 mg, 85%) as a colorless oil.

$^1$H NMR (300 MHz, CDCl$_3$) δ ppm 0.91 (d, J=6.6 Hz, 3H), 1.00 (d, J=6.6 Hz, 3H), 1.23 (t, J=7.1 Hz, 3H), 1.49-1.64 (m, 1H), 1.84 (t, J=7.3 Hz, 2H), 2.25 (s, 3H), 2.56-2.67 (m, 2H), 3.01 (s, 3H), 3.70 (t, J=7.0 Hz, 2H), 4.06-4.17 (m, 2H), 4.19-4.29 (m, 1H), 4.63-4.73 (m, 1H), 6.56 (d, J=8.5 Hz, 2H), 7.14-7.19 (m, 1H), 7.22 (d, J=8.5 Hz, 2H), 7.25-7.29 (m, 1H), 7.38 (d, J=2.2 Hz, 1H).

(2) 3-{[(4-{[1-(5-chloro-3-methyl-1-benzofuran-2-yl)-3-methylbutyl]amino}phenyl)carbonyl](methyl)amino}propanoic acid To a mixture of ethyl 3-{[(4-{[1-(5-chloro-3-methyl-1-benzofuran-2-yl)-3-methylbutyl]amino}phenyl)carbonyl](methyl)amino}propanoate (199 mg) synthesized above, tetrahydrofuran (5 mL) and ethanol (5 mL) was added 1N aqueous sodium hydroxide solution (1.50 mL), and the mixture was stirred at room temperature for 2 hr, and concentrated under reduced pressure. The residue was dissolved in water (10 mL), and 1N hydrochloric acid (1.50 mL) was added at 0° C. The resulting precipitate was collected by filtration to give the title object compound (174 mg, 93%) as a white solid.

$^1$H NMR (300 MHz, CDCl$_3$) δ ppm 0.92 (d, J=6.8 Hz, 3H), 1.00 (d, J=6.8 Hz, 3H), 1.48-1.64 (m, 1H), 1.85 (t, J=7.2 Hz, 2H), 2.25 (s, 3H), 2.67 (t, J=6.3 Hz, 2H), 3.04 (s, 3H), 3.71 (t, J=6.3 Hz, 2H), 4.69 (t, J=7.6 Hz, 1H), 6.57 (d, J=8.7 Hz, 2H), 7.15-7.20 (m, 1H), 7.22-7.31 (m, 3H), 7.39 (d, J=1.9 Hz, 1H).

Example A102

3-{[(4-{[(3-bromo-5-methoxy-1-benzofuran-2-yl)(cyclohexyl)methyl]amino}phenyl)carbonyl]amino}propanoic acid

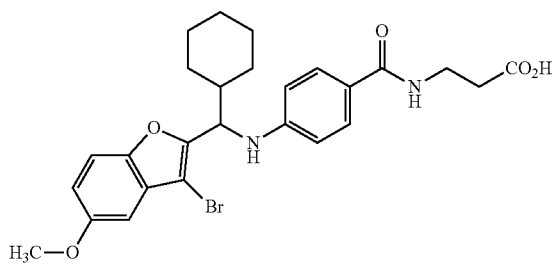 [SMILES: COc1ccc2oc(C(Nc3ccc(C(=O)NCCC(=O)O)cc3)C3CCCCC3)c(Br)c2c1]

(1) N,5-dimethoxy-N-methyl-1-benzofuran-2-carboxamide

To a solution (100 mL) of 2-hydroxy-5-methoxybenzaldehyde (10.0 g) in N,N-dimethylformamide were added 2-chloro-N-methoxy-N-methylacetamide (12.1 g), sodium iodide (24.0 g) and potassium carbonate (22.1 g), and the mixture was stirred at 50° C. overnight. The reaction mixture was cooled to room temperature, and insoluble material was filtered off. To the filtrate was added 1,8-diazabicyclo[5.4.0]undec-7-ene (9.82 mL), and the mixture was stirred at 120° C. for 2 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (40% ethyl acetate/hexane) to give the title object compound (9.42 g, 61%) as a yellow oil.

$^1$H NMR (300 MHz, CDCl$_3$) δ ppm 3.42 (s, 3H), 3.83 (s, 3H), 3.85 (s, 3H), 7.01-7.06 (m, 1H), 7.07-7.09 (m, 1H), 7.43-7.45 (m, 1H), 7.46-7.51 (m, 1H).

(2) 3-bromo-N,5-dimethoxy-N-methyl-1-benzofuran-2-carboxamide

To a solution (100 mL) of N,5-dimethoxy-N-methyl-1-benzofuran-2-carboxamide (9.24 g) synthesized above in acetic acid was added dropwise bromine (2.21 mL), and the mixture was stirred overnight at room temperature. The resulting precipitate was collected by filtration and washed with diisopropyl ether to give the title object compound (9.48 g, 77%) as an orange solid.

$^1$H NMR (300 MHz, CDCl$_3$) δ ppm 3.43 (s, 3H), 3.85 (s, 3H), 3.95 (s, 3H), 7.09 (d, J=9.0 Hz, 1H), 7.46-7.54 (m, 2H).

(3) 3-bromo-5-methoxy-1-benzofuran-2-carbaldehyde

To a solution (40 mL) of 3-bromo-N,5-dimethoxy-N-methyl-1-benzofuran-2-carboxamide (4.00 g) synthesized above in tetrahydrofuran was added lithium aluminum hydride (241 mg) at 0° C., and the mixture was stirred for 1 hr. Lithium aluminum hydride (241 mg) was additionally added, and the mixture was stirred at 0° C. for 1 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (880 mg, 27%) as a pale-yellow solid.

$^1$H NMR (300 MHz, CDCl$_3$) δ ppm 3.96 (s, 3H), 7.17 (d, J=9.1 Hz, 1H), 7.48-7.53 (m, 1H), 7.55-7.56 (m, 1H), 9.85 (s, 1H).

(4) (3-bromo-5-methoxy-1-benzofuran-2-yl)(cyclohexyl)methanol

To a solution (50 mL) of 3-bromo-5-methoxy-1-benzofuran-2-carbaldehyde (2.26 g) synthesized above in tetrahydrofuran was added a 1.0M solution (13.3 mL) of cyclohexylmagnesium bromide in tetrahydrofuran at −78° C., and the mixture was stirred at −78° C. for 30 min then at 0° C. for 1 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (1.82 g, 67%) as a yellow oil.

$^1$H NMR (300 MHz, CDCl$_3$) δ ppm 0.99-1.37 (m, 5H), 1.49-1.60 (m, 1H), 1.62-2.02 (m, 6H), 3.93 (s, 3H), 4.53 (t, J=6.0 Hz, 1H), 6.63 (s, 1H), 6.89 (d, J=8.8 Hz, 1H), 7.34 (d, J=8.8 Hz, 1H).

(5) 3-bromo-2-[chloro(cyclohexyl)methyl]-5-methoxy-1-benzofuran

To a solution (20 mL) of (3-bromo-5-methoxy-1-benzofuran-2-yl)(cyclohexyl)methanol (1.82 g) synthesized above in toluene was added thionyl chloride (469 μL) and the mixture was stirred at 100° C. for 1.5 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (1.73 g, 90%) as a yellow solid.

$^1$H NMR (300 MHz, CDCl$_3$) δ ppm 0.98-1.39 (m, 5H), 1.51-1.87 (m, 4H), 2.03-2.21 (m, 2H), 3.92 (s, 3H), 4.74 (d, J=8.0 Hz, 1H), 6.68 (s, 1H), 6.92 (d, J=8.8 Hz, 1H), 7.36 (d, J=8.8 Hz, 1H).

(6) 4-{[(3-bromo-5-methoxy-1-benzofuran-2-yl)(cyclohexyl)methyl]amino}benzoic acid To a mixture of 3-bromo-2-[chloro(cyclohexyl)methyl]-5-methoxy-1-benzofuran (1.73 g) synthesized above, methyl 4-aminobenzoate (878 mg), sodium iodide (1.45 g) and N,N-dimethylformamide (30 mL) was added sodium carbonate (1.03 g), and the mixture was stirred at 80° C. for 8 hr. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (25% ethyl acetate/hexane) to give a yellow oil. To a mixture of the obtained oil, tetrahydrofuran (10 mL) and ethanol (10 mL) was added 1N aqueous sodium hydroxide solution (10.0 mL), and the mixture was stirred with heating under reflux for 5 hr, and concentrated under reduced pressure. The residue was dissolved in water (20 mL), and 1N hydrochloric acid (10.0 mL) was added at 0° C. The resulting precipitate was collected by filtration to give the title object compound (318 mg, 14%) as a pale-brown solid.

$^1$H NMR (300 MHz, CDCl$_3$) δ ppm 1.04-1.37 (m, 5H), 1.55-1.86 (m, 4H), 1.87-2.02 (m, 2H), 3.90 (s, 3H), 4.44 (d, J=6.6 Hz, 1H), 6.56 (s, 1H), 6.61 (d, J=8.9 Hz, 2H), 6.87 (d, J=9.0 Hz, 1H), 7.29-7.35 (m, 1H), 7.87 (d, J=8.9 Hz, 2H).

(7) ethyl 3-{[(4-{[(3-bromo-5-methoxy-1-benzofuran-2-yl)(cyclohexyl)methyl]amino}phenyl)carbonyl]amino}propanoate To a mixture of 4-{[(3-bromo-5-methoxy-1-benzofuran-2-yl)(cyclohexyl)methyl]amino}benzoic acid (125 mg) synthesized above, β-alanine ethyl ester hydrochloride (63.0 mg), 1-hydroxybenzotriazole monohydrate (62.9 mg), triethylamine (114 μL) and N,N-dimethylformamide (10 mL) was added 1-ethyl-3-(3-dimethylaminopropyl)carbodiimide hydrochloride (78.6 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (134 mg, 88%) as a pale-yellow oil.

$^1$H NMR (300 MHz, CDCl$_3$) δ ppm 1.03-1.37 (m, 8H), 1.54-1.85 (m, 4H), 1.87-1.99 (m, 2H), 2.56-2.61 (m, 2H), 3.62-3.70 (m, 2H), 3.90 (s, 3H), 4.14 (q, J=7.1 Hz, 2H), 4.36-4.41 (m, 2H), 6.53 (d, J=0.8 Hz, 1H), 6.56-6.64 (m, 3H), 6.86 (d, J=8.8 Hz, 1H), 7.29 (dd, J=8.8, 0.8 Hz, 1H), 7.56 (d, J=8.8 Hz, 2H).

(8) 3-{[(4-{[(3-bromo-5-methoxy-1-benzofuran-2-yl)(cyclohexyl)methyl]amino}phenyl)carbonyl]amino}propanoic acid To a mixture of ethyl 3-{[(4-{[(3-bromo-5-methoxy-1-benzofuran-2-yl)(cyclohexyl)methyl]amino}phenyl)carbonyl]amino}propanoate (134 mg) synthesized above, tetrahydrofuran (5 mL) and ethanol (5 mL) was added 1N aqueous sodium hydroxide solution (1.00 mL), and the mixture was stirred at room temperature for 2.5 hr, and concentrated under reduced pressure. The residue was dissolved in water (10 mL), and 1N hydrochloric acid (1.00 mL) was added at 0° C. The resulting precipitate was collected by filtration to give the title object compound (116 mg, 91%) as a pale-brown solid.

$^1$H NMR (300 MHz, CDCl$_3$) δ ppm 1.02-1.35 (m, 5H), 1.53-1.84 (m, 4H), 1.84-1.99 (m, 2H), 2.61 (t, J=5.7 Hz, 2H), 3.59-3.68 (m, 2H), 3.89 (s, 3H), 4.38 (d, J=6.4 Hz, 1H), 6.52-6.66 (m, 4H), 6.85 (d, J=8.9 Hz, 1H), 7.30 (dd, J=8.9, 0.8 Hz, 1H), 7.54 (d, J=8.7 Hz, 2H).

Example A103

3-{[(4-{[(3-bromo-5-methoxy-1-benzofuran-2-yl)(cyclohexyl)methyl]amino}phenyl)carbonyl](methyl)amino}-propanoic acid

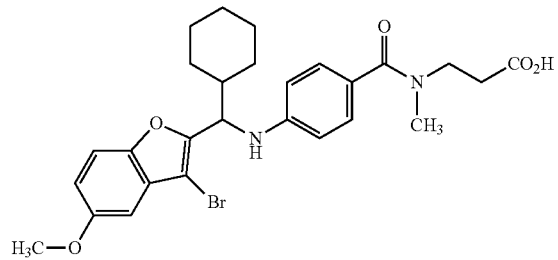 [SMILES: COc1ccc2oc(C(Nc3ccc(C(=O)N(C)CCC(=O)O)cc3)C3CCCCC3)c(Br)c2c1]

(1) ethyl 3-{[(4-{[(3-bromo-5-methoxy-1-benzofuran-2-yl)(cyclohexyl)methyl]amino}phenyl)carbonyl](methyl)amino}-propanoate To a mixture of 4-{[(3-bromo-5-methoxy-1-benzofuran-2-yl)(cyclohexyl)methyl]amino}benzoic acid (125 mg) synthesized in Example A102(6), ethyl 3-(methylamino)propanoate (53.8 mg), 1-hydroxybenzotriazole monohydrate (62.9 mg), triethylamine (114 μL) and N,N-dimethylformamide (10 mL) was added 1-ethyl-3-(3-dimethylaminopropyl)carbodiimide hydrochloride (78.6 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (35% ethyl acetate/hexane) to give the title object compound (124 mg, 79%) as a pale-yellow oil.

$^1$H NMR (300 MHz, CDCl$_3$) δ ppm 1.04-1.36 (m, 8H), 1.55-1.85 (m, 4H), 1.86-2.00 (m, 2H), 2.62 (t, J=7.0 Hz, 2H), 3.02 (s, 3H), 3.72 (t, J=7.0 Hz, 2H), 3.91 (s, 3H), 4.12 (q, J=7.1 Hz, 2H), 4.24-4.41 (m, 2H), 6.54-6.55 (m, 1H), 6.58 (d, J=8.8 Hz, 2H), 6.86 (d, J=8.8 Hz, 1H), 7.24 (d, J=8.8 Hz, 2H), 7.30 (dd, J=8.8, 0.8 Hz, 1H).

(2) 3-{[(4-{[(3-bromo-5-methoxy-1-benzofuran-2-yl)(cyclohexyl)methyl]amino}phenyl)carbonyl](methyl)amino}-propanoic acid To a mixture of ethyl 3-{[(4-{[(3-bromo-5-methoxy-1-benzofuran-2-yl)(cyclohexyl)methyl]amino}phenyl)carbonyl]methyl)amino}-propanoate (124 mg) synthesized above, tetrahydrofuran (5 mL) and ethanol (5 mL) was added 1N aqueous sodium hydroxide solution (1.00 mL), and the mixture was stirred at room temperature for 2 hr, and concentrated under reduced pressure. The residue was dissolved in water (10 mL), and 1N hydrochloric acid (1.00 mL) was added at 0° C., and the mixture was extracted with ethyl acetate. The extract was washed with saturated brine, dried over magnesium sulfate, and concentrated under reduced pressure. The residue was dissolved in ethanol (5 mL), 1N aqueous sodium hydroxide solution (500 μL) was added, and the mixture was concentrated under reduced pressure. The residue was dissolved in water (5 mL), and 1N hydrochloric acid (500 μL) was added at 0° C. The resulting precipitate was collected by filtration to give the title object compound (107 mg, 91%) as a white solid.

$^1$H NMR (300 MHz, CDCl$_3$) δ ppm 1.03-1.36 (m, 5H), 1.53-1.84 (m, 4H), 1.85-2.00 (m, 2H), 2.62-2.75 (m, 2H), 3.05 (s, 3H), 3.70 (t, J=6.2 Hz, 2H), 3.90 (s, 3H), 4.37 (d, J=6.4 Hz, 1H), 6.55 (s, 1H), 6.58 (d, J=8.7 Hz, 2H), 6.87 (d, J=8.9 Hz, 1H), 7.22-7.35 (m, 3H).

Example A104

3-{[(4-{[2-ethyl-1-(5-methoxy-3-methyl-1-benzofuran-2-yl)butyl]amino}phenyl)carbonyl]amino}propanoic acid

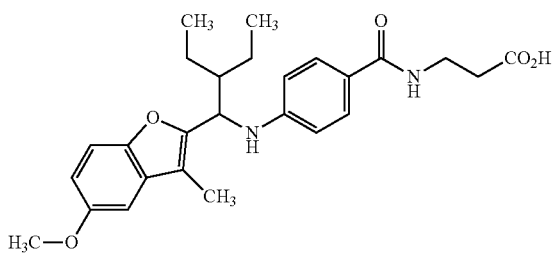 [SMILES: CCC(CC)C(Nc1ccc(C(=O)NCCC(=O)O)cc1)c1oc2ccc(OC)cc2c1C]

(1) (2-acetyl-4-methoxyphenoxy)acetic acid

To a mixture of 1-(2-hydroxy-5-methoxyphenyl)ethanone (25.0 g), methyl bromoacetate (15.5 mL) and N,N-dimethylformamide (250 mL) was added potassium carbonate (31.1 g), and the mixture was stirred overnight at room temperature. The insoluble material was filtered off, 1N hydrochloric acid was added to the filtrate, and the mixture was extracted with ethyl acetate. The extract was washed with saturated brine, dried over magnesium sulfate, and concentrated under reduced pressure to give a brown solid. To a mixture of the obtained solid, tetrahydrofuran (300 mL) and ethanol (300 mL) was added 1N aqueous sodium hydroxide solution (300 mL), and the mixture was stirred overnight at room temperature, and concentrated under reduced pressure. 1N Hydrochloric acid (300 mL) was added to the residue at 0° C., and the resulting precipitate was collected by filtration to give the title object compound (34.2 g, quantitative) as a white solid.

$^1$H NMR (300 MHz, CDCl$_3$) δ ppm 2.67 (s, 3H), 3.83 (s, 3H), 4.72 (s, 2H), 6.92 (d, J=9.0 Hz, 1H), 7.04-7.09 (m, 1H), 7.29 (d, J=3.0 Hz, 1H).

(2) 5-methoxy-3-methyl-1-benzofuran

A mixture of (2-acetyl-4-methoxyphenoxy)acetic acid (10.0 g) synthesized above, acetic anhydride (18.3 g) and acetic acid (100 mL) was stirred at 110° C. for 5 hr, poured into water, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (5% ethyl acetate/hexane) to give the title object compound (5.87 g, 81%) as a colorless oil.

$^1$H NMR (300 MHz, CDCl$_3$) δ ppm 2.21 (d, J=1.1 Hz, 3H), 3.86 (s, 3H), 6.85-6.91 (m, 1H), 6.95 (d, J=2.7 Hz, 1H), 7.33 (d, J=8.8 Hz, 1H), 7.35-7.39 (m, 1H).

(3) 2-ethyl-1-(5-methoxy-3-methyl-1-benzofuran-2-yl)butan-1-one

To a mixture of 5-methoxy-3-methyl-1-benzofuran (2.00 g) synthesized above, 2-ethylbutanoyl chloride (1.85 mL) and nitromethane (30 mL) was added aluminum chloride (3.28 g), and the mixture was stirred at room temperature for 1.5 hr. Water was added to quench the reaction, and the reaction mixture was extracted with ethyl acetate. The extract was washed with saturated brine, dried over magnesium sulfate, and concentrated under reduced pressure. The residue was purified by silica gel column chromatography (6% ethyl acetate/hexane) to give the title object compound (3.12 g, 97%) as a pale-yellow oil.

$^1$H NMR (300 MHz, CDCl$_3$) δ ppm 0.86-0.95 (m, 6H), 1.52-1.66 (m, 2H), 1.72-1.88 (m, 2H), 2.59 (s, 3H), 3.29-3.41 (m, 1H), 3.88 (s, 3H), 7.00-7.02 (m, 1H), 7.06-7.11 (m, 1H), 7.37-7.42 (m, 1H).

(4) methyl 4-{[2-ethyl-1-(5-methoxy-3-methyl-1-benzofuran-2-yl)butyl]amino}benzoate To a mixture of 2-ethyl-1-(5-methoxy-3-methyl-1-benzofuran-2-yl)butan-1-one (800 mg) synthesized above, methyl 4-aminobenzoate (464 mg), triethylamine (3.43 mL) and methylene chloride (10 mL) was added titanium (IV) chloride (404 μL), and the mixture was stirred overnight at room temperature under argon atmosphere. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (882 μL) and sodium cyanoborohydride (386 mg), and the mixture was stirred at room temperature for 1.5 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (718 mg, 59%) as a brown oil.

$^1$H NMR (300 MHz, CDCl$_3$) δ ppm 0.85 (t, J=7.4 Hz, 3H), 0.95 (t, J=7.3 Hz, 3H), 1.14-1.74 (m, 4H), 1.81-1.95 (m, 1H), 2.23 (s, 3H), 3.81 (s, 3H), 3.83 (s, 3H), 4.47-4.53 (m, 1H), 4.59 (t, J=8.1 Hz, 1H), 6.56 (d, J=8.8 Hz, 2H), 6.81 (dd, J=8.8, 2.6 Hz, 1H), 6.86 (d, J=2.6 Hz, 1H), 7.24 (d, J=8.8 Hz, 1H), 7.79 (d, J=8.8 Hz, 2H).

(5) 4-{[2-ethyl-1-(5-methoxy-3-methyl-1-benzofuran-2-yl)butyl]amino}benzoic acid To a mixture of methyl 4-{[2-ethyl-1-(5-methoxy-3-methyl-1-benzofuran-2-yl)butyl]amino}benzoate (718 mg) synthesized above, tetrahydrofuran (5 mL) and ethanol (5 mL) was added 1N aqueous sodium hydroxide solution (5.00 mL), and the mixture was stirred overnight with heating under reflux, and concentrated under reduced pressure. The residue was dissolved in water (10 mL), and 1N hydrochloric acid (5.00 mL) was added at 0° C. The resulting precipitate was collected by filtration to give the title object compound (574 mg, 83%) as a white solid.

$^1$H NMR (300 MHz, CDCl$_3$) δ ppm 0.85 (t, J=7.4 Hz, 3H), 0.95 (t, J=7.3 Hz, 3H), 1.16-1.74 (m, 4H), 1.82-1.95 (m, 1H), 2.24 (s, 3H), 3.83 (s, 3H), 4.54-4.66 (m, 2H), 6.58 (d, J=8.8 Hz, 2H), 6.83 (dd, J=8.8, 2.6 Hz, 1H), 6.88 (d, J=2.6 Hz, 1H), 7.25 (d, J=8.8 Hz, 1H), 7.85 (d, J=8.8 Hz, 2H).

(6) ethyl 3-{[(4-{[2-ethyl-1-(5-methoxy-3-methyl-1-benzofuran-2-yl)butyl]amino}phenyl)carbonyl]amino}propanoate To a mixture of 4-{[2-ethyl-1-(5-methoxy-3-methyl-1-benzofuran-2-yl)butyl]amino}benzoic acid (250 mg) synthesized above, β-alanine ethyl ester hydrochloride (151 mg), 1-hydroxybenzotriazole monohydrate (151 mg), triethylamine (275 µL) and N,N-dimethylformamide (10 mL) was added 1-ethyl-3-(3-dimethylaminopropyl)carbodiimide hydrochloride (188 mg), and the mixture was stirred at room temperature for 1 day. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (55% ethyl acetate/hexane) to give the title object compound (85.0 mg, 27%) as a pale-yellow oil.

$^1$H NMR (300 MHz, CDCl$_3$) δ ppm 0.87 (t, J=7.4 Hz, 3H), 0.95 (t, J=7.4 Hz, 3H), 1.24 (t, J=7.1 Hz, 3H), 1.30-1.74 (m, 4H), 1.81-1.93 (m, 1H), 2.23 (s, 3H), 2.54-2.62 (m, 2H), 3.65 (q, J=6.1 Hz, 2H), 3.83 (s, 3H), 4.13 (q, J=7.1 Hz, 2H), 4.40 (d, J=8.8 Hz, 1H), 4.52-4.60 (m, 1H), 6.53-6.62 (m, 3H), 6.78-6.84 (m, 1H), 6.86 (d, J=2.7 Hz, 1H), 7.22 (s, 1H), 7.54 (d, J=8.8 Hz, 2H).

(7) 3-{[(4-{[2-ethyl-1-(5-methoxy-3-methyl-1-benzofuran-2-yl)butyl]amino}phenyl)carbonyl]amino}propanoic acid To a mixture of ethyl 3-{[(4-{[2-ethyl-1-(5-methoxy-3-methyl-1-benzofuran-2-yl)butyl]amino}phenyl)carbonyl]amino}propanoate (85.0 mg) synthesized above, tetrahydrofuran (5 mL) and ethanol (5 mL) was added 1N aqueous sodium hydroxide solution (1.00 mL), and the mixture was stirred at room temperature for 2 hr, and concentrated under reduced pressure. The residue was dissolved in water (10 mL), and 1N hydrochloric acid (1.00 mL) was added at 0° C. The resulting precipitate was collected by filtration to give the title object compound (75.4 mg, 94%) as a white solid.

$^1$H NMR (300 MHz, CDCl$_3$) δ ppm 0.84 (t, J=7.3 Hz, 3H), 0.94 (t, J=7.3 Hz, 3H), 1.14-1.72 (m, 4H), 1.79-1.93 (m, 1H), 2.22 (s, 3H), 2.62 (t, J=5.7 Hz, 2H), 3.58-3.68 (m, 2H), 3.82 (s, 3H), 4.57 (d, J=7.7 Hz, 1H), 6.52-6.62 (m, 3H), 6.81 (dd, J=8.9, 2.5 Hz, 1H), 6.86 (d, J=2.5 Hz, 1H), 7.24 (d, J=8.9 Hz, 1H), 7.52 (d, J=8.9 Hz, 2H).

Example A105

3-{[(4-{[2-ethyl-1-(5-methoxy-3-methyl-1-benzofuran-2-yl)butyl]amino}phenyl)carbonyl](methyl)amino}propanoic acid

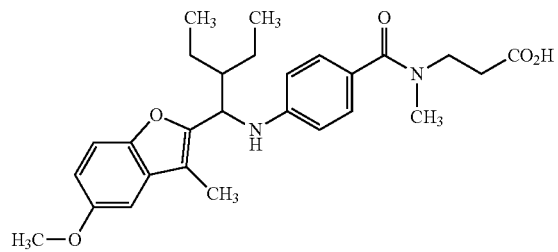 [SMILES: CCC(CC)C(Nc1ccc(C(=O)N(C)CCC(=O)O)cc1)c1oc2ccc(OC)cc2c1C]

(1) ethyl 3-{[(4-{[2-ethyl-1-(5-methoxy-3-methyl-1-benzofuran-2-yl)butyl]amino}phenyl)carbonyl]methyl)amino}propanoate To a mixture of 4-{[2-ethyl-1-(5-methoxy-3-methyl-1-benzofuran-2-yl)butyl]amino}benzoic acid (250 mg) synthesized in Example A104(5), ethyl 3-(methylamino)propanoate (129 mg), 1-hydroxybenzotriazole monohydrate (151 mg), triethylamine (275 µL) and N,N-dimethylformamide (10 mL) was added 1-ethyl-3-(3-dimethylaminopropyl)carbodiimide hydrochloride (188 mg), and the mixture was stirred at room temperature for 1 day. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (55% ethyl acetate/hexane) to give the title object compound (261 mg, 81%) as a pale-yellow oil.

$^1$H NMR (300 MHz, CDCl$_3$) δ ppm 0.85 (t, J=7.4 Hz, 3H), 0.94 (t, J=7.4 Hz, 3H), 1.23 (t, J=7.1 Hz, 3H), 1.29-1.73 (m, 4H), 1.79-1.93 (m, 1H), 2.22 (s, 3H), 2.61 (t, J=7.1 Hz, 2H), 3.01 (s, 3H), 3.70 (t, J=7.1 Hz, 2H), 3.83 (s, 3H), 4.11 (q, J=7.1 Hz, 2H), 4.28 (d, J=8.5 Hz, 1H), 4.50-4.58 (m, 1H), 6.55 (d, J=8.7 Hz, 2H), 6.79-6.83 (m, 1H), 6.86 (d, J=2.5 Hz, 1H), 7.20 (d, J=8.7 Hz, 2H), 7.24 (d, J=8.8 Hz, 1H).

(2) 3-{[(4-{[2-ethyl-1-(5-methoxy-3-methyl-1-benzofuran-2-yl)butyl]amino}phenyl)carbonyl](methyl)amino}propanoic acid To a mixture of ethyl 3-{[(4-{[2-ethyl-1-(5-methoxy-3-methyl-1-benzofuran-2-yl)butyl]amino}phenyl)carbonyl](methyl)amino}propanoate (261 mg) synthesized above, tetrahydrofuran (5 mL) and ethanol (5 mL) was added 1N aqueous sodium hydroxide solution (1.00 mL), and the mixture was stirred at room temperature for 1 hr, and concentrated under reduced pressure. The residue was dissolved in water (10 mL), and 1N hydrochloric acid (1.00 mL) was added at 0° C. The resulting precipitate was collected by filtration to give the title object compound (231 mg, 94%) as a pale-brown solid.

¹H NMR (300 MHz, CDCl₃) δ ppm 0.85 (t, J=7.3 Hz, 3H), 0.94 (t, J=7.4 Hz, 3H), 1.15-1.73 (m, 4H), 1.80-1.93 (m, 1H), 2.23 (s, 3H), 2.65 (t, J=6.6 Hz, 2H), 3.03 (s, 3H), 3.69 (t, J=6.6 Hz, 2H), 3.83 (s, 3H), 4.55 (d, J=7.7 Hz, 1H), 6.56 (d, J=8.9 Hz, 2H), 6.82 (dd, J=8.8, 2.4 Hz, 1H), 6.87 (d, J=2.4 Hz, 1H), 7.20-7.28 (m, 3H).

Example A106

3-[({4-[(1-{5-chloro-1-[3-(trifluoromethyl)phenyl]-1H-indol-2-yl}heptyl)amino]phenyl}carbonyl)amino]propanoic acid

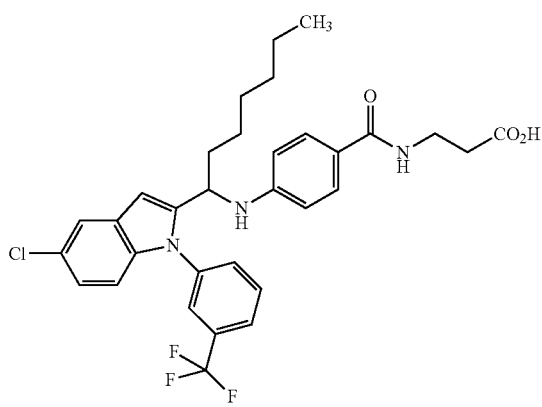 [SMILES: CCCCCCC(Nc1ccc(C(=O)NCCC(=O)O)cc1)c1cc2cc(Cl)ccc2n1-c1cccc(C(F)(F)F)c1]

(1) 5-chloro-N-methoxy-N-methyl-1H-indole-2-carboxamide

To a mixture of 5-chloro-1H-indole-2-carboxylic acid (15.0 g), N,O-dimethylhydroxylamine hydrochloride (8.97 g), 1-hydroxybenzotriazole monohydrate (14.1 g), triethylamine (25.6 mL) and N,N-dimethylformamide (200 mL) was added 1-ethyl-3-(3-dimethylaminopropyl)carbodiimide hydrochloride (17.6 g), and the mixture was stirred overnight at room temperature. 1N Hydrochloric acid was added to quench the reaction, the resulting precipitate was collected by filtration to give the title object compound (15.5 g, 84%) as a pale-brown solid.

¹H NMR (300 MHz, CDCl₃) δ ppm 3.43 (s, 3H), 3.85 (s, 3H), 7.14-7.18 (m, 1H), 7.25 (dd, J=8.7, 1.9 Hz, 1H), 7.36 (d, J=8.7 Hz, 1H), 7.66 (d, J=1.9 Hz, 1H), 9.32 (br s, 1H).

(2) 1-(5-chloro-1H-indol-2-yl)heptan-1-one

To a solution (100 mL) of 5-chloro-N-methoxy-N-methyl-1H-indole-2-carboxamide (9.14 g) synthesized above in tetrahydrofuran was added a 2.3M solution (50.0 mL) of hexyllithium in hexane at −78° C., and the mixture was stirred under nitrogen atmosphere for 1.5 hr. A 2.3M solution (38.3 mL) of hexyllithium in hexane was additionally added, and the mixture was stirred at −78° C. for 2 hr. 1N Hydrochloric acid was added to quench the reaction, and the mixture was extracted with ethyl acetate. The extract was washed with saturated brine, dried over magnesium sulfate, and concentrated under reduced pressure. The residue was washed with hexane to give the title object compound (6.90 g, 68%) as a pale-yellow solid.

¹H NMR (300 MHz, CDCl₃) δ ppm 0.86-0.95 (m, 3H), 1.26-1.48 (m, 6H), 1.71-1.85 (m, 2H), 2.92 (t, J=7.7 Hz, 2H), 7.11-7.14 (m, 1H), 7.29 (dd, J=8.8, 1.9 Hz, 1H), 7.36 (d, J=8.8 Hz, 1H), 7.66-7.70 (m, 1H), 9.05-9.19 (m, 1H).

(3) 1-{5-chloro-1-[3-(trifluoromethyl)phenyl]-1H-indol-2-yl}heptan-1-one

A mixture of 1-(5-chloro-1H-indol-2-yl)heptan-1-one (9.14 g) synthesized above, 3-iodobenzotrifluoride (1.97 mL), copper(I) bromide (327 mg), potassium carbonate (2.36 g) and N-methyl-2-pyrrolidone (30 mL) was deaerated, and the mixture was stirred under argon atmosphere at 180° C. for 1 day. 1N Hydrochloric acid was added to the reaction mixture, and the mixture was extracted with ethyl acetate. The extract was washed with saturated brine, dried over magnesium sulfate, and concentrated under reduced pressure. The residue was purified by silica gel column chromatography (10% ethyl acetate/hexane) to give the title object compound (0.78 g, 17%) as a brown oil.

¹H NMR (300 MHz, CDCl₃) δ ppm 0.84-0.92 (m, 3H), 1.22-1.41 (m, 6H), 1.62-1.74 (m, 2H), 2.90-2.97 (m, 2H), 6.95 (d, J=8.8 Hz, 1H), 7.25 (dd, J=8.8, 1.9 Hz, 1H), 7.35 (s, 1H), 7.42-7.47 (m, 1H), 7.49-7.53 (m, 1H), 7.59-7.66 (m, 1H), 7.69-7.74 (m, 2H).

(4) methyl 4-[(1-{5-chloro-1-[3-(trifluoromethyl)phenyl]-1H-indol-2-yl}heptyl)amino]benzoate To a mixture of 1-{5-chloro-1-[3-(trifluoromethyl)phenyl]-1H-indol-2-yl}heptan-1-one (709 mg) synthesized above, methyl 4-aminobenzoate (263 mg), triethylamine (1.94 mL) and methylene chloride (10 mL) was added titanium (IV) chloride (229 μL), and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (10 mL) of the obtained oil in tetrahydrofuran were added acetic acid (498 μL) and sodium cyanoborohydride (219 mg), and the mixture was stirred at room temperature for 1.5 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (15% ethyl acetate/hexane) to give the title object compound (645 mg, 68%) as a brown oil.

¹H NMR (300 MHz, CDCl₃) δ ppm 0.84 (t, J=6.9 Hz, 3H), 1.12-1.41 (m, 8H), 1.74-1.93 (m, 2H), 3.83 (s, 3H), 4.03-4.15 (m, 1H), 4.41-4.52 (m, 1H), 6.33 (d, J=8.8 Hz, 2H), 6.57 (s, 1H), 6.88 (d, J=8.8 Hz, 1H), 7.09 (dd, J=8.8, 1.9 Hz, 1H), 7.45-7.52 (m, 1H), 7.54-7.65 (m, 3H), 7.68-7.79 (m, 3H).

(5) 4-[(1-{5-chloro-1-[3-(trifluoromethyl)phenyl]-1H-indol-2-yl}heptyl)amino]benzoic acid To a mixture of methyl 4-[(1-{5-chloro-1-[3-(trifluoromethyl)phenyl]-1H-indol-2-yl}heptyl)amino]benzoate (645 mg) synthesized above, tetrahydrofuran (5 mL) and ethanol (5 mL) was added 1N aqueous sodium hydroxide solution (5.00 mL), and the mixture was stirred overnight with heating under reflux, and concentrated under reduced pressure. The residue was dissolved in water (10 mL), and 1N hydrochloric acid (5.00 mL) was added at 0° C. The resulting precipitate was collected by filtration to give the title object compound (589 mg, 94%) as a white solid.

$^1$H NMR (300 MHz, CDCl$_3$) δ ppm 0.80 (t, J=6.8 Hz, 3H), 1.03-1.34 (m, 6H), 1.63-1.83 (m, 2H), 4.29-4.44 (m, 1H), 6.18 (d, J=8.3 Hz, 2H), 6.49 (s, 1H), 6.82 (d, J=8.5 Hz, 1H), 7.02 (dd, J=8.5, 1.9 Hz, 1H), 7.34-7.56 (m, 4H), 7.60 (d, J=7.6 Hz, 1H), 7.70 (d, J=8.3 Hz, 2H).

(6) ethyl 3-[({4-[(1-{5-chloro-1-[3-(trifluoromethyl)phenyl]-1H-indol-2-yl}heptyl)amino]phenyl}carbonyl)amino]propanoate To a mixture of 4-[(1-{5-chloro-1-[3-(trifluoromethyl)phenyl]-1H-indol-2-yl}heptyl)amino]benzoic acid (250 mg) synthesized above, β-alanine ethyl ester hydrochloride (109 mg), 1-hydroxybenzotriazole monohydrate (109 mg), triethylamine (198 μL) and N,N-dimethylformamide (10 mL) was added 1-ethyl-3-(3-dimethylaminopropyl)carbodiimide hydrochloride (136 mg), and the mixture was stirred at room temperature for 3 days. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (272 mg, 92%) as a pale-yellow oil.

$^1$H NMR (300 MHz, CDCl$_3$) δ ppm 0.83 (t, J=6.7 Hz, 3H), 1.11-1.39 (m, 11H), 1.75-1.90 (m, 2H), 2.60 (t, J=5.8 Hz, 2H), 3.63-3.72 (m, 2H), 3.93-4.04 (m, 1H), 4.15 (q, J=7.1 Hz, 2H), 4.38-4.50 (m, 1H), 6.35 (d, J=8.5 Hz, 2H), 6.53-6.64 (m, 2H), 6.87 (d, J=8.6 Hz, 1H), 7.08 (dd, J=8.6, 2.1 Hz, 1H), 7.45-7.66 (m, 6H), 7.70 (d, J=7.1 Hz, 1H).

(7) 3-[({4-[(1-{5-chloro-1-[3-(trifluoromethyl)phenyl]-1H-indol-2-yl}heptyl)amino]phenyl}carbonyl)amino]propanoic acid To a mixture of ethyl 3-[({4-[(1-{5-chloro-1-[3-(trifluoromethyl)phenyl]-1H-indol-2-yl}heptyl)amino]phenyl}carbonyl)amino]propanoate (273 mg) synthesized above, tetrahydrofuran (5 mL) and ethanol (5 mL) was added 1N aqueous sodium hydroxide solution (5.00 mL), and the mixture was stirred at room temperature for 2 hr, and concentrated under reduced pressure. The residue was dissolved in water (10 mL), and 1N hydrochloric acid (5.00 mL) was added at 0° C. The resulting precipitate was collected by filtration to give the title object compound (253 mg, 97%) as a white solid.

$^1$H NMR (300 MHz, CDCl$_3$) δ ppm 0.78 (t, J=6.8 Hz, 3H), 1.01-1.32 (m, 8H), 1.64-1.78 (m, 2H), 2.30-2.43 (m, 2H), 3.37-3.53 (m, 2H), 4.29-4.43 (m, 1H), 6.27 (d, J=8.7 Hz, 2H), 6.47 (s, 1H), 6.76-6.89 (m, 2H), 7.00 (dd, J=8.7, 1.9 Hz, 1H), 7.39-7.59 (m, 6H), 7.63 (d, J=7.6 Hz, 1H).

Example A107

3-[({4-[(1-{5-chloro-1-[3-(trifluoromethyl)phenyl]-1H-indol-2-yl}heptyl)amino]phenyl}carbonyl)(methyl)amino]propanoic acid

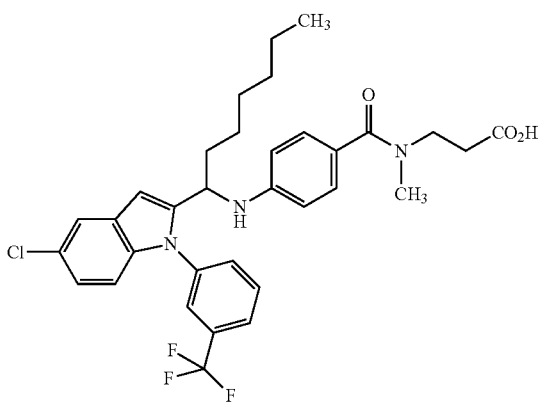 [SMILES: CCCCCCC(Nc1ccc(C(=O)N(C)CCC(=O)O)cc1)c1cc2cc(Cl)ccc2n1-c1cccc(C(F)(F)F)c1]

(1) ethyl 3-[({4-[(1-{5-chloro-1-[3-(trifluoromethyl)phenyl]-1H-indol-2-yl}heptyl)amino]phenyl}carbonyl)(methyl)amino]propanoate To a mixture of 4-[(1-{5-chloro-1-[3-(trifluoromethyl)phenyl]-1H-indol-2-yl}heptyl)amino]benzoic acid (250 mg) synthesized in Example A106(5), ethyl 3-(methylamino)propanoate (93.1 mg), 1-hydroxybenzotriazole monohydrate (109 mg), triethylamine (198 μL) and N,N-dimethylformamide (10 mL) was added 1-ethyl-3-(3-dimethylaminopropyl)carbodiimide hydrochloride (136 mg), and the mixture was stirred at room temperature for 3 days. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (40% ethyl acetate/hexane) to give the title object compound (254 mg, 84%) as a pale-yellow oil.

$^1$H NMR (300 MHz, CDCl$_3$) δ ppm 0.83 (t, J=6.9 Hz, 3H), 1.11-1.37 (m, 11H), 1.76-1.86 (m, 2H), 2.62 (t, J=7.3 Hz, 2H), 3.02 (s, 3H), 3.72 (t, J=7.3 Hz, 2H), 3.88 (d, J=7.7 Hz, 1H), 4.07-4.17 (m, 2H), 4.35-4.46 (m, 1H), 6.34 (d, J=8.5 Hz, 2H), 6.56 (s, 1H), 6.88 (d, J=8.8 Hz, 1H), 7.08 (dd, J=8.8, 2.0 Hz, 1H), 7.17 (d, J=8.5 Hz, 2H), 7.51 (d, J=7.7 Hz, 1H), 7.56 (d, J=2.0 Hz, 1H), 7.57-7.66 (m, 2H), 7.71 (d, J=7.7 Hz, 1H).

(2) 3-[({4-[(1-{5-chloro-1-[3-(trifluoromethyl)phenyl]-1H-indol-2-yl}heptyl)amino]phenyl}carbonyl)(methyl)amino]propanoic acid To a mixture of ethyl 3-[({4-[(1-{5-chloro-1-[3-(trifluoromethyl)phenyl]-1H-indol-2-yl}heptyl)amino]phenyl}carbonyl)(methyl)amino]propanoate (254 mg) synthesized above, tetrahydrofuran (5 mL) and ethanol (5 mL) was added 1N aqueous sodium hydroxide solution (1.00 mL), and the mixture was stirred overnight at room temperature, and concentrated under reduced pressure. The residue was dissolved in water (10 mL), and 1N hydrochloric acid (1.00 mL) was added at 0° C. The resulting precipitate was collected by filtration to give the title object compound (223 mg, 92%) as a white solid.

$^1$H NMR (300 MHz, CDCl$_3$) δ ppm 0.81 (t, J=6.8 Hz, 3H), 1.06-1.35 (m, 8H), 1.70-1.82 (m, 2H), 2.39-2.49 (m, 2H), 2.92 (s, 3H), 3.51-3.72 (m, 2H), 4.38 (t, J=6.8 Hz, 1H), 6.32 (d, J=8.5 Hz, 2H), 6.53 (s, 1H), 6.86 (d, J=8.7 Hz, 1H), 7.05 (dd, J=8.7, 1.9 Hz, 1H), 7.14 (d, J=8.5 Hz, 2H), 7.47-7.55 (m, 2H), 7.55-7.67 (m, 2H), 7.70 (d, J=7.6 Hz, 1H).

Example A108

3-{[(4-{[(3-cyano-5-methoxy-1-benzofuran-2-yl)(cyclohexyl)methyl]amino}phenyl)carbonyl]amino}propanoic acid

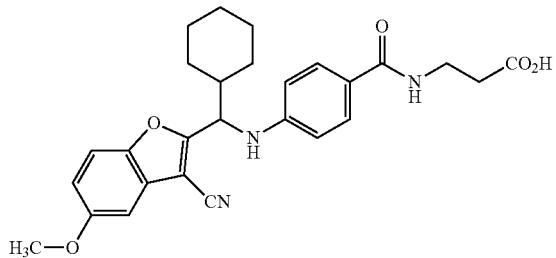

(1) (3-bromo-5-methoxy-1-benzofuran-2-yl)(cyclohexyl)methanone

To a mixture of dimethyl sulfoxide (831 mL) and tetrahydrofuran (20 mL) was added trifluoroacetic acid anhydride (1.63 mL) at −78° C., and the mixture was stirred for 30 min, and a solution (20 mL) of (3-bromo-5-methoxy-1-benzofuran-2-yl)(cyclohexyl)methanol (2.03 g) synthesized in Example A102(4) in tetrahydrofuran was added. The reaction mixture was stirred under argon atmosphere at −78° C. for 1 hr, triethylamine (3.33 mL) was added, and the mixture was stirred at room temperature for 1 hr. The reaction mixture was concentrated under reduced pressure, and the residue was purified by silica gel column chromatography (15% ethyl acetate/hexane) to give the title object compound (1.52 g, 75%) as a white solid.

$^1$H NMR (300 MHz, CDCl$_3$) δ ppm 1.20-1.63 (m, 5H), 1.70-1.81 (m, 1H), 1.82-2.00 (m, 4H), 3.13-3.24 (m, 1H), 3.95 (s, 3H), 7.12 (d, J=9.3 Hz, 1H), 7.46-7.50 (m, 2H).

(2) methyl 4-{[(3-bromo-5-methoxy-1-benzofuran-2-yl)(cyclohexyl)methyl]amino}benzoate To a mixture of (3-bromo-5-methoxy-1-benzofuran-2-yl)(cyclohexyl)methanone (1.52 g) synthesized above, methyl 4-aminobenzoate (682 mg), triethylamine (5.03 mL) and methylene chloride (20 mL) was added titanium (IV) chloride (593 μL), and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (1.29 mL) and sodium cyanoborohydride (567 mg), and the mixture was stirred at room temperature for 1.5 hr. Saturated aqueous sodium hydrogen carbonate solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (25% ethyl acetate/hexane) to give the title object compound (1.46 g, 69%) as a yellow solid.

$^1$H NMR (300 MHz, CDCl$_3$) δ ppm 1.03-1.38 (m, 5H), 1.54-1.85 (m, 4H), 1.85-2.01 (m, 2H), 3.82 (s, 3H), 3.90 (s, 3H), 4.36-4.56 (m, 2H), 6.54 (s, 1H), 6.58 (d, J=9.0 Hz, 2H), 6.86 (d, J=8.8 Hz, 1H), 7.30 (d, J=8.8 Hz, 1H), 7.81 (d, J=9.0 Hz, 2H).

(3) 4-{[(3-cyano-5-methoxy-1-benzofuran-2-yl)(cyclohexyl)methyl]amino}benzoic acid To a mixture of methyl 4-{[(3-bromo-5-methoxy-1-benzofuran-2-yl)(cyclohexyl)methyl]amino}benzoate (1.46 g) synthesized above, zinc cyanide (362 mg) and N,N-dimethylformamide (30 mL) was added tetrakis(triphenylphosphine)palladium (0) (357 mg), and after deaeration, the mixture was stirred under argon atmosphere at 80° C. overnight. Water was added to the reaction mixture, and the mixture was extracted with ethyl acetate. The extract was washed with saturated brine, dried over magnesium sulfate, and concentrated under reduced pressure. The residue was purified by silica gel column chromatography (40% ethyl acetate/hexane) to give a yellow solid. To a solution (10 mL) of the obtained solid in tetrahydrofuran was added 1N lithium hydroxide aqueous solution (2.88 mL), and the mixture was stirred overnight with heating under reflux. Ethanol (10 mL) and water (10 mL) were added to the reaction mixture, and the mixture was stirred with heating under reflux for 3 hr. 1N lithium hydroxide aqueous solution (1.44 mL) was additionally added, and the mixture was stirred overnight with heating under reflux, and concentrated under reduced pressure. The residue was dissolved in water (20 mL), and 1N hydrochloric acid (4.35 mL) was added at 0° C. The resulting precipitate was collected by filtration to give the title object compound (547 mg, 94%) as a pale-yellow solid.

$^1$H NMR (300 MHz, CDCl$_3$) δ ppm 1.05-1.38 (m, 5H), 1.53-1.87 (m, 4H), 1.87-2.01 (m, 2H), 3.94 (s, 3H), 4.42-4.60 (m, 2H), 6.58 (d, J=8.8 Hz, 2H), 6.68 (d, J=0.8 Hz, 1H), 6.84 (d, J=9.1 Hz, 1H), 7.53 (dd, J=9.1, 0.8 Hz, 1H), 7.87 (d, J=8.8 Hz, 2H).

(4) ethyl 3-{[(4-{[(3-cyano-5-methoxy-1-benzofuran-2-yl)(cyclohexyl)methyl]amino}phenyl)carbonyl]amino}propanoate To a mixture of 4-{[(3-cyano-5-methoxy-1-benzofuran-2-yl)(cyclohexyl)methyl]amino}benzoic acid (240 mg) synthesized above, β-alanine ethyl ester hydrochloride (137 mg), 1-hydroxybenzotriazole monohydrate (136 mg), triethylamine (248 μL) and N,N-dimethylformamide (10 mL) was added 1-ethyl-3-(3-dimethylaminopropyl)carbodiimide hydrochloride (171 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (60% ethyl acetate/hexane) to give the title object compound (285 mg, 95%) as a yellow solid.

¹H NMR (300 MHz, CDCl₃) δ ppm 1.05-1.37 (m, 8H), 1.53-1.86 (m, 4H), 1.86-2.00 (m, 2H), 2.59 (t, J=6.3 Hz, 2H), 3.62-3.70 (m, 2H), 3.93 (s, 3H), 4.14 (q, J=7.1 Hz, 2H), 4.35-4.45 (m, 2H), 6.57 (d, J=8.8 Hz, 2H), 6.60 (t, J=5.2 Hz, 1H), 6.65 (d, J=0.5 Hz, 1H), 6.83 (d, J=9.1 Hz, 1H), 7.51-7.60 (m, 3H).

(5) 3-{[(4-{[(3-cyano-5-methoxy-1-benzofuran-2-yl)(cyclohexyl)methyl]amino}phenyl)carbonyl]amino}propanoic acid To a mixture of ethyl 3-{[(4-{[(3-cyano-5-methoxy-1-benzofuran-2-yl)(cyclohexyl)methyl]amino}phenyl)carbonyl]amino}propanoate (285 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), and 1N hydrochloric acid (1.00 mL) was added at 0° C. The resulting precipitate was collected by filtration to give the title object compound (246 mg, 92%) as a pale-yellow solid.

¹H NMR (300 MHz, CDCl₃) δ ppm 1.04-1.37 (m, 5H), 1.50-1.63 (m, 1H), 1.63-1.85 (m, 3H), 1.85-2.01 (m, 2H), 2.64 (t, J=5.7 Hz, 2H), 3.60-3.70 (m, 2H), 3.93 (s, 3H), 4.42 (d, J=6.4 Hz, 1H), 6.58 (d, J=8.7 Hz, 2H), 6.62-6.70 (m, 2H), 6.83 (d, J=9.2 Hz, 1H), 7.50-7.59 (m, 3H).

Example A109

3-{[(4-{[(3-cyano-5-methoxy-1-benzofuran-2-yl)(cyclohexyl)methyl]amino}phenyl)carbonyl](methyl)amino}-propanoic acid

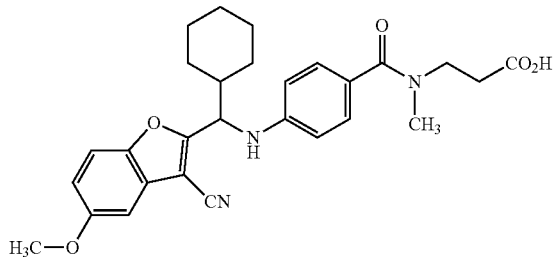

(1) ethyl 3-{[(4-{[(3-cyano-5-methoxy-1-benzofuran-2-yl)(cyclohexyl)methyl]amino}phenyl)carbonyl]methyl)amino}-propanoate To a mixture of 4-{[(3-cyano-5-methoxy-1-benzofuran-2-yl)(cyclohexyl)methyl]amino}benzoic acid (240 mg) synthesized in Example A108(3), ethyl 3-(methylamino)propanoate (117 mg), 1-hydroxybenzotriazole monohydrate (136 mg), triethylamine (248 μL) and N,N-dimethylformamide (10 mL) was added 1-ethyl-3-(3-dimethylaminopropyl)carbodiimide hydrochloride (171 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (60% ethyl acetate/hexane) to give the title object compound (253 mg, 82%) as a pale-yellow oil.

¹H NMR (300 MHz, CDCl₃) δ ppm 1.04-1.36 (m, 8H), 1.52-1.85 (m, 4H), 1.85-1.99 (m, 2H), 2.62 (t, J=6.9 Hz, 2H), 3.02 (s, 3H), 3.71 (t, J=6.9 Hz, 2H), 3.94 (s, 3H), 4.11 (q, J=7.1 Hz, 2H), 4.27-4.33 (m, 1H), 4.35-4.43 (m, 1H), 6.56 (d, J=8.5 Hz, 2H), 6.66-6.67 (m, 1H), 6.83 (d, J=9.1 Hz, 1H), 7.23 (d, J=8.5 Hz, 2H), 7.52 (dd, J=9.1, 0.8 Hz, 1H).

(2) 3-{[(4-{[(3-cyano-5-methoxy-1-benzofuran-2-yl)(cyclohexyl)methyl]amino}phenyl)carbonyl](methyl)amino}-propanoic acid To a mixture of ethyl 3-{[(4-{[(3-cyano-5-methoxy-1-benzofuran-2-yl)(cyclohexyl)methyl]amino}phenyl)carbonyl](methyl)amino}-propanoate (253 mg) synthesized above, tetrahydrofuran (5 mL) and ethanol (5 mL) was added 1N aqueous sodium hydroxide solution (1.00 mL), and the mixture was stirred at room temperature for 3 hr, and concentrated under reduced pressure. The residue was dissolved in water (10 mL), and 1N hydrochloric acid (1.00 mL) was added at 0° C. The resulting precipitate was collected by filtration to give the title object compound (218 mg, 91%) as a pale-yellow solid.

¹H NMR (300 MHz, CDCl₃) δ ppm 1.04-1.36 (m, 5H), 1.53-1.63 (m, 1H), 1.63-1.84 (m, 3H), 1.85-2.00 (m, 2H), 2.61-2.73 (m, 2H), 3.05 (s, 3H), 3.71 (t, J=6.6 Hz, 2H), 3.94 (s, 3H), 4.40 (d, J=6.4 Hz, 1H), 6.57 (d, J=8.7 Hz, 2H), 6.67 (d, J=0.8 Hz, 1H), 6.84 (d, J=9.1 Hz, 1H), 7.26 (d, J=8.7 Hz, 2H), 7.55 (dd, J=9.1, 0.8 Hz, 1H).

Example A110

3-[{[4-({[5-(acetylamino)-3-methyl-1-benzofuran-2-yl](cyclohexyl)methyl}amino)phenyl]carbonyl}(methyl)amino]-propanoic acid

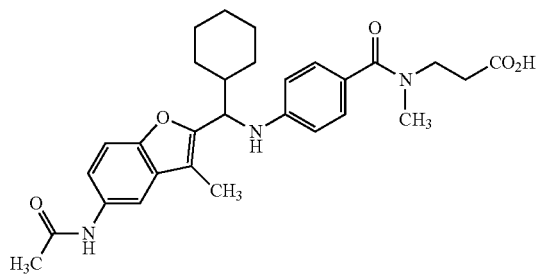 [SMILES: CC(=O)Nc1ccc2oc(C(Nc3ccc(C(=O)N(C)CCC(=O)O)cc3)C3CCCCC3)c(C)c2c1]

(1) cyclohexyl(3-methyl-5-nitro-1-benzofuran-2-yl)methanone

To a mixture of 2'-hydroxy-5'-nitroacetophenone (5.00 g), 2-bromo-1-cyclohexylethanone (6.79 g) synthesized in Example A51(1) and N,N-dimethylformamide (50 mL) was added potassium carbonate (7.63 g), and the mixture was stirred overnight at room temperature. 1N Hydrochloric acid was added to quench the reaction, and the mixture was extracted with ethyl acetate. The extract was washed with saturated brine, dried over magnesium sulfate, and concentrated under reduced pressure. The residue was washed with diisopropyl ether to give the title object compound (4.18 g, 53%) as a yellow solid.

¹H NMR (300 MHz, CDCl₃) δ ppm 1.19-1.54 (m, 5H), 1.70-1.81 (m, 1H), 1.82-1.92 (m, 2H), 1.92-2.02 (m, 2H), 2.65 (s, 3H), 3.24-3.36 (m, 1H), 7.62 (d, J=9.2 Hz, 1H), 8.37 (dd, J=9.2, 2.4 Hz, 1H), 8.59 (d, J=2.4 Hz, 1H).

(2) methyl 4-{[cyclohexyl(3-methyl-5-nitro-1-benzofuran-2-yl)methyl]amino}benzoate To a mixture of cyclohexyl(3-methyl-5-nitro-1-benzofuran-2-yl)methanone (3.00 g) synthesized above, methyl 4-aminobenzoate (1.57 g), triethylamine (11.6 mL) and methylene chloride (40 mL) was added titanium (IV) chloride (1.37 mL), and the mixture was stirred overnight under argon atmosphere at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (40 mL) of the obtained oil in tetrahydrofuran were added acetic acid (2.98 mL) and sodium cyanoborohydride (1.31 g), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (25% ethyl acetate/hexane) to give the title object compound (2.66 g, 61%) as an orange solid.
$^1$H NMR (300 MHz, CDCl$_3$) δ ppm 0.96-1.38 (m, 5H), 1.45-1.59 (m, 1H), 1.62-2.01 (m, 4H), 2.05-2.15 (m, 1H), 2.32 (s, 3H), 3.81 (s, 3H), 4.41-4.56 (m, 2H), 6.55 (d, J=9.1 Hz, 2H), 7.43 (d, J=8.9 Hz, 1H), 7.80 (d, J=9.1 Hz, 2H), 8.16 (dd, J=8.9, 2.4 Hz, 1H), 8.36 (d, J=2.4 Hz, 1H).

(3) 4-{[cyclohexyl(3-methyl-5-nitro-1-benzofuran-2-yl)methyl]amino}benzoic acid

To a mixture of methyl 4-{[cyclohexyl(3-methyl-5-nitro-1-benzofuran-2-yl)methyl]amino}benzoate (2.66 g) synthesized above, tetrahydrofuran (20 mL) and ethanol (20 mL) was added 1N aqueous sodium hydroxide solution (20.0 mL), and the mixture was stirred overnight with heating under reflux, and concentrated under reduced pressure. The residue was dissolved in water (40 mL), and 1N hydrochloric acid (20.0 mL) was added at 0° C. The resulting precipitate was collected by filtration and the obtained solid was dissolved in ethyl acetate. The solution was washed with saturated brine, dried over magnesium sulfate, and concentrated under reduced pressure. The residue was washed with diisopropyl ether to give the title object compound (2.22 g, 86%) as a pale-brown solid.
$^1$H NMR (300 MHz, CDCl$_3$) δ ppm 0.96-1.40 (m, 5H), 1.45-1.58 (m, 1H), 1.63-2.02 (m, 4H), 2.04-2.16 (m, 1H), 2.33 (s, 3H), 4.48 (d, J=8.0 Hz, 1H), 6.57 (d, J=9.1 Hz, 2H), 7.43 (d, J=8.9 Hz, 1H), 7.86 (d, J=9.1 Hz, 2H), 8.17 (dd, J=8.9, 2.4 Hz, 1H), 8.37 (d, J=2.4 Hz, 1H).

(4) ethyl 3-{[(4-{[cyclohexyl(3-methyl-5-nitro-1-benzofuran-2-yl)methyl]amino}phenyl)carbonyl](methyl)amino}propanoate To a mixture of 4-{[cyclohexyl(3-methyl-5-nitro-1-benzofuran-2-yl)methyl]amino}benzoic acid (1.54 g) synthesized above, ethyl 3-(methylamino)propanoate (593 mg), 1-hydroxybenzotriazole monohydrate (692 mg), triethylamine (1.26 mL) and N,N-dimethylformamide (15 mL) was added 1-ethyl-3-(3-dimethylaminopropyl)carbodiimide hydrochloride (867 mg), and the mixture was stirred overnight at room temperature. 1N Hydrochloric acid was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50% ethyl acetate/hexane) to give the title object compound (1.41 g, 72%) as a yellow solid.
$^1$H NMR (300 MHz, CDCl$_3$) δ ppm 0.96-1.40 (m, 8H), 1.44-1.56 (m, 1H), 1.58-2.00 (m, 3H), 2.06-2.17 (m, 1H), 2.31 (s, 3H), 2.61 (t, J=7.0 Hz, 2H), 3.01 (s, 3H), 3.70 (t, J=7.0 Hz, 2H), 4.06-4.16 (m, 2H), 4.28-4.34 (m, 1H), 4.42 (t, J=8.0 Hz, 1H), 6.55 (d, J=8.7 Hz, 2H), 7.22 (d, J=8.7 Hz, 2H), 7.43 (d, J=9.1 Hz, 1H), 8.16 (dd, J=9.1, 2.5 Hz, 1H), 8.35-8.37 (m, 1H).

(5) ethyl 3-{[(4-{[(5-amino-3-methyl-1-benzofuran-2-yl)(cyclohexyl)methyl]amino}phenyl)carbonyl](methyl)amino}-propanoate To a solution (20 mL) of ethyl 3-{[(4-{[cyclohexyl(3-methyl-5-nitro-1-benzofuran-2-yl)methyl]amino}phenyl)carbonyl]methyl)amino}propanoate (600 mg) synthesized above in ethanol was added platinum (IV) oxide (60.0 mg), and the mixture was stirred under hydrogen atmosphere at room temperature for 1 hr. Platinum oxide was filtered off, and the filtrate was concentrated to give the title object compound (579 mg, quantitative) as a white solid.
$^1$H NMR (300 MHz, CDCl$_3$) δ ppm 0.93-1.35 (m, 8H), 1.49-1.60 (m, 1H), 1.60-1.95 (m, 4H), 2.01-2.12 (m, 1H), 2.17 (s, 3H), 2.61 (t, J=7.1 Hz, 2H), 3.01 (s, 3H), 3.56 (br s, 2H), 3.70 (t, J=7.1 Hz, 2H), 4.11 (q, J=7.1 Hz, 2H), 4.30-4.34 (m, 2H), 6.55 (d, J=8.7 Hz, 2H), 6.59 (dd, J=8.5, 2.5 Hz, 1H), 6.69 (d, J=2.5 Hz, 1H), 7.14 (d, J=8.5 Hz, 1H), 7.20 (d, J=8.7 Hz, 2H).

(6) ethyl 3-[{[4-({[5-(acetylamino)-3-methyl-1-benzofuran-2-yl](cyclohexyl)methyl}amino)phenyl]carbonyl}(methyl)amino]-propanoate To a solution (10 mL) of ethyl 3-{[(4-{[(5-amino-3-methyl-1-benzofuran-2-yl)(cyclohexyl)methyl]amino}phenyl)carbonyl](methyl)amino}-propanoate (480 mg) synthesized above in tetrahydrofuran were added triethylamine (204 μL) and acetic anhydride (138 μL), and the mixture was stirred at room temperature for 2.5 days. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (90% ethyl acetate/hexane) to give the title object compound (366 mg, 70%) as a pale-brown oil
$^1$H NMR (300 MHz, CDCl$_3$) δ ppm 0.92-1.38 (m, 8H), 1.45-1.57 (m, 1H), 1.60-1.97 (m, 4H), 2.01-2.13 (m, 1H), 2.17 (s, 3H), 2.22 (s, 3H), 2.61 (t, J=7.1 Hz, 2H), 3.01 (s, 3H), 3.71 (t, J=7.1 Hz, 2H), 4.06-4.17 (m, 2H), 4.31-4.41 (m, 2H), 6.55 (d, J=8.5 Hz, 2H), 7.09 (dd, J=8.8, 2.1 Hz, 1H), 7.20 (d, J=8.5 Hz, 2H), 7.26 (d, J=8.8 Hz, 1H), 7.39-7.50 (m, 1H), 7.71 (d, J=2.1 Hz, 1H).

(7) 3-[{[4-({[5-(acetylamino)-3-methyl-1-benzofuran-2-yl](cyclohexyl)methyl}amino)phenyl]carbonyl}(methyl)amino]-propanoic acid To a mixture of ethyl 3-[{[4-({[5-(acetylamino)-1-benzofuran-2-yl](cyclohexyl)methyl}amino)phenyl]carbonyl}(methyl)amino]-propanoate (366 mg) synthesized above, tetrahydrofuran (5 mL) and ethanol (5 mL) was added 1N lithium hydroxide aqueous solution (1.00 mL), and the mixture was stirred at room temperature for 1 hr. 1N Lithium hydroxide aqueous solution (1.00 mL) was additionally added, and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (292 mg, 84%) as a white solid.

¹H NMR (300 MHz, CDCl₃) δ ppm 0.93-1.37 (m, 5H), 1.45-1.57 (m, 1H), 1.60-1.99 (m, 4H), 2.04-2.25 (m, 7H), 2.44-2.68 (m, 2H), 2.99 (s, 3H), 3.45-3.73 (m, 2H), 4.35 (d, J=7.9 Hz, 1H), 6.54 (d, J=8.7 Hz, 2H), 7.03-7.11 (m, 1H), 7.12-7.28 (m, 3H), 7.57-7.68 (m, 2H).

Example A111

3-[({4-[(cyclohexyl{3-methyl-5-[(methylsulfonyl)amino]-1-benzofuran-2-yl}methyl)amino]phenyl}carbonyl)(methyl)amino]propanoic acid

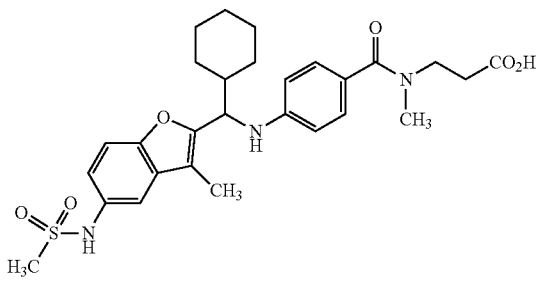 [SMILES: Cc1c(C(Nc2ccc(C(=O)N(C)CCC(=O)O)cc2)C2CCCCC2)oc2ccc(NS(C)(=O)=O)cc12]

To a solution (10 mL) of ethyl 3-{[(4-{[(5-amino-3-methyl-1-benzofuran-2-yl)(cyclohexyl)methyl]amino}phenyl)carbonyl](methyl)amino}-propanoate (412 mg) synthesized in Example A110(5) in N,N-dimethylacetamide were added triethylamine (160 μL) and methanesulfonyl chloride (89.0 μL), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (60% ethyl acetate/hexane) to give a yellow oil. To a mixture of the obtained oil, tetrahydrofuran (5 mL), ethanol (5 mL) and water (1 mL) was added 4N lithium hydroxide aqueous solution (500 μL), and the mixture was stirred at room temperature for 4 hr, and concentrated under reduced pressure. The residue was dissolved in water (10 mL), and 1N hydrochloric acid (2.00 mL) was added at 0° C. The resulting precipitate was collected by filtration to give the title object compound (379 mg, 91%) as a white solid.

¹H NMR (300 MHz, CDCl₃) δ ppm 0.92-1.39 (m, 5H), 1.45-1.57 (m, 1H), 1.62-1.98 (m, 4H), 2.06-2.15 (m, 1H), 2.22 (s, 3H), 2.64 (t, J=6.2 Hz, 2H), 2.93 (s, 3H), 3.03 (s, 3H), 3.68 (t, J=6.2 Hz, 2H), 4.37 (d, J=8.0 Hz, 1H), 6.55 (d, J=8.7 Hz, 2H), 6.65-6.71 (m, 1H), 7.06 (dd, J=8.6, 2.2 Hz, 1H), 7.23 (d, J=8.7 Hz, 2H), 7.31 (d, J=8.6 Hz, 1H), 7.34 (d, J=2.2 Hz, 1H).

Example A112

3-{[(4-{[cyclohexyl(3-methylfuro[3,2-b]pyridin-2-yl)methyl]amino}phenyl)carbonyl]amino}propanoic acid

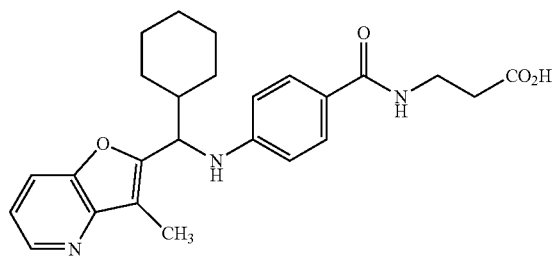 [SMILES: Cc1c(C(Nc2ccc(C(=O)NCCC(=O)O)cc2)C2CCCCC2)oc2cccnc12]

(1) cyclohexyl(3-methylfuro[3,2-b]pyridin-2-yl)methanone

To a mixture of 1-(3-hydroxypyridin-2-yl)ethanone (4.37 g), 2-bromo-1-cyclohexylethanone (9.82 g) synthesized in Example A51(1) and N,N-dimethylformamide (50 mL) was added potassium carbonate (13.2 g), and the mixture was stirred at room temperature for 2.5 days. 1N Hydrochloric acid was added to quench the reaction, and the mixture was extracted with ethyl acetate. The extract was washed with saturated brine, dried over magnesium sulfate, and concentrated under reduced pressure. The residue was purified by silica gel column chromatography (20% ethyl acetate/hexane) to give the title object compound (4.09 g, 53%) as a brown solid.

¹H NMR (300 MHz, CDCl₃) δ ppm 1.19-1.59 (m, 5H), 1.70-1.92 (m, 3H), 1.92-2.03 (m, 2H), 2.69 (s, 3H), 3.26-3.39 (m, 1H), 7.39 (dd, J=8.3, 4.6 Hz, 1H), 7.82 (dd, J=8.3, 1.4 Hz, 1H), 8.65 (dd, J=4.6, 1.4 Hz, 1H).

(2) methyl 4-{[cyclohexyl(3-methylfuro[3,2-b]pyridin-2-yl)methyl]amino}benzoate

To a mixture of cyclohexyl(3-methylfuro[3,2-b]pyridin-2-yl)methanone (1.08 g) synthesized above, methyl 4-aminobenzoate (738 mg), triethylamine (4.95 mL) and methylene chloride (20 mL) was added titanium (IV) chloride (584 μL), and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (1.27 mL) and sodium cyanoborohydride (558 mg), and the mixture was stirred at room temperature for 1 hr. Saturated aqueous sodium hydrogen carbonate solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (50% ethyl acetate/hexane) to give the title object compound (789 mg, 47%) as a pale-brown solid.

$^1$H NMR (300 MHz, CDCl$_3$) δ ppm 0.99-1.38 (m, 5H), 1.42-1.53 (m, 1H), 1.64-2.01 (m, 4H), 2.06-2.16 (m, 1H), 2.77 (s, 3H), 3.81 (s, 3H), 4.50-4.63 (m, 2H), 6.54 (d, J=9.1 Hz, 2H), 7.37 (dd, J=8.2, 5.8 Hz, 1H), 7.81 (d, J=9.1 Hz, 2H), 7.98 (dd, J=8.2, 1.1 Hz, 1H), 8.49 (dd, J=5.8, 1.1 Hz, 1H).

(3) 4-{[cyclohexyl(3-methylfuro[3,2-b]pyridin-2-yl)methyl]amino}benzoic acid To a mixture of methyl 4-{[cyclohexyl(3-methylfuro[3,2-b]pyridin-2-yl)methyl]amino}benzoate (789 mg) synthesized above, tetrahydrofuran (10 mL) and ethanol (10 mL) was added 1N aqueous sodium hydroxide solution (10.0 mL), and the mixture was stirred overnight with heating under reflux, and concentrated under reduced pressure. The residue was dissolved in water (20 mL), and 1N hydrochloric acid (10.0 mL) was added at 0° C. The resulting precipitate was collected by filtration to give the title object compound (718 mg, 94%) as a white solid.

$^1$H NMR (300 MHz, CDCl$_3$) δ ppm 0.96-1.39 (m, 5H), 1.47-1.60 (m, 1H), 1.62-2.02 (m, 4H), 2.03-2.17 (m, 1H), 2.38 (s, 3H), 4.47-4.72 (m, 2H), 6.58 (d, J=8.9 Hz, 2H), 7.18 (dd, J=8.3, 4.9 Hz, 1H), 7.65 (dd, J=8.3, 1.2 Hz, 1H), 7.86 (d, J=8.9 Hz, 2H), 8.51 (dd, J=4.9, 1.2 Hz, 1H).

(4) ethyl 3-{[(4-{[cyclohexyl(3-methylfuro[3,2-b]pyridin-2-yl)methyl]amino}phenyl)carbonyl]amino}propanoate To a mixture of 4-{[cyclohexyl(3-methylfuro[3,2-b]pyridin-2-yl)methyl]amino}benzoic acid (330 mg) synthesized above, β-alanine ethyl ester hydrochloride (209 mg), 1-hydroxybenzotriazole monohydrate (208 mg), triethylamine (379 μL) and N,N-dimethylformamide (10 mL) was added 1-ethyl-3-(3-dimethylaminopropyl)carbodiimide hydrochloride (261 mg), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (70% ethyl acetate/hexane) to give the title object compound (383 mg, 91%) as a pale-brown oil $^1$H NMR (300 MHz, CDCl$_3$) δ ppm 0.96-1.38 (m, 8H), 1.47-1.58 (m, 1H), 1.61-2.00 (m, 4H), 2.05-2.16 (m, 1H), 2.35 (s, 3H), 2.58 (t, J=5.8 Hz, 2H), 3.61-3.69 (m, 2H), 4.13 (q, J=7.1 Hz, 2H), 4.42-4.52 (m, 2H), 6.53-6.65 (m, 3H), 7.13 (dd, J=8.2, 4.7 Hz, 1H), 7.54 (d, J=8.8 Hz, 2H), 7.58-7.62 (m, 1H), 8.45-8.49 (m, 1H).

(5) 3-{[(4-{[cyclohexyl(3-methylfuro[3,2-b]pyridin-2-yl)methyl]amino}phenyl)carbonyl]amino}propanoic acid To a mixture of ethyl 3-{[(4-{[cyclohexyl(3-methylfuro[3,2-b]pyridin-2-yl)methyl]amino}phenyl)carbonyl]amino}propanoate (383 mg) synthesized above, tetrahydrofuran (5 mL) and ethanol (5 mL) was added 1N aqueous sodium hydroxide solution (2.00 mL), and the mixture was stirred overnight at room temperature, and concentrated under reduced pressure. The residue was dissolved in water (10 mL), and 1N hydrochloric acid (2.00 mL) was added at 0° C. The resulting precipitate was collected by filtration to give the title object compound (315 mg, 88%) as a white solid.

$^1$H NMR (300 MHz, CDCl$_3$) δ ppm 0.97-1.38 (m, 5H), 1.44-1.57 (m, 1H), 1.61-2.00 (m, 4H), 2.05-2.18 (m, 1H), 2.35 (s, 3H), 2.64 (t, J=5.7 Hz, 2H), 3.56-3.78 (m, 2H), 4.46 (d, J=8.0 Hz, 1H), 6.55 (d, J=8.7 Hz, 2H), 6.72 (t, J=6.1 Hz, 1H), 7.18 (dd, J=8.3, 4.9 Hz, 1H), 7.54 (d, J=8.7 Hz, 2H), 7.66 (dd, J=8.3, 1.3 Hz, 1H), 8.49 (dd, J=4.9, 1.3 Hz, 1H).

Example A113

3-{[(4-{[cyclohexyl(3-methylfuro[3,2-b]pyridin-2-yl)methyl]amino}phenyl)carbonyl](methyl)amino}propanoic acid

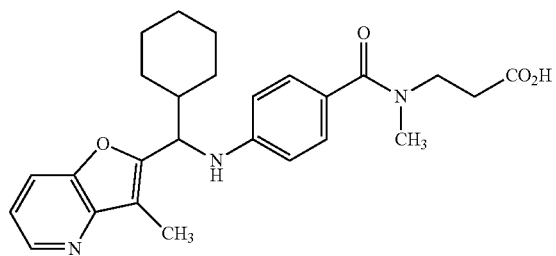

(1) ethyl 3-{[(4-{[cyclohexyl(3-methylfuro[3,2-b]pyridin-2-yl)methyl]amino}phenyl)carbonyl]methyl)amino}propanoate To a mixture of 4-{[cyclohexyl(3-methylfuro[3,2-b]pyridin-2-yl)methyl]amino}benzoic acid (330 mg) synthesized in Example A112(3), ethyl 3-(methylamino)propanoate (178 mg), 1-hydroxybenzotriazole monohydrate (208 mg), triethylamine (379 μL) and N,N-dimethylformamide (10 mL) was added 1-ethyl-3-(3-dimethylaminopropyl)carbodiimide hydrochloride (261 mg), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (80% ethyl acetate/hexane) to give the title object compound (292 mg, 67%) as a pale-brown oil $^1$H NMR (300 MHz, CDCl$_3$) δ ppm 0.97-1.38 (m, 8H), 1.47-1.58 (m, 1H), 1.61-2.00 (m, 4H), 2.05-2.16 (m, 1H), 2.35 (s, 3H), 2.60 (t, J=6.9 Hz, 2H), 3.00 (s, 3H), 3.69 (t, J=6.9 Hz, 2H), 4.10 (q, J=7.0 Hz, 2H), 4.35 (d, J=8.3 Hz, 1H), 4.45 (t, J=8.3 Hz, 1H), 6.56 (d, J=8.5 Hz, 2H), 7.13 (dd, J=8.2, 4.9 Hz, 1H), 7.20 (d, J=8.5 Hz, 2H), 7.60 (dd, J=8.2, 1.4 Hz, 1H), 8.47 (dd, J=4.9, 1.4 Hz, 1H).

(2) 3-{[(4-{[cyclohexyl(3-methylfuro[3,2-b]pyridin-2-yl)methyl]amino}phenyl)carbonyl]methyl)amino}propanoic acid To a mixture of ethyl 3-{[(4-{[cyclohexyl(3-methylfuro[3,2-b]pyridin-2-yl)methyl]amino}phenyl)carbonyl](methyl)amino}propanoate (292 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), and the mixture was acidified with acetic acid, and extracted with ethyl acetate. The extract was washed with saturated brine, dried over magnesium sulfate, and concentrated under reduced pressure to give the title object compound (278 mg, quantitative) as a yellow solid.

$^1$H NMR (300 MHz, CDCl$_3$) δ ppm 0.95-1.39 (m, 5H), 1.47-1.58 (m, 1H), 1.61-2.00 (m, 4H), 2.06-2.16 (m, 1H), 2.34 (s, 3H), 2.60-2.73 (m, 2H), 3.03 (s, 3H), 3.70 (t, J=6.8 Hz, 2H), 4.45 (d, J=8.0 Hz, 1H), 6.56 (d, J=8.5 Hz, 2H), 7.17 (dd, J=8.2, 4.8 Hz, 1H), 7.23 (d, J=8.5 Hz, 2H), 7.65 (dd, J=8.2, 1.3 Hz, 1H), 8.50 (dd, J=4.8, 1.3 Hz, 1H).

Example A114

3-{[(4-{[(5-methoxy-3-methyl-1-benzofuran-2-yl)(phenyl)methyl]amino}phenyl)carbonyl](methyl)amino}-propanoic acid

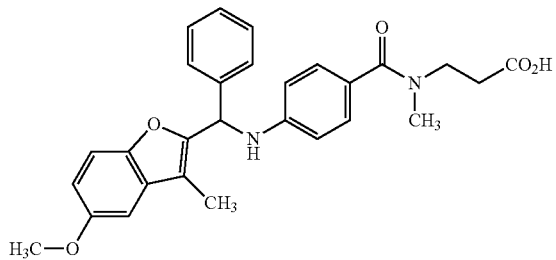 [SMILES: COc1ccc2oc(C(Nc3ccc(C(=O)N(C)CCC(=O)O)cc3)c3ccccc3)c(C)c2c1]

(1) (5-methoxy-3-methyl-1-benzofuran-2-yl)(phenyl)methanone

To a mixture of 5-methoxy-3-methyl-1-benzofuran (2.00 g) synthesized in Example A104(2), benzoyl chloride (1.68 mL) and nitromethane (20 mL) was added aluminum chloride (3.28 g), and the mixture was stirred at room temperature for 2 hr. Water was added to quench the reaction, and the reaction mixture was extracted with ethyl acetate. The extract was washed with saturated brine, dried over magnesium sulfate, and concentrated under reduced pressure. The residue was purified by silica gel column chromatography (30% ethyl acetate/hexane) and further by silica gel column chromatography (20% ethyl acetate/hexane) to give the title object compound (2.03 g, 62%) as a yellow oil.

$^1$H NMR (300 MHz, CDCl$_3$) δ ppm 2.62 (s, 3H), 3.89 (s, 3H), 7.05 (d, J=2.5 Hz, 1H), 7.10 (dd, J=9.1, 2.5 Hz, 1H), 7.42 (d, J=9.1 Hz, 1H), 7.47-7.63 (m, 3H), 8.04-8.09 (m, 2H).

(2) methyl 4-{[(5-methoxy-3-methyl-1-benzofuran-2-yl)(phenyl)methyl]amino}benzoate To a mixture of (5-methoxy-3-methyl-1-benzofuran-2-yl)(phenyl)methanone (2.03 g) synthesized above, methyl 4-aminobenzoate (1.27 g), triethylamine (8.50 mL) and methylene chloride (30 mL) was added titanium (IV) chloride (1.00 mL), and the mixture was stirred under argon atmosphere overnight at room temperature. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (30 mL) of the obtained oil in tetrahydrofuran were added acetic acid (2.18 mL) and sodium cyanoborohydride (955 mg), and the mixture was stirred at room temperature for 2.5 hr. Saturated aqueous sodium hydrogen carbonate solution was added to quench the reaction, the organic solvent was evaporated in an evaporator, and the residue was extracted with ethyl acetate. The extract was washed with saturated brine, dried over magnesium sulfate, and concentrated under reduced pressure. The residue was purified by silica gel column chromatography (30% ethyl acetate/hexane) to give the title object compound (2.36 g, 77%) as a brown solid.

$^1$H NMR (300 MHz, CDCl$_3$) δ ppm 2.26 (s, 3H), 3.82 (s, 3H), 3.84 (s, 3H), 4.98 (d, J=6.0 Hz, 1H), 5.82 (d, J=6.0 Hz, 1H), 6.60 (d, J=8.7 Hz, 2H), 6.84 (dd, J=8.8, 2.6 Hz, 1H), 6.90 (d, J=2.6 Hz, 1H), 7.23-7.37 (m, 4H), 7.39-7.44 (m, 2H), 7.82 (d, J=8.7 Hz, 2H).

(3) 4-{[(5-methoxy-3-methyl-1-benzofuran-2-yl)(phenyl)methyl]amino}benzoic acid

To a mixture of methyl 4-{[(5-methoxy-3-methyl-1-benzofuran-2-yl)(phenyl)methyl]amino}benzoate (2.36 g) synthesized above, tetrahydrofuran (20 mL) and ethanol (20 mL) was added 1N aqueous sodium hydroxide solution (20.0 mL), and the mixture was stirred overnight with heating under reflux, and concentrated under reduced pressure. The residue was dissolved in water (40 mL), and 1N hydrochloric acid (20.0 mL) was added at 0° C. The resulting precipitate was collected by filtration and the obtained solid was dissolved in ethyl acetate. The solution was washed with saturated brine, dried over magnesium sulfate, and concentrated under reduced pressure to give the title object compound (1.09 g, 48%) as a pale-red solid.

$^1$H NMR (300 MHz, CDCl$_3$) δ ppm 2.27 (s, 3H), 3.84 (s, 3H), 5.00-5.11 (m, 1H), 5.84 (br s, 1H), 6.61 (d, J=8.8 Hz, 2H), 6.81-6.88 (m, 1H), 6.91 (d, J=2.7 Hz, 1H), 7.24-7.38 (m, 4H), 7.39-7.45 (m, 2H), 7.88 (d, J=8.8 Hz, 2H).

(4) ethyl 3-{[(4-{[(5-methoxy-3-methyl-1-benzofuran-2-yl)(phenyl)methyl]amino}phenyl)carbonyl](methyl)amino}-propanoate To a mixture of 4-{[(5-methoxy-3-methyl-1-benzofuran-2-yl)(phenyl)methyl]amino}benzoic acid (400 mg) synthesized above, ethyl 3-(methylamino)propanoate (203 mg), 1-hydroxybenzotriazole monohydrate (237 mg), triethylamine (431 μL) and N,N-dimethylformamide (10 mL) was added 1-ethyl-3-(3-dimethylaminopropyl)carbodiimide hydrochloride (297 mg), and the mixture was stirred overnight at room temperature. Water was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (486 mg, 94%) as a pale-brown oil $^1$H NMR (300 MHz, CDCl$_3$) δ ppm 1.24 (t, J=7.1 Hz, 3H), 2.26 (s, 3H), 2.56-2.67 (m, 2H), 3.02 (s, 3H), 3.71 (t, J=7.1 Hz, 2H), 3.84 (s, 3H), 4.12 (q, J=7.1 Hz, 2H), 4.76 (d, J=6.0 Hz, 1H), 5.77 (d, J=6.0 Hz, 1H), 6.60 (d, J=8.5 Hz, 2H), 6.84 (dd, J=8.9, 2.6 Hz, 1H), 6.90 (d, J=2.6 Hz, 1H), 7.20-7.37 (m, 6H), 7.39-7.45 (m, 2H).

(5) 3-{[(4-{[(5-methoxy-3-methyl-1-benzofuran-2-yl)(phenyl)methyl]amino}phenyl)carbonyl](methyl)amino}-propanoic acid To a mixture of ethyl 3-{[(4-{[(5-methoxy-3-methyl-1-benzofuran-2-yl)(phenyl)methyl]amino}phenyl)carbonyl]

methyl)amino}-propanoate (486 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration to give the title object compound (412 mg, 90%) as a white solid.

$^1$H NMR (300 MHz, CDCl$_3$) δ ppm 2.26 (s, 3H), 2.68 (t, J=6.4 Hz, 2H), 3.05 (s, 3H), 3.72 (t, J=6.4 Hz, 2H), 3.84 (s, 3H), 5.78 (s, 1H), 6.60 (d, J=8.7 Hz, 2H), 6.84 (dd, J=8.9, 2.5 Hz, 1H), 6.91 (d, J=2.5 Hz, 1H), 7.23-7.39 (m, 6H), 7.39-7.47 (m, 2H).

Example A115

3-[({4-[(cyclohexyl{5-[(ethylcarbamoyl)amino]-3-methyl-1-benzofuran-2-yl}methyl)amino]phenyl}carbonyl)(methyl)amino]propanoic acid

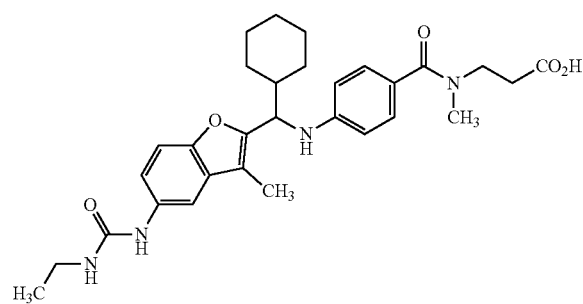 [SMILES: CCNC(=O)Nc1ccc2oc(C(Nc3ccc(C(=O)N(C)CCC(=O)O)cc3)C3CCCCC3)c(C)c2c1]

(1) ethyl 3-[({4-[(cyclohexyl{5-[(ethylcarbamoyl)amino]-3-methyl-1-benzofuran-2-yl}methyl)amino]phenyl}carbonyl)(methyl)amino]propanoate To a solution (10 mL) of ethyl 3-{[(4-{[(5-amino-3-methyl-1-benzofuran-2-yl)(cyclohexyl)methyl]amino}phenyl)carbonyl](methyl)amino}-propanoate (280 mg) synthesized in Example A110(5) in tetrahydrofuran were added triethylamine (95 μL) and ethyl isocyanate (54 μL), and the mixture was stirred at room temperature for 1 day. Triethylamine (95 μL) and ethyl isocyanate (54 μL) were additionally added, and the mixture was stirred overnight at room temperature. The reaction mixture was concentrated under reduced pressure, and the residue was purified by silica gel column chromatography (60-100% ethyl acetate/hexane) to give the title object compound (304 mg, 95%) as a colorless oil.

$^1$H NMR (300 MHz, CDCl$_3$) δ ppm 0.93-1.37 (m, 11H), 1.44-1.57 (m, 1H), 1.59-1.96 (m, 4H), 2.04-2.15 (m, 1H), 2.19 (s, 3H), 2.56-2.66 (m, 2H), 3.02 (s, 3H), 3.14-3.28 (m, 2H), 3.71 (t, J=7.0 Hz, 2H), 4.11 (q, J=7.1 Hz, 2H), 4.29-4.45 (m, 2H), 6.55 (d, J=8.8 Hz, 2H), 6.72-6.83 (m, 1H), 7.15-7.23 (m, 3H), 7.43-7.48 (m, 1H).

(2) 3-[({4-[(cyclohexyl{5-[(ethylcarbamoyl)amino]-3-methyl-1-benzofuran-2-yl}methyl)amino]phenyl}carbonyl)(methyl)amino]propanoic acid To a mixture of ethyl 3-[({4-[(cyclohexyl{5-[(ethylcarbamoyl)amino]-3-methyl-1-benzofuran-2-yl}methyl)amino]phenyl}carbonyl)(methyl)amino]propanoate (304 mg) synthesized above, tetrahydrofuran (5 mL) and ethanol (5 mL) was added 1N lithium hydroxide aqueous solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (258 mg, 89%) as a white solid.

$^1$H NMR (300 MHz, CDCl$_3$) δ ppm 0.93-1.39 (m, 8H), 1.45-1.57 (m, 1H), 1.61-1.98 (m, 4H), 2.06-2.20 (m, 4H), 2.47-2.65 (m, 2H), 2.99 (s, 3H), 3.12-3.25 (m, 2H), 3.52-3.70 (m, 2H), 4.34 (d, J=8.1 Hz, 1H), 4.94-5.06 (m, 1H), 6.53 (d, J=8.7 Hz, 2H), 6.88 (dd, J=8.7, 2.0 Hz, 1H), 7.14-7.24 (m, 3H), 7.35 (d, J=2.0 Hz, 1H).

Example A116

3-{[(4-{[cyclohexyl(6-methoxy-1-methyl-1H-benzimidazol-2-yl)methyl]amino}phenyl)carbonyl]amino}propanoic acid

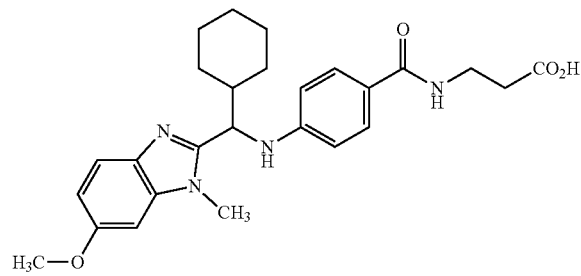 [SMILES: COc1ccc2nc(C(Nc3ccc(C(=O)NCCC(=O)O)cc3)C3CCCCC3)n(C)c2c1]

(1) 5-methoxy-N-methyl-2-nitroaniline

A mixture of formic acid (7.64 g) and acetic anhydride (16.9 g) was stirred at 60° C. for 2 hr then a solution (100 mL) of 5-methoxy-2-nitroaniline (9.30 g) in tetrahydrofuran was added dropwise, and the mixture was stirred overnight at room temperature. The reaction mixture was concentrated under reduced pressure, and the residue was dissolved in ethyl acetate. The solution was washed with saturated aqueous sodium hydrogen carbonate solution and saturated brine, dried over sodium sulfate, and concentrated under reduced pressure. To a solution (200 mL) of the residue in tetrahydrofuran was added a 1.0M solution (140 mL) of borane-tetrahydrofuran complex in tetrahydrofuran at 0° C., and the mixture was stirred with heating under reflux for 2 hr. Methanol was added to the reaction mixture at 0° C., and the mixture was stirred at room temperature for 30 min. After stirring, 1N hydrochloric acid was added to adjust to pH=2. The reaction mixture was stirred with heating under reflux for 1 hr, and concentrated under reduced pressure, and the residue was dissolved in ethyl acetate. The solution was washed with water and saturated brine, dried over sodium sulfate, and concentrated under reduced pressure to give the title object compound (6.30 g, 62%) as a colorless oil.

$^1$H NMR (300 MHz, CDCl$_3$) δ ppm 3.01 (d, J=5.1 Hz, 3H), 3.88 (s, 3H), 6.12 (d, J=2.7 Hz, 1H), 6.24 (dd, J=9.6, 2.4 Hz, 1H), 8.14 (d, J=9.6 Hz, 1H), 8.29 (br, 1H).

(2) 6-methoxy-1-methyl-1H-benzoimidazole

To a solution (200 mL) of 5-methoxy-N-methyl-2-nitroaniline (6.30 g) synthesized above in methanol was added 10% palladium/carbon (1.00 g) and the mixture was stirred under hydrogen atmosphere overnight at room temperature. Palladium/carbon was filtered off, and the filtrate was concentrated. A solution (150 mL) of the residue in formic acid was stirred overnight with heating under reflux, and concentrated under reduced pressure. The residue was purified by silica gel column chromatography (25% ethyl acetate/petroleum ether) to give the title object compound (4.07 g, 60%) as a white solid.

$^1$H NMR (300 MHz, CDCl$_3$) δ ppm 3.78 (s, 3H), 3.87 (s, 3H), 6.81 (d, J=2.4 Hz, 1H), 6.91 (dd, J=8.7, 2.4 Hz, 1H), 7.66 (d, J=9.0 Hz, 1H), 7.75 (s, 1H).

(3) N-methoxy-N-methylcyclohexanecarboxamide

A mixture of cyclohexanecarboxylic acid (6.10 g), N,O-dimethylhydroxyamine hydrochloride (7.31 g), 1-ethyl-3-(3-dimethylaminopropyl)carbodiimide hydrochloride (14.4 g), N,N-diisopropylethylamine (9.68 g), 4-dimethylaminopyridine (600 mg) and methylene chloride (150 mL) was stirred overnight at room temperature. water was added to quench the reaction, and the reaction mixture was extracted with methylene chloride. The extract was washed with saturated brine, dried over sodium sulfate, and concentrated under reduced pressure to give the title object compound (7.57 g, 88%).

$^1$H NMR (300 MHz, CDCl$_3$) δ ppm 1.21-1.30 (m, 3H), 1.42-1.50 (m, 2H), 1.64-1.80 (m, 5H), 2.65 (m, 1H), 3.14 (s, 3H), 3.66 (s, 3H).

(4) cyclohexyl(6-methoxy-1-methyl-1H-benzimidazol-2-yl)methanone

To a solution (100 mL) of 6-methoxy-1-methyl-1H-benzoimidazole (4.07 g) synthesized in the above-mentioned (2) in tetrahydrofuran was added a 1.6M solution (30.1 mL) of n-butyllithium in hexane at −78° C., and the mixture was stirred under nitrogen atmosphere for 30 min. A solution (50 mL) of N-methoxy-N-methylcyclohexanecarboxamide (5.15 g) synthesized in the above-mentioned (3) in tetrahydrofuran was added, and the mixture was stirred at −78° C. for 1 hr and at room temperature for 2 hr. Saturated aqueous ammonium chloride solution was added to quench the reaction, and the reaction mixture was extracted with ethyl acetate. The extract was washed with saturated brine, dried over sodium sulfate, and concentrated under reduced pressure. The residue was purified by silica gel column chromatography (ethyl acetate/petroleum ether=1:5, volume ratio) to give the title object compound (5.80 g, 85%) as white crystals.

$^1$H NMR (300 MHz, CDCl$_3$) δ ppm 1.23-1.33 (m, 1H), 1.45-1.52 (m, 4H), 1.64-1.72 (m, 1H), 1.78-1.86 (m, 2H), 1.96-2.01 (m, 2H), 3.82-3.90 (m, 1H), 3.91 (s, 3H), 4.09 (s, 3H), 6.77 (d, J=2.4 Hz, 1H), 7.00 (dd, J=9.0, 2.4 Hz, 1H), 7.76 (dd, J=9.0, 2.4 Hz, 1H).

(5) methyl 4-{[cyclohexyl(6-methoxy-1-methyl-1H-benzimidazol-2-yl)methyl]amino}benzoate To a mixture of cyclohexyl(6-methoxy-1-methyl-1H-benzimidazol-2-yl)methanone (1.00 g) synthesized above, methyl 4-aminobenzoate (611 mg), triethylamine (4.10 mL) and methylene chloride (20 mL) was added titanium (IV) chloride (482 μL), and the mixture was stirred under argon atmosphere overnight at room temperature. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown solid. To a solution (20 mL) of the obtained solid in tetrahydrofuran were added acetic acid (1.05 mL) and sodium cyanoborohydride (461 mg), and the mixture was stirred at room temperature for 1 hr. Saturated aqueous sodium hydrogen carbonate solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (625 mg, 42%) as a pale-brown solid.

$^1$H NMR (300 MHz, CDCl$_3$) δ ppm 1.02-1.34 (m, 5H), 1.46-1.58 (m, 1H), 1.59-1.84 (m, 4H), 1.95-2.11 (m, 1H), 3.77 (s, 3H), 3.82 (s, 3H), 3.86 (s, 3H), 4.59 (t, J=8.0 Hz, 1H), 5.04 (d, J=8.0 Hz, 1H), 6.63 (d, J=8.8 Hz, 2H), 6.76 (d, J=2.4 Hz, 1H), 6.88 (dd, J=8.7, 2.4 Hz, 1H), 7.59 (d, J=8.7 Hz, 1H), 7.80 (d, J=8.8 Hz, 2H).

(6) 4-{[cyclohexyl(6-methoxy-1-methyl-1H-benzimidazol-2-yl)methyl]amino}benzoic acid To a mixture of methyl 4-{[cyclohexyl(6-methoxy-1-methyl-1H-benzimidazol-2-yl)methyl]amino}benzoate (625 mg) synthesized above, tetrahydrofuran (10 mL) and ethanol (10 mL) was added 1N aqueous sodium hydroxide solution (5.00 mL), and the mixture was stirred overnight with heating under reflux, and concentrated under reduced pressure. The residue was dissolved in water (20 mL), and 1N hydrochloric acid (5.00 mL) was added at 0° C. The resulting precipitate was collected by filtration to give the title object compound (600 mg, quantitative) as a pale-brown solid.

$^1$H NMR (300 MHz, CDCl$_3$) δ ppm 1.01-1.36 (m, 5H), 1.40-1.53 (m, 1H), 1.56-1.86 (m, 3H), 1.98-2.19 (m, 2H), 3.83 (s, 3H), 3.87 (s, 3H), 4.59-4.69 (m, 1H), 5.82-5.96 (m, 1H), 6.68 (d, J=8.9 Hz, 2H), 6.78 (d, J=2.3 Hz, 1H), 6.91 (dd, J=8.9, 2.3 Hz, 1H), 7.64 (d, J=8.9 Hz, 1H), 7.88 (d, J=8.9 Hz, 2H).

(7) ethyl 3-{[(4-{[cyclohexyl(6-methoxy-1-methyl-1H-benzimidazol-2-yl)methyl]amino}phenyl)carbonyl]amino}propanoate To a mixture of 4-{[cyclohexyl(6-methoxy-1-methyl-1H-benzimidazol-2-yl)methyl]amino}benzoic acid (270 mg) synthesized above, β-alanine ethyl ester hydrochloride (158 mg), 1-hydroxybenzotriazole monohydrate (158 mg), triethylamine (287 μL) and N,N-dimethylformamide (10 mL) was added 1-ethyl-3-(3-dimethylaminopropyl)carbodiimide hydrochloride (198 mg), and the mixture was stirred overnight at room temperature. Saturated aqueous ammonium chloride solution was added to quench the reaction, and the reaction mixture was extracted with ethyl acetate. The extract was washed with 1N hydrochloric acid, saturated aqueous sodium hydrogen carbonate solution and saturated brine, dried over magnesium sulfate, and concentrated under reduced pressure. The residue was purified by silica gel column chromatography (60-100% ethyl acetate/hexane) to give the title object compound (151 mg, 45%) as a pale-yellow oil.

$^1$H NMR (300 MHz, CDCl$_3$) δ ppm 1.03-1.35 (m, 8H), 1.45-1.55 (m, 1H), 1.58-1.85 (m, 3H), 1.94-2.11 (m, 2H), 2.58 (t, J=6.1 Hz, 2H), 3.66 (q, J=6.1 Hz, 2H), 3.76 (s, 3H), 3.86 (s, 3H), 4.14 (q, J=7.1 Hz, 2H), 4.56 (t, J=7.8 Hz, 1H), 4.90 (d, J=7.8 Hz, 1H), 6.58-6.67 (m, 3H), 6.75 (d, J=2.5 Hz, 1H), 6.88 (dd, J=8.8, 2.5 Hz, 1H), 7.55 (d, J=8.8 Hz, 2H), 7.58 (d, J=8.8 Hz, 1H).

(8) 3-{[(4-{[cyclohexyl(6-methoxy-1-methyl-1H-benzimidazol-2-yl)methyl]amino}phenyl)carbonyl]amino}propanoic acid To a mixture of ethyl 3-{[(4-{[cyclohexyl(6-methoxy-1-methyl-1H-benzimidazol-2-yl)methyl]amino}phenyl)carbonyl]amino}propanoate (151 mg) synthesized above, tetrahydrofuran (5 mL) and ethanol (5 mL) was added 1N aqueous sodium hydroxide solution (1.00 mL), and the mixture was stirred at room temperature for 2.5 hr, and concentrated under reduced pressure. The residue was dissolved in water (10 mL), and 1N hydrochloric acid (1.00 mL) was added at 0° C. The resulting precipitate was collected by filtration to give the title object compound (124 mg, 87%) as a white solid.
$^1$H NMR (300 MHz, CDCl$_3$) δ ppm 0.96-1.30 (m, 5H), 1.30-1.40 (m, 1H), 1.60-1.70 (m, 2H), 1.71-1.83 (m, 1H), 1.90-2.05 (m, 1H), 2.12-2.23 (m, 1H), 2.71 (t, J=5.4 Hz, 2H), 3.72-3.84 (m, 2H), 3.86 (s, 3H), 3.87 (s, 3H), 4.57-4.66 (m, 1H), 6.74 (d, J=8.9 Hz, 2H), 6.78 (d, J=2.4 Hz, 1H), 6.90 (dd, J=8.9, 2.4 Hz, 1H), 7.24-7.32 (m, 1H), 7.52 (d, J=8.9 Hz, 1H), 7.66 (d, J=8.9 Hz, 2H).

Example A117

3-{[(4-{[cyclohexyl(6-methoxy-1-methyl-1H-benzimidazol-2-yl)methyl]amino}phenyl)carbonyl]methyl)amino}propanoic acid

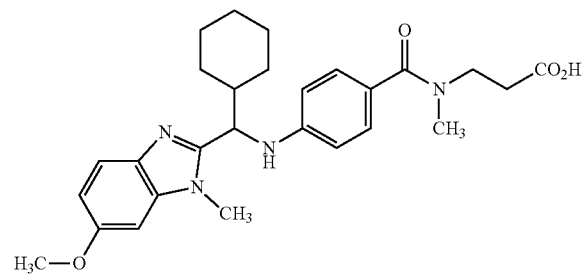 [SMILES: COc1ccc2nc(C(Nc3ccc(C(=O)N(C)CCC(=O)O)cc3)C3CCCCC3)n(C)c2c1]

(1) ethyl 3-{[(4-{[cyclohexyl(6-methoxy-1-methyl-1H-benzimidazol-2-yl)methyl]amino}phenyl)carbonyl]methyl)amino}propanoate To a mixture of 4-{[cyclohexyl(6-methoxy-1-methyl-1H-benzimidazol-2-yl)methyl]amino}benzoic acid (270 mg) synthesized in Example A116(6), ethyl 3-(methylamino)propanoate (135 mg), 1-hydroxybenzotriazole monohydrate (158 mg), triethylamine (287 μL) and N,N-dimethylformamide (10 mL) was added 1-ethyl-3-(3-dimethylaminopropyl)carbodiimide hydrochloride (198 mg), and the mixture was stirred overnight at room temperature. Saturated aqueous ammonium chloride solution was added to quench the reaction, and the reaction mixture was extracted with ethyl acetate. The extract was washed with 1N hydrochloric acid, saturated aqueous sodium hydrogen carbonate solution and saturated brine, dried over magnesium sulfate, and concentrated under reduced pressure. The residue was purified by silica gel column chromatography (60-100% ethyl acetate/hexane) to give the title object compound (103 mg, 30%) as a pale-yellow oil.
$^1$H NMR (300 MHz, CDCl$_3$) δ ppm 1.02-1.33 (m, 8H), 1.45-1.55 (m, 1H), 1.59-1.92 (m, 3H), 1.92-2.13 (m, 2H), 2.61 (t, J=7.0 Hz, 2H), 3.01 (s, 3H), 3.70 (t, J=7.0 Hz, 2H), 3.76 (s, 3H), 3.86 (s, 3H), 4.11 (q, J=7.1 Hz, 2H), 4.49-4.57 (m, 1H), 4.75 (d, J=8.2 Hz, 1H), 6.63 (d, J=8.5 Hz, 2H), 6.76 (d, J=2.4 Hz, 1H), 6.88 (dd, J=8.8, 2.4 Hz, 1H), 7.22 (d, J=8.5 Hz, 2H), 7.59 (d, J=8.8 Hz, 1H).

(2) 3-{[(4-{[cyclohexyl(6-methoxy-1-methyl-1H-benzimidazol-2-yl)methyl]amino}phenyl)carbonyl](methyl)amino}propanoic acid To a mixture of ethyl 3-{[(4-{[cyclohexyl(6-methoxy-1-methyl-1H-benzimidazol-2-yl)methyl]amino}phenyl)carbonyl](methyl)amino}propanoate (103 mg) synthesized above, tetrahydrofuran (5 mL) and ethanol (5 mL) was added 1N aqueous sodium hydroxide solution (1.00 mL), and the mixture was stirred at room temperature for 2 hr, and concentrated under reduced pressure. The residue was dissolved in water (10 mL), and 1N hydrochloric acid (1.00 mL) was added at 0° C. The resulting precipitate was collected by filtration to give the title object compound (72.1 mg, 74%) as a pale-brown solid.
$^1$H NMR (300 MHz, CDCl$_3$) δ ppm 1.00-1.30 (m, 5H), 1.31-1.41 (m, 1H), 1.57-1.81 (m, 3H), 1.88-2.03 (m, 1H), 2.07-2.19 (m, 1H), 2.69-2.81 (m, 2H), 3.10 (s, 3H), 3.73-3.82 (m, 2H), 3.84 (s, 3H), 3.85 (s, 3H), 4.54 (d, J=8.1 Hz, 1H), 6.59 (d, J=8.5 Hz, 2H), 6.77 (d, J=2.4 Hz, 1H), 6.88 (dd, J=8.9, 2.4 Hz, 1H), 7.20-7.28 (m, 2H), 7.54 (d, J=8.9 Hz, 1H).

Example A118

3-{[(4-{[1-(5-methoxy-3-methyl-1-benzofuran-2-yl)heptyl]amino}phenyl)carbonyl]amino}propanoic acid

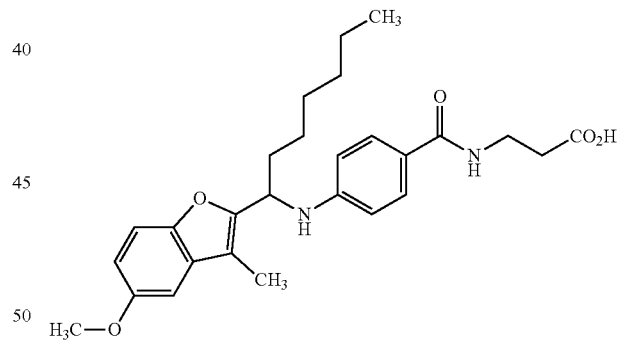

(1) 1-(5-methoxy-3-methyl-1-benzofuran-2-yl)heptan-1-one

To a mixture of 5-methoxy-3-methyl-1-benzofuran (1.87 g) synthesized in Example A104(2), heptanoyl chloride (2.14 mL) and nitromethane (20 mL) was added aluminum chloride (3.07 g), and the mixture was stirred overnight at room temperature. Water was added to quench the reaction, and the reaction mixture was extracted with ethyl acetate. The extract was washed with saturated brine, dried over magnesium sulfate, and concentrated under reduced pressure. The residue was purified by silica gel column chromatography (7% ethyl acetate/hexane) to give the title object compound (2.34 g, 74%) as a pale-yellow solid.

¹H NMR (300 MHz, CDCl₃) δ ppm 0.84-0.95 (m, 3H), 1.24-1.48 (m, 6H), 1.67-1.82 (m, 2H), 2.57 (s, 3H), 2.96 (t, J=7.4 Hz, 2H), 3.87 (s, 3H), 7.00 (d, J=2.6 Hz, 1H), 7.07 (dd, J=9.1, 2.6 Hz, 1H), 7.38 (d, J=9.1 Hz, 1H).

(2) methyl 4-{[1-(5-methoxy-3-methyl-1-benzofuran-2-yl)heptyl]amino}benzoate

To a mixture of 1-(5-methoxy-3-methyl-1-benzofuran-2-yl)heptan-1-one (1.18 g) synthesized above, methyl 4-aminobenzoate (715 mg), triethylamine (4.79 mL) and methylene chloride (20 mL) was added titanium (IV) chloride (566 μL), and the mixture was stirred under argon atmosphere overnight at room temperature. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (1.23 mL) and sodium cyanoborohydride (540 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-20% ethyl acetate/hexane) to give the title object compound (1.17 g, 66%) as a pale-brown oil ¹H NMR (300 MHz, CDCl₃) δ ppm 0.82-0.88 (m, 3H), 1.18-1.40 (m, 8H), 1.88-2.03 (m, 2H), 2.24 (s, 3H), 3.81 (s, 3H), 3.83 (s, 3H), 4.51 (d, J=7.7 Hz, 1H), 4.58-4.68 (m, 1H), 6.56 (d, J=8.8 Hz, 2H), 6.82 (dd, J=8.8, 2.5 Hz, 1H), 6.87 (d, J=2.5 Hz, 1H), 7.25 (d, J=8.8 Hz, 1H), 7.80 (d, J=8.8 Hz, 2H).

(3) 4-{[1-(5-methoxy-3-methyl-1-benzofuran-2-yl)heptyl]amino}benzoic acid

To a mixture of methyl 4-{[1-(5-methoxy-3-methyl-1-benzofuran-2-yl)heptyl]amino}benzoate (1.17 g) synthesized above, tetrahydrofuran (20 mL) and ethanol (20 mL) was added 1N aqueous sodium hydroxide solution (20.0 mL), and the mixture was stirred overnight with heating under reflux, and concentrated under reduced pressure. The residue was dissolved is in water (20 mL), and 1N hydrochloric acid (20.0 mL) was added at 0° C. The resulting precipitate was collected by filtration to give the title object compound (1.02 g, 90%) as a pale-brown solid.

¹H NMR (300 MHz, CDCl₃) δ ppm 0.80-0.92 (m, 3H), 1.16-1.44 (m, 8H), 1.90-2.03 (m, 2H), 2.25 (s, 3H), 3.84 (s, 3H), 4.65 (t, J=7.3 Hz, 1H), 6.58 (d, J=8.8 Hz, 2H), 6.84 (dd, J=8.9, 2.5 Hz, 1H), 6.89 (d, J=2.5 Hz, 1H), 7.26 (d, J=8.9 Hz, 1H), 7.87 (d, J=8.8 Hz, 2H).

(4) ethyl 3-{[(4-{[1-(5-methoxy-3-methyl-1-benzofuran-2-yl)heptyl]amino}phenyl)carbonyl]amino}propanoate To a mixture of 4-{[1-(5-methoxy-3-methyl-1-benzofuran-2-yl)heptyl]amino}benzoic acid (300 mg) synthesized above, β-alanine ethyl ester hydrochloride (175 mg), 1-hydroxybenzotriazole monohydrate (175 mg), triethylamine (318 μL) and N,N-dimethylformamide (10 mL) was added 1-ethyl-3-(3-dimethylaminopropyl)carbodiimide hydrochloride (219 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-100% ethyl acetate/hexane) to give the title object compound (320 mg, 85%) as a colorless oil.

¹H NMR (300 MHz, CDCl₃) δ ppm 0.81-0.90 (m, 3H), 1.17-1.44 (m, 11H), 1.89-2.00 (m, 2H), 2.24 (s, 3H), 2.58 (t, J=6.0 Hz, 2H), 3.66 (q, J=6.0 Hz, 2H), 3.83 (s, 3H), 4.14 (q, J=7.1 Hz, 2H), 4.37-4.44 (m, 1H), 4.55-4.66 (m, 1H), 6.53-6.64 (m, 3H), 6.82 (dd, J=8.8, 2.4 Hz, 1H), 6.87 (d, J=2.4 Hz, 1H), 7.24 (d, J=8.8 Hz, 1H), 7.55 (d, J=8.8 Hz, 2H).

(5) 3-{[(4-{[1-(5-methoxy-3-methyl-1-benzofuran-2-yl)heptyl]amino}phenyl)carbonyl]amino}propanoic acid To a mixture of ethyl 3-{[(4-{[1-(5-methoxy-3-methyl-1-benzofuran-2-yl)heptyl]amino}phenyl)carbonyl]amino}propanoate (320 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration to give the title object compound (213 mg, 71%) as a pale-brown solid.

¹H NMR (300 MHz, CDCl₃) δ ppm 0.85 (t, J=6.8 Hz, 3H), 1.16-1.43 (m, 8H), 1.85-2.03 (m, 2H), 2.23 (s, 3H), 2.63 (t, J=5.8 Hz, 2H), 3.59-3.69 (m, 2H), 3.83 (s, 3H), 4.60 (t, J=7.3 Hz, 1H), 6.56 (d, J=8.9 Hz, 2H), 6.64 (t, J=6.1 Hz, 1H), 6.82 (dd, J=8.9, 2.5 Hz, 1H), 6.88 (d, J=2.5 Hz, 1H), 7.23-7.27 (m, 1H), 7.53 (d, J=8.9 Hz, 2H).

Example A119

3-{[(4-{[1-(5-methoxy-3-methyl-1-benzofuran-2-yl)heptyl]amino}phenyl)carbonyl](methyl)amino}propanoic acid

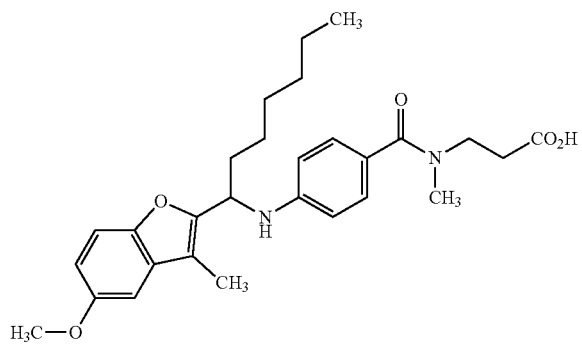

(1) ethyl 3-{[(4-{[1-(5-methoxy-3-methyl-1-benzofuran-2-yl)heptyl]amino}phenyl)carbonyl]methyl)amino}propanoate To a mixture of 4-{[1-(5-methoxy-3-methyl-1-benzofuran-2-yl)heptyl]amino}benzoic acid (300 mg) synthesized in Example A118(3), ethyl 3-(methylamino)propanoate (150 mg), 1-hydroxybenzotriazole monohydrate (175 mg), triethylamine (318 μL) and N,N-dimethylformamide (10 mL) was added 1-ethyl-3-(3-dimethylaminopropyl)carbodiimide hydrochloride (219 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (289 mg, 75%) as a colorless oil.

$^1$H NMR (300 MHz, CDCl$_3$) δ ppm 0.86 (t, J=6.9 Hz, 3H), 1.17-1.45 (m, 11H), 1.88-2.01 (m, 2H), 2.24 (s, 3H), 2.61 (t, J=7.0 Hz, 2H), 3.01 (s, 3H), 3.70 (t, J=7.0 Hz, 2H), 3.84 (s, 3H), 4.11 (q, J=7.1 Hz, 2H), 4.23-4.37 (m, 1H), 4.54-4.63 (m, 1H), 6.56 (d, J=8.8 Hz, 2H), 6.82 (dd, J=8.8, 2.4 Hz, 1H), 6.88 (d, J=2.4 Hz, 1H), 7.22 (d, J=8.8 Hz, 2H), 7.25 (d, J=8.8 Hz, 1H).

(2) 3-{[(4-{[1-(5-methoxy-3-methyl-1-benzofuran-2-yl)heptyl]amino}phenyl)carbonyl](methyl)amino}propanoic acid To a mixture of ethyl 3-{[(4-{[1-(5-methoxy-3-methyl-1-benzofuran-2-yl)heptyl]amino}phenyl)carbonyl](methyl)amino}propanoate (289 mg) synthesized above, tetrahydrofuran (5 mL) and ethanol (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (153 mg, 56%) as a pale-yellow solid.

$^1$H NMR (300 MHz, CDCl$_3$) δ ppm 0.85 (t, J=6.6 Hz, 3H), 1.16-1.44 (m, 8H), 1.86-2.02 (m, 2H), 2.24 (s, 3H), 2.64 (t, J=6.6 Hz, 2H), 3.02 (s, 3H), 3.69 (t, J=6.6 Hz, 2H), 3.84 (s, 3H), 4.59 (t, J=7.3 Hz, 1H), 6.56 (d, J=8.7 Hz, 2H), 6.83 (dd, J=8.8, 2.5 Hz, 1H), 6.89 (d, J=2.5 Hz, 1H), 7.20-7.29 (m, 3H).

Example A120

3-{[(4-{[1-(5-methoxy-3-methyl-1-benzofuran-2-yl)-5-(methylsulfanyl)pentyl]amino}phenyl)carbonyl]amino}propanoic acid

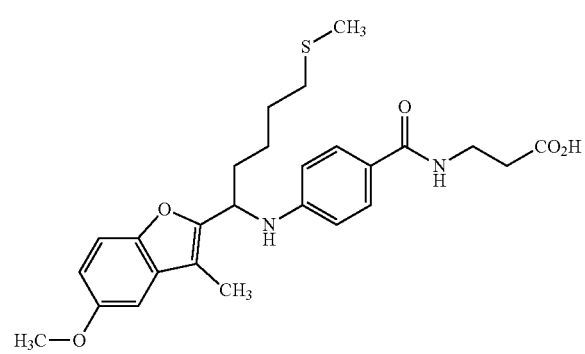 [SMILES: CCCCCCC(Nc1ccc(C(=O)NCCC(=O)O)cc1)c1oc2ccc(OC)cc2c1C]

(1) 5-chloro-1-(5-methoxy-3-methyl-1-benzofuran-2-yl)pentan-1-one

To a mixture of 5-methoxy-3-methyl-1-benzofuran (2.00 g) synthesized in Example A104(2) above, 5-chlorovaleryl chloride (1.74 mL) and nitromethane (40 mL) was added aluminum chloride (2.47 g) at 0° C., and the mixture was stirred for 2 hr. Water was added to quench the reaction, and the reaction mixture was extracted with ethyl acetate. The extract was washed with saturated brine, dried over magnesium sulfate, and concentrated under reduced pressure. The residue was purified by silica gel column chromatography (5% ethyl acetate/hexane) to give the title object compound (2.63 g, 76%) as a pale-yellow solid.

$^1$H NMR (300 MHz, CDCl$_3$) δ ppm 1.83-1.97 (m, 4H), 2.58 (s, 3H), 2.98-3.05 (m, 2H), 3.56-3.63 (m, 2H), 3.87 (s, 3H), 7.00 (d, J=2.7 Hz, 1H), 7.08 (dd, J=9.0, 2.7 Hz, 1H), 7.38 (d, J=9.0 Hz, 1H).

(2) 1-(5-methoxy-3-methyl-1-benzofuran-2-yl)-5-(methylsulfanyl)pentan-1-one

To a mixture of 5-chloro-1-(5-methoxy-3-methyl-1-benzofuran-2-yl)pentan-1-one (1.30 g) synthesized above, methanol (15 mL) and tetrahydrofuran (15 mL) was added a 15% aqueous solution (4.33 mL) of sodium methanethiolate, and the mixture was stirred at room temperature for 1 hr and at 50° C. for 1 hr. Sodium methanethiolate (325 mg) was additionally added and the mixture was stirred at 50° C. for 1 hr. Sodium methanethiolate (325 mg) was additionally added again, and the mixture was stirred at 50° C. for 1 hr. Water was added to quench the reaction, and the reaction mixture was extracted with ethyl acetate. The extract was washed with saturated brine, dried over magnesium sulfate, and concentrated under reduced pressure. The residue was washed with hexane to give the title object compound (492 mg, 36%) as a yellow solid.

$^1$H NMR (300 MHz, CDCl$_3$) δ ppm 1.64-1.79 (m, 2H), 1.79-1.92 (m, 2H), 2.11 (s, 3H), 2.51-2.62 (m, 5H), 3.00 (t, J=7.3 Hz, 2H), 3.87 (s, 3H), 7.00 (d, J=2.5 Hz, 1H), 7.08 (dd, J=9.1, 2.5 Hz, 1H), 7.38 (d, J=9.1 Hz, 1H).

(3) methyl 4-{[1-(5-methoxy-3-methyl-1-benzofuran-2-yl)-5-(methylsulfanyl)pentyl]amino}benzoate To a mixture of 1-(5-methoxy-3-methyl-1-benzofuran-2-yl)-5-(methylsulfanyl)pentan-1-one (658 mg) synthesized above, methyl 4-aminobenzoate (375 mg), triethylamine (2.50 mL) and methylene chloride (10 mL) was added a 1.0M solution (2.70 mL) of titanium (IV) chloride in methylene chloride at 0° C., and the mixture was stirred under argon atmosphere at room temperature for 3.5 days. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a solution (10 mL) of the obtained oil in tetrahydrofuran were added acetic acid (647 μL) and sodium cyanoborohydride (283 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-50% ethyl acetate/hexane) to give the so title object compound (645 mg, 67%) as a brown oil.

$^1$H NMR (300 MHz, CDCl$_3$) δ ppm 1.30-1.71 (m, 4H), 1.91-2.08 (m, 5H), 2.25 (s, 3H), 2.46 (t, J=7.3 Hz, 2H), 3.81 (s, 3H), 3.83 (s, 3H), 4.52 (d, J=8.0 Hz, 1H), 4.59-4.70 (m, 1H), 6.57 (d, J=8.8 Hz, 2H), 6.83 (dd, J=8.7, 2.5 Hz, 1H), 6.87 (d, J=2.5 Hz, 1H), 7.25 (d, J=8.7 Hz, 1H), 7.80 (d, J=8.8 Hz, 2H).

(4) 4-{[1-(5-methoxy-3-methyl-1-benzofuran-2-yl)-5-(methylsulfanyl)pentyl]amino}benzoic acid To a mixture of methyl 4-{[1-(5-methoxy-3-methyl-1-benzofuran-2-yl)-5-(methylsulfanyl)pentyl]amino}benzoate (1.01 g) synthesized above, tetrahydrofuran (10 mL) and ethanol (10 mL) was added 1N aqueous sodium hydroxide solution (10.0 mL), and the mixture was stirred overnight with heating under reflux, and concentrated under reduced pressure. The residue was dissolved in water (20 mL), and 1N hydrochloric acid (10.0 mL) was added at 0° C. The resulting precipitate was collected by filtration to give the title object compound (915 mg, 94%) as a brown solid.

$^1$H NMR (300 MHz, CDCl$_3$) δ ppm 1.29-1.70 (m, 4H), 1.93-2.09 (m, 5H), 2.25 (s, 3H), 2.46 (t, J=7.3 Hz, 2H), 3.83 (s, 3H), 4.65 (t, J=7.3 Hz, 1H), 6.57 (d, J=8.8 Hz, 2H), 6.83 (dd, J=8.8, 2.5 Hz, 1H), 6.88 (d, J=2.5 Hz, 1H), 7.25 (d, J=8.8 Hz, 1H), 7.86 (d, J=8.8 Hz, 2H).

(5) ethyl 3-{[(4-{[1-(5-methoxy-3-methyl-1-benzofuran-2-yl)-5-(methylsulfanyl)pentyl]amino}phenyl)carbonyl]amino}propanoate To a mixture of 4-{[1-(5-methoxy-3-methyl-1-benzofuran-2-yl)-5-(methylsulfanyl)pentyl]amino}benzoic acid (450 mg) synthesized above, β-alanine ethyl ester hydrochloride (252 mg), 1-hydroxybenzotriazole monohydrate (251 mg), triethylamine (456 µL) and N,N-dimethylformamide (10 mL) was added 1-ethyl-3-(3-dimethylaminopropyl)carbodiimide hydrochloride (314 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (518 mg, 93%) as a pale-yellow oil.

$^1$H NMR (300 MHz, CDCl$_3$) δ ppm 1.25 (t, J=7.1 Hz, 3H), 1.31-1.72 (m, 4H), 1.91-2.10 (m, 5H), 2.25 (s, 3H), 2.42-2.50 (m, 2H), 2.59 (t, J=5.8 Hz, 2H), 3.61-3.71 (m, 2H), 3.84 (s, 3H), 4.07-4.19 (m, 2H), 4.38-4.45 (m, 1H), 4.57-4.68 (m, 1H), 6.54-6.66 (m, 3H), 6.83 (dd, J=8.7, 2.5 Hz, 1H), 6.88 (d, J=2.5 Hz, 1H), 7.25 (d, J=8.7 Hz, 1H), 7.56 (d, J=8.8 Hz, 2H).

(6) 3-{[(4-{[1-(5-methoxy-3-methyl-1-benzofuran-2-yl)-5-(methylsulfanyl)pentyl]amino}phenyl)carbonyl]amino}propanoic acid To a mixture of ethyl 3-{[(4-{[1-(5-methoxy-3-methyl-1-benzofuran-2-yl)-5-(methylsulfanyl)pentyl]amino}phenyl)carbonyl]amino}propanoate (253 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration to give the title object compound (133 mg, 56%) as a pale-brown solid.

$^1$H NMR (300 MHz, CDCl$_3$) δ ppm 1.30-1.69 (m, 4H), 1.90-2.04 (m, 2H), 2.05 (s, 3H), 2.24 (s, 3H), 2.41-2.50 (m, 2H), 2.63 (t, J=5.8 Hz, 2H), 3.59-3.69 (m, 2H), 3.83 (s, 3H), 4.62 (t, J=7.3 Hz, 1H), 6.57 (d, J=8.7 Hz, 2H), 6.65 (t, J=5.9 Hz, 1H), 6.83 (dd, J=8.8, 2.5 Hz, 1H), 6.88 (d, J=2.5 Hz, 1H), 7.22-7.28 (m, 1H), 7.54 (d, J=8.7 Hz, 2H).

Example A121

3-{[(4-{[1-(5-methoxy-3-methyl-1-benzofuran-2-yl)-5-(methylsulfanyl)pentyl]amino}phenyl)carbonyl](methyl)amino}-propanoic acid

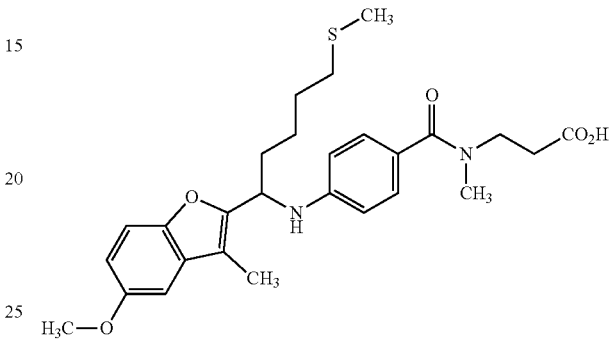

(1) ethyl 3-{[(4-{[1-(5-methoxy-3-methyl-1-benzofuran-2-yl)-5-(methylsulfanyl)pentyl]amino}phenyl)carbonyl](methyl)amino}-propanoate To a mixture of 4-{[1-(5-methoxy-3-methyl-1-benzofuran-2-yl)-5-(methylsulfanyl)pentyl]amino}benzoic acid (460 mg) synthesized in Example A120(4), ethyl 3-(methylamino)propanoate (219 mg), 1-hydroxybenzotriazole monohydrate (256 mg), triethylamine (464 µL) and N,N-dimethylformamide (10 mL) was added 1-ethyl-3-(3-dimethylaminopropyl)carbodiimide hydrochloride (320 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-50% ethyl acetate/hexane) to give the title object compound (514 mg, 88%) as a pale-brown oil $^1$H NMR (300 MHz, CDCl$_3$) δ ppm 1.23 (t, J=7.1 Hz, 3H), 1.30-1.73 (m, 4H), 1.88-2.10 (m, 5H), 2.24 (s, 3H), 2.41-2.50 (m, 2H), 2.55-2.67 (m, 2H), 3.01 (s, 3H), 3.70 (t, J=7.3 Hz, 2H), 3.84 (s, 3H), 4.11 (q, J=7.1 Hz, 2H), 4.27-4.35 (m, 1H), 4.54-4.65 (m, 1H), 6.57 (d, J=8.8 Hz, 2H), 6.83 (dd, J=8.8, 2.6 Hz, 1H), 6.88 (d, J=2.6 Hz, 1H), 7.18-7.30 (m, 3H).

(2) 3-{[(4-{[1-(5-methoxy-3-methyl-1-benzofuran-2-yl)-5-(methylsulfanyl)pentyl]amino}phenyl)carbonyl](methyl)amino}-propanoic acid To a mixture of ethyl 3-{[(4-{[1-(5-methoxy-3-methyl-1-benzofuran-2-yl)-5-(methylsulfanyl)pentyl]amino}phenyl)carbonyl](methyl)amino}-propanoate (251 mg) synthesized above, tetrahydrofuran (5 mL) and ethanol (5 mL) was added 1N aqueous sodium hydroxide solution (1.00 mL), and the mixture was stirred at room temperature for 3 hr, and concentrated under reduced pressure. The residue was dissolved in water (10 mL), and 1N hydrochloric acid (1.00 mL) was added at 0° C. The resulting precipitate was collected by filtration to give the title object compound (74.8 mg, 33%) as a pale-brown solid.

$^1$H NMR (300 MHz, CDCl$_3$) δ ppm 1.30-1.69 (m, 4H), 1.90-2.05 (m, 2H), 2.06 (s, 3H), 2.24 (s, 3H), 2.46 (t, J=6.8 Hz, 2H), 2.66 (t, J=6.6 Hz, 2H), 3.03 (s, 3H), 3.70 (t, J=6.6 Hz, 2H), 3.84 (s, 3H), 4.60 (t, J=7.3 Hz, 1H), 6.57 (d, J=8.9 Hz, 2H), 6.84 (dd, J=8.9, 2.5 Hz, 1H), 6.89 (d, J=2.5 Hz, 1H), 7.21-7.30 (m, 3H).

Example A122

3-{[4-{[1-(5-methoxy-3-methyl-1-benzofuran-2-yl-5-(methylsulfonyl)pentyl]amino}phenyl)carbonyl](methyl)amino}propanoic acid

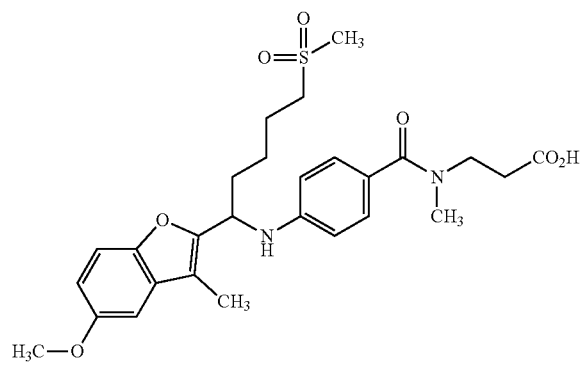 [SMILES: COc1ccc2oc(C(CCCCS(C)(=O)=O)Nc3ccc(C(=O)N(C)CCC(=O)O)cc3)c(C)c2c1]

(1) ethyl 3-{[(4-{[1-(5-methoxy-3-methyl-1-benzo-furan-2-yl)-5-(methylsulfonyl)pentyl]amino}phenyl)carbonyl](methyl)amino}-propanoate To a solution (10 mL) of ethyl 3-{[(4-{[1-(5-methoxy-3-methyl-1-benzofuran-2-yl)-5-(methylsulfanyl)pentyl]amino}phenyl)carbonyl](methyl)amino}-propanoate (263 mg) synthesized in Example A121(1) in acetone was added m-chloroperbenzoic acid (water-containing, purity 69-75%) (344 mg) at 0° C., and the mixture was stirred overnight at room temperature. Saturated aqueous sodium sulfite solution was added to quench the reaction, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane), then by NH silica gel column chromatography (ethyl acetate) to give the title object compound (104 mg, 37%) as a pale-yellow oil.

$^1$H NMR (300 MHz, CDCl$_3$) δ ppm 1.24 (t, J=7.1 Hz, 3H), 1.34-1.69 (m, 2H), 1.76-2.14 (m, 4H), 2.24 (s, 3H), 2.62 (t, J=6.9 Hz, 2H), 2.85 (s, 3H), 2.97 (t, J=8.0 Hz, 2H), 3.02 (s, 3H), 3.71 (t, J=6.9 Hz, 2H), 3.84 (s, 3H), 4.12 (q, J=7.1 Hz, 2H), 4.30 (d, J=8.0 Hz, 1H), 4.57-4.68 (m, 1H), 6.58 (d, J=8.7 Hz, 2H), 6.85 (dd, J=8.7, 2.5 Hz, 1H), 6.89 (d, J=2.5 Hz, 1H), 7.19-7.31 (m, 3H).

(2) 3-{[(4-{[1-(5-methoxy-3-methyl-1-benzofuran-2-yl)-5-(methylsulfonyl)pentyl]amino}phenyl)carbonyl](methyl)amino}-propanoic acid To a mixture of ethyl 3-{[(4-{[1-(5-methoxy-3-methyl-1-benzofuran-2-yl)-5-(methylsulfonyl)pentyl]amino}phenyl)carbonyl]methyl)amino}-propanoate (104 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), and 1N hydrochloric acid (1.00 mL) was added at 0° C. The resulting precipitate was collected by filtration to give the title object compound (52.7 mg, 53%) as a yellow solid.

$^1$H NMR (300 MHz, CDCl$_3$) δ ppm 1.34-1.69 (m, 2H), 1.76-2.13 (m, 4H), 2.23 (s, 3H), 2.66 (t, J=6.4 Hz, 2H), 2.85 (s, 3H), 2.96 (t, J=7.8 Hz, 2H), 3.04 (s, 3H), 3.70 (t, J=6.4 Hz, 2H), 3.84 (s, 3H), 4.59-4.66 (m, 1H), 6.58 (d, J=8.7 Hz, 2H), 6.85 (dd, J=9.1, 2.5 Hz, 1H), 6.89 (d, J=2.5 Hz, 1H), 7.21-7.30 (m, 3H).

Example A123

3-{[(4-{[5-methoxy-1-(5-methoxy-3-methyl-1-benzofuran-2-yl)pentyl]amino}phenyl)carbonyl]amino}propanoic acid

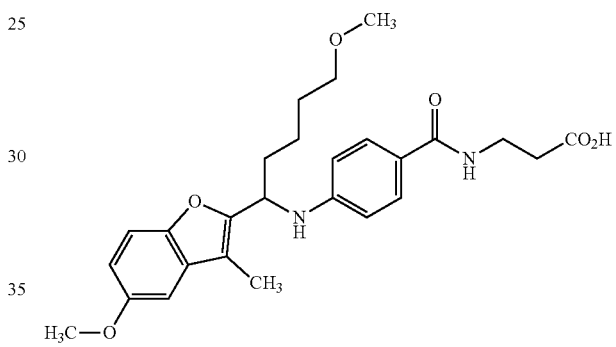

(1) 5-methoxy-1-(5-methoxy-3-methyl-1-benzofuran-2-yl)pentan-1-one

To a solution (20 mL) of 5-chloro-1-(5-methoxy-3-methyl-1-benzofuran-2-yl)pentan-1-one (1.93 g) synthesized in Example A120(1) in methanol were added sodium iodide (1.54 g) and sodium methoxide (1.86 g), and the mixture was stirred overnight with heating under reflux, and concentrated under reduced pressure. Water was added to the residue, and the mixture was extracted with ethyl acetate. The extract was washed with saturated brine, dried over magnesium sulfate, and concentrated under reduced pressure. The residue was purified by silica gel column chromatography (0-20% ethyl acetate/hexane) to give the title object compound (797 mg, 42%) as a white solid.

$^1$H NMR (300 MHz, CDCl$_3$) δ ppm 1.62-1.75 (m, 2H), 1.76-1.89 (m, 2H), 2.58 (s, 3H), 3.00 (t, J=7.3 Hz, 2H), 3.33 (s, 3H), 3.43 (t, J=6.3 Hz, 2H), 3.87 (s, 3H), 7.00 (d, J=2.4 Hz, 1H), 7.07 (dd, J=9.0, 2.4 Hz, 1H), 7.38 (d, J=9.0 Hz, 1H).

(2) methyl 4-{[5-methoxy-1-(5-methoxy-3-methyl-1-benzofuran-2-yl)pentyl]amino}benzoate To a mixture of 5-methoxy-1-(5-methoxy-3-methyl-1-benzofuran-2-yl)pentan-1-one (797 mg) synthesized above, methyl 4-aminobenzoate (479 mg), triethylamine (3.21 mL) and methylene chloride (10 mL) was added a 1.0M solution (3.46 mL) of titanium (IV) chloride in methylene chloride at 0° C., and the mixture was stirred under argon atmosphere at room temperature for 3.5 days. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (10 mL) of the obtained oil in tetrahydrofuran were added acetic acid (824 μL) and sodium cyanoborohydride (362 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (1.07 g, 90%) as a brown oil.

$^1$H NMR (300 MHz, CDCl$_3$) δ ppm 1.27-1.67 (m, 4H), 1.91-2.08 (m, 2H), 2.24 (s, 3H), 3.30 (s, 3H), 3.31-3.37 (m, 2H), 3.81 (s, 3H), 3.83 (s, 3H), 4.51-4.56 (m, 1H), 4.60-4.69 (m, 1H), 6.56 (d, J=8.8 Hz, 2H), 6.83 (dd, J=8.8, 2.5 Hz, 1H), 6.87 (d, J=2.5 Hz, 1H), 7.25 (d, J=8.8 Hz, 1H), 7.80 (d, J=8.8 Hz, 2H).

(3) 4-{[5-methoxy-1-(5-methoxy-3-methyl-1-benzofuran-2-yl)pentyl]amino}benzoic acid To a mixture of methyl 4-{[5-methoxy-1-(5-methoxy-3-methyl-1-benzofuran-2-yl)pentyl]amino}benzoate (1.07 g) synthesized above, tetrahydrofuran (10 mL) and ethanol (10 mL) was added 1N aqueous sodium hydroxide solution (10.0 mL), and the mixture was stirred with heating under reflux for 1 day, and concentrated under reduced pressure. The residue was dissolved in water (10 mL), and 1N hydrochloric acid (10.0 mL) was added at 0° C. The resulting precipitate was collected by filtration to give the title object compound (875 mg, 85%) as a brown solid.

$^1$H NMR (300 MHz, CDCl$_3$) δ ppm 1.26-1.68 (m, 4H), 1.90-2.10 (m, 2H), 2.25 (s, 3H), 3.30 (s, 3H), 3.35 (t, J=6.5 Hz, 2H), 3.84 (s, 3H), 4.66 (t, J=7.3 Hz, 1H), 6.58 (d, J=8.8 Hz, 2H), 6.84 (dd, J=8.9, 2.5 Hz, 1H), 6.89 (d, J=2.5 Hz, 1H), 7.26 (d, J=8.9 Hz, 1H), 7.86 (d, J=8.8 Hz, 2H).

(4) ethyl 3-{[(4-{[5-methoxy-1-(5-methoxy-3-methyl-1-benzofuran-2-yl)pentyl]amino}phenyl)carbonyl]amino}propanoate To a mixture of 4-{[5-methoxy-1-(5-methoxy-3-methyl-1-benzofuran-2-yl)pentyl]amino}benzoic acid (400 mg) synthesized above, β-alanine ethyl ester hydrochloride (234 mg), 1-hydroxybenzotriazole monohydrate (233 mg), triethylamine (422 μL) and N,N-dimethylformamide (10 mL) was added 1-ethyl-3-(3-dimethylaminopropyl)carbodiimide hydrochloride (291 mg), and the mixture was stirred at room temperature for 2.5 days. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (40-80% ethyl acetate/hexane) to give the title object compound (489 mg, 97%) as a pale-brown oil $^1$H NMR (300 MHz, CDCl$_3$) δ ppm 1.25 (t, J=7.1 Hz, 3H), 1.30-1.69 (m, 4H), 1.88-2.08 (m, 2H), 2.24 (s, 3H), 2.55-2.62 (m, 2H), 3.30 (s, 3H), 3.34 (t, J=6.7 Hz, 2H), 3.62-3.70 (m, 2H), 3.83 (s, 3H), 4.14 (q, J=7.1 Hz, 2H), 4.39-4.47 (m, 1H), 4.57-4.68 (m, 1H), 6.54-6.64 (m, 3H), 6.82 (dd, J=8.8, 2.4 Hz, 1H), 6.87 (d, J=2.4 Hz, 1H), 7.24 (d, J=8.8 Hz, 1H), 7.55 (d, J=8.8 Hz, 2H).

(5) 3-{[(4-{[5-methoxy-1-(5-methoxy-3-methyl-1-benzofuran-2-yl)pentyl]amino}phenyl)carbonyl]amino}propanoic acid To a mixture of ethyl 3-{[(4-{[5-methoxy-1-(5-methoxy-3-methyl-1-benzofuran-2-yl)pentyl]amino}phenyl)carbonyl]amino}propanoate (489 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration, and the obtained solid was dissolved in ethyl acetate. The solution was washed with saturated brine, dried over magnesium sulfate, and concentrated under reduced pressure to give the title object compound (453 mg, 98%) as a pale-brown solid.

$^1$H NMR (300 MHz, CDCl$_3$) δ ppm 1.27-1.67 (m, 4H), 1.91-2.03 (m, 2H), 2.23 (s, 3H), 2.63 (t, J=5.7 Hz, 2H), 3.30 (s, 3H), 3.35 (td, J=6.3, 1.2 Hz, 2H), 3.60-3.69 (m, 2H), 3.83 (s, 3H), 4.61 (t, J=7.2 Hz, 1H), 6.56 (d, J=8.8 Hz, 2H), 6.66 (t, J=6.0 Hz, 1H), 6.82 (dd, J=8.9, 2.5 Hz, 1H), 6.87 (d, J=2.5 Hz, 1H), 7.22-7.27 (m, 1H), 7.54 (d, J=8.8 Hz, 2H).

Example A124

3-{[(4-{[5-methoxy-1-(5-methoxy-3-methyl-1-benzofuran-2-yl)pentyl]amino}phenyl)carbonyl](methyl)amino}propanoic acid

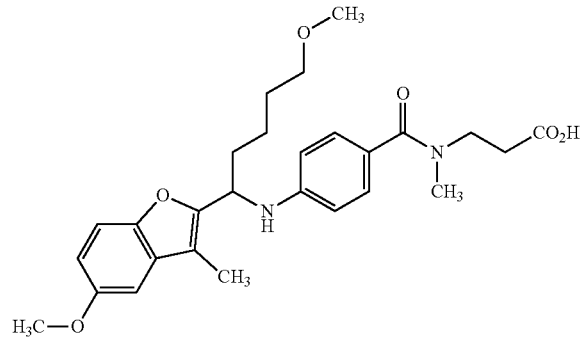 [SMILES: COCCCCC(Nc1ccc(C(=O)N(C)CCC(=O)O)cc1)c1oc2ccc(OC)cc2c1C]

(1) ethyl 3-{[(4-{[5-methoxy-1-(5-methoxy-3-methyl-1-benzofuran-2-yl)pentyl]amino}phenyl)carbonyl](methyl)amino}propanoate To a mixture of 4-{[5-methoxy-1-(5-methoxy-3-methyl-1-benzofuran-2-yl)pentyl]amino}benzoic acid (400 mg) synthesized in Example A123(3), ethyl 3-(methylamino)propanoate (199 mg), 1-hydroxybenzotriazole monohydrate (233 mg), triethylamine (422 μL) and N,N-dimethylformamide (10 mL) was added 1-ethyl-3-(3-dimethylaminopropyl)carbodiimide hydrochloride (291 mg), and the mixture was stirred at room temperature for 2.5 days. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (40-80% ethyl acetate/hexane) to give the title object compound (460 mg, 89%) as a pale-yellow oil.

$^1$H NMR (300 MHz, CDCl$_3$) δ ppm 1.24 (t, J=7.1 Hz, 3H), 1.30-1.67 (m, 4H), 1.88-2.06 (m, 2H), 2.24 (s, 3H), 2.62 (t, J=7.0 Hz, 2H), 3.02 (s, 3H), 3.30 (s, 3H), 3.35 (t, J=6.3 Hz, 2H), 3.71 (t, J=7.0 Hz, 2H), 3.84 (s, 3H), 4.12 (q, J=7.1 Hz, 2H), 4.27-4.36 (m, 1H), 4.55-4.66 (m, 1H), 6.57 (d, J=8.8 Hz, 2H), 6.83 (dd, J=8.8, 2.5 Hz, 1H), 6.88 (d, J=2.5 Hz, 1H), 7.18-7.28 (m, 3H).

(2) 3-{[(4-{[5-methoxy-1-(5-methoxy-3-methyl-1-benzofuran-2-yl)pentyl]amino}phenyl)carbonyl](methyl)amino}propanoic acid To a mixture of ethyl 3-{[(4-{[5-methoxy-1-(5-methoxy-3-methyl-1-benzofuran-2-yl)pentyl]amino}phenyl)carbonyl](methyl)amino}propanoate (460 mg) synthesized above, tetrahydrofuran (5 mL) and ethanol (5 mL) was added 1N aqueous sodium hydroxide solution (2.00 mL), and the mixture was stirred overnight at room temperature, and concentrated under reduced pressure. The residue was dissolved in water (10 mL), and 1N hydrochloric acid (2.00 mL) was added at 0° C. The resulting precipitate was collected by filtration to give the title object compound (428 mg, 99%) as a pale-yellow solid.

$^1$H NMR (300 MHz, CDCl$_3$) δ ppm 1.27-1.67 (m, 4H), 1.88-2.06 (m, 2H), 2.23 (s, 3H), 2.67 (t, J=6.6 Hz, 2H), 3.04 (s, 3H), 3.30 (s, 3H), 3.35 (td, J=6.4, 1.0 Hz, 2H), 3.70 (t, J=6.6 Hz, 2H), 3.84 (s, 3H), 4.61 (t, J=7.2 Hz, 1H), 6.56 (d, J=8.7 Hz, 2H), 6.83 (dd, J=8.8, 2.4 Hz, 1H), 6.88 (d, J=2.4 Hz, 1H), 7.21-7.30 (m, 3H).

Example A125

3-{[(4-{[(5-bromo-3-methylfuro[3,2-b]pyridin-2-yl)(cyclohexyl)methyl]amino}phenyl)carbonyl]amino}propanoic acid

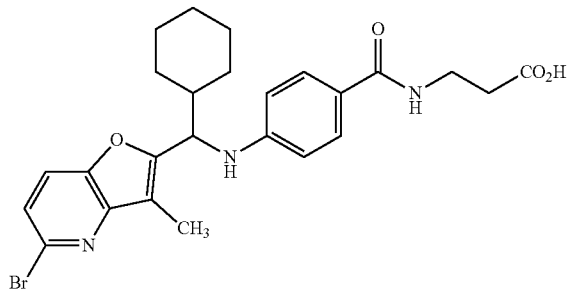

(1) 3-(benzyloxy)-6-bromopyridine-2-carbonitrile

To a mixture of 2-cyano-3-hydroxypyridine (10.0 g), water (40 mL) and acetonitrile (200 mL) was added N-bromosuccinimide (17.8 g) at 0° C., and the mixture was stirred at 0° C. for 2 hr, and at room temperature for 1 hr. Ethyl acetate was added to the reaction mixture. The solution was washed with water and saturated brine, dried over magnesium sulfate, and concentrated under reduced pressure to give a white solid. To a solution (200 mL) of the obtained solid in acetone were added benzyl bromide (11.9 mL) and potassium carbonate (23.1 g), and the mixture was stirred overnight with heating under reflux. Insoluble material was filtered off, and the filtrate was concentrated under reduced pressure. The residue was washed with methanol and toluene to give the title object compound (3.17 g, 13%) as a white solid.

$^1$H NMR (300 MHz, DMSO-d) δ ppm 5.36 (s, 2H), 7.32-7.50 (m, 5H), 7.87 (d, J=9.1 Hz, 1H), 7.96 (d, J=9.1 Hz, 1H).

(2) 1-[3-(benzyloxy)-6-bromopyridin-2-yl]ethanone

To a solution (40 mL) of 3-(benzyloxy)-6-bromopyridine-2-carbonitrile (4.00 g) synthesized above in tetrahydrofuran was added a 1.0M solution (27.6 mL) of methylmagnesium bromide in tetrahydrofuran at 0° C., and the mixture was stirred at room temperature for 5 hr. A 1.0 M solution (13.8 mL) of methylmagnesium bromide in tetrahydrofuran was additionally added, and the mixture was further stirred at room temperature for 1 hr, then 1N hydrochloric acid (80 mL) was added. The mixture was stirred overnight at room temperature, 1N aqueous sodium hydroxide solution (100 mL) was added, and the mixture was extracted with ethyl acetate. The extract was washed with saturated brine, dried over magnesium sulfate, and concentrated under reduced pressure. The residue was purified by silica gel column chromatography (10-90% ethyl acetate/hexane) to give the title object compound (1.45 g, 34%) as a yellow solid.

$^1$H NMR (300 MHz, CDCl$_3$) δ ppm 2.65 (s, 3H), 5.18 (s, 2H), 7.25 (d, J=8.5 Hz, 1H), 7.28-7.46 (m, 5H), 7.48 (d, J=8.5 Hz, 1H).

(3) 1-(6-bromo-3-hydroxypyridin-2-yl)ethanone

To a suspension (30 mL) of aluminum chloride (3.96 g) in toluene was added trimethylammonium chloride (1.32 g), and the mixture was stirred under argon atmosphere at room temperature for 1 hr. A solution (30 mL) of 1-[3-(benzyloxy)-6-bromopyridin-2-yl]ethanone (2.81 g) synthesized above in toluene was added to the mixture, and the mixture was stirred at room temperature for 3 hr. The reaction mixture was concentrated under reduced pressure, saturated aqueous Rochelle salt solution was added to the residue, and the mixture was extracted with ethyl acetate. The extract was washed with saturated brine, dried over magnesium sulfate, and concentrated under reduced pressure. The residue was purified by silica gel column chromatography (0-5% ethyl acetate/hexane) to give the title object compound (1.64 g, 83%) as a yellow solid.

$^1$H NMR (300 MHz, CDCl$_3$) δ ppm 2.74 (s, 3H), 7.23 (d, J=8.8 Hz, 1H), 7.52 (d, J=8.8 Hz, 1H), 11.77 (s, 1H).

(4) (5-bromo-3-methylfuro[3,2-b]pyridin-2-yl)(cyclohexyl)methanone

To a mixture of 1-(6-bromo-3-hydroxypyridin-2-yl)ethanone (1.64 g) synthesized above, 2-bromo-1-cyclohexylethanone (2.34 g) synthesized in Example A51(1) and N,N-dimethylformamide (20 mL) was added potassium carbonate (3.15 g), and the mixture was stirred overnight at room temperature. Saturated aqueous ammonium chloride solution was added to quench the reaction, and the mixture was extracted with ethyl acetate. The extract was washed with saturated brine, dried over magnesium sulfate, and concentrated under reduced pressure. The residue was washed with diisopropyl ether to give the title object compound (865 mg, 35%) as a white solid.

$^1$H NMR (300 MHz, CDCl$_3$) δ ppm 1.19-1.54 (m, 5H), 1.70-1.81 (m, 1H), 1.81-2.00 (m, 4H), 2.63 (s, 3H), 3.23-3.35 (m, 1H), 7.52 (d, J=8.7 Hz, 1H), 7.69 (d, J=8.7 Hz, 1H).

(5) methyl 4-{[(5-bromo-3-methylfuro[3,2-b]pyridin-2-yl)(cyclohexyl)methyl]amino}benzoate To a mixture of (5-bromo-3-methylfuro[3,2-b]pyridin-2-yl)(cyclohexyl)methanone (1.46 g) synthesized above, methyl 4-aminobenzoate (753 mg), triethylamine (5.05 mL) and methylene chloride (15 mL) was added a 1.0M solution (5.44 mL) of titanium (IV) chloride in methylene chloride at 0° C., and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (1.30 mL) and sodium cyanoborohydride (569 mg), and the mixture was stirred at room temperature for 2 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (1.86 g, 90%) as a pale-brown solid.
$^1$H NMR (300 MHz, CDCl$_3$) δ ppm 1.00-1.35 (m, 5H), 1.45-1.55 (m, 1H), 1.63-2.00 (m, 4H), 2.04-2.14 (m, 1H), 2.33 (s, 3H), 3.82 (s, 3H), 4.43-4.54 (m, 2H), 6.55 (d, J=9.0 Hz, 2H), 7.29 (d, J=8.5 Hz, 1H), 7.48 (d, J=8.5 Hz, 1H), 7.80 (d, J=9.0 Hz, 2H).

(6) 4-{[(5-bromo-3-methylfuro[3,2-b]pyridin-2-yl)(cyclohexyl)methyl]amino}benzoic acid To a solution (20 mL) of methyl 4-{[(5-bromo-3-methylfuro[3,2-b]pyridin-2-yl)(cyclohexyl)methyl]amino}benzoate (1.86 g) synthesized above in tetrahydrofuran was added 2N lithium hydroxide aqueous solution (10.2 mL), and the mixture was stirred with heating under reflux for 2 hr. A 4N aqueous lithium hydroxide solution (5.10 mL) was additionally added, and the mixture was stirred with heating under reflux for 4 hr. A 4N aqueous lithium hydroxide solution (5.10 mL) and ethanol (20 mL) were further added, and the mixture was stirred with heating under reflux for 4 hr, and concentrated under reduced pressure. The residue was dissolved in water (40 mL), and 1N hydrochloric acid (61.2 mL) was added at 0° C. The resulting precipitate was collected by filtration to give the title object compound (1.74 g, 96%) as a pale-brown solid.
$^1$H NMR (300 MHz, CDCl$_3$) δ ppm 0.95-1.41 (m, 6H), 1.54-1.81 (m, 3H), 1.87-2.02 (m, 1H), 2.02-2.15 (m, 1H), 2.27 (s, 3H), 4.52-4.62 (m, 1H), 6.63 (d, J=8.7 Hz, 2H), 6.92 (d, J=8.0 Hz, 1H), 7.43 (d, J=8.7 Hz, 1H), 7.61 (d, J=8.7 Hz, 2H), 7.90 (d, J=8.7 Hz, 1H), 12.01 (br s, 1H).

(7) ethyl 3-{[(4-{[(5-bromo-3-methylfuro[3,2-b]pyridin-2-yl)(cyclohexyl)methyl]amino}phenyl)carbonyl]amino}propanoate To a mixture of 4-{[(5-bromo-3-methylfuro[3,2-b]pyridin-2-yl)(cyclohexyl)methyl]amino}benzoic acid (300 mg) synthesized above, β-alanine ethyl ester hydrochloride (157 mg), 1-hydroxybenzotriazole monohydrate (156 mg), triethylamine (283 μL) and N,N-dimethylformamide (10 mL) was added 1-ethyl-3-(3-dimethylaminopropyl)carbodiimide hydrochloride (196 mg) and the mixture was stirred at room temperature for 1.5 days. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (20-60% ethyl acetate/hexane) to give the title object compound (343 mg, 93%) as a pale-yellow oil.
$^1$H NMR (300 MHz, CDCl$_3$) δ ppm 0.95-1.37 (m, 8H), 1.44-1.55 (m, 1H), 1.61-1.98 (m, 4H), 2.02-2.13 (m, 1H), 2.31 (s, 3H), 2.58 (t, J=5.9 Hz, 2H), 3.61-3.70 (m, 2H), 4.13 (q, J=7.1 Hz, 2H), 4.40-4.50 (m, 2H), 6.55 (d, J=8.8 Hz, 2H), 6.63 (t, J=5.9 Hz, 1H), 7.27 (d, J=8.5 Hz, 1H), 7.47 (d, J=8.5 Hz, 1H), 7.54 (d, J=8.8 Hz, 2H).

(8) 3-{[(4-{[(5-bromo-3-methylfuro[3,2-b]pyridin-2-yl)(cyclohexyl)methyl]amino}phenyl)carbonyl]amino}propanoic acid To a mixture of ethyl 3-{[(4-{[(5-bromo-3-methylfuro[3,2-b]pyridin-2-yl)(cyclohexyl)methyl]amino}phenyl)carbonyl]amino}propanoate (343 mg) synthesized above, tetrahydrofuran (5 mL) and ethanol (5 mL) was added 1N lithium hydroxide aqueous solution (1.00 mL), and the mixture was stirred at room temperature for 5 hr, and concentrated under reduced pressure. The residue was dissolved in water (10 mL), and 1N hydrochloric acid (1.00 mL) was added at 0° C. The resulting precipitate was collected by filtration to give the title object compound (307 mg, 94%) as a pale-yellow solid.
$^1$H NMR (300 MHz, DMSO-d$_6$) δ ppm 0.94-1.30 (m, 5H), 1.30-1.42 (m, 1H), 1.53-1.82 (m, 3H), 1.86-2.02 (m, 1H), 2.03-2.15 (m, 1H), 2.26 (s, 3H), 2.41 (t, J=7.1 Hz, 2H), 3.29-3.41 (m, 2H), 4.56 (t, J=8.2 Hz, 1H), 6.60 (d, J=8.9 Hz, 2H), 6.66 (d, J=8.2 Hz, 1H), 7.42 (d, J=8.6 Hz, 1H), 7.52 (d, J=8.9 Hz, 2H), 7.89 (d, J=8.6 Hz, 1H), 8.01 (t, J=5.5 Hz, 1H).

Example A126

3-{[(4-{[(5-bromo-3-methylfuro[3,2-b]pyridin-2-yl)(cyclohexyl)methyl]amino}phenyl)carbonyl](methyl)amino}-propanoic acid

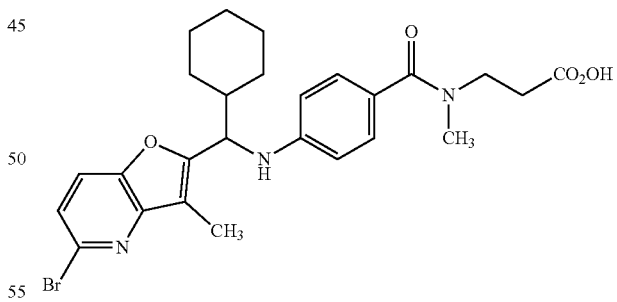

(1) ethyl 3-{[(4-{[(5-bromo-3-methylfuro[3,2-b]pyridin-2-yl)(cyclohexyl)methyl]amino}phenyl)carbonyl](methyl)amino}-propanoate To a mixture of 4-{[(5-bromo-3-methylfuro[3,2-b]pyridin-2-yl)(cyclohexyl)methyl]amino}benzoic acid (300 mg) synthesized in Example A125(6), ethyl 3-(methylamino)propanoate (134 mg), 1-hydroxybenzotriazole monohydrate (156 mg), triethylamine (283 μL) and N,N-dimethylformamide (10 mL) was added 1-ethyl-3-(3-dimethylaminopropyl)

carbodiimide hydrochloride (196 mg), and the mixture was stirred at room temperature for 1.5 days. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (20-60% ethyl acetate/hexane) to give the title object compound (317 mg, 84%) as a pale-yellow oil.

$^1$H NMR (300 MHz, CDCl$_3$) δ ppm 0.94-1.38 (m, 8H), 1.44-1.55 (m, 1H), 1.59-2.00 (m, 4H), 2.02-2.14 (m, 1H), 2.32 (s, 3H), 2.56-2.66 (m, 2H), 3.00 (s, 3H), 3.69 (t, J=7.0 Hz, 2H), 4.06-4.17 (m, 2H), 4.27-4.34 (m, 1H), 4.39-4.46 (m, 1H), 6.53 (d, J=8.7 Hz, 2H), 7.20 (d, J=8.7 Hz, 2H), 7.28 (d, J=8.5 Hz, 1H), 7.48 (d, J=8.5 Hz, 1H).

(2) 3-{[(4-{[(5-bromo-3-methylfuro[3,2-b]pyridin-2-yl)(cyclohexyl)methyl]amino}phenyl)carbonyl](methyl)amino}-propanoic acid To a mixture of ethyl 3-{[(4-{[(5-bromo-3-methylfuro[3,2-b]pyridin-2-yl)(cyclohexyl)methyl]amino}phenyl)carbonyl](methyl)amino}-propanoate (271 mg) synthesized above, tetrahydrofuran (5 mL) and ethanol (5 mL) was added 1N lithium hydroxide aqueous solution (1.00 mL), and the mixture was stirred overnight at room temperature, and concentrated under reduced pressure. The residue was dissolved in water (10 mL), and 1N hydrochloric acid (1.00 mL) was added at 0° C. The resulting precipitate was collected by filtration to give the title object compound (271 mg, 90%) as a pale-yellow solid.

$^1$H NMR (300 MHz, CDCl$_3$) δ ppm 0.95-1.37 (m, 5H), 1.44-1.55 (m, 1H), 1.60-1.97 (m, 4H), 2.03-2.14 (m, 1H), 2.31 (s, 3H), 2.64 (t, J=6.3 Hz, 2H), 3.02 (s, 3H), 3.69 (t, J=6.3 Hz, 2H), 4.43 (d, J=7.9 Hz, 1H), 6.54 (d, J=8.6 Hz, 2H), 7.23 (d, J=8.6 Hz, 2H), 7.29 (d, J=8.6 Hz, 1H), 7.49 (d, J=8.6 Hz, 1H).

Example A127

3-{[(4-{[(5-chloro-3-methylfuro[3,2-b]pyridin-2-yl)(cyclohexyl)methyl]amino}phenyl)carbonyl]amino}propanoic acid

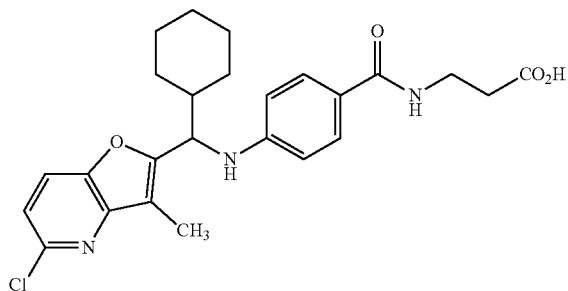 [SMILES: Cc1c(C(Nc2ccc(C(=O)NCCC(=O)O)cc2)C2CCCCC2)oc2ccc(Cl)nc12]

(1) 3-(benzyloxy)-6-chloro-2-iodopyridine

To an aqueous solution (100 mL) of 2-chloro-5-hydroxypyridine (10.0 g) were added sodium carbonate (16.3 g) and iodine (10.8 g), and the mixture was stirred at room temperature for 5 days. The reaction mixture was acidified to pH=5 with 1N hydrochloric acid, and the mixture was extracted with ethyl acetate. The extract was washed with saturated brine, dried over magnesium sulfate, and concentrated under reduced pressure to give a yellow solid. The obtained solid was recrystallized from methanol to give a brown solid. To a solution (200 mL) of the obtained solid in acetone were added benzyl bromide (8.02 mL) and potassium carbonate (15.5 g), and the mixture was stirred overnight with heating under reflux. Insoluble material was filtered off, and the filtrate was concentrated under reduced pressure. The residue was purified by silica gel column chromatography (0-30% ethyl acetate/hexane) to give the title object compound (18.4 g, 69%) as a yellow oil. $^1$H NMR (300 MHz, CDCl$_3$) δ ppm 5.17 (s, 2H), 6.97 (d, J=8.4 Hz, 1H), 7.15 (d, J=8.4 Hz, 1H), 7.30-7.47 (m, 5H).

(2) 1-[3-(benzyloxy)-6-chloropyridin-2-yl]ethanol

To a solution (100 mL) of 3-(benzyloxy)-6-chloro-2-iodopyridine (17.4 g) synthesized above in tetrahydrofuran was added a 1.0 M solution (60.2 mL) of isopropylmagnesium bromide in tetrahydrofuran at −45° C., and the mixture was stirred at the same temperature for 1 hr. Acetaldehyde (10.2 mL) was added to the reaction mixture, and the mixture was stirred at −45° C. for 30 min then at room temperature for 2 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (0-30% ethyl acetate/hexane) to give the title object compound (6.82 g, 52%) as a pale-yellow oil.

$^1$H NMR (300 MHz, CDCl$_3$) δ ppm 1.46 (d, J=6.6 Hz, 3H), 3.95 (d, J=7.7 Hz, 1H), 5.06-5.18 (m, 3H), 7.14 (d, J=8.5 Hz, 1H), 7.17 (d, J=8.5 Hz, 1H), 7.31-7.44 (m, 5H).

(3) 1-[3-(benzyloxy)-6-chloropyridin-2-yl]ethanone

To a mixture of 1-[3-(benzyloxy)-6-chloropyridin-2-yl]ethanol (7.04 g) synthesized above, 4-methylmorpholine N-oxide (6.26 g) and acetonitrile (140 mL) was added tetrapropylammonium perruthenate (938 mg), and the mixture was stirred at room temperature for 3 hr, and concentrated under reduced pressure. The residue was purified by silica gel column chromatography (0-10% ethyl acetate/hexane) to give the title object compound (6.26 g, 90%) as a white solid.

$^1$H NMR (300 MHz, CDCl$_3$) δ ppm 2.66 (s, 3H), 5.19 (s, 2H), 7.27-7.47 (m, 7H).

(4) 1-(6-chloro-3-hydroxypyridin-2-yl)ethanone

To a suspension (80 mL) of aluminum chloride (14.3 g) in toluene was added trimethylammonium chloride (4.75 g), and the mixture was stirred under argon atmosphere at room temperature for 1 hr. To the mixture was added a solution (80 mL) of 1-[3-(benzyloxy)-6-chloropyridin-2-yl]ethanone (8.66 g) synthesized above in toluene, and the mixture was stirred at room temperature for 4 hr. The reaction mixture was concentrated under reduced pressure, saturated aqueous Rochelle salt solution was added to the residue, and the mixture was extracted with ethyl acetate. The extract was washed with saturated brine, dried over magnesium sulfate, and concentrated under reduced pressure. The residue was purified by silica gel column chromatography (0-5% ethyl acetate/hexane) to give the title object compound (4.89 g, 86%) as a pale-yellow solid.

¹H NMR (300 MHz, CDCl₃) δ ppm 2.74 (s, 3H), 7.31 (d, J=8.8 Hz, 1H), 7.39 (d, J=8.8 Hz, 1H), 11.77 (s, 1H).

(5) (5-chloro-3-methylfuro[3,2-b]pyridin-2-yl)(cyclohexyl)methanone

To a mixture of 1-(6-chloro-3-hydroxypyridin-2-yl)ethanone (4.89 g) synthesized above, 2-bromo-1-cyclohexylethanone (7.01 g) synthesized in Example A51(1) and N,N-dimethylformamide (50 mL) was added potassium carbonate (11.8 g), and the mixture was stirred overnight at room temperature. Saturated aqueous ammonium chloride solution was added to quench the reaction, and the mixture was extracted with ethyl acetate. The extract was washed with saturated brine, dried over magnesium sulfate, and concentrated under reduced pressure. The residue was washed with diisopropyl ether to give the title object compound (5.78 g, 73%) as a white solid.

¹H NMR (300 MHz, CDCl₃) δ ppm 1.19-1.61 (m, 5H), 1.70-1.80 (m, 1H), 1.81-2.01 (m, 4H), 2.63 (s, 3H), 3.23-3.35 (m, 1H), 7.39 (d, J=8.7 Hz, 1H), 7.78 (d, J=8.7 Hz, 1H).

(6) methyl 4-{[(5-chloro-3-methylfuro[3,2-b]pyridin-2-yl)(cyclohexyl)methyl]amino}benzoate To a mixture of (5-chloro-3-methylfuro[3,2-b]pyridin-2-yl)(cyclohexyl)methanone (1.00 g) synthesized above, methyl 4-aminobenzoate (599 mg), triethylamine (4.01 mL) and methylene chloride (10 mL) was added a 1.0M solution (4.32 mL) of titanium (IV) chloride in methylene chloride at 0° C., and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (15 mL) of the obtained oil in tetrahydrofuran were added acetic acid (1.03 mL) and sodium cyanoborohydride (452 mg), and the mixture was stirred at room temperature for 2 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (1.31 g, 81%) as an orange solid.

¹H NMR (300 MHz, CDCl₃) δ ppm 0.96-1.37 (m, 5H), 1.45-1.56 (m, 1H), 1.63-1.99 (m, 4H), 2.03-2.14 (m, 1H), 2.32 (s, 3H), 3.81 (s, 3H), 4.43-4.56 (m, 2H), 6.54 (d, J=9.0 Hz, 2H), 7.14 (d, J=8.5 Hz, 1H), 7.56 (d, J=8.5 Hz, 1H), 7.79 (d, J=9.0 Hz, 2H).

(7) 4-{[(5-chloro-3-methylfuro[3,2-b]pyridin-2-yl)(cyclohexyl)methyl]amino}benzoic acid To a mixture of methyl 4-{[(5-chloro-3-methylfuro[3,2-b]pyridin-2-yl)(cyclohexyl)methyl]amino}benzoate (1.31 g) synthesized above, ethanol (20 mL) and tetrahydrofuran (20 mL) was added 1N lithium hydroxide aqueous solution (20 mL), and the mixture was stirred with heating under reflux for 3 hr, and concentrated under reduced pressure. The residue was dissolved in water (40 mL), and 1N hydrochloric acid (20 mL) was added at 0° C. The resulting precipitate was collected by filtration and the obtained solid was dissolved in ethyl acetate. The solution was washed with saturated brine, dried over magnesium sulfate, and concentrated under reduced pressure. The residue was washed with diisopropyl ether to give the title object compound (1.21 g, 96%) as a pale-yellow solid.

¹H NMR (300 MHz, DMSO-d₆) δ ppm 0.96-1.42 (m, 6H), 1.54-1.82 (m, 3H), 1.87-2.03 (m, 1H), 2.04-2.16 (m, 1H), 2.28 (s, 3H), 4.53-4.64 (m, 1H), 6.64 (d, J=8.9 Hz, 2H), 6.95 (d, J=7.9 Hz, 1H), 7.32 (d, J=8.6 Hz, 1H), 7.62 (d, J=8.9 Hz, 2H), 7.99 (d, J=8.6 Hz, 1H), 12.02 (br s, 1H).

(8) ethyl 3-{[(4-{[(5-chloro-3-methylfuro[3,2-b]pyridin-2-yl)(cyclohexyl)methyl]amino}phenyl)carbonyl]amino}propanoate To a mixture of 4-{[(5-chloro-3-methylfuro[3,2-b]pyridin-2-yl)(cyclohexyl)methyl]amino}benzoic acid (300 mg) synthesized above, β-alanine ethyl ester hydrochloride (174 mg), 1-hydroxybenzotriazole monohydrate (173 mg), triethylamine (315 μL) and N,N-dimethylformamide (10 mL) was added 1-ethyl-3-(3-dimethylaminopropyl)carbodiimide hydrochloride (217 mg), and the mixture was stirred at room temperature for 2.5 days. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (383 mg, quantitative) as a pale-yellow oil.

¹H NMR (300 MHz, CDCl₃) δ ppm 0.96-1.37 (m, 8H), 1.45-1.56 (m, 1H), 1.61-1.99 (m, 4H), 2.02-2.14 (m, 1H), 2.31 (s, 3H), 2.54-2.62 (m, 2H), 3.60-3.69 (m, 2H), 4.13 (q, J=7.1 Hz, 2H), 4.40-4.50 (m, 2H), 6.55 (d, J=8.8 Hz, 2H), 6.62 (t, J=5.9 Hz, 1H), 7.14 (d, J=8.5 Hz, 1H), 7.54 (d, J=8.8 Hz, 2H), 7.55 (d, J=8.5 Hz, 1H).

(9) 3-{[(4-{[(5-chloro-3-methylfuro[3,2-b]pyridin-2-yl)(cyclohexyl)methyl]amino}phenyl)carbonyl]amino}propanoic acid To a mixture of ethyl 3-{[(4-{[(5-chloro-3-methylfuro[3,2-b]pyridin-2-yl)(cyclohexyl)methyl]amino}phenyl)carbonyl]amino}propanoate (383 mg) synthesized above, tetrahydrofuran (5 mL) and ethanol (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (328 mg, 93%) as a white solid.

¹H NMR (300 MHz, DMSO-d₆) δ ppm 0.95-1.30 (m, 5H), 1.30-1.41 (m, 1H), 1.55-1.82 (m, 3H), 1.87-2.01 (m, 1H), 2.04-2.16 (m, 1H), 2.26 (s, 3H), 2.42 (t, J=7.2 Hz, 2H), 3.26-3.42 (m, 2H), 4.56 (t, J=8.2 Hz, 1H), 6.60 (d, J=8.9 Hz, 2H), 6.68 (d, J=8.2 Hz, 1H), 7.31 (d, J=8.5 Hz, 1H), 7.52 (d, J=8.9 Hz, 2H), 7.93-8.06 (m, 2H).

Example A128

3-{[(4-{[(5-chloro-3-methylfuro[3,2-b]pyridin-2-yl)(cyclohexyl)methyl]amino}phenyl)carbonyl](methyl)amino}-propanoic acid

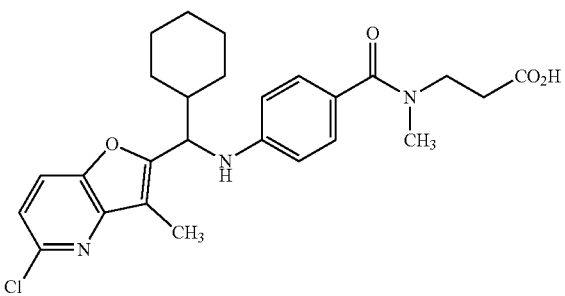 [SMILES: Cc1c(C(Nc2ccc(C(=O)N(C)CCC(=O)O)cc2)C2CCCCC2)oc2ccc(Cl)nc12]

(1) ethyl 3-{[(4-{[(5-chloro-3-methylfuro[3,2-b]pyridin-2-yl)(cyclohexyl)methyl]amino}phenyl)carbonyl]methyl)amino}-propanoate To a mixture of 4-{[(5-chloro-3-methylfuro[3,2-b]pyridin-2-yl)(cyclohexyl)methyl]amino}benzoic acid (300 mg) synthesized in Example A127(7), ethyl 3-(methylamino)propanoate (148 mg), 1-hydroxybenzotriazole monohydrate (173 mg), triethylamine (315 µL) and N,N-dimethylformamide (10 mL) was added 1-ethyl-3-(3-dimethylaminopropyl)carbodiimide hydrochloride (217 mg), and the mixture was stirred at room temperature for 2.5 days. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (332 mg, 86%) as a pale-yellow oil.

$^1$H NMR (300 MHz, CDCl$_3$) δ ppm 0.96-1.38 (m, 8H), 1.44-1.56 (m, 1H), 1.61-1.99 (m, 4H), 2.03-2.15 (m, 1H), 2.31 (s, 3H), 2.61 (t, J=6.9 Hz, 2H), 3.00 (s, 3H), 3.69 (t, J=6.9 Hz, 2H), 4.06-4.17 (m, 2H), 4.29-4.36 (m, 1H), 4.39-4.47 (m, 1H), 6.54 (d, J=8.7 Hz, 2H), 7.14 (d, J=8.5 Hz, 1H), 7.21 (d, J=8.7 Hz, 2H), 7.56 (d, J=8.5 Hz, 1H).

(2) 3-{[(4-{[(5-chloro-3-methylfuro[3,2-b]pyridin-2-yl)(cyclohexyl)methyl]amino}phenyl)carbonyl](methyl)amino}-propanoic acid To a mixture of ethyl 3-{[(4-{[(5-chloro-3,2-b]pyridin-2-yl)(cyclohexyl)methyl]amino}phenyl)carbonyl](methyl)amino}-propanoate (332 mg) synthesized above, tetrahydrofuran (5 mL) and ethanol (5 mL) was added 1N lithium hydroxide aqueous solution (3.00 mL), and the mixture was stirred overnight at room temperature, and concentrated under reduced pressure. The residue was dissolved in water (10 mL), and 1N hydrochloric acid (3.00 mL) was added at 0° C. The resulting precipitate was collected by filtration to give the title object compound (278 mg, 89%) as a pale-yellow solid.

$^1$H NMR (300 MHz, CDCl$_3$) δ ppm 0.94-1.38 (m, 5H), 1.44-1.56 (m, 1H), 1.61-1.98 (m, 4H), 2.02-2.15 (m, 1H), 2.31 (s, 3H), 2.62 (t, J=6.3 Hz, 2H), 3.00 (s, 3H), 3.68 (t, J=6.3 Hz, 2H), 4.43 (d, J=8.0 Hz, 1H), 6.54 (d, J=8.5 Hz, 2H), 7.14 (d, J=8.5 Hz, 1H), 7.22 (d, J=8.5 Hz, 2H), 7.57 (d, J=8.5 Hz, 1H).

Example A129

3-[({4-[(cyclohexyl{3-methyl-5-[(phenylcarbonyl)amino]-1-benzofuran-2-yl]methyl)amino}phenyl]carbonyl)(methyl)amino}propanoic acid

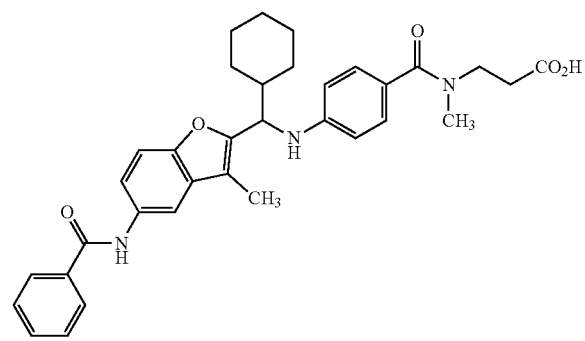 [SMILES: Cc1c(C(Nc2ccc(C(=O)N(C)CCC(=O)O)cc2)C2CCCCC2)oc2ccc(NC(=O)c3ccccc3)cc12]

To a solution (10 mL) of ethyl 3-{[(4-{[(5-amino-3-methyl-1-benzofuran-2-yl)(cyclohexyl)methyl]amino}phenyl)carbonyl](methyl)amino}-propanoate (280 mg) synthesized in Example A110(5) in N,N-dimethylacetamide was added benzoyl chloride (99 µL), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give a pale-red oil. To a mixture of the obtained oil, tetrahydrofuran (5 mL) and ethanol (5 mL) was added 1N lithium hydroxide aqueous solution (2.00 mL), and the mixture was stirred at room temperature for 5 hr, and concentrated under reduced pressure. The residue was dissolved in water (10 mL), and 1N hydrochloric acid (2.00 mL) was added at 0° C. The resulting precipitate was collected by filtration to give the title object compound (303 mg, 94%) as a white solid.

$^1$H NMR (300 MHz, CDCl$_3$) δ ppm 0.93-1.38 (m, 5H), 1.46-1.58 (m, 1H), 1.60-1.99 (m, 4H), 2.03-2.16 (m, 1H), 2.19 (s, 3H), 2.44-2.60 (m, 2H), 2.96 (s, 3H), 3.49-3.64 (m, 2H), 4.36 (d, J=8.0 Hz, 1H), 6.54 (d, J=8.7 Hz, 2H), 7.13-7.33 (m, 4H), 7.39-7.56 (m, 3H), 7.80 (s, 1H), 7.85-7.92 (m, 2H), 8.21 (s, 1H).

Example A130

3-[({4-[(cyclohexyl{3-methyl-5-[(phenylsulfonyl)amino]-1-benzofuran-2-yl}methyl)amino]phenyl}carbonyl)(methyl)amino]propanoic acid

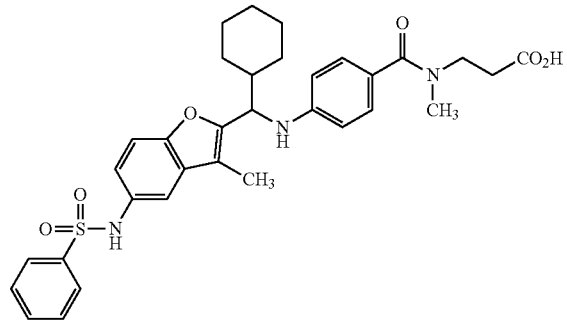 [SMILES: Cc1c(C(Nc2ccc(C(=O)N(C)CCC(=O)O)cc2)C2CCCCC2)oc2ccc(NS(=O)(=O)c3ccccc3)cc12]

(1) ethyl 3-[({4-[(cyclohexyl{3-methyl-5-[(phenylsulfonyl)amino]-1-benzofuran-2-yl}methyl)amino]phenyl}carbonyl)(methyl)amino]propanoate To a solution (10 mL) of ethyl 3-{[(4-{[(5-amino-3-methyl-1-benzofuran-2-yl)(cyclohexyl)methyl]amino}phenyl)carbonyl](methyl)amino}-propanoate (254 mg) synthesized in Example A110(5) in N,N-dimethylacetamide was added benzenesulfonyl chloride (99 µL), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (312 mg, 96%) as a colorless oil.

$^1$H NMR (300 MHz, CDCl$_3$) δ ppm 0.95-1.34 (m, 8H), 1.41-1.54 (m, 1H), 1.58-1.95 (m, 4H), 2.04-2.12 (m, 1H), 2.18 (s, 3H), 2.56-2.68 (m, 2H), 3.02 (s, 3H), 3.71 (t, J=6.7 Hz, 2H), 4.12 (q, J=7.1 Hz, 2H), 4.28-4.39 (m, 2H), 6.51-6.58 (m, 3H), 6.78 (dd, J=8.8, 2.2 Hz, 1H), 7.14-7.24 (m, 4H), 7.37-7.46 (m, 2H), 7.48-7.56 (m, 1H), 7.68-7.74 (m, 2H).

(2) 3-[({4-[(cyclohexyl{3-methyl-5-[(phenylsulfonyl)amino]-1-benzofuran-2-yl}methyl)amino]phenyl}carbonyl)(methyl)amino]propanoic acid To a mixture of ethyl 3-[({4-[(cyclohexyl{3-methyl-5-[(phenylsulfonyl)amino]-1-benzofuran-2-yl}methyl)amino]phenyl}carbonyl)(methyl)amino]propanoate (312 mg) synthesized above, tetrahydrofuran (5 mL) and ethanol (5 mL) was added 1N aqueous sodium hydroxide solution (2.00 mL), and the mixture was stirred at room temperature for 5 hr, and concentrated under reduced pressure. The residue was dissolved in water (10 mL), and 1N hydrochloric acid (2.00 mL) was added at 0° C. The resulting precipitate was collected by filtration to give the title object compound (240 mg, 80%) as a white solid.

$^1$H NMR (300 MHz, CDCl$_3$) δ ppm 0.89-1.37 (m, 5H), 1.40-1.55 (m, 1H), 1.58-1.97 (m, 4H), 2.02-2.13 (m, 1H), 2.16 (s, 3H), 2.62 (t, J=6.1 Hz, 2H), 3.01 (s, 3H), 3.68 (t, J=6.1 Hz, 2H), 4.34 (d, J=8.0 Hz, 1H), 6.53 (d, J=8.7 Hz, 2H), 6.79 (dd, J=8.7, 2.3 Hz, 1H), 6.84-6.98 (m, 1H), 7.11-7.25 (m, 4H), 7.34-7.42 (m, 2H), 7.45-7.53 (m, 1H), 7.67-7.74 (m, 2H).

Example A131

3-[{[4-({[5-(benzylamino)-3-methyl-1-benzofuran-2-yl](cyclohexyl)methyl}amino)phenyl]carbonyl}(methyl)amino]-propanoic acid

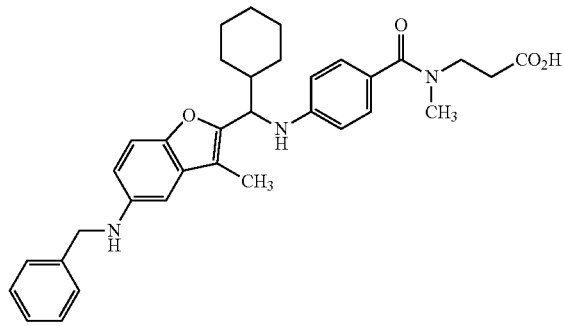 [SMILES: Cc1c(C(Nc2ccc(C(=O)N(C)CCC(=O)O)cc2)C2CCCCC2)oc2ccc(NCc3ccccc3)cc12]

(1) ethyl 3-[{[4-({[5-(benzylamino)-3-methyl-1-benzofuran-2-yl](cyclohexyl)methyl}amino)phenyl]carbonyl}(methyl)amino]-propanoate To a mixture of ethyl 3-{[(4-{[(5-amino-3-methyl-1-benzofuran-2-yl)(cyclohexyl)methyl]amino}phenyl)carbonyl](methyl)amino}-propanoate (322 mg) synthesized in Example A110(5), benzaldehyde (100 μL) and ethanol (10 mL) were added acetic acid (56 μL) and sodium cyanoborohydride (61.6 mg), and the mixture was stirred at room temperature for 1.5 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (354 mg, 93%) as a colorless oil.

$^1$H NMR (300 MHz, CDCl$_3$) δ ppm 0.92-1.37 (m, 8H), 1.47-1.96 (m, 5H), 2.01-2.12 (m, 1H), 2.17 (s, 3H), 2.56-2.67 (m, 2H), 3.02 (s, 3H), 3.66-3.77 (m, 3H), 4.06-4.18 (m, 2H), 4.29-4.39 (m, 4H), 6.51-6.64 (m, 4H), 7.14-7.43 (m, 8H).

(2) 3-[{[4-({[5-(benzylamino)-3-methyl-1-benzofuran-2-yl](cyclohexyl)methyl}amino)phenyl]carbonyl}(methyl)amino]-propanoic acid To a mixture of ethyl 3-[{[4-({[5-(benzylamino)-3-methyl-1-benzofuran-2-yl](cyclohexyl)methyl}amino)phenyl]carbonyl}(methyl)amino]-propanoate (354 mg) synthesized above, tetrahydrofuran (5 mL) and ethanol (5 mL) was added 1N aqueous sodium hydroxide solution (2.00 mL), and the mixture was stirred at room temperature for 1.5 hr, and concentrated under reduced pressure. The residue was dissolved in water (10 mL), and 1N hydrochloric acid (2.00 mL) was added at 0° C. The resulting precipitate was collected by filtration to give the title object compound (310 mg, 92%) as a white solid.

$^1$H NMR (300 MHz, CDCl$_3$) δ ppm 0.92-1.34 (m, 5H), 1.47-1.58 (m, 1H), 1.60-1.97 (m, 4H), 2.01-2.12 (m, 1H), 2.17 (s, 3H), 2.67 (t, J=6.4 Hz, 2H), 3.04 (s, 3H), 3.65-3.73 (m, 2H), 4.30-4.36 (m, 3H), 6.55 (d, J=8.7 Hz, 2H), 6.59 (dd, J=8.7, 2.7 Hz, 1H), 6.63-6.67 (m, 1H), 7.17 (d, J=8.7 Hz, 1H), 7.20-7.42 (m, 7H).

Example A132

3-[({4-[(cyclohexyl{5-fluoro-3-[(2-methoxyethoxy)methyl]-1-benzofuran-2-yl}methyl)amino]phenyl}carbonyl)amino]propanoic acid

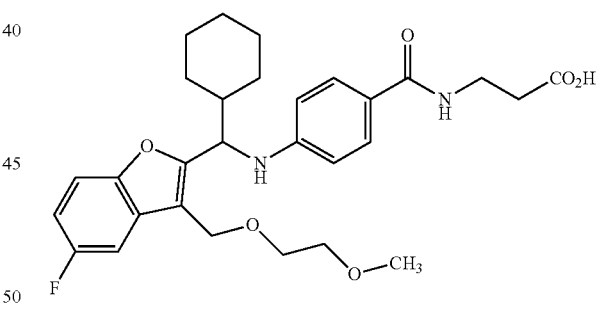

(1) methyl 5-fluoro-3-[(2-methoxyethoxy)methyl]-1-benzofuran-2-carboxylate

To a solution (25 mL) of 2-methoxyethanol (2.74 mL) in N,N-dimethylformamide was added sodium hydride (60%, oily, 835 mg) at 0° C., and the mixture was stirred at room temperature for 30 min. After stirring, a solution (25 mL) of methyl 3-(bromomethyl)-5-fluoro-1-benzofuran-2-carboxylate (5.00 g) synthesized in Example A47(2) in N,N-dimethylformamide was added at 0° C. The reaction mixture was stirred at 80° C. for 5 hr, then saturated aqueous ammonium chloride solution was added, and the mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (1.54 g, 31%) as a pale-yellow oil.

$^1$H NMR (300 MHz, CDCl$_3$) δ ppm 3.40 (s, 3H), 3.57-3.62 (m, 2H), 3.66-3.72 (m, 2H), 3.99 (s, 3H), 5.11 (s, 2H), 7.14-7.22 (m, 1H), 7.45-7.51 (m, 1H), 7.60-7.65 (m, 1H).

(2) {5-fluoro-3-[(2-methoxyethoxy)methyl]-1-benzofuran-2-yl}methanol

To a mixture of methyl 5-fluoro-3-[(2-methoxyethoxy)methyl]-1-benzofuran-2-carboxylate (1.54 g) synthesized above, calcium chloride (1.21 g), ethanol (15 mL) and tetrahydrofuran (15 mL) was added sodium borohydride (825 mg) at 0° C., and the mixture was stirred at room temperature for 3 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give the title object compound (1.34 g, 97%) as a pale-yellow oil.

$^1$H NMR (300 MHz, CDCl$_3$) δ ppm 3.38 (s, 3H), 3.55-3.60 (m, 2H), 3.63-3.68 (m, 2H), 4.73 (s, 2H), 4.76 (br s, 2H), 6.95-7.04 (m, 1H), 7.17-7.23 (m, 1H), 7.33-7.40 (m, 1H).

(3) 5-fluoro-3-[(2-methoxyethoxy)methyl]-1-benzofuran-2-carbaldehyde

To a mixture of {5-fluoro-3-[(2-methoxyethoxy)methyl]-1-benzofuran-2-yl}methanol (2.65 g) synthesized above, 4-methylmorpholine N-oxide (2.44 g) and acetonitrile (50 mL) was added tetrapropylammonium perruthenate (366 mg), and the mixture was stirred for 5 hr, and concentrated under reduced pressure. The residue was purified by silica gel column chromatography (0-30% ethyl acetate/hexane) to give the title object compound (1.33 g, 51%) as a yellow oil.

$^1$H NMR (300 MHz, CDCl$_3$) δ ppm 3.41 (s, 3H), 3.58-3.64 (m, 2H), 3.72-3.77 (m, 2H), 5.07 (s, 2H), 7.21-7.29 (m, 1H), 7.48-7.57 (m, 2H), 10.09 (s, 1H).

(4) cyclohexyl{5-fluoro-3-[(2-methoxyethoxy)methyl]-1-benzofuran-2-yl}methanone

To a solution (20 mL) of 5-fluoro-3-[(2-methoxyethoxy)methyl]-1-benzofuran-2-carbaldehyde (1.33 g) synthesized above in tetrahydrofuran was added a 1.0M solution (7.91 mL) of cyclohexylmagnesium bromide in tetrahydrofuran at 0° C., and the mixture was stirred for 2 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give a pale-yellow oil. To a mixture of the obtained oil, 4-methylmorpholine N-oxide (933 mg) and acetonitrile (20 mL) was added tetrapropylammonium perruthenate (140 mg), and the mixture was stirred overnight at room temperature, and concentrated under reduced pressure. The residue was purified by silica gel column chromatography (0-20% ethyl acetate/hexane) to give the title object compound (881 mg, 50%) as a colorless oil.

$^1$H NMR (300 MHz, CDCl$_3$) δ ppm 1.17-1.55 (m, 5H), 1.70-1.80 (m, 1H), 1.80-2.01 (m, 4H), 3.24-3.37 (m, 1H), 3.40 (s, 3H), 3.57-3.63 (m, 2H), 3.66-3.72 (m, 2H), 5.11 (s, 2H), 7.14-7.23 (m, 1H), 7.41-7.48 (m, 1H), 7.64-7.70 (m, 1H).

(5) methyl 4-[(cyclohexyl{5-fluoro-3-[(2-methoxyethoxy)methyl]-1-benzofuran-2-yl}methyl)amino]benzoate To a mixture of cyclohexyl{5-fluoro-3-[(2-methoxyethoxy)methyl]-1-benzofuran-2-yl}methanone (881 mg) synthesized above, methyl 4-aminobenzoate (440 mg), triethylamine (2.93 mL) and methylene chloride (10 mL) was added a 1.0M solution (3.16 mL) of titanium (IV) chloride in methylene chloride, and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown solid. To a solution (10 mL) of the obtained solid in tetrahydrofuran were added acetic acid (301 μL) and sodium cyanoborohydride (331 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (482 mg, 39%) as a brown oil.

$^1$H NMR (300 MHz, CDCl$_3$) δ ppm 0.96-1.35 (m, 5H), 1.41-1.51 (m, 1H), 1.58-1.85 (m, 3H), 1.86-2.01 (m, 1H), 2.01-2.13 (m, 1H), 3.43 (s, 3H), 3.53-3.60 (m, 2H), 3.60-3.67 (m, 2H), 3.80 (s, 3H), 4.46-4.72 (m, 3H), 4.99 (d, J=8.8 Hz, 1H), 6.60 (d, J=9.0 Hz, 2H), 6.88-6.98 (m, 1H), 7.13-7.19 (m, 1H), 7.27-7.34 (m, 1H), 7.78 (d, J=9.0 Hz, 2H).

(6) 4-[(cyclohexyl{5-fluoro-3-[(2-methoxyethoxy)methyl]-1-benzofuran-2-yl}methyl)amino]benzoic acid To a mixture of methyl 4-[(cyclohexyl{5-fluoro-3-[(2-methoxyethoxy)methyl]-1-benzofuran-2-yl}methyl)amino]benzoate (482 mg) synthesized above, tetrahydrofuran (5 mL) and ethanol (5 mL) was added 1N aqueous sodium hydroxide solution (5.00 mL), and the mixture was stirred overnight with heating under reflux, and concentrated under reduced pressure. The residue was dissolved in water (10 mL), and 1N hydrochloric acid (5.00 mL) was added at 0° C. The resulting precipitate was collected by filtration to give the title object compound (437 mg, 93%) as a pale-red solid.

$^1$H NMR (300 MHz, CDCl$_3$) δ ppm 0.99-1.35 (m, 5H), 1.40-1.53 (m, 1H), 1.59-1.85 (m, 3H), 1.86-2.14 (m, 2H), 3.44 (s, 3H), 3.52-3.70 (m, 4H), 4.49-4.73 (m, 3H), 6.62 (d, J=8.9 Hz, 2H), 6.91-7.00 (m, 1H), 7.14-7.20 (m, 1H), 7.29-7.36 (m, 1H), 7.84 (d, J=8.9 Hz, 2H).

(7) ethyl 3-[({4-[(cyclohexyl{5-fluoro-3-[(2-methoxyethoxy)methyl]-1-benzofuran-2-yl}methyl)amino]phenyl}carbonyl)amino]propanoate To a mixture of 4-[(cyclohexyl{5-fluoro-3-[(2-methoxyethoxy)methyl]-1-benzofuran-2-yl}methyl)amino]benzoic acid (200 mg) synthesized above, β-alanine ethyl ester hydrochloride (101 mg), 1-hydroxybenzotriazole monohydrate (101 mg), triethylamine (184 μL) and N,N-dimethylformamide (10 mL) was added 1-ethyl-3-(3-dimethylaminopropyl) carbodiimide hydrochloride (126 mg), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (216 mg, 89%) as a pale-yellow oil.

$^1$H NMR (300 MHz, CDCl$_3$) δ ppm 1.00-1.34 (m, 8H), 1.41-1.52 (m, 1H), 1.60-2.01 (m, 4H), 2.03-2.13 (m, 1H), 2.58 (t, J=5.9 Hz, 2H), 3.43 (s, 3H), 3.54-3.69 (m, 6H), 4.13 (q, J=7.1 Hz, 2H), 4.45-4.53 (m, 1H), 4.57 (d, J=12.1 Hz, 1H), 4.65 (d, J=12.1 Hz, 1H), 4.87 (d, J=8.5 Hz, 1H), 6.56-6.65 (m, 3H), 6.88-6.98 (m, 1H), 7.14-7.20 (m, 1H), 7.28-7.34 (m, 1H), 7.53 (d, J=8.8 Hz, 2H).

(8) 3-[({4-[(cyclohexyl{5-fluoro-3-[(2-methoxyethoxy)methyl]-1-benzofuran-2-yl}methyl)amino]phenyl}carbonyl)amino]propanoic acid To a mixture of ethyl 3-[({4-[(cyclohexyl{5-fluoro-3-[(2-methoxyethoxy)methyl]-1-benzofuran-2-yl}methyl)amino]phenyl}carbonyl)amino]propanoate (216 mg) synthesized above, tetrahydrofuran (5 mL) and ethanol (5 mL) was added 1N aqueous sodium hydroxide solution (1.00 mL), and the mixture was stirred at room temperature for 3 hr, and concentrated under reduced pressure. The residue was dissolved in water (10 mL), and 1N hydrochloric acid (1.00 mL) was added at 0° C. The resulting precipitate was collected by filtration to give the title object compound (69.6 mg, 34%) as a pale-yellow solid.

$^1$H NMR (300 MHz, CDCl$_3$) δ ppm 0.99-1.35 (m, 5H), 1.40-1.51 (m, 1H), 1.59-1.85 (m, 3H), 1.84-2.00 (m, 1H), 2.01-2.12 (m, 1H), 2.63 (t, J=5.7 Hz, 2H), 3.42 (s, 3H), 3.54-3.69 (m, 6H), 4.49 (d, J=8.3 Hz, 1H), 4.56 (d, J=12.1 Hz, 1H), 4.64 (d, J=12.1 Hz, 1H), 6.53-6.67 (m, 3H), 6.88-6.99 (m, 1H), 7.12-7.20 (m, 1H), 7.27-7.34 (m, 1H), 7.52 (d, J=8.7 Hz, 2H).

Example A133

3-[({4-[(cyclohexyl{5-fluoro-3-[(2-methoxyethoxy)methyl]-1-benzofuran-2-yl}methyl)amino]phenyl}carbonyl)(methyl)amino]propanoic acid

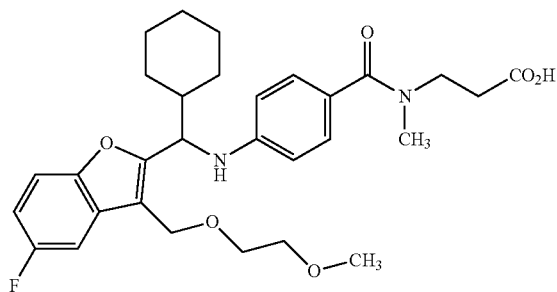 [SMILES: COCCOCc1c(C(Nc2ccc(C(=O)N(C)CCC(=O)O)cc2)C2CCCCC2)oc2ccc(F)cc12]

(1) ethyl 3-[({4-[(cyclohexyl{5-fluoro-3-[(2-methoxyethoxy)methyl]-1-benzofuran-2-yl}methyl)amino]phenyl}carbonyl)(methyl)amino]propanoate To a mixture of 4-[(cyclohexyl{5-fluoro-3-[(2-methoxyethoxy)methyl]-1-benzofuran-2-yl}methyl)amino]benzoic acid (200 mg) synthesized in Example A132(6), ethyl 3-(methylamino)propanoate (86.4 mg), 1-hydroxybenzotriazole monohydrate (101 mg), triethylamine (184 μL) and N,N-dimethylformamide (10 mL) was added 1-ethyl-3-(3-dimethylaminopropyl)carbodiimide hydrochloride (126 mg), and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (175 mg, 70%) as a pale-brown oil.

$^1$H NMR (300 MHz, CDCl$_3$) δ ppm 1.00-1.37 (m, 8H), 1.42-1.53 (m, 1H), 1.59-2.00 (m, 4H), 2.03-2.14 (m, 1H), 2.61 (t, J=7.0 Hz, 2H), 3.01 (s, 3H), 3.42 (s, 3H), 3.54-3.75 (m, 6H), 4.11 (q, J=7.1 Hz, 2H), 4.42-4.51 (m, 1H), 4.59 (d, J=12.1 Hz, 1H), 4.65 (d, J=12.1 Hz, 1H), 4.71 (d, J=8.5 Hz, 1H), 6.59 (d, J=8.8 Hz, 2H), 6.89-6.98 (m, 1H), 7.16-7.23 (m, 3H), 7.28-7.34 (m, 1H).

(2) 3-[({4-[(cyclohexyl{5-fluoro-3-[(2-methoxyethoxy)methyl]-1-benzofuran-2-yl}methyl)amino]phenyl}carbonyl)(methyl)amino]propanoic acid To a mixture of ethyl 3-[({4-[(cyclohexyl{5-fluoro-3-[(2-methoxyethoxy)methyl]-1-benzofuran-2-yl}methyl)amino]phenyl}carbonyl)(methyl)amino]propanoate (175 mg) synthesized above, tetrahydrofuran (5 mL) and ethanol (5 mL) was added 1N aqueous sodium hydroxide solution (1.00 mL), and the mixture was stirred at room temperature for 1 hr, and concentrated under reduced pressure. The residue was dissolved in water (10 mL), 1N hydrochloric acid (1.00 mL) was added at 0° C., and the mixture was extracted with ethyl acetate. The extract was washed with saturated brine, dried over magnesium sulfate, and concentrated under reduced pressure to give the title object compound (143 mg, 82%) as a yellow solid.

$^1$H NMR (300 MHz, CDCl$_3$) δ ppm 0.99-1.35 (m, 5H), 1.40-1.51 (m, 1H), 1.60-2.00 (m, 4H), 2.02-2.15 (m, 1H), 2.64 (t, J=6.4 Hz, 2H), 3.02 (s, 3H), 3.42 (s, 3H), 3.54-3.75 (m, 6H), 4.47 (d, J=8.3 Hz, 1H), 4.59 (d, J=12.3 Hz, 1H), 4.66 (d, J=12.3 Hz, 1H), 6.60 (d, J=8.7 Hz, 2H), 6.89-6.99 (m, 1H), 7.16-7.25 (m, 3H), 7.28-7.35 (m, 1H).

Example A134

3-{[(4-{[2-ethyl-1-(3-methyl-1-benzothiophene-2-yl)butyl]amino}phenyl)carbonyl]amino}propanoic acid

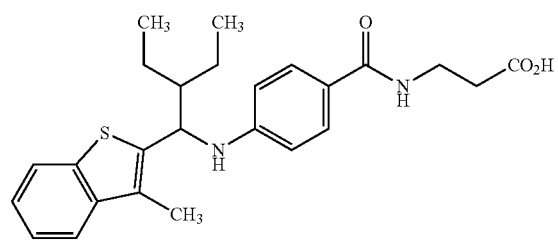 [SMILES: CCC(CC)C(Nc1ccc(C(=O)NCCC(=O)O)cc1)c1sc2ccccc2c1C]

(1) 2-ethyl-1-(3-methyl-1-benzothiophene-2-yl)butan-1-one

To a mixture of 3-methyl-1-benzothiophene (1.00 g), 2-ethylbutyryl chloride (1.02 mL) and nitromethane (10 mL) was added aluminum chloride (1.35 g) at 0° C., and the mixture was stirred for 3 hr. Water was added to quench the reaction, and the reaction mixture was extracted with ethyl acetate. The extract was washed with saturated brine, dried over magnesium sulfate, and concentrated under reduced pressure. The residue was purified by silica gel column chromatography (0-10% ethyl acetate/hexane) to give the title object compound (1.65 g, 99%) as a pale-yellow oil.

$^1$H NMR (300 MHz, CDCl$_3$) δ ppm 0.93 (t, J=7.4 Hz, 6H), 1.51-1.67 (m, 2H), 1.75-1.92 (m, 2H), 2.78 (s, 3H), 2.97-3.08 (m, 1H), 7.40-7.53 (m, 2H), 7.81-7.91 (m, 2H).

(2) methyl 4-{[2-ethyl-1-(3-methyl-1-benzothiophen-2-yl)butyl]amino}benzoate

To a mixture of 2-ethyl-1-(3-methyl-1-benzothiophen-2-yl)butan-1-one (1.65 g) synthesized above, methyl 4-aminobenzoate (1.15 g), triethylamine (7.47 mL) and methylene chloride (15 mL) was added a 1.0M solution (8.04 mL) of titanium (IV) chloride in methylene chloride, and the mixture was stirred under argon atmosphere overnight at room temperature. Saturated aqueous sodium hydrogen carbonate solution was added to quench the reaction, methylene chloride was evaporated in an evaporator, and the residue was extracted with ethyl acetate. The extract was washed with saturated brine, dried over magnesium sulfate, and concentrated under reduced pressure to give a dark brown oil. To a mixture of the obtained oil, methyl 4-aminobenzoate (506 mg), triethylamine (7.47 mL) and methylene chloride (30 mL) was added titanium (IV) chloride (882 μL), and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (30 mL) of the obtained oil in tetrahydrofuran were added acetic acid (797 μL) and sodium cyanoborohydride (842 mg) and the mixture was stirred at room temperature stirred for 1.5 hr. Saturated aqueous sodium hydrogen carbonate solution was added to quench the reaction, the organic solvent was evaporated in an evaporator, and the residue was extracted with ethyl acetate. The extract was washed with saturated brine, dried over magnesium sulfate, and concentrated under reduced pressure. The residue was purified by silica gel column chromatography (10-40% ethyl acetate/hexane) to give the title object compound (580 mg, 23%) as a pale-brown solid.

$^1$H NMR (300 MHz, CDCl$_3$) δ ppm 0.84-0.99 (m, 6H), 1.33-1.56 (m, 3H), 1.67-1.84 (m, 2H), 2.46 (s, 3H), 3.79 (s, 3H), 4.45 (d, J=6.6 Hz, 1H), 4.81-4.89 (m, 1H), 6.52 (d, J=9.0 Hz, 2H), 7.22-7.29 (m, 1H), 7.31-7.38 (m, 1H), 7.61-7.66 (m, 1H), 7.67-7.71 (m, 1H), 7.77 (d, J=9.0 Hz, 2H).

(3) 4-{[2-ethyl-1-(3-methyl-1-benzothiophen-2-yl)butyl]amino}benzoic acid

To a mixture of methyl 4-{[2-ethyl-1-(3-methyl-1-benzothiophen-2-yl)butyl]amino}benzoate (580 mg) synthesized above, tetrahydrofuran (10 mL) and ethanol (10 mL) was added 1N aqueous sodium hydroxide solution (10.0 mL), and the mixture was stirred overnight with heating under reflux, and concentrated under reduced pressure. The residue was dissolved in water (20 mL), and 1N hydrochloric acid (10.0 mL) was added at 0° C. The resulting precipitate was collected by filtration to give the title object compound (529 mg, 95%) as a white solid.

$^1$H NMR (300 MHz, CDCl$_3$) δ ppm 0.87-0.99 (m, 6H), 1.32-1.56 (m, 3H), 1.67-1.83 (m, 2H), 2.46 (s, 3H), 4.46-4.54 (m, 1H), 4.82-4.91 (m, 1H), 6.53 (d, J=8.7 Hz, 2H), 7.22-7.30 (m, 1H), 7.32-7.39 (m, 1H), 7.65 (d, J=7.6 Hz, 1H), 7.70 (d, J=7.6 Hz, 1H), 7.81 (d, J=8.7 Hz, 2H).

(4) ethyl 3-{[(4-{[2-ethyl-1-(3-methyl-1-benzothiophen-2-yl)butyl]amino}phenyl)carbonyl]amino}propanoate To a mixture of 4-{[2-ethyl-1-(3-methyl-1-benzothiophen-2-yl)butyl]amino}benzoic acid (250 mg) synthesized above, β-alanine ethyl ester hydrochloride (157 mg), 1-hydroxybenzotriazole monohydrate (156 mg), triethylamine (284 μL) and N,N-dimethylformamide (10 mL) was added 1-ethyl-3-(3-dimethylaminopropyl)carbodiimide hydrochloride (196 mg), and the mixture was stirred at room temperature for 2.5 days. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (330 mg, quantitative) as a pale-yellow oil.

$^1$H NMR (300 MHz, CDCl$_3$) δ ppm 0.86-0.97 (m, 6H), 1.24 (t, J=7.1 Hz, 3H), 1.33-1.55 (m, 3H), 1.67-1.83 (m, 2H), 2.46 (s, 3H), 2.54-2.60 (m, 2H), 3.60-3.68 (m, 2H), 4.12 (q, J=7.1 Hz, 2H), 4.35 (d, J=6.6 Hz, 1H), 4.79-4.86 (m, 1H), 6.50-6.61 (m, 3H), 7.22-7.29 (m, 1H), 7.31-7.37 (m, 1H), 7.52 (d, J=8.5 Hz, 2H), 7.61-7.66 (m, 1H), 7.66-7.71 (m, 1H).

(5) 3-{[(4-{[2-ethyl-1-(3-methyl-1-benzothiophen-2-yl)butyl]amino}phenyl)carbonyl]amino}propanoic acid To a mixture of ethyl 3-{[(4-{[2-ethyl-1-(3-methyl-1-benzothiophen-2-yl)butyl]amino}phenyl)carbonyl]amino}propanoate (330 mg) synthesized above, tetrahydrofuran (5 mL) and ethanol (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (272 mg, 91%) as a pale-yellow solid.

$^1$H NMR (300 MHz, CDCl$_3$) δ ppm 0.86-0.97 (m, 6H), 1.32-1.56 (m, 3H), 1.66-1.83 (m, 2H), 2.45 (s, 3H), 2.60 (t, J=5.5 Hz, 2H), 3.57-3.66 (m, 2H), 4.82 (d, J=6.0 Hz, 1H), 6.47-6.58 (m, 3H), 7.22-7.29 (m, 1H), 7.31-7.38 (m, 1H), 7.50 (d, J=8.7 Hz, 2H), 7.64 (d, J=7.5 Hz, 1H), 7.69 (d, J=7.9 Hz, 1H).

Example A135

3-{[(4-{[2-ethyl-1-(3-methyl-1-benzothiophen-2-yl)butyl]amino}phenyl)carbonyl](methyl)amino}propanoic acid

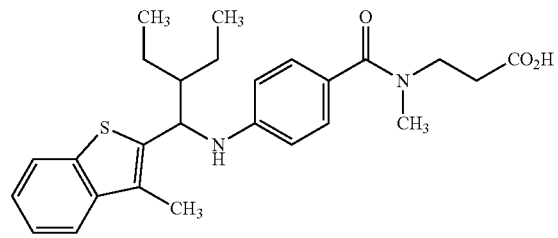 [SMILES: CCC(CC)C(Nc1ccc(C(=O)N(C)CCC(=O)O)cc1)c1sc2ccccc2c1C]

(1) ethyl 3-{[(4-{[2-ethyl-1-(3-methyl-1-benzothiophen-2-yl)butyl]amino}phenyl)carbonyl](methyl)amino}propanoate To a mixture of 4-{[2-ethyl-1-(3-methyl-1-benzothiophen-2-yl)butyl]amino}benzoic acid (250 mg) synthesized in Example A134(3), ethyl 3-(methylamino)propanoate (134 mg), 1-hydroxybenzotriazole monohydrate (156 mg), triethylamine (284 μL) and N,N-dimethylformamide (10 mL) was added 1-ethyl-3-(3-dimethylaminopropyl)carbodiimide hydrochloride (196 mg), and the mixture was stirred at room temperature 2.5 days. Saturated aqueous ammonium chloride solution was added to quench the reaction, and the reaction mixture was extracted with ethyl acetate. The extract was washed with saturated brine and saturated aqueous sodium hydrogen carbonate solution, dried over magnesium sulfate, and concentrated under reduced pressure. The residue was purified by silica gel column chromatography (30-70% ethyl acetate/hexane) to give the title object compound (253 mg, 77%) as a colorless oil.

$^1$H NMR (300 MHz, CDCl$_3$) δ ppm 0.87-0.97 (m, 6H), 1.22 (t, J=7.1 Hz, 3H), 1.32-1.54 (m, 3H), 1.67-1.82 (m, 2H), 2.45 (s, 3H), 2.60 (t, J=7.0 Hz, 2H), 3.00 (s, 3H), 3.69 (t, J=7.0 Hz, 2H), 4.10 (q, J=7.1 Hz, 2H), 4.23 (d, J=6.3 Hz, 1H), 4.76-4.83 (m, 1H), 6.51 (d, J=8.8 Hz, 2H), 7.19 (d, J=8.8 Hz, 2H), 7.22-7.29 (m, 1H), 7.31-7.38 (m, 1H), 7.61-7.66 (m, 1H), 7.68-7.72 (m, 1H).

(2) 3-{[(4-{[2-ethyl-1-(3-methyl-1-benzothiophen-2-yl)butyl]amino}phenyl)carbonyl](methyl)amino}propanoic acid To a mixture of ethyl 3-{[(4-{[2-ethyl-1-(3-methyl-1-benzothiophen-2-yl)butyl]amino}phenyl)carbonyl](methyl)amino}propanoate (253 mg) synthesized above, tetrahydrofuran (5 mL) and ethanol (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (225 mg, 95%) as a white solid.

$^1$H NMR (300 MHz, CDCl$_3$) δ ppm 0.84-0.99 (m, 6H), 1.30-1.56 (m, 3H), 1.66-1.81 (m, 2H), 2.45 (s, 3H), 2.64 (t, J=6.4 Hz, 2H), 3.01 (s, 3H), 3.68 (t, J=6.4 Hz, 2H), 4.80 (d, J=6.4 Hz, 1H), 6.52 (d, J=8.7 Hz, 2H), 7.21 (d, J=8.7 Hz, 2H), 7.23-7.30 (m, 1H), 7.31-7.38 (m, 1H), 7.64 (d, J=7.9 Hz, 1H), 7.71 (d, J=7.5 Hz, 1H).

Example A136

3-{[(4-{[cyclohexyl(3-methylthieno[2,3-c]pyridin-2-yl)methyl]amino}phenyl)carbonyl](methyl)amino}propanoic acid

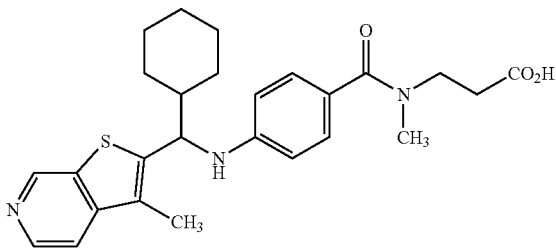 [SMILES: Cc1c(C(Nc2ccc(C(=O)N(C)CCC(=O)O)cc2)C2CCCCC2)sc2cnccc12]

(1) ethyl 3-methylthieno[2,3-c]pyridine-2-carboxylate

To a solution (120 mL) of 3-chloropyridine-4-carbonitrile (10.3 g) in tetrahydrofuran was added a 3.0M solution (49.8 mL) of methylmagnesium chloride in tetrahydrofuran under nitrogen atmosphere at 0° C., and the mixture was stirred at room temperature for 2 hr. Water (50 mL) was added to the reaction mixture, then 10% sulfuric acid (100 mL) was added to the reaction mixture, and the mixture was stirred overnight. Sodium carbonate was added to acidify the solution to pH=9, and the mixture was extracted with ethyl acetate. The extract was dried over sodium sulfate, and concentrated under reduced pressure. The residue was purified by silica gel column chromatography to give a colorless oil (6.10 g). To a mixture of the obtained oil (6.00 g), ethyl mercaptoacetate (11.6 mL) and anhydrous N,N-dimethylformamide (100 mL) was added sodium hydride (60%, oily, 4.0 g) at 5° C. over 30 min, and the mixture was stirred at 5° C. for 20 min then at room temperature overnight. Saturated aqueous sodium hydrogen carbonate solution was added to quench the reaction, and the reaction mixture was poured into water. The precipitated solid was collected by filtration and recrystallized from petroleum ether/ethyl acetate to give the title object compound (5.12 g, 31%) as a yellow solid.

$^1$H NMR (300 MHz, CDCl$_3$) δ ppm 1.42 (t, J=7.2 Hz, 3H), 2.76 (s, 3H), 4.41 (q, J=7.2 Hz, 2H), 7.69 (dd, J=5.7, 0.9 Hz, 1H), 8.57 (d, J=5.7 Hz, 1H), 9.14 (d, J=0.6 Hz, 1H).

(2) 3-methylthieno[2,3-c]pyridine-2-carbaldehyde

To a mixture of ethyl 3-methylthieno[2,3-c]pyridine-2-carboxylate (2.00 g) synthesized above, calcium chloride (2.01 g), ethanol (30 mL) and tetrahydrofuran (30 mL) was added sodium borohydride (1.37 g) at 0° C., and the mixture was stirred at room temperature for 3 hr. Saturated aqueous ammonium chloride solution was added to quench the reaction, and the reaction mixture was extracted with ethyl acetate. The extract was washed with saturated brine, dried over magnesium sulfate, and concentrated under reduced pressure to give a pale-yellow solid. To a solution (40 mL) of the obtained solid in tetrahydrofuran was added active manganese dioxide (8.10 g), and the mixture was stirred at 50° C. for 8 hr. Manganese dioxide was filtered off, and the filtrate was concentrated under reduced pressure to give the title object compound (1.39 g, 87%) as a pale-brown solid.

$^1$H NMR (300 MHz, CDCl$_3$) δ ppm 2.81 (s, 3H), 7.75 (dd, J=5.5, 1.1 Hz, 1H), 8.61 (d, J=5.5 Hz, 1H), 9.20 (d, J=1.1 Hz, 1H), 10.41 (s, 1H).

(3) cyclohexyl(3-methylthieno[2,3-c]pyridin-2-yl)methanone

To a solution (30 mL) of 3-methylthieno[2,3-c]pyridine-2-carbaldehyde (1.39 g) synthesized above in tetrahydrofuran was added a 1.0M solution (15.7 mL) of cyclohexylmagnesium bromide in tetrahydrofuran at 0° C., and the mixture was stirred for 1.5 hr. Saturated aqueous ammonium chloride solution was added to quench the reaction, tetrahydrofuran was evaporated in an evaporator, and the residue was extracted with ethyl acetate. The extract was washed with saturated brine, dried over magnesium sulfate, and concentrated under reduced pressure. The residue was purified by silica gel column chromatography (30-70% ethyl acetate/hexane) to give a pale-yellow solid. To a mixture of the obtained solid, 4-methylmorpholine N-oxide (680 mg) and acetonitrile (20 mL) was added tetrapropylammonium perruthenate (113 mg), and the mixture was stirred at room temperature for 1 hr, and concentrated under reduced pressure. The residue was purified by silica gel column chromatography (0-40% ethyl acetate/hexane) to give the title object compound (628 mg, 31%) as a colorless oil.

¹H NMR (300 MHz, CDCl₃) δ ppm 1.22-1.62 (m, 5H), 1.70-1.81 (m, 1H), 1.82-1.94 (m, 2H), 1.95-2.06 (m, 2H), 2.73 (s, 3H), 2.97-3.09 (m, 1H), 7.71 (dd, J=5.5, 1.1 Hz, 1H), 8.58 (d, J=5.5 Hz, 1H), 9.16 (d, J=1.1 Hz, 1H).

(4) 4-{[cyclohexyl(3-methylthieno[2,3-c]pyridin-2-yl)methyl]amino}benzoic acid

To a mixture of cyclohexyl(3-methylthieno[2,3-c]pyridin-2-yl)methanone (628 mg) synthesized above, methyl 4-aminobenzoate (402 mg), triethylamine (2.70 mL) and methylene chloride (10 mL) was added titanium (IV) chloride (318 μL), and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (30 mL) of the obtained oil in tetrahydrofuran were added acetic acid (277 μL) and sodium cyanoborohydride (304 mg), and the mixture was stirred at room temperature for 2 hr. Saturated aqueous sodium hydrogen carbonate solution was added to quench the reaction, the organic solvent was evaporated in an evaporator, and the residue was extracted with ethyl acetate. The extract was washed with saturated brine, dried over magnesium sulfate, and concentrated under reduced pressure. The residue was purified by silica gel column chromatography (30-70% ethyl acetate/hexane) to give an orange solid. To a mixture of the obtained solid, tetrahydrofuran (5 mL) and ethanol (5 mL) was added 1N aqueous sodium hydroxide solution (5.00 mL), and the mixture was stirred with heating under reflux for 4 hr. 1N Hydrochloric acid (5.00 mL) was added to the reaction mixture, and the mixture was extracted with ethyl acetate. The extract was washed with saturated brine, dried over magnesium sulfate, and concentrated under reduced pressure. The residue was purified by silica gel column chromatography (40-100% ethyl acetate/hexane) to give the title object compound (202 mg, 22%) as a yellow solid.

¹H NMR (300 MHz, CDCl₃) δ ppm 1.07-1.34 (m, 5H), 1.40-1.93 (m, 5H), 2.01-2.16 (m, 1H), 2.50 (s, 3H), 4.58-4.69 (m, 2H), 6.51 (d, J=8.8 Hz, 2H), 7.52 (dd, J=5.6, 0.9 Hz, 1H), 7.82 (d, J=8.8 Hz, 2H), 8.49 (d, J=5.6 Hz, 1H), 8.95 (d, J=0.9 Hz, 1H).

(5) ethyl 3-{[(4-{[cyclohexyl(3-methylthieno[2,3-c]pyridin-2-yl)methyl]amino}phenyl)carbonyl](methyl)amino}propanoate To a mixture of 4-{[cyclohexyl(3-methylthieno[2,3-c]pyridin-2-yl)methyl]amino}benzoic acid (202 mg) synthesized above, ethyl 3-(methylamino)propanoate (104 mg), 1-hydroxybenzotriazole monohydrate (122 mg), triethylamine (222 μL) and N,N-dimethylformamide (10 mL) was added 1-ethyl-3-(3-dimethylaminopropyl)carbodiimide hydrochloride (152 mg), and the mixture was stirred at room temperature for 1 day. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-100% ethyl acetate/hexane, then 0-10% methanol/acetic acid) to give the title object compound (151 mg, 58%) as a pale-yellow oil.

¹H NMR (300 MHz, CDCl₃) δ ppm 1.06-1.36 (m, 8H), 1.53-1.88 (m, 5H), 2.03-2.16 (m, 1H), 2.48 (s, 3H), 2.60 (t, J=7.0 Hz, 2H), 2.99 (s, 3H), 3.69 (t, J=7.0 Hz, 2H), 4.10 (q, J=7.1 Hz, 2H), 4.35 (d, J=5.7 Hz, 1H), 4.58 (dd, J=7.3, 5.7 Hz, 1H), 6.49 (d, J=8.7 Hz, 2H), 7.19 (d, J=8.7 Hz, 2H), 7.51 (dd, J=5.7, 1.1 Hz, 1H), 8.48 (d, J=5.7 Hz, 1H), 8.95 (d, J=1.1 Hz, 1H).

(6) 3-{[(4-{[cyclohexyl(3-methylthieno[2,3-c]pyridin-2-yl)methyl]amino}phenyl)carbonyl](methyl)amino}propanoic acid To a mixture of ethyl 3-{[(4-{[cyclohexyl(3-methylthieno[2,3-c]pyridin-2-yl)methyl]amino}phenyl)carbonyl](methyl)amino}propanoate (151 mg) synthesized above, tetrahydrofuran (5 mL) and ethanol (5 mL) was added 1N aqueous sodium hydroxide solution (1.00 mL), and the mixture was stirred at room temperature for 5 hr, and concentrated under reduced pressure. The residue was dissolved in water (10 mL), and 1N hydrochloric acid (1.00 mL) was added at 0° C. The resulting precipitate was collected by filtration to give the title object compound (80.2 mg, 56%) as a white solid.

¹H NMR (300 MHz, CDCl₃) δ ppm 1.04-1.34 (m, 5H), 1.50-1.62 (m, 1H), 1.63-1.88 (m, 4H), 2.02-2.14 (m, 1H), 2.48 (s, 3H), 2.53-2.68 (m, 2H), 3.00 (s, 3H), 3.58-3.74 (m, 2H), 4.57 (d, J=7.5 Hz, 1H), 6.47 (d, J=8.5 Hz, 2H), 7.19 (d, J=8.5 Hz, 2H), 7.55 (d, J=5.7 Hz, 1H), 8.43 (d, J=5.7 Hz, 1H), 8.94 (s, 1H).

Example A137

3-{[(4-{[cyclohexyl(3-methylthieno[2,3-c]pyridin-2-yl)methyl]amino}phenyl)carbonyl]amino}propanoic acid

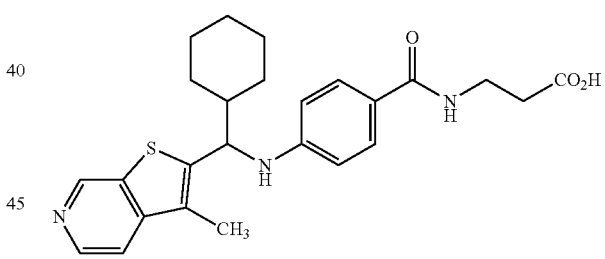

(1) ethyl 3-{[(4-{[cyclohexyl(3-methylthieno[2,3-c]pyridin-2-yl)methyl]amino}phenyl)carbonyl]amino}propanoate To a mixture of 4-{[cyclohexyl(3-methylthieno[2,3-c]pyridin-2-yl)methyl]amino}benzoic acid (201 mg) synthesized in Example A136(4), β-alanine ethyl ester hydrochloride (122 mg), 1-hydroxybenzotriazole monohydrate (121 mg), triethylamine (220 μL) and N,N-dimethylformamide (10 mL) was added 1-ethyl-3-(3-dimethylaminopropyl)carbodiimide hydrochloride (152 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (60-100% ethyl acetate/hexane) to give the title object compound (209 mg, 83%) as a pale-yellow oil.

$^1$H NMR (300 MHz, CDCl$_3$) δ ppm 1.06-1.37 (m, 8H), 1.53-1.89 (m, 5H), 2.05-2.16 (m, 1H), 2.48 (s, 3H), 2.56 (t, J=5.8 Hz, 2H), 3.59-3.68 (m, 2H), 4.12 (q, J=7.1 Hz, 2H), 4.50 (d, J=5.8 Hz, 1H), 4.58-4.64 (m, 1H), 6.50 (d, J=8.8 Hz, 2H), 6.61 (t, J=5.9 Hz, 1H), 7.51 (dd, J=5.5, 1.1 Hz, 1H), 7.52 (d, J=8.8 Hz, 2H), 8.47 (d, J=5.5 Hz, 1H), 8.93 (d, J=1.1 Hz, 1H).

(2) 3-{[(4-{[cyclohexyl(3-methylthieno[2,3-c]pyridin-2-yl)methyl]amino}phenyl)carbonyl]amino}propanoic acid To a mixture of ethyl 3-{[(4-{[cyclohexyl(3-methylthieno[2,3-c]pyridin-2-yl)methyl]amino}phenyl)carbonyl]amino}propanoate (209 mg) synthesized above, tetrahydrofuran (5 mL) and ethanol (5 mL) was added 1N aqueous sodium hydroxide solution (1.00 mL), and the mixture was stirred at room temperature for 1 hr, and concentrated under reduced pressure. The residue was dissolved in water (10 mL), and 1N hydrochloric acid (1.00 mL) was added at 0° C. The resulting precipitate was collected by filtration to give the title object compound (169 mg, 86%) as a white solid.

$^1$H NMR (300 MHz, CDCl$_3$) δ ppm 1.04-1.36 (m, 5H), 1.49-1.89 (m, 5H), 2.02-2.14 (m, 1H), 2.48 (s, 3H), 2.59 (t, J=5.7 Hz, 2H), 3.51-3.77 (m, 2H), 4.59 (d, J=7.2 Hz, 1H), 6.47 (d, J=8.7 Hz, 2H), 6.85 (t, J=5.8 Hz, 1H), 7.48-7.60 (m, 3H), 8.42 (d, J=5.7 Hz, 1H), 8.88 (s, 1H).

Example A138

3-{[(4-{[cyclohexyl(3-methylthieno[3,2-c]pyridin-2-yl)methyl]amino}phenyl)carbonyl]amino}propanoic acid

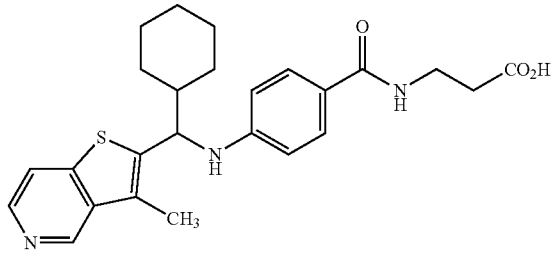 [SMILES: Cc1c(C(Nc2ccc(C(=O)NCCC(=O)O)cc2)C2CCCCC2)sc2ccncc12]

(1) ethyl 3-methylthieno[3,2-c]pyridine-2-carboxylate

Thionyl chloride (100 mL) was added to 4-chloronicotinic acid (22.4 g), and the mixture was stirred with heating under reflux for 4 hr, and concentrated under reduced pressure. To a solution (300 mL) of the residue in methylene chloride were added N,O-dimethylhydroxylamine hydrochloride (13.8 g) and triethylamine (60 mL), and the mixture was stirred at room temperature for 5 hr. Water was added to the reaction mixture, and the reaction mixture was extracted with methylene chloride. The extract was dried over sodium sulfate, and concentrated under reduced pressure. To a solution (300 mL) of the residue in tetrahydrofuran was added a 3.0 M solution (54 mL) of methylmagnesium chloride in ether at −78° C. and the mixture was stirred under nitrogen atmosphere at room temperature for 10 hr. The reaction mixture was acidified with aqueous sodium carbonate solution to pH=9, and extracted with ethyl acetate. The extract was dried over sodium sulfate, and concentrated under reduced pressure to give a colorless oil. To a mixture of the obtained oil, ethyl mercaptoacetate (21 mL) and anhydrous N,N-dimethylformamide (200 mL) was added sodium hydride (60%, oily, 7.34 g) at 5° C. over 30 min, and the mixture was stirred at 5° C. for 20 min then at room temperature for 18 hr. Water was added to quench the reaction, and the reaction mixture was extracted with ethyl acetate. The extract was dried over sodium sulfate, and concentrated under reduced pressure. The obtained solid was recrystallized from petroleum ether/ethyl acetate to give the title object compound (5.45 g, 17%) as a white solid.

$^1$H NMR (300 MHz, CDCl$_3$) δ ppm 1.43 (t, J=7.2 Hz, 3H), 2.85 (s, 3H), 4.42 (q, J=7.2 Hz, 2H), 7.74 (dd, J=5.7, 0.9 Hz, 1H), 8.55 (d, J=6.0 Hz, 1H), 9.14 (d, J=1.2 Hz, 1H).

(2) 3-methylthieno[3,2-c]pyridine-2-carbaldehyde

To a mixture of ethyl 3-methylthieno[3,2-c]pyridine-2-carboxylate (3.40 g) synthesized above, calcium chloride (3.42 g), ethanol (30 mL) and tetrahydrofuran (30 mL) was added sodium borohydride (2.33 g) at 0° C., and the mixture was stirred at room temperature for 3 hr. Saturated aqueous ammonium chloride solution was added to quench the reaction, and the reaction mixture was extracted with ethyl acetate. The extract was washed with saturated brine, dried over magnesium sulfate, and concentrated under reduced pressure to give a pale-yellow oil. To a solution (60 mL) of the obtained oil in tetrahydrofuran was added active manganese dioxide (14.4 g) and the mixture was stirred at 50° C. overnight. Manganese dioxide was filtered off, and the filtrate was concentrated under reduced pressure. The residue was washed with diisopropyl ether to give the title object compound (1.54 g, 56%) as a pale-brown solid.

$^1$H NMR (300 MHz, CDCl$_3$) δ ppm 2.89 (s, 3H), 7.79 (dd, J=5.5, 0.8 Hz, 1H), 8.58 (d, J=5.5 Hz, 1H), 9.21 (d, J=0.8 Hz, 1H), 10.35 (s, 1H).

(3) cyclohexyl(3-methylthieno[3,2-c]pyridin-2-yl)methanone

To a solution (40 mL) of 3-methylthieno[3,2-c]pyridine-2-carbaldehyde (1.87 g) synthesized above in tetrahydrofuran was added a 1.0M solution (21.2 mL) of cyclohexylmagnesium bromide in tetrahydrofuran at 0° C., and the mixture was stirred for 1 hr. A 1.0M solution (10.0 mL) of cyclohexylmagnesium bromide in tetrahydrofuran was additionally added, and the mixture was further stirred at 0° C. for 1 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-90% ethyl acetate/hexane) to give a pale-yellow solid. To a mixture of the obtained solid, 4-methylmorpholine N-oxide (1.24 mg) and acetonitrile (30 mL) was added tetrapropylammonium perruthenate (164 mg), and the mixture was stirred at room temperature for 4 hr, and concentrated under reduced pressure. The residue was purified by silica gel column chromatography (10-50% ethyl acetate/hexane) to give the title object compound (864 mg, 31%) as a white solid.

$^1$H NMR (300 MHz, CDCl$_3$) δ ppm 1.19-1.61 (m, 5H), 1.69-1.80 (m, 1H), 1.81-1.92 (m, 2H), 1.93-2.04 (m, 2H), 2.82 (s, 3H), 2.93-3.05 (m, 1H), 7.75 (dd, J=5.7, 1.0 Hz, 1H), 8.55 (d, J=5.7 Hz, 1H), 9.17 (d, J=1.0 Hz, 1H).

(4) 4-{[cyclohexyl(3-methylthieno[3,2-c]pyridin-2-yl)methyl]amino}benzoic acid To a mixture of cyclohexyl(3-methylthieno[3,2-c]pyridin-2-yl)methanone (864 mg) synthesized above, methyl 4-aminobenzoate (553 mg), triethylamine (3.71 mL) and methylene chloride (20 mL) was added titanium (IV) chloride (439 μL) at 0° C., and the mixture was stirred under argon atmosphere overnight at room temperature. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (20 mL) of the obtained oil in tetrahydrofuran were added acetic acid (268 μL) and sodium cyanoborohydride (419 mg), and the mixture was stirred at room temperature stirred for 1.5 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give a pale-brown solid. To a mixture of the obtained solid, tetrahydrofuran (5 mL) and ethanol (5 mL) was added 1N aqueous sodium hydroxide solution (5.00 mL), and the mixture was stirred overnight with heating under reflux. Tetrahydrofuran (5 mL), ethanol (5 mL) and 1N aqueous sodium hydroxide solution (5.00 mL) were additionally added, and the mixture was stirred with heating under reflux for 2.5 hr, and ethylenediamine (1.00 mL) was added. The mixture was stirred with heating under reflux for 4 hr, and concentrated under reduced pressure. The residue was acidified with 1N hydrochloric acid to pH=4, and the mixture was extracted with ethyl acetate. The extract was washed with saturated brine, dried over magnesium sulfate, and concentrated under reduced pressure. The residue was purified by silica gel column chromatography (50-100% ethyl acetate/hexane) to give the title object compound (432 mg, 34%) as a pale-yellow solid.

$^1$H NMR (300 MHz, CDCl$_3$) δ ppm 1.04-1.37 (m, 5H), 1.53-1.90 (m, 5H), 2.03-2.15 (m, 1H), 2.56 (s, 3H), 4.55-4.66 (m, 2H), 6.51 (d, J=8.7 Hz, 2H), 7.63 (dd, J=5.5, 1.1 Hz, 1H), 7.84 (d, J=8.7 Hz, 2H), 8.39 (d, J=5.5 Hz, 1H), 8.97 (d, J=1.1 Hz, 1H).

(5) ethyl 3-{[(4-{[cyclohexyl(3-methylthieno[3,2-c]pyridin-2-yl)methyl]amino}phenyl)carbonyl]amino}propanoate To a mixture of 4-{[cyclohexyl(3-methylthieno[3,2-c]pyridin-2-yl)methyl]amino}benzoic acid (211 mg) synthesized above, β-alanine ethyl ester hydrochloride (128 mg), 1-hydroxybenzotriazole monohydrate (128 mg), triethylamine (233 μL) and N,N-dimethylformamide (10 mL) was added 1-ethyl-3-(3-dimethylaminopropyl)carbodiimide hydrochloride (160 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (60-100% ethyl acetate/hexane) to give the title object compound (214 mg, 80%) as a white solid.

$^1$H NMR (300 MHz, CDCl$_3$) δ ppm 1.05-1.37 (m, 8H), 1.53-1.91 (m, 5H), 2.04-2.16 (m, 1H), 2.50-2.63 (m, 5H), 3.58-3.70 (m, 2H), 4.12 (q, J=7.1 Hz, 2H), 4.42 (d, J=5.8 Hz, 1H), 4.52-4.62 (m, 1H), 6.51 (d, J=8.7 Hz, 2H), 6.59 (t, J=5.8 Hz, 1H), 7.52 (d, J=8.7 Hz, 2H), 7.60 (d, J=5.5 Hz, 1H), 8.37 (d, J=5.5 Hz, 1H), 8.93 (s, 1H).

(6) 3-{[(4-{[cyclohexyl(3-methylthieno[3,2-c]pyridin-2-yl)methyl]amino}phenyl)carbonyl]amino}propanoic acid To a mixture of ethyl 3-{[(4-{[cyclohexyl(3-methylthieno[3,2-c]pyridin-2-yl)methyl]amino}phenyl)carbonyl]amino}propanoate (186 mg) synthesized above, tetrahydrofuran (5 mL) and ethanol (5 mL) was added 1N aqueous sodium hydroxide solution (1.00 mL), and the mixture was stirred at room temperature for 1 hr, and concentrated under reduced pressure. The residue was dissolved in water (10 mL), and 1N hydrochloric acid (1.00 mL) was added at 0° C. The resulting precipitate was collected by filtration to give the title object compound (186 mg, 93%) as a white solid.

$^1$H NMR (300 MHz, CDCl$_3$) δ ppm 1.05-1.36 (m, 5H), 1.55-1.64 (m, 1H), 1.65-1.90 (m, 4H), 2.03-2.15 (m, 1H), 2.56 (s, 3H), 2.61 (t, J=5.1 Hz, 2H), 3.52-3.67 (m, 1H), 3.73-3.89 (m, 1H), 4.56 (d, J=7.2 Hz, 1H), 6.48 (d, J=8.7 Hz, 2H), 6.89-6.99 (m, 1H), 7.58 (d, J=8.7 Hz, 2H), 7.69 (d, J=5.7 Hz, 1H), 8.31 (d, J=5.7 Hz, 1H), 8.96 (s, 1H).

Example A139

3-{[(4-{[cyclohexyl(3-methylthieno[3,2-c]pyridin-2-yl)methyl]amino}phenyl)carbonyl](methyl)amino}propanoic acid

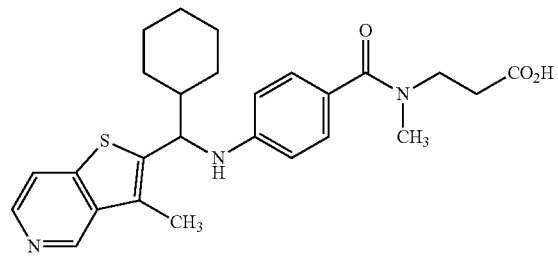 [SMILES: Cc1c(C(Nc2ccc(C(=O)N(C)CCC(=O)O)cc2)C2CCCCC2)sc2ccncc12]

(1) ethyl 3-{[(4-{[cyclohexyl(3-methylthieno[3,2-c]pyridin-2-yl)methyl]amino}phenyl)carbonyl](methyl)amino}propanoate To a mixture of 4-{[cyclohexyl(3-methylthieno[3,2-c]pyridin-2-yl)methyl]amino}benzoic acid (209 mg) synthesized in Example A138(4), ethyl 3-(methylamino)propanoate (108 mg), 1-hydroxybenzotriazole monohydrate (126 mg), triethylamine (229 μL) and N,N-dimethylformamide (10 mL) was added 1-ethyl-3-(3-dimethylaminopropyl)carbodiimide hydrochloride (158 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (60-100% ethyl acetate/hexane, then 0-10% methanol/ethyl acetate) to give the title object compound (180 mg, 66%) as a colorless oil.

$^1$H NMR (300 MHz, CDCl$_3$) δ ppm 1.04-1.38 (m, 8H), 1.52-1.94 (m, 5H), 2.02-2.16 (m, 1H), 2.55 (s, 3H), 2.60 (t, J=6.9 Hz, 2H), 2.99 (s, 3H), 3.69 (t, J=6.9 Hz, 2H), 4.10 (q, J=6.8 Hz, 2H), 4.27-4.39 (m, 1H), 4.49-4.59 (m, 1H), 6.49 (d, J=8.5 Hz, 2H), 7.19 (d, J=8.5 Hz, 2H), 7.62 (d, J=5.5 Hz, 1H), 8.38 (d, J=5.5 Hz, 1H), 8.93 (s, 1H).

(2) 3-{[(4-{[cyclohexyl(3-methylthieno[3,2-c]pyridin-2-yl)methyl]amino}phenyl)carbonyl](methyl)amino}propanoic acid To a mixture of ethyl 3-{[(4-{[cyclohexyl(3-methylthieno[3,2-c]pyridin-2-yl)methyl]amino}phenyl)carbonyl]methyl)amino}propanoate (180 mg) synthesized above, tetrahydrofuran (5 mL) and ethanol (5 mL) 1N aqueous sodium hydroxide solution (1.00 mL) was added, and the mixture was stirred at room temperature for 1 hr, and concentrated under reduced pressure. The residue was dissolved in water (10 mL), and 1N hydrochloric acid (1.00 mL) was added at 0° C. The resulting precipitate was collected by filtration to give the title object compound (136 mg, 80%) as a white solid.

$^1$H NMR (300 MHz, CDCl$_3$) δ ppm 1.03-1.32 (m, 5H), 1.52-1.63 (m, 1H), 1.63-1.89 (m, 4H), 2.03-2.15 (m, 1H), 2.53 (s, 3H), 2.58-2.74 (m, 2H), 3.03 (s, 3H), 3.62-3.79 (m, 2H), 4.54 (d, J=7.5 Hz, 1H), 6.48 (d, J=8.7 Hz, 2H), 7.22 (d, J=8.7 Hz, 2H), 7.67 (d, J=5.5 Hz, 1H), 8.34 (d, J=5.5 Hz, 1H), 8.93 (s, 1H).

Example A140

3-{[(4-{[1-(5-chloro-1-methyl-1H-indol-2-yl)heptyl]amino}phenyl)carbonyl]amino}propanoic acid

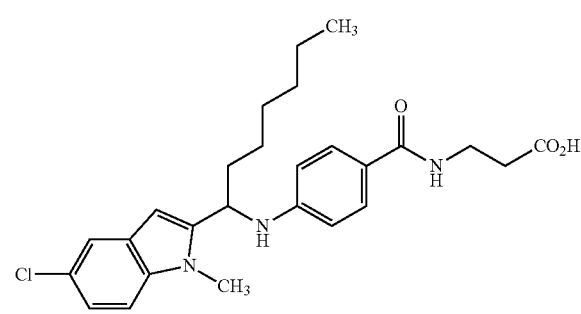 [SMILES: CCCCCCC(Nc1ccc(C(=O)NCCC(=O)O)cc1)c1cc2cc(Cl)ccc2n1C]

(1) 1-(5-chloro-1-methyl-1H-indol-2-yl)heptan-1-one

To a solution (10 mL) of 1-(5-chloro-1H-indol-2-yl)heptan-1-one (1.00 g) synthesized in Example A106(2) in N,N-dimethylformamide was added sodium hydride (60%, oily, 182 mg) at 0° C. and the mixture was stirred under argon atmosphere for 30 min. After stirring, methyl iodide (354 μL) was added. The reaction mixture was stirred at room temperature overnight, saturated aqueous ammonium chloride solution was added to quench the reaction, and the mixture was extracted with ethyl acetate. The extract was washed with saturated brine, dried over magnesium sulfate, and concentrated under reduced pressure. The residue was washed with hexane to give the title object compound (367 mg, 35%) as a pale-brown solid.

$^1$H NMR (300 MHz, CDCl$_3$) δ ppm 0.85-0.94 (m, 3H), 1.24-1.46 (m, 6H), 1.68-1.81 (m, 2H), 2.90-2.98 (m, 2H), 4.05 (s, 3H), 7.19 (s, 1H), 7.28-7.31 (m, 2H), 7.63-7.66 (m, 1H).

(2) methyl 4-{[1-(5-chloro-1-methyl-1H-indol-2-yl)heptyl]amino}benzoate

To a mixture of 1-(5-chloro-1-methyl-1H-indol-2-yl)heptan-1-one (1.05 g) synthesized above, methyl 4-aminobenzoate (629 mg), triethylamine (4.21 mL) and methylene chloride (10 mL) was added a 1.0M solution (4.54 mL) of titanium (IV) chloride in methylene chloride at 0° C., and the mixture was stirred overnight at room temperature under argon atmosphere. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown solid. To a solution (10 mL) of the obtained solid in tetrahydrofuran were added acetic acid (1.08 mL) and sodium cyanoborohydride (475 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-30% ethyl acetate/hexane) to give the title object compound (1.15 g, 74%) as a pale-brown solid.

$^1$H NMR (300 MHz, CDCl$_3$) δ ppm 0.83-0.91 (m, 3H), 1.21-1.53 (m, B H), 1.88-2.08 (m, 2H), 3.68 (s, 3H), 3.83 (s, 3H), 4.25 (d, J=7.1 Hz, 1H), 4.60-4.70 (m, 1H), 6.37 (s, 1H), 6.55 (d, J=8.8 Hz, 2H), 7.13 (dd, J=8.7, 1.9 Hz, 1H), 7.19 (d, J=8.7 Hz, 1H), 7.49 (d, J=1.9 Hz, 1H), 7.83 (d, J=8.8 Hz, 2H).

(3) 4-{[1-(5-chloro-1-methyl-1H-indol-2-yl)heptyl]amino}benzoic acid

To a mixture of methyl 4-{[1-(5-chloro-1-methyl-1H-indol-2-yl)heptyl]amino}benzoate (1.15 g) synthesized above, tetrahydrofuran (15 mL) and ethanol (15 mL) was added 1N is aqueous sodium hydroxide solution (15 mL), and the mixture was stirred overnight with heating under reflux, and concentrated under reduced pressure. The residue was dissolved in water (30 mL), and 1N hydrochloric acid (15 mL) was added at 0° C. The resulting precipitate was collected by filtration to give the title object compound (1.09 g, 98%) as a white solid.

$^1$H NMR (300 MHz, CDCl$_3$) δ ppm 0.86 (t, J=6.5 Hz, 3H), 1.11-1.51 (m, 8H), 1.79-2.04 (m, 2H), 3.58 (s, 3H), 4.49-4.63 (m, 1H), 6.31 (s, 1H), 6.42 (d, J=8.3 Hz, 2H), 7.05-7.17 (m, 2H), 7.46 (s, 1H), 7.80 (d, J=8.3 Hz, 2H).

(4) ethyl 3-{[(4-{[1-(5-chloro-1-methyl-1H-indol-2-yl)heptyl]amino}phenyl)carbonyl]amino}propanoate To a mixture of 4-{[1-(5-chloro-1-methyl-1H-indol-2-yl)heptyl]amino}benzoic acid (300 mg) synthesized above, β-alanine ethyl ester hydrochloride (174 mg), 1-hydroxybenzotriazole monohydrate (173 mg), triethylamine (158 μL) and N,N-dimethylformamide (10 mL) was added 1-ethyl-3-(3-dimethylaminopropyl)carbodiimide hydrochloride (217 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (349 mg, 93%) as a pale-yellow oil.

$^1$H NMR (300 MHz, CDCl$_3$) δ ppm 0.88 (t, J=6.9 Hz, 3H), 1.18-1.55 (m, 11H), 1.87-2.10 (m, 2H), 2.60 (t, J=5.8 Hz, 2H), 3.61-3.76 (m, 5H), 4.06-4.23 (m, 3H), 4.57-4.69 (m, 1H), 6.37 (s, 1H), 6.57 (d, J=8.5 Hz, 2H), 6.64 (t, J=5.8 Hz, 1H), 7.11-7.16 (m, 1H), 7.17-7.23 (m, 1H), 7.50 (d, J=1.6 Hz, 1H), 7.59 (d, J=8.5 Hz, 2H).

(5) 3-{[(4-{[1-(5-chloro-1-methyl-1H-indol-2-yl)heptyl]amino}phenyl)carbonyl]amino}propanoic acid To a mixture of ethyl 3-{[(4-{[1-(5-chloro-1-methyl-1H-indol-2-yl)heptyl]amino}phenyl)carbonyl]amino}propanoate (349 mg) synthesized above, tetrahydrofuran (5 mL) and ethanol (5 mL) was added 1N aqueous sodium hydroxide solution (2.00 mL), and the mixture was stirred at room temperature for 3 hr, and concentrated under reduced pressure. The residue was dissolved in water (10 mL), and 1N hydrochloric acid (2.00 mL) was added at 0° C. The resulting precipitate was collected by filtration to give the title object compound (302 mg, 92%) as a pale-brown solid.

$^1$H NMR (300 MHz, CDCl$_3$) δ ppm 0.86 (t, J=6.4 Hz, 3H), 1.17-1.55 (m, 8H), 1.84-2.05 (m, 2H), 2.62 (t, J=5.7 Hz, 2H), 3.58-3.72 (m, 5H), 4.60 (t, J=6.8 Hz, 1H), 6.33 (s, 1H), 6.52 (d, J=8.7 Hz, 2H), 6.69 (t, J=5.8 Hz, 1H), 7.12 (dd, J=9.0, 2.1 Hz, 1H), 7.17 (d, J=9.0 Hz, 1H), 7.47 (d, J=2.1 Hz, 1H), 7.55 (d, J=8.7 Hz, 2H).

Example A141

3-{[(4-{[1-(5-chloro-1-methyl-1H-indol-2-yl)heptyl]amino}phenyl)carbonyl](methyl)amino}propanoic acid

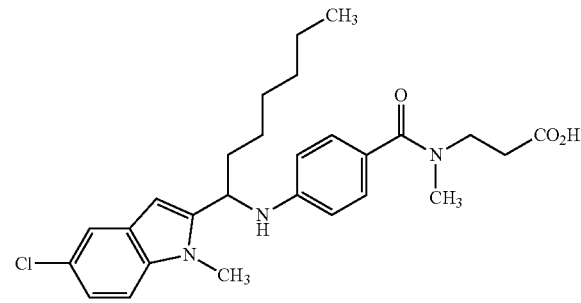 [SMILES: CCCCCCC(Nc1ccc(C(=O)N(C)CCC(=O)O)cc1)c1cc2cc(Cl)ccc2n1C]

(1) ethyl 3-{[(4-{[1-(5-chloro-1-methyl-1H-indol-2-yl)heptyl]amino}phenyl)carbonyl](methyl)amino}propanoate To a mixture of 4-{[1-(5-chloro-1-methyl-1H-indol-2-yl)heptyl]amino}benzoic acid (300 mg) synthesized in Example A140(3), ethyl 3-(methylamino)propanoate (148 mg), 1-hydroxybenzotriazole monohydrate (173 mg), triethylamine (158 µL) and N,N-dimethylformamide (10 mL) was added 1-ethyl-3-(3-dimethylaminopropyl)carbodiimide hydrochloride (217 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-70% ethyl acetate/hexane) to give the title object compound (235 mg, 61%) as a pale-yellow oil.

$^1$H NMR (300 MHz, CDCl$_3$) δ ppm 0.87 (t, J=6.6 Hz, 3H), 1.17-1.53 (m, 11H), 1.89-2.06 (m, 2H), 2.63 (t, J=6.7 Hz, 2H), 3.04 (s, 3H), 3.65-3.79 (m, 5H), 4.02 (d, J=7.1 Hz, 1H), 4.12 (q, J=7.1 Hz, 2H), 4.54-4.65 (m, 1H), 6.37 (s, 1H), 6.55 (d, J=8.4 Hz, 2H), 7.13 (dd, J=8.8, 1.8 Hz, 1H), 7.20 (d, J=8.8 Hz, 1H), 7.25 (d, J=8.4 Hz, 2H), 7.50 (d, J=1.8 Hz, 1H).

(2) 3-{[(4-{[1-(5-chloro-1-methyl-1H-indol-2-yl)heptyl]amino}phenyl)carbonyl]methyl)amino}propanoic acid To a mixture of ethyl 3-{[(4-{[1-(5-chloro-1-methyl-1H-indol-2-yl)heptyl]amino}phenyl)carbonyl]methyl)amino}propanoate (235 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (211 mg, 95%) as a pale-yellow solid.

$^1$H NMR (300 MHz, CDCl$_3$) δ ppm 0.87 (t, J=6.8 Hz, 3H), 1.16-1.54 (m, 8H), 1.84-2.05 (m, 2H), 2.63 (t, J=5.8 Hz, 2H), 3.02 (s, 3H), 3.62-3.76 (m, 5H), 4.59 (t, J=6.8 Hz, 1H), 6.35 (s, 1H), 6.53 (d, J=8.5 Hz, 2H), 7.12 (dd, J=8.7, 1.9 Hz, 1H), 7.19 (d, J=8.7 Hz, 1H), 7.24 (d, J=8.5 Hz, 2H), 7.49 (d, J=1.9 Hz, 1H).

Example A142

3-{[(4-{[cyclohexyl(3-methylthieno[2,3-b]pyridin-2-yl)methyl]amino}phenyl)carbonyl]amino}propanoic acid

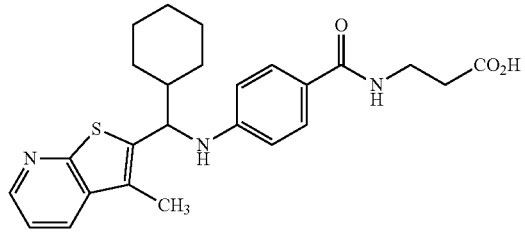 [SMILES: Cc1c(C(Nc2ccc(C(=O)NCCC(=O)O)cc2)C2CCCCC2)sc2ncccc12]

(1) ethyl 3-methylthieno[2,3-b]pyridine-2-carboxylate

To a solution (300 mL) of 2-chloropyridine-3-carbonitrile (15.0 g) in tetrahydrofuran was added a 3.0M solution (72.5 mL) of methylmagnesium chloride in tetrahydrofuran at −78° C., and the mixture was stirred at room temperature for 10 hr under nitrogen atmosphere. To the reaction mixture was added water (50 mL), and then added 10% sulfuric acid (100 mL), and the mixture was stirred overnight. Sodium carbonate was added to acidify the reaction mixture to pH=9, and the mixture was extracted with ethyl acetate. The extract was dried with sodium sulfate, and concentrated under reduced pressure. The residue was purified by silica gel column chromatography to give a colorless oil (7.68 g). To a mixture of the obtained oil (7.00 g), ethyl mercaptoacetate (13 mL) and anhydrous N,N-dimethylformamide (200 mL) was added sodium hydride (60%, oily, 4.68 g) at 5° C. over 30 min, and the mixture was stirred at 5° C. for 20 min then at room temperature for 18 hr. Saturated aqueous sodium hydrogen carbonate solution was added to quench the reaction, and the mixture was poured into water. The precipitated solid was collected by filtration and recrystallized from petroleum ether/ethyl acetate to give the title object compound (6.14 g, 29%) as a white solid.

$^1$H NMR (400 MHz, CDCl$_3$) δ ppm 1.45 (t, J=7.2 Hz, 3H), 2.78 (s, 3H), 4.43 (q, J=7.2 Hz, 2H), 7.38-7.40 (m, 1H), 8.11-8.13 (m, 1H), 8.70-8.72 (m, 1H).

(2) 3-methylthieno[2,3-b]pyridine-2-carbaldehyde

To a mixture of ethyl 3-methylthieno[2,3-b]pyridine-2-carboxylate (3.00 g) synthesized above, calcium chloride (3.02 g), ethanol (50 mL) and tetrahydrofuran (50 mL) was added sodium borohydride (2.06 g) at 0° C., and the mixture was stirred at room temperature for 4 hr. Saturated aqueous ammonium chloride solution was added to quench the reaction, and the reaction mixture was extracted with ethyl acetate. The extract was washed with saturated brine, dried over magnesium sulfate, and concentrated under reduced pressure to give a white solid. To a solution (50 mL) of the obtained solid in tetrahydrofuran was added active manganese dioxide (12.5 g), and the mixture was stirred at 50° C. overnight. Manganese dioxide was filtered off, and the filtrate was concentrated under reduced pressure. The residue was washed with diisopropyl ether to give the title object compound (2.07 g, 86%) as a pale-yellow solid.

$^1$H NMR (300 MHz, CDCl$_3$) δ ppm 2.79 (s, 3H), 7.39 (dd, J=8.2, 4.5 Hz, 1H), 8.16 (dd, J=8.2, 1.6 Hz, 1H), 8.72 (dd, J=4.5, 1.6 Hz, 1H), 10.36 (s, 1H).

(3) cyclohexyl(3-methylthieno[2,3-b]pyridin-2-yl)methanone

To a solution (60 mL) of 3-methylthieno[2,3-b]pyridine-2-carbaldehyde (2.07 g) synthesized above in tetrahydrofuran was added a 1.0M solution (17.6 mL) of cyclohexylmagnesium bromide in tetrahydrofuran at 0° C., and the mixture was stirred for 1 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (10-50% ethyl acetate/hexane) to give a yellow solid. To a mixture of the obtained solid, 4-methylmorpholine N-oxide (1.81 g) and acetonitrile (40 mL) was added tetrapropylammonium perruthenate (238 mg), and the mixture was stirred at room temperature for 3 hr, and concentrated under reduced pressure. The residue was purified by silica gel column chromatography (0-30% ethyl acetate/hexane) to give the title object compound (1.50 g, 85%) as a white solid.

$^1$H NMR (300 MHz, CDCl$_3$) δ ppm 1.18-1.62 (m, 5H), 1.69-1.80 (m, 1H), 1.81-1.91 (m, 2H), 1.95-2.06 (m, 2H), 2.73 (s, 3H), 2.95-3.07 (m, 1H), 7.37 (m, J=8.2, 4.4 Hz, 1H), 8.13 (dd, J=8.2, 1.6 Hz, 1H), 8.70 (dd, J=4.4, 1.6 Hz, 1H).

(4) methyl 4-{[cyclohexyl(3-methylthieno[2,3-b]pyridin-2-yl)methyl]amino}benzoate To a mixture of cyclohexyl(3-methylthieno[2,3-b]pyridin-2-yl)methanone (1.00 g) synthesized above, methyl 4-aminobenzoate (642 mg), triethylamine (4.31 mL) and methylene chloride (20 mL) was added titanium (IV) chloride (508 μL) at 0° C., and the mixture was stirred at room temperature for 1.5 days under argon atmosphere. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown solid. To a solution (20 mL) of the obtained solid in tetrahydrofuran were added acetic acid (442 μL) and sodium cyanoborohydride (485 mg), and the mixture was stirred at room temperature for 1.5 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (975 mg, 64%) as a pale-brown solid.

$^1$H NMR (300 MHz, CDCl$_3$) δ ppm 1.00-1.35 (m, 5H), 1.48-1.96 (m, 5H), 2.02-2.19 (m, 1H), 2.55 (s, 3H), 3.81 (s, 3H), 4.54-4.70 (m, 2H), 6.51 (d, J=8.8 Hz, 2H), 7.59 (dd, J=7.6, 5.7 Hz, 1H), 7.78 (d, J=8.8 Hz, 2H), 8.22 (d, J=7.6 Hz, 1H), 8.63 (d, J=5.7 Hz, 1H).

(5) 4-{[cyclohexyl(3-methylthieno[2,3-b]pyridin-2-yl)methyl]amino}benzoic acid

To a mixture of methyl 4-{[cyclohexyl(3-methylthieno[2,3-b]pyridin-2-yl)methyl]amino}benzoate (975 mg) synthesized above, tetrahydrofuran (10 mL) and ethanol (10 mL) was added 1N aqueous sodium hydroxide solution (10 mL), and the mixture was stirred overnight with heating under reflux, and concentrated under reduced pressure. The residue was dissolved in water (20 mL), 1N hydrochloric acid (10 mL) was added, and the mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (701 mg, 75%) as a pale-yellow solid.

$^1$H NMR (300 MHz, CDCl$_3$) δ ppm 1.01-1.39 (m, 5H), 1.53-1.92 (m, 5H), 2.07-2.20 (m, 1H), 2.46 (s, 3H), 4.60 (d, J=8.0 Hz, 1H), 6.53 (d, J=8.5 Hz, 2H), 7.21-7.31 (m, 1H), 7.82 (d, J=8.5 Hz, 2H), 7.87 (dd, J=8.1, 1.3 Hz, 1H), 8.47 (dd, J=4.4, 1.3 Hz, 1H).

(6) ethyl 3-{[(4-{[cyclohexyl(3-methylthieno[2,3-b]pyridin-2-yl)methyl]amino}phenyl)carbonyl]amino}propanoate To a mixture of 4-{[cyclohexyl(3-methylthieno[2,3-b]pyridin-2-yl)methyl]amino}benzoic acid (300 mg) synthesized above, β-alanine ethyl ester hydrochloride (181 mg), 1-hydroxybenzotriazole monohydrate (181 mg), triethylamine (329 μL) and N,N-dimethylformamide (10 mL) was added 1-ethyl-3-(3-dimethylaminopropyl)carbodiimide hydrochloride (226 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (30-100% ethyl acetate/hexane) to give the title object compound (335 mg, 89%) as a pale-yellow solid.

$^1$H NMR (300 MHz, CDCl$_3$) δ ppm 1.02-1.38 (m, 8H), 1.54-1.90 (m, 5H), 2.08-2.21 (m, 1H), 2.45 (s, 3H), 2.56 (t, J=5.9 Hz, 2H), 3.59-3.69 (m, 2H), 4.12 (q, J=7.1 Hz, 2H), 4.40 (d, J=6.3 Hz, 1H), 4.53-4.61 (m, 1H), 6.48-6.64 (m, 3H), 7.21-7.30 (m, 1H), 7.52 (d, J=8.5 Hz, 2H), 7.86 (dd, J=8.1, 1.5 Hz, 1H), 8.45 (dd, J=4.5, 1.5 Hz, 1H).

(7) 3-{[(4-{[cyclohexyl(3-methylthieno[2,3-b]pyridin-2-yl)methyl]amino}phenyl)carbonyl]amino}propanoic acid To a mixture of ethyl 3-[{(4-{[cyclohexyl(3-methylthieno[2,3-b]pyridin-2-yl)methyl]amino}phenyl)carbonyl]amino}propanoate (335 mg) synthesized above, tetrahydrofuran (5 mL) and ethanol (5 mL) was added 1N aqueous sodium hydroxide solution (2.00 mL), and the mixture was stirred at room temperature for 2 hr, and concentrated under reduced pressure. The residue was dissolved in water (10 mL), and 1N hydrochloric acid (2.00 mL) was added at 0° C. The resulting precipitate was collected by filtration to give the title object compound (281 mg, 89%) as a white solid.

$^1$H NMR (300 MHz, CDCl$_3$) δ ppm 1.00-1.34 (m, 5H), 1.51-1.87 (m, 5H), 2.06-2.19 (m, 1H), 2.44 (s, 3H), 2.52-2.64 (m, 2H), 3.53-3.68 (m, 2H), 4.55 (d, J=8.0 Hz, 1H), 6.49 (d, J=8.7 Hz, 2H), 6.71 (t, J=5.3 Hz, 1H), 7.23-7.31 (m, 1H), 7.49 (d, J=8.7 Hz, 2H), 7.88 (dd, J=8.0, 1.1 Hz, 1H), 8.45 (dd, J=4.5, 1.1 Hz, 1H).

Example A143

3-{[(4-{[cyclohexyl(3-methylthieno[2,3-b]pyridin-2-yl)methyl]amino}phenyl)carbonyl](methyl)amino}propanoic acid

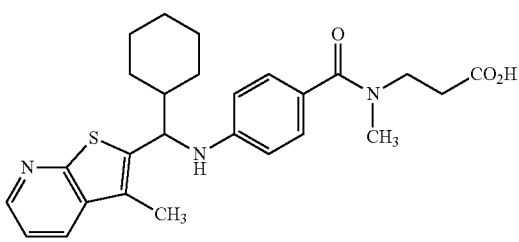 [SMILES: Cc1c(C(Nc2ccc(C(=O)N(C)CCC(=O)O)cc2)C2CCCCC2)sc2ncccc12]

(1) ethyl 3-{[(4-{[cyclohexyl(3-methylthieno[2,3-b]pyridin-2-yl)methyl]amino}phenyl)carbonyl](methyl)amino}propanoate To a mixture of 4-{[cyclohexyl(3-methylthieno[2,3-b]pyridin-2-yl)methyl]amino}benzoic acid (300 mg) synthesized in Example A142(5), ethyl 3-(methylamino)propanoate (155 mg), 1-hydroxybenzotriazole monohydrate (181 mg), triethylamine (329 μL) and N,N-dimethylformamide (10 mL) was added 1-ethyl-3-(3-dimethylaminopropyl)carbodiimide hydrochloride (226 mg), and the mixture was stirred overnight at room temperature. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (40-100% ethyl acetate/hexane) to give the title object compound (333 mg, 85%) as a pale-yellow oil.

$^1$H NMR (300 MHz, CDCl$_3$) δ ppm 1.00-1.37 (m, 8H), 1.52-1.89 (m, 5H), 2.07-2.21 (m, 1H), 2.45 (s, 3H), 2.60 (t, J=6.8 Hz, 2H), 2.99 (s, 3H), 3.69 (t, J=6.8 Hz, 2H), 4.02-4.17 (m, 2H), 4.32 (d, J=5.8 Hz, 1H), 4.49-4.58 (m, 1H), 6.52 (d, J=8.5 Hz, 2H), 7.19 (d, J=8.5 Hz, 2H), 7.22-7.31 (m, 1H), 7.86 (dd, J=8.0, 1.1 Hz, 1H), 8.43-8.50 (m, 1H).

(2) 3-{[(4-{[cyclohexyl(3-methylthieno[2,3-b]pyridin-2-yl)methyl]amino}phenyl)carbonyl](methyl)amino}propanoic acid To a mixture of ethyl 3-{[(4-{[cyclohexyl(3-methylthieno[2,3-b]pyridin-2-yl)methyl]amino}phenyl)carbonyl](methyl)amino}propanoate (333 mg) synthesized above, tetrahydrofuran (5 mL) and ethanol (5 mL) was added 1N aqueous sodium hydroxide solution (2.00 mL), and the mixture was stirred at room temperature for 4 hr, and concentrated under reduced pressure. The residue was dissolved in water (10 mL), and 1N hydrochloric acid (2.00 mL) was added at 0° C. The resulting precipitate was collected by filtration to give the title object compound (275 mg, 88%) as a white solid.

$^1$H NMR (300 MHz, CDCl$_3$) δ ppm 1.02-1.35 (m, 5H), 1.54-1.88 (m, 5H), 2.07-2.19 (m, 1H), 2.45 (s, 3H), 2.58-2.70 (m, 2H), 3.01 (s, 3H), 3.68 (t, J=6.6 Hz, 2H), 4.54 (d, J=7.6 Hz, 1H), 6.51 (d, J=8.7 Hz, 2H), 7.20 (d, J=8.7 Hz, 2H), 7.27 (dd, J=8.1, 4.7 Hz, 1H), 7.88 (dd, J=8.1, 1.6 Hz, 1H), 8.47 (dd, J=4.7, 1.6 Hz, 1H).

Example A144

3-{[(4-{[cyclohexyl(3-methylthieno[3,2-b]pyridin-2-yl)methyl]amino}phenyl)carbonyl]amino}propanoic acid

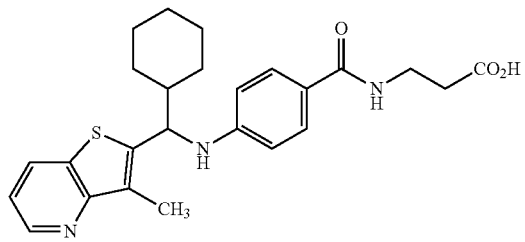 [SMILES: Cc1c(C(Nc2ccc(C(=O)NCCC(=O)O)cc2)C2CCCCC2)sc2cccnc12]

(1) ethyl 3-methylthieno[3,2-b]pyridine-2-carboxylate

To a solution (100 mL) of 3-chloropyridine-2-carbonitrile (10.0 g) in tetrahydrofuran was added a 3.0M solution (48.0 mL) of methylmagnesium bromide in diethyl ether, and the mixture was stirred at room temperature for 3 hr. To the reaction mixture was added 2N hydrochloric acid (300 mL), tetrahydrofuran was evaporated in an evaporator, and the residue was extracted with ethyl acetate. The extract was washed with saturated brine, dried over anhydrous magnesium sulfate, and concentrated under reduced pressure. The residue was purified by silica gel column chromatography (30-70% ethyl acetate/hexane) to give a pale-yellow oil. To a mixture of the obtained oil, ethyl mercaptoacetate (4.23 mL) and N,N-dimethylformmide (60 mL) was added and potassium carbonate (16.0 g), and the mixture was stirred overnight at 50° C. Water was added to quench the reaction, and the precipitated solid was collected by filtration to give the title object compound (6.75 g, 79%) as a white solid.

$^1$H NMR (400 MHz, CDCl$_3$) δ ppm 1.44 (t, J=7.2 Hz, 3H), 2.87 (s, 3H), 4.44 (q, J=7.2 Hz, 2H), 7.37 (dd, J=8.3, 4.4 Hz, 1H), 8.17 (dd, J=8.3, 1.5 Hz, 1H), 8.78 (dd, J=4.4, 1.5 Hz, 1H).

(2) 3-methylthieno[3,2-b]pyridine-2-carbaldehyde

To a mixture of ethyl 3-methylthieno[3,2-b]pyridine-2-carboxylate (3.00 g) synthesized above, calcium chloride (3.02 g), ethanol (30 mL) and tetrahydrofuran (30 mL) was added sodium borohydride (2.06 g) at 0° C., and the mixture was stirred at room temperature for 5 hr. Saturated aqueous ammonium chloride solution was added to quench the reaction, and the reaction mixture was extracted with ethyl acetate. The extract was washed with saturated brine, dried over magnesium sulfate, and concentrated under reduced pressure to give a white solid. To a solution (50 mL) of the obtained solid in tetrahydrofuran was added active manganese dioxide (12.2 g), and the mixture was stirred at 50° C. overnight. Manganese dioxide was filtered off, and the filtrate was concentrated under reduced pressure to give the title object compound (2.24 g, 93%) as a white solid.

$^1$H NMR (300 MHz, CDCl$_3$) δ ppm 2.90 (s, 3H), 7.40 (dd, J=8.2, 4.6 Hz, 1H), 8.21 (dd, J=8.2, 1.4 Hz, 1H), 8.79 (dd, J=4.6, 1.4 Hz, 1H), 10.43 (s, 1H).

(3) cyclohexyl(3-methylthieno[3,2-b]pyridin-2-yl)methanone

To a solution (50 mL) of 3-methylthieno[3,2-b]pyridine-2-carbaldehyde (2.24 g) synthesized above in tetrahydrofuran was added a 1.0M solution (18.9 mL) of cyclohexylmagnesium bromide in tetrahydrofuran at 0° C., and the mixture was stirred at 0° C. for 1.5 hr under argon atmosphere. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (10-50% ethyl acetate/hexane) to give a pale-yellow oil. To a mixture of the obtained oil, 4-methylmorpholine N-oxide (1.81 g) and acetonitrile (40 mL) was added tetrapropylammonium perruthenate (238 mg), and the mixture was stirred at room temperature for 2 hr, and concentrated under reduced pressure. The residue was purified by silica gel column chromatography (0-30% ethyl acetate/hexane) to give the title object compound (1.38 g, 79%) as a colorless oil.

$^1$H NMR (300 MHz, CDCl$_3$) δ ppm 1.19-1.65 (m, 5H), 1.70-1.81 (m, 1H), 1.82-1.94 (m, 2H), 1.94-2.08 (m, 2H), 2.86 (s, 3H), 3.01-3.15 (m, 1H), 7.37 (dd, J=8.2, 4.4 Hz, 1H), 8.17 (dd, J=8.2, 1.5 Hz, 1H), 8.78 (dd, J=4.4, 1.5 Hz, 1H).

(4) methyl 4-{[cyclohexyl(3-methylthieno[3,2-b]pyridin-2-yl)methyl]amino}benzoate To a mixture of cyclohexyl(3-methylthieno[3,2-b]pyridin-2-yl)methanone (1.38 g) synthesized above, methyl 4-aminobenzoate (884 mg), triethylamine (5.94 mL) and methylene chloride (30 mL) was added titanium (IV) chloride (700 μL) at 0° C., and the mixture was stirred at room temperature for 3.5 days under argon atmosphere. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (30 mL) of the obtained oil in tetrahydrofuran were added acetic acid (607 μL) and sodium cyanoborohydride (666 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (10-50% ethyl acetate/hexane) to give the title object compound (1.31 g, 62%) as a brown solid.

$^1$H NMR (300 MHz, CDCl$_3$) δ ppm 1.07-1.37 (m, 5H), 1.55-1.90 (m, 5H), 2.03-2.16 (m, 1H), 2.59 (s, 3H), 3.79 (s, 3H), 4.56 (d, J=5.8 Hz, 1H), 4.63-4.72 (m, 1H), 6.51 (d, J=8.5 Hz, 2H), 7.16 (dd, J=8.1, 4.6 Hz, 1H), 7.77 (d, J=8.5 Hz, 2H), 7.98 (dd, J=8.1, 1.2 Hz, 1H), 8.64 (dd, J=4.6, 1.2 Hz, 1H).

(5) 4-{[cyclohexyl(3-methylthieno[3,2-b]pyridin-2-yl)methyl]amino}benzoic acid To a mixture of methyl 4-{[cyclohexyl(3-methylthieno[3,2-b]pyridin-2-yl)methyl]amino}benzoate (1.31 g) synthesized above, tetrahydrofuran (10 mL) and ethanol (10 mL) was added 1N aqueous sodium hydroxide solution (10 mL), and the mixture was stirred overnight with heating under reflux. 1N Aqueous sodium hydroxide solution (5 mL) was additionally added, and the mixture was further stirred with heating under reflux for 7 hr, and concentrated under reduced pressure. The residue was dissolved in water (20 mL), and 1N hydrochloric acid (15 mL) was added at 0° C. The resulting precipitate was collected by filtration, and the obtained brown solid was dissolved in ethyl acetate. The solution was washed with saturated brine, dried over magnesium sulfate, and concentrated under reduced pressure. The residue was washed with diisopropyl ether to give the title object compound (804 mg, 64%) as a brown solid.

$^1$H NMR (300 MHz, CDCl$_3$) δ ppm 1.07-1.36 (m, 5H), 1.55-1.91 (m, 5H), 2.02-2.15 (m, 1H), 2.60 (s, 3H), 4.52-4.74 (m, 2H), 6.52 (d, J=8.7 Hz, 2H), 7.17 (dd, J=8.0, 4.6 Hz, 1H), 7.82 (d, J=8.7 Hz, 2H), 7.99 (dd, J=8.0, 1.4 Hz, 1H), 8.66 (dd, J=4.6, 1.4 Hz, 1H).

(6) ethyl 3-{[(4-{[cyclohexyl(3-methylthieno[3,2-b]pyridin-2-yl)methyl]amino}phenyl)carbonyl]amino}propanoate To a mixture of 4-{[cyclohexyl(3-methylthieno[3,2-b]pyridin-2-yl)methyl]amino}benzoic acid (300 mg) synthesized above, β-alanine ethyl ester hydrochloride (181 mg), 1-hydroxybenzotriazole monohydrate (181 mg), triethylamine (329 μL) and N,N-dimethylformamide (10 mL) was added 1-ethyl-3-(3-dimethylaminopropyl)carbodiimide hydrochloride (226 mg), and the mixture was stirred at room temperature for 1 day. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (60-100% ethyl acetate/hexane) to give the title object compound (330 mg, 87%) as a pale-brown solid.

$^1$H NMR (300 MHz, CDCl$_3$) δ ppm 1.07-1.36 (m, 8H), 1.56-1.90 (m, 5H), 2.02-2.16 (m, 1H), 2.52-2.63 (m, 5H), 3.59-3.68 (m, 2H), 4.12 (q, J=7.1 Hz, 2H), 4.49 (d, J=5.8 Hz, 1H), 4.62-4.69 (m, 1H), 6.52 (d, J=8.5 Hz, 2H), 6.59 (t, J=5.8 Hz, 1H), 7.16 (dd, J=8.1, 4.6 Hz, 1H), 7.52 (d, J=8.5 Hz, 2H), 7.99 (dd, J=8.1, 1.4 Hz, 1H), 8.64 (dd, J=4.6, 1.4 Hz, 1H).

(7) 3-{[(4-{[cyclohexyl(3-methylthieno[3,2-b]pyridin-2-yl)methyl]amino}phenyl)carbonyl]amino}propanoic acid To a mixture of ethyl 3-{[(4-{[cyclohexyl(3-methylthieno[3,2-b]pyridin-2-yl)methyl]amino}phenyl)carbonyl]amino}propanoate (330 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (291 mg, 94%) as a white solid.

$^1$H NMR (300 MHz, CDCl$_3$) δ ppm 1.07-1.36 (m, 5H), 1.55-1.89 (m, 5H), 2.03-2.14 (m, 1H), 2.57 (s, 3H), 2.63 (t, J=5.7 Hz, 2H), 3.55-3.77 (m, 2H), 4.64 (d, J=7.2 Hz, 1H), 6.49 (d, J=8.9 Hz, 2H), 6.78 (t, J=6.0 Hz, 1H), 7.19 (dd, J=8.0, 4.6 Hz, 1H), 7.53 (d, J=8.9 Hz, 2H), 8.01 (dd, J=8.0, 1.5 Hz, 1H), 8.64 (dd, J=4.6, 1.5 Hz, 1H).

Example A145

3-{[(4-{[cyclohexyl(3-methylthieno[3,2-b]pyridin-2-yl)methyl]amino}phenyl)carbonyl](methyl)amino}propanoic acid

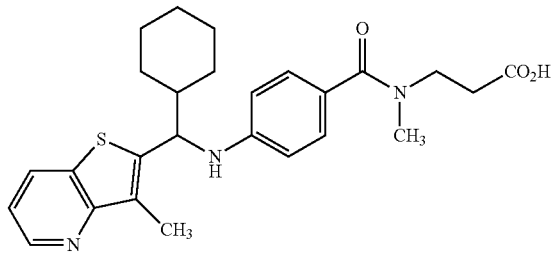 [SMILES: Cc1c(C(Nc2ccc(C(=O)N(C)CCC(=O)O)cc2)C2CCCCC2)sc2cccnc12]

(1) ethyl 3-{[(4-{[cyclohexyl(3-methylthieno[3,2-b]pyridin-2-yl)methyl]amino}phenyl)carbonyl](methyl)amino}propanoate To a mixture of 4-{[cyclohexyl(3-methylthieno[3,2-b]pyridin-2-yl)methyl]amino}benzoic acid (300 mg) synthesized in Example A144(5), ethyl 3-(methylamino)propanoate (155 mg), 1-hydroxybenzotriazole monohydrate (181 mg), triethylamine (329 μL) and N,N-dimethylformamide (10 mL) was added 1-ethyl-3-(3-dimethylaminopropyl)carbodiimide hydrochloride (226 mg), and the mixture was stirred at room temperature for 1 day. Saturated aqueous ammonium chloride solution was added to quench the reaction, and the reaction mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50-100% ethyl acetate/hexane) to give the title object compound (325 mg, 84%) as a pale-yellow oil.

$^1$H NMR (300 MHz, CDCl$_3$) δ ppm 1.07-1.36 (m, 8H), 1.54-1.92 (m, 5H), 2.01-2.16 (m, 1H), 2.51-2.68 (m, 5H), 2.99 (s, 3H), 3.69 (t, J=7.0 Hz, 2H), 4.10 (q, J=6.9 Hz, 2H), 4.36 (d, J=5.2 Hz, 1H), 4.58-4.67 (m, 1H), 6.51 (d, J=8.5 Hz, 2H), 7.13-7.23 (m, 3H), 8.00 (d, J=8.0 Hz, 1H), 8.64 (d, J=4.4 Hz, 1H).

(2) 3-{[(4-{[cyclohexyl(3-methylthieno[3,2-b]pyridin-2-yl)methyl]amino}phenyl)carbonyl]methyl)amino}propanoic acid To a mixture of ethyl 3-{[(4-{[cyclohexyl(3-methylthieno[3,2-b]pyridin-2-yl)methyl]amino}phenyl)carbonyl](methyl)amino}propanoate (325 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (277 mg, 90%) as a white solid.

$^1$H NMR (300 MHz, CDCl$_3$) δ ppm 1.06-1.34 (m, 5H), 1.55-1.88 (m, 5H), 2.03-2.15 (m, 1H), 2.58 (s, 3H), 2.66 (t, J=6.3 Hz, 2H), 3.02 (s, 3H), 3.70 (t, J=6.3 Hz, 2H), 4.62 (d, J=7.5 Hz, 1H), 6.50 (d, J=8.7 Hz, 2H), 7.15-7.25 (m, 3H), 8.01 (dd, J=8.3, 1.5 Hz, 1H), 8.66 (dd, J=4.5, 1.5 Hz, 1H).

Example A146

3-[{[4-({cyclohexyl[3-methyl-6-(trifluoromethyl)thieno[3,2-b]pyridin-2-yl]methyl}amino)phenyl]carbonyl}(methyl)amino]propanoic acid

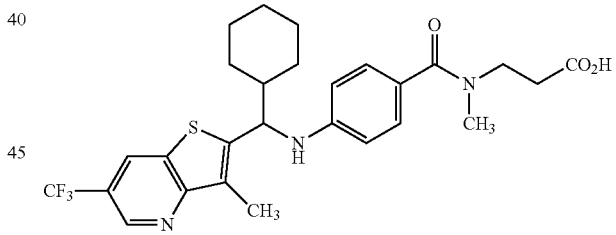

(1) ethyl 3-methyl-6-(trifluoromethyl)thieno[3,2-b]pyridine-2-carboxylate

To a solution (50 mL) of 3-chloro-5-(trifluoromethyl)pyridine-2-carbonitrile (5.00 g) in tetrahydrofuran was added 3.0M solution (16.1 mL) of methylmagnesium bromide in diethyl ether at 0° C., and the mixture was stirred for 3 hr under argon atmosphere. To the reaction mixture was added 1N hydrochloric acid (300 mL) to acidify the solution to pH=3-4, and the mixture was extracted with ethyl acetate. The extract was washed with saturated brine, dried over anhydrous magnesium sulfate, and concentrated under reduced pressure. The residue was purified by silica gel column chromatography (0-10% ethyl acetate/hexane) to give a pale-yellow solid. To a mixture of the obtained solid, ethyl mercaptoacetate (1.61 mL) and N,N-dimethylformamide (30 mL) was added potassium carbonate (5.56 g), and the mixture was stirred at 50° C. for 10 hr. Water was added to quench the reaction, and the precipitated solid was collected by filtration to give the title object compound (3.76 g, 54%) as a white solid.

$^1$H NMR (300 MHz, CDCl$_3$) δ ppm 1.45 (t, J=7.1 Hz, 3H), 2.88 (s, 3H), 4.45 (q, J=7.1 Hz, 2H), 8.39-8.45 (m, 1H), 8.94-9.02 (m, 1H).

(2) 3-methyl-6-(trifluoromethyl)thieno[3,2-b]pyridine-2-carbaldehyde

To a mixture of ethyl 3-methyl-6-(trifluoromethyl)thieno[3,2-b]pyridine-2-carboxylate (3.69 g) synthesized above, calcium chloride (2.84 g), ethanol (40 mL) and tetrahydrofuran (40 mL) was added sodium borohydride (1.94 g) at 0° C., and the mixture was stirred overnight at room temperature. Saturated aqueous ammonium chloride solution was added to quench the reaction, and the reaction mixture was extracted with ethyl acetate. The extract was washed with saturated brine, dried over magnesium sulfate, and concentrated under reduced pressure to give a white solid. To a solution (60 mL) of the obtained solid in tetrahydrofuran was added active manganese dioxide (16.3 g), and the mixture was stirred at 50° C. for 5 hr. Manganese dioxide was filtered off, and the filtrate was concentrated under reduced pressure to give the title object compound (2.88 g, 92%) as a white solid.

$^1$H NMR (300 MHz, CDCl$_3$) δ ppm 2.93 (s, 3H), 8.47-8.50 (m, 1H), 9.00 (d, J=1.6 Hz, 1H), 10.46 (s, 1H).

(3) cyclohexyl[3-methyl-6-(trifluoromethyl)thieno[3,2-b]pyridin-2-yl]methanone

To a solution (15 mL) of 3-methyl-6-(trifluoromethyl)thieno[3,2-b]pyridine-2-carbaldehyde (1.44 g) synthesized above in tetrahydrofuran was added 1.0M solution (8.81 mL) of cyclohexylmagnesium bromide in tetrahydrofuran at 0° C., and the mixture was stirred for 1 hr under argon atmosphere. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (10-50% ethyl acetate/hexane) to give a yellow oil. To a mixture of the obtained oil, 4-methylmorpholine N-oxide (817 mg) and acetonitrile (20 mL) was added tetrapropylammonium perruthenate (108 mg), and the mixture was stirred at room temperature for 1 hr, and concentrated under reduced pressure. The residue was purified by silica gel column chromatography (0-10% ethyl acetate/hexane) to give the title object compound (805 mg, 42%) as a yellow solid.

$^1$H NMR (300 MHz, CDCl$_3$) δ ppm 1.19-1.65 (m, 5H), 1.70-1.81 (m, 1H), 1.82-2.07 (m, 4H), 2.86 (s, 3H), 3.01-3.15 (m, 1H), 8.42 (s, 1H), 8.98 (s, 1H).

(4) methyl 4-({cyclohexyl[3-methyl-6-(trifluoromethyl)thieno[3,2-b]pyridin-2-yl]methyl}amino)benzoate To a mixture of cyclohexyl[3-methyl-6-(trifluoromethyl)thieno[3,2-b]pyridin-2-yl]methanone (805 mg) synthesized above, methyl 4-aminobenzoate (410 mg), triethylamine (2.75 mL) and methylene chloride (10 mL) was added titanium (IV) chloride (323 μL) at 0° C., and the mixture was stirred at room temperature for 1 day under argon atmosphere. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure to give a dark brown oil. To a solution (10 mL) of the obtained oil in tetrahydrofuran were added acetic acid (282 μL) and sodium cyanoborohydride (309 mg), and the mixture was stirred at room temperature for 1 hr. Saturated aqueous sodium hydrogen carbonate solution was added to quench the reaction, and the reaction mixture was extracted with ethyl acetate. The extract was washed with saturated brine, dried over magnesium sulfate, and concentrated under reduced pressure. The residue was purified by silica gel column chromatography (0-40% ethyl acetate/hexane) to give the title object compound (775 mg, 68%) as a pale-brown solid.

$^1$H NMR (300 MHz, CDCl$_3$) δ ppm 1.05-1.36 (m, 5H), 1.53-1.91 (m, 5H), 2.02-2.15 (m, 1H), 2.62 (s, 3H), 3.79 (s, 3H), 4.58 (d, J=5.5 Hz, 1H), 4.66-4.74 (m, 1H), 6.50 (d, J=8.8 Hz, 2H), 7.77 (d, J=8.8 Hz, 2H), 8.23 (d, J=1.3 Hz, 1H), 8.87 (d, J=1.3 Hz, 1H).

(5) 4-({cyclohexyl[3-methyl-6-(trifluoromethyl)thieno[3,2-b]pyridin-2-yl]methyl}amino)benzoic acid To a mixture of methyl 4-({cyclohexyl[3-methyl-6-(trifluoromethyl)thieno[3,2-b]pyridin-2-yl]methyl}amino)benzoate (775 mg) synthesized above, tetrahydrofuran (10 mL) and ethanol (10 mL) was added 1N aqueous sodium hydroxide solution (10 mL), and the mixture was stirred for 1 day with heating under reflux, and concentrated under reduced pressure. The residue was dissolved in water (20 mL), and 1N hydrochloric acid (10 mL) was added at 0° C., and the mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (671 mg, 87%) as a pale-brown solid.

$^1$H NMR (300 MHz, CDCl$_3$) δ ppm 1.07-1.38 (m, 5H), 1.53-1.93 (m, 5H), 2.00-2.14 (m, 1H), 2.62 (s, 3H), 4.55-4.80 (m, 2H), 6.50 (d, J=8.8 Hz, 2H), 7.82 (d, J=8.8 Hz, 2H), 8.23 (d, J=1.3 Hz, 1H), 8.88 (d, J=1.3 Hz, 1H).

(6) ethyl 3-[{[4-({cyclohexyl[3-methyl-6-(trifluoromethyl)thieno[3,2-b]pyridin-2-yl]methyl}amino)phenyl]carbonyl}(methyl)amino]propanoate To a mixture of 4-({cyclohexyl[3-methyl-6-(trifluoromethyl)thieno[3,2-b]pyridin-2-yl]methyl}amino)benzoic acid (343 mg) synthesized above, ethyl 3-(methylamino)propanoate (151 mg), 1-hydroxybenzotriazole monohydrate (176 mg), triethylamine (321 μL) and N,N-dimethylformamide (10 mL) was added 1-ethyl-3-(3-dimethylaminopropyl)carbodiimide hydrochloride (221 mg), and the mixture was stirred at room temperature for 2.5 days. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (310 mg, 72%) as a white solid.

$^1$H NMR (300 MHz, CDCl$_3$) δ ppm 1.08-1.35 (m, 8H), 1.54-1.92 (m, 5H), 2.01-2.13 (m, 1H), 2.51-2.68 (m, 5H), 2.99 (s, 3H), 3.69 (t, J=7.0 Hz, 2H), 4.10 (q, J=7.1 Hz, 2H), 4.37-4.46 (m, 1H), 4.60-4.68 (m, 1H), 6.49 (d, J=8.7 Hz, 2H), 7.19 (d, J=8.7 Hz, 2H), 8.24 (s, 1H), 8.87 (s, 1H).

(7) 3-[{[4-({cyclohexyl[3-methyl-6-(trifluoromethyl)thieno[3,2-b]pyridin-2-yl]methyl}amino)phenyl]carbonyl}(methyl)amino]propanoic acid To a mixture of ethyl 3-[{[4-({cyclohexyl[3-methyl-6-(trifluoromethyl)thieno[3,2-b]pyridin-2-yl]methyl}amino)phenyl]carbonyl}(methyl)amino]propanoate (310 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), 1N hydrochloric acid (2.00 mL) was added at 0° C. The resulting precipitate was collected by filtration to give the title object compound (284 mg, 96%) as a white solid.
$^1$H NMR (300 MHz, CDCl$_3$) δ ppm 1.07-1.35 (m, 5H), 1.53-1.89 (m, 5H), 2.00-2.12 (m, 1H), 2.54-2.69 (m, 5H), 3.00 (s, 3H), 3.68 (t, J=6.6 Hz, 2H), 4.64 (d, J=7.2 Hz, 1H), 6.49 (d, J=8.3 Hz, 2H), 7.20 (d, J=8.3 Hz, 2H), 8.25 (s, 1H), 8.88 (s, 1H).

Example A147

3-[({4-[(cyclohexyl{3-methyl-5-[2-(methylthio)ethoxy]-1-benzofuran-2-yl}methyl)amino]phenyl}carbonyl)(methyl)amino]propanoic acid

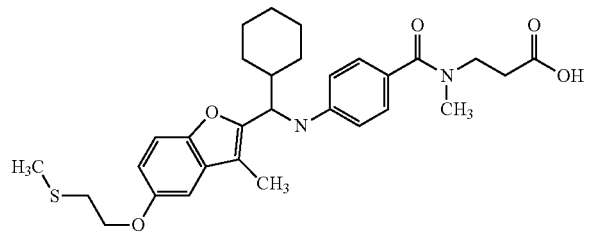 [SMILES: CSCCOc1ccc2oc(C(Nc3ccc(C(=O)N(C)CCC(=O)O)cc3)C3CCCCC3)c(C)c2c1]

(1) cyclohexyl{3-methyl-5-[2-(methylsulfanyl)ethoxy]-1-benzofuran-2-yl}methanone Cyclohexyl(5-hydroxy-3-methyl-1-benzofuran-2-yl)methanone (0.76 g) synthesized in Example A82(3) was dissolved in tetrahydrofuran (15 mL), and 2-(methylthio)ethanol (0.26 mL), tributylphosphine (1.5 mL) and 1,1'-(azodicarbonyl)dipiperidine (1.46 g) were added to the solution under ice-cooling. The ice bath was removed, and the reaction mixture was stirred at room temperature for 12 hr. Hexane (15 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:4, volume ratio) to give the title object compound (0.73 g, 76%) as a pale-yellow oil.
$^1$H NMR (300 MHz, CDCl$_3$) δ ppm 1.18-2.01 (m, 10H), 2.24 (s, 3H), 2.57 (s, 3H), 2.92 (t, J=6.8 Hz, 2H), 3.25-3.40 (m, 1H), 4.21 (t, J=6.8 Hz, 2H), 7.03-7.41 (m, 3H).

(2) cyclohexyl{3-methyl-5-[2-(methylsulfanyl)ethoxy]-1-benzofuran-2-yl}methanol

Cyclohexyl{3-methyl-5-[2-(methylsulfanyl)ethoxy]-1-benzofuran-2-yl}methanone (0.73 g) synthesized in the above-mentioned (1) was dissolved in a tetrahydrofuran (10 mL) and methanol (5 mL), and sodium borohydride (90%, 0.18 g) was added to the solution under ice-cooling. The ice bath was removed, and the reaction mixture was stirred at room temperature for 1 hr. The mixture was ice-cooled again, water (1 mL) and 1N hydrochloric acid (5 mL) were carefully added, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (0.67 g, 91%) as a pale-yellow oil.
$^1$H NMR (300 MHz, CDCl$_3$) δ ppm 0.86-1.99 (m, 11H), 2.19 (s, 3H), 2.23 (s, 3H), 2.91 (t, J=6.9 Hz, 2H), 4.20 (t, J=6.9 Hz, 2H), 4.51 (dd, J=8.5, 6.0 Hz, 1H), 6.79-6.98 (m, 2H), 7.31 (d, J=9.0 Hz, 1H).

(3) ethyl 3-[({4-[(cyclohexyl{3-methyl-5-[2-(methylsulfanyl)ethoxy]-1-benzofuran-2-yl}methyl)amino]phenyl}carbonyl)(methyl)amino]propanoate Cyclohexyl{3-methyl-5-[2-(methylsulfanyl)ethoxy]-1-benzofuran-2-yl}methanol (0.34 g) synthesized in the above-mentioned (2) was dissolved in tetrahydrofuran (5 mL), and thionyl chloride (0.13 mL) was added to the solution at room temperature. The reaction mixture was stirred at room temperature for 30 min then ice-cooled, and saturated aqueous sodium hydrogen carbonate solution (10 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (5 mL), sodium iodide (0.23 g), sodium carbonate (0.15 g) and ethyl 3-{[(4-aminophenyl)carbonyl](methyl)amino}propanoate (0.25 g) synthesized in Example 2(2) were added to the solution, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (0.33 g, 59%) as a yellow oil.
$^1$H NMR (300 MHz, CDCl$_3$) δ ppm 1.00-2.00 (m, 15H), 2.05 (s, 3H), 2.22 (s, 3H), 2.61 (t, J=6.8 Hz, 2H), 2.89 (t, J=6.9 Hz, 2H), 3.01 (s, 3H), 3.70 (t, J=6.8 Hz, 2H), 4.00-4.20 (m, 4H), 4.36 (d, J=8.0 Hz, 1H), 6.56 (d, J=8.7 Hz, 2H), 6.78-6.94 (m, 2H), 7.14-7.25 (m, 3H).

(4) 3-[({4-[(cyclohexyl{3-methyl-5-[2-(methylthio)ethoxy]-1-benzofuran-2-yl}methyl)amino]phenyl}carbonyl)(methyl)amino]propanoic acid Ethyl 3-[({4-[(cyclohexyl{3-methyl-5-[2-(methylsulfanyl)ethoxy]-1-benzofuran-2-yl}methyl)amino]phenyl}carbonyl)(methyl)amino]propanoate (0.33 g) synthesized in the above-mentioned (3) was dissolved in ethanol (2 mL), 1N aqueous sodium hydroxide solution (1.5 mL) was added to the solution at room temperature, and the mixture was stirred at 50° C. for 0.5 hr. Ethanol was evaporated under reduced pressure, 1N hydrochloric acid (1.5 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.20 g, 63%) as a colorless solid.

¹H NMR (300 MHz, DMSO-d₆) δ ppm 0.88-2.11 (m, 12H), 2.15 (s, 3H), 2.23 (s, 3H), 2.40-2.46 (m, 2H), 2.76-2.96 (m, 5H), 3.50 (t, J=7.3 Hz, 2H), 4.15 (t, J=6.7 Hz, 2H), 4.37 (t, J=8.3 Hz, 1H), 6.46 (d, J=8.1 Hz, 1H), 6.59 (d, J=8.7 Hz, 2H), 6.80 (dd, J=8.7, 2.6 Hz, 1H), 7.03 (d, J=2.6 Hz, 1H), 7.09 (d, J=8.7 Hz, 2H), 7.32 (d, J=8.7 Hz, 1H).

Example A148

3-[({4-[(cyclohexyl{3-methyl-5-[2-(methylthio)ethoxy]-1-benzofuran-2-yl}methyl)amino]phenyl}carbonyl)amino]propanoic acid

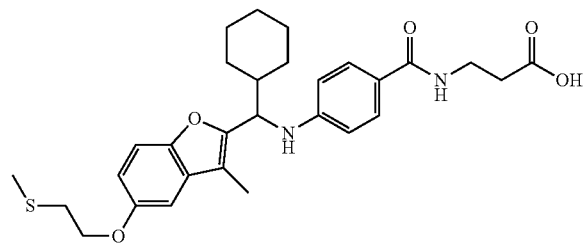

Cyclohexyl{3-methyl-5-[2-(methylsulfanyl)ethoxy]-1-benzofuran-2-yl}methanol synthesized in Example A147(2) was dissolved in tetrahydrofuran (5 mL), and thionyl chloride (0.13 mL) was added to the solution at room temperature. The reaction mixture was stirred at room temperature for 30 min then ice-cooled, and saturated aqueous sodium hydrogen carbonate solution (10 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (5 mL), sodium iodide (0.23 g), sodium carbonate (0.15 g) and ethyl 3-{[(4-aminophenyl)carbonyl]amino}propanoate (0.25 g) synthesized in Example 1(2) were added, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (0.38 g, 69%) as a yellow oil. This was dissolved in ethanol (2 mL), 1N aqueous sodium hydroxide solution (1.5 mL) was added to the solution at room temperature, and the mixture was stirred at 50° C. for 0.5 hr. Ethanol was evaporated under reduced pressure, 1N hydrochloric acid (1.5 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.18 g, 49%) as a colorless solid.

¹H NMR (300 MHz, DMSO-d₆) δ ppm 0.88-2.10 (m, 12H), 2.15 (s, 3H), 2.23 (s, 3H), 2.42 (t, J=7.2 Hz, 2H), 2.84 (t, J=6.5 Hz, 2H), 3.47-3.55 (m, 2H), 4.15 (t, J=6.6 Hz, 2H), 4.41 (t, J=8.4 Hz, 1H), 6.49-6.64 (m, 3H), 6.79 (dd, J=8.9, 2.5 Hz, 1H), 7.03 (d, J=2.4 Hz, 1H), 7.32 (d, J=8.9 Hz, 1H), 7.51 (d, J=8.7 Hz, 2H), 7.99 (t, J=5.5 Hz, 1H).

Example A149

3-[{[4-({cyclohexyl[5-(2-methoxyethoxy)-3-methyl-1-benzofuran-2-yl]methyl}amino)phenyl]carbonyl}amino]propanoic acid

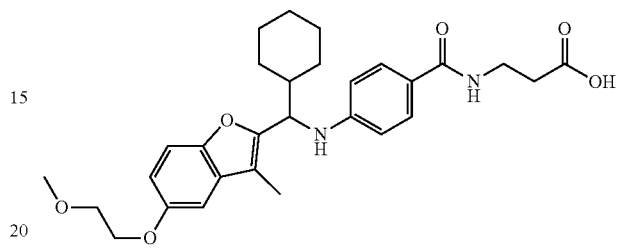

To a solution (15 mL) of cyclohexyl[5-(2-methoxyethoxy)-3-methyl-1-benzofuran-2-yl]methanol (0.86 g) synthesized in Example A79(3) in tetrahydrofuran was added thionyl chloride (0.35 mL) at room temperature. The reaction mixture was stirred at room temperature for 30 min then ice-cooled, and saturated aqueous sodium hydrogen carbonate solution (20 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (15 mL), sodium iodide (0.61 g), sodium carbonate (0.41 g) and ethyl 3-{[(4-aminophenyl)carbonyl]amino}propanoate (0.64 g) synthesized in Example 1(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[5-(2-methoxyethoxy)-3-methyl-1-benzofuran-2-yl]methyl}amino)phenyl]carbonyl}amino]propanoate (0.62 g, 43%) as a yellow oil. This was dissolved in ethanol (5 mL), 1N aqueous sodium hydroxide solution (3.0 mL) was added to the solution at room temperature, and the mixture was stirred at 50° C. for 0.5 hr. Ethanol was evaporated under reduced pressure, 1N hydrochloric acid (3.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.54 g, 91%) as a colorless solid.

¹H NMR (300 MHz, CDCl₃) δ ppm 0.93-2.13 (m, 12H), 2.21 (s, 3H), 2.66 (t, J=5.7 Hz, 2H), 3.46 (s, 3H), 3.58-3.71 (m, 2H), 3.76 (dd, J=5.6, 4.1 Hz, 2H), 4.14 (dd, J=5.7, 4.1 Hz, 2H), 4.38 (d, J=7.9 Hz, 1H), 6.57-6.65 (m, 3H), 6.80-6.98 (m, 2H), 7.22-7.26 (m, 1H), 7.53 (d, J=8.7 Hz, 2H).

Example A150

3-[({4-[(cyclohexyl{3-methyl-5-[3-(methylsulfanyl)propoxy]-1-benzofuran-2-yl}methyl)amino]phenyl}carbonyl)(methyl)amino]propanoic acid

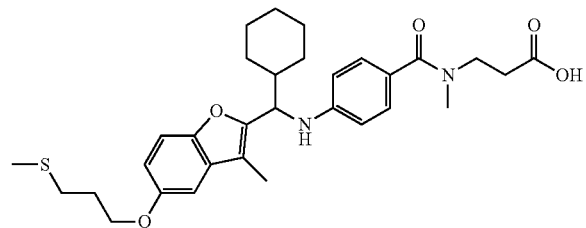 [SMILES: CSCCCOc1ccc2oc(C(Nc3ccc(C(=O)N(C)CCC(=O)O)cc3)C3CCCCC3)c(C)c2c1]

(1) cyclohexyl{3-methyl-5-[3-(methylsulfanyl)propoxy]-1-benzofuran-2-yl}methanone Cyclohexyl(5-hydroxy-3-methyl-1-benzofuran-2-yl)methanone (2.4 g) synthesized in Example A82(3) was dissolved in tetrahydrofuran (50 mL), and 3-(methylthio)propanol (1.0 mL), tributylphosphine (4.7 mL) and 1,1'-(azodicarbonyl)dipiperidine (4.7 g) were added to the solution under ice-cooling. The ice bath was removed and the reaction mixture was stirred at room temperature for 12 hr. Hexane (50 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:4, volume ratio) to give the title object compound (3.1 g, 95%) as a pale-yellow oil.
$^1$H NMR (300 MHz, CDCl$_3$) δ ppm 1.18-2.01 (m, 12H), 2.14 (s, 3H), 2.56 (s, 3H), 2.72 (t, J=7.2 Hz, 2H), 3.25-3.40 (m, 1H), 4.08-4.20 (m, 2H), 7.03-7.42 (m, 3H).

(2) cyclohexyl{3-methyl-5-[3-(methylsulfanyl)propoxy]-1-benzofuran-2-yl}methanol Cyclohexyl{3-methyl-5-[3-(methylsulfanyl)propoxy]-1-benzofuran-2-yl}methanone (3.1 g) synthesized in the above-mentioned (1) was dissolved in tetrahydrofuran (50 mL) and methanol (10 mL), and sodium borohydride (90%, 0.73 g) was added to the solution under ice-cooling. The ice bath was removed, the reaction mixture was stirred at room temperature for 1 hr then ice-cooled again, and water (5 mL) and 1N hydrochloric acid (25 mL) were carefully added to the mixture, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (3.0 g, 95%) as a pale-yellow oil.
$^1$H NMR (300 MHz, CDCl$_3$) δ ppm 1.18-2.01 (m, 14H), 2.13 (s, 3H), 2.19 (s, 3H), 2.72 (t, J=7.2 Hz, 2H), 4.11 (t, J=7.2 Hz, 2H), 4.40-4.55 (m, 1H), 6.80-7.42 (m, 3H).

(3) ethyl 3-[({4-[(cyclohexyl{3-methyl-5-[3-(methylsulfanyl)propoxy]-1-benzofuran-2-yl}methyl)amino]phenyl}carbonyl)(methyl)amino]propanoate Cyclohexyl{3-methyl-5-[3-(methylsulfanyl)propoxy]-1-benzofuran-2-yl}methanol (1.5 g) synthesized in the above-mentioned (2) was dissolved in tetrahydrofuran (10 mL), and thionyl chloride (0.56 mL) was added to the solution at room temperature. The reaction mixture was stirred at room temperature for 30 min then ice-cooled, and saturated aqueous sodium hydrogen carbonate solution (30 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (10 mL), sodium iodide (0.95 g), sodium carbonate (0.63 g) and ethyl 3-{[(4-aminophenyl)carbonyl](methyl)amino}propanoate (1.1 g) synthesized in Example 2(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (1.4 g, 56%) as a yellow oil.
$^1$H NMR (300 MHz, CDCl$_3$) δ ppm 1.00-2.00 (m, 17H), 2.12 (s, 3H), 2.21 (s, 3H), 2.52-2.79 (m, 4H), 3.01 (s, 3H), 3.70 (t, J=7.2 Hz, 2H), 4.00-4.36 (m, 5H), 6.56 (d, J=8.7 Hz, 2H), 6.78-6.94 (m, 2H), 7.14-7.25 (m, 3H).

(4) 3-[({4-[(cyclohexyl{3-methyl-5-[3-(methylsulfanyl)propoxy]-1-benzofuran-2-yl}methyl)amino]phenyl}carbonyl)(methyl)amino]propanoic acid Ethyl 3-[({4-[(cyclohexyl{3-methyl-5-[3-(methylsulfanyl)propoxy]-1-benzofuran-2-yl}methyl)amino]phenyl}carbonyl)(methyl)amino]propanoate (0.37 g) synthesized in the above-mentioned (3) was dissolved in ethanol (5 mL), 1N aqueous sodium hydroxide solution (2.0 mL) was added to the solution at room temperature, and the mixture was stirred at 50° C. for 0.5 hr. Ethanol was evaporated under reduced pressure, 1N hydrochloric acid (2.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.28 g, 79%) as a colorless solid.
$^1$H NMR (300 MHz, CDCl$_3$) δ ppm 0.89-2.10 (m, 14H), 2.12 (s, 3H), 2.21 (s, 3H), 2.52-2.81 (m, 4H), 3.04 (s, 3H), 3.70 (q, J=6.4 Hz, 2H), 4.09 (t, J=6.4 Hz, 2H), 4.36 (d, J=7.9 Hz, 1H), 6.56 (d, J=8.7 Hz, 2H), 6.77-6.96 (m, 2H), 7.20-7.26 (m, 3H).

Example A151

3-[({4-[(cyclohexyl{3-methyl-5-[3-(methylsulfanyl)propoxy]-1-benzofuran-2-yl}methyl)amino]phenyl}carbonyl)amino]propanoic acid

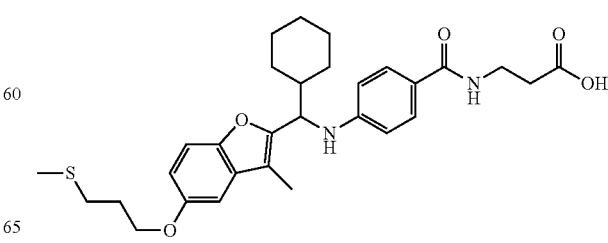

(1) ethyl 3-[({4-[(cyclohexyl{3-methyl-5-[3-(methylsulfanyl)propoxy]-1-benzofuran-2-yl}methyl)amino]phenyl}carbonyl)amino]propanoate Cyclohexyl{3-methyl-5-[3-(methylsulfanyl)propoxy]-1-benzofuran-2-yl}methanol (1.5 g) synthesized in Example A150(2) was dissolved in tetrahydrofuran (10 mL), and thionyl chloride (0.56 mL) was added to the solution at room temperature. The reaction mixture was stirred at room temperature for 30 min then ice-cooled, and saturated aqueous sodium hydrogen carbonate solution (30 mL) was carefully added. The reaction mixture was stirred for 10 min, and extracted with ethyl acetate. The extract was washed with saturated brine, dried over magnesium sulfate, and concentrated under reduced pressure. The residue was dissolved in N,N-dimethylacetamide (10 mL), sodium iodide (0.95 g), sodium carbonate (0.63 g) and ethyl 3-{[(4-aminophenyl)carbonyl]amino}propanoate (1.0 g) synthesized in Example 1(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (1.8 g, 77%) as a yellow oil.

$^1$H NMR (300 MHz, CDCl$_3$) δ ppm 1.00-2.00 (m, 17H), 2.12 (s, 3H), 2.21 (s, 3H), 2.52-2.79 (m, 4H), 3.66 (q 3=6.0 Hz, 2H), 4.00-4.60 (m, 5H), 6.56 (d, J=8.9 Hz, 2H), 6.58 (br. s. 1H), 6.78-6.94 (m, 2H), 7.20-7.60 (m, 3H).

(2) 3-[({4-[(cyclohexyl{3-methyl-5-[3-(methylsulfanyl)propoxy]-1-benzofuran-2-yl}methyl)amino]phenyl}carbonyl)amino]propanoic acid Ethyl 3-[({4-[(cyclohexyl{3-methyl-5-[3-(methylsulfanyl)propoxy]-1-benzofuran-2-yl}methyl)amino]phenyl}carbonyl)amino]propanoate (0.25 g) synthesized in the above-mentioned (1) was dissolved in ethanol (5 mL), 1N aqueous sodium hydroxide solution (2.0 mL) was added to the solution at room temperature, and the mixture was stirred at 50° C. for 0.5 hr. Ethanol was evaporated under reduced pressure, 1N hydrochloric acid (2.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.07 g, 31%) as a colorless solid.

$^1$H NMR (300 MHz, CDCl$_3$) δ ppm 0.82-2.16 (m, 14H), 2.22 (s, 3H), 2.52-2.81 (m, 4H), 3.66 (q, J=6.0 Hz, 2H), 4.08 (t, J=6.0 Hz, 2H), 4.38 (d, J=7.9 Hz, 1H), 6.43-6.66 (m, 3H), 6.74-6.96 (m, 2H), 7.20-7.26 (m, 1H), 7.53 (d, J=8.9 Hz, 2H).

Example A152

3-[({4-[(cyclohexyl{3-methyl-5-[3-(methylsulfonyl)propoxy]-1-benzofuran-2-yl}methyl)amino]phenyl}carbonyl)(methyl)amino]propanoic acid

(1) ethyl 3-[({4-[(cyclohexyl{3-methyl-5-[3-(methylsulfonyl)propoxy]-1-benzofuran-2-yl}methyl)amino]phenyl}carbonyl)(methyl)amino]propanoate Ethyl 3-[({4-[(cyclohexyl{3-methyl-5-[3-(methylsulfanyl)propoxy]-1-benzofuran-2-yl}methyl)amino]phenyl}carbonyl)(methyl)amino]propanoate (0.61 g) synthesized in Example A150(3) was dissolved in methanol (15 mL) and water (2 mL), oxone (2.1 g) was added to the solution at room temperature, and the mixture was stirred for 30 min. Water was added to the reaction mixture, and the mixture was extracted with diethyl ether. The extract was concentrated under reduced pressure, and the residue was purified by silica gel column chromatography (ethyl acetate:hexane=1:1, volume ratio) to give the title object compound (0.48 g, 75%) as a yellow oil.

$^1$H NMR (300 MHz, CDCl$_3$) δ ppm 0.94-2.01 (m, 17H), 2.21 (s, 3H), 2.28-2.42 (m, 2H), 2.61 (t, J=6.9 Hz, 2H), 2.95 (s, 3H), 3.01 (s, 3H), 3.20-3.36 (m, 2H), 3.70 (t, J=6.9 Hz, 2H), 4.04-4.19 (m, 2H), 4.26-4.44 (m, 1H), 6.56 (d, J=8.7 Hz, 2H), 6.74-6.91 (m, 2H), 7.15-7.25 (m, 3H).

(2) 3-[({4-[(cyclohexyl{3-methyl-5-[3-(methylsulfonyl)propoxy]-1-benzofuran-2-yl}methyl)amino]phenyl}carbonyl)(methyl)amino]propanoic acid Ethyl 3-[({4-[(cyclohexyl{3-methyl-5-[3-(methylsulfonyl)propoxy]-1-benzofuran-2-yl}methyl)amino]phenyl}carbonyl)(methyl)amino]propanoate (0.48 g) synthesized in the above-mentioned (1) was dissolved in ethanol (5 mL), 1N aqueous sodium hydroxide solution (1.5 mL) was added to the solution at room temperature, and the mixture was stirred at 50° C. for 0.5 hr. Ethanol was evaporated under reduced pressure, 1N hydrochloric acid (1.5 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.35 g, 78%) as a colorless solid.

$^1$H NMR (300 MHz, CDCl$_3$) δ ppm 0.87-2.15 (m, 12H), 2.21 (s, 3H), 2.25-2.45 (m, 2H), 2.67 (br. s., 2H), 2.95 (s, 3H), 3.04 (s, 3H), 3.17-3.36 (m, 2H), 3.69 (t, J=6.5 Hz, 2H), 4.13 (t, J=5.7 Hz, 2H), 4.36 (d, J=7.9 Hz, 1H), 6.56 (d, J=8.7 Hz, 2H), 6.70-6.93 (m, 2H), 7.16-7.26 (m, 3H).

Example A153

3-[({4-[(cyclohexyl{3-methyl-5-[3-(methylsulfonyl)propoxy]-1-benzofuran-2-yl}methyl)amino]phenyl}carbonyl)amino]propanoic acid

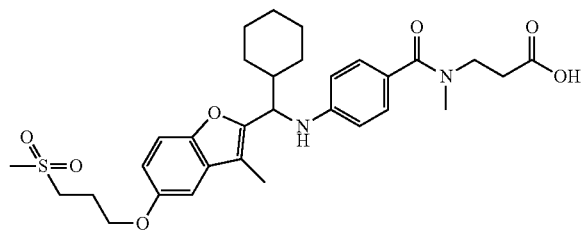 [SMILES: Cc1c(C(Nc2ccc(C(=O)N(C)CCC(=O)O)cc2)C2CCCCC2)oc2ccc(OCCCS(C)(=O)=O)cc12]

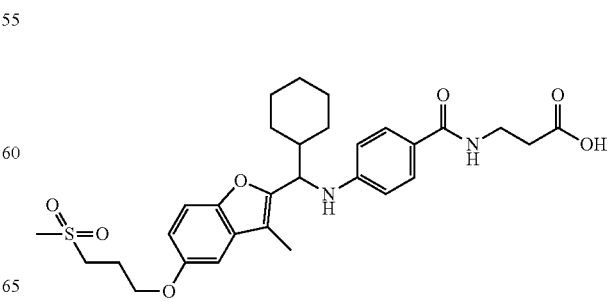

(1) ethyl 3-[({4-[(cyclohexyl{3-methyl-5-[3-(methylsulfonyl)propoxy]-1-benzofuran-2-yl}methyl)amino]phenyl}carbonyl)amino]propanoate Ethyl 3-[({4-[(cyclohexyl{3-methyl-5-[3-(methylsulfanyl)propoxy]-1-benzofuran-2-yl}methyl)amino]phenyl}carbonyl)amino]propanoate (0.16 g) synthesized in Example A151(1) was dissolved in acetone (5 mL), metachloroperbenzoic acid (0.2 g) was added to the solution under ice-cooling, and the mixture was stirred for 15 min. To the reaction mixture was added sodium sulfite aqueous solution, and the mixture was extracted with ethyl acetate. The extract was concentrated under reduced pressure, and the residue was purified by silica gel column chromatography (ethyl acetate:hexane=1:1, volume ratio) to give the title object compound (0.11 g, 68%) as a yellow oil.
$^1$H NMR (300 MHz, CDCl$_3$) δ ppm 0.89-1.92 (m, 17H), 2.22 (s, 3H), 2.25-2.44 (m, 2H), 2.58 (t, J=5.8 Hz, 2H), 2.95 (s, 3H), 3.14-3.35 (m, 2H), 3.66 (q, J=6.8 Hz, 2H), 4.13 (q, J=7.2 Hz, 2H), 4.38 (d, J=7.9 Hz, 1H), 6.43-6.64 (m, 3H), 6.73-6.90 (m, 2H), 7.16-7.25 (m, 1H), 7.54 (d, J=8.7 Hz, 2H).

(2) 3-[({4-[(cyclohexyl{3-methyl-5-[3-(methylsulfonyl)propoxy]-1-benzofuran-2-yl}methyl)amino]phenyl}carbonyl)amino]propanoic acid Ethyl 3-[({4-[(cyclohexyl{3-methyl-5-[3-(methylsulfonyl)propoxy]-1-benzofuran-2-yl}methyl)amino]phenyl}carbonyl)amino]propanoate (0.11 g) synthesized in the above-mentioned (1) was dissolved in ethanol (3 mL), 1N aqueous sodium hydroxide solution (1.0 mL) was added to the solution at room temperature, and the mixture was stirred at 50° C. for 0.5 hr. Ethanol was evaporated under reduced pressure, 1N hydrochloric acid (1.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.9 g, 80%) as a colorless solid.
$^1$H NMR (300 MHz, CDCl$_3$) δ ppm 0.90-2.14 (m, 14H), 2.22 (s, 3H), 2.26-2.42 (m, 2H), 2.60-2.72 (m, 2H), 2.95 (s, 3H), 3.17-3.33 (m, 2H), 3.66 (q, J=5.7 Hz, 2H), 4.13 (t, J=5.7 Hz, 2H), 4.38 (d, J=7.9 Hz, 1H), 6.47-6.62 (m, 3H), 6.74-6.90 (m, 2H), 7.20-7.26 (m, 1H), 7.53 (d, J=8.7 Hz, 2H).

Example A154

3-[{[4-({[5-(benzyloxy)-3-methyl-1-benzofuran-2-yl](cyclohexyl)methyl}amino)phenyl]carbonyl}(methyl)amino]-propanoic acid

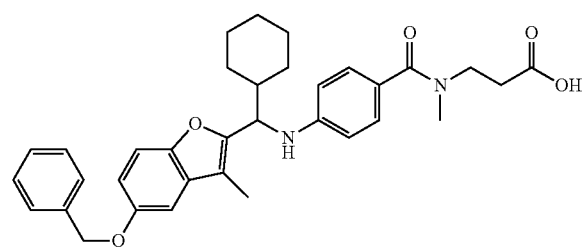

(1) [5-(benzyloxy)-3-methyl-1-benzofuran-2-yl](cyclohexyl)methanol

[5-(Benzyloxy)-3-methyl-1-benzofuran-2-yl](cyclohexyl)methanone (1.5 g) synthesized in Example A82(2) was dissolved in tetrahydrofuran (25 mL) and methanol (5 mL), and sodium borohydride (90%, 0.36 g) was added to the solution under ice-cooling. The ice bath was removed, the reaction mixture was stirred at room temperature for 1 hr then ice-cooled again, and water (5 mL) and 1N hydrochloric acid (10 mL) were carefully added, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (1.4 g, 95%) as a pale-yellow oil.
$^1$H NMR (300 MHz, CDCl$_3$) δ ppm 0.81-2.00 (m, 12H), 2.18 (s, 3H), 4.51 (d, J=8.3 Hz, 1H), 5.10 (s, 2H), 6.87-7.06 (m, 2H), 7.29-7.58 (m, 6H).

(2) ethyl 3-[{[4-({[5-(benzyloxy)-3-methyl-1-benzofuran-2-yl](cyclohexyl)methyl}amino)phenyl]carbonyl}(methyl)amino]-propanoate

[5-(Benzyloxy)-3-methyl-1-benzofuran-2-yl](cyclohexyl)methanol (1.5 g) synthesized in the above-mentioned (1) was dissolved in tetrahydrofuran (20 mL), and thionyl chloride (0.57 mL) was added to the solution at room temperature. The reaction mixture was stirred at room temperature for 30 min then ice-cooled, and saturated aqueous sodium hydrogen carbonate solution (30 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (15 mL), sodium iodide (0.98 g), sodium carbonate (0.65 g) and ethyl 3-{[(4-aminophenyl)carbonyl](methyl)amino}propanoate (1.1 g) synthesized in Example 2(2) were added, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (1.8 g, 72%) as a yellow oil.
$^1$H NMR (300 MHz, CDCl$_3$) δ ppm 0.86-2.00 (m, 15H), 2.21 (s, 3H), 2.61 (t, J=7.1 Hz, 2H), 3.01 (s, 3H), 3.70 (t, J=7.1 Hz, 2H), 4.12 (q, J=7.2 Hz, 2H), 4.27-4.43 (m, 2H), 5.08 (s, 2H), 6.56 (d, J=8.7 Hz, 2H), 6.79-7.01 (m, 2H), 7.13-7.24 (m, 3H), 7.30-7.59 (m, 5H).

(3) 3-[{[4-({[5-(benzyloxy)-3-methyl-1-benzofuran-2-yl](cyclohexyl)methyl}amino)phenyl]carbonyl}(methyl)amino]-propanoic acid Ethyl 3-[{[4-({[5-(benzyloxy)-3-methyl-1-benzofuran-2-yl](cyclohexyl)methyl}amino)phenyl]carbonyl}(methyl)amino]-propanoate (0.2 g) synthesized in the above-mentioned (2) was dissolved in ethanol (5 mL), 1N aqueous sodium hydroxide solution (1.5 mL) was added to the solution at room temperature, and the mixture was stirred at room temperature for 0.5 hr. Ethanol was evaporated under reduced pressure, 1N hydrochloric acid (1.5 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.18 g, 94%) as a colorless solid.
$^1$H NMR (300 MHz, CDCl$_3$) δ ppm 0.79-2.14 (m, 12H), 2.21 (s, 3H), 2.63 (t, J=6.2 Hz, 2H), 3.01 (s, 3H), 3.68 (t, J=6.2

Hz, 2H), 4.36 (d, J=7.9 Hz, 1H), 5.08 (s, 2H), 6.55 (d, J=8.7 Hz, 2H), 6.80-7.03 (m, 2H), 7.13-7.52 (m, 8H).

Example A155

3-[{[4-({cyclohexyl[3-methyl-5-(pyridin-2-yl-methoxy)-1-benzofuran-2-yl]methyl}amino)phenyl]carbonyl}(methyl)amino]propanoic acid

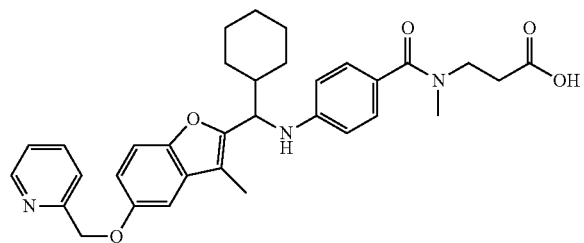 [SMILES: Cc1c(C(Nc2ccc(C(=O)N(C)CCC(=O)O)cc2)C2CCCCC2)oc2ccc(OCc3ccccn3)cc12]

(1) ethyl 3-{[(4-{[cyclohexyl(5-hydroxy-3-methyl-1-benzofuran-2-yl)methyl]amino}phenyl)carbonyl](methyl)amino}propanoate Ethyl 3-[{[4-({[5-(benzyloxy)-3-methyl-1-benzofuran-2-yl](cyclohexyl)methyl}amino)phenyl]carbonyl}(methyl)amino]-propanoate (2.46 g) synthesized in Example A154(2) was dissolved in ethanol (50 mL), and platinum oxide (0.33 g) was added to the solution. The reaction mixture was stirred under hydrogen atmosphere (1 atm) at room temperature overnight. The reaction mixture was filtered, and the residue was washed with ethanol. The filtrate was concentrated under reduced pressure, and the residue was purified by silica gel column chromatography (ethyl acetate:hexane=1:1, volume ratio) to give the title object compound (1.64 g, 79%) as a yellow oil.

$^1$H NMR (300 MHz, CDCl$_3$) δ ppm 0.91-1.91 (m, 15H), 2.18 (s, 3H), 2.61 (t, J=7.1 Hz, 2H), 3.01 (s, 3H), 3.71 (t, J=7.1 Hz, 2H), 4.02-4.18 (m, 2H), 4.28-4.41 (m, 1H), 4.86 (s, 1H), 6.55 (d, J=8.7 Hz, 2H), 6.66-6.87 (m, 2H), 7.14-7.25 (m, 3H).

(2) ethyl 3-[{[4-({cyclohexyl[3-methyl-5-(pyridin-2-ylmethoxy)-1-benzofuran-2-yl]methyl}amino)phenyl]carbonyl}(methyl)amino]propanoate Ethyl 3-{[(4-{[cyclohexyl(5-hydroxy-3-methyl-1-benzofuran-2-yl)methyl]amino}phenyl)carbonyl](methyl)amino}propanoate (0.23 g) synthesized in the above-mentioned (1) was dissolved in tetrahydrofuran (5 mL), and 2-pyridinemethanol (62 mg), tributylphosphine (0.21 mL) and 1,1'-(azodicarbonyl)dipiperidine (0.21 g) were added to the solution under ice-cooling. The ice bath was removed, the reaction mixture was stirred at room temperature for 12 hr, then hexane (15 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:1, volume ratio) to give the title object compound (0.19 g, 70%) as a pale-yellow oil.

$^1$H NMR (300 MHz, CDCl$_3$) δ ppm 0.88-1.95 (m, 15H), 2.21 (s, 3H), 2.54-2.72 (m, 2H), 3.01 (s, 3H), 3.70 (t, J=7.2 Hz, 2H), 4.01-4.21 (m, 2H), 4.22-4.54 (m, 1H), 5.10 (s, 2H), 6.56 (d, J=8.7 Hz, 2H), 6.80-7.05 (m, 2H), 7.21 (d, J=8.7 Hz, 2H), 7.28-7.40 (m, 2H), 7.79 (d, J=8.0 Hz, 1H), 8.58 (d, J=4.5 Hz, 1H), 8.70 (s, 1H).

(3) 3-[{[4-({cyclohexyl[3-methyl-5-(pyridin-2-ylmethoxy)-1-benzofuran-2-yl]methyl}amino)phenyl]carbonyl}(methyl)amino]propanoic acid Ethyl 3-[{[4-({cyclohexyl[3-methyl-5-(pyridin-2-ylmethoxy)-1-benzofuran-2-yl]methyl}amino)phenyl]carbonyl}(methyl)amino]propanoate (0.19 g) synthesized in the above-mentioned (2) was dissolved in ethanol (5 mL), 1N aqueous sodium hydroxide solution (1.0 mL) was added to the solution at room temperature, and the mixture was stirred at room temperature for 0.5 hr. Ethanol was evaporated under reduced pressure, 1N hydrochloric acid (1.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.11 g, 41%) as a yellow solid.

$^1$H NMR (300 MHz, CDCl$_3$) δ ppm 0.92-2.16 (m, 12H), 2.20 (s, 3H), 2.62 (br. s., 2H), 3.02 (s, 3H), 3.65 (br. s., 2H), 4.34 (d, J=7.9 Hz, 1H), 5.15 (s, 2H), 6.54 (d, J=8.3 Hz, 2H), 6.75-6.98 (m, 2H), 7.11-7.30 (m, 4H), 7.35-7.52 (m, 1H), 7.93 (d, J=7.9 Hz, 1H), 8.50-8.70 (m, 2H).

Example A156

3-[{[4-({cyclohexyl[3-methyl-5-(pyridin-3-ylmethoxy)-1-benzofuran-2-yl]methyl}amino)phenyl]carbonyl}(methyl)amino]propanoic acid

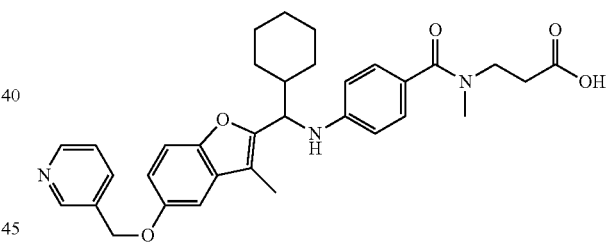

(1) ethyl 3-[{[4-({cyclohexyl[3-methyl-5-(pyridin-3-ylmethoxy)-1-benzofuran-2-yl]methyl}amino)phenyl]carbonyl}(methyl)amino]propanoate Ethyl 3-{[(4-{[cyclohexyl(5-hydroxy-3-methyl-1-benzofuran-2-yl)methyl]amino}phenyl)carbonyl]methyl)amino}propanoate (0.23 g) synthesized in Example A155(1) was dissolved in tetrahydrofuran (5 mL), and 3-pyridinemethanol (62 mg), tributylphosphine (0.21 mL) and 1,1'-(azodicarbonyl)dipiperidine (0.21 g) were added to the solution under ice-cooling. The ice bath was removed, the reaction mixture was stirred at room temperature for 12 hr, then hexane (5 mL) was added to the mixture, and the precipitate was filtered off through celite. Water was added to the filtrate and the mixture was extracted with ethyl acetate. The extract was concentrated under reduced pressure, and the residue was purified by silica gel column chromatography (ethyl acetate:hexane=1:1, volume ratio) to give the title object compound (0.13 g, 49%) as a pale-yellow oil.

$^1$H NMR (300 MHz, CDCl$_3$) δ ppm 0.85-1.95 (m, 15H), 2.19 (s, 3H), 2.61 (br. s., 2H), 3.01 (s, 3H), 3.70 (t, J=7.2 Hz, 2H), 4.12 (q, J=7.2, 2.8 Hz, 2H), 4.25-4.45 (m, 2H), 5.24 (s, 2H), 6.55 (d, J=8.7 Hz, 2H), 6.84-7.02 (m, 2H), 7.13-7.30 (m, 4H), 7.55 (d, J=7.9 Hz, 1H), 7.67-7.82 (m, 1H), 8.48-8.71 (m, 1H).

(2) 3-[{[4-({cyclohexyl[3-methyl-5-(pyridin-3-yl-methoxy)-1-benzofuran-2-yl]methyl}amino)phenyl]carbonyl}(methyl)amino]propanoic acid Ethyl 3-[{[4-({cyclohexyl[3-methyl-5-(pyridin-3-yl-methoxy)-1-benzofuran-2-yl]methyl}amino)phenyl]carbonyl}(methyl)amino]propanoate (0.13 g) synthesized in the above-mentioned (1) was dissolved in ethanol (5 mL), 1N aqueous sodium hydroxide solution (3.0 mL) was added to the solution at room temperature, and the mixture was stirred at room temperature for 0.5 hr. Ethanol was evaporated under reduced pressure, 1N hydrochloric acid (3.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.08 g, 95%) as a pale-yellow solid.

$^1$H NMR (300 MHz, CDCl$_3$) δ ppm 0.83-2.13 (m, 12H), 2.18 (s, 3H), 2.50-2.75 (br. s., 2H), 3.01 (s, 3H), 3.64 (br. s., 2H), 4.35 (d, J=7.9 Hz, 1H), 5.44 (s, 2H), 6.55 (d, J=8.7 Hz, 2H), 6.79-7.09 (m, 2H), 7.12-7.25 (m, 3H), 7.45-8.01 (m, 3H), 8.66 (br. s., 1H).

Example A157

3-[{[4-({cyclohexyl[3-methyl-5-(pyridin-4-yl-methoxy)-1-benzofuran-2-yl]methyl}amino)phenyl]carbonyl}(methyl)amino]propanoic acid

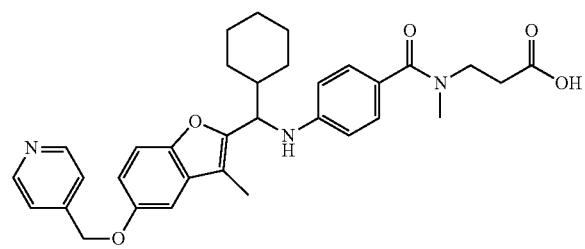 [SMILES: Cc1c(C(Nc2ccc(C(=O)N(C)CCC(=O)O)cc2)C2CCCCC2)oc2ccc(OCc3ccncc3)cc12]

(1) ethyl 3-[{[4-({cyclohexyl[3-methyl-5-(pyridin-4-ylmethoxy)-1-benzofuran-2-yl]methyl}amino)phenyl]carbonyl}(methyl)amino]propanoate Ethyl 3-{[(4-{[cyclohexyl(5-hydroxy-3-methyl-1-benzofuran-2-yl)methyl]amino}phenyl)carbonyl](methyl)amino}propanoate (0.23 g) synthesized in Example A155(1) was dissolved in tetrahydrofuran (5 mL), and 4-pyridinemethanol (62 mg), tributylphosphine (0.21 mL) and 1,1'-(azodicarbonyl)dipiperidine (0.21 g) were added to the solution under ice-cooling. The ice bath was removed, the reaction mixture was stirred at room temperature for 12 hr, then hexane (5 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:1, volume ratio) to give the title object compound (0.18 g, 64%) as a pale-yellow oil.

$^1$H NMR (300 MHz, CDCl$_3$) δ ppm 0.89-1.97 (m, 15H), 2.20 (s, 3H), 2.61 (t, J=7.2 Hz, 2H), 3.01 (s, 3H), 3.70 (t, J=7.2 Hz, 2H), 4.06-4.18 (q, J=7.2 Hz, 2H), 4.74 (d, J=4.0 Hz, 1H), 5.11 (s, 2H), 6.56 (d, J=8.7 Hz, 2H), 6.82-6.99 (m, 2H), 7.14-7.31 (m, 3H), 7.38 (d, J=6.0 Hz, 2H), 8.60-8.69 (m, 2H).

(2) 3-[{[4-({cyclohexyl[3-methyl-5-(pyridin-4-yl-methoxy)-1-benzofuran-2-yl]methyl}amino)phenyl]carbonyl}(methyl)amino]propanoic acid Ethyl 3-[{[4-({cyclohexyl[3-methyl-5-(pyridin-4-yl-methoxy)-1-benzofuran-2-yl]methyl}amino)phenyl]carbonyl}(methyl)amino]propanoate (0.17 g) synthesized in the above-mentioned (1) was dissolved in ethanol (5 mL), 1N aqueous sodium hydroxide solution (3.0 mL) was added to the solution at room temperature, and the mixture was stirred at room temperature for 0.5 hr. Ethanol was evaporated under reduced pressure, 1N hydrochloric acid (3.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.13 g, 77%) as a pale-yellow solid.

$^1$H NMR (300 MHz, CDCl$_3$) δ ppm 0.81-2.13 (m, 12H), 2.19 (s, 3H), 2.50-2.75 (br. s., 2H), 3.03 (s, 3H), 3.60-3.75 (m, 2H), 4.34 (d, J=7.9 Hz, 1H), 5.16 (s, 2H), 6.53 (d, J=8.5 Hz, 2H), 6.78-6.97 (m, 2H), 7.12-7.31 (m, 3H), 7.44 (d, J=5.8 Hz, 2H), 8.60 (d, J=5.8 Hz, 2H).

Example A158

3-({[4-({[5-(benzyloxy)-3-methyl-1-benzofuran-2-yl](cyclohexyl)methyl}amino)phenyl]carbonyl}amino)propanoic acid

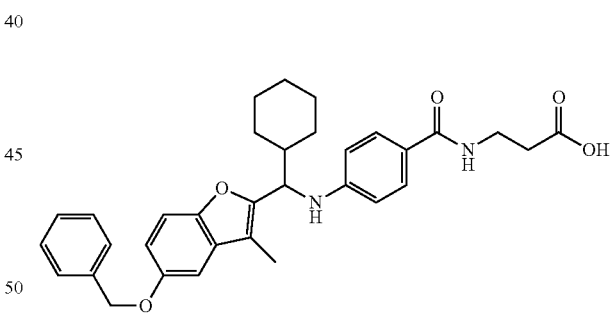

(1) ethyl 3-({[4-({[5-(benzyloxy)-3-methyl-1-benzofuran-2-yl](cyclohexyl)methyl}amino)phenyl]carbonyl}amino)propanoate

[5-(Benzyloxy)-3-methyl-1-benzofuran-2-yl](cyclohexyl)methanol (1.0 g) synthesized in Example A154(1) was dissolved in tetrahydrofuran (15 mL), and thionyl chloride (0.38 mL) was added to the solution at room temperature. The reaction mixture was stirred at room temperature for 30 min then ice-cooled, and saturated aqueous sodium hydrogen carbonate solution (30 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (20 mL), sodium iodide (0.65 g), sodium carbonate (0.43 g) and ethyl 3-{[(4-aminophenyl)carbonyl]amino}propanoate (0.68 g) synthesized in Example 1(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (0.78 g, 48%) as a yellow oil.

$^1$H NMR (300 MHz, CDCl$_3$) δ ppm 0.92-1.98 (m, 15H), 2.21 (s, 3H), 2.58 (t, J=5.7 Hz, 2H), 3.48 (q, J=7.0 Hz, 1H), 3.66 (q, J=5.7 Hz, 2H), 4.11 (q, J=7.2 Hz, 2H), 4.30-4.54 (m, 2H), 5.08 (s, 2H), 6.57-6.62 (m, 3H), 6.82-7.02 (m, 2H), 7.18-7.60 (m, 8H).

(2) 3-[{[4-({[5-(benzyloxy)-3-methyl-1-benzofuran-2-yl](cyclohexyl)methyl}amino)phenyl]carbonyl}(methyl)amino]-propanoic-acid Ethyl 3-({[4-({[5-(benzyloxy)-3-methyl-1-benzofuran-2-yl](cyclohexyl)methyl}amino)phenyl]carbonyl}amino)propanoate (0.78 g) synthesized in the above-mentioned (1) was dissolved in ethanol (5 mL), 1N aqueous sodium hydroxide solution (3.0 mL) was added to the solution at room temperature, and the mixture was stirred at room temperature for 0.5 hr. Ethanol was evaporated under reduced pressure, 1N hydrochloric acid (3.0 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.70 g, 94%) as a colorless solid.

$^1$H NMR (300 MHz, CDCl$_3$) δ ppm 0.81-2.10 (m, 12H), 2.17 (s, 3H), 2.50 (br. s., 2H), 3.55 (br. s., 2H), 4.32 (br. s., 1H), 5.04 (s, 2H), 6.51 (d, J=8.7 Hz, 2H), 6.68 (br. s., 1H), 6.81-6.99 (m, 2H), 7.23-7.59 (m, 8H).

Example A159

3-[{[4-({1-[5-(benzyloxy)-3-methyl-1-benzofuran-2-yl]-3-methylbutyl}amino)phenyl]carbonyl}(methyl)amino]propanoic acid

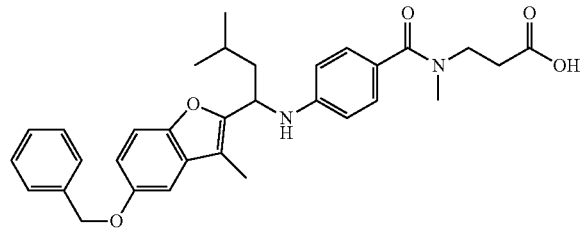 [SMILES: Cc1c(C(CC(C)C)Nc2ccc(C(=O)N(C)CCC(=O)O)cc2)oc2ccc(OCc3ccccc3)cc12]

(1) ethyl 5-(benzyloxy)-3-methyl-1-benzofuran-2-carboxylate

To a solution (200 mL) of 1-[5-(benzyloxy)-2-hydroxyphenyl]ethanone (15.3 g) synthesized in Example A82(1) in N,N-dimethylformamide were added potassium carbonate (13.1 g) and ethyl bromoacetate (7.7 mL) at room temperature, and the mixture was stirred at room temperature for 1 hr. Water was added to the reaction mixture, and the mixture was extracted with diethyl ether. The extract was concentrated under reduced pressure, the obtained residue was dissolved in N,N-dimethylformamide (100 mL) again, and 1,8-diazabicyclo[5.4.0]undec-7-ene (12.2 mL) was added to the solution. The reaction mixture was stirred at 80° C. overnight. After cooling to room temperature, water was added to the reaction mixture, and the mixture was extracted with diethyl ether. The extract was concentrated under reduced pressure and the obtained solid was washed with ethanol-isopropyl ether to give the title object compound (3.3 g, 17%) as a colorless solid.

$^1$H NMR (300 MHz, CDCl$_3$) 3 ppm 1.44 (t, J=7.2 Hz, 3H), 2.55 (s, 3H), 4.45 (q, J=7.2 Hz, 2H), 5.12 (s, 2H), 7.01-7.21 (m, 2H), 7.30-7.60 (m, 6H).

(2)[5-(benzyloxy)-3-methyl-1-benzofuran-2-yl]methanol

To a solution (50 mL) of ethyl 5-(benzyloxy)-3-methyl-1-benzofuran-2-carboxylate (3.3 g) synthesized in the above-mentioned (1) in tetrahydrofuran was added lithium aluminum hydride (0.42 g) under ice-cooling. The ice bath was removed, and the reaction mixture was stirred at room temperature for 1 hr then ice-cooled again. water (1.1 mL), 1N aqueous sodium hydroxide solution (5.5 mL), and water (1.1 mL) were successively added dropwise to quench the reaction. The residue was filtered through celite, and the filtrate was concentrated under reduced pressure to give the title object compound (2.8 g, quantitative) as a pale-yellow solid.

$^1$H NMR (300 MHz, CDCl$_3$) δ ppm 1.70-1.90 (br. s., 1H), 2.22 (s, 3H), 4.73 (d, J=6.0 Hz, 2H), 5.10 (s, 2H), 6.88-7.06 (m, 2H), 7.28-7.56 (m, 6H).

(3) 5-(benzyloxy)-3-methyl-1-benzofuran-2-carbaldehyde

To a solution (30 mL) of [5-(benzyloxy)-3-methyl-1-benzofuran-2-yl]methanol (2.8 g) synthesized in the above-mentioned (2) in toluene was added manganese dioxide (5 g), and the mixture was heated under reflux with a Dean-Stark trap for 1 hr. The reaction mixture was allowed to cool to room temperature, catalyst was filtered through celite. The filtrate was concentrated under reduced pressure to give the title object compound (2.68 g, 94%) as a colorless solid.

$^1$H NMR (300 MHz, CDCl$_3$) δ ppm 2.58 (s, 3H), 5.12 (s, 2H), 7.06-7.25 (m, 2H), 7.32-7.57 (m, 6H), 10.00 (s, 1H).

(4) ethyl 3-[{[4-({1-[5-(benzyloxy)-3-methyl-1-benzofuran-2-yl]-3-methylbutyl}amino)phenyl]carbonyl}(methyl)amino]propanoate To a solution (15 mL) of 5-(benzyloxy)-3-methyl-1-benzofuran-2-carbaldehyde (1.2 g) synthesized in the above-mentioned (3) in tetrahydrofuran was added dropwise isobutylmagnesium bromide (1M, tetrahydrofuran solution) under ice-cooling. The ice bath was removed, the reaction mixture was stirred at room temperature for 15 min, and aqueous ammonium chloride solution was added to quench the reaction. The reaction mixture was extracted with ethyl acetate, and the residue was purified by silica gel column chromatography (ethyl acetate:hexane=1:4, volume ratio) to give 1-[5-(benzyloxy)-3-methyl-1-benzofuran-2-yl]-3-methylbutan-1-ol (0.82 g, 56%) as a pale-yellow oil. This was dissolved in tetrahydrofuran (15 mL), and thionyl chloride (0.35 mL) was added to the solution at room temperature. The reaction mixture was stirred at room temperature for 30 min then ice-cooled, and saturated aqueous sodium hydrogen carbonate solution (15 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (15 mL), sodium iodide (0.56 g), sodium carbonate (0.38 g) and ethyl 3-{[(4-aminophenyl)carbonyl](methyl)amino}propanoate (0.63 g) synthesized in Example 2(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (0.46 g, 33%) as a yellow oil.

$^1$H NMR (300 MHz, CDCl$_3$) δ ppm 0.76-1.05 (m, 6H), 1.11-1.90 (m, 6H), 2.24 (s, 3H), 2.47-2.69 (m, 2H), 3.01 (s, 3H), 3.56-3.80 (m, 2H), 3.95-4.32 (m, 3H), 4.56-4.78 (m, 1H), 5.09 (s, 2H), 6.57 (d, J=8.7 Hz, 2H), 6.80-7.02 (m, 2H), 7.12-7.53 (m, 8H).

(5) 3-[{[4-({1-[5-(benzyloxy)-3-methyl-1-benzofuran-2-yl]-3-methylbutyl}amino)phenyl]carbonyl}(methyl)amino]propanoic acid Ethyl 3-[{[4-({1-[5-(benzyloxy)-3-methyl-1-benzofuran-2-yl]-3-methylbutyl}amino)phenyl]carbonyl}(methyl)amino]propanoate (0.46 g) synthesized in the above-mentioned (4) was dissolved in ethanol (5 mL), 1N aqueous sodium hydroxide solution (1.5 mL) was added to the solution at room temperature, and the mixture was stirred at room temperature for 0.5 hr. Ethanol was evaporated under reduced pressure, 1N hydrochloric acid (1.5 mL) was added to the residue, and the mixture was extracted with ethyl acetate. The extract was washed with saturated brine, dried over magnesium sulfate, and concentrated under reduced pressure. The residue was washed with ethanol-water to give the title object compound (0.45 g, quantitative) as a colorless solid.

$^1$H NMR (300 MHz, CDCl$_3$) δ ppm 0.90 (d, 3H, J=6.0 Hz), 0.99 (d, 3H, J=6.0 Hz), 1.25-2.00 (m, 4H), 2.24 (s, 3H), 2.67 (br. s., 2H), 3.03 (s, 3H), 3.71 (br. s., 2H), 4.20-4.40 (m, 2H), 5.08 (s, 2H), 6.59-7.05 (m, 4H), 7.31-7.57 (m, 8H).

Example A160

3-[{[4-({cyclohexyl[3-methyl-5-(tetrahydro-2H-thiopyran-4-yloxy)-1-benzofuran-2-yl]methyl}amino)phenyl]carbonyl}(methyl)amino]propanoic acid (1) ethyl 3-[{[4-({cyclohexyl[3-methyl-5-(tetrahydro-2H-thiopyran-4-yloxy)-1-benzofuran-2-yl]methyl}amino)phenyl]carbonyl}(methyl)amino]propanoate Ethyl 3-{[(4-{[cyclohexyl(5-hydroxy-3-methyl-1-benzofuran-2-yl)methyl]amino}phenyl)carbonyl](methyl)amino}propanoate (0.50 g) synthesized in Example A155(1) was dissolved in tetrahydrofuran (10 mL), and tetrahydrothiopyran-4-ol (142 mg), tributylphosphine (0.45 mL) and 1,1'-(azodicarbonyl)dipiperidine (0.45 g) were added to the solution under ice-cooling. The ice bath was removed, the reaction mixture was stirred at room temperature for 12 hr, then hexane (10 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:2, volume ratio) to give the title object compound (0.14 g, 23%) as a yellow oil.

$^1$H NMR (300 MHz, CDCl$_3$) δ 0.91-2.14 (m, 18H), 2.20 (s, 3H), 2.46-2.99 (m, 6H), 3.01 (s, 3H), 3.33-3.49 (m, 1H), 3.70 (t, J=7.1 Hz, 2H), 4.12 (q, J=7.2 Hz, 2H), 4.25-4.40 (m, 1H), 6.56 (d, J=8.7 Hz, 2H), 6.78-6.94 (m, 2H), 7.16-7.30 (m, 3H).

(2) 3-[{[4-({cyclohexyl[3-methyl-5-(tetrahydro-2H-thiopyran-4-yloxy)-1-benzofuran-2-yl]methyl}amino)phenyl]carbonyl}(methyl)amino]propanoic acid Ethyl 3-[{[4-({cyclohexyl[3-methyl-5-(tetrahydro-2H-thiopyran-4-yloxy)-1-benzofuran-2-yl]methyl}amino)phenyl]carbonyl}(methyl)amino]propanoate (0.14 g) synthesized in the above-mentioned (1) was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, 1N hydrochloric acid (1.0 mL) was added to the residue, and the mixture was extracted with ethyl acetate. The extract was washed with saturated brine, dried over magnesium sulfate, and concentrated under reduced pressure. The residue was purified by silica gel column chromatography (ethyl acetate:hexane=3:1, volume ratio) to give the title object compound (0.06 g, 46%) as a colorless solid.

$^1$H NMR (300 MHz, CDCl$_3$) δ ppm 0.86-2.15 (m, 16H), 2.21 (s, 3H), 2.41-2.95 (m, 6H), 3.06 (s, 3H), 3.72 (t, J=6.4 Hz, 2H), 4.21-4.46 (m, 2H), 6.56 (d, J=8.7 Hz, 2H), 6.76-6.95 (m, 2H), 7.22-7.26 (m, 3H).

Example A161

3-{[(4-{[cyclohexyl(4-fluoro-3-methyl-1-benzofuran-2-yl)methyl]amino}phenyl)carbonyl]amino}propanoic acid

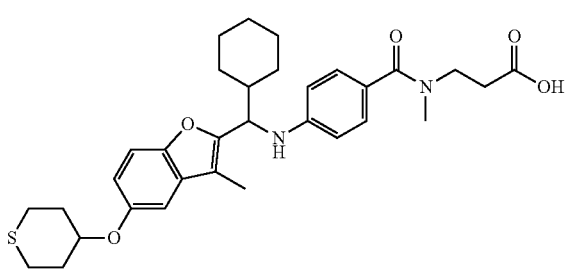 [SMILES: Cc1c(C(Nc2ccc(C(=O)N(C)CCC(=O)O)cc2)C2CCCCC2)oc2ccc(OC3CCSCC3)cc12]

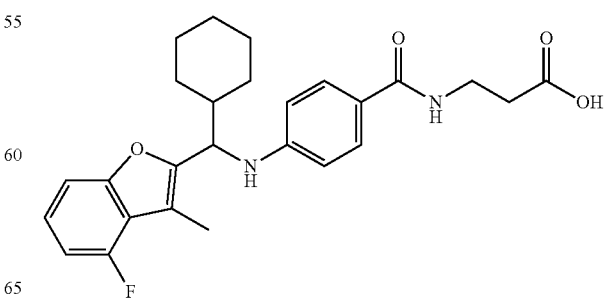

(1) cyclohexyl(4-fluoro-3-methyl-1-benzofuran-2-yl) methanone

To a solution (50 mL) of 1-(2-fluoro-6-hydroxyphenyl) ethanone (2.5 g) in N,N-dimethylformamide were added potassium carbonate (6.7 g) and 2-bromo-1-cyclohexyletha none (4.0 g) synthesized in Example A51(1) at room temperature, and the mixture was stirred at room temperature for 16 hr. The reaction mixture was allowed to cool to room temperature and filtered through celite. Water was added to the filtrate, and the mixture was extracted with diethyl ether. The extract was washed with saturated brine, dried over magnesium sulfate, and concentrated under reduced pressure. The obtained residue was dissolved in N,N-dimethylformamide (50 mL) again, 1,8-diazabicyclo[5.4.0]undec-7-ene (2.6 mL) was added to the solution, and the mixture was stirred at 110° C. for 1 hr with heating. After cooling to room temperature, the reaction mixture was quenched with 1N hydrochloric acid, and the reaction mixture was extracted with diethyl ether. The extract was concentrated under reduced pressure, and the precipitated compound was recrystallized from diisopropyl ether-hexane to give the title object compound (2.6 g, 62%) as a colorless solid.

$^1$H NMR (300 MHz, CDCl$_3$) δ ppm 1.20-2.07 (m, 10H), 2.73 (s, 3H), 3.20-3.36 (m, 1H), 6.92 (ddd, J=10.0, 7.8, 0.8 Hz, 1H), 7.27-7.44 (m, 2H).

(2) cyclohexyl(4-fluoro-3-methyl-1-benzofuran-2-yl) methanol

Cyclohexyl(4-fluoro-3-methyl-1-benzofuran-2-yl)methanone (2.6 g) synthesized in the above-mentioned (1) was dissolved to in tetrahydrofuran (40 mL) and methanol (4 mL), and sodium borohydride (90%, 0.83 g) was added to the solution under ice-cooling. The ice bath was removed, the reaction mixture was stirred at room temperature for 1 hr then ice-cooled again, and water (5 mL) and 1N hydrochloric acid (10 mL) were carefully added to the mixture, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (2.5 g, quantitative) as a pale-yellow oil.

$^1$H NMR (300 MHz, CDCl$_3$) δ ppm 0.72-2.22 (m, 12H), 2.35 (s, 3H), 4.50 (dd, J=8.6, 6.1 Hz, 1H), 6.86 (ddd, J=10.1, 7.6, 1.3 Hz, 1H), 7.11-7.24 (m, 2H).

(3) 3-{[(4-{[cyclohexyl(4-fluoro-3-methyl-1-benzofuran-2-yl)methyl]amino}phenyl)carbonyl]amino}propanoic acid Cyclohexyl(4-fluoro-3-methyl-1-benzofuran-2-yl)methanol (0.52 g) synthesized in the above-mentioned (2) was dissolved in tetrahydrofuran (10 mL), and thionyl chloride (0.27 mL) was added to the solution at room temperature. The reaction mixture was stirred at room temperature for 30 min then ice-cooled, and saturated aqueous sodium hydrogen carbonate solution (5 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (10 mL), sodium iodide (0.45 g), sodium carbonate (0.30 g) and ethyl 3-{[(4-aminophenyl)carbonyl]amino}propanoate (0.45 g) synthesized in Example 1(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[cyclohexyl(4-fluoro-3-methyl-1-benzofuran-2-yl) methyl]amino}phenyl)carbonyl]amino}propanoate (0.12 g, 13%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.11 g, 95%) as a colorless solid.

$^1$H NMR (300 MHz, CDCl$_3$) δ ppm 0.85-2.18 (m, 12H), 2.37 (s, 3H), 2.54 (t, J=5.6 Hz, 2H), 3.41-3.75 (m, 2H), 4.35 (d, J=8.1 Hz, 1H), 6.44-6.64 (m, 3H), 6.72-6.89 (m, 1H), 7.02-7.19 (m, 2H), 7.52 (d, J=8.5 Hz, 2H).

Example A162

3-{[(4-{[cyclohexyl(4-fluoro-3-methyl-1-benzofuran-2-yl)methyl]amino}phenyl)carbonyl]methyl) amino}propanoic acid

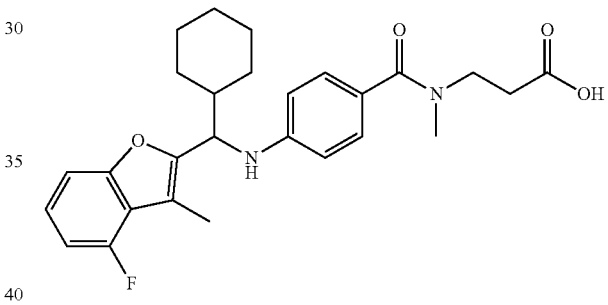

Cyclohexyl(4-fluoro-3-methyl-1-benzofuran-2-yl)methanol (520 mg) synthesized in Example A161(2) was dissolved in tetrahydrofuran (10 mL), and thionyl chloride (0.27 mL) was added to the solution at room temperature. The reaction mixture was stirred at room temperature for 30 min then ice-cooled, and saturated aqueous sodium hydrogen carbonate solution (10 mL) was carefully added to the mixture. The mixture was stirred for 10 min, and extracted with ethyl acetate. The extract was washed with saturated brine, dried over magnesium sulfate, and concentrated under reduced pressure. The residue was dissolved in N,N-dimethylacetamide (10 mL), sodium iodide (0.45 g), sodium carbonate (0.30 g) and ethyl 3-{[(4-aminophenyl)carbonyl](methyl) amino}propanoate (0.50 g) synthesized in Example 2(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[cyclohexyl(4-fluoro-3-methyl-1-benzofuran-2-yl)methyl] amino}phenyl)carbonyl](methyl)amino}propanoate (0.15 g, 15%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.14 g, 95%) as a colorless solid.

$^1$H NMR (300 MHz, CDCl$_3$) δ ppm 0.88-2.16 (m, 12H), 2.38 (s, 3H), 2.65 (t, J=6.4 Hz, 2H), 3.03 (s, 3H), 3.69 (t, J=6.4 Hz, 2H), 4.35 (d, J=8.3 Hz, 1H), 6.56 (d, J=8.7 Hz, 2H), 6.75-6.91 (m, 1H), 7.03-7.18 (m, 2H), 7.23 (d, J=8.7 Hz, 2H).

Example A163

3-{[(4-{[cyclohexyl(5,7-difluoro-3-methyl-1-benzofuran-2-yl)methyl]amino}phenyl)carbonyl]amino}propanoic acid

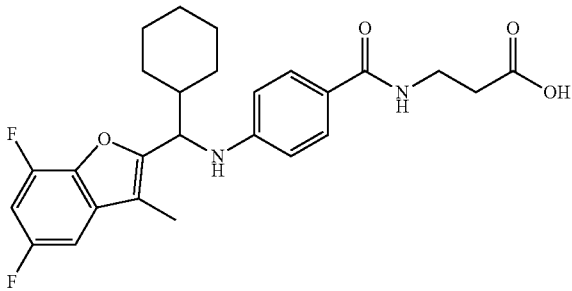 [SMILES: Cc1c(C(Nc2ccc(C(=O)NCCC(=O)O)cc2)C2CCCCC2)oc2c(F)cc(F)cc12]

(1) cyclohexyl(5,7-difluoro-3-methyl-1-benzofuran-2-yl)methanone

To a solution (50 mL) of 1-(3,5-difluoro-2-hydroxyphenyl)ethanone (2.8 g) in N,N-dimethylformamide were added potassium carbonate (6.7 g) and 2-bromo-1-cyclohexylethanone (4.0 g) synthesized in Example A51(1) at room temperature, and the mixture was stirred at room temperature for 16 hr. The reaction mixture was allowed to cool to room temperature, and filtered through celite. Water was added to the filtrate, and the mixture was extracted with diethyl ether. The extract was washed with saturated brine, dried over magnesium sulfate, and concentrated under reduced pressure. The obtained residue was dissolved in N,N-dimethylformamide (50 mL) again, 1,8-diazabicyclo[5.4.0]undec-7-ene (2.6 mL) was added to the solution, and the mixture was stirred at 110° C. 1 hr with heating. After cooling to room temperature, the reaction mixture was quenched with 1N hydrochloric acid, and the reaction mixture was extracted with diethyl ether. The extract was concentrated under reduced pressure, and the precipitated compound was recrystallized from diisopropyl ether-hexane to give the title object compound (3.1 g, 70%) as a colorless solid.

$^1$H NMR (300 MHz, CDCl$_3$) δ ppm 1.09-2.09 (m, 10H), 2.56 (s, 3H), 3.17-3.47 (m, 1H), 6.93-7.16 (m, 2H).

(2) cyclohexyl(5,7-difluoro-3-methyl-1-benzofuran-2-yl)methanol

Cyclohexyl(5,7-difluoro-3-methyl-1-benzofuran-2-yl)methanone (3.1 g) synthesized in the above-mentioned (1) was dissolved in tetrahydrofuran (50 mL) and methanol (5 mL), and sodium borohydride (90%, 0.93 g) was added to the solution under ice-cooling. The ice bath was removed, and the reaction mixture was stirred at room temperature for 1 hr then ice-cooled again, and water (5 mL) and 1N hydrochloric acid (10 mL) were carefully added to the mixture, and the mixture was extracted with ethyl acetate. The extract was washed with saturated brine, dried over magnesium sulfate, and concentrated under reduced pressure. The residue was purified by silica gel column chromatography (ethyl acetate:hexane=1:4, volume ratio) to give the title object compound (3.1 g, quantitative) as a pale-yellow oil.

$^1$H NMR (300 MHz, CDCl$_3$) δ ppm 0.83-2.00 (m, 12H), 2.20 (s, 3H), 4.52 (dd, J=8.5, 6.8 Hz, 1H), 6.79-6.93 (m, 2H).

(3) 3-{[(4-{[cyclohexyl(5,7-difluoro-3-methyl-1-benzofuran-2-yl)methyl]amino}phenyl)carbonyl]amino}propanoic acid Cyclohexyl (5,7-difluoro-3-methyl-1-benzofuran-2-yl)methanol (0.56 g) synthesized in the above-mentioned (2) was dissolved in tetrahydrofuran (10 mL), and thionyl chloride (0.26 mL) was added to the solution at room temperature. The reaction mixture was stirred at room temperature for 30 min then ice-cooled, and saturated aqueous sodium hydrogen carbonate solution (10 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (10 mL), sodium iodide (0.45 g), sodium carbonate (0.30 g) and ethyl 3-{[(4-aminophenyl)carbonyl]amino}propanoate (0.45 g) synthesized in Example 1(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[cyclohexyl(4-fluoro-3-methyl-1-benzofuran-2-yl)methyl]amino}phenyl)carbonyl]amino}propanoate (0.17 g, 17%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.16 g, 95%) as a colorless solid.

$^1$H NMR (300 MHz, CDCl$_3$) δ ppm 0.87-2.14 (m, 12H), 2.21 (s, 3H), 2.61 (t, J=5.7 Hz, 2H), 3.63 (q, J=5.7 Hz, 2H), 4.39 (d, J=8.3 Hz, 1H), 6.45-6.64 (m, 3H), 6.67-6.81 (m, 1H), 6.87 (dd, J=8.3, 2.3 Hz, 1H), 7.53 (d, J=8.7 Hz, 2H).

Example A164

3-{[(4-{[cyclohexyl(5,7-difluoro-3-methyl-1-benzofuran-2-yl)methyl]amino}phenyl)carbonyl](methyl)amino}propanoic acid

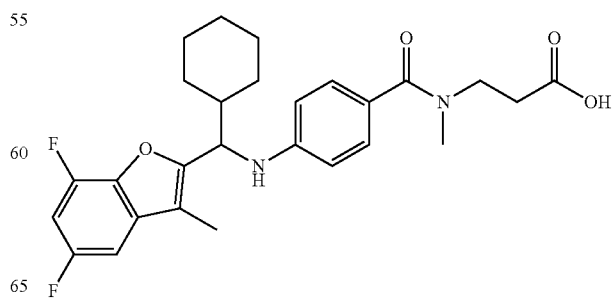

Cyclohexyl(5,7-difluoro-3-methyl-1-benzofuran-2-yl)methanol (0.56 g) synthesized in Example A163(2) was dissolved in tetrahydrofuran (10 mL), and thionyl chloride (0.26 mL) was added to the solution at room temperature. The reaction mixture was stirred at room temperature for 30 min then ice-cooled, and saturated aqueous sodium hydrogen carbonate solution (10 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (10 mL), sodium iodide (0.45 g), sodium carbonate (0.30 g) and ethyl 3-{[(4-aminophenyl)carbonyl](methyl)amino}propanoate (0.50 g) synthesized in Example 2(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[cyclohexyl(4-fluoro-3-methyl-1-benzofuran-2-yl)methyl]amino}phenyl)carbonyl](methyl)amino}propanoate (0.17 g, 17%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.15 g, 93%) as a colorless solid.

$^1$H NMR (300 MHz, CDCl$_3$) δ ppm 0.88-2.16 (m, 12H), 2.21 (s, 3H), 2.67 (t, J=6.4 Hz, 2H), 3.04 (s, 3H), 3.70 (t, J=6.4 Hz, 2H), 4.38 (d, J=8.1 Hz, 1H), 6.56 (d, J=8.7 Hz, 2H), 6.75-6.88 (m, 2H), 7.23 (d, J=8.7 Hz, 2H).

Example A165

3-({[4-({1-[5-(benzyloxy)-3-methyl-1-benzofuran-2-yl]ethyl}amino)phenyl]carbonyl}amino)propanoic acid

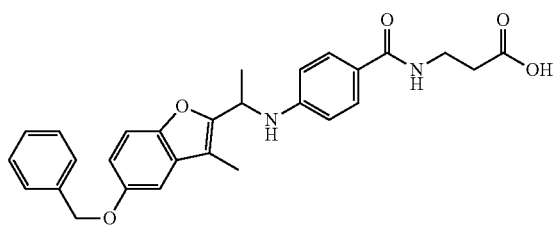 [SMILES: Cc1c(C(C)Nc2ccc(C(=O)NCCC(=O)O)cc2)oc2ccc(OCc3ccccc3)cc12]

(1) 1-[5-(benzyloxy)-3-methyl-1-benzofuran-2-yl]ethanone

To a solution (120 mL) of 1-[5-(benzyloxy)-2-hydroxyphenyl]ethanone (6.4 g) synthesized in Example A82(1) in N,N-dimethylformamide were added potassium carbonate (10.8 g) and bromoacetone (4.8 g) at room temperature, and the mixture was stirred at 80° C. for 1 hr. Water was added to the reaction mixture, and the mixture was extracted with diethyl ether. The extract was concentrated under reduced pressure, and the obtained residue was dissolved in N,N-dimethylformamide (120 mL) again, and 1,8-diazabicyclo[5.4.0]undec-7-ene (5.1 mL) was added to the solution. The reaction mixture was stirred at 80° C. for 2 hr. After cooling to room temperature, water was added to the reaction mixture, and the mixture was extracted with diethyl ether. The extract was concentrated under reduced pressure, and the obtained solid was washed with ethanol-isopropyl ether to give the title object compound (2.5 g, 34%) as a colorless solid.

$^1$H NMR (300 MHz, CDCl$_3$) δ ppm 2.56 (s, 3H), 2.60 (s, 3H), 5.12 (s, 2H), 7.11 (d, J=2.3 Hz, 1H), 7.17 (dd, J=8.9, 2.3 Hz, 1H), 7.30-7.55 (m, 6H).

(2) 1-[5-(benzyloxy)-3-methyl-1-benzofuran-2-yl]ethanol

1-[5-(Benzyloxy)-3-methyl-1-benzofuran-2-yl]ethanone (0.53 g) synthesized in the above-mentioned (1) was dissolved in tetrahydrofuran (10 mL) and methanol (1 mL), and sodium borohydride (90%, 0.16 g) was added to the solution under ice-cooling. The ice bath was removed, and the reaction mixture was stirred at room temperature for 1 hr then ice-cooled again, and water (1 mL) and 1N hydrochloric acid (5 mL) were carefully added to the mixture, and the mixture was extracted with ethyl acetate. The extract was washed with saturated brine, dried over magnesium sulfate, and concentrated under reduced pressure to give a crude product (0.53 g, quantitative) of the title object compound as a pale-yellow oil.

$^1$H NMR (300 MHz, CDCl$_3$) δ ppm 1.62 (d, J=6.6 Hz, 3H), 1.91 (br. s., 1H), 2.21 (s, 3H), 4.95-5.21 (m, 3H), 6.87-7.07 (m, 2H), 7.28-7.58 (m, 6H).

(3) 3-({[4-({1-[5-(benzyloxy)-3-methyl-1-benzofuran-2-yl]ethyl}amino)phenyl]carbonyl}amino)propanoic acid 1-[5-(Benzyloxy)-3-methyl-1-benzofuran-2-yl]ethanol (0.27 g) synthesized in the above-mentioned (2) was dissolved in tetrahydrofuran (5 mL), and thionyl chloride (0.13 mL) was added to the solution at room temperature. The reaction mixture was stirred at room temperature for 30 min then ice-cooled, and saturated aqueous sodium hydrogen carbonate solution (10 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (10 mL), sodium iodide (0.21 g), sodium carbonate (0.14 g) and ethyl 3-{[(4-aminophenyl)carbonyl]amino}propanoate (0.23 g) synthesized in Example 1(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-[{[4-({1-[5-(benzyloxy)-3-methyl-1-benzofuran-2-yl]ethyl}amino)phenyl]carbonyl}amino)propanoate (0.15 g, 31%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.13 g, 88%) as a colorless solid.

¹H NMR (300 MHz, CDCl₃) δ ppm 1.62 (d, J=7.0 Hz, 3H), 2.22 (s, 3H), 2.69 (d, J=5.7 Hz, 2H), 3.57-3.76 (m, 2H), 4.65-4.88 (m, 1H), 5.08 (s, 2H), 6.59-6.75 (m, 3H), 6.82-7.04 (m, 2H), 7.29-7.62 (m, 8H).

Example A166

3-[{[4-({1-[5-(benzyloxy)-3-methyl-1-benzofuran-2-yl]ethyl}amino)phenyl]carbonyl}(methyl)amino]propanoic acid

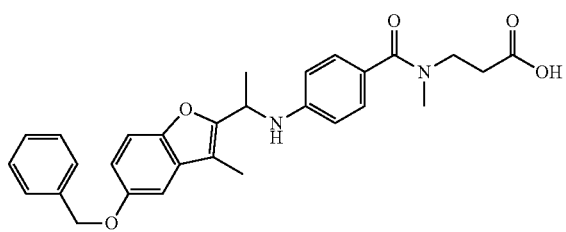 [SMILES: Cc1c(C(C)Nc2ccc(C(=O)N(C)CCC(=O)O)cc2)oc2ccc(OCc3ccccc3)cc12]

1-[5-(Benzyloxy)-3-methyl-1-benzofuran-2-yl]ethanol (0.27 g) synthesized in Example A165(2) was dissolved in tetrahydrofuran (5 mL), and thionyl chloride (0.13 mL) was added to the solution at room temperature. The reaction mixture was stirred at room temperature for 30 min then ice-cooled, and saturated aqueous sodium hydrogen carbonate solution (5 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (10 mL), sodium iodide (0.21 g), sodium carbonate (0.14 g) and ethyl 3-{[(4-aminophenyl)carbonyl](methyl)amino}propanoate (0.24 g) synthesized in Example 2(2) were added to the solution, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[cyclohexyl(4-fluoro-3-methyl-1-benzofuran-2-yl)methyl]amino}phenyl)carbonyl](methyl)amino}propanoate (0.10 g, 20%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.09 g, 90%) as a colorless solid.

¹H NMR (300 MHz, CDCl₃) δ ppm 1.63 (d, J=6.8 Hz, 3H), 2.21 (s, 3H), 2.69 (t, J=6.5 Hz, 2H), 3.05 (s, 3H), 3.71 (t, J=6.5 Hz, 2H), 4.79 (q, J=6.9 Hz, 1H), 5.09 (s, 2H), 6.60 (d, J=8.3 Hz, 2H), 6.84-7.02 (m, 2H), 7.27-7.51 (m, 8H).

Example A167

3-[({4-[(cyclohexyl{5-[(2-fluoropyridin-4-yl)methoxy]-3-methyl-1-benzofuran-2-yl}methyl)amino]phenyl}carbonyl)amino]propanoic acid

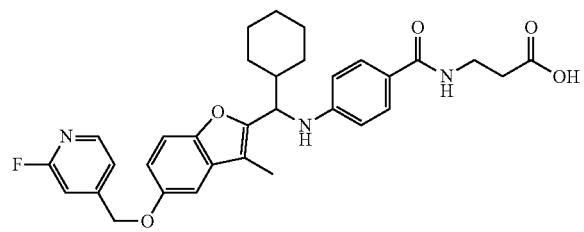 [SMILES: Cc1c(C(Nc2ccc(C(=O)N(C)CCC(=O)O)cc2)C2CCCCC2)oc2ccc(OCc3ccnc(F)c3)cc12]

(1) ethyl 3-{[(4-{[cyclohexyl(5-hydroxy-3-methyl-1-benzofuran-2-yl)methyl]amino}phenyl)carbonyl]amino}propanoate Ethyl 3-[{[4-({[5-(benzyloxy)-3-methyl-1-benzofuran-2-yl](cyclohexyl)methyl}amino)phenyl]carbonyl}amino]propanoate (5.6 g) synthesized in Example A158(1) was dissolved in ethanol (100 mL), and platinum oxide (0.50 g) was added to the solution. The reaction mixture was stirred under hydrogen atmosphere (1 atm) at room temperature overnight. The reaction mixture was filtered, and the residue was washed with ethanol. The filtrate was concentrated under reduced pressure, and the residue was purified by silica gel column chromatography (ethyl acetate:hexane=1:1, volume ratio) to give the title object compound (3.2 g, 68%) as a yellow oil.

¹H NMR (300 MHz, CDCl₃) δ ppm 0.94-1.94 (m, 14H), 2.16 (s, 3H), 2.59 (t, J=5.8 Hz, 2H), 3.66 (q, J=5.8 Hz, 2H), 4.03-4.14 (m, 2H), 4.26-4.56 (m, 2H), 5.57 (br. s., 1H), 6.56 (d, J=8.7 Hz, 2H), 6.61-6.68-6.71 (m, 1H), 6.73 (dd, J=8.7, 2.3 Hz, 1H), 6.83 (d, J=2.3 Hz, 1H), 7.19 (d, J=8.7 Hz, 1H), 7.55 (d, J=8.7 Hz, 2H).

(2) ethyl 3-[({4-[(cyclohexyl{5-[(2-fluoropyridin-4-yl)methoxy]-3-methyl-1-benzofuran-2-yl}methyl)amino]phenyl}carbonyl)amino]propanoate Ethyl 3-{[(4-{[cyclohexyl(5-hydroxy-3-methyl-1-benzofuran-2-yl)methyl]amino}phenyl)carbonyl]amino}propanoate (0.36 g) synthesized in the above-mentioned (1) was dissolved in tetrahydrofuran (5 mL), and 2-fluoro-4-pyridinemethanol (114 mg), tributylphosphine (0.35 mL) and 1,1'-(azodicarbonyl)dipiperidine (0.34 g) were added to the solution under ice-cooling. The ice bath was removed, the reaction mixture was stirred at room temperature for 12 hr, then hexane (5 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:2, volume ratio) to give the title object compound (0.23 g, 54%) as a yellow oil.

¹H NMR (300 MHz, CDCl₃) δ ppm 0.90-2.00 (m, 14H), 2.22 (s, 3H), 2.58 (t, J=5.8 Hz, 2H), 3.66 (q, J=5.8 Hz, 2H), 4.15 (q, J=7.0 Hz, 2H), 4.30-4.54 (m, 2H), 5.13 (s, 2H), 6.57-6.75 (m, 3H), 6.83-6.96 (m, 2H), 7.05 (s, 1H), 7.18-7.32 (m, 2H), 7.55 (d, J=8.9 Hz, 2H), 8.22 (d, J=5.1 Hz, 1H).

(3) 3-[({4-[(cyclohexyl{5-[(2-fluoropyridin-4-yl)methoxy]-3-methyl-1-benzofuran-2-yl}methyl)amino]phenyl}carbonyl)amino]propanoic acid Ethyl 3-[({4-[(cyclohexyl{5-[(2-fluoropyridin-4-yl)methoxy]-3-methyl-1-benzofuran-2-yl}methyl)amino]phenyl}carbonyl)amino]propanoate (0.24 g) synthesized in the above-mentioned (2) was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.17 g, 75%) as a colorless solid.

$^1$H NMR (300 MHz, CDCl$_3$) δ ppm 0.83-2.13 (m, 12H), 2.20 (s, 3H), 2.52-2.77 (m, 2H), 3.52-3.77 (m, 2H), 4.38 (d, J=8.0 Hz, 1H), 5.14 (s, 2H), 6.38-6.93 (m, 5H), 7.04 (s, 1H), 7.17-7.25 (m, 2H), 7.53 (d, J=8.7 Hz, 2H), 8.21 (d, J=5.3 Hz, 1H).

Example A168

3-[({4-[(cyclohexyl{5-[(2-fluoropyridin-4-yl)methoxy]-3-methyl-1-benzofuran-2-yl}methyl)amino]phenyl}carbonyl)(methyl)amino]propanoic acid

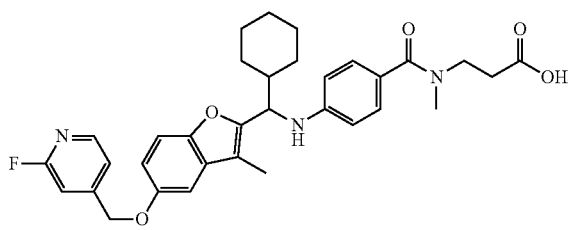

(1) ethyl 3-[({4-[(cyclohexyl{5-[(2-fluoropyridin-4-yl)methoxy]-3-methyl-1-benzofuran-2-yl}methyl)amino]phenyl}carbonyl)(methyl)amino]propanoate Ethyl 3-{[(4-{[cyclohexyl(5-hydroxy-3-methyl-1-benzofuran-2-yl)methyl]amino}phenyl)carbonyl]methyl)amino}propanoate (0.35 g) synthesized in Example A155(1) was dissolved in tetrahydrofuran (5 mL), and 2-fluoro-4-pyridinemethanol (108 mg), tributylphosphine (0.32 mL) and 1,1'-(azodicarbonyl)dipiperidine (0.32 g) were added to the solution under ice-cooling. The ice bath was removed, the reaction mixture was stirred at room temperature for 12 hr then hexane (5 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:2, volume ratio) to give the title object compound (0.27 g, 62%) as a yellow oil.

$^1$H NMR (300 MHz, CDCl$_3$) δ ppm 0.94-1.99 (m, 14H), 2.21 (s, 3H), 2.61 (br. s., 2H), 3.01 (s, 3H), 3.70 (t, J=7.1 Hz, 2H), 4.12 (q, J=7.0 Hz, 2H), 4.24-4.49 (m, 2H), 5.14 (s, 2H), 6.56 (d, J=8.5 Hz, 2H), 6.83-6.95 (m, 2H), 7.06 (s, 1H), 7.21-7.28 (m, 4H), 8.22 (d, J=5.1 Hz, 1H).

(2) 3-[({4-[(cyclohexyl{5-[(2-fluoropyridin-4-yl)methoxy]-3-methyl-1-benzofuran-2-yl}methyl)amino]phenyl}carbonyl)(methyl)amino]propanoic acid Ethyl 3-[({4-[(cyclohexyl{5-[(2-fluoropyridin-4-yl)methoxy]-3-methyl-1-benzofuran-2-yl}methyl)amino]phenyl}carbonyl)(methyl)amino]propanoate (0.27 g) synthesized in the above-mentioned (1) was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.21 g, 82%) as a colorless solid.

$^1$H NMR (300 MHz, CDCl$_3$) δ ppm 0.86-2.14 (m, 12H), 2.21 (s, 3H), 2.67 (t, J=6.4 Hz, 2H), 3.04 (s, 3H), 3.70 (t, J=6.4 Hz, 2H), 4.36 (d, J=8.0 Hz, 1H), 5.14 (s, 2H), 6.55 (d, J=8.7 Hz, 2H), 6.79-6.96 (m, 2H), 7.05 (s, 1H), 7.20-7.35 (m, 4H), 8.21 (d, J=5.3 Hz, 1H).

Example A169

3-{[(4-{[{5-[(6-chloropyridin-3-yl)methoxy]-3-methyl-1-benzofuran-2-yl}(cyclohexyl)methyl]amino}phenyl)carbonyl]amino}propanoic acid

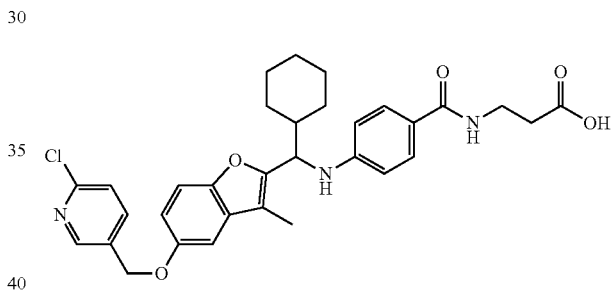

(1) ethyl 3-{[(4-{[{5-[(6-chloropyridin-3-yl)methoxy]-3-methyl-1-benzofuran-2-yl}(cyclohexyl)methyl]amino}phenyl)carbonyl]amino}propanoate Ethyl 3-{[(4-{[cyclohexyl(5-hydroxy-3-methyl-1-benzofuran-2-yl)methyl]amino}phenyl)carbonyl]amino}propanoate (0.35 g) synthesized in Example A167(1) was dissolved in tetrahydrofuran (5 mL), and 6-chloro-3-pyridinemethanol (0.13 g), tributylphosphine (0.33 mL) and 1,1'-(azodicarbonyl)dipiperidine (0.33 g) were added to the solution under ice-cooling. The ice bath was removed, the reaction mixture was stirred at room temperature for 12 hr then hexane (5 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:2, volume ratio) to give the title object compound (0.31 g, 65%) as a yellow oil.

$^1$H NMR (300 MHz, CDCl$_3$) δ ppm 0.95-2.13 (m, 14H), 2.22 (s, 2H), 2.58 (t, J=5.9 Hz, 2H), 3.65 (q, J=5.9 Hz, 2H), 4.25 (q, J=7.0 Hz, 2H), 4.29-4.54 (m, 1H), 4.71 (d, J=5.3 Hz, 1H), 5.07 (s, 2H), 6.48-6.68 (m, 3H), 6.77-7.03 (m, 2H), 7.25 (s, 1H), 7.24-7.40 (m, 2H), 7.54 (d, J=8.7 Hz, 2H), 7.68-7.76 (m, 1H), 8.34-8.47 (m, 1H).

(2) 3-{[(4-{[{5-[(6-chloropyridin-3-yl)methoxy]-3-methyl-1-benzofuran-2-yl}(cyclohexyl)methyl]amino}phenyl)carbonyl]amino}propanoic acid Ethyl 3-{[(4-{[{5-[(6-chloropyridin-3-yl)methoxy]-3-methyl-1-benzofuran-2-yl}(cyclohexyl)methyl]amino}phenyl)carbonyl]amino}propanoate (0.31 g) synthesized in the above-mentioned (1) was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.22 g, 74%) as a colorless solid.

$^1$H NMR (300 MHz, CDCl$_3$) δ ppm 0.88-2.13 (m, 12H), 2.21 (s, 3H), 2.62 (t, J=5.7 Hz, 2H), 3.45-3.77 (m, 2H), 4.37 (d, J=8.0 Hz, 1H), 5.07 (s, 2H), 6.43-6.64 (m, 3H), 6.75-6.99 (m, 2H), 7.23-7.26 (m, 1H), 7.35 (d, J=8.0 Hz, 1H), 7.52 (d, J=8.7 Hz, 2H), 7.76 (dd, J=8.0, 1.9 Hz, 1H), 8.43 (d, J=1.9 Hz, 1H).

Example A170

3-{[(4-{[{5-[(6-chloropyridin-3-yl)methoxy]-3-methyl-1-benzofuran-2-yl}(cyclohexyl)methyl]amino}phenyl)carbonyl](methyl)amino}-propanoic acid

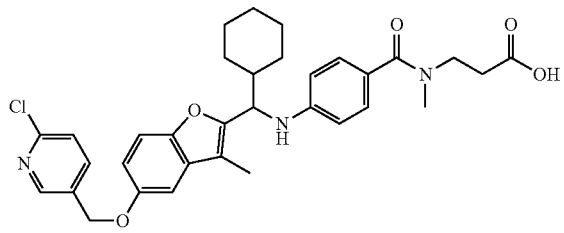 [SMILES: Cc1c(C(Nc2ccc(C(=O)N(C)CCC(=O)O)cc2)C2CCCCC2)oc2ccc(OCc3ccc(Cl)nc3)cc12]

(1) ethyl 3-{[(4-{[{5-[(6-chloropyridin-3-yl)methoxy]-3-methyl-1-benzofuran-2-yl}(cyclohexyl)methyl]amino}phenyl)carbonyl](methyl)amino}-propanoate Ethyl 3-{[(4-{[cyclohexyl(5-hydroxy-3-methyl-1-benzofuran-2-yl)methyl]amino}phenyl)carbonyl](methyl)amino}propanoate (0.39 g) synthesized in Example A155(1) was dissolved in tetrahydrofuran (5 mL), 6-chloro-3-pyridinemethanol (140 mg), tributylphosphine (0.35 mL) and 1,1'-(azodicarbonyl)dipiperidine (0.36 g) were added to the solution under ice-cooling. The ice bath was removed, the reaction mixture was stirred at room temperature for 12 hr then hexane (5 mL) was added to the mixture, and the precipitate was filtered off through celite. Water was added to the filtrate, and the mixture was extracted with ethyl acetate. The extract was concentrated under reduced pressure, and the residue was purified by silica gel column chromatography (ethyl acetate:hexane=1:2, volume ratio) to give the title object compound (0.32 g, 66%) as a yellow oil.

$^1$H NMR (300 MHz, CDCl$_3$) δ ppm 0.95-2.13 (m, 14H), 2.22 (s, 3H), 2.61 (t, J=5.9 Hz, 2H), 3.01 (s, 3H), 3.70 (t, J=5.9 Hz, 2H), 4.25 (q, J=7.0 Hz, 2H), 4.29-4.71 (m, 2H), 5.07 (s, 2H), 6.55 (d, J=8.7 Hz, 2H), 6.77-7.03 (m, 2H), 7.10-7.40 (m, 4H), 7.68-7.76 (m, 1H), 8.34-8.47 (m, 1H).

(2) 3-{[(4-{[{5-[(6-chloropyridin-3-yl)methoxy]-3-methyl-1-benzofuran-2-yl}(cyclohexyl)methyl]amino}phenyl)carbonyl](methyl)amino}-propanoic acid Ethyl 3-{[(4-{[{5-[(6-chloropyridin-3-yl)methoxy]-3-methyl-1-benzofuran-2-yl}(cyclohexyl)methyl]amino}phenyl)carbonyl](methyl)amino}-propanoate (0.32 g) synthesized in the above-mentioned (1) was dissolved in ethanol (3 mL), 1N aqueous sodium hydroxide solution (1.0 mL) was added to the solution at room temperature and the mixture was stirred at room temperature for 0.5 hr. Ethanol was evaporated under reduced pressure, and 1N hydrochloric acid (1.0 mL) was added to the residue. The precipitate was washed with water to give the title object compound (0.26 g, 85%) as a colorless solid.

$^1$H NMR (300 MHz, CDCl$_3$) δ ppm 0.86-2.15 (m, 12H), 2.21 (s, 3H), 2.52-2.77 (m, 2H), 3.04 (s, 3H), 3.69 (t, J=6.4 Hz, 2H), 4.36 (d, J=8.0 Hz, 1H), 5.08 (s, 2H), 6.56 (d, J=8.7 Hz, 2H), 6.71-7.00 (m, 2H), 7.14-7.26 (m, 3H), 7.36 (d, J=8.0 Hz, 1H), 7.77 (dd, J=8.0, 1.9 Hz, 1H), 8.44 (d, J=1.9 Hz, 1H).

Example A171

3-({[4-({1-[5-(benzyloxy)-3-methyl-1-benzofuran-2-yl]-2-methylpropyl}amino)phenyl]carbonyl}amino)propanoic acid

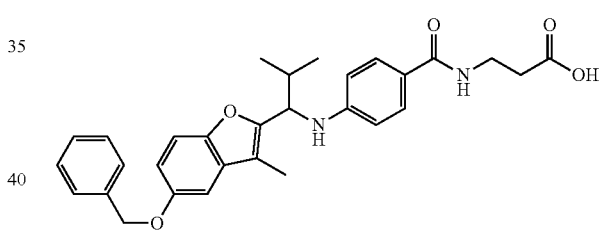

(1) ethyl 3-({[4-({1-[5-(benzyloxy)-3-methyl-1-benzofuran-2-yl]-2-methylpropyl}amino)phenyl]carbonyl}amino)propanoate 1-[5-(Benzyloxy)-3-methyl-1-benzofuran-2-yl]-2-methylpropan-1-ol (1.0 g) synthesized in Example A85(2) was dissolved in tetrahydrofuran (15 mL), and thionyl chloride (0.43 mL) was added to the solution at room temperature. The reaction mixture was stirred at room temperature for 30 min then ice-cooled, and saturated aqueous sodium hydrogen carbonate solution (15 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (15 mL), sodium iodide (0.74 g), sodium carbonate (0.50 g) and ethyl 3-{[(4-aminophenyl)carbonyl]amino}propanoate (0.76 g) synthesized in Example 1(2) were added to the solution, and the mixture was stirred at 80° C. for 12 hr. After allowed to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (0.43 g, 25%) as a yellow oil.

$^1$H NMR (300 MHz, CDCl$_3$) δ ppm 0.91 (d, J=6.4 Hz, 3H), 1.12 (d, J=7.0 Hz, 3H), 1.25 (t, J=7.0 Hz, 3H), 2.16-2.34 (m, 4H), 2.58 (t, J=6.0 Hz, 2H), 3.66 (q, J=6.0 Hz, 2H), 4.15 (q, J=7.0 Hz, 2H), 4.25-4.54 (m, 2H), 5.08 (s, 2H), 6.48-6.66 (m, 3H), 6.80-7.04 (m, 2H), 7.20-7.48 (m, 6H), 7.55 (d, J=9.0 Hz, 2H).

(2) 3-({[4-({1-[5-(benzyloxy)-3-methyl-1-benzofuran-2-yl]-2-methylpropyl}amino)phenyl]carbonyl}amino)propanoic acid Ethyl 3-({[4-({1-[5-(benzyloxy)-3-methyl-1-benzofuran-2-yl]-2-methylpropyl}amino)phenyl]carbonyl}amino)propanoate (0.43 g) synthesized in the above-mentioned (1) was dissolved in ethanol (10 mL), 1N aqueous sodium hydroxide solution (2.0 mL) was added to the solution at room temperature, and the mixture was stirred at room temperature for 0.5 hr. Ethanol was evaporated under reduced pressure, and 1N hydrochloric acid (2.0 mL) was added to the residue. The precipitate was washed with water to give the title object compound (0.36 g, 89%) as a colorless solid.

$^1$H NMR (300 MHz, CDCl$_3$) δ ppm 0.93 (d, J=6.4 Hz, 3H), 1.13 (d, J=6.4 Hz, 3H), 2.10-2.40 (m, 4H), 2.67 (br. s., 2H), 3.66 (br. s., 2H), 4.35 (br. s., 1H), 5.08 (s., 2H), 6.44-6.69 (m, 3H), 6.79-7.68 (m, 10H).

Example A172

3-[{[5-({1-[5-(benzyloxy)-3-methyl-1-benzofuran-2-yl]-2-methylpropyl}amino)pyridin-2-yl]carbonyl}(methyl)amino]propanoic acid

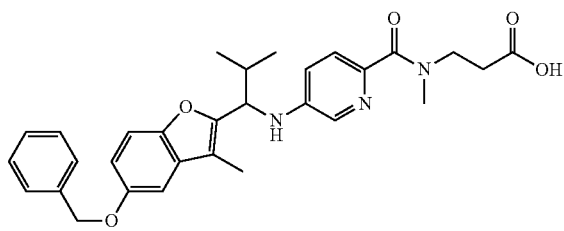 [SMILES: Cc1c(C(Nc2ccc(C(=O)N(C)CCC(=O)O)nc2)C(C)C)oc2ccc(OCc3ccccc3)cc12]

(1) methyl 5-({1-[5-(benzyloxy)-3-methyl-1-benzofuran-2-yl]-2-methylpropyl}amino)pyridine-2-carboxylate 1-[5-(Benzyloxy)-3-methyl-1-benzofuran-2-yl]-2-methylpropan-1-ol (1.0 g) synthesized in Example A58(2) was dissolved in tetrahydrofuran (15 mL), and thionyl chloride (0.43 mL) was added to the solution at room temperature. The reaction mixture was stirred at room temperature for 30 min then ice-cooled, and saturated aqueous sodium hydrogen carbonate solution (15 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in N,N-dimethylacetamide (15 mL), sodium iodide (0.74 g), sodium carbonate (0.50 g) and methyl 5-aminopyridine-2-carboxylate (0.50 g) were added to the solution, and the mixture was stirred at 80° C. for 12 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give the title object compound (0.22 g, 15%) as a yellow oil.

$^1$H NMR (300 MHz, CDCl$_3$) δ ppm 0.93 (d, J=6.8 Hz, 3H), 1.15 (d, J=6.8 Hz, 3H), 2.16-2.40 (m, 4H), 3.91 (s, 3H), 4.35 (t, J=8.1 Hz, 1H), 4.65 (d, J=8.7 Hz, 1H), 5.08 (s, 2H), 6.72-7.03 (m, 3H), 7.18-7.53 (m, 6H), 7.89 (d, J=8.3 Hz, 1H), 8.10 (d, J=2.6 Hz, 1H).

(2) ethyl 3-[{[5-({1-[5-(benzyloxy)-3-methyl-1-benzofuran-2-yl]-2-methylpropyl}amino)pyridin-2-yl]carbonyl}(methyl)amino]propanoate Methyl 5-({1-[5-(benzyloxy)-3-methyl-1-benzofuran-2-yl]-2-methylpropyl}amino)pyridine-2-carboxylate (0.22 g) synthesized in the above-mentioned (1) was dissolved in ethanol (5 mL), and 1N aqueous sodium hydroxide solution (1 mL) was added to the solution at room temperature. The reaction mixture was stirred at 70° C. for 30 min, allowed to cool to room temperature, and concentrated under reduced pressure. The residue was dissolved in N,N-dimethylformamide (1 mL), and 1-ethyl-3-(3-dimethylaminopropyl)carbodiimide hydrochloride (0.17 g), 1-hydroxybenzotriazole.monohydrate (0.14 g) and ethyl 3-(methylamino)propanoate (0.10 g) were added to the solution at room temperature, and the mixture was stirred overnight. Water was added to the reaction mixture, and the mixture was extracted with diethyl ether. The extract was concentrated under reduced pressure, and the residue was purified by silica gel column chromatography (ethyl acetate:hexane=1:1, volume ratio) to give the title object compound (0.15 g, 56%) as a yellow oil.

$^1$H NMR (300 MHz, CDCl$_3$) δ ppm 0.93 (d, J=6.4 Hz, 3H), 1.14 (d, J=6.4 Hz, 3H), 1.26 (t, J=7.2 Hz, 3H), 2.16-2.36 (m, 4H), 2.60-2.80 (m, 2H), 3.80 (br. s., 2H), 4.12 (q, J=7.2 Hz, 2H), 4.22-4.48 (m, 2H), 5.09 (s, 2H), 6.79-7.05 (m, 3H), 7.24-7.51 (m, 7H), 7.93 (br. s., 1H).

(3) 3-[{[5-({1-[5-(benzyloxy)-3-methyl-1-benzofuran-2-yl]-2-methylpropyl}amino)pyridin-2-yl]carbonyl}(methyl)amino]propanoic acid Ethyl 3-[{[5-({1-[5-(benzyloxy)-3-methyl-1-benzofuran-2-yl]-2-methylpropyl}amino)pyridin-2-yl]carbonyl}(methyl)amino]propanoate (0.15 g) synthesized in the above-mentioned (2) was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.14 g, quantitative) as a colorless solid.

$^1$H NMR (300 MHz, CDCl$_3$) δ ppm 0.93 (d, J=6.8 Hz, 3H), 1.15 (d, J=6.8 Hz, 3H), 2.24 (s, 3H), 2.27-2.39 (m, 1H), 2.82 (br. s., 2H), 3.10 (s, 3H), 3.77 (t, J=6.4 Hz, 2H), 4.31 (d, J=7.9 Hz, 1H), 5.09 (s, 2H), 6.85-7.03 (m, 3H), 7.29-7.61 (m, 7H), 8.04 (br. s., 1H).

Example A173

3-[{[4-({1-[5-(2-methoxyethoxy)-3-methyl-1-benzofuran-2-yl]-2-methylpropyl}amino)phenyl]carbonyl}(methyl)amino]propanoic acid

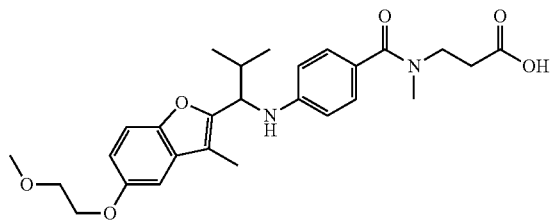 [SMILES: COCCOc1ccc2oc(C(Nc3ccc(C(=O)N(C)CCC(=O)O)cc3)C(C)C)c(C)c2c1]

(1) 1-[5-(2-methoxyethoxy)-3-methyl-1-benzofuran-2-yl]-2-methylpropan-1-one

To a solution (10 mL) of 1-[2-hydroxy-5-(2-methoxyethoxy)phenyl]ethanone (0.55 g) synthesized in Example A79(1) in N,N-dimethylformamide were added potassium carbonate (1.1 g) and 1-bromo-3-methylbutan-2-one (0.56 g) synthesized in Example A75(1) at room temperature, and the mixture was stirred for 15 hr. The reaction mixture was filtered through celite, water (200 mL) was added and the mixture was extracted with diethyl ether (10 mL×2). The extract was washed with saturated brine, dried over magnesium sulfate, and concentrated under reduced pressure. The residue was dissolved in N,N-dimethylformamide (10 mL), and 1,8-diazabicyclo[5.4.0]undec-7-ene (0.41 mL) was added to the solution at room temperature. The reaction mixture was stirred at 100° C. for 1 hr. The reaction mixture was allowed to cool to room temperature, 1N hydrochloric acid (10 mL) was added, and the mixture was extracted with diethyl ether (10 mL×2). The extract was washed with water, saturated aqueous sodium hydrogen carbonate solution and saturated brine, dried over magnesium sulfate, and concentrated under reduced pressure. The residue was purified by silica gel column chromatography (ethyl acetate:hexane=1:1, volume ratio) to give the title object compound (0.71 g, 98%) as a pale-yellow oil.

$^1$H NMR (300 MHz, CDCl$_3$) δ ppm 1.23 (d, J=6.8 Hz, 6H), 2.57 (s, 3H), 3.48 (s, 3H), 3.56 (quin, J=6.8 Hz, 1H), 3.74-3.85 (m, 2H), 4.10-4.24 (m, 2H), 7.05 (d, J=2.6 Hz, 1H), 7.14 (dd, J=9.0, 2.6 Hz, 1H), 7.39 (d, J=9.0 Hz, 1H).

(2) 1-[5-(2-methoxyethoxy)-3-methyl-1-benzofuran-2-yl]-2-methylpropan-1-ol

1-[5-(2-Methoxyethoxy)-3-methyl-1-benzofuran-2-yl]-2-methylpropan-1-one (0.71 g) synthesized in the above-mentioned (1) was dissolved in tetrahydrofuran (5 mL) and methanol (0.5 mL), and sodium borohydride (90%, 0.21 g) was added to the solution under ice-cooling. The ice bath was removed, and the reaction mixture was stirred at room temperature for 1 hr then ice-cooled again, and water (1 mL) and 1N hydrochloric acid (5 mL) were carefully added to the mixture, and the mixture was extracted with ethyl acetate. The extract was washed with saturated brine, dried over magnesium sulfate, and concentrated under reduced pressure to give a crude product (0.70 g, quantitative) of the title object compound as a pale-yellow oil.

$^1$H NMR (300 MHz, CDCl$_3$) δ ppm 0.82 (d, J=6.8 Hz, 3H), 1.12 (d, J=6.8 Hz, 3H), 1.96 (br. s., 1H), 2.12-2.33 (m, 4H), 3.47 (s, 3H), 3.70-3.85 (m, 2H), 4.10-4.23 (m, 2H), 4.46 (d, J=8.3 Hz, 1H), 6.79-7.01 (m, 2H), 7.30 (d, J=8.7 Hz, 1H).

(3) 3-[{[4-({1-[5-(2-methoxyethoxy)-3-methyl-1-benzofuran-yl]-2-methylpropyl}amino)phenyl]carbonyl}(methyl)amino]propanoic acid 1-[5-(2-Methoxyethoxy)-3-methyl-1-benzofuran-2-yl]-2-methylpropan-1-ol (0.70 g) synthesized in the above-mentioned (2) was dissolved in tetrahydrofuran (10 mL), and thionyl chloride (0.34 mL) was added to the solution at room temperature. The reaction mixture was stirred at room temperature for 30 min then ice-cooled, and saturated aqueous sodium hydrogen carbonate solution (5 mL) was carefully added to the mixture. The reaction mixture was stirred for 10 min, and extracted with ethyl acetate. The extract was washed with saturated brine, dried over magnesium sulfate, and concentrated under reduced pressure. The residue was dissolved in dimethylacetamide (10 mL), sodium iodide (0.56 g), sodium carbonate (0.38 g) and ethyl 3-{[(4-aminophenyl)carbonyl](methyl)amino}propanoate (0.63 g) synthesized in Example 2(2) were added to the solution and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-[{[4-({1-[5-(2-methoxyethoxy)-3-methyl-1-benzofuran-2-yl]-2-methylpropyl}amino)phenyl]carbonyl}(methyl)amino]propanoate (0.10 g, 8%) as a yellow oil. The obtained oil was dissolved in ethanol (3 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.05 g, 52%) as a colorless solid.

$^1$H NMR (300 MHz, CDCl$_3$) δ ppm 0.91 (d, J=6.4 Hz, 3H), 1.12 (d, J=6.4 Hz, 3H), 2.21 (s, 3H), 2.23-2.36 (m, 1H), 2.67 (t, J=6.4 Hz, 2H), 3.04 (s, 3H), 3.46 (s, 3H), 3.69 (t, J=6.4 Hz, 2H), 3.73-3.84 (m, 2H), 4.15 (dd, J=5.7, 3.8 Hz, 2H), 4.32 (d, J=7.5 Hz, 1H), 6.57 (d, J=8.7 Hz, 2H), 6.76-6.98 (m, 2H), 7.15-7.25 (m, 3H).

Example A174

3-[{[4-({cyclohexyl[5-(6-methoxypyridin-3-yl)-3-methyl-1-benzofuran-2-yl]methyl}amino)phenyl]carbonyl}(methyl)amino]propanoic acid

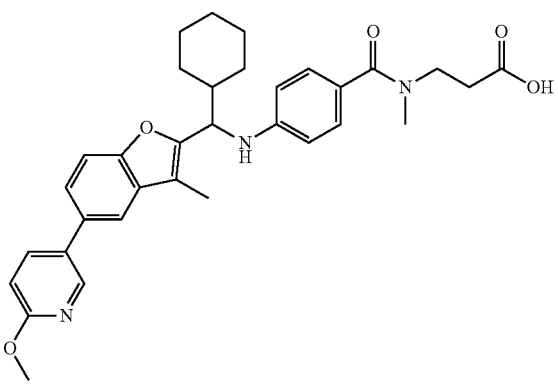 [SMILES: COc1ccc(-c2ccc3oc(C(Nc4ccc(C(=O)N(C)CCC(=O)O)cc4)C4CCCCC4)c(C)c3c2)cn1]

(1) (5-bromo-3-methyl-1-benzofuran-2-yl)(cyclohexyl)methanone

1-[5-Bromo-2-hydroxyphenyl]ethanone (13.4 g) was dissolved in N,N-dimethylformamide (300 mL). To the reaction mixture were added potassium carbonate (25.8 g) and 2-bromo-1-cyclohexylethanone (19.0 g) synthesized in Example A51(1) at room temperature, and the mixture was stirred for 3 hr. The reaction mixture was filtered through celite, water (200 mL) was added, and the mixture was extracted with diethyl ether (100 mL×2). The extract was washed with saturated brine, dried over magnesium sulfate, and concentrated under reduced pressure. The residue was dissolved in N,N-dimethylformamide (150 mL), 1,8-diazabicyclo[5.4.0]undec-7-ene (9.3 mL) was added to the solution at room temperature, and the mixture was stirred at 100° C. for 1 hr. The reaction mixture was allowed to cool to room temperature, 1N hydrochloric acid (70 mL) was added, and the mixture was extracted with diethyl ether (100 mL×2). The extract was washed with water, saturated aqueous sodium hydrogen carbonate solution and saturated brine, dried over magnesium sulfate, and concentrated under reduced pressure. The precipitate was washed with diisopropyl ether to give the title object compound (15.4 g, 77%) as a pale-yellow solid.

$^1$H NMR (300 MHz, CDCl$_3$) δ ppm 1.16-2.05 (m, 10H), 2.56 (s, 3H), 3.20-3.36 (m, 1H), 7.40 (d, J=8.9 Hz, 1H), 7.55 (dd, J=8.9, 1.5 Hz, 1H), 7.77 (d, J=1.5 Hz, 1H).

(2) (5-bromo-3-methyl-1-benzofuran-2-yl)(cyclohexyl)methanol (5-Bromo-3-methyl-1-benzofuran-2-yl)(cyclohexyl)methanone (7.5 g) synthesized in the above-mentioned (1) was dissolved in tetrahydrofuran (100 mL) and methanol (15 mL), and sodium borohydride (90%, 1.9 g) was added to the solution under ice-cooling. The ice bath was removed, and the reaction mixture was stirred at room temperature for 1 hr then ice-cooled again, and water (10 mL) and 1N hydrochloric acid (50 mL) were carefully added to the mixture, and the mixture was extracted with ethyl acetate. The extract was washed with saturated brine, dried over magnesium sulfate, and concentrated under reduced pressure to give a crude product (7.4 g, quantitative) of the title object compound as a pale-yellow oil.

$^1$H NMR (300 MHz, CDCl$_3$) δ ppm 0.83-2.11 (m, 11H), 2.19 (s, 3H), 3.62-3.85 (m, 1H), 4.51 (br. s., 1H), 7.27-7.59 (m, 3H).

(3) ethyl 3-{[(4-{[(5-bromo-3-methyl-1-benzofuran-2-yl)(cyclohexyl)methyl]amino}phenyl)carbonyl](methyl)amino}-propanoate (5-Bromo-3-methyl-1-benzofuran-2-yl)(cyclohexyl)methanol (7.5 g) synthesized in the above-mentioned (2) was dissolved in tetrahydrofuran (150 mL), and thionyl chloride (3.1 mL) was added to the solution at room temperature. The reaction mixture was stirred at room temperature for 30 min then ice-cooled, and saturated aqueous sodium hydrogen carbonate solution (75 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (100 mL), sodium iodide (5.2 g), sodium carbonate (3.5 g) and ethyl 3-{[(4-aminophenyl)carbonyl](methyl)amino}propanoate (5.8 g) synthesized in Example 2(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (6.0 g, 47%) as a pale-yellow solid.

$^1$H NMR (300 MHz, CDCl$_3$) δ ppm 0.88-1.97 (m, 14H), 2.22 (s, 3H), 2.61 (t, J=7.1 Hz, 2H), 3.01 (s, 3H), 3.70 (t, J=7.1 Hz, 2H), 3.99-4.17 (m, 2H), 4.23-4.47 (m, 2H), 6.55 (d, J=8.7 Hz, 2H), 7.11-7.37 (m, 4H), 7.54 (d, J=1.7 Hz, 1H).

(4) 3-[{[4-({cyclohexyl[5-(6-methoxypyridin-3-yl)-3-methyl-1-benzofuran-2-yl]methyl}amino)phenyl]carbonyl}(methyl)amino]propanoic acid To a solution (5 mL) of ethyl 3-{[(4-{[(5-bromo-3-methyl-1-benzofuran-2-yl)(cyclohexyl)methyl]amino}phenyl)carbonyl]methyl)amino}propanoate (0.25 g) synthesized in the above-mentioned (3) in N,N-dimethylacetamide were added (6-methoxypyridin-3-yl)boronic acid (0.14 g), potassium carbonate (0.13 g) and tetrakistriphenylphosphine palladium (0.05 g), and the mixture was stirred at 90° C. for 12 hr under nitrogen atmosphere. The reaction mixture was cooled to room temperature, and filtered-through celite and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-[{[4-({cyclohexyl[5-(6-methoxypyridin-3-yl)-3-methyl-1-benzofuran-2-yl]methyl}amino)phenyl]carbonyl}(methyl)amino]propanoate (0.15 g, 58%) as a pale-yellow oil. The obtained oil was dissolved in ethanol (1 mL), 1N aqueous sodium hydroxide solution (1.0 mL) was added at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.12 g, 85%) as a pale-yellow solid.

$^1$H NMR (300 MHz, CDCl$_3$) δ ppm 1.27-2.19 (m, 12H), 2.29 (s, 3H), 2.69 (t, J=6.4 Hz, 2H), 3.05 (s, 3H), 3.70 (t, J=6.4 Hz, 2H), 3.99 (s, 3H), 4.41 (d, J=7.9 Hz, 1H), 6.58 (d, J=8.7 Hz, 2H), 6.83 (d, J=9.0 Hz, 1H), 7.19-7.26 (m, 2H), 7.32-7.53 (m, 3H), 7.81 (dd, J=8.5, 2.4 Hz, 1H), 8.38 (d, J=2.3 Hz, 1H).

Example A175

3-{[(4-{[1-(4-fluoro-3-methyl-1-benzofuran-2-yl)-2-methylpropyl]amino}phenyl)carbonyl](methyl)amino}propanoic acid

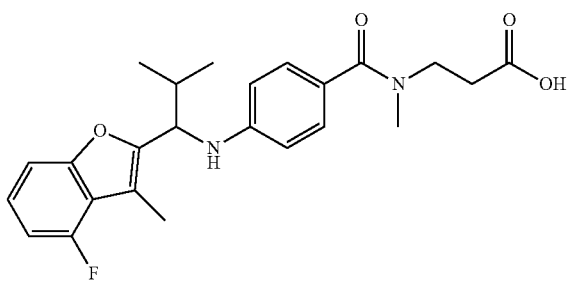 [SMILES: Cc1c(C(Nc2ccc(C(=O)N(C)CCC(=O)O)cc2)C(C)C)oc2cccc(F)c12]

(1) 1-(4-fluoro-3-methyl-1-benzofuran-2-yl)-2-methylpropan-1-one

To a solution (25 mL) of 1-(2-fluoro-6-hydroxyphenyl)ethanone (1.3 g) in N,N-dimethylformamide were added potassium carbonate (3.5 g) and 1-bromo-3-methylbutan-2-one (1.7 g) synthesized in Example A75(1) at room temperature, and the mixture was stirred at room temperature for 3 hr. The reaction mixture was allowed to cool to room temperature, and filtered through celite. Water was added to the filtrate, and the mixture was extracted with diethyl ether. The extract was washed with saturated brine, dried over magnesium sulfate, and concentrated under reduced pressure. The obtained residue was dissolved in N,N-dimethylformamide (15 mL) again, 1,8-diazabicyclo[5.4.0]undec-7-ene (1.3 mL) was added to the mixture, and the mixture was stirred at 110° C. for 1 hr with heating. After cooling to room temperature, the reaction mixture was quenched with 1N hydrochloric acid, and the mixture was extracted with diethyl ether. The extract was concentrated under reduced pressure, and the precipitated compound was recrystallized from diisopropyl ether-hexane to give the title object compound (1.4 g, 77%) as a colorless solid.

$^1$H NMR (300 MHz, CDCl$_3$) δ ppm 1.24 (d, J=6.8 Hz, 6H), 2.74 (s, 3H), 3.50-3.66 (m, 1H), 6.93 (dd, J=10.2, 7.9 Hz, 1H), 7.28-7.50 (m, 2H).

(2) 1-(4-fluoro-3-methyl-1-benzofuran-2-yl)-2-methylpropan-1-ol 1-(4-Fluoro-3-methyl-1-benzofuran-2-yl)-2-methylpropan-1-one (1.4 g) synthesized in the above-mentioned (1) was dissolved in tetrahydrofuran (20 mL) and methanol (2 mL), and sodium borohydride (90%, 0.53 g) was added to the solution under ice-cooling. The ice bath was removed, and the reaction mixture was stirred at room temperature for 1 hr then ice-cooled again, and water (2 mL) and 1N hydrochloric acid (5 mL) were carefully added to the mixture, and the mixture was extracted with ethyl acetate. The extract was washed with saturated brine, dried over magnesium sulfate, and concentrated under reduced pressure to give a crude product (1.4 g, quantitative) of the title object compound as a pale-yellow oil.

$^1$H NMR (300 MHz, CDCl$_3$) δ ppm 0.82 (d, J=6.8 Hz, 3H), 1.13 (d, J=6.8 Hz, 3H), 1.99 (d, J=5.7 Hz, 1H), 2.22 (dt, J=8.3, 6.8 Hz, 1H), 2.36 (s, 3H), 4.46 (dd, J=8.3, 5.7 Hz, 1H), 6.77-7.23 (m, 3H).

(3) 3-{[(4-{[1-(4-fluoro-3-methyl-1-benzofuran-2-yl)-2-methylpropyl]amino}phenyl)carbonyl](methyl)amino}propanoic acid 1-(4-Fluoro-3-methyl-1-benzofuran-2-yl)-2-methylpropan-1-ol (1.4 g) synthesized in the above-mentioned (2) was dissolved in tetrahydrofuran (20 mL), and thionyl chloride (0.84 mL) was added to the solution at room temperature. The reaction mixture was stirred at room temperature for 30 min then ice-cooled, and saturated aqueous sodium hydrogen carbonate solution (20 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (30 mL), sodium iodide (1.4 g), sodium carbonate (0.96 g) and ethyl 3-{[(4-aminophenyl)carbonyl](methyl)amino}propanoate (1.6 g) synthesized in Example 2(2) were added to the solution, and the mixture was stirred at 80° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[1-(4-fluoro-3-methyl-1-benzofuran-2-ylpropyl]amino}phenyl)carbonyl](methyl)amino}propanoate (0.20 g, 7%) as a yellow oil. The obtained oil was dissolved in ethanol (2 mL), 1N aqueous sodium hydroxide solution (2.0 mL) was added to the solution at room temperature, and the mixture was stirred at room temperature for 0.5 hr. Ethanol was evaporated under reduced pressure, and 1N hydrochloric acid (2.0 mL) was added to the residue. The precipitate was washed with water to give the title object compound (0.06 g, 32%) as a pale-yellow solid.

$^1$H NMR (300 MHz, CDCl$_3$) δ ppm 0.92 (d, J=6.4 Hz, 3H), 1.14 (d, J=6.4 Hz, 3H), 2.09-2.32 (m, 1H), 2.39 (s, 3H), 2.69 (t, J=6.2 Hz, 2H), 3.05 (s, 3H), 3.71 (t, J=6.2 Hz, 2H), 4.31 (d, J=7.9 Hz, 1H), 6.58 (d, J=8.7 Hz, 2H), 6.76-7.19 (m, 3H), 7.25 (d, J=8.7 Hz, 2H).

Example A176

3-{[(4-{[cyclohexyl(3-methyl-5-phenyl-1-benzofuran-2-yl)methyl]amino}phenyl)carbonyl](methyl)amino}propanoic acid

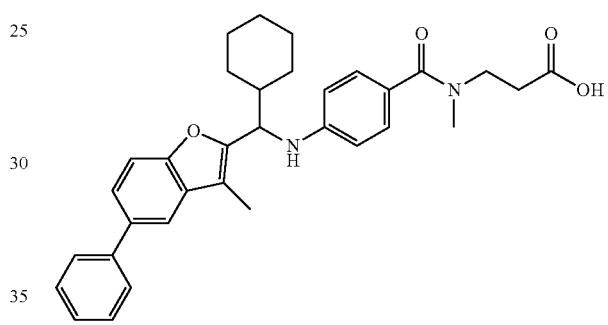

To a solution (5 mL) of ethyl 3-{[(4-{[(5-bromo-3-methyl-1-benzofuran-2-yl)(cyclohexyl)methyl]amino}phenyl)carbonyl](methyl)amino}-propanoate (0.28 g) synthesized in Example A174 (3) in N,N-dimethylacetamide were added phenylboronic acid (0.12 g), potassium carbonate (0.14 g) and tetrakistriphenylphosphine palladium (0.10 g), and the mixture was stirred at 70° C. for 12 hr under nitrogen atmosphere. The reaction mixture was cooled to room temperature, and filtered through celite, and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-{[(4-{[cyclohexyl(3-methyl-5-phenyl-1-benzofuran-2-yl)methyl]amino}phenyl)carbonyl](methyl)amino}propanoate (0.15 g, 54%) as a pale-yellow oil. The obtained oil was dissolved in ethanol (1 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title, object compound (0.09 g, 67%) as a colorless solid.

$^1$H NMR (300 MHz, CDCl$_3$) δ ppm 0.97-2.16 (m, 11H), 2.29 (s, 3H), 2.69 (t, J=6.2 Hz, 2H), 3.05 (s, 3H), 3.72 (t, J=6.2 Hz, 2H), 4.41 (d, J=7.9 Hz, 1H), 6.58 (d, J=8.7 Hz, 2H), 7.23-7.66 (m, 10H).

Example A177

3-[{[4-({cyclohexyl[5-(2-methoxypyridin-3-yl)-3-methyl-1-benzofuran-2-yl]methyl}amino)phenyl]carbonyl}(methyl)amino]propanoic acid

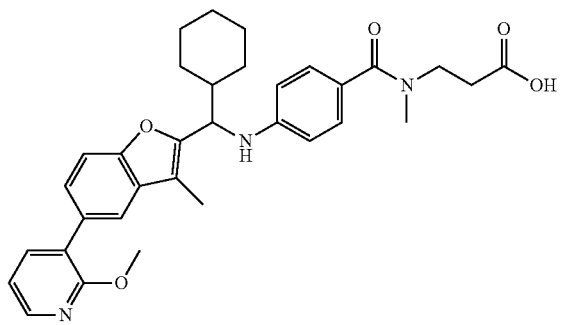 [SMILES: COc1ncccc1-c1ccc2oc(C(Nc3ccc(C(=O)N(C)CCC(=O)O)cc3)C3CCCCC3)c(C)c2c1]

To a solution (15 mL) of ethyl 3-{[(4-{[(5-bromo-3-methyl-1-benzofuran-2-yl)(cyclohexyl)methyl]amino}phenyl)carbonyl](methyl)amino}-propanoate (0.53 g) synthesized in Example A174(3) in N,N-dimethylacetamide were added (2-methoxypyridin-3-yl)boronic acid (0.29 g), potassium carbonate (0.27 g) and tetrakistriphenylphosphine palladium (0.05 g), and the mixture was stirred at 90° C. for 12 hr under nitrogen atmosphere. The reaction mixture was cooled to room temperature and filtered through celite, and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-[{[4-({cyclohexyl[5-(2-methoxypyridin-3-yl)-3-methyl-1-benzofuran-2-yl]methyl}amino)phenyl]carbonyl}(methyl)amino]propanoate (0.50 g, 89%) as a pale-yellow oil. The obtained oil was dissolved in ethanol (1 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.47 g, quantitative) as a colorless solid.

$^1$H NMR (300 MHz, CDCl$_3$) δ ppm 0.97-2.15 (m, 11H), 2.27 (s, 3H), 2.49-2.65 (m, 2H), 2.99 (s, 3H), 3.65 (br. s., 2H), 3.95 (s, 3H), 4.39 (d, J=7.9 Hz, 1H), 6.56 (d, J=8.7 Hz, 2H), 6.97 (dd, J=7.2, 4.9 Hz, 1H), 7.23 (d, J=8.7 Hz, 2H), 7.38-7.66 (m, 4H), 8.15 (dd, J=5.1, 2.1 Hz, 1H).

Example A178

3-[{[4-({cyclohexyl[5-(3,5-dimethylisoxazol-4-yl)-3-methyl-1-benzofuran-2-yl]methyl}amino)phenyl]carbonyl}(methyl)amino]propanoic acid

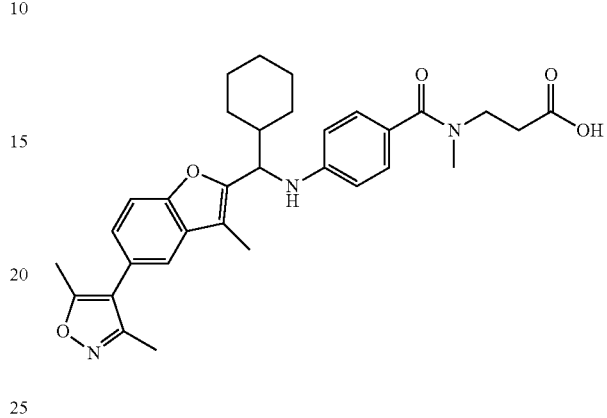

To a solution (15 mL) of ethyl 3-{[(4-{[(5-bromo-3-methyl-1-benzofuran-2-yl)(cyclohexyl)methyl]amino}phenyl)carbonyl](methyl)amino}-propanoate (0.54 g) synthesized in Example A174(3) in toluene were added (3,5-dimethylisoxazol-4-yl)boronic acid (0.41 g) and 2N aqueous sodium carbonate solution (1.46 mL), and the mixture was stirred at room temperature for 10 min under argon atmosphere. To the reaction mixture were added 2-dicyclohexylphosphino-2',6'-dimethoxybiphenyl (0.05 g) and tris(dibenzylideneacetone)dipalladium (0) (0.03 g), and the mixture was heated under reflux under argon atmosphere overnight. The reaction mixture was cooled to room temperature and filtered through celite, and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-[{[4-({cyclohexyl[5-(3,5-dimethylisoxazol-4-yl)-3-methyl-1-benzofuran-2-yl]methyl}amino)phenyl]carbonyl}(methyl)amino]propanoate (0.13 g, 23%) as a pale-yellow oil. The obtained oil was dissolved in ethanol (1 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.12 g, 96%) as a colorless solid.

$^1$H NMR (300 MHz, CDCl$_3$) δ ppm 0.93-2.19 (m, 11H), 2.26 (s, 3H), 2.27 (s, 3H), 2.39 (s, 3H), 2.71 (t, J=6.2 Hz, 2H), 3.07 (s, 3H), 3.73 (t, J=6.2 Hz, 2H), 4.41 (d, J=7.9 Hz, 1H), 6.58 (d, J=8.7 Hz, 2H), 7.08 (dd, J=8.3, 1.5 Hz, 1H), 7.20-7.26 (m, 3H), 7.42 (d, J=8.3 Hz, 1H).

Example A179

3-[{[4-({1-[5-(benzyloxy)-3-methyl-1-benzofuran-2-yl]propyl}amino)phenyl]carbonyl}(methyl)amino]propanoic acid

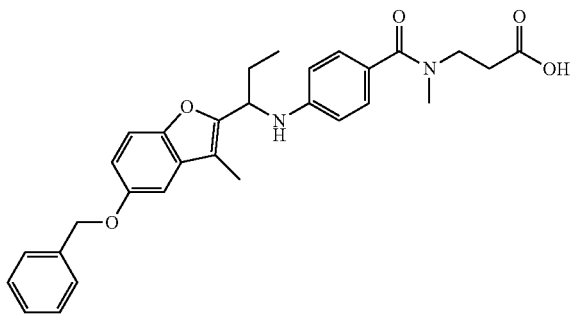 [SMILES: CCC(Nc1ccc(C(=O)N(C)CCC(=O)O)cc1)c1oc2ccc(OCc3ccccc3)cc2c1C]

(1) 1-[5-(benzyloxy)-3-methyl-1-benzofuran-2-yl]propan-1-one

To a solution (150 mL) of 1-[5-(benzyloxy)-2-hydroxyphenyl]ethanone (7.8 g) synthesized in Example 82(1) in N,N-dimethylformamide were added potassium carbonate (13.2 g) and 1-bromobutan-2-one (5.0 mL) at room temperature, and the mixture was stirred at room temperature for 3 hr. The reaction mixture was allowed to cool to room temperature, and filtered through celite. Water was added to the filtrate, and the mixture was extracted with diethyl ether. The extract was washed with saturated brine, dried over magnesium sulfate, and concentrated under reduced pressure. The obtained residue was dissolved in N,N-dimethylformamide (100 mL) again, 1,8-diazabicyclo[5.4.0]undec-7-ene (4.9 mL) was added to the solution, and the mixture was stirred at 110° C. with heating for 1 hr. After cooling to room temperature, the reaction mixture was quenched with 1N hydrochloric acid, and the mixture was extracted with diethyl ether. The extract was concentrated under reduced pressure, and the precipitated compound was recrystallized from diisopropyl ether-hexane to give the title object compound (6.2 g, 66%) as a colorless solid.

$^1$H NMR (300 MHz, CDCl$_3$) δ ppm 1.22 (t, J=7.2 Hz, 3H), 2.57 (s, 3H), 3.01 (q, J=7.2 Hz, 2H), 5.12 (s, 2H), 7.04-7.52 (m, 8H).

(2) 1-[5-(benzyloxy)-3-methyl-1-benzofuran-2-yl]propan-1-ol

1-[5-(Benzyloxy)-3-methyl-1-benzofuran-2-yl]propan-1-one (0.88 g) synthesized in the above-mentioned (1) was dissolved in tetrahydrofuran (15 mL) and methanol (1 mL), and sodium borohydride (90%, 0.25 g) was added to the solution under ice-cooling. The ice bath was removed, and the reaction mixture was stirred at room temperature for 1 hr then ice-cooled again, and water (2 mL) and 1N hydrochloric acid (5 mL) were carefully added to the mixture, and the mixture was extracted with ethyl acetate. The extract was washed with saturated brine, dried over magnesium sulfate, and concentrated under reduced pressure to give a crude product (0.85 g, quantitative) of the title object compound as a pale-yellow oil.

$^1$H NMR (300 MHz, CDCl$_3$) δ ppm 0.93 (t, J=7.4 Hz, 3H), 1.92-2.03 (m, 3H), 2.21 (s, 3H), 4.69-4.87 (m, 1H), 5.11 (s, 2H), 6.89-7.51 (m, 8H).

(3) 3-[{[4-({1-[5-(benzyloxy)-3-methyl-1-benzofuran-2-yl]propyl}amino)phenyl]carbonyl}(methyl)amino]propanoic acid 1-[5-(Benzyloxy)-3-methyl-1-benzofuran-2-yl]propan-1-ol (0.85 g) synthesized in the above-mentioned (2) was dissolved in tetrahydrofuran (15 mL), and thionyl chloride (0.40 mL) was added to the solution at room temperature. The reaction mixture was stirred at room temperature for 30 min then ice-cooled, and saturated aqueous sodium hydrogen carbonate solution (20 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15 mL), sodium iodide (0.67 g), sodium carbonate (0.45 g) and ethyl 3-{[(4-aminophenyl)carbonyl](methyl)amino}propanoate (0.75 g) synthesized in Example 2(2) were added to the solution and the mixture was stirred at 80° C. for 4 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-[{[4-({1-[5-(benzyloxy)-3-methyl-1-benzofuran-2-yl]propyl}amino)phenyl]carbonyl}(methyl)amino]propanoate (0.15 g, 9%) as a yellow oil. The obtained oil was dissolved in ethanol (2 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.10 g, 71%) as a colorless solid.

$^1$H NMR (300 MHz, CDCl$_3$) δ ppm 0.94 (t, J=7.3 Hz, 3H), 1.87-2.08 (m, 2H), 2.23 (s, 3H), 2.66 (t, J=6.2 Hz, 2H), 3.03 (s, 3H), 3.70 (t, J=6.2 Hz, 2H), 4.52 (dd, J=8.3, 6.2 Hz, 1H), 5.09 (s, 2H), 6.57 (d, J=8.7 Hz, 2H), 6.82-7.02 (m, 2H), 7.18-7.51 (m, 8H).

Example A180

3-(methyl{[4-({2-methyl-1-[3-methyl-5-(tetrahydro-2H-pyran-4-yloxy)-1-benzofuran-2-yl]propyl}amino)phenyl]carbonyl}amino)propanoic acid

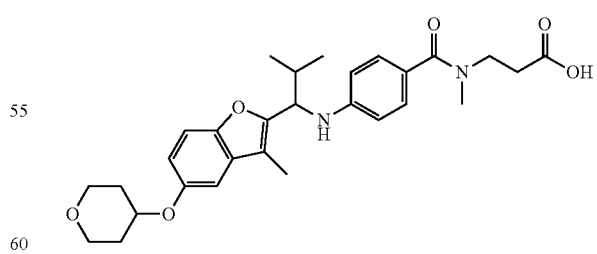

(1) 1-(5-hydroxy-3-methyl-1-benzofuran-2-yl)-2-methylpropan-1-one

To a solution of 1-[5-(benzyloxy)-3-methyl-1-benzofuran-2-yl]-2-methylpropan-1-one (11.4 g) synthesized in Example A85(1) in ethanol (200 mL) was added palladium carbonethylenediamine complex (1.1 g) at room temperature. The reaction mixture was stirred under hydrogen atmosphere (1 atm) at room temperature for 16 hr, and the catalyst was filtered off. The filtrate was concentrated under reduced pressure to give a crude product (8.0 g, quantitative) of the title object compound as a colorless solid.

$^1$H NMR (300 MHz, CDCl$_3$) δ ppm 1.24 (d, J=6.8 Hz, 6H), 2.55 (s, 3H), 3.48-3.63 (m, 1H), 6.95-7.40 (m, 3H).

(2) 3-(methyl{[4-({2-methyl-1-[3-methyl-5-(tetrahydro-2H-pyran-4-yloxy)-1-benzofuran-2-yl] propyl}amino)phenyl]carbonyl}amino)propanoic acid 1-(5-Hydroxy-3-methyl-1-benzofuran-2-yl)-2-methylpropan-1-one (1.0 g) synthesized in the above-mentioned (1) was dissolved in N,N-dimethylforamide (20 mL) and was added potassium phosphate (1.3 g) and tetrahydro-2H-pyran-4-yl 4-methylbenzenesulfonate (2.8 g) at room temperature. The reaction mixture was stirred at 80° C. for 4 hr, then again added potassium phosphate (1.3 g) and tetrahydro-2H-pyran-4-yl 4-methylbenzenesulfonate (2.8 g). After being stirred for 12 h at 80° C., then cooled to room temperature and quenched with water. The mixture was extracted with diethyl ether then washed with saturated brine, dried over magnesium sulfate, and concentrated under reduced pressure. The residue was purified by silica gel column chromatography (ethyl acetate:hexane=1:4, volume ratio) to give 1-(5-(tetrahydro-2H-pyran-4-yl)-3-methyl-1-benzofuran-2-yl)-2-methylpropan-1-one (1.1 g, 78%) as a colorless oil. Obtained oil (1.1 g) was dissolved in tetrahydrofuran (15 mL) and methanol (1 mL), and sodium borohydride (90%, 0.30 g) was added to the solution under ice-cooling. The ice bath was removed, and the reaction mixture was stirred at room temperature for 1 hr then ice-cooled again, and water (5 mL) and 1N hydrochloric acid (15 mL) were carefully added to the mixture, and the mixture was extracted with ethyl acetate. The extract was washed with saturated brine, dried over magnesium sulfate, and concentrated under reduced pressure to give 1-(5 (tetrahydro-2H-pyran-4-yl)-3-methyl-1-benzofuran-2-yl)-2-methylpropan-1-ol (0.71 g, 65%) as a pale-yellow oil. The obtained oil was dissolved in tetrahydrofuran (15 mL), and thionyl chloride (0.30 mL) was added to the solution at room temperature. The reaction mixture was stirred at room temperature for 30 min then ice-cooled, and saturated aqueous sodium hydrogen carbonate solution (20 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15 mL), sodium iodide (0.52 g), sodium carbonate (0.35 g) and ethyl 3-{[(4-aminophenyl)carbonyl] (methyl)amino}propanoate (0.58 g) synthesized in Example 2(2) were added to the mixture, and the mixture was stirred at 70° C. for 4 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-(methyl{[4-({2-methyl-1-[3-methyl-5-(tetrahydro-2H-pyran-4-yloxy)-1-benzofuran-2-yl]propyl}amino)phenyl] carbonyl}amino)propanoate (0.54 g, 46%) as a yellow oil. The obtained oil was dissolved in ethanol (3 mL), 1N aqueous sodium hydroxide solution (3.0 mL) was added to the solution at room temperature, and the mixture was stirred at room temperature for 0.5 hr. Ethanol was evaporated under reduced pressure, and 1N hydrochloric acid (3.0 mL) was added to the residue. The precipitate was washed with water to give the title object compound (0.53 g, 98%) as a colorless solid.

$^1$H NMR (300 MHz, CDCl$_3$) δ ppm 0.92 (d, J=6.8 Hz, 3H), 1.13 (d, J=6.8 Hz, 3H), 1.70-2.09 (m, 4H), 2.21 (s, 3H), 2.22-2.27 (m, 1H), 2.67 (t, J=6.2 Hz, 2H), 3.04 (s, 3H), 3.56 (ddd, J=11.5, 8.5, 3.4 Hz, 2H), 3.70 (t, J=6.2 Hz, 2H), 3.91-4.08 (m, 2H), 4.32 (d, J=7.6 Hz, 1H), 4.43 (tt, J=7.9, 3.8 Hz, 1H), 6.57 (d, J=8.7 Hz, 2H), 6.85 (dd, J=8.7, 2.7 Hz, 1H), 6.93 (d, J=2.3 Hz, 1H), 7.19-7.26 (m, 3H).

Example A181

3-[{[4-({cyclohexyl[3-methyl-5-(1-methyl-1H-pyrazol-4-yl)-1-benzofuran-2-yl]methyl}amino)phenyl] carbonyl}(methyl)amino]propanoic acid

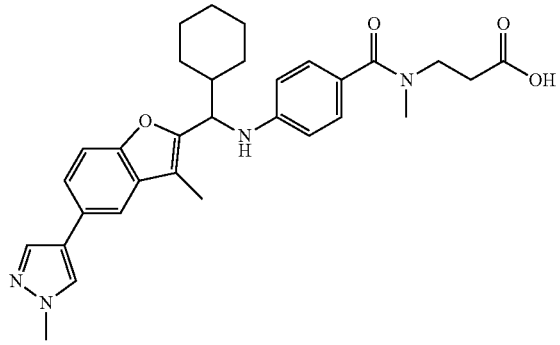 [SMILES: Cc1c(C(Nc2ccc(C(=O)N(C)CCC(=O)O)cc2)C2CCCCC2)oc2ccc(-c3cnn(C)c3)cc12]

To a solution (15 mL) of ethyl 3-{[(4-{[(5-bromo-3-methyl-1-benzofuran-2-yl)(cyclohexyl)methyl]amino}phenyl) carbonyl](methyl)amino}-propanoate (0.59 g) synthesized in Example A174(3) in N,N-dimethylacetamide were added 1-methyl-4-(4,4,5,5-tetramethyl-1,3,2-dioxaborolan-2-yl)-1H-pyrazole (0.44 g), potassium carbonate (0.29 g) and tetrakistriphenylphosphine palladium (0.06 g), and the mixture was stirred at 70° C. for 24 hr under argon atmosphere. The reaction mixture was cooled to room temperature, and filtered through celite, and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-[{[4-({cyclohexyl[3-methyl-5-(1-methyl-1H-pyrazol-4-yl)-1-benzofuran-2-yl] methyl}amino)phenyl]carbonyl}(methyl)amino]propanoate (0.23 g, 39%) as a pale-yellow oil. The obtained oil was dissolved in ethanol (1 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.04 g, 16%) as a colorless solid.

$^1$H NMR (300 MHz, CDCl$_3$) δ ppm 0.93-2.11 (m, 11H), 2.27 (s, 3H), 2.67 (br. s., 2H), 3.03 (s, 3H), 3.70 (t, J=6.2 Hz, 2H), 3.94 (s, 3H), 4.38 (d, J=7.8 Hz, 1H), 6.57 (d, J=8.6 Hz, 2H), 7.23 (d, J=8.6 Hz, 2H), 7.29-7.39 (m, 2H), 7.49 (s, 1H), 7.59 (s, 1H), 7.75 (s, 1H).

Example A182

3-[{[4-({1-[5-(6-methoxypyridin-3-yl)-3-methyl-1-benzofuran-2-yl]-2-methylpropyl}amino)phenyl]carbonyl}(methyl)amino]propanoic acid

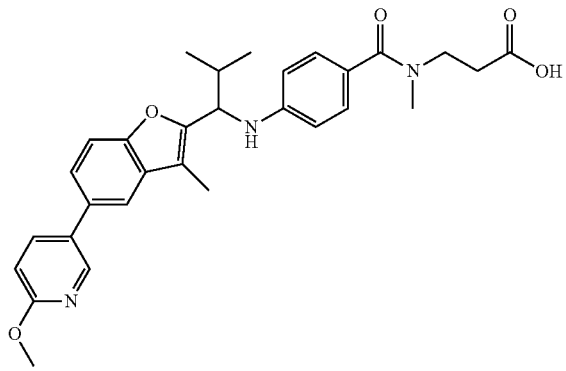 [SMILES: COc1ccc(-c2ccc3oc(C(Nc4ccc(C(=O)N(C)CCC(=O)O)cc4)C(C)C)c(C)c3c2)cn1]

(1) 1-(5-bromo-3-methyl-1-benzofuran-2-yl)-2-methylpropan-1-one

1-[5-Bromo-2-hydroxyphenyl]ethanone (8.4 g) was dissolved in N,N-dimethylformamide (50 mL). To the reaction mixture were added carbonate (16.2 g) and 1-bromo-3-methylbutan-2-one (8.4 g) synthesized in Example A75(1) at room temperature potassium, and the mixture was stirred at 60° C. for 1 hr. The reaction mixture was filtered through celite, water (100 mL) was added, and the mixture was extracted with diethyl ether (50 mL×2). The extract was washed with saturated brine, dried over magnesium sulfate, and concentrated under reduced pressure. The precipitate was washed with diisopropyl ether to give the title object compound (10.2 g, 77%) as a pale-yellow solid.

$^1$H NMR (300 MHz, CDCl$_3$) δ ppm 1.25 (d, J=6.8 Hz, 6H), 2.57 (s, 3H), 3.48-3.70 (m. 1H), 7.39 (d, J=8.7 Hz, 1H), 7.55 (dd, J=8.7, 1.9 Hz, 1H), 7.78 (d, J=1.9 Hz, 1H).

(2) ethyl 3-{[(4-{[1-(5-bromo-3-methyl-1-benzofuran-2-yl)-2-methylpropyl]amino}phenyl)carbonyl](methyl)amino}propanoate 1-(5-Bromo-3-methyl-1-benzofuran-2-yl)-2-methylpropan-1-one (6.2 g) synthesized in the above-mentioned (1) was dissolved in tetrahydrofuran (100 mL) and methanol (10 mL), and sodium borohydride (90%, 1.8 g) was added to the solution under ice-cooling. The ice bath was removed, and the reaction mixture was stirred at room temperature for 1 hr then ice-cooled again, and water (10 mL) and 1N hydrochloric acid (50 mL) were carefully added to the mixture, and the mixture was extracted with ethyl acetate. The extract was washed with saturated brine, dried over magnesium sulfate, and concentrated under reduced pressure to give 1-(5-bromo-3-methyl-1-benzofuran-2-yl)-2-methylpropan-1-ol (6.1 g, quantitative) as a pale-yellow oil. The obtained oil was dissolved in tetrahydrofuran (50 mL), and thionyl chloride (2.3 mL) was added to the solution at room temperature. The reaction mixture was stirred at room temperature for 30 min then ice-cooled, and saturated aqueous sodium hydrogen carbonate solution (30 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (100 mL), sodium iodide (3.9 g), sodium carbonate (2.7 g) and ethyl 3-{[(4-aminophenyl)carbonyl](methyl)amino}propanoate (4.4 g) synthesized in Example 2(2) were added to the solution, and the mixture was stirred at 70° C. for 4 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (1.12 g, 12%) as a yellow oil.

$^1$H NMR (300 MHz, CDCl$_3$) δ ppm 0.91 (d, J=6.4 Hz, 3H), 1.13 (d, J=6.4 Hz, 3H), 1.18-1.26 (t, J=7.2 Hz, 3H), 2.20-2.35 (m, 4H), 2.61 (t, J=7.0 Hz, 2H), 3.01 (s, 4H), 3.70 (t, J=7.0 Hz, 2H), 4.09-4.17 (m, 2H), 4.24-4.41 (m, 2H), 6.56 (d, J=8.7 Hz, 2H), 7.15-7.36 (m, 4H), 7.55 (d, J=1.9 Hz, 1H).

(3) 3-[{[4-({1-[5-(6-methoxypyridin-3-yl)-3-methyl-1-benzofuran-2-yl]-2-methylpropyl}amino)phenyl]carbonyl}(methyl)amino]propanoic acid To a solution (10 mL) of ethyl 3-{[(4-{[1-(5-bromo-3-methyl-1-benzofuran-2-yl)-2-methylpropyl]amino}phenyl)carbonyl](methyl)amino}propanoate (0.55 g) synthesized in the above-mentioned (2) in N,N-dimethylacetamide were added (6-methoxypyridin-3-yl)boronic acid (0.33 g), potassium carbonate (0.29 g) and tetrakistriphenylphosphine palladium (0.12 g), and the mixture was stirred at 70° C. for 24 hr under argon atmosphere. The reaction mixture was cooled to room temperature, and filtered through celite, and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-[{[4-({1-[5-(6-methoxypyridin-3-yl)-3-methyl-1-benzofuran-2-yl]-2-methylpropyl}amino)phenyl]carbonyl}(methyl)amino]propanoate (0.10 g) as a pale-yellow oil. The obtained oil was dissolved in ethanol (1 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.06 g, 10%) as a colorless solid.

$^1$H NMR (300 MHz, CDCl$_3$) δ ppm 0.94 (d, J=6.8 Hz, 3H), 1.15 (d, J=6.8 Hz, 3H), 2.15-2.37 (m, 1H), 2.29 (s, 3H), 2.66 (t, J=6.2 Hz, 2H), 3.03 (s, 3H), 3.70 (t, J=6.2 Hz, 2H), 3.98 (s, 3H), 4.36 (d, J=7.5 Hz, 1H), 6.58 (d, J=8.7 Hz, 2H), 6.82 (d, J=8.7 Hz, 1H), 7.23 (d, J=8.7 Hz, 2H), 7.30-7.46 (m, 2H), 7.53 (d, J=1.9 Hz, 1H), 7.79 (dd, J=8.5, 2.4 Hz, 1H), 8.38 (d, J=2.4 Hz, 1H).

Example A183

3-[{[4-({1-[5-(2-methoxypyridin-3-yl)-3-methyl-1-benzofuran-2-yl]-2-methylpropyl}amino)phenyl]carbonyl}(methyl)amino]propanoic acid

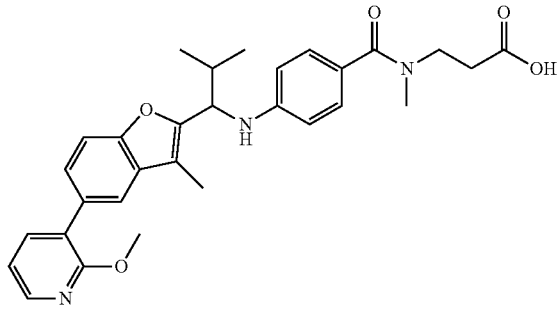 [SMILES: COc1ncccc1-c1ccc2oc(C(Nc3ccc(C(=O)N(C)CCC(=O)O)cc3)C(C)C)c(C)c2c1]

To a solution (10 mL) of ethyl 3-{[(4-{[1-(5-bromo-3-methyl-1-benzofuran-2-yl)-2-methylpropyl]amino}phenyl)carbonyl]methyl)amino}propanoate (0.55 g) synthesized in Example A182(2) in N,N-dimethylacetamide were added (2-methoxypyridin-3-yl)boronic acid (0.33 g), potassium carbonate (0.29 g) and tetrakistriphenylphosphine palladium (0.12 g), and the mixture was stirred at 70° C. for 24 hr under argon atmosphere. The reaction mixture was cooled to room temperature, and filtered through celite, and the residue was washed with diethyl ether. Water was added to the filtrate, and the organic layer was concentrated under reduced pressure. The residue was purified by silica gel column chromatography (ethyl acetate:hexane=1:1, volume ratio) to give ethyl 3-[{[4-({1-[5-(2-methoxypyridin-3-yl)-3-methyl-1-benzofuran-2-yl]-2-methylpropyl}amino)phenyl]carbonyl}(methyl)amino]propanoate (0.10 g) as a pale-yellow oil. The obtained oil was dissolved in ethanol (1 mL), 1N aqueous sodium hydroxide solution (1.0 mL) was added to the solution at room temperature, and the mixture was stirred at room temperature for 0.5 hr. Ethanol was evaporated under reduced pressure, 1N hydrochloric acid (1.0 mL) was added to the residue. The precipitate was washed with water to give the title object compound (0.18 g, 33%) as a colorless solid.

$^1$H NMR (300 MHz, CDCl$_3$) δ ppm 0.94 (d, J=6.4 Hz, 3H), 1.15 (d, J=6.4 Hz, 3H), 2.12-2.40 (m, 1H), 2.27 (s, 3H), 2.67 (t, J=6.2 Hz, 2H), 3.04 (s, 3H), 3.70 (t, J=6.2 Hz, 2H), 3.96 (s, 3H), 4.36 (d, J=7.9 Hz, 1H), 6.58 (d, J=8.7 Hz, 2H), 6.97 (d, J=7.2, 4.9 Hz, 1H), 7.23 (d, J=8.7 Hz, 2H), 7.33-7.77 (m, 4H), 8.16 (dd, J=4.9, 1.9 Hz, 1H).

Example A184

3-{[(4-{[1-(5-cyclopropyl-3-methyl-1-benzofuran-2-yl)-2-methylpropyl]amino}phenyl)carbonyl](methyl)amino}propanoic acid

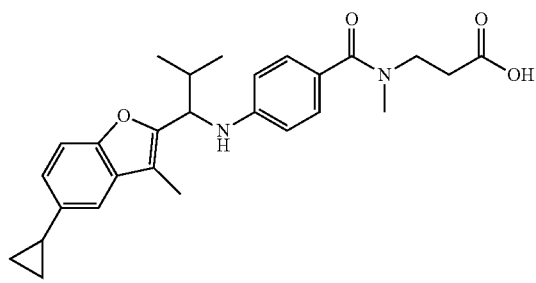 [SMILES: Cc1c(C(Nc2ccc(C(=O)N(C)CCC(=O)O)cc2)C(C)C)oc2ccc(C3CC3)cc12]

(1) 1-(5-cyclopropyl-3-methyl-1-benzofuran-2-yl)-2-methylpropan-1-one

To a solution (20 mL) of 1-(5-bromo-3-methyl-1-benzofuran-2-yl)-2-methylpropan-1-one (1.0 g) synthesized in Example A182(1) in toluene were added cyclopropaneboronic acid (0.92 g), 2N aqueous sodium carbonate solution (5.3 mL), and the mixture was stirred at room temperature for 10 min under argon atmosphere. To the reaction mixture were added 2-dicyclohexylphosphino-2',6'-dimethoxybiphenyl (0.18 g) and tris(dibenzylideneacetone)dipalladium (0) (0.10 g), and the mixture was heated under reflux under argon atmosphere overnight. The reaction mixture was cooled to room temperature, and filtered through celite, and the residue was washed with diethyl ether. Water was added to the filtrate, and the organic layer was concentrated under reduced pressure. The residue was purified by silica gel column chromatography (ethyl acetate:hexane=1:10, volume ratio) to give the title object compound (0.80 g, 93%) as a yellow oil.

$^1$H NMR (300 MHz, CDCl$_3$) δ ppm 0.59-1.08 (m, 4H), 1.23 (d, J=6.8 Hz, 6H), 1.91-2.11 (m, 1H), 2.35 (s, 1H), 2.58 (s, 3H), 7.07-7.51 (m, 3H).

(2) 1-(5-cyclopropyl-3-methyl-1-benzofuran-2-yl)-2-methylpropan-1-ol 1-(5-Cyclopropyl-3-methyl-1-benzofuran-2-yl)-2-methylpropan-1-one (0.80 g) synthesized in the above-mentioned (1) was dissolved in tetrahydrofuran (10 mL) and methanol (1 mL), and sodium borohydride (90%, 0.34 g) was added to the solution under ice-cooling. The ice bath was removed, and the reaction mixture was stirred at room temperature for 1 hr then ice-cooled again, and water (1 mL) and 1N hydrochloric acid (5 mL) were carefully added to the mixture, and the mixture was extracted with ethyl acetate. The extract was washed with saturated brine, dried over magnesium sulfate, and concentrated under reduced pressure to give the title object compound (0.4 g, 50%) as a yellow oil.

$^1$H NMR (300 MHz, CDCl$_3$) δ ppm 0.63-0.75 (m, 2H), 0.80 (d, J=6.8 Hz, 3H), 0.88-1.01 (m, 2H), 1.11 (d, J=6.8 Hz, 3H), 1.20-1.30 (m, 1H), 1.93-2.03 (m, 1H), 2.12-2.30 (m, 4H), 4.46 (d, J=8.3 Hz, 1H), 7.01 (dd, J=8.3, 1.9 Hz, 1H), 7.17 (d, J=1.9 Hz, 1H), 7.29 (d, J=8.3 Hz, 1H).

(3) 3-{[(4-{[1-(5-cyclopropyl-3-methyl-1-benzofuran-2-yl)-2-methylpropyl]amino}phenyl)carbonyl](methyl)amino}propanoic acid To a solution (5 mL) of 1-(5-cyclopropyl-3-methyl-1-benzofuran-2-yl)-2-methylpropan-1-ol (0.40 g) synthesized in the above-mentioned (2) in tetrahydrofuran was added thionyl chloride (0.22 mL) at room temperature. The reaction mixture was stirred at room temperature for 30 min then ice-cooled, and saturated aqueous sodium hydrogen carbonate solution (5 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5 sodium iodide (0.373 g), sodium carbonate (0.25 g) and ethyl 3-{[(4-aminophenyl)carbonyl](methyl)amino}propanoate (0.41 g) synthesized in Example 2(2) were added to the solution, and the mixture was stirred at 70° C. for 12 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-{[(4-{[1-(5-cyclopropyl-3-methyl-1-benzofuran-2-yl)-2-methylpropyl]amino}phenyl)carbonyl](methyl)amino}propanoate (0.25 g) as a pale-yellow oil. The obtained oil was dissolved in ethanol (2 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.24 g, 32%) as a colorless solid.

¹H NMR (300 MHz, CDCl₃) δ ppm 0.62-0.73 (m, 2H), 0.82-1.00 (m, 5H), 1.12 (d, J=6.8 Hz, 3H), 1.90-2.07 (m, 1H), 2.14-2.32 (m, 4H), 2.67 (t, J=6.2 Hz, 2H), 3.03 (s, 3H), 3.70 (t, J=6.2 Hz, 2H), 4.32 (d, J=7.9 Hz, 1H), 6.56 (d, J=8.7 Hz, 2H), 6.98 (dd, J=8.7, 1.9 Hz, 1H), 7.13 (d, J=1.9 Hz, 1H), 7.19-7.25 (m, 3H).

Example A185

3-{[(6-{[cyclohexyl(5,7-difluoro-3-methyl-1-benzofuran-2-yl)methyl]amino}pyridin-3-yl)carbonyl](methyl)amino}propanoic acid

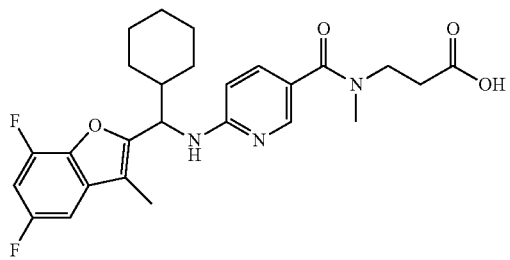 [SMILES: Cc1c(C(Nc2ccc(C(=O)N(C)CCC(=O)O)cn2)C2CCCCC2)oc2c(F)cc(F)cc12]

Cyclohexyl(5,7-difluoro-3-methyl-1-benzofuran-2-yl)methanol (0.52 g) synthesized in Example A163(2) was dissolved in tetrahydrofuran (5 mL), and thionyl chloride (0.24 mL) was added to the solution at room temperature. The reaction mixture was stirred at room temperature for 30 min then ice-cooled, and saturated aqueous sodium hydrogen carbonate solution (3 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5 mL), sodium iodide (0.45 g), sodium carbonate (0.30 g), ethyl 6-aminopyridine-3-carboxylate (0.45 g) were added to the solution, and the mixture was stirred at 60° C. overnight. After allowing to cool, water was added to the reaction mixture, and the mixture was extracted with diethyl ether. The extract was concentrated under reduced pressure, and the residue was purified by silica gel column chromatography (ethyl acetate:hexane=1:1, volume ratio) to give ethyl 6-{[cyclohexyl(5,7-difluoro-3-methyl-1-benzofuran-2-yl)methyl]amino}pyridine-3-carboxylate (0.10 g) as a yellow oil. The obtained oil was dissolved in tetrahydrofuran (2 mL) and ethanol (2 mL), and the mixture was stirred in the presence of 1N aqueous sodium hydroxide solution (2 mL) at 100° C. for 12 hr. The reaction mixture was allowed to cool to room temperature, and concentrated under reduced pressure. The residue was dissolved in N,N-dimethylformamide (20 mL), ethyl 3-(methylamino)propanoate (0.24 g), 1-ethyl-3-(3-dimethylaminopropyl)carbodiimide hydrochloride (0.48 g) and hydroxybenzotriazole monohydrate (0.38 g) were added to the solution, and the mixture was stirred at 70° C. for 4 hr. The reaction mixture was allowed to cool to room temperature, water was added and the mixture was extracted with diethyl ether. The extract was washed with saturated brine, and dried over magnesium sulfate. The solvent was evaporated under reduced pressure, ethanol (5 mL) and 1N aqueous sodium hydroxide solution (1.0 mL) were added to the residue, and the mixture was stirred at room temperature for 1 hr. The reaction mixture was concentrated under reduced pressure, neutralized with 1N hydrochloric acid (1.0 mL), and extracted with ethyl acetate. The extract was evaporated under reduced pressure, and the residue was purified by silica gel column chromatography (ethyl acetate:hexane=1:4, volume ratio) to give the title object compound (0.05 g, 6%) as a yellow oil.

¹H NMR (300 MHz, CDCl₃) δ ppm 1.00-1.93 (m, 11H), 2.22 (s, 3H), 2.68-2.75 (m, 2H), 3.09 (s, 3H), 3.70-3.80 (m, 2H), 4.10-4.20 (m, 1H), 6.36 (d, J=8.7 Hz, 1H), 6.69-6.94 (m, 2H), 7.50-7.58 (m, 1H), 8.15 (d, J=1.9 Hz, 1H).

Example A186

3-[{[4-({cyclohexyl[3-methyl-5-(morpholin-4-yl)-1-benzofuran-2-yl]methyl}amino)phenyl]carbonyl}(methyl)amino]propanoic acid

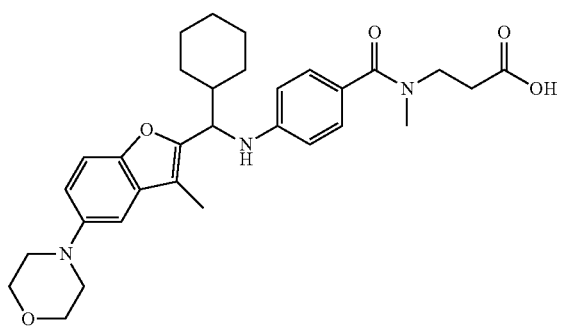 [SMILES: Cc1c(C(Nc2ccc(C(=O)N(C)CCC(=O)O)cc2)C2CCCCC2)oc2ccc(N3CCOCC3)cc12]

(1) methyl 5-bromo-3-methyl-1-benzofuran-2-carboxylate

To a solution (200 mL) of 1-(5-bromo-2-hydroxyphenyl)ethanone (25.0 g) in N,N-dimethylformamide were added potassium carbonate (24.0 g) and methyl bromoacetate (11.5 mL) at room temperature, and the mixture was stirred at room temperature for 15 hr. The reaction mixture was filtered, 1,8-diazabicyclo[5.4.0]undec-7-ene (23.2 mL) was added to the filtrate, and the mixture was stirred at 100° C. for 3 hr. The reaction mixture was allowed to cool to room temperature, and ice water was added. The precipitate was washed with ethanol-water to give the title object compound (16.8 g, 52%) as a pale-red solid.

¹H NMR (300 MHz, CDCl₃) δ ppm 2.56 (s, 3H), 3.99 (s, 3H), 7.36-7.46 (m, 1H), 7.49-7.60 (m, 1H), 7.77 (d, J=2.3 Hz, 1H).

(2) methyl 3-methyl-5-(morpholin-4-yl)-1-benzofuran-2-carboxylate

To a solution (100 mL) of methyl 5-bromo-3-methyl-1-benzofuran-2-carboxylate (5.4 g) synthesized in the above-mentioned (1) in toluene were added morpholine (5.2 mL), cesium carbonate (13.0 g), tris(dibenzylideneacetone)dipalladium (0) (0.92 g) and 9,9-dimethyl-4,5-bis(diphenylphosphino)xanthene (1.1 g), and the mixture was heated under reflux under argon atmosphere for 20 hr. The reaction mixture was cooled to room temperature, and filtered through celite. Water was added to the residue, and the mixture was extracted with ethyl acetate. The extract was concentrated, and the residue was purified by silica gel column chromatography (ethyl acetate:hexane=1:2, volume ratio) to give the title object compound (0.69 g, 13%) as a yellow oil.

¹H NMR (300 MHz, CDCl₃) δ ppm 2.57 (s, 3H), 3.06-3.22 (m, 4H), 3.83-3.94 (m, 4H), 3.97 (s, 3H), 7.02 (d, J=2.3 Hz, 1H), 7.15 (dd, J=9.0, 2.3 Hz, 1H), 7.45 (d, J=9.0 Hz, 1H).

(3) 3-methyl-5-(morpholin-4-yl)-1-benzofuran-2-carbaldehyde

A solution (2 mL) of methyl 3-methyl-5-(morpholin-4-yl)-1-benzofuran-2-carboxylate (0.69 g) synthesized in the above-mentioned (2) in tetrahydrofuran was added to an ice-cooled solution (5 mL) of lithium aluminum hydride (0.25 g) in tetrahydrofuran. The ice bath was removed, and the reaction mixture was stirred at room temperature for 1 hr then ice-cooled again, and water (0.65 mL), 1N aqueous sodium hydroxide solution (3.2 mL) and water (0.65 mL) were successively added dropwise to quench the reaction. The residue was filtered through celite, and the filtrate was concentrated under reduced pressure to give a crude product (0.48 g) of [3-methyl-5-(morpholin-4-yl)-1-benzofuran-2-yl]methanol as a pale-yellow oil. The obtained oil was dissolved in acetonitrile (5 mL), tetrapropylammonium perruthenate (0.07 g) and N-methylmorpholine N-oxide (0.46 g) were added to the solution at room temperature, and the mixture was stirred for 30 min. The solvent was evaporated under reduced pressure, and the residue was purified by silica gel column chromatography (ethyl acetate:hexane=1:2, volume ratio) to give the title object compound (0.24 g, 40%) as a yellow oil.

¹H NMR (300 MHz, CDCl₃) δ ppm 2.59 (s, 3H), 3.09-3.22 (m, 4H), 3.79-3.98 (m, 4H), 7.05 (d, J=2.3 Hz, 1H), 7.23 (dd, J=9.2, 2.3 Hz, 1H), 7.46 (d, J=9.2 Hz, 1H), 10.00 (s, 1H).

(4) cyclohexyl[3-methyl-5-(morpholin-4-yl)-1-benzofuran-2-yl]methanol

To a solution (5 mL) of 3-methyl-5-(morpholin-4-yl)-1-benzofuran-2-carbaldehyde (0.24 g) synthesized in the above-mentioned (3) in tetrahydrofuran was added dropwise cyclohexylmagnesium bromide (2 mL, 1M tetrahydrofuran solution) under ice-cooling. After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give cyclohexyl[3-methyl-5-(morpholin-4-yl)-1-benzofuran-2-yl]methanol (0.39 g, quantitative) as a pale-yellow oil.

¹H NMR (300 MHz, CDCl₃) δ ppm 1.07-2.01 (m, 12H), 2.19 (s, 3H), 3.11-3.21 (m, 4H), 3.83-3.95 (m, 4H), 4.50 (d, J=8.7 Hz, 1H), 6.90-7.01 (m, 2H), 7.33 (d, J=9.8 Hz, 1H).

(5) 3-[{[4-({cyclohexyl[3-methyl-5-(morpholin-4-yl)-1-benzofuran-2-yl]methyl}amino)phenyl]carbonyl}(methyl)amino]propanoic acid To a solution (5 mL) of cyclohexyl[3-methyl-5-(morpholin-4-yl)-1-benzofuran-2-yl]methanol (0.39 g) synthesized in the above-mentioned (4) in tetrahydrofuran was added thionyl chloride (0.13 mL) at room temperature. The reaction mixture was stirred at room temperature for 30 min then ice-cooled, and saturated aqueous sodium hydrogen carbonate solution (5 mL) was carefully added. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5 mL), sodium iodide (0.23 g), sodium carbonate (0.15 g) and ethyl 3-{[(4-aminophenyl)carbonyl](methyl)amino}propanoate (0.25 g) synthesized in Example 2(2) were added to the solution and the mixture was stirred at 70° C. for 15 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[3-methyl-5-(morpholin-4-yl)-1-benzofuran-2-yl]methyl}amino)phenyl]carbonyl}(methyl)amino]propanoate (0.25 g) as a pale-yellow oil. The obtained oil was dissolved in ethanol (2 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.19 g, 33%) as a colorless solid.

¹H NMR (300 MHz, CDCl₃) δ ppm 0.90-2.16 (m, 11H), 2.22 (s, 3H), 2.68 (br. s., 2H), 3.04 (s, 3H), 3.14 (br. s., 4H), 3.58-3.77 (m, 2H), 3.89 (br. s., 4H), 4.36 (d, J=8.3 Hz, 1H), 6.56 (d, J=9.0 Hz, 2H), 6.84-7.02 (m, 2H), 7.17-7.27 (m, 3H).

Example A187

3-[{[4-({cyclohexyl[3-methyl-5-(thiomorpholin-4-yl)-1-benzofuran-2-yl]methyl}amino)phenyl]carbonyl}(methyl)amino]propanoic acid

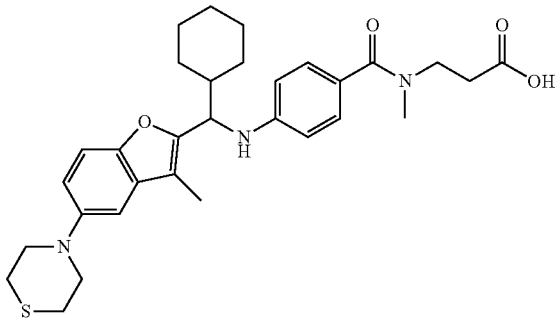

(1) cyclohexyl[3-methyl-5-(thiomorpholin-4-yl)-1-benzofuran-2-yl]methanone

To a solution (15 mL) of (5-bromo-3-methyl-1-benzofuran-2-yl)(cyclohexyl)methanone (0.75 g) synthesized in Example A174(1) in toluene were added thiomorpholine (0.72 g), cesium carbonate (2.3 g), tris(dibenzylideneacetone)dipalladium (0) (0.16 g) and 9,9-dimethyl-4,5-bis(diphenylphosphino)xanthene (0.2 g), and the mixture was heated under reflux under argon atmosphere for 18 hr. The reaction mixture was cooled to room temperature and filtered through celite, water was added to the residue, and the mixture was extracted with ethyl acetate. The extract was concentrated to give a crude product (0.83 g, quantitative) of the title object compound as a yellow oil.

¹H NMR (300 MHz, CDCl₃) δ ppm 1.37-2.01 (m, 10H), 2.56 (s, 3H), 2.70-2.88 (m, 4H), 3.25-3.40 (m, 1H), 3.42-3.70 (m, 4H), 7.00-7.78 (m, 3H).

(2) cyclohexyl[3-methyl-5-(thiomorpholin-4-yl)-1-benzofuran-2-yl]methanol

Cyclohexyl[3-methyl-5-(thiomorpholin-4-yl)-1-benzofuran-2-yl]methanone (0.83 g) synthesized in the above-mentioned (1) was dissolved in tetrahydrofuran (10 mL) and methanol (1 mL), and sodium borohydride (90%, 0.2 g) was added to the solution under ice-cooling. The ice bath was removed, and the reaction mixture was stirred at room temperature for 1 hr then ice-cooled again, and water (1 mL) and 1N hydrochloric acid (5 mL) were carefully added, and the mixture was extracted with ethyl acetate. The extract was washed with saturated brine, dried over magnesium sulfate, and concentrated under reduced pressure. The residue was purified by silica gel column chromatography (ethyl acetate: hexane=1:4, volume ratio) to give the title object compound (0.18 g, 22%) as a yellow oil.
$^1$H NMR (300 MHz, CDCl$_3$) δ ppm 0.81-1.93 (m, 11H), 2.20 (s, 3H), 2.70-2.91 (m, 4H), 3.34-3.53 (m, 4H), 4.50 (d, J=8.3 Hz, 1H), 4.99 (t, J=6.4 Hz, 1H), 6.90-7.40 (m, 3H).

(3) 3-[{[4-({cyclohexyl[3-methyl-5-(thiomorpholin-4-yl)-1-benzofuran-2-yl]methyl}amino)phenyl]carbonyl}(methyl)amino]propanoic acid To a solution (5 mL) of cyclohexyl[3-methyl-5-(thiomorpholin-4-yl)-1-benzofuran-2-yl]methanol (0.18 g) synthesized in the above-mentioned (2) in tetrahydrofuran was added thionyl chloride (0.07 mL) at room temperature. The reaction mixture was stirred at room temperature for 30 min then ice-cooled, and saturated aqueous sodium hydrogen carbonate solution (5 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (5 mL), sodium iodide (0.15 g), sodium carbonate (0.10 g) and ethyl 3-{[(4-aminophenyl)carbonyl](methyl)amino}propanoate (0.13 g) synthesized in Example 2(2) were added to the solution, and the mixture was stirred at 70° C. for 15 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[{[4-({cyclohexyl[3-methyl-5-(thiomorpholin-4-yl)-1-benzofuran-2-yl]methyl}amino)phenyl]carbonyl}(methyl)amino]propanoate (0.08 g) as a pale-yellow oil. The obtained oil was dissolved in ethanol (2 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.05 g, 18%) as a colorless solid.
$^1$H NMR (300 MHz, CDCl$_3$) δ ppm 0.88-2.17 (m, 11H), 2.20 (s, 3H), 2.59 (br. s., 2H), 2.80-3.20 (m, 7H), 3.50-3.70 (m, 6H), 4.38 (d, J=7.9 Hz, 1H), 6.55 (d, J=8.7 Hz, 2H), 7.08-7.47 (m, 5H).

Example A188

3-[({4-[(cyclohexyl{5-[(2-methoxyethyl)(methyl)amino]-3-methyl-1-benzofuran-2-yl}methyl)amino]phenyl}carbonyl)(methyl)amino]propanoic acid

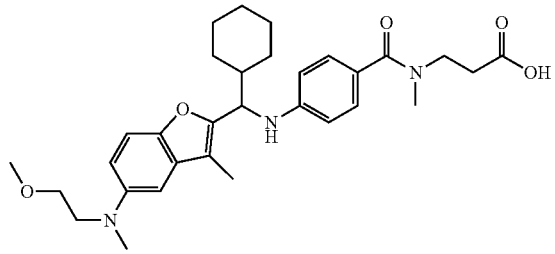 [SMILES: COCCN(C)c1ccc2oc(C(Nc3ccc(C(=O)N(C)CCC(=O)O)cc3)C3CCCCC3)c(C)c2c1]

(1) methyl 5-[(2-methoxyethyl)(methyl)amino]-3-methyl-1-benzofuran-2-carboxylate To a solution (50 mL) of methyl 5-bromo-3-methyl-1-benzofuran-2-carboxylate (2.7 g) synthesized in Example A186(1) in toluene were added 2-methoxy-N-methylethanamine (2.7 g), cesium carbonate (9.8 g), tris(dibenzylideneacetone)dipalladium (0) (0.69 g) and 9,9-dimethyl-4,5-bis(diphenylphosphino)xanthene (0.87 g), and the mixture was heated under reflux under argon atmosphere for 6 hr. The reaction mixture was cooled to room temperature, and filtered through celite, water was added to the filtrate, and the mixture was extracted with ethyl acetate. The extract was concentrated, and the residue was purified by silica gel column chromatography (ethyl acetate:hexane=1:4, volume ratio) to give the title object compound (2.7 g, quantitative) as a yellow oil.
$^1$H NMR (300 MHz, CDCl$_3$) δ ppm 2.55 (s, 3H), 3.01 (s, 3H), 3.37 (s, 3H), 3.40-3.70 (m, 4H), 3.97 (s, 3H), 6.77-7.15 (m, 3H).

(2) 5-[(2-methoxyethyl)(methyl)amino]-3-methyl-1-benzofuran-2-carbaldehyde

A solution (10 mL) of methyl 5-[(2-methoxyethyl)(methyl)amino]-3-methyl-1-benzofuran-2-carboxylate (2.7 g) synthesized in the above-mentioned (1) in tetrahydrofuran was added to an ice-cooled solution (40 mL) of lithium aluminum hydride (0.38 g) in tetrahydrofuran. The ice bath was removed, and the reaction mixture was stirred at room temperature for 1 hr then ice-cooled again, and water (1.0 mL), 1N aqueous sodium hydroxide solution (5.0 mL) and water (1.0 mL) were successively added dropwise to quench the reaction. The residue was filtered through celite, and the filtrate was concentrated under reduced pressure to give a crude product (0.41 g) of {5-[(2-methoxyethyl)(methyl)amino]-3-methyl-1-benzofuran-2-yl}methanol as a pale-yellow oil. The obtained oil was dissolved in acetonitrile (20 mL), tetrapropylammonium perruthenate (0.07 g) and N-methylmorpholine N-oxide (0.46 g) were added to the solution at room temperature, and the mixture was stirred for 30 min. The solvent was evaporated under reduced pressure, and the residue was purified by silica gel column chromatography (ethyl acetate:hexane=1:2, volume ratio) to give the title object compound (0.09 g, 3%) as a yellow oil.
$^1$H NMR (300 MHz, CDCl$_3$) δ ppm 2.58 (s, 3H), 3.02 (s, 3H), 3.38 (s, 3H), 3.47-3.66 (m, 4H), 6.81 (d, J=2.6 Hz, 1H), 7.10 (dd, J=9.0, 2.6 Hz, 1H), 7.40 (d, J=9.0 Hz, 1H), 9.97 (s, 1H).

(3) cyclohexyl{5-[(2-methoxyethyl)(methyl)amino]-3-methyl-1-benzofuran-2-yl}methanol To a solution (5 mL) of 5-[(2-methoxyethyl)(methyl)amino]-3-methyl-1-benzofuran-2-carbaldehyde (0.09 g) synthesized in the above-mentioned (2) in tetrahydrofuran was added dropwise cyclohexylmagnesium bromide (2 mL, 1M tetrahydrofuran solution) under ice-cooling. After the completion of the dropwise addition, the ice bath was removed, and the mixture was stirred at room temperature for 15 min. To the reaction mixture was added aqueous ammonium chloride solution, and the mixture was extracted with ethyl acetate. The extract was concentrated under reduced pressure, and the residue was purified by silica gel column chromatography (ethyl acetate:hexane=1:2, volume ratio) to give the title object compound (0.11 g, quantitative) as a yellow oil.
$^1$H NMR (300 MHz, CDCl$_3$) δ ppm 0.99-1.96 (m, 12H), 2.18 (s, 3H), 2.99 (s, 3H), 3.37 (s, 3H), 3.45-3.72 (m, 4H), 4.49 (d, J=8.7 Hz, 1H), 6.77-7.30 (m, 3H).

(4) 3-[({4-[(cyclohexyl{5-[(2-methoxyethyl)(methyl)amino]-3-methyl-1-benzofuran-2-yl}methyl)amino]phenyl}carbonyl)(methyl)amino]propanoic acid To a solution (10 mL) of cyclohexyl{5-[(2-methoxyethyl)(methyl)amino]-3-methyl-1-benzofuran-2-yl}methanol (0.11 g) synthesized in the above-mentioned (3) in tetrahydrofuran was added thionyl chloride (0.10 mL) at room temperature. The reaction mixture was stirred at room temperature for 30 min then ice-cooled, and saturated aqueous sodium hydrogen carbonate solution (5 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (10 mL), sodium iodide (0.14 g), sodium carbonate (0.09 g) and ethyl 3-{[(4-aminophenyl)carbonyl](methyl)amino}propanoate (0.15 g) synthesized in Example 2(2) were added to the solution, and the mixture was stirred at 70° C. for 4 hr. After allowing to cool, water was added to the reaction mixture and the mixture was extracted with ethyl acetate. The extract was concentrated under reduced pressure, and the residue was purified by silica gel column chromatography (ethyl acetate:hexane=1:1, volume ratio) to give ethyl 3-[({4-[(cyclohexyl{5-[(2-methoxyethyl)(methyl)amino]-3-methyl-1-benzofuran-2-yl}methyl)amino]phenyl}carbonyl)(methyl)amino]propanoate (0.03 g) as a pale-yellow oil. The obtained oil was dissolved in ethanol (2 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.02 g, 11%) as a colorless solid.

$^1$H NMR (300 MHz, CDCl$_3$) δ ppm 0.90-2.13 (m, 11H), 2.21 (s, 3H), 2.68 (br. s., 2H), 2.98 (s, 3H), 3.05 (s, 3H), 3.36 (s, 3H), 3.41-3.62 (m, 4H), 3.68 (br. s., 2H), 4.35 (d, J=8.0 Hz, 1H), 6.56 (d, J=8.7 Hz, 2H), 6.67-6.88 (m, 2H), 7.13-7.25 (m, 3H).

Example A189 ethyl 3-{[(4-{[cyclopentyl(5-fluoro-3-methyl-1-benzofuran-2-yl)methyl]amino}phenyl)carbonyl]amino}propanoate

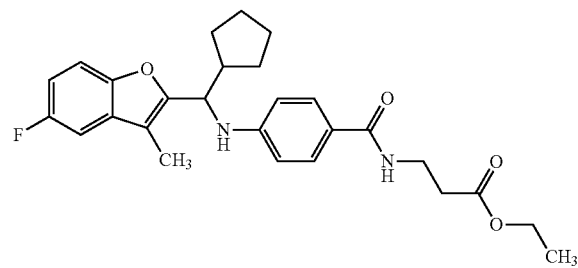 [SMILES: CCOC(=O)CCNC(=O)c1ccc(NC(c2oc3ccc(F)cc3c2C)C2CCCC2)cc1]

(1) methyl 4-{[cyclopentyl(5-fluoro-3-methyl-1-benzofuran-2-yl)methyl]amino}benzoate To a mixture of cyclopentyl(5-fluoro-3-methyl-1-benzofuran-2-yl)methanone (1.3 g) synthesized in Example A67(3), methyl 4-aminobenzoate (798 mg), triethylamine (5.88 mL) and dichloromethane (13 mL) was added titanium (IV) chloride (1.0M dichloromethane solution, 6.3 mL) at 0° C., and the mixture was stirred at room temperature for 2 hr under nitrogen atmosphere. Saturated aqueous sodium hydrogen carbonate solution was added to quench the reaction. The solvent was concentrated under reduced pressure, and the residue was extracted with ethyl acetate. The extract was washed with saturated brine, dried over magnesium sulfate, and concentrated under reduced pressure to give a dark brown solid. To a solution of the obtained solid in tetrahydrofuran (20 mL) were added sodium cyanoborohydride (657 mg) and acetic acid (1.50 mL), and the mixture was stirred at room temperature for 16 hr. Saturated aqueous sodium hydrogen carbonate solution was added to quench the reaction, and the mixture was extracted with ethyl acetate. The extract was washed with saturated brine, dried over magnesium sulfate, and concentrated under reduced pressure. The residue was subjected to silica gel column chromatography (hexane-ethyl acetate 90:10) to give the title compound (1.27 g, 63%) as a yellow amorphous compound.

$^1$H NMR (300 MHz, CDCl$_3$) δ ppm 1.49-1.69 (m, 8H), 2.26 (s, 3H), 2.43-2.56 (m, 1H), 3.82 (s, 3H), 4.34-4.45 (m, 1H), 4.55 (d, J=8.3 Hz, 1H), 6.56 (d, J=9.0 Hz, 2H), 6.86-6.98 (m, 1H), 7.02-7.14 (m, 1H), 7.23-7.35 (m, 1H), 7.79 (d, J=9.0 Hz, 2H).

(2) 4-{[cyclopentyl(5-fluoro-3-methyl-1-benzofuran-2-yl)methyl]amino}benzoic acid To a mixture of methyl 4-{[cyclopentyl(5-fluoro-3-methyl-1-benzofuran-2-yl)methyl]amino}benzoate (1.19 g) synthesized above, tetrahydrofuran (6 mL) and ethanol (6 mL) was added 1N aqueous sodium hydroxide solution (6 mL), and the mixture was stirred with heating under reflux for 3.5 hr. 1N Aqueous sodium hydroxide solution (6 mL) was additionally added to the mixture, and the mixture was stirred with heating under reflux for 14 hr. The reaction mixture was concentrated under reduced pressure, 1N hydrochloric acid (11 mL) was added to the residue, and the mixture was extracted with ethyl acetate. The extract was washed with saturated brine, dried over magnesium sulfate, and concentrated under reduced pressure to give the title compound (1.08 g, 94%) as a colorless amorphous form.

$^1$H NMR (300 MHz, CDCl$_3$) δ ppm 1.39-1.76 (m, 8H), 1.89-1.99 (m, 1H), 2.24 (s, 3H), 2.40-2.55 (m, 1H), 4.40 (d, J=9.1 Hz, 1H), 6.52 (d, J=8.7 Hz, 2H), 6.82-6.98 (m, 1H), 7.02-7.13 (m, 1H), 7.03-7.11 (m, 1H), 7.22-7.29 (m, 1H), 7.81 (d, J=8.7 Hz, 2H).

(3) ethyl 3-{[(4-{[cyclopentyl(5-fluoro-3-methyl-1-benzofuran-2-yl)methyl]amino}phenyl)carbonyl]amino}propanoate A solution of 4-{[cyclopentyl(5-fluoro-3-methyl-1-benzofuran-2-yl)methyl]amino}benzoic acid (483 mg) synthesized above, β-alanine ethyl ester hydrochloride (241 mg), 1-hydroxybenzotriazole monohydrate (240 mg), triethylamine (438 μL) and 1-ethyl-3-(3-dimethylaminopropyl)carbodiimide hydrochloride (301 mg) in N,N-dimethylformamide (10 mL) was stirred at room temperature for 3 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was subjected to silica gel column chromatography (hexane-ethyl acetate 100:0-60:40, v/v) to give the title compound (397 mg, 65%) as a colorless amorphous form.

$^1$H NMR (300 MHz, CDCl$_3$) δ ppm 1.21-1.31 (m, 3H), 1.50-1.70 (m, 8H), 1.92-2.01 (m, 1H), 2.25 (s, 3H), 2.42-2.55 (m, 1H), 2.58 (t, J=5.9 Hz, 2H), 3.65 (q, J=6.1 Hz, 2H), 4.31-4.49 (m, 2H), 6.57 (d, J=8.7 Hz, 3H), 6.84-6.98 (m, 1H), 7.06 (dd, J=8.3, 2.7 Hz, 1H), 7.21-7.32 (m, 1H), 7.54 (d, J=8.7 Hz, 2H).

Example A190

3-{[(4-{[cyclopentyl(5-fluoro-3-methyl-1-benzofuran-2-yl)methyl]amino}phenyl)carbonyl]amino}propanoic acid

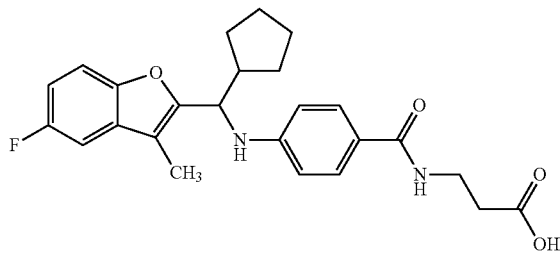 [SMILES: Cc1c(C(Nc2ccc(C(=O)NCCC(=O)O)cc2)C2CCCC2)oc2ccc(F)cc12]

Ethyl 3-{[(4-{[cyclopentyl(5-fluoro-3-methyl-1-benzofuran-2-yl)methyl]amino}phenyl)carbonyl]amino}propanoate (363 mg) synthesized in Example A189 was dissolved in ethanol (1.5 mL) and tetrahydrofuran (1.5 mL), 1N aqueous sodium hydroxide solution (1.5 mL) was added to the solution, and the mixture was stirred at room temperature for 30 min. The solvent was evaporated under reduced pressure, water (4 mL) was added to the mixture, and the mixture was neutralized with 1N hydrochloric acid under ice-cooling, and the mixture was stirred for 30 min. The resulting precipitate was collected by filtration, and dried to give the title compound (283 mg, 83%) as a colorless solid.

$^1$H NMR (300 MHz, CDCl$_3$) δ ppm 1.21-1.72 (m, 7H), 1.91-2.04 (m, 1H), 2.24 (s, 3H), 2.47 (q, J=8.1 Hz, 1H), 2.62 (t, J=5.9 Hz, 2H), 3.63 (q, J=6.1 Hz, 2H), 4.38 (d, J=9.1 Hz, 1H), 6.51-6.64 (m, 3H), 6.86-6.97 (m, 1H), 7.06 (dd, J=8.5, 2.5 Hz, 1H), 7.19-7.32 (m, 2H), 7.52 (d, J=8.7 Hz, 2H).

Example A191

3-{[(4-{[2-ethyl-1-(5-fluoro-3-methyl-1-benzofuran-2-yl)butyl]amino}phenyl)carbonyl]amino}propanoic acid

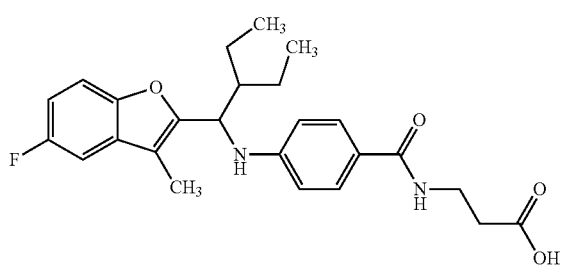 [SMILES: CCC(CC)C(Nc1ccc(C(=O)NCCC(=O)O)cc1)c1oc2ccc(F)cc2c1C]

A solution of 4-{[2-ethyl-1-(5-fluoro-3-methyl-1-benzofuran-2-yl)butyl]amino}benzoic acid (180 mg) synthesized in Example A71(4), β-alanine ethyl ester hydrochloride (89 mg), 1-hydroxybenzotriazole monohydrate (89 mg), triethylamine (163 µL) and 1-ethyl-3-(3-dimethylaminopropyl)carbodiimide hydrochloride (111 mg) in N,N-dimethylformamide (5 mL) was stirred at room temperature for 6 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was subjected to silica gel column chromatography (hexane-ethyl acetate 100:0-60:40, v/v) to give a colorless oil (159 mg). The obtained colorless oil (159 mg) was dissolved in ethanol (1.0 mL) and tetrahydrofuran (1.0 mL), 1N aqueous sodium hydroxide solution (0.66 mL) was added to the solution, and the mixture was stirred at room temperature for 1 hr. The solvent was evaporated under reduced pressure, water (4 mL) was added, neutralized with 1N hydrochloric acid under ice-cooling, and the mixture was stirred for 30 min. The resulting precipitate was collected by filtration, and dried to give the title compound (87 mg, 41%) as a colorless solid.

$^1$H NMR (300 MHz, CDCl$_3$) δ ppm 0.85 (t, J=7.4 Hz, 3H), 0.94 (t, J=7.6 Hz, 3H), 1.14-1.68 (m, 4H), 1.80-1.92 (m, 1H), 2.21 (s, 3H), 2.63 (t, J=5.7 Hz, 2H), 3.64 (q, J=6.1 Hz, 2H), 4.58 (d, J=7.6 Hz, 1H), 6.49-6.64 (m, 3H), 6.92 (td, J=9.1, 2.7 Hz, 1H), 7.05 (dd, J=8.5, 2.5 Hz, 1H), 7.22-7.29 (m, 1H), 7.53 (d, J=8.7 Hz, 2H).

Example A192

3-{[(4-{[1-(5-fluoro-3-methyl-1-benzofuran-2-yl)-2-methylpropyl]amino}phenyl)carbonyl]methyl)amino}propanoic acid

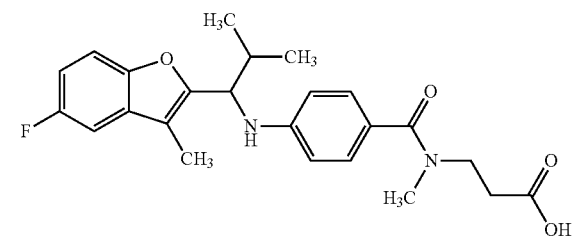 [SMILES: Cc1c(C(Nc2ccc(C(=O)N(C)CCC(=O)O)cc2)C(C)C)oc2ccc(F)cc12]

(1) 1-(5-fluoro-3-methyl-1-benzofuran-2-yl)-2-methylpropan-1-one

To a solution of 5-fluoro-3-methyl-1-benzofuran (2.0 g) synthesized in Example A67(2) and isobutyryl chloride (1.56 g) in nitromethane (40 mL) was added aluminum chloride (anhydrous) (2.66 g) at 0° C., and the mixture was stirred at 0° C. for 1 hr, and at room temperature for 12 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-90:10, v/v) to give the title compound (1.933 g, 66%) as a colorless oil.

¹H NMR (300 MHz, CDCl₃) δ ppm 1.24 (d, J=7.2 Hz, 6H), 2.57 (s, 3H), 3.44-3.65 (m, 1H), 7.11-7.33 (m, 2H), 7.41-7.50 (m, 1H).

(2) 1-(5-fluoro-3-methyl-1-benzofuran-2-yl)-2-methylpropan-1-ol 1-(5-Fluoro-3-methyl-1-benzofuran-2-yl)-2-methylpropan-1-one (11.66 g) synthesized above was dissolved in methanol (4 mL)-tetrahydrofuran (20 mL), and sodium tetrahydroborate (90%) (446 mg) was added to the solution at 0° C. The reaction mixture was stirred at 0° C. for 1 hr. Water was added to the reaction mixture, and the mixture was extracted with ethyl acetate. The organic layer was washed with saturated brine, and dried over anhydrous magnesium sulfate. After filtration, the filtrate was concentrated to give the title compound (1.193 g, 100%) as a colorless oil.

¹H NMR (300 MHz, CDCl₃) δ ppm 0.82 (d, J=6.8 Hz, 3H), 1.12 (d, J=6.8 Hz, 3H), 1.99-2.06 (m, 1H), 2.15-2.27 (m, 4H), 4.43-4.52 (m, 1H), 6.91-7.01 (m, 1H), 7.11 (dd, J=8.7, 2.6 Hz, 1H), 7.33 (dd, 1H).

(3) 3-{[(4-{[1-(5-fluoro-3-methyl-1-benzofuran-2-yl)-2-methylpropyl]amino}phenyl)carbonyl]methyl)amino}propanoic acid To a solution of 1-(5-fluoro-3-methyl-1-benzofuran-2-yl)-2-methylpropan-1-ol (1.128 g) obtained above in tetrahydrofuran (10 mL) was added thionyl chloride (0.45 mL) at room temperature. The reaction mixture was stirred at room temperature for 2 hr. To the reaction mixture was added aqueous sodium hydrogen carbonate solution, and the mixture was extracted with ethyl acetate. The organic layer was washed with saturated brine, and dried over anhydrous magnesium sulfate. After filtration, the filtrate was concentrated to give a crude 2-(1-chloro-2-methylpropyl)-5-fluoro-3-methyl-1-benzofuran (1.10 g). To the obtained 2-(1-chloro-2-methylpropyl)-5-fluoro-3-methyl-1-benzofuran (500 mg) were added ethyl 3-{[(4-aminophenyl)carbonyl](methyl)amino}propanoate (546 mg) obtained in Example 2 (2), sodium iodide (623 mg), sodium carbonate (441 mg) and N,N-dimethylformamide (5 mL), and the mixture was stirred at 80° C. for 13 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give a yellow amorphous compound (287 mg). The obtained amorphous compound (280 mg) was dissolved in ethanol (2.4 mL) and tetrahydrofuran (2.4 mL), and 1N aqueous sodium hydroxide solution (1.2 mL) was added to the solution, and the mixture was stirred at room temperature for 1.5 hr. The solvent was evaporated under reduced pressure, water (4 mL) was added, the mixture was neutralized with 1N hydrochloric acid (1.2 mL) under ice-cooling, and the mixture was stirred for 1.5 hr. The resulting precipitate was collected by filtration, and dried to give the title compound (231 mg, 23%) as a yellow amorphous compound.

¹H NMR (300 MHz, CDCl₃) δ ppm 0.91 (d, 3H), 1.13 (d, J=6.4 Hz, 3H), 2.18-2.30 (m, 4H), 2.66 (t, J=6.4 Hz, 2H), 3.03 (s, 3H), 3.70 (t, J=6.6 Hz, 2H), 4.33 (d, J=7.5 Hz, 1H), 6.56 (d, J=8.7 Hz, 2H), 6.93 (td, J=9.0, 2.6 Hz, 1H), 7.07 (dd. J=8.7, 2.6 Hz, 1H), 7.22-7.32 (m, 3H).

Example A193

3-{[(4-{[1-(5-fluoro-3-methyl-1-benzofuran-2-yl)-2-methylpropyl]amino}phenyl)carbonyl]amino}propanoic acid

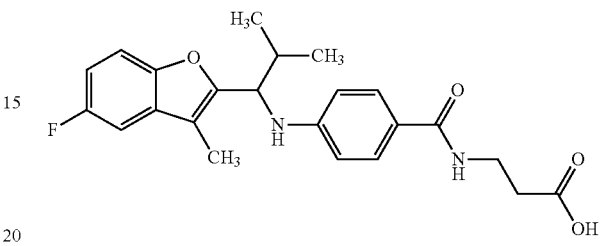

To a solution of 1-(5-fluoro-3-methyl-1-benzofuran-2-yl)-2-methylpropan-1-ol (1.128 g) obtained in Example A192(2) in tetrahydrofuran (10 mL) was added thionyl chloride (0.45 mL) at room temperature. The reaction mixture was stirred at room temperature for 2 hr. To the reaction mixture was added aqueous sodium hydrogen carbonate solution, and the mixture was extracted with ethyl acetate. The organic layer was washed with saturated brine, and dried over anhydrous magnesium sulfate. After filtration, the filtrate was concentrated to give a crude 2-(1-chloro-2-methylpropyl)-5-fluoro-3-methyl-1-benzofuran (1.10 g). To the obtained 2-(1-chloro-2-methylpropyl)-5-fluoro-3-methyl-1-benzofuran (485 mg) were added ethyl 3-{[(4-aminophenyl)carbonyl]amino}propanoate (500 mg) obtained in Example 1(2), sodium iodide (599 mg), sodium carbonate (424 mg) and N,N-dimethylformamide (5 mL) and the mixture was stirred at 80° C. for 13 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give a colorless amorphous compound (123 mg). The obtained amorphous compound (123 mg) was dissolved in ethanol (2.0 mL) and tetrahydrofuran (2.0 mL), 1N aqueous sodium hydroxide solution (1.0 mL) was added to the solution, and the mixture was stirred at room temperature for 1 hr. The solvent was evaporated under reduced pressure, water (4 mL) was added to the residue, and the mixture was neutralized with 1N hydrochloric acid (1.0 mL) under ice-cooling and the mixture was stirred for 20 min. The resulting precipitate was collected by filtration, and dried to give the title compound (97 mg, 11%) as a yellow amorphous compound.

¹H NMR (300 MHz, CHLOROFORM-d) δ ppm 0.91 (d, 3H), 1.13 (d, J=6.8 Hz, 3H), 2.18-2.29 (m, 4H), 2.64 (t, J=5.7 Hz, 2H), 3.65 (q, J=6.0 Hz, 2H), 4.35 (d, J=7.9 Hz, 1H), 6.57

(d, J=8.7 Hz, 3H), 6.92 (td, J=9.0, 2.6 Hz, 1H), 7.06 (dd, J=8.5, 2.4 Hz, 1H), 7.23-7.30 (m, 1H), 7.54 (d, J=8.7 Hz, 2H).

Example A194

3-[({4-[(cyclohexyl{3-methyl-5-[(5-methylisoxazol-3-yl)methoxy]-1-benzofuran-2-yl}methyl)amino]phenyl}carbonyl)(methyl)amino]propanoic acid

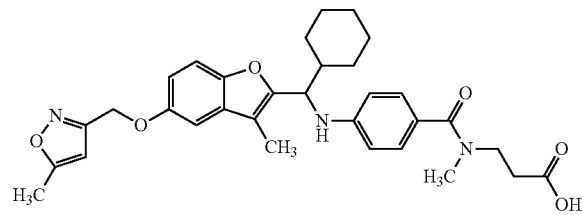 [SMILES: Cc1cc(COc2ccc3oc(C(Nc4ccc(C(=O)N(C)CCC(=O)O)cc4)C4CCCCC4)c(C)c3c2)no1]

(1) [5-(benzyloxy)-3-methyl-1-benzofuran-2-yl](cyclohexyl)methanol

[5-(Benzyloxy)-3-methyl-1-benzofuran-2-yl](cyclohexyl)methanone (23.4 g) synthesized in Example A82(2) was dissolved in methanol (40 mL)-tetrahydrofuran (400 mL), and sodium tetrahydroborate (90%) (5.64 g) was added to the solution at 0° C. The reaction mixture was stirred at 0° C. for 1 hr. Water was added to the reaction mixture, and the mixture was extracted with ethyl acetate. The organic layer was washed with saturated brine, and dried over anhydrous magnesium sulfate. After filtration, the filtrate was concentrated to give the title compound (25.17 g, 100%) as a colorless oil.

$^1$H NMR (300 MHz, CDCl$_3$) δ ppm 0.88-1.40 (m, 7H), 1.61-1.70 (m, 2H), 1.75-1.92 (m, 2H), 1.95-1.99 (m, 1H), 2.18 (s, 3H), 4.45-4.54 (m, 1H), 5.10 (s, 2H), 6.94 (dd, J=9.0, 2.6 Hz, 1H), 7.00 (d, J=2.3 Hz, 1H), 7.28-7.49 (m, 6H).

(2) 5-(benzyloxy)-2-[chloro(cyclohexyl)methyl]-3-methyl-1-benzofuran

To a solution of [5-(benzyloxy)-3-methyl-1-benzofuran-2-yl](cyclohexyl)methanol (25.17 g) synthesized above in tetrahydrofuran (250 mL) was added thionyl chloride (9.44 mL) at room temperature. The reaction mixture was stirred at room temperature for 1 hr. To the reaction mixture was added aqueous sodium hydrogen carbonate solution cooled to 0° C., and the mixture was extracted with ethyl acetate. The organic layer was washed with saturated brine, and dried over anhydrous magnesium sulfate. After filtration, the filtrate was concentrated to give the title compound (25.39 g, 96%) as a yellow solid.

$^1$H NMR (300 MHz, CDCl$_3$) 3 ppm 0.87-1.52 (m, 6H), 1.58-1.71 (m, 4H), 2.19 (s, 3H), 2.29-2.38 (m, 1H), 4.80 (d, 1H), 5.10 (s, 2H), 6.94-7.02 (m, 2H), 7.32-7.56 (m, 6H).

(3) ethyl 3-[{[4-({[5-(benzyloxy)-3-methyl-1-benzofuran-2-yl](cyclohexyl)methyl}amino)phenyl]carbonyl}(methyl)amino]propanoate To 5-(benzyloxy)-2-[chloro(cyclohexyl)methyl]-3-methyl-1-benzofuran (8.48 g) obtained above were added ethyl 3-{[(4-aminophenyl)carbonyl](methyl)amino}propanoate (12.5 g) obtained in Example 2(2), sodium iodide (7.62 g), sodium carbonate (5.39 mg) and N,N-dimethylacetamide (125 mL), and the mixture was stirred at 60° C. for 14 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (14.20 g, 72%) as a yellow amorphous compound.

$^1$H NMR (300 MHz, CDCl$_3$) δ ppm 0.88-1.26 (m, 5H), 1.50-2.09 (m, 7H), 2.21 (s, 3H), 2.56-2.73 (m, 2H), 3.01 (s, 3H), 3.70 (t, J=7.0 Hz, 2H), 4.06-4.18 (m, 2H), 4.32-4.42 (m, 2H), 4.32-4.39 (m, 2H), 5.08 (s, 2H), 6.56 (d, J=8.7 Hz, 2H), 6.86-6.92 (m, 1H), 6.97 (d, J=2.3 Hz, 1H), 7.17-7.53 (m, 8H).

(4) ethyl 3-{[(4-{[cyclohexyl(5-hydroxy-3-methyl-1-benzofuran-2-yl)methyl]amino}phenyl)carbonyl](methyl)amino}propanoate Ethyl 3-[{[4-({[5-(benzyloxy)-3-methyl-1-benzofuran-2-yl](cyclohexyl)methyl}amino)phenyl]carbonyl}(methyl)amino]propanoate (10.11 g) obtained above was dissolved in ethanol (200 mL), and 10% palladium carbon (containing water) (1.0 g) was added to the solution at room temperature. The reaction mixture was stirred under hydrogen atmosphere (1 atm) at room temperature for 24 hr, and the catalyst was filtered off. The filtrate was concentrated under reduced pressure to give the title compound (8.98 g, 100%) as a brown amorphous compound.

$^1$H NMR (300 MHz, CDCl$_3$) δ ppm 0.93-1.16 (m, 3H), 1.22-1.27 (m, 5H), 1.52 (d, J=12.5 Hz, 1H), 1.65-1.95 (m, 4H), 2.08-2.13 (m, 1H), 2.15 (s, 3H), 2.62 (t, J=6.8 Hz, 2H), 3.02 (s, 3H), 3.72 (t, J=7.0 Hz, 2H), 4.05-4.17 (m, 2H), 4.30-4.38 (m, 2H), 5.58 (s, 1H), 6.55 (d, J=8.7 Hz, 2H), 6.70 (dd, J=8.5, 2.5 Hz, 1H), 6.80 (d, J=2.7 Hz, 1H), 7.17 (d, J=8.7 Hz, 1H), 7.22 (d, J=8.3 Hz, 2H).

(5) 3-[({4-[(cyclohexyl{3-methyl-5-[(5-methylisoxazol-3-yl)methoxy]-1-benzofuran-2-yl}methyl)amino]phenyl}carbonyl)(methyl)amino]propanoic acid A solution of ethyl 3-{[(4-{[cyclohexyl(5-hydroxy-3-methyl-1-benzofuran-2-yl)methyl]amino}phenyl)carbonyl](methyl)amino}propanoate (300 mg) obtained above, (5-methylisoxazol-3-yl)methanol (83 mg) and tributylphosphine (308 mg) in tetrahydrofuran (30 mL) was cooled to 0° C. in an ice-bath, and 1,1'-(azodicarbonyl)dipiperidine (308 mg) was added to the solution. The reaction mixture was stirred at room temperature for 3.5 hr. (5-Methylisoxazol-3-yl)methanol (83 mg), tributylphosphine (154 mg) and 1,1'-(azodicarbonyl)dipiperidine (154 mg) were further added to the mixture, and the mixture was stirred at room temperature for 14 hr. To the reaction mixture was added hexane (60 mL). The insoluble material was filtered off, and the filtrate was concentrated under reduced pressure. The residue was subjected to silica gel column chromatography (hexane-ethyl acetate 100:0-50:50, v/v) to give a colorless amorphous compound (105 mg). The obtained colorless amorphous compound (105 mg) was dissolved in ethanol (0.5 mL) and tetrahydrofuran (0.5 mL), 1N aqueous sodium hydroxide solution (0.36 mL) was added to the solution, and the mixture was stirred at room temperature for 30 min. The solvent was evaporated under reduced pressure, water (2 mL) was added to the residue, and the mixture was neutralized with 1N hydrochloric acid (0.36 mL) under ice-cooling. The resulting precipitate was collected by filtration, and dried to give the title compound (72 mg, 21%) as a colorless amorphous form.

$^1$H NMR (300 MHz, CDCl$_3$) δ ppm 1.01-1.25 (m, 5H), 1.42-1.83 (m, 6H), 2.07 (br. s., 1H), 2.21 (s, 3H), 2.41 (s, 3H), 2.61-2.69 (m, 2H), 3.02 (s, 3H), 3.68 (t, J=6.4 Hz, 2H), 4.35 (d, J=7.9 Hz, 1H), 5.13 (s, 2H), 6.11 (s, 1H), 6.55 (d, J=8.3 Hz, 2H), 6.87 (dd, J=8.9, 2.4 Hz, 1H), 6.97 (d, J=2.6 Hz, 1H), 7.19-7.26 (m, 3H).

Example A195

3-[{[4-({cyclohexyl[5-(2-hydroxy-2-methylpropoxy)-3-methyl-1-benzofuran-2-yl]methyl}amino)phenyl]carbonyl}(methyl)amino]propanoic acid

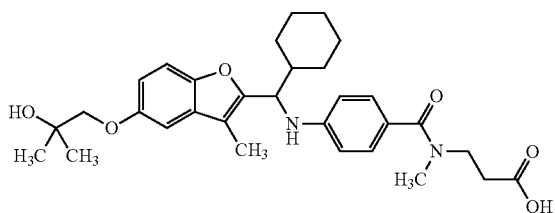 [SMILES: Cc1c(C(Nc2ccc(C(=O)N(C)CCC(=O)O)cc2)C2CCCCC2)oc2ccc(OCC(C)(C)O)cc12]

A solution of ethyl 3-{[(4-{[cyclohexyl(5-hydroxy-3-methyl-1-benzofuran-2-yl)methyl]amino}phenyl)carbonyl](methyl)amino}propanoate (300 mg) obtained in Example A194(4), isobutylene oxide (439 mg), potassium carbonate (422 mg) and sodium iodide (457 mg) in N,N-dimethylformamide (6 mL) was stirred at 80° C. for 9 hr. Isobutylene oxide (2.0 g) was further added to the mixture, and the mixture was stirred at 120° C. for 14 hr. Isobutylene oxide (2.0 g) was further added to the mixture, and the mixture was stirred at 120° C. for 5 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give a colorless oil (103 mg). The obtained colorless oil (103 mg) was dissolved in ethanol (0.5 mL) and tetrahydrofuran (0.5 mL), 1N aqueous sodium hydroxide solution (0.36 mL) was added to the solution, and the mixture was stirred at room temperature for 30 min. The solvent was evaporated under reduced pressure, water (4 mL) was added to the residue, and the mixture was neutralized with 1N hydrochloric acid (0.36 mL) under ice-cooling. The resulting precipitate was collected by filtration, and dried to give the title compound (88 mg, 26%) as a colorless solid.

$^1$H NMR (300 MHz, CDCl$_3$) δ ppm 0.85-1.27 (m, 6H), 1.35 (s, 6H), 1.47-1.91 (m, 5H), 2.04-2.13 (m, 1H), 2.21 (s, 3H), 2.62 (t, J=6.2 Hz, 2H), 3.01 (s, 3H), 3.67 (t, J=6.6 Hz, 2H), 3.82 (s, 2H), 4.35 (d, J=7.9 Hz, 1H), 6.55 (d, J=9.0 Hz, 2H), 6.84 (dd, J=8.7, 2.6 Hz, 1H), 6.90 (d, J=2.3 Hz, 1H), 7.22 (d, J=9.8 Hz, 2H), 7.26-7.28 (m, 1H).

Example A196

3-[({4-[(cyclohexyl{3-methyl-5-[(3-methyloxetan-3-yl)methoxy]-1-benzofuran-2-yl}methyl)amino]phenyl}carbonyl)(methyl)amino]propanoic acid

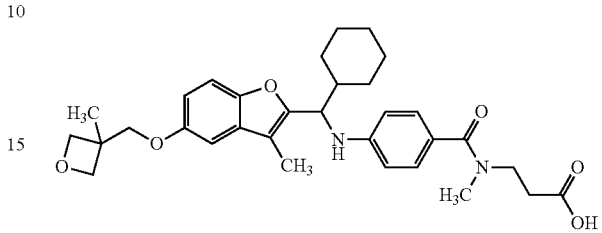

A solution of ethyl 3-{[(4-{[cyclohexyl(5-hydroxy-3-methyl-1-benzofuran-2-yl)methyl]amino}phenyl)carbonyl](methyl)amino}propanoate (300 mg) obtained in Example A194(4), (3-methyloxetan-3-yl)methanol (75 mg) and tributylphosphine (308 mg) in tetrahydrofuran (30 mL) was cooled to 0° C. in an ice-bath, and 1,1'-(azodicarbonyl)dipiperidine (308 mg) was added to the solution. The reaction mixture was stirred at room temperature for 18 hr. To the reaction mixture was added hexane (60 mL). The insoluble material was filtered off, and the filtrate was concentrated under reduced pressure. The residue was subjected to silica gel column chromatography (NH silica, hexane-ethyl acetate 100:0-50:50, v/v), and then preparative HPLC" instrument: Gilson Inc., preparative HPLC system; column: Develosil ODS-UG-10, S-5 μm, 50×100 mm; solvent: SOLUTION A; 0.1% trifluoroacetic acid-containing water, SOLUTION B; 0.1% trifluoroacetic acid-containing acetonitrile, (SOLUTION A:SOLUTION B=95:5-0:100); flow rate: 150 mL/min; detection method: UV 220 nm". The fractionated fraction was concentrated and acetonitrile was evaporated. Saturated aqueous sodium hydrogen carbonate solution (0° C.) was added to the aqueous layer, and the mixture was extracted with ethyl acetate. The organic layer was washed with saturated brine, and dried over anhydrous magnesium sulfate. After filtration, the filtrate was concentrated to give a colorless oil (100 mg). The obtained colorless oil (100 mg) was dissolved in ethanol (0.5 mL) and tetrahydrofuran (0.5 mL), 1N aqueous sodium hydroxide solution (0.34 mL) was added to the solution, and the mixture was stirred at room temperature for 30 min. The solvent was evaporated under reduced pressure, water (4 mL) was added to the residue, and the mixture was neutralized with 1N hydrochloric acid (0.34 mL) under ice-cooling and stirred at 0° C. for 30 min. The resulting precipitate was collected by filtration, and dried to give the title compound (73 mg, 22%) as a colorless solid.

$^1$H NMR (300 MHz, CDCl$_3$) δ ppm 0.91-1.33 (m, 5H), 1.45 (s, 3H), 1.52-1.95 (m, 5H), 2.09 (d, J=8.7 Hz, 1H), 2.22 (s, 3H), 2.55-2.74 (m, 2H), 3.03 (s, 3H), 3.65-3.76 (m, 3H), 4.05 (s, 2H), 4.36 (d, J=7.9 Hz, 1H), 4.47 (d, J=6.0 Hz, 2H), 4.64 (d, J=5.7 Hz, 2H), 6.56 (d, J=8.7 Hz, 2H), 6.80-6.89 (m, 1H), 6.92 (d, J=2.6 Hz, 1H), 7.14-7.32 (m, 3H).

Example A197 ethyl 3-{[(4-{[{5-[(3-cyanopyridin-2-yl)oxy]-3-methyl-1-benzofuran-2-yl}(cyclohexyl)methyl]amino}phenyl)carbonyl]methyl)amino}-propanoate

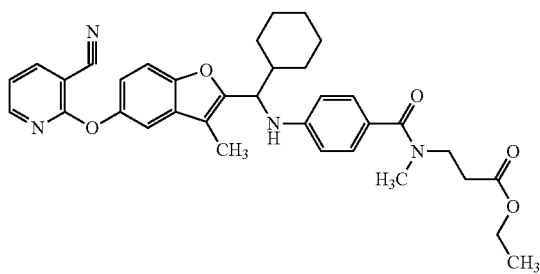 [SMILES: CCOC(=O)CCN(C)C(=O)c1ccc(NC(c2oc3ccc(Oc4ncccc4C#N)cc3c2C)C2CCCCC2)cc1]

A solution of ethyl 3-{[(4-{[cyclohexyl(5-hydroxy-3-methyl-1-benzofuran-2-yl)methyl]amino}phenyl)carbonyl](methyl)amino}propanoate (300 mg) obtained in Example A194(4), 2-chloro-3-cyanopyridine (126 mg) and potassium carbonate (125 mg) in N,N-dimethylformamide (3 mL) was stirred at 80° C. for 2.5 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (250 mg, 69%) as a colorless amorphous form.

$^1$H NMR (300 MHz, CDCl$_3$) δ ppm 0.99-1.31 (m, 6H), 1.48-1.96 (m, 6H), 2.06-2.14 (m, 2H), 2.23 (s, 3H), 2.62 (t, J=7.0 Hz, 2H), 3.02 (s, 3H), 3.71 (t, J=7.0 Hz, 2H), 4.12 (q, J=7.2 Hz, 2H), 4.31-4.44 (m, 2H), 6.56 (d, J=8.3 Hz, 2H), 6.98-7.11 (m, 2H), 7.19-7.25 (m, 3H), 7.40 (d, J=8.7 Hz, 1H), 8.00 (dd, J=7.6, 1.9 Hz, 1H), 8.29 (dd, J=4.9, 1.9 Hz, 1H).

Example A198

3-{[(4-{[{5-[(3-cyanopyridin-2-yl)oxy]-3-methyl-1-benzofuran-2-yl}(cyclohexyl)methyl]amino}phenyl)carbonyl](methyl)amino}-propanoic acid

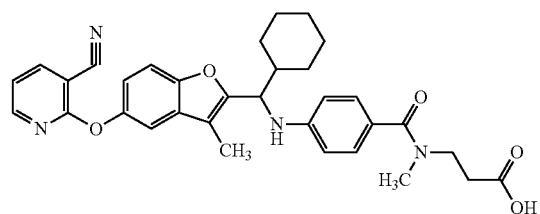 [SMILES: Cc1c(C(Nc2ccc(C(=O)N(C)CCC(=O)O)cc2)C2CCCCC2)oc2ccc(Oc3ncccc3C#N)cc12]

Ethyl 3-{[(4-{[{5-[(3-cyanopyridin-2-yl)oxy]-3-methyl-1-benzofuran-2-yl}(cyclohexyl)methyl]amino}phenyl)carbonyl](methyl)amino}-propanoate (234 mg) obtained in Example A197 was dissolved in ethanol (1.5 mL) and tetrahydrofuran (1.5 mL), 1N aqueous sodium hydroxide solution (0.78 mL) was added to the solution, and the mixture was stirred at room temperature for 30 min. The solvent was evaporated under reduced pressure, water (4 mL) was added, and the mixture was neutralized with 1N hydrochloric acid (0.78 mL) under ice-cooling. The resulting precipitate was collected by filtration and dried. The obtained residue was purified by preparative HPLC "instrument: Gilson Inc., preparative HPLC system; column: Develosil ODS-UG-10, S-5 μm, 50×100 mm; solvent: SOLUTION A; 0.1% trifluoroacetic acid-containing water, SOLUTION B; 0.1% trifluoroacetic acid-containing acetonitrile, (SOLUTION A:SOLUTION B=95:5-0:100); flow rate: 150 mL/min; detection method: UV 220 nm". To the fractionated fraction was added saturated aqueous sodium hydrogen carbonate solution, and the mixture was extracted with ethyl acetate. The organic layer was washed with saturated brine, and dried over anhydrous magnesium sulfate. After filtration, the filtrate was concentrated to give the title compound (73 mg, 33%) as a colorless amorphous form.

$^1$H NMR (300 MHz, CDCl$_3$) δ ppm 1.12 (br. s., 4H), 1.42-1.91 (m, 6H), 2.04 (s, 3H), 2.20 (s, 3H), 2.39-2.63 (m, 1H), 2.89-3.03 (m, 3H), 3.58 (m, 2H), 4.37 (d, J=8.0 Hz, 1H), 6.54 (d, J=8.3 Hz, 2H), 6.94-7.10 (m, 2H), 7.17-7.24 (m, 3H), 7.37 (d, J=8.7 Hz, 1H), 7.99 (dd, J=7.6, 1.9 Hz, 1H), 8.28 (d, J=3.4 Hz, 1H).

Example A199

3-[({4-[(cyclohexyl{5-[(1,1-dioxidotetrahydro-2H-thiopyran-4-yl)oxy]-3-methyl-1-benzofuran-2-yl}methyl)amino]phenyl}carbonyl)(methyl)amino]propanoic acid

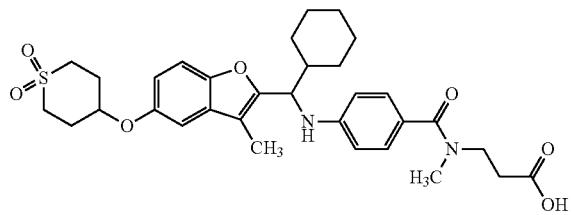 [SMILES: Cc1c(C(Nc2ccc(C(=O)N(C)CCC(=O)O)cc2)C2CCCCC2)oc2ccc(OC3CCS(=O)(=O)CC3)cc12]

(1) 1,1-dioxidotetrahydro-2H-thiopyran-4-yl 4-methylbenzenesulfonate

To a solution of tetrahydro-2H-thiopyran-4-yl 4-methylbenzenesulfonate (3.0 g) in acetic acid (9 mL) was added 30% hydrogen peroxide (3 mL), and the mixture was stirred at 50° C. for 3.5 hr. The reaction mixture was cooled to room temperature, water (30 mL) was added to the mixture, and the mixture was stirred at 0° C. for 5 min. The obtained solid was collected by filtration and washed with water to give the title compound (2.84 g, 85%) as a colorless solid.

$^1$H NMR (300 MHz, CDCl$_3$) δ ppm 2.26-2.36 (m, 4H), 2.47 (s, 3H), 2.84-3.00 (m, 2H), 3.10-3.43 (m, 2H), 4.74-4.86 (m, 1H), 7.38 (d, J=8.0 Hz, 2H), 7.81 (d, J=8.3 Hz, 2H).

(2) 3-[({4-[(cyclohexyl{5-[(1,1-dioxidotetrahydro-2H-thiopyran-4-yl)oxy]-3-methyl-1-benzofuran-2-yl}methyl)amino]phenyl}carbonyl)(methyl)amino]propanoic acid A solution of ethyl 3-{[(4-{[cyclohexyl(5-hydroxy-3-methyl-1-benzofuran-2-yl)methyl]amino}phenyl)carbonyl](methyl)amino}propanoate (400 mg) obtained in Example A194(4), 1,1-dioxidotetrahydro-2H-thiopyran-4-yl 4-methylbenzenesulfonate (593 mg) synthesized above and tripotassium phosphate (223 mg) in N,N-dimethylformamide (4 mL) was stirred at 100° C. for 14 hr. 1,1-Dioxidotetrahydro-2H-thiopyran-4-yl 4-methylbenzenesulfonate (593 mg) and tripotassium phosphate (112 mg) were further added to the mixture, and the mixture was stirred at 100° C. for 2 hr then at 120° C. for 3 hr. Water was added to the reaction mixture and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-34:66, v/v) to give a colorless amorphous form (200 mg). The colorless amorphous form (200 mg) was dissolved in ethanol (1.5 mL) and tetrahydrofuran (1.5 mL), and 1N aqueous sodium hydroxide solution (0.64 mL) was added to the solution, and the mixture was stirred at room temperature for 30 min. The solvent was evaporated under reduced pressure, water (4 mL) was added to the residue, and the mixture was neutralized with 1N hydrochloric acid (0.64 mL) under ice-cooling and stirred at 0° C. for 30 min. The resulting precipitate was collected by filtration, and dried to give the title compound (136 mg, 29%) as a colorless amorphous form.

$^1$H NMR (300 MHz, CDCl$_3$) δ ppm 0.99-2.00 (m, 8H), 2.21 (s, 3H), 2.31-2.73 (m, 10H), 2.86-2.99 (m, 1H), 3.03 (s, 3H), 3.36-3.53 (m, 2H), 3.65-3.76 (m, 2H), 4.36 (d, J=8.3 Hz, 1H), 4.54-4.82 (m, 3H), 6.55 (d, J=8.3 Hz, 2H), 6.78-6.87 (m, 1H), 6.93 (d, J=2.6 Hz, 1H), 7.17-7.30 (m, 3H).

Example A200

3-[{[4-({cyclohexyl[3-methyl-5-(pyridin-2-yloxy)-1-benzofuran-2-yl]methyl}amino)phenyl]carbonyl}(methyl)amino]propanoic acid

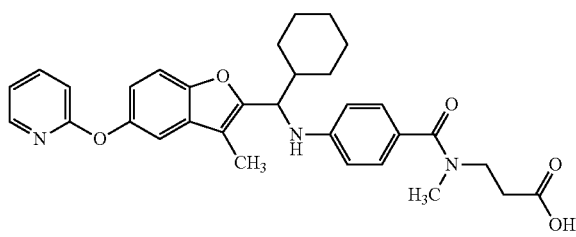 [SMILES: Cc1c(C(Nc2ccc(C(=O)N(C)CCC(=O)O)cc2)C2CCCCC2)oc2ccc(Oc3ccccn3)cc12]

A solution of ethyl 3-{[(4-{[cyclohexyl(5-hydroxy-3-methyl-1-benzofuran-2-yl)methyl]amino}phenyl)carbonyl](methyl)amino}propanoate (300 mg) obtained in Example A194(4), 2-fluoropyridine (88 mg) and potassium carbonate (126 mg) in N,N-dimethylformamide (3 mL) was stirred at 80° C. for 8 hr then at room temperature for 48 hr. 2-Fluoropyridine (88 mg) was added to the mixture, and the mixture was stirred at 120° C. for 4 hr. 2-Fluoropyridine (352 mg) was added to the mixture, and the mixture was stirred at 120° C. for 10 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give a colorless oil (35 mg). The obtained oil (35 mg) was dissolved in tetrahydrofuran (0.5 mL), and 1N aqueous sodium hydroxide solution (0.12 mL) was added to the solution, and the mixture was stirred at 50° C. for 1 hr. The solvent was evaporated under reduced pressure, water (4 mL) was added to the residue, and the mixture was neutralized with 1N hydrochloric acid (0.12 mL) under ice-cooling and stirred at 0° C. for 20 min. The resulting precipitate was collected by filtration, and dried to give the title compound (22 mg, 7%) as a colorless amorphous form.

$^1$H NMR (300 MHz, CDCl$_3$) δ ppm 0.86-1.42 (m, 6H), 1.51-1.96 (m, 5H), 2.13 (br. s., 1H), 2.19 (s, 3H), 2.36-2.69 (m, 2H), 3.01 (s, 3H), 3.54 (br. s., 2H), 4.39 (d, J=7.9 Hz, 1H), 6.58 (d, J=8.7 Hz, 2H), 6.88-7.05 (m, 3H), 7.12-7.24 (m, 3H), 7.33 (d, J=8.7 Hz, 1H), 7.65-7.74 (m, 1H), 8.09-8.20 (m, 1H).

Example A201

Ethyl 3-{[(4-{[{5-[(5-cyanopyridin-2-yl)oxy]-3-methyl-1-benzofuran-2-yl}(cyclohexyl)methyl]amino}phenyl)carbonyl]methyl)amino}-propanoate

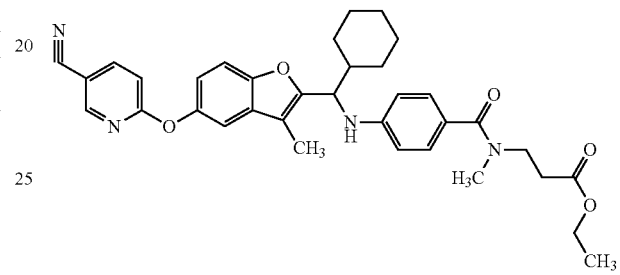

A solution of ethyl 3-{[(4-{[cyclohexyl(5-hydroxy-3-methyl-1-benzofuran-2-yl)methyl]amino}phenyl)carbonyl](methyl)amino}propanoate (400 mg) obtained in Example A194(4), 2-chloro-5-cyanopyridine (167 mg) and potassium carbonate (168 mg) in N,N-dimethylformamide (4 mL) was stirred at 80° C. for 14 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (340 mg, 70%) as a colorless amorphous form.

$^1$H NMR (300 MHz, CDCl$_3$) δ ppm 1.01-1.30 (m, 8H), 1.55-1.96 (m, 5H), 2.09-2.15 (m, 1H), 2.22 (s, 3H), 2.62 (t, J=6.8 Hz, 2H), 3.03 (s, 3H), 3.71 (t, J=7.0 Hz, 2H), 4.04-4.18 (m, 2H), 4.27-4.48 (m, 2H), 6.56 (d, J=8.7 Hz, 2H), 6.90-7.07 (m, 2H), 7.17 (d, J=2.3 Hz, 1H), 7.22 (d, J=8.7 Hz, 2H), 7.40 (d, J=8.7 Hz, 1H), 7.90 (dd, J=8.7, 2.3 Hz, 1H), 8.46 (d, J=2.3 Hz, 1H).

Example A202

3-{[(4-{[{5-[(5-cyanopyridin-2-yl)oxy]-3-methyl-1-benzofuran-2-yl}(cyclohexyl)methyl]amino}phenyl)carbonyl](methyl)amino}-propanoic acid

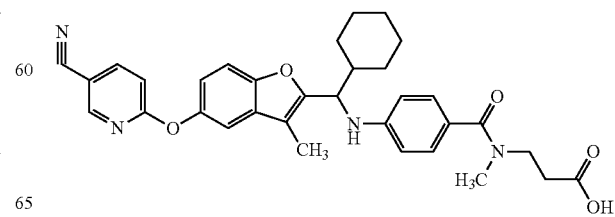

Ethyl 3-{[(4-{[{5-[(5-cyanopyridin-2-yl)oxy]-3-methyl-1-benzofuran-2-yl}(cyclohexyl)methyl]amino}phenyl)carbonyl](methyl)amino}-propanoate (300 mg) obtained in Example A201 was dissolved in tetrahydrofuran (4.0 mL), and 1N aqueous sodium hydroxide solution (1.1 mL) was added to the solution, and the mixture was stirred at 50° C. for 1 hr. The solvent was evaporated under reduced pressure, water (4 mL) was added to the residue, and the mixture was neutralized with 1N hydrochloric acid (1.1 mL) under ice-cooling and stirred at 0° C. for 30 min. The resulting precipitate was collected by filtration, and dried to give the title compound (271 mg, 87%) as a colorless amorphous form.

$^1$H NMR (300 MHz, CDCl$_3$) δ ppm 0.93-1.36 (m, 5H), 1.52-2.11 (m, 7H), 2.22 (s, 3H), 2.61 (br. s., 2H), 3.03 (s, 3H), 3.66 (br. s., 2H), 4.39 (d, J=7.9 Hz, 1H), 6.56 (d, J=8.7 Hz, 2H), 6.91-7.08 (m, 2H), 7.12-7.25 (m, 3H), 7.39 (d, J=8.7 Hz, 1H), 7.90 (dd, J=8.7, 2.3 Hz, 1H), 8.45 (d, J=2.3 Hz, 1H).

Example A203 ethyl 3-(methyl{[4-({2-methyl-1-[3-methyl-5-(tetrahydro-2H-thiopyran-4-yloxy)-1-benzofuran-2-yl]propyl}amino)phenyl]carbonyl}amino)propanoate

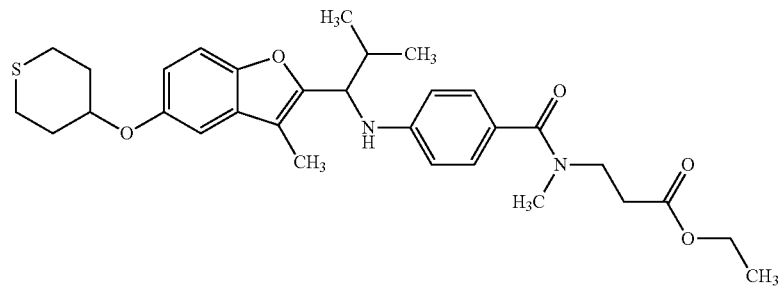 [SMILES: CCOC(=O)CCN(C)C(=O)c1ccc(NC(c2oc3ccc(OC4CCSCC4)cc3c2C)C(C)C)cc1]

(1) 1-(5-hydroxy-3-methyl-1-benzofuran-2-yl)-2-methylpropan-1-one

1-[5-(Benzyloxy)-3-methyl-1-benzofuran-2-yl]-2-methylpropan-1-one (4.0 g) synthesized in Example A85(1) was dissolved in ethanol (80 mL), and palladium carbon-ethylenediamine complex (400 mg) was added to the solution at room temperature. The reaction mixture was stirred under hydrogen atmosphere (1 atm) at room temperature for 9.5 hr. The catalyst was filtered off, and the filtrate was concentrated under reduced pressure to give the title compound (2.82 g, 100%) as a colorless solid.

$^1$H NMR (300 MHz, CDCl$_3$) δ ppm 1.24 (d, J=6.8 Hz, 6H), 2.55 (s, 3H), 3.48-3.63 (m, 1H), 6.95-7.08 (m, 2H), 7.32-7.40 (m, 1H).

(2) 2-methyl-1-[3-methyl-5-(tetrahydro-2H-thiopyran-4-yloxy)-1-benzofuran-2-yl]propan-1-one A solution of 1-(5-hydroxy-3-methyl-1-benzofuran-2-yl)-2-methylpropan-1-one (1.0 g) synthesized above, tetrahydro-2H-thiopyran-4-yl 4-methylbenzenesulfonate (2.99 g) and tripotassium phosphate (1.26 g) in N,N-dimethylformamide (10 mL) was stirred at 80° C. for 3 hr then at 100° C. for 14 hr. Tetrahydro-2H-thiopyran-4-yl 4-methylbenzenesulfonate (2.99 g) was added to the mixture, and the mixture was stirred at 100° C. for 20 min. Tripotassium phosphate (600 mg) was added to the mixture, and the mixture was stirred at 100° C. for 2 hr then at 120° C. for 3 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-90:10, v/v) to give the title compound (886 mg, 61%) as an orange oil.

$^1$H NMR (300 MHz, CDCl$_3$) δ ppm 1.23 (d, J=6.8 Hz, 5H), 1.82-2.29 (m, 4H), 2.49-2.68 (m, 6H), 2.88-3.00 (m, 2H), 3.38-3.71 (m, 1H), 4.25-4.50 (m, 1H), 6.99-7.16 (m, 2H), 7.40 (d, J=9.5 Hz, 1H).

(3) 2-methyl-1-[3-methyl-5-(tetrahydro-2H-thiopyran-4-yloxy)-1-benzofuran-2-yl]propan-1-ol 2-Methyl-1-[3-methyl-5-(tetrahydro-2H-thiopyran-4-yloxy)-1-benzofuran-2-yl]propan-1-one (849 mg) synthesized above was dissolved in methanol (3 mL)-tetrahydrofuran (15 mL), and sodium tetrahydroborate (90%) (202 mg) was added to the solution at 0° C. The reaction mixture was stirred at 0° C. for 30 min. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-85:15, v/v) to give the title compound (621 mg, 73%) as a colorless oil.

$^1$H NMR (300 MHz, CDCl$_3$) δ ppm 0.82 (d, J=6.8 Hz, 3H), 1.12 (d, J=6.4 Hz, 3H), 1.92-2.13 (m, 2H), 2.16-2.27 (m, 6H), 2.48-2.70 (m, 2H), 2.89-3.01 (m, 2H), 4.28-4.37 (m, 1H), 4.46 (dd, J=8.3, 6.0 Hz, 1H), 6.87 (dd, 1H), 6.96 (d, J=2.6 Hz, 1H), 7.30 (d, J=8.7 Hz, 1H).

(4) ethyl 3-(methyl{[4-({2-methyl-1-[3-methyl-5-(tetrahydro-2H-thiopyran-4-yloxy)-1-benzofuran-2-yl]propyl}amino)phenyl]carbonyl}amino)propanoate To a solution of 2-methyl-1-[3-methyl-5-(tetrahydro-2H-thiopyran-4-yloxy)-1-benzofuran-2-yl]propan-1-ol (621 mg) obtained above in tetrahydrofuran (5 mL) was added thionyl chloride (0.17 mL) at room temperature. The reaction mixture was stirred at room temperature for 2 hr. To the reaction mixture was added aqueous sodium hydrogen carbonate solution, and the mixture was extracted with ethyl acetate. The organic layer was washed with saturated brine, and dried over anhydrous magnesium sulfate. After filtration, the filtrate was concentrated to give a colorless oil (648 mg). To the obtained colorless oil (648 mg) were added ethyl 3-{[(4-aminophenyl)carbonyl](methyl)amino}propanoate (509 mg) obtained in Example 2 (2), sodium iodide (581 mg), sodium carbonate (411 mg) and N,N-dimethylacetamide (5 mL), and the mixture was stirred at 80° C. for 19 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (495 mg, 46%) as a colorless oil.

$^1$H NMR (300 MHz, CDCl$_3$) δ ppm 0.92 (d, J=6.8 Hz, 3H), 1.13 (d, J=6.8 Hz, 3H), 1.21-1.30 (m, 3H), 1.95-2.09 (m, 2H), 2.13-2.27 (m, 6H), 2.49-2.67 (m, 4H), 2.87-2.96 (m, 2H), 3.01 (s, 3H), 3.70 (t, J=7.2 Hz, 2H), 4.07-4.16 (m, 2H), 4.26-4.36 (m, 3H), 6.57 (d, J=8.7 Hz, 2H), 6.83 (dd, J=8.7, 2.6 Hz, 1H), 6.91 (d, J=2.6 Hz, 1H), 7.16-7.25 (m, 3H).

Example A204

3-(methyl{[4-({2-methyl-1-[3-methyl-5-(tetrahydro-2H-thiopyran-4-yloxy)-1-benzofuran-2-yl]propyl}amino)phenyl]carbonyl}amino)propanoic acid

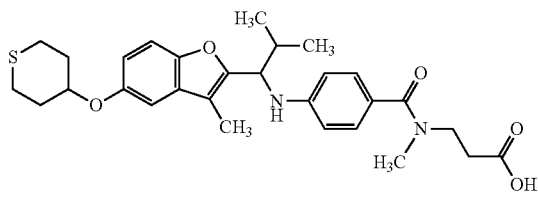 [SMILES: Cc1c(C(Nc2ccc(C(=O)N(C)CCC(=O)O)cc2)C(C)C)oc2ccc(OC3CCSCC3)cc12]

Ethyl 3-(methyl{[4-({2-methyl-1-[3-methyl-5-(tetrahydro-2H-thiopyran-4-yloxy)-1-benzofuran-2-yl]propyl}amino)phenyl]carbonyl}amino)propanoate (485 mg) synthesized in Example A203 was dissolved in ethanol (2.0 mL) and tetrahydrofuran (2.0 mL), and 1N aqueous sodium hydroxide solution (1.96 mL) was added to the solution, and the mixture was stirred at room temperature for 0.5 hr. The solvent was evaporated under reduced pressure, water (4 mL) was added to the residue, and the mixture was neutralized with 1N hydrochloric acid (1.96 mL) under ice-cooling, and stirred for 30 min. The resulting precipitate was collected by filtration, and dried to give the title compound (421 mg, 91%) as a colorless amorphous form.

$^1$H NMR (300 MHz, CDCl$_3$) δ ppm 0.91 (d, J=6.8 Hz, 3H), 1.12 (d, J=6.8 Hz, 3H), 1.96-2.07 (m, 2H), 2.15-2.28 (m, 6H), 2.48-2.71 (m, 5H), 3.02 (s, 3H), 3.62-3.75 (m, 2H), 4.21-4.35 (m, 2H), 4.55-4.73 (m, 2H), 6.56 (d, J=8.7 Hz, 2H), 6.83 (dd, J=8.7, 2.7 Hz, 1H), 6.91 (d, J=2.7 Hz, 1H), 7.20-7.26 (m, 3H).

Example A205 ethyl 3-{methyl[(4-{[2-methyl-1-(3-methyl-5-{[5-(trifluoromethyl)pyridin-2-yl]oxy}-1-benzofuran-2-yl)propyl]amino}phenyl)carbonyl]amino}propanoate

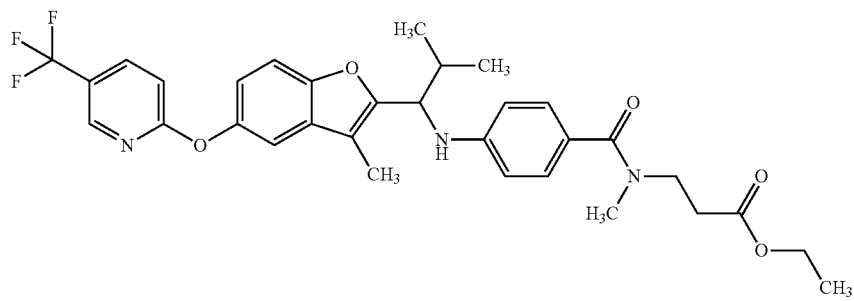 [SMILES: CCOC(=O)CCN(C)C(=O)c1ccc(NC(c2oc3ccc(Oc4ccc(C(F)(F)F)cn4)cc3c2C)C(C)C)cc1]

(1)-2-methyl-1-(3-methyl-5-{[5-(trifluoromethyl)pyridin-2-yl]oxy}-1-benzofuran-2-yl)propan-1-one A solution of 1-(5-hydroxy-3-methyl-1-benzofuran-2-yl)-2-methylpropan-1-one (900 mg) synthesized in Example A203(1), 2-chloro-5-(trifluoromethyl)pyridine (898 mg) and potassium carbonate (854 mg) in N,N-dimethylformamide (5 mL) was stirred at 120° C. for 1 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-90:10, is v/v) to give the title compound (1.23 g, 82%) as a colorless solid.

$^1$H NMR (300 MHz, CDCl$_3$) δ ppm 1.25 (d, J=6.8 Hz, 6H), 2.58 (s, 3H), 3.47-3.71 (m, 1H), 7.06 (d, J=8.7 Hz, 1H), 7.21-7.29 (m, 1H), 7.42 (d, J=2.6 Hz, 1H), 7.55 (d, J=8.7 Hz, 1H), 7.92 (dd, J=8.7, 1.9 Hz, 1H), 8.43 (s, 1H).

(2)-2-methyl-1-(3-methyl-5-{[5-(trifluoromethyl)pyridin-2-yl]oxy}-1-benzofuran-2-yl)propan-1-ol 2-Methyl-1-(3-methyl-5-{[5-(trifluoromethyl)pyridin-2-yl]oxy}-1-benzofuran-2-yl)propan-1-one (1.22 g) synthesized above was dissolved in methanol (40 mL)-tetrahydrofuran (4 mL), and sodium tetrahydroborate (90%)(253 mg) was added to the solution at 0° C. The reaction mixture was stirred at 0° C. for 2 hr. Water was added to the reaction mixture, and the mixture was extracted with ethyl acetate. The organic layer was washed with saturated brine, and dried over anhydrous magnesium sulfate. After filtration, the filtrate was concentrated to give the title compound (1.22 g, 100%) as a colorless oil.

$^1$H NMR (300 MHz, CDCl$_3$) δ ppm 0.85 (d, 3H), 1.13 (d, J=6.4 Hz, 3H), 1.98-2.04 (m, 1H), 2.15-2.30 (m, 4H), 4.50 (dd, J=7.9, 3.8 Hz, 1H), 6.94-7.09 (m, 2H), 7.24 (d, J=2.3 Hz, 1H), 7.45 (d, J=9.0 Hz, 1H), 7.89 (dd, J=8.7, 2.3 Hz, 1H), 8.45 (s, 1H).

(3) ethyl 3-{methyl[(4-{[2-methyl-1-(3-methyl-5-{[5-(trifluoromethyl)pyridin-2-yl]oxy}-1-benzofuran-2-yl)propyl]amino}phenyl)carbonyl]amino}propanoate To a solution of 2-methyl-1-(3-methyl-5-{[5-(trifluoromethyl)pyridin-2-yl]oxy}-1-benzofuran-2-yl)propan-1-ol (776 mg) obtained above in tetrahydrofuran (5 mL) was added thionyl chloride (0.19 mL) at room temperature. The reaction mixture was stirred at room temperature for 3 hr. To the reaction mixture was added aqueous sodium hydrogen carbonate solution, and the mixture was extracted with ethyl acetate. The organic layer was washed with saturated brine, and dried over anhydrous magnesium sulfate. After filtration, the filtrate was concentrated. To the obtained residue were added ethyl 3-{[(4-aminophenyl)carbonyl](methyl)amino}propanoate (557 mg) obtained in Example 2 (2), sodium iodide (636 mg), sodium carbonate (449 mg) and N,N-dimethylacetamide (5 mL), and the mixture was stirred at 80° C. for 14 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (436 mg, 34%) as a yellow amorphous compound.

$^1$H NMR (300 MHz, CDCl$_3$) δ ppm 0.94 (d, J=6.4 Hz, 3H), 1.15 (d, J=6.8 Hz, 3H), 1.21-1.29 (m, 3H), 1.60 (s, 3H), 2.20-2.31 (m, 4H), 2.62 (t, J=6.8 Hz, 2H), 3.72 (t, J=7.2 Hz, 2H), 4.12 (q, J=7.2 Hz, 2H), 4.34 (d, 2H), 6.58 (d, 2H), 6.99 (td, J=5.8, 3.0 Hz, 2H), 7.15-7.25 (m, 3H), 7.39 (d, J=9.0 Hz, 1H), 7.88 (dd, J=8.7, 2.3 Hz, 1H), 8.43 (d, J=2.6 Hz, 1H).

Example A206

3-{methyl[(4-{[2-methyl-1-(3-methyl-5-{[5-(trifluoromethyl)pyridin-2-yl]oxy}-1-benzofuran-2-yl)propyl]amino}phenyl)carbonyl]amino}propanoic acid

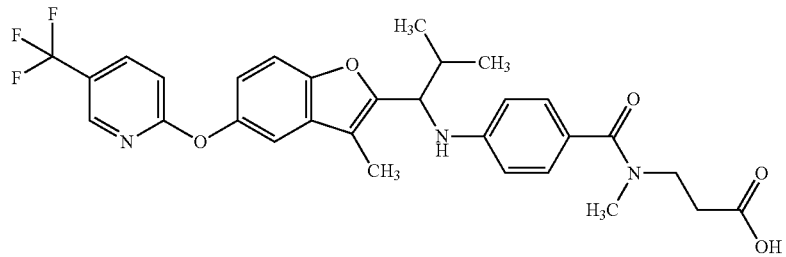 [SMILES: Cc1c(C(Nc2ccc(C(=O)N(C)CCC(=O)O)cc2)C(C)C)oc2ccc(Oc3ccc(C(F)(F)F)cn3)cc12]

Ethyl 3-{methyl[(4-{[2-methyl-1-(3-methyl-5-{[5-(trifluoromethyl)pyridin-2-yl]oxy}-1-benzofuran-2-yl)propyl]amino}phenyl)carbonyl]amino}propanoate (425 mg) synthesized in Example A205 was dissolved in tetrahydrofuran (4.0 mL), 1N aqueous sodium hydroxide solution (1.4 mL) was added to the solution, and the mixture was stirred at 50° C. for 1.5 hr. The solvent was evaporated under reduced pressure, water (4 mL) was added to the residue, and the mixture was neutralized with 1N hydrochloric acid (1.4 mL) under ice-cooling and stirred for 20 min. The resulting precipitate was collected by filtration, and dried to give the title compound (378 mg, 94%) as a colorless amorphous form.

$^1$H NMR (300 MHz, CDCl$_3$) δ ppm 0.93 (d, J=6.8 Hz, 3H), 1.14 (d, J=6.4 Hz, 3H), 2.16-2.30 (m, 4H), 2.52 (br. s., 2H), 2.99 (s, 3H), 3.62 (br. s., 2H), 4.34 (d, J=7.5 Hz, 1H), 6.57 (d, J=8.7 Hz, 2H), 6.89-7.05 (m, 2H), 7.14-7.25 (m, 3H), 7.37 (d, J=9.0 Hz, 1H), 7.89 (dd, J=8.9, 2.4 Hz, 1H), 8.42 (s, 1H).

Example A207 ethyl 3-{[(4-{[cyclopentyl(5,7-difluoro-3-methyl-1-benzofuran-2-yl)methyl]amino}phenyl)carbonyl](methyl)amino}propanoate

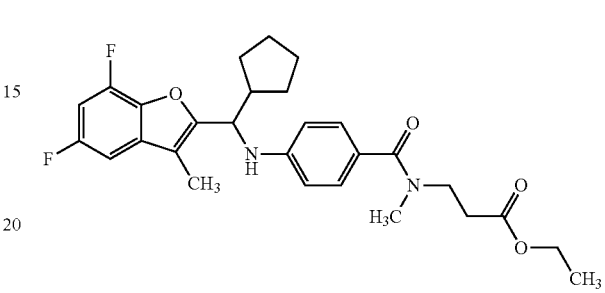

(1)(2-acetyl-4,6-difluorophenoxy)acetic acid

A solution of 3',5'-difluoro-2'-hydroxyacetophenone (5.0 g), methyl bromoacetate (4.89 g) and potassium carbonate (6.01 g) in N,N-dimethylformamide (50 mL) was stirred at room temperature for 4 hr. The insoluble material was filtered off, 1N hydrochloric acid was added to the filtrate, and the mixture was extracted with ethyl acetate. The extract was washed with saturated brine, dried over magnesium sulfate, and concentrated under reduced pressure to give a brown oil. To the obtained oil were added tetrahydrofuran (60 mL), ethanol (60 mL) and 1N aqueous sodium hydroxide solution (60 mL), and the mixture was stirred at room temperature for 30 min. The solvent was concentrated under reduced pressure, 1N hydrochloric acid (60 mL) was added, and the mixture was extracted with ethyl acetate. The extract was washed with saturated brine, dried over magnesium sulfate, and concentrated under reduced pressure to give the title compound (6.67 g, 100%) as a pale-yellow solid.

$^1$H NMR (300 MHz, CDCl$_3$) δ ppm 2.67 (s, 3H), 4.81 (s, 2H), 7.01-7.12 (m, 1H), 7.20-7.26 (m, 1H), 9.19 (br. s., 1H).

(2) 5,7-difluoro-3-methyl-1-benzofuran

A mixture of (2-acetyl-4,6-difluorophenoxy)acetic acid (6.60 g) obtained above, sodium acetate (11.76 g) and acetic anhydride (40 mL) was stirred at 110° C. for 8 hr. The reaction mixture was cooled to room temperature, water was added to the mixture, and the mixture was extracted with ethyl acetate.

The organic layer was washed with saturated aqueous sodium hydrogen carbonate solution, saturated brine, and dried over anhydrous magnesium sulfate. After filtration, the filtrate was concentrated. The residue was subjected to silica gel column chromatography (NH silica, hexane) to give the title compound (2.42 g, 50%) as a colorless solid.

$^1$H NMR (300 MHz, CDCl$_3$) δ ppm 2.21 (s, 3H), 6.70-6.90 (m, 1H), 6.97 (dd, J=8.0, 2.3 Hz, 1H), 7.46 (s, 1H).

(3) cyclopentyl(5,7-difluoro-3-methyl-1-benzofuran-2-yl)methanone

To a solution of 5,7-difluoro-3-methyl-1-benzofuran (1.0 g) synthesized above, and cyclopentanecarbonylchloride (867 mg) in nitromethane (20 mL) was added aluminum chloride (anhydrous) (1.19 g) at 0° C., and the mixture was stirred for 2 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-95:5, v/v) to give the title compound (1.25 g, 80%) as a colorless solid.

$^1$H NMR (300 MHz, CDCl$_3$) δ ppm 1.62-2.16 (m, 8H), 2.57 (s, 3H), 3.66-3.85 (m, 1H), 6.90-7.05 (m, 1H), 7.10 (dd, J=7.3, 2.8 Hz, 1H).

(4) cyclopentyl(5,7-difluoro-3-methyl-1-benzofuran-2-yl)methanol

Cyclopentyl(5,7-difluoro-3-methyl-1-benzofuran-2-yl)methanone (1.24 g) synthesized above was dissolved in methanol (4 mL)-tetrahydrofuran (20 mL), and sodium tetrahydroborate (90%)(355 mg) was added to the solution at 0° C. The reaction mixture was stirred at 0° C. for 2 hr. Water was added to the reaction mixture, and the mixture was extracted with ethyl acetate. The organic layer was washed with saturated brine, and dried over anhydrous magnesium sulfate. After filtration, the filtrate was concentrated to give the title compound (1.18 g, 100%) as a yellow oil.

$^1$H NMR (300 MHz, CDCl$_3$) δ ppm 1.04-1.22 (m, 1H), 1.43-1.75 (m, 6H), 1.93-2.03 (m, 2H), 2.22 (s, 3H), 2.40-2.63 (m, 1H), 4.56 (dd, J=9.0, 6.4 Hz, 1H), 6.72-6.85 (m, 1H), 6.87-6.95 (m, 1H).

(5) ethyl 3-{[(4-{[cyclopentyl(5,7-difluoro-3-methyl-1-benzofuran-2-yl)methyl]amino}phenyl)carbonyl](methyl)amino}propanoate To a solution of cyclopentyl(5,7-difluoro-3-methyl-1-benzofuran-2-yl)methanol (1.1 g) obtained above in tetrahydrofuran (10 mL) was added thionyl chloride (0.46 mL) at room temperature. The reaction mixture was stirred at room temperature for 2 hr. Thionyl chloride (0.46 mL) was further added to the mixture, and the mixture was stirred at room temperature for 30 min. To the reaction mixture was added aqueous sodium hydrogen carbonate solution, and the mixture was extracted with ethyl acetate. The organic layer was washed with saturated brine, and dried over anhydrous magnesium sulfate. After filtration, the filtrate was concentrated. To the obtained residue were added ethyl 3-{[(4-aminophenyl)carbonyl](methyl)amino}propanoate (1.09 g) obtained in Example 2 (2), sodium iodide (1.24 g), sodium carbonate (875 mg) and N,N-dimethylacetamide (10 mL), and the mixture was stirred at 80° C. for 2 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (252 mg, 12%) as a yellow amorphous compound.

$^1$H NMR (300 MHz, CDCl$_3$) δ ppm 1.24 (dt, J=9.4, 7.1 Hz, 3H), 1.46-1.79 (m, 7H), 1.91-2.02 (m, 1H), 2.25 (s, 3H), 2.42-2.67 (m, 3H), 3.01 (s, 3H), 3.70 (t, J=7.2 Hz, 2H), 4.04-4.16 (m, 2H), 4.31-4.41 (m, 2H), 6.56 (d, J=8.7 Hz, 2H), 6.68-6.79 (m, 1H), 6.88 (dd, J=8.0, 2.3 Hz, 1H), 7.22 (d, J=8.3 Hz, 2H).

Example A208

3-{[(4-{[cyclopentyl(5,7-difluoro-3-methyl-1-benzofuran-2-yl)methyl]amino}phenyl)carbonyl](methyl)amino}propanoic acid

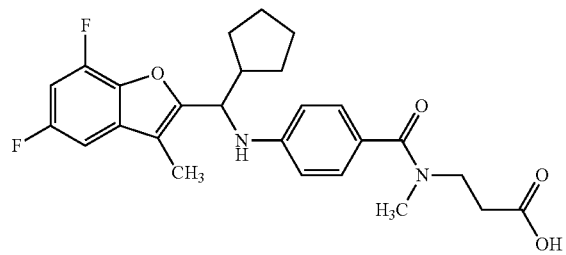 [SMILES: Cc1c(C(Nc2ccc(C(=O)N(C)CCC(=O)O)cc2)C2CCCC2)oc2c(F)cc(F)cc12]

Ethyl 3-{[(4-{[cyclopentyl(5,7-difluoro-3-methyl-1-benzofuran-2-yl)methyl]amino}phenyl)carbonyl](methyl)amino}propanoate (240 mg) synthesized in Example A207 was dissolved in ethanol (1.0 mL)-tetrahydrofuran (1.0 mL), 1N aqueous sodium hydroxide solution (0.96 mL) was added to the solution, and the mixture was stirred at room temperature for 30 min. The solvent was evaporated under reduced pressure, water (4 mL) was added to the residue, and the mixture was neutralized with 1N hydrochloric acid (0.96 mL) under ice-cooling, and stirred for 15 min. The resulting precipitate was collected by filtration, and dried to give the title compound (185 mg, 82%) as a colorless amorphous form.

$^1$H NMR (300 MHz, CDCl$_3$) δ ppm 1.16-1.39 (m, 1H), 1.43-1.75 (m, 7H), 1.86-2.06 (m, 1H), 2.24 (s, 3H), 2.38-2.56 (m, 1H), 2.66 (t, J=6.4 Hz, 2H), 3.03 (s, 3H), 3.70 (t, J=6.8 Hz, 2H), 4.37 (d, J=9.4 Hz, 1H), 6.55 (d, J=8.7 Hz, 2H), 6.68-6.80 (m, 1H), 6.88 (dd, J=7.9, 2.3 Hz, 1H), 7.24 (d, J=8.7 Hz, 2H).

Example A209

3-[{[4-({cyclohexyl[3-methyl-5-(tetrahydrofuran-2-ylmethoxy)-1-benzofuran-2-yl]methyl}amino)phenyl]carbonyl}(methyl)amino]propanoic acid

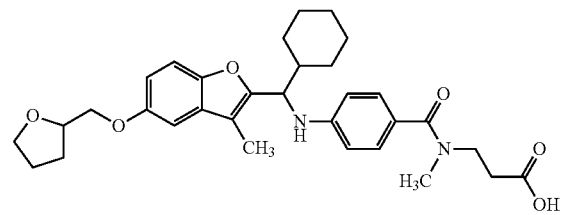 [SMILES: Cc1c(C(Nc2ccc(C(=O)N(C)CCC(=O)O)cc2)C2CCCCC2)oc2ccc(OCC3CCCO3)cc12]

(1) cyclohexyl[3-methyl-5-(tetrahydrofuran-2-yl-methoxy)-1-benzofuran-2-yl]methanone A solution of 1-(5-hydroxy-3-methyl-1-benzofuran-2-yl)-2-methylpropan-1-one (300 mg) synthesized in Example A203(1), tetrahydrofurfuryl bromide (230 mg), potassium carbonate (240 mg) in N,N-dimethylformamide (3 mL) was stirred at 80° C. for 2 hr then at 120° C. for 4 hr. Tetrahydrofurfuryl bromide (230 mg) was added to the mixture, and the mixture was stirred at 120° C. for 60 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-90:10, v/v) to give the title compound (275 mg, 69%) as a colorless oil.

$^1$H NMR (300 MHz, CDCl$_3$) δ ppm 1.20-1.51 (m, 5H), 1.68-2.17 (m, 9H), 2.56 (s, 3H), 3.20-3.39 (m, 1H), 3.76-3.98 (m, 2H), 4.02 (d, J=5.3 Hz, 2H), 4.24-4.37 (m, 1H), 7.03 (d, J=2.6 Hz, 1H), 7.13 (dd, J=9.0, 2.6 Hz, 1H), 7.39 (d, J=8.7 Hz, 1H).

(2) cyclohexyl[3-methyl-5-(tetrahydrofuran-2-yl-methoxy)-1-benzofuran-2-yl]methanol Cyclohexyl[3-methyl-5-(tetrahydrofuran-2-ylmethoxy)-1-benzofuran-2-yl]methanone (260 mg) synthesized above was dissolved in methanol (0.5 mL)-tetrahydrofuran (2.5 mL), and sodium tetrahydroborate (90%) (64 mg) was added to the solution at 0° C. The reaction mixture was stirred at 0° C. for 2.5 hr. Water was added to the reaction mixture, and the mixture was extracted with ethyl acetate. The organic layer was washed with saturated brine, and dried over anhydrous magnesium sulfate. After filtration, the filtrate was concentrated to give the title compound (235 mg, 90%) as a colorless oil.

$^1$H NMR (300 MHz, CDCl$_3$) δ ppm 0.77-1.46 (m, 8H), 1.61-1.69 (m, 2H), 1.72-2.01 (m, 6H), 2.18 (s, 3H), 3.78-3.89 (m, 1H), 3.92-4.05 (m, 3H), 4.22-4.39 (m, 1H), 4.50 (d, J=8.7 Hz, 1H), 6.87-6.92 (m, 1H), 6.94 (d, J=2.6 Hz, 1H), 7.29 (d, J=9.1 Hz, 1H).

(3) 3-[{[4-({cyclohexyl[3-methyl-5-(tetrahydrofuran-2-ylmethoxy)-1-benzofuran-2-yl]methyl}amino)phenyl]carbonyl}(methyl)amino]propanoic acid To a solution of cyclohexyl[3-methyl-5-(tetrahydrofuran-2-ylmethoxy)-1-benzofuran-2-yl]methanol (220 mg) obtained above in tetrahydrofuran (2 mL) was added thionyl chloride (70 μL) at room temperature. The reaction mixture was stirred at room temperature for 2 hr. To the reaction mixture was added aqueous sodium hydrogen carbonate solution, and the mixture was extracted with ethyl acetate. The organic layer was washed with saturated brine, and dried over anhydrous magnesium sulfate. After filtration, the filtrate was concentrated. To the obtained residue were added ethyl 3-{[(4-aminophenyl)carbonyl](methyl)amino}propanoate (168 mg) obtained in Example 2 (2), sodium iodide (192 mg), sodium carbonate (136 mg) and N,N-dimethylacetamide (3.0 mL), and the mixture was stirred at 80° C. for 14 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-0:100, v/v) to give a colorless, amorphous form (120 mg). The obtained colorless amorphous form (120 mg) was dissolved in ethanol (1.0 mL)-tetrahydrofuran (1.0 mL), 1N aqueous sodium hydroxide solution (0.44 mL) was added to the solution, and the mixture was stirred at room temperature for 1 hr. The solvent was evaporated under reduced pressure, water (1 mL) was added to the residue, and the mixture was neutralized with 1N hydrochloric acid (0.44 mL) under ice-cooling and stirred for 10 min. The resulting precipitate was collected by filtration, and dried to give the title compound (97 mg, 80%) as a colorless solid.

$^1$H NMR (300 MHz, CDCl$_3$) δ ppm 0.93-1.29 (m, 5H), 1.47-2.14 (m, 11H), 2.20 (s, 3H), 2.54-2.72 (m, 2H), 3.02 (s, 3H), 3.67 (t, J=6.4 Hz, 2H), 3.77-3.90 (m, 1H), 3.91-4.03 (m, 3H), 4.19-4.32 (m, 1H), 4.35 (d, J=7.9 Hz, 1H), 6.55 (d, J=8.7 Hz, 2H), 6.79-6.95 (m, 2H), 7.16-7.25 (m, 3H).

Example A210 ethyl 3-[{[6-({1-[5-(cyclopropylmethoxy)-3-methyl-1-benzofuran-2-yl]-2-methylpropyl}amino)pyridin-3-yl]carbonyl}(methyl)amino]propanoate

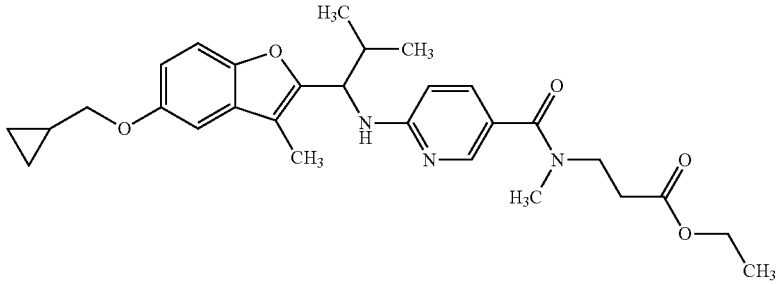

(1) methyl 6-({1-[5-(cyclopropylmethoxy)-3-methyl-1-benzofuran-2-yl]-2-methylpropyl}amino)pyridine-3-carboxylate To a solution of 1-[5-(cyclopropylmethoxy)-3-methyl-1-benzofuran-2-yl]-2-methylpropan-1-ol (1.41 g) obtained in Example A75(3) in tetrahydrofuran (10 mL) was added thionyl chloride (0.45 mL) at room temperature. The reaction mixture was stirred at room temperature for 2 hr. To the reaction mixture was added aqueous sodium hydrogen carbonate solution ice-cooled to 0° C., and the mixture was extracted with ethyl acetate. The organic layer was washed with saturated brine, and dried over anhydrous magnesium sulfate. After filtration, the filtrate was concentrated to give a colorless solid (1.42 g). To the obtained colorless solid (710 mg) were added methyl 6-aminopyridine-3-carboxylate (411 mg), sodium iodide (770 mg), sodium carbonate (545 mg) and N,N-dimethylacetamide (6 mL), and the mixture was stirred at 80° C. for 22 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (265 mg, 25%) as a brown oil.

$^1$H NMR (300 MHz, CDCl$_3$) δ ppm 0.33-0.39 (m, 2H), 0.60-0.69 (m, 2H), 0.88-0.95 (m, 3H), 1.10 (d, J=6.8 Hz, 3H), 2.94 (s, 3H), 3.01 (s, 3H), 3.82-3.88 (m, 4H), 5.01 (t, 1H), 5.40 (d, J=8.7 Hz, 1H), 6.34 (d, J=8.3 Hz, 1H), 6.85-6.95 (m, 2H), 7.21-7.27 (m, 1H), 7.91 (dd, J=9.0, 2.3 Hz, 1H), 8.74 (d, J=1.9 Hz, 1H).

(2)-6-({1-[5-(cyclopropylmethoxy)-3-methyl-1-benzofuran-2-yl]-2-methylpropyl}amino)pyridine-3-carboxylic acid To a mixture of methyl 6-({1-[5-(cyclopropylmethoxy)-3-methyl-1-benzofuran-2-yl]-2-methylpropyl}amino)pyridine-3-carboxylate (260 mg) obtained above, tetrahydrofuran (1.2 mL) and ethanol (1.2 mL) was added 1N aqueous sodium hydroxide solution (1.2 mL), and the mixture was stirred with heating under reflux for 5 hr. 1N Aqueous sodium hydroxide solution (1.2 mL) was added to the mixture, and the mixture was stirred with heating under reflux for 16 hr. 8N Aqueous sodium hydroxide solution (1.2 mL) was added to the mixture, and the mixture was further stirred with heating under reflux for 1 hr. The reaction mixture was concentrated under reduced pressure, water (4 mL) was added to the residue, and 1N hydrochloric acid (10.8 mL) was added to the mixture under ice-cooling, and the mixture was stirred for 10 min. The resulting precipitate was collected by filtration, and dried to give the title compound (145 mg, 58%) as a colorless solid.

$^1$H NMR (300 MHz, CDCl$_3$) δ ppm 0.31-0.37 (m, 2H), 0.61-0.66 (m, 2H), 0.94 (d, J=6.8 Hz, 3H), 1.15 (d, J=6.8 Hz, 3H), 1.21-1.37 (m, 1H), 2.22 (s, 3H), 2.31-2.48 (m, 1H), 3.82 (d, J=6.8 Hz, 2H), 4.66 (br. s., 1H), 6.36 (d, J=8.7 Hz, 1H), 6.79-6.92 (m, 2H), 7.22-7.29 (m, 1H), 8.05 (dd, J=9.1, 1.9 Hz, 1H), 8.75 (d, J=1.9 Hz, 1H).

(3) ethyl 3-[{[6-({1-[5-(cyclopropylmethoxy)-3-methyl-1-benzofuran-2-yl]-2-methylpropyl}amino)pyridin-3-yl]carbonyl}(methyl)amino]propanoate A mixture of 6-({1-[5-(cyclopropylmethoxy)-3-methyl-1-benzofuran-2-yl]-2-methylpropyl}amino)pyridine-3-carboxylic acid (145 mg) synthesized above, ethyl 3-(methylamino)propanoate (58 mg), 1-hydroxybenzotriazole.monohydrate (67 mg), triethylamine (122 μL), 1-ethyl-3-(3-dimethylaminopropyl)carbodiimide hydrochloride (84 mg) and N,N-dimethylformamide (2 mL) was stirred at room temperature for 18 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (hexane-ethyl acetate 100:0-0:100, v/v) to give the title compound (104 mg, 56%) as a colorless amorphous form.

$^1$H NMR (300 MHz, CDCl$_3$) δ ppm 0.26-0.49 (m, 2H), 0.58-0.70 (m, 2H), 0.86-1.00 (m, 3H), 1.04-1.15 (m, 3H), 1.18-1.31 (m, 4H), 2.18-2.30 (m, 4H), 2.63 (t, J=6.8 Hz, 2H), 3.06 (s, 3H), 3.73 (t, J=7.0 Hz, 2H), 3.82 (d, J=6.8 Hz, 2H), 4.13 (q, J=7.2 Hz, 2H), 4.94 (t, J=8.5 Hz, 1H), 5.18 (d, J=8.7 Hz, 1H), 6.34 (d, J=8.3 Hz, 1H), 6.79-6.91 (m, 2H), 7.22-7.26 (m, 1H), 7.47 (dd, J=8.3, 2.3 Hz, 1H).

Example A211

3-[{[6-({1-[5-(cyclopropylmethoxy)-3-methyl-1-benzofuran-2-yl]-2-methylpropyl}amino)pyridin-3-yl]carbonyl}(methyl)amino]propanoic acid

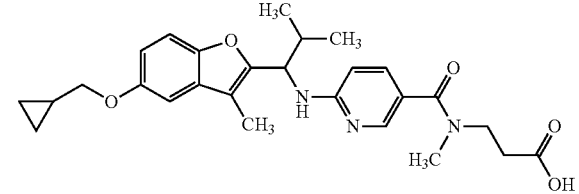

Ethyl 3-[{[6-({1-[5-(cyclopropylmethoxy)-3-methyl-1-benzofuran-2-yl]-2-methylpropyl}amino)pyridin-3-yl]carbonyl}(methyl)amino]propanoate (100 mg) synthesized in Example A210 was dissolved in ethanol (0.5 mL)-tetrahydrofuran (0.5 mL), 1N aqueous sodium hydroxide solution (0.4 mL) was added to the solution, and the mixture was stirred at room temperature for 2 hr. The solvent was evaporated under reduced pressure, water (0.5 mL) was added to the residue, and the mixture was neutralized with 1N hydrochloric acid (0.4 mL) under ice-cooling, and the mixture was stirred for 20 min. The resulting precipitate was collected by filtration, and dried to give the title compound (77 mg, 80%) as a colorless solid.

$^1$H NMR (300 MHz, CDCl$_3$) δ ppm 0.30-0.43 (m, 2H), 0.57-0.69 (m, 2H), 0.92 (d, J=6.4 Hz, 3H), 1.15 (d, J=6.4 Hz, 3H), 1.23-1.35 (m, 1H), 2.21 (s, 3H), 2.30-2.43 (m, 1H), 2.66 (t, J=6.2 Hz, 2H), 3.06 (s, 3H), 3.70-3.77 (m, 2H), 3.82 (d, J=7.2 Hz, 2H), 4.43 (br. s., 1H), 6.38 (d, J=9.1 Hz, 1H), 6.80-6.91 (m, 2H), 7.26-7.30 (m, 1H), 7.57 (dd, J=8.7, 1.9 Hz, 1H), 8.10 (br. s., 1H).

Example A212 ethyl 3-[{[5-({1-[5-(cyclopropylmethoxy)-3-methyl-1-benzofuran-2-yl]-2-methylpropyl}amino)pyridin-2-yl]carbonyl}(methyl)amino]propanoate

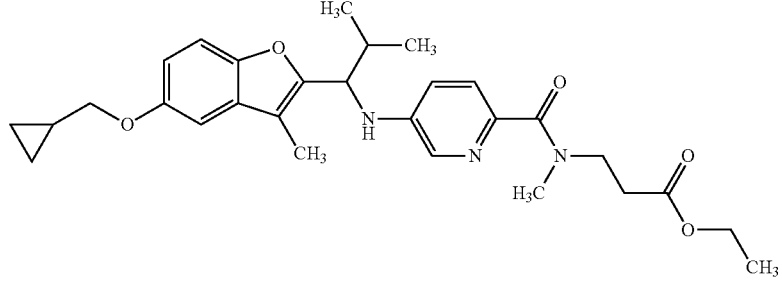 [SMILES: CCOC(=O)CCN(C)C(=O)c1ccc(NC(c2oc3ccc(OCC4CC4)cc3c2C)C(C)C)cn1]

(1) methyl 5-({1-[5-(cyclopropylmethoxy)-3-methyl-1-benzofuran-2-yl]-2-methylpropyl}amino)pyridine-2-carboxylate To a solution of 1-[5-(cyclopropylmethoxy)-3-methyl-1-benzofuran-2-yl]-2-methylpropan-1-ol (1.41 g) obtained in Example A75(3) in tetrahydrofuran (10 mL) was added thionyl chloride (0.45 mL) at room temperature. The reaction mixture was stirred at room temperature for 2 hr. To the reaction mixture was added aqueous sodium hydrogen carbonate solution ice-cooled to 0° C., and the mixture was extracted with ethyl acetate. The organic layer was washed with saturated brine, and dried over anhydrous magnesium sulfate. After filtration, the filtrate was concentrated to give a colorless solid (1.42 g). To the obtained colorless solid (710 mg) were added methyl 5-aminopyridine-2-carboxylate (411 mg), sodium iodide (770 mg), sodium carbonate (545 mg) and N,N-dimethylacetamide (6 mL), and the mixture was stirred at 80° C. for 2 hr. Water was added to the reaction mixture, and the mixture was extracted with ethyl acetate. The organic layer was washed with saturated brine, and dried over anhydrous magnesium sulfate. After filtration, the filtrate was concentrated. The residue was subjected to silica gel column chromatography (hexane-ethyl acetate 100:0-50:50, v/v) to give the title compound (424 mg, 40%) as a brown oil.

$^1$H NMR (300 MHz, CDCl$_3$) δ ppm 0.29-0.40 (m, 2H), 0.60-0.69 (m, 2H), 0.93 (d, J=6.8 Hz, 3H), 1.14 (d, J=6.8 Hz, 3H), 2.20-2.31 (m, 4H), 3.82 (d, J=6.8 Hz, 3H), 3.91 (s, 3H), 4.34 (t, J=8.0 Hz, 1H), 4.65 (d, J=8.3 Hz, 1H), 6.81-6.91 (m, 3H), 7.23 (d, J=9.5 Hz, 1H), 7.89 (d, J=8.3 Hz, 1H), 8.10 (d, J=2.7 Hz, 1H).

(2) 5-({1-[5-(cyclopropylmethoxy)-3-methyl-1-benzofuran-2-yl]-2-methylpropyl}amino)pyridine-2-carboxylic acid To a mixture of methyl 5-({1-[5-(cyclopropylmethoxy)-3-methyl-1-benzofuran-2-yl]-2-methylpropyl}amino)pyridine-2-carboxylate (410 mg) synthesized above, tetrahydrofuran (2.0 mL) and ethanol (2.0 mL) was added 1N aqueous sodium hydroxide solution (2.0 mL), and the mixture was stirred with heating under reflux for 14 hr. The reaction mixture was concentrated under reduced pressure, water (4 mL) was added to the residue, 1N hydrochloric acid (2 mL) was added under ice-cooling, and the mixture was stirred for 20 min. The resulting precipitate was collected by filtration, and dried to give the title compound (323 mg, 80%) as a colorless solid.

$^1$H NMR (300 MHz, CDCl$_3$) δ ppm 0.35 (q, 2H), 0.60-0.68 (m, 2H), 0.94 (d, J=6.8 Hz, 3H), 1.15 (d, J=6.8 Hz, 3H), 1.24-1.35 (m, 1H), 2.18-2.38 (m, 4H), 3.82 (d, J=7.2 Hz, 2H), 4.35 (br. s., 1H), 4.98 (br. s., 1H), 6.82-6.90 (m, 2H), 6.96 (dd, J=8.7, 2.6 Hz, 1H), 7.20-7.28 (m, 1H), 7.95 (d, J=8.7 Hz, 1H), 8.08 (br. s., 1H).

(3) ethyl 3-[{[5-({1-[5-(cyclopropylmethoxy)-3-methyl-1-benzofuran-2-yl]-2-methylpropyl}amino)pyridin-2-yl]carbonyl}(methyl)amino]propanoate A mixture of 5-({1-[5-(cyclopropylmethoxy)-3-methyl-1-benzofuran-2-yl]-2-methylpropyl}amino)pyridine-2-carboxylic acid (311 mg) synthesized above, ethyl 3-(methylamino)propanoate (131 mg), 1-hydroxybenzotriazole.monohydrate (145 mg), triethylamine (265 µL), 1-ethyl-3-(3-dimethylaminopropyl)carbodiimide hydrochloride (182 mg) and N,N-dimethylformamide (2 mL) was stirred at room temperature for 16 hr. Saturated aqueous ammonium chloride solution was added to quench the reaction, and the reaction mixture was extracted with ethyl acetate. The extract was washed with saturated brine, dried over magnesium sulfate, and concentrated under reduced pressure. The residue was purified by silica gel column chromatography (hexane-ethyl acetate 100:0-0:100, v/v) to give the title compound (291 mg, 73%) as a colorless amorphous form.

$^1$H NMR (300 MHz, CDCl$_3$) δ ppm 0.31-0.39 (m, 2H), 0.64 (q, J=6.1 Hz, 2H), 0.92 (d, J=6.8 Hz, 3H), 1.14 (d, 3H), 1.22-1.31 (m, 3H), 1.63 (s, 3H), 2.17-2.30 (m, 4H), 2.62-2.75 (m, 2H), 3.71-3.93 (m, 4H), 4.01-4.18 (m, 3H), 4.24-4.36 (m, 1H), 4.40-4.47 (m, 1H), 6.75-6.92 (m, 3H), 7.20-7.25 (m, 1H), 7.53 (br. s., 1H), 7.93 (br. s., 1H).

Example A213

3-[{[5-({1-[5-(cyclopropylmethoxy)-3-methyl-1-benzofuran-2-yl]-2-methylpropyl}amino)pyridin-2-yl]carbonyl}(methyl)amino]propanoic acid

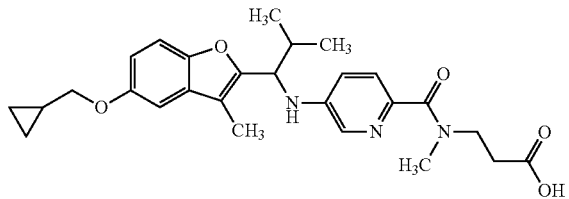

Ethyl 3-[{[5-({1-[5-(cyclopropylmethoxy)-3-methyl-1-benzofuran-2-yl]-2-methylpropyl}amino)pyridin-2-yl]carbonyl}(methyl)amino]propanoate (280 mg) synthesized in Example A212 was dissolved in ethanol (1.0 mL)-tetrahydrofuran (1.0 mL), 1N aqueous sodium hydroxide solution (1.1 mL) was added to the solution, and the mixture was stirred at room temperature for 1 hr. The solvent was evaporated under reduced pressure, water (2.0 mL) was added to the residue, and the mixture was neutralized with 1N hydrochloric acid (1.1 mL) under ice-cooling, and stirred for 30 min. The resulting precipitate was collected by filtration, and dried to give the title compound (238 mg, 90%) as a colorless solid.

$^1$H NMR (300 MHz, CDCl$_3$) δ ppm 0.28-0.41 (m, 2H), 0.57-0.68 (m, 2H), 0.91 (d, J=6.4 Hz, 3H), 1.12 (d, J=6.4 Hz, 3H), 2.18-2.31 (m, 4H), 2.77 (br. s., 2H), 3.06 (br. s., 3H), 3.68-3.77 (m, 2H), 3.80-3.85 (m, 2H), 4.29 (d, J=7.6 Hz, 2H), 4.66 (br. s., 1H), 6.80-7.00 (m, 3H), 7.24 (d, J=8.7 Hz, 1H), 7.61 (br. s., 1H), 7.93 (br. s., 1H).

Example A214

3-{[(4-{[cyclohexyl(5-fluoro-3-methoxy-1-benzofuran-2-yl)methyl]amino}phenyl)carbonyl](methyl)amino}propanoic acid

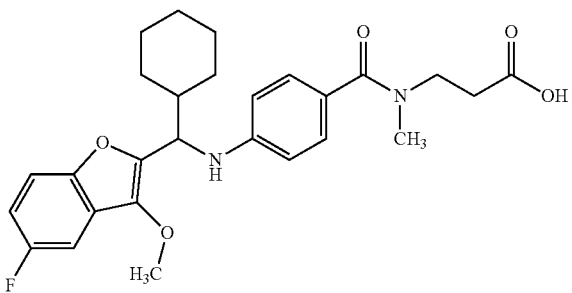 [SMILES: COc1c(C(Nc2ccc(C(=O)N(C)CCC(=O)O)cc2)C2CCCCC2)oc2ccc(F)cc12]

(1) cyclohexyl(5-fluoro-3-hydroxy-1-benzofuran-2-yl)methanone 1-(5-Fluoro-2-hydroxyphenyl)ethanone (4.0 g) was dissolved in acetonitrile (80 mL). To the reaction mixture were added potassium carbonate (4.8 g) and 2-bromo-1-cyclohexylethanone (7.3 g) synthesized in Example A51(1) at room temperature, and the mixture was stirred at room temperature for 8 hr. The reaction mixture was filtered through celite, rinsed with ethyl acetate, and the filtrate was concentrated under reduced pressure. The residue was dissolved in N,N-dimethylformamide (50 mL), 1,8-diazabicyclo[5.4.0]undec-7-ene (5.3 mL) was added to the solution, and the mixture was stirred with heating at 110° C. for 1 hr. After cooling to room temperature, the reaction mixture was quenched with 1N hydrochloric acid, and the mixture was extracted with diethyl ether. The extract was concentrated under reduced pressure, and the precipitated compound was recrystallized from diisopropyl ether-ethanol to give the title object compound (4.7 g, 76%) as a colorless solid.
$^1$H NMR (300 MHz, CDCl$_3$) δ ppm 1.03-2.12 (m, 10H), 3.00-3.26 (m, 1H), 5.24 (s, 1H), 7.14-7.50 (m, 3H).

(2) cyclohexyl(5-fluoro-3-methoxy-1-benzofuran-2-yl)methanone

Cyclohexyl(5-fluoro-3-hydroxy-1-benzofuran-2-yl)methanone (3.0 g) synthesized in the above-mentioned (1) was dissolved in tetrahydrofuran (15 mL) and N,N-dimethylformamide (15 mL). The reaction mixture was ice-cooled, sodium hydride (0.69 mg) was added to the solution, and the mixture was stirred for 15 min. Dimethyl sulfate (1.6 mL) was added to the mixture, and the mixture was stirred at room temperature overnight. The solvent was evaporated under reduced pressure, water was added to the residue, and the mixture was extracted with ethyl acetate. The extract was concentrated under reduced pressure, and the precipitate was recrystallized from diisopropyl ether-hexane to give the title object compound (2.0 g, 63%) as a colorless solid.
$^1$H NMR (300 MHz, CDCl$_3$) δ ppm 1.16-2.03 (m, 10H), 3.23 (tt, J=11.2, 3.1 Hz, 1H), 4.26 (s, 3H), 7.20-7.54 (m, 3H).

(3) cyclohexyl(5-fluoro-3-methoxy-1-benzofuran-2-yl)methanol

Cyclohexyl(5-fluoro-3-methoxy-1-benzofuran-2-yl)methanone (2.0 g) synthesized in the above-mentioned (2) was dissolved in tetrahydrofuran (15 mL) and methanol (3 mL), and sodium borohydride (90%, 0.59 g) was added to the solution under ice-cooling. The ice bath was removed, and the reaction mixture was stirred at room temperature for 1 hr then ice-cooled again, and water (2 mL) and 1N hydrochloric acid (10 mL) were carefully added to the mixture, and the mixture was extracted with ethyl acetate. The extract was washed with saturated brine, dried over magnesium sulfate, and concentrated under reduced pressure to give a crude product (1.9 g, quantitative) of the title object compound as a yellow oil.
$^1$H NMR (300 MHz, CDCl$_3$) δ ppm 0.86-2.19 (m, 12H), 3.97 (s, 3H), 4.61 (d, J=8.3 Hz, 1H), 6.98-7.33 (m, 3H).

(4) ethyl 3-{[(4-{[cyclohexyl(5-fluoro-3-methoxy-1-benzofuran-2-yl)methyl]amino}phenyl)carbonyl](methyl)amino}propanoate To a solution (15 mL) of cyclohexyl(5-fluoro-3-methoxy-1-benzofuran-2-yl)methanol (1.9 g) synthesized in the above-mentioned (3) in tetrahydrofuran was added thionyl chloride (0.48 mL) at room temperature. The reaction mixture was stirred at room temperature for 30 min then ice-cooled, and saturated aqueous sodium hydrogen carbonate solution (15 mL) was carefully added to the mixture. The reaction mixture was stirred for 10 min, and the mixture was extracted with ethyl acetate. The extract was washed with saturated brine, dried over magnesium sulfate, and concentrated under reduced pressure. The residue was dissolved in dimethylacetamide (15 mL), sodium iodide (0.98 g), sodium carbonate (0.65 g) and ethyl 3-{[(4-aminophenyl)carbonyl](methyl)amino}propanoate (0.90 g) synthesized in Example 2(2) were added to the solution, and the mixture was stirred at 70° C. for 4 hr. After allowing to cool, water was added to the reaction mixture, and the mixture was extracted with ethyl acetate. The extract was concentrated under reduced pressure, and the residue was purified by silica gel column chromatography (ethyl acetate:hexane=1:1, volume ratio) to give the title object compound (0.30 g, 16%) as a pale-yellow oil.
$^1$H NMR (300 MHz, CDCl$_3$) δ ppm 0.91-2.19 (m, 14H), 2.61 (t, J=7.2 Hz, 2H), 3.01 (s, 3H), 3.70 (t, J=7.2 Hz, 2H), 3.94 (s, 3H), 4.11 (q, J=7.2 Hz, 2H), 4.30-4.46 (m, 2H), 6.63 (d, J=8.7 Hz, 2H), 6.93-7.25 (m, 5H).

(5) 3-{[(4-{[cyclohexyl(5-fluoro-3-methoxy-1-benzofuran-2-yl)methyl]amino}phenyl)carbonyl](methyl)amino}propanoic acid Ethyl 3-{[(4-{[cyclohexyl(5-fluoro-3-methoxy-1-benzofuran-2-yl)methyl]amino}phenyl)carbonyl](methyl)amino}propanoate (0.30 g) synthesized in the above-mentioned (4) was dissolved in ethanol (5 mL), 1N aqueous sodium hydroxide solution (1.0 mL) was added to the solution at room temperature, and the mixture was stirred at room temperature for 0.5 hr. Ethanol was evaporated under reduced pressure, and 1N hydrochloric acid (1.0 mL) was added to the residue. The precipitate was washed with water to give the title object compound (0.15 g, 52%) as a colorless solid.
$^1$H NMR (300 MHz, CDCl$_3$) δ ppm 0.94-2.20 (m, 11H), 2.70 (t, J=6.4 Hz, 2H), 3.05 (s, 3H), 3.71 (t, J=6.4 Hz, 2H), 3.94 (s, 3H), 4.46 (d, J=8.3 Hz, 1H), 6.64 (d, J=9.0 Hz, 2H), 6.94 (td, J=9.0, 2.6 Hz, 1H), 7.14-7.31 (m, 4H).

Example A215

3-{[(4-{[cyclohexyl(6-methoxy-2-methyl-1-benzofuran-3-yl)methyl]amino}phenyl)carbonyl](methyl)amino}propanoic acid

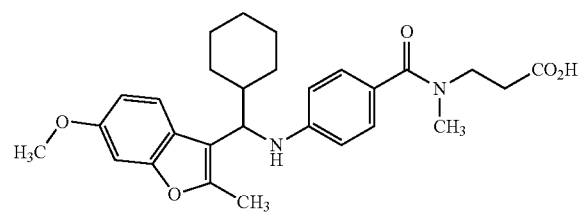 [SMILES: COc1ccc2c(C(Nc3ccc(C(=O)N(C)CCC(=O)O)cc3)C3CCCCC3)c(C)oc2c1]

(1) cyclohexyl(6-methoxy-2-methyl-1-benzofuran-3-yl)methanone

To a mixture of 6-methoxy-2-methyl-1-benzofuran (1.50 g), cyclohexanecarbonyl chloride (1.36 mL) and nitromethane (15 mL) was added aluminum chloride (1.85 g) at 0° C., and the mixture was stirred for 1 hr. Water was added to quench the reaction, and the reaction mixture was extracted with ethyl acetate. The extract was washed with saturated brine, dried over magnesium sulfate, and concentrated under reduced pressure. The residue was purified by silica gel column chromatography (0-10% ethyl acetate/hexane) to give the title object compound (1.18 g, 47%) as a yellow oil.

$^1$H NMR (300 MHz, CDCl$_3$) δ ppm 1.20-1.62 (m, 5H), 1.69-1.81 (m, 1H), 1.82-2.02 (m, 4H), 2.73 (s, 3H), 2.95-3.09 (m, 1H), 3.85 (s, 3H), 6.93 (dd, J=8.7, 2.2 Hz, 1H), 6.97 (d, J=2.2 Hz, 1H), 7.68 (d, J=8.7 Hz, 1H).

(2) cyclohexyl(6-methoxy-2-methyl-1-benzofuran-3-yl)methanol

To a mixture of cyclohexyl(6-methoxy-2-methyl-1-benzofuran-3-yl)methanone (1.18 g) synthesized above, methanol (1 mL) and tetrahydrofuran (10 mL) was added sodium borohydride (246 mg) at 0° C., and the mixture was stirred for 30 min. 1N Hydrochloric acid was added to quench the reaction, the organic solvent was evaporated in an evaporator, and the residue was extracted with ethyl acetate. The extract was washed with saturated brine, dried over magnesium sulfate, and concentrated under reduced pressure to give the title object compound (906 mg, 76%) as a pale-yellow oil.

$^1$H NMR (300 MHz, CDCl$_3$) δ ppm 0.76-0.97 (m, 1H), 0.99-1.38 (m, 4H), 1.37-1.50 (m, 1H), 1.51-1.72 (m, 2H), 1.74-2.00 (m, 2H), 2.11-2.24 (m, 1H), 2.38 (s, 3H), 3.83 (s, 3H), 4.50 (d, J=8.0 Hz, 1H), 6.81 (dd, J=8.5, 2.2 Hz, 1H), 6.93 (d, J=2.2 Hz, 1H), 7.51 (d, J=8.5 Hz, 1H).

(3) 3-[chloro(cyclohexyl)methyl]-6-methoxy-2-methyl-1-benzofuran

To a solution (10 mL) of cyclohexyl(6-methoxy-2-methyl-1-benzofuran-3-yl)methanol (499 mg) synthesized above in toluene was added thionyl chloride (159 µL), and the mixture was stirred at room temperature for 1 hr. The reaction mixture was poured into ice-cooled saturated aqueous sodium hydrogen carbonate solution, and the mixture was extracted with ethyl acetate. The extract was washed with saturated brine, dried over magnesium sulfate, and concentrated under reduced pressure to give the title object compound (530 mg, 99%) as a pale-yellow oil.

$^1$H NMR (300 MHz, CDCl$_3$) δ ppm 0.72-0.92 (m, 1H), 0.97-1.40 (m, 4H), 1.44-1.72 (m, 3H), 1.76-1.89 (m, 1H), 2.05-2.22 (m, 1H), 2.29-2.46 (m, 4H), 3.83 (s, 3H), 4.74 (d, J=9.3 Hz, 1H), 6.84 (dd, J=8.5, 2.4 Hz, 1H), 6.93 (d, J=2.4 Hz, 1H), 7.55 (d, J=8.5 Hz, 1H).

(4) ethyl 3-{[(4-{[cyclohexyl(6-methoxy-2-methyl-1-benzofuran-3-yl)methyl]amino}phenyl)carbonyl](methyl)amino}propanoate To a mixture of 3-[chloro(cyclohexyl)methyl]-6-methoxy-2-methyl-1-benzofuran (530 mg) synthesized above, ethyl 3-{[(4-aminophenyl)carbonyl](methyl)amino}propanoate (498 mg) synthesized in Example 2(2) and N,N-dimethylformamide (10 mL) were added sodium iodide (408 mg) and sodium carbonate (288 mg), and the mixture was stirred at 80° C. overnight. Saturated aqueous ammonium chloride solution was added to quench the reaction, and the mixture was extracted with ethyl acetate. The extract was washed with saturated brine, dried over magnesium sulfate, and concentrated under reduced pressure. The residue was purified by silica gel column chromatography (30-70% ethyl acetate/hexane) to give the title object compound (781 mg, 85%) as a white solid.

$^1$H NMR (300 MHz, CDCl$_3$) δ ppm 0.91-1.37 (m, 8H), 1.54-1.96 (m, 5H), 1.99-2.12 (m, 1H), 2.42 (s, 3H), 2.60 (t, J=6.9 Hz, 2H), 3.00 (s, 3H), 3.69 (t, J=6.9 Hz, 2H), 3.82 (s, 3H), 4.11 (q, J=7.1 Hz, 2H), 4.19-4.32 (m, 2H), 6.47 (d, J=8.5 Hz, 2H), 6.79 (dd, J=8.5, 2.2 Hz, 1H), 6.91 (d, J=2.2 Hz, 1H), 7.17 (d, J=8.5 Hz, 2H), 7.40 (d, J=8.5 Hz, 1H).

(5) 3-{[(4-{[cyclohexyl(6-methoxy-2-methyl-1-benzofuran-3-yl)methyl]amino}phenyl)carbonyl](methyl)amino}propanoic acid To a mixture of ethyl 3-{[(4-{[cyclohexyl(6-methoxy-2-methyl-1-benzofuran-3-yl)methyl]amino}phenyl)carbonyl](methyl)amino}propanoate (781 mg) synthesized above, tetrahydrofuran (5 mL) and ethanol (5 mL) was added 1N aqueous sodium hydroxide solution (2.00 mL), and the mixture was stirred at room temperature for 1 hr, and concentrated under reduced pressure. The residue was dissolved in water (10 mL), and 1N hydrochloric acid (2.00 mL) was added at 0° C. The resulting precipitate was collected by filtration to give the title object compound (702 mg, 95%) as a white solid.

$^1$H NMR (300 MHz, CDCl$_3$) δ ppm 0.91-1.36 (m, 5H), 1.57-1.97 (m, 5H), 1.99-2.11 (m, 1H), 2.41 (s, 3H), 2.64 (t, J=6.6 Hz, 2H), 3.01 (s, 3H), 3.68 (t, J=6.6 Hz, 2H), 3.81 (s, 3H), 4.24 (d, J=7.5 Hz, 1H), 6.47 (d, J=8.7 Hz, 2H), 6.79 (dd, J=8.7, 2.3 Hz, 1H), 6.91 (d, J=2.3 Hz, 1H), 7.18 (d, J=8.7 Hz, 2H), 7.40 (d, J=8.7 Hz, 1H).

Experimental Example 1

The glucagon binding inhibitory action of the compound of the present invention was evaluated by the following method.
(1) Cloning of Human Glucagon Receptor Gene Human glucagon receptor gene was cloned by PCR reaction using human pancreas Marathon-ready cDNA (Clontech) as a template and the following primer set.

```
GGR-U:
                                          (SEQ ID NO: 1)
 5'-AATAGAATTCATGCCCCCCTGCCAGCCACAG-3'

GGR-L:
                                          (SEQ ID NO: 2)
 5'-CTAAGCGGCCGCTCAGAAGGGGCTCTCAGCCAATCT-3'
```

PCR reaction was performed using Advantage 2 polymerase (Clontech) and according to the attached protocol. The obtained PCR product was electrophoresed on an agarose gel (1%). An about 1.4 kb of DNA fragment containing a glucagon receptor gene was recovered from the gel and digested with restriction enzymes EcoRI and NotI. DNA treated with the restriction enzymes was electrophoresed on an agarose gel (1%). An about 1.4 kb of DNA fragment was recovered and ligated to plasmid pMSRαneo digested with restriction enzymes EcoRI and NotI to construct a human-type glucagon receptor expression plasmid DNA "pMSRα-neo/hGCGR". The base sequence of an inserted fragment was confirmed and the base sequence was confirmed to be in consistency with that of the object sequence.
(2) Preparation of Glucagon Receptor Membrane Protein A human-type glucagon receptor was expressed using FreeStyle CHO Expression System (Invitrogen). A transient expression in FreeStyle CHO cell was performed using a human-type glucagon receptor expression plasmid DNA "pMSRαneo/hGCGR" and according to the manual attached to the FreeStyle CHO Expression System. The above-mentioned DNA was transfected and the cultured with shaking for 2 days (37° C., 8% $CO_2$, 125 rpm). 2400 ml of culture medium was centrifuged at 2,000 rpm for 10 min and the cells were collected. The collected cells were washed with PBS, suspended in homogenate buffer [10 mM $NaHCO_3$ (pH 7.4), 1 mM EDTA, Complete EDTA-free (Roche, 1 tablet/50 ml)] and disrupted by polytron cell disrupter (Kinematica AG). Disruption solution was centrifuged at 2,000 rpm for 10 min and the supernatant was collected. The supernatant was centrifuged at 35,000 rpm for 60 min and the precipitate was suspended in a buffer [20 mM Tris-HCl (pH 7.4), 5 mM EDTA, Complete EDTA-free (Roche, 1 tablet/50 ml)] to give a glucagon receptor membrane protein (452 mg).

(3) Measurement of Glucagon Binding Inhibitory Activity

To each well of 96 well plate (Corning Incorporated) were added 25 µl of test compound (containing 0.4% DMSO), 50 µl of glucagon receptor membrane protein diluted with reaction buffer [50 mM Tris-HCl (pH 7.4), 5 mM EGTA, 5 mM magnesium chloride, 0.1% BSA, 0.005% Tween20] to 100 µg/ml, and 25 µl of radioactive labeled glucagon ([$^{125}$I]-Receptor Grade Glucagon; Perkin Elmer Inc.) diluted with the reaction buffer to 200 µM, whereby the reaction was started. The plate was stood for 90 min at room temperature. The reaction solution was transferred from the reaction plate to a 96 well unifilter GF/C plate (Perkin Elmer Inc.) using a cell harvester (Perkin Elmer Inc.) and the membrane fraction was collected on the filter by suction. The filter was presoaked in 2 mg/ml of polyethyleneimine to prevent non-specific adsorption of labeled ligand. The filter was washed 4 times with a reaction buffer and dried for 2 hr at 42° C. To each well was added 25 µl of scintillator (MicroScint0; Perkin Elmer Inc.), and the fluorescence amount was measured using a microplate scintillation counter (TopCount NXT™; Perkin Elmer Inc.). The glucagon binding inhibitory activity ($IC_{50}$ value) of the well added with the test compound (containing 0.4% DMSO) was calculated, using the reaction rate of the well added only with 0.4% DMSO as 0% inhibitory rate, and the reaction rate of the well added with non-labeled glucagon (final concentration 1 µM) as 100% inhibitory rate. The results are shown in Table 1.

TABLE 1

| test compound | $IC_{50}$ value (nM) |
|---|---|
| Example 8 | 410 |
| Example 41 | 2300 |
| Example 61 | 320 |
| Example A3 | 1700 |
| Example A7 | 1800 |
| Example A12 | 210 |
| Example A17 | 230 |
| Example A49 | 640 |
| Example A53 | 570 |
| Example A73 | 900 |
| Example A78 | 280 |
| Example A83 | 84 |

In addition, the inhibitory rate (%) of the well added with the test compound (10 µM; containing 0.4% DMSO) was calculated, using the reaction rate of the well added only with 0.4% DMSO as 0% inhibitory rate, and the reaction rate of the well added with non-labeled glucagon (final concentration 1 µM) as 100% inhibitory rate. The results are shown in Table 2.

TABLE 2

| test compound | inhibitory rate (%) at 10 µM |
|---|---|
| Example 1 | 73 |
| Example 2 | 72 |
| Example 3 | 74 |
| Example 4 | 77 |
| Example 5 | 73 |
| Example 6 | 75 |
| Example 7 | 72 |
| Example 8 | 75 |
| Example 9 | 74 |
| Example 10 | 76 |
| Example 11 | 73 |
| Example 12 | 74 |
| Example 13 | 71 |
| Example 14 | 71 |
| Example 15 | 72 |
| Example 16 | 63 |
| Example 17 | 80 |
| Example 18 | 72 |
| Example 19 | 80 |
| Example 20 | 79 |
| Example 21 | 77 |
| Example 22 | 61 |
| Example 23 | 71 |
| Example 24 | 73 |
| Example 25 | 78 |
| Example 26 | 72 |
| Example 27 | 70 |
| Example 28 | 71 |
| Example 29 | 77 |
| Example 30 | 75 |
| Example 31 | 67 |
| Example 32 | 59 |
| Example 33 | 75 |
| Example 34 | 79 |
| Example 35 | 75 |
| Example 36 | 69 |
| Example 37 | 70 |
| Example 38 | 53 |
| Example 41 | 60 |
| Example 43 | 54 |
| Example 44 | 69 |
| Example 45 | 60 |
| Example 46 | 71 |
| Example 47 | 66 |
| Example 48 | 63 |
| Example 50 | 68 |
| Example 51 | 60 |
| Example 52 | 63 |
| Example 54 | 62 |
| Example 56 | 76 |
| Example 58 | 69 |
| Example 59 | 61 |
| Example 60 | 71 |
| Example 61 | 75 |
| Example 62 | 68 |
| Example 63 | 72 |
| Example 64 | 70 |
| Example 65 | 64 |
| Example 66 | 74 |
| Example 67 | 72 |
| Example 68 | 66 |
| Example 70 | 75 |
| Example 71 | 71 |
| Example 72 | 51 |
| Example 73 | 59 |
| Example 75 | 61 |
| Example 76 | 68 |
| Example 77 | 55 |
| Example 78 | 69 |
| Example 79 | 67 |
| Example 81 | 82 |
| Example 82 | 78 |
| Example 83 | 78 |
| Example 84 | 76 |
| Example 85 | 68 |
| Example 86 | 76 |
| Example 87 | 64 |
| Example 88 | 71 |

TABLE 2-continued

| test compound | inhibitory rate (%) at 10 μM |
|---|---|
| Example 89 | 62 |
| Example 90 | 66 |
| Example 91 | 71 |
| Example 92 | 56 |
| Example A1 | 76 |
| Example A2 | 64 |
| Example A3 | 55 |
| Example A4 | 66 |
| Example A5 | 77 |
| Example A6 | 87 |
| Example A7 | 60 |
| Example A8 | 78 |
| Example A9 | 67 |
| Example A10 | 80 |
| Example A11 | 74 |
| Example A12 | 72 |
| Example A13 | 85 |
| Example A14 | 73 |
| Example A15 | 72 |
| Example A16 | 74 |
| Example A17 | 72 |
| Example A19 | 71 |
| Example A20 | 72 |
| Example A21 | 62 |
| Example A22 | 66 |
| Example A23 | 77 |
| Example A24 | 70 |
| Example A25 | 60 |
| Example A26 | 64 |
| Example A27 | 80 |
| Example A28 | 62 |
| Example A29 | 77 |
| Example A30 | 76 |
| Example A31 | 62 |
| Example A32 | 72 |
| Example A33 | 76 |
| Example A34 | 75 |
| Example A35 | 71 |
| Example A36 | 73 |
| Example A37 | 78 |
| Example A38 | 56 |
| Example A39 | 78 |
| Example A41 | 86 |
| Example A43 | 80 |
| Example A44 | 82 |
| Example A46 | 78 |
| Example A47 | 67 |
| Example A48 | 66 |
| Example A49 | 86 |
| Example A51 | 71 |
| Example A52 | 64 |
| Example A53 | 83 |
| Example A54 | 52 |
| Example A55 | 90 |
| Example A56 | 76 |
| Example A57 | 85 |
| Example A59 | 77 |
| Example A60 | 85 |
| Example A62 | 81 |
| Example A63 | 90 |
| Example A64 | 84 |
| Example A65 | 79 |
| Example A68 | 82 |
| Example A69 | 89 |
| Example A72 | 79 |
| Example A73 | 87 |
| Example A76 | 83 |
| Example A78 | 90 |
| Example A79 | 73 |
| Example A80 | 92 |
| Example A82 | 89 |
| Example A83 | 93 |
| Example A85 | 82 |
| Example A86 | 89 |
| Example A88 | 75 |
| Example A89 | 80 |
| Example A90 | 77 |
| Example A91 | 79 |
| Example A92 | 76 |
| Example A93 | 70 |
| Example A94 | 57 |
| Example A96 | 76 |
| Example A97 | 76 |
| Example A98 | 78 |
| Example A99 | 80 |
| Example A100 | 78 |
| Example A101 | 76 |
| Example A102 | 68 |
| Example A103 | 66 |
| Example A104 | 68 |
| Example A105 | 67 |
| Example A106 | 69 |
| Example A107 | 74 |
| Example A108 | 58 |
| Example A109 | 58 |
| Example A111 | 70 |
| Example A112 | 85 |
| Example A113 | 68 |
| Example A114 | 70 |
| Example A115 | 53 |
| Example A116 | 58 |
| Example A118 | 70 |
| Example A119 | 70 |
| Example A120 | 73 |
| Example A121 | 59 |
| Example A123 | 71 |
| Example A124 | 51 |
| Example A125 | 69 |
| Example A126 | 68 |
| Example A127 | 71 |
| Example A128 | 83 |
| Example A129 | 82 |
| Example A130 | 76 |
| Example A131 | 87 |
| Example A132 | 83 |
| Example A133 | 80 |
| Example A134 | 82 |
| Example A135 | 76 |
| Example A136 | 62 |
| Example A137 | 75 |
| Example A138 | 85 |
| Example A139 | 76 |
| Example A140 | 83 |
| Example A141 | 86 |
| Example A142 | 87 |
| Example A143 | 75 |
| Example A144 | 82 |
| Example A145 | 76 |
| Example A146 | 77 |
| Example A147 | 99 |
| Example A148 | 94 |
| Example A149 | 69 |
| Example A150 | 81 |
| Example A151 | 78 |
| Example A152 | 76 |
| Example A153 | 74 |
| Example A154 | 82 |
| Example A155 | 81 |
| Example A156 | 80 |
| Example A157 | 80 |
| Example A158 | 79 |
| Example A159 | 74 |
| Example A160 | 92 |
| Example A161 | 84 |
| Example A162 | 79 |
| Example A163 | 87 |
| Example A164 | 85 |
| Example A165 | 85 |
| Example A166 | 75 |
| Example A167 | 86 |
| Example A168 | 90 |
| Example A169 | 86 |
| Example A170 | 89 |
| Example A171 | 86 |
| Example A172 | 82 |
| Example A173 | 74 |

TABLE 2-continued

| test compound | inhibitory rate (%) at 10 μM |
| --- | --- |
| Example A174 | 98 |
| Example A175 | 68 |
| Example A176 | 96 |
| Example A177 | 90 |
| Example A178 | 86 |
| Example A179 | 84 |
| Example A180 | 83 |
| Example A181 | 88 |
| Example A182 | 95 |
| Example A183 | 88 |
| Example A184 | 74 |
| Example A185 | 71 |
| Example A186 | 85 |
| Example A187 | 90 |
| Example A188 | 77 |
| Example A190 | 86 |
| Example A191 | 82 |
| Example A192 | 72 |
| Example A193 | 80 |
| Example A194 | 88 |
| Example A195 | 84 |
| Example A196 | 87 |
| Example A198 | 87 |
| Example A199 | 88 |
| Example A200 | 89 |
| Example A202 | 86 |
| Example A204 | 86 |
| Example A206 | 70 |
| Example A208 | 83 |
| Example A209 | 90 |
| Example A211 | 70 |
| Example A213 | 70 |
| Example A214 | 75 |
| Example A215 | 72 |

As mentioned above, it has been shown that the compound of the present invention has a superior glucagon binding inhibitory action.

Experimental Example 2

Suppressive Action Test for Glucagon-Induced Blood Glucose Increase (Rat)

Full feeding SD rats (male, 7- to 9-week-old) were fasted, 0.5% methylcellulose suspension containing a test compound (10 mg/kg body weight) (compound administration group, 5 rats per group) or 0.5% methylcellulose suspension (compound non-administration group, 12 rats, per group) was orally administered, and 60 min later, glucagon (15 μg/kg body weight, Novo Nordisk Pharma Ltd.) was subcutaneously administered. At 20 min from the glucagon administration, blood samples were collected from the rat tail vein and the blood glucose was measured using a self-testing glucose kit ACCU-CHEK (Roche Diagnostics K.K.). In addition, as a non-treatment group (5 rats per group), the blood glucose of rat (compound non-treatment group) free of glucagon administration was measured in the same manner as above.

The difference between the blood glucose of compound non-administration group or compound administration group and the blood glucose of non-treatment group was calculated. The percentage of "the difference between blood glucose of compound administration group and blood glucose of non-treatment group" was obtained as "blood glucose increase rate (% of control)" where "the difference between blood glucose of compound non-administration group and that of non-treatment group" is 100%. The results are shown in Table 3.

TABLE 3

| test compound | compound administration dose (mg/kg) | blood glucose increasing rate (% of control) |
| --- | --- | --- |
| Example A41 | 10 | 16.6 |
| Example A53 | 10 | 27.4 |
| Example A73 | 10 | 24.2 |
| Example A78 | 10 | 26.3 |
| Example A83 | 10 | 43.0 |

As mentioned above, it has been shown that the compound of the present invention has a superior blood glucose increase-suppressive action.

Formulation Example 1

Production of Capsule

| | |
| --- | --- |
| 1) compound of Example 1 | 30 mg |
| 2) finely powdered cellulose | 10 mg |
| 3) lactose | 19 mg |
| 4) magnesium stearate | 1 mg |
| Total | 60 mg |

1), 2), 3) and 4) are mixed and filled into a gelatin capsule.

Formulation Example 2

Production of Tablet

| | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

Total amount of 1), 2) and 3) and 30 g of 4) are kneaded with water, dried in vacuo and sieved. To this sieved powder are added 14 g of 4) and 1 g of 5), and the mixture is tabletted by tableting machine. In this way, 1000 tablets containing 30 mg of Example 1 compound per tablet are obtained.

INDUSTRIAL APPLICABILITY

The compound of the present invention has a glucagon antagonistic action, and is useful for the prophylaxis or treatment of diabetes and the like.

This application is based on patent application Nos. 2008-055250 and 2009-025511 filed in Japan, the contents of which are incorporated in full herein by this reference.

The invention claimed is:

1. A compound represented by the following formula:

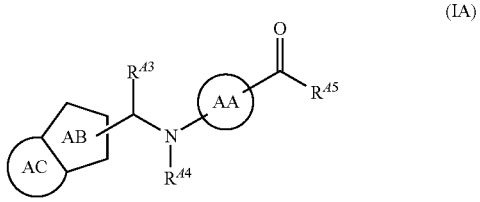

(IA)

wherein ring AA is an optionally substituted benzene ring;
ring AB is an optionally substituted furan ring;
ring AC is an optionally substituted benzene ring;
$R^{A3}$ is a $C_{1-6}$ alkyl group or a $C_{3-10}$ cycloalkyl group;
$R^{A4}$ is a hydrogen atom or a $C_{1-6}$ alkyl group;
$R^{A5}$ is $NR^{A6}$—$CR^{A7}R^{A8}$—$CR^{A9}R^{A10}$—$COOR^{A11}$;
$R^{A6}$, $R^{A7}$, $R^{A8}$, $R^{A9}$ and $R^{A11}$ are each independently a hydrogen atom or a $C_{1-6}$ alkyl group; and
$R^{A10}$ is a hydrogen atom, a $C_{1-6}$ alkyl group or a hydroxy group,
or a salt thereof.

2. The compound of claim 1, wherein
$R^{A4}$ is a hydrogen atom;
$R^{A5}$ is $NR^{A6}$—$(CH_2)_2$—$COOR^{A11}$;

$R^{A6}$ is a hydrogen atom or methyl; and
$R^{A11}$ is a hydrogen atom, methyl or ethyl.

3. 3-{[(4-{[Cyclohexyl(3-methyl-1-benzofuran-2-yl)methyl]amino}phenyl)carbonyl](methyl)amino}propanoic acid or a salt thereof.

4. 3-{[(4-{[2-Ethyl-1-(5-fluoro-3-methyl-1-benzofuran-2-yl)butyl]amino}phenyl)carbonyl](methyl)amino}propanoic acid or a salt thereof.

5. 3-[{[4-({1-[5-(Cyclopropylmethoxy)-3-methyl-1-benzofuran-2-yl]-2-methylpropyl}amino)phenyl]carbonyl}(methyl)amino]propanoic acid or a salt thereof.

6. 3-[{[4-({Cyclohexyl[3-methyl-5-(tetrahydro-2H-pyran-4-yloxy)-1-benzofuran-2-yl]methyl}amino)phenyl]carbonyl}(methyl)amino]propanoic acid or a salt thereof.

7. A pharmaceutical composition comprising the compound of claim 1 or a salt thereof, and a pharmacologically acceptable carrier.

8. A method of suppressing sugar production in a mammal, comprising administering the compound of claim 1 or a salt thereof to the mammal.

9. A method for the prophylaxis or treatment of diabetes in a mammal, comprising administering the compound of claim 1 or a salt thereof to the mammal.

10. 3-{[(4-{[Cyclopentyl(5-fluoro-3-methyl-1-benzofuran-2-yl)methyl]amino}phenyl)carbonyl](methyl)amino}propanoic acid or a salt thereof.

* * * * *